(12) United States Patent
Wang et al.

(10) Patent No.: US 10,391,175 B2
(45) Date of Patent: *Aug. 27, 2019

(54) BET BROMODOMAIN INHIBITORS AND THERAPEUTIC METHODS USING THE SAME

(71) Applicant: THE REGENTS OF THE UNIVERSITY OF MICHIGAN, Ann Arbor, MI (US)

(72) Inventors: Shaomeng Wang, Superior Township, MI (US); Xu Ran, Ann Arbor, MI (US); Yujun Zhao, Ann Arbor, MI (US); Chao-Yie Yang, Ann Arbor, MI (US); Liu Liu, Ann Arbor, MI (US); Longchuan Bai, Ann Arbor, MI (US); Donna McEachern, Ann Arbor, MI (US); Jeanne Stuckey, Fenton, MI (US); Jennifer Lynn Meagher, Ann Arbor, MI (US); Duxin Sun, Ann Arbor, MI (US); Xiaoqin Li, Ann Arbor, MI (US); Bing Zhou, Ann Arbor, MI (US); Hacer Karatas, Ann Arbor, MI (US); Ruijuan Luo, Ann Arbor, MI (US); Arul Chinnaiyan, Ann Arbor, MI (US); Irfan A. Asangani, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 22 days.

This patent is subject to a terminal disclaimer.

(21) Appl. No.: 15/619,671

(22) Filed: Jun. 12, 2017

(65) Prior Publication Data
US 2017/0281773 A1 Oct. 5, 2017

Related U.S. Application Data

(63) Continuation of application No. 14/204,076, filed on Mar. 11, 2014, now Pat. No. 9,675,697.

(60) Provisional application No. 61/936,949, filed on Feb. 7, 2014, provisional application No. 61/866,126, filed on Aug. 15, 2013, provisional application No. 61/775,886, filed on Mar. 11, 2013.

(51) Int. Cl.
| | |
|---|---|
| *A61K 31/519* | (2006.01) |
| *C07D 471/04* | (2006.01) |
| *A61K 45/06* | (2006.01) |
| *C07D 487/04* | (2006.01) |
| *C07D 491/056* | (2006.01) |

(52) U.S. Cl.
CPC ............ *A61K 45/06* (2013.01); *C07D 471/04* (2013.01); *C07D 487/04* (2013.01); *C07D 491/056* (2013.01)

(58) Field of Classification Search
CPC ............................ C07D 471/04; A61K 31/519
See application file for complete search history.

(56) References Cited

U.S. PATENT DOCUMENTS

| | | | |
|---|---|---|---|
| 7,067,507 B2* | 6/2006 | Pulley | C07D 273/02 514/183 |
| 8,044,042 B2 | 10/2011 | Adachi et al. | |
| 8,114,995 B2 | 2/2012 | Hansen et al. | |
| 8,476,260 B2 | 7/2013 | Miyoshi et al. | |
| 8,557,984 B2 | 10/2013 | Bouillot et al. | |
| 8,580,957 B2 | 11/2013 | Demont et al. | |
| 9,675,697 B2* | 6/2017 | Wang | C07D 487/04 |
| 2010/0286127 A1 | 11/2010 | Miyoshi et al. | |
| 2011/0178053 A1* | 7/2011 | Arendt | C07D 213/73 514/189 |
| 2012/0059002 A1 | 3/2012 | Hansen et al. | |
| 2012/0157428 A1 | 6/2012 | Albrecht et al. | |
| 2012/0202799 A1 | 8/2012 | Crowe et al. | |
| 2012/0208800 A1 | 8/2012 | Chung et al. | |
| 2012/0252781 A1 | 10/2012 | Bailey et al. | |
| 2013/0079335 A1 | 3/2013 | Bailey | |
| 2013/0184264 A1 | 7/2013 | Bradner et al. | |
| 2013/0252331 A1 | 9/2013 | Bradner et al. | |
| 2013/0281399 A1 | 10/2013 | McLure et al. | |
| 2013/0281450 A1 | 10/2013 | Pratt et al. | |
| 2013/0331382 A1 | 12/2013 | Hubbard et al. | |
| 2014/0005169 A1 | 1/2014 | Albrecht et al. | |

(Continued)

FOREIGN PATENT DOCUMENTS

| | | |
|---|---|---|
| EP | 0989131 | 3/2000 |
| WO | WO-2008/092231 A1 | 8/2008 |

(Continued)

OTHER PUBLICATIONS

Garnier, Jean-Marc, et al. "BET bromodomain inhibitors: a patent review." Expert Opinion on Therapeutic Patents. © Nov. 22, 2013. Accessed Jun. 10, 2018. Available from: < http://www.tandfonline.com/doi/pdf/10.1517/13543776.2014.859244 >. (Year: 2013).*

Mayo Clinic. "Cancer". © 2015. Accessed Jun. 10, 2018. Available from: <http://www.mayoclinic.org/diseases-conditions/cancer/basics/prevention/con-20032378 >. (Year: 2015).*

Sepsis Alliance. "Sepsis and Prevention: Vaccinations." © 2018. Accessed Jun. 10, 2018. Available from: < https://www.sepsis.org/sepsis-and/sepsis-prevention-vaccinations/ >. (Year: 2018).*

American Cancer Society. "Treating Squamous Cell Carcinoma of the Skin." © 2018. Accessed Jul. 2, 2018. Available from: < https://www.cancer.org/cancer/basal-and-squamous-cell-skin-cancer/treating/squamousl-cell-carcinoma.html >. (Year: 2018).*

(Continued)

*Primary Examiner* — Andrew D Kosar
*Assistant Examiner* — John S Kenyon
(74) *Attorney, Agent, or Firm* — Marshall, Gerstein & Borun LLP

(57) ABSTRACT

Inhibitors of BET bromodomains and compositions containing the same are disclosed. Methods of using the BET bromodomain inhibitors in the treatment of diseases and conditions wherein inhibition of BET bromodomain provides a benefit, like cancers, also are disclosed.

18 Claims, 13 Drawing Sheets

(56) References Cited

U.S. PATENT DOCUMENTS

| | | |
|---|---|---|
| 2014/0011862 A1 | 1/2014 | Bradner et al. |
| 2014/0066410 A1 | 3/2014 | Zhou et al. |
| 2014/0135316 A1 | 5/2014 | Albrecht et al. |
| 2014/0142102 A1 | 5/2014 | Fairfax et al. |
| 2014/0162971 A1 | 6/2014 | Wang et al. |
| 2015/0246923 A1 | 9/2015 | Wang et al. |

FOREIGN PATENT DOCUMENTS

| | | | |
|---|---|---|---|
| WO | WO-2008/137816 A2 | 11/2008 | |
| WO | WO-2009/075830 A1 | 6/2009 | |
| WO | WO-2011/143669 A2 | 11/2011 | |
| WO | WO-2012/075383 | 6/2012 | |
| WO | WO-2012/075456 A1 | 6/2012 | |
| WO | WO-2012/174487 | 12/2012 | |
| WO | WO-2013/024104 | 2/2013 | |
| WO | WO-2013/027168 | 2/2013 | |
| WO | WO-2013/030150 | 3/2013 | |
| WO | WO-2013/033268 | 3/2013 | |
| WO | WO-2013/110198 A1 | 8/2013 | |
| WO | WO-2014/134232 A1 | 9/2014 | |
| WO | WO-2015131005 A1 * | 9/2015 | ........... C07D 487/04 |
| WO | WO-2016/138332 A1 | 9/2016 | |

OTHER PUBLICATIONS

Hirshberg Foundation for Pancreatic Cancer Research. "Prognosis." © 2018. Accessed Jul. 2, 2018. Available from: < http://pancreatic.org/pancreatic-cancer/about-the-pancreas/prognosis/ >. (Year: 2018).*

Mayo Clinic. "Heart Transplant." © 2018. Accessed: Jul. 2, 2018. Available from: < https://www.mayoclinic.org/tests-procedures/heart-transplant/about/pac-20384750 >. (Year: 2018).*

Mayo Clinic. "Hepatitis B." © 2018. Accessed Jul. 2, 2018. Available from: < https://www.mayoclinic.org/diseases-conditions/hepatitis-b/diagnosis-treatment/drc-20366821 >. (Year: 2018).*

Children's Oncology Group. © Sep. 2011. Accessed Jul. 2, 2018. Available from: < https://www.childrensoncologygroup.org/index.php/osteosarcoma >. (Year: 2011).*

"Sepsis can strike, kill shockingly fast." Jan. 29, 2009. Accessed Jul. 2, 2018. Available from: < http://www.cnn.com/2009/HEALTH/01/29/ep.sepsis.infection/index.html >. (Year: 2009).*

Belkina et al., BET domain co-regulators in obesity, inflammation and cancer, Nat. Rev. Cancer, 12(7):465-77 (2012).

Extended European Search Report for European Patent Application No. 14779458.0, dated Jul. 13, 2016.

Ferguson et al., Targeting Low-Druggability Bromodomains: Fragment Based Screening and Inhibitor Design against the BAZ2B Bromodomain, J. Med. Chem., 56:10183-10187 (2013).

Filippakopoulos et al., Histone recognition and large-scale structural analysis of the human bromodomain family, Cell, 149(1):214-31 (2012).

Garnier et al., BET bromodomain inhibitors: a patent review, Exp. Opin. Ther. Patents, 24:1-15 (2013).

Haynes et al., The bromodomain: a conserved sequence found in human, *Drosophila* and yeast proteins, Nucleic Acids Res., 20(10):2603 (1992).

International Search Report in international application No. PCT/US2014/022953, dated Jul. 24, 2014.

Mayo Clinic. "Cancer". . . Copyrgt. 2015. Available from: < http://www.mayoclinic.org/diseases-conditions/cancer/basics/prevention/co- n-20032378 >.

Muller et al., Bromodomains as therapeutic targets, Expert Rev. Mol. Med., 13:e29 (2011).

Sanchez et al., The role of human bromodomains in chromatin biology and gene transcription, Curr. Opin. Drug Discov. Devel., 12(5):659-65 (2009).

* cited by examiner

BET BROMODOMAIN INHIBITORS AND THERAPEUTIC METHODS USING THE SAME

FIELD OF THE INVENTION

The present invention relates to BET bromodomain inhibitors and to therapeutic methods of treating conditions and diseases wherein inhibition of BET bromodomains provides a benefit.

BACKGROUND OF THE INVENTION

The genomes of eukaryotic organisms are highly organized within the nucleus of the cell. The long strands of duplex DNA are wrapped around an octamer of histone proteins (usually comprising two copies of histones H2A, H2B, H3, and H4) to form a nucleosome, which then is further compressed to form a highly condensed chromatin structure. A range of different condensation states are possible, and the tightness of this structure varies during the cell cycle. The chromatin structure plays a critical role in regulating gene transcription, which cannot occur efficiently from highly condensed chromatin. The chromatin structure is controlled by a series of post translational modifications to histone proteins, notably histones H3 and H4. These modifications include acetylation, methylation, phosphorylation, ubiquitinylation, and SUMOylation.

Histone acetylation usually is associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (about 110 amino acid) distinct domains within proteins that bind to acetylated lysine resides commonly, but not exclusively, in the context of histones. There is a family of about 50 proteins known to contain bromodomains, which have a range of functions within the cell.

The BET family of bromodomain-containing proteins includes four proteins, i.e., BRD2, BRD3, BRD4, and BRD-t, which contain tandem bromodomains capable of binding to two acetylated lysine residues in close proximity, thereby increasing the specificity of the interaction. BRD2 and BRD3 associate with histones along actively transcribed genes and may be involved in facilitating transcriptional elongation, while BRD4 may be involved in the recruitment of the pTEF-β complex to inducible genes, resulting in phosphorylation of RNA polymerase and increased transcriptional output. BRD4 or BRD3 also may fuse with NUT (nuclear protein in testis) forming novel fusion oncogenes, BRD4-NUT or BRD3-NUT, in a highly malignant form of epithelial neoplasia. Data suggests that BRD-NUT fusion proteins contribute to carcinogenesis. BRD-t is uniquely expressed in the testes and ovary. All family members have been reported to have some function in controlling or executing aspects of the cell cycle, and have been shown to remain in complex with chromosomes during cell division, which suggests a role in the maintenance of epigenetic memory. In addition, some viruses make use of these proteins to tether their genomes to the host cell chromatin as part of the process of viral replication.

A discussion of BET proteins can be found in WO 2012/075456, WO 2012/075383, and WO 2011/054864, each designating the U.S. and each incorporated herein by reference in its entirety. A discussion of BET bromodomain inhibitors, e.g., I-BET-151 and I-BET-762, can be found in Delmore et al., *Cell* 146:904-917 (2011) and Seal et al., *Bioorg. Med. Chem. Lett.* 22:2968-2972 (2012).

Despite research directed to BET bromodomains and BET bromodomain inhibitors, the design of potent, non-peptide inhibitors of BET bromodomains remains a significant challenge in modern drug discovery. Accordingly, a need still exists in the art for BET bromodomain inhibitors having physical and pharmacological properties that permit use of the inhibitors in therapeutic applications. The present invention provides compounds designed to bind to BET bromodomains and inhibit BET bromodomain activity.

SUMMARY OF THE INVENTION

The present invention is directed to inhibitors of BET bromodomains, to compositions comprising the inhibitors, and to methods of using the inhibitors in a therapeutic treatment of conditions and diseases wherein inhibition of BET bromodomain activity provides a benefit.

In one aspect, the present invention is directed to compounds having a structural formula (I):

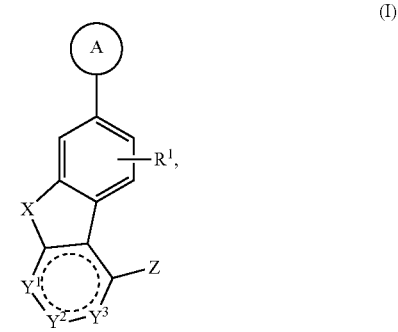

wherein:
X is $N(R^a)$, O, or S;
$Y^1$ and $Y^3$, independently, are CH or N;
$Y^2$ is CH, $CR^a$, N, or null;
Z is H,

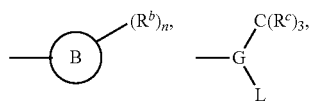

halo, OH, or null;
A is an unsubstituted or substituted 5-membered heterocyclic ring;
B is aryl, $CH(R^a)$-aryl, $C_{3-10}$cycloalkyl, $CH(R^a)$—$C_{3-10}$cycloalkyl, heteroaryl, $CH(R^a)$-heteroaryl, $C_{3-10}$heterocycloalkyl, or $CH(R^a)$—$C_{3-10}$heterocycloalkyl, each unsubstituted or substituted;
G is N, O, or S;
L is null, H, or $C(R^d)_3$;
$R^1$ is H, halo, OH, $OR^a$, or $N(R^a)_2$;
$R^a$, independently, is H, $C_{1-3}$alkyl, or benzyl;
$R^b$, independently, is $C_{1-6}$alkyl, halo, aryl, unsubstituted or substituted $CH_2$-aryl, unsubstituted or substituted $C_{3-10}$cycloalkyl, unsubstituted or substituted $CH_2$—$C_{3-10}$cycloalkyl, heteroaryl, unsubstituted or substituted $CH_2$-heteroaryl, unsubstituted or substituted $C_{3-10}$heterocycloalkyl, or unsubstituted or substituted $CH_2$—$C_{3-10}$heterocycloalkyl, or CHO;
n is an integer 0, 1, 2, or 3;

$R^c$ and $R^d$, each independently, are hydrogen, $C_{1-6}$alkyl, unsubstituted or substituted aryl, unsubstituted or substituted $CH_2$-aryl, unsubstituted or substituted $C_{3-10}$cycloalkyl, unsubstituted or substituted $CH_2$—$C_{3-10}$cycloalkyl, heteroaryl, unsubstituted or substituted $CH_2$-heteroaryl, unsubstituted or substituted $C_{3-10}$heterocycloalkyl, or unsubstituted or substituted $CH_2$—$C_{3-10}$heterocycloalkyl;

or a pharmaceutically acceptable salt, hydrate, or solvate thereof.

In another aspect, the present invention is directed to compounds having a structural formula (I):

(I)

wherein:

X is $N(R^{a1})$, O, or S;
$Y^1$ and $Y^3$, independently, are CH or N;
$Y^2$ is $CR^2$, N, or null;
Z is H, halo, or OH;

A is an unsubstituted or substituted 5-membered heterocyclic ring;

B is aryl, $CH(R^{a2})$-aryl, $C_{3-10}$cycloalkyl, $CH(R^{a2})$—$C_{3-10}$cycloalkyl, heteroaryl, $CH(R^{a2})$-heteroaryl, $C_{3-10}$heterocycloalkyl, $CH(R^{a2})$—$C_{3-10}$heterocycloalkyl, each unsubstituted or substituted;
G is N, O, or S;
L is null, H, or $C(R^d)_3$;
$R^1$ is H, halo, OH, $OR^{a3}$, $R^{a3}$, or $N(R^{a3})_2$;
$R^{a1}$, $R^{a2}$, $R^{a3}$, $R^{a4}$, and $R^{a5}$ each independently, is H, $C_{1-3}$alkyl, phenyl, or benzyl;
$R^2$, independently, is
H,
$C_{1-3}$alkyl,
$(CH_2)_{1-3}C_{4-7}$heterocycloalkyl,
$C_{4-7}$heterocycloalkyl,
$CO_2H$,
$CO_2(C_{1-3}$alkyl$)$,
$NH_2$,
$NH(C_{1-3}$alkyl$)$,
$N(C_{1-3}$alkyl$)_2$,
$(CH_2)_{1-3}NMe_2$,
$(CH_2)_{1-3}OH$,
$C(Me)_2OH$,
$CH(Me)OH$,
$C(Me_2)NH_2$,
phenyl,
benzyl,
$C(=O)OR^{a4}$
$C(=O)N(R^{a4})_2$,
$C(=O)$-unsubstituted or substituted $C_{3-10}$heterocycloalkyl,
$C(=O)$-unsubstituted or substituted hydroxy$C_{3-10}$heterocycloalkyl,
$C(=O)N(R^{a1})(CH_2)_{2-3}N(C_{1-3}$ alkyl$)_2$,
$C(=O)N(R^{a1})(CH_2)_{2-3}$unsubstituted or substituted $C_{3-10}$heterocycloalkyl,
$C(=O)N(R^{a1})$-unsubstituted or substituted $C_{3-10}$heterocycloalkyl,
$C(=O)N(R^{a1})$-hydroxycycloalkyl,
$C(=O)N(R^{a1})$—$C_{1-6}$hydroxyalkyl,

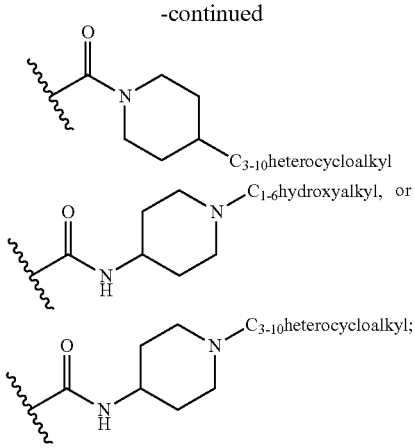

$R^b$, independently, is:
$C_{1-6}$alkyl,
$C_{1-6}$hydroxyalkyl,
halo,
aryl,
unsubstituted or substituted $CH_2$-aryl,
unsubstituted or substituted $C_{3-10}$cycloalkyl,
unsubstituted or substituted $CH_2$—$C_{3-10}$cycloalkyl,
unsubstituted or substituted heteroaryl,
unsubstituted or substituted $CH_2$-heteroaryl,
unsubstituted or substituted $C_{3-10}$heterocycloalkyl,
unsubstituted or substituted $CH_2$—$C_{3-10}$heterocycloalkyl,
$CF_3$,
CN,
$OR^{a5}$
$N(R^{a5})_2$,
$N(R^{a1})C_{1-6}$hydroxyalkyl
$N(R^{a1})C(=O)(C_{1-6}$alkyl),
$N(R^{a1})C(=O)(CH_2)_{1-3}$-unsubstituted or substituted $C_{3-10}$heterocycloalkyl,
$N(R^{a1})C(=O)(CH_2)_{1-3}$-hydroxy$C_{3-10}$heterocycloalkyl,
$NH(CH_2)_{2-3}CO_2H$,
$NH(CH_2)_{2-3}C(=O)N(R^{a5})_2$,
$N(R^{a1})C(=O)(CH_2)_{1-3}N(H)$-unsubstituted or substituted $C_{3-10}$heterocycloalkyl,
$N(R^{a1})C(=O)(CH_2)_{1-3}$-unsubstituted or substituted $C_{3-10}$heterocycloalkyl,
$N(R^{a1})C(=O)(CH_2)_{1-3}N(H)$—$C_{1-6}$hydroxyalkyl,
$N(R^{a1})C(=O)N(R^{a2})_2$,
$N(R^{a1})C(=O)N(R^{a2})$-unsubstituted or substituted $C_{3-10}$heterocycloalkyl
$N(R^{a1})C(=O)N(R^{a2})_2$,
$N(R^{a1})C(=O)N(R^{a2})$-unsubstituted or substituted $C_{3-10}$heterocycloalkyl
$NH(CH_2)_{2-3}N(C_{1-3}$alkyl$)_2$,
$NH(CH_2)_{2-3}$—$C_{3-10}$heterocycloalkyl,
$N[(CH_2)_{2-3}$—$C_{3-10}$heterocycloalkyl$]_2$,
$O(CH_2)_{2-3}N(C_{1-3}$alkyl$)_2$,
$O(CH_2)_{2-3}$—$C_{3-10}$heterocycloalkyl,
$C(=O)N(R^{a5})_2$
$C(=O)N(R^{a1})(CH_2)_{2-3}$-unsubstituted or substituted $C_{3-10}$heterocycloalkyl,
$C(=O)$-unsubstituted or substituted $C_{3-10}$heterocycloalkyl,
$N(R^{a1})C(=O)$-hydroxy$C_{3-10}$heterocycloalkyl,
$C(=O)N(R^{a1})(CH_2)_{2-3}$—$N(H)C(=O)NH_2$,
$C(=O)N(R^{a1})(CH_2)_{2-3}N(C_{1-3}$ alkyl$)_2$
$C(=O)N(R^{a1})(CH_2)_{2-3}$—$CO_2R^{a1}$,
$C(=O)N(R^{a1})$-alkyl,
$C(=O)N(R^{a1})$—$C_{1-6}$hydroxyalkyl,
$C(=O)N(R^{a1})$-unsubstituted or substituted $C_{3-10}$heterocycloalkyl,
$C(=O)N(R^{a1})$—$C_{1-6}$hydroxyalkyl,
$C(=O)N(R^{a1})CH_2CH_2OCH_2CH_2OCH_3$,
$C(=O)N(R^{a1})CH_2CH_2SO_2Me$,
$CO_2R^{a1}$,
$C(R^{a1})_2CO_2R^{a2}$,
$C(R^{a1})_2C(=O)N(R^{a5})_2$,
$C(R^{a1})_2C(=O)N(R^{a2})$-unsubstituted or substituted $C_{3-10}$heterocycloalkyl,
$C(R^{a1})_2CN$,

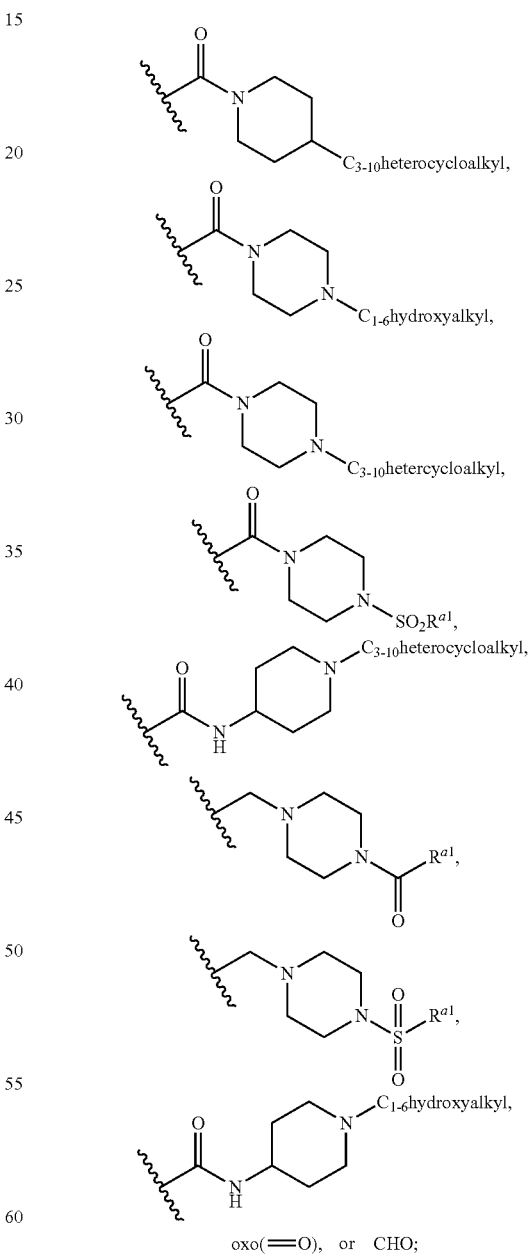

oxo(=O), or CHO;

n is an integer 0, 1, 2, or 3;
m is an integer 0, 1, 2, or 3;
$R^c$ and $R^d$, each independently, are hydrogen, $C_{1-6}$alkyl, unsubstituted or substituted aryl, unsubstituted or substituted CH$_2$-aryl, unsubstituted or substituted C$_{3-10}$cycloalkyl, unsubstituted or substituted CH$_2$—C$_{3-10}$cycloalkyl, heteroaryl, unsubstituted or substituted CH$_2$-heteroaryl, unsubstituted or substituted C$_{3-10}$heterocycloalkyl, hydroxycycloalkyl, or unsubstituted or substituted CH$_2$—C$_{3-10}$heterocycloalkyl, or R$^c$ and R$^d$ taken together form an unsubstituted or substituted C$_{3-10}$heterocycloalkyl or hydroxyC$_{3-10}$heterocycloalkyl;

Q$^-$ is a pharmaceutically acceptable anion;

or a pharmaceutically acceptable salt, hydrate, or solvate thereof.

In one embodiment, the present invention provides a method of treating a condition or disease by administering a therapeutically effective amount of a compound of structural formula (I) to an individual in need thereof. The disease or condition of interest is treatable by inhibition of BET bromodomains, for example, a cancer, a chronic autoimmune disorder, an inflammatory condition, a proliferative disorder, sepsis, or a viral infection.

Another embodiment of the present invention is to provide a composition comprising (a) a BET bromodomain inhibitor of structural formula (I) and (b) an excipient and/or pharmaceutically acceptable carrier useful in treating diseases or conditions wherein inhibition of BET bromodomains provides a benefit.

Another embodiment of the present invention is to utilize a composition comprising a compound of structural formula (I) and a second therapeutically active agent in a method of treating an individual for a disease or condition wherein inhibition of BET bromodomains, e.g., BRD2, BRD3, BRD4, BRD-t, or an isoform or mutant thereof, provides a benefit.

In a further embodiment, the invention provides for use of a composition comprising a BET bromodomain inhibitor of structural formula (I) and an optional second therapeutic agent for the manufacture of a medicament for treating a disease or condition of interest, e.g., a cancer.

Still another embodiment of the present invention is to provide a kit for human pharmaceutical use comprising (a) a container, (b1) a packaged composition comprising a BET bromodomain inhibitor of structural formula (I), and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition.

A BET bromodomain inhibitor of structural formula (I) and the second therapeutic agent can be administered together as a single-unit dose or separately as multi-unit doses, wherein the BET bromodomain inhibitor of structural formula (I) is administered before the second therapeutic agent or vice versa. It is envisioned that one or more dose of a BET bromodomain inhibitor of structural formula (I) and/or one or more dose of a second therapeutic agent can be administered.

In one embodiment, a BET bromodomain inhibitor of structural formula (I) and a second therapeutic agent are administered simultaneously. In related embodiments, a BET bromodomain inhibitor of structural formula (I) and a second therapeutic agent are administered from a single composition or from separate compositions. In a further embodiment, the BET bromodomain inhibitor of structural formula (I) and second therapeutic agent are administered sequentially. A BET bromodomain inhibitor of structural formula (I), as used in the present invention, can be administered in an amount of about 0.005 to about 500 milligrams per dose, about 0.05 to about 250 milligrams per dose, or about 0.5 to about 100 milligrams per dose.

These and other embodiments and features of the present invention will become apparent from the following detailed description of the preferred embodiments.

DETAILED DESCRIPTION OF THE PREFERRED EMBODIMENTS

Figure 1:
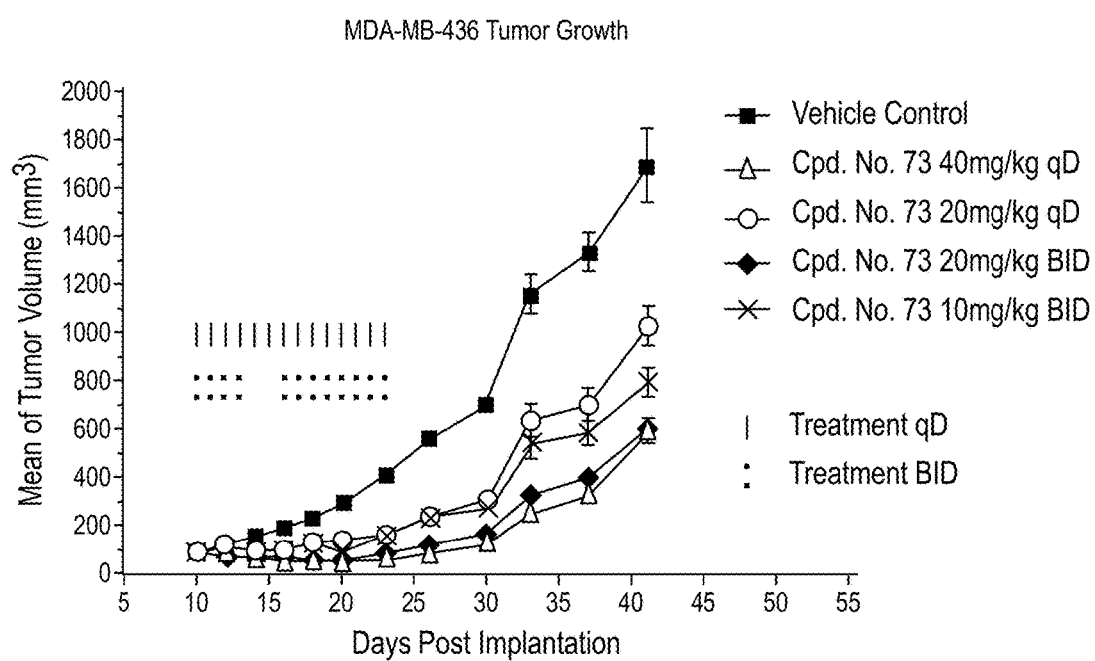
FIG. 1 is a line graph showing in vivo antitumor activity of Cpd. No. 73 in the MDA-MB-436 breast cancer xenograft model in SCID mice. Tumors were grown s.c. to an average size of 100 mm$^3$, and Cpd. No. 73 was administered orally at the indicated dose and schedule. Vehicle Control (PEG200) was given twice daily.
Figure 2:
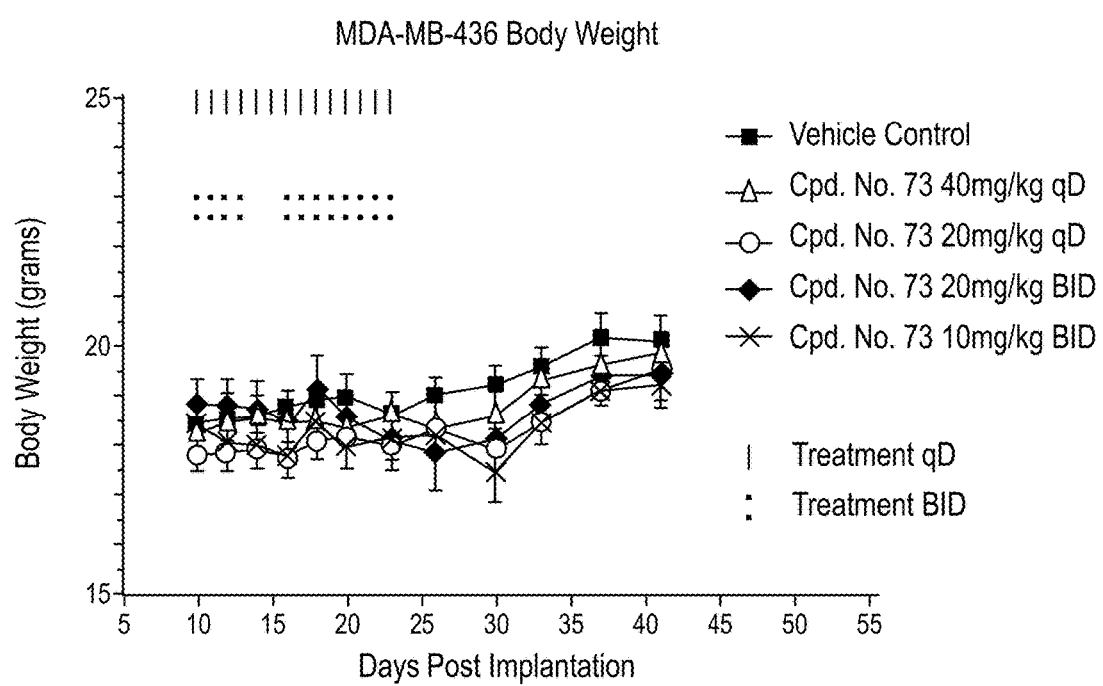
FIG. 2 is a line graph showing the animal weight following administration of Cpd. No. 73 in MDA-MB-436 tumor-bearing SCID mice. Cpd. No. 73 was administered orally at the indicated dose and schedule. Vehicle Control (PEG200) was given twice daily.
Figure 3:
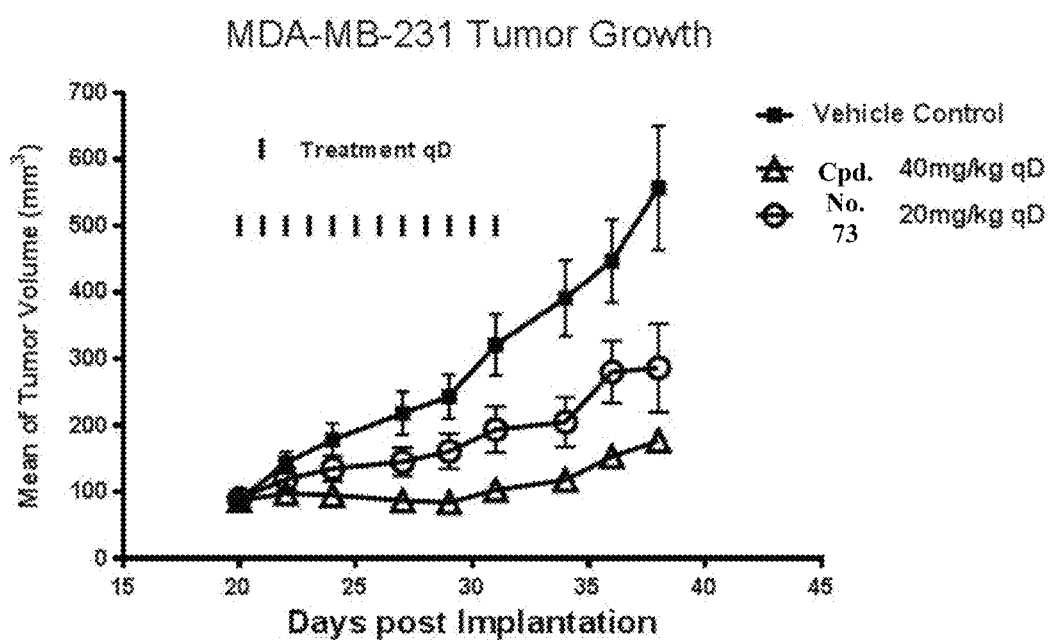
FIG. 3 is a line graph showing in vivo antitumor activity of Cpd. No. 73 in the MDA-MB-231 breast cancer xenograft model in mice. Cpd. No. 73 was administered with daily oral, dosing via oral gavage with either 20 or 40 mg/kg for 12 days. Each group had eight mice and each mouse bearing one tumor.
Figure 4:
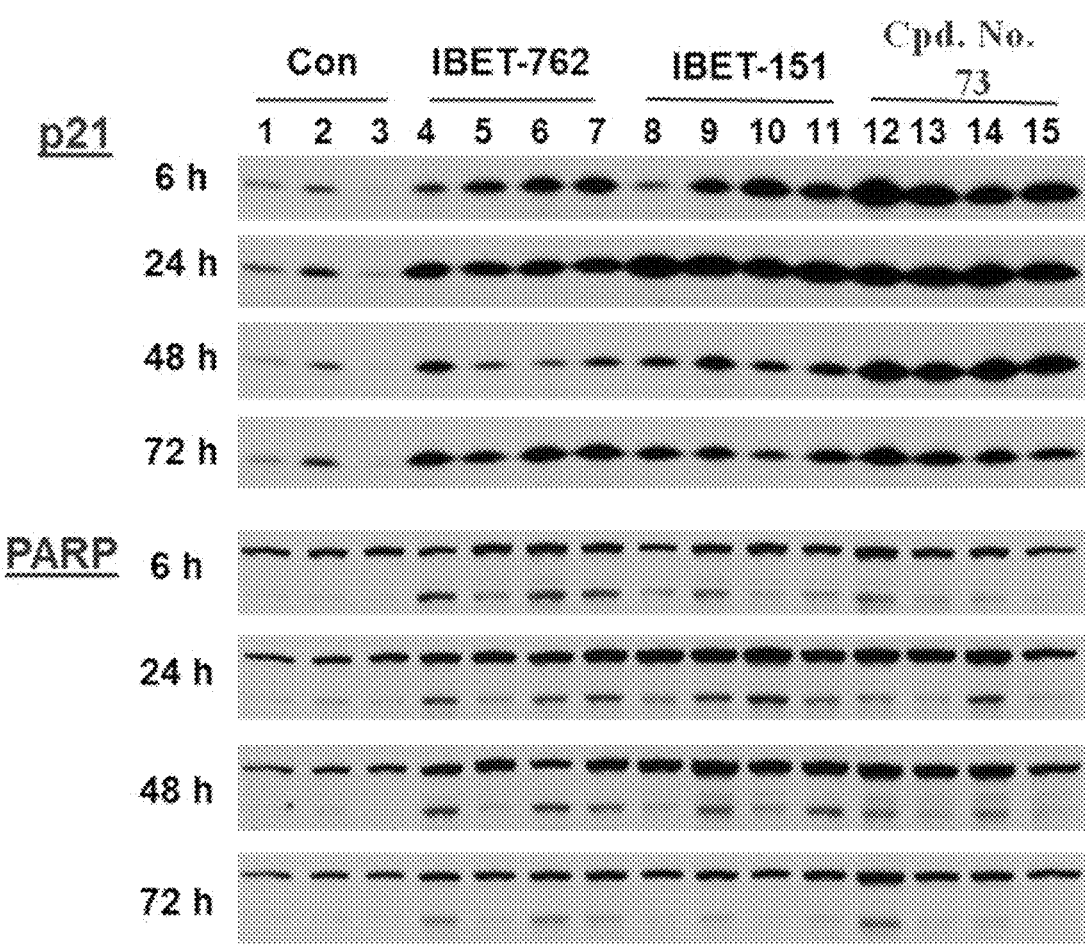
FIG. 4 is an illustration showing western blot analysis of in vivo upregulation of p21 and by BET inhibitors in MV-4; 11 xenograft tumors in SCID mice. Compounds were dosed orally at 100 mg/kg for up to 72 hours. Resected xenograft tumor tissues were grinded into powder in liquid nitrogen and lysed in lysis buffer [1% CHAPS, 150 mM NaCl, 20 mM Tris-HCl, 1 mM. EDTA, 1 mM EGTA, and COMPLETE proteinase inhibitor (Roche)] for 2 freeze-thaw (−80° C. to room temperature) cycles then another 30 minutes on ice. Protein concentrations were determined using the Bio-Rad Protein Assay Dye reagent. Whole tumor lysates (20 μg) were separated on a 4-20% Novex gels (Invitrogen). The separated proteins were transferred to a PVDF membrane (BIO-RAD) and the PVDF membrane was then blotted with 5% Blotting-Grade Blocker (BIO-RAD) for 1 hour at room temperature. The primary antibodies used were: p21Waf1/Cip1 (12D1) Rabbit mAb [Cell Signaling technology (CST), Cat#2947] and PARP (46D11) Rabbit mAb [CST #9532]. The secondary antibody used was horseradish peroxidase conjugated goat anti-rabbit (Thermo Scientific Cat#31460). The BIO-RAD Clarity Western ECL Substrates (BIO-RAD) and HyBlot CL film (Denville) were used for signal development and detection using a SRX-101A tabletop processor (Konica Minolta).
Figure 5:
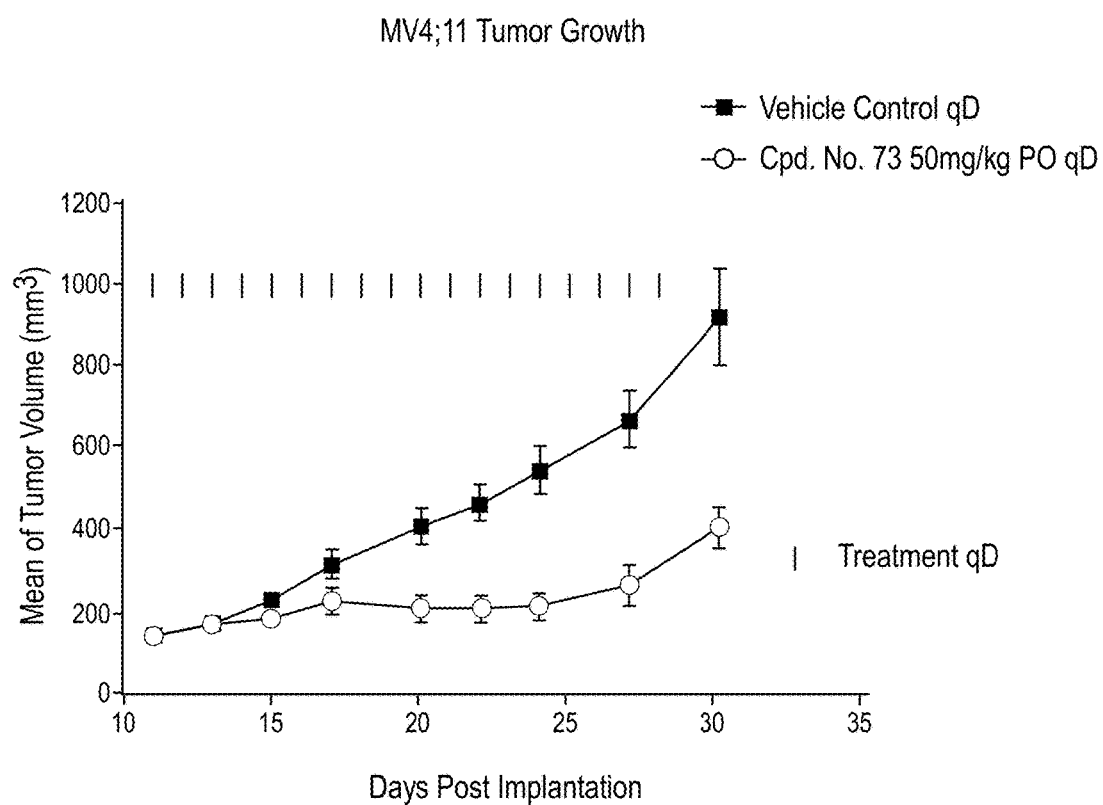
FIG. 5 is a line graph showing in vivo antitumor activity of BET inhibitors in the MV4; 11 acute myeloid leukemia (AML) xenograft model in SCID mice. Tumors were grown s.c. to an average size of 150 mm$^3$, and Cpd. No. 73 was administered orally at the indicated dose and schedule.
Figure 6:
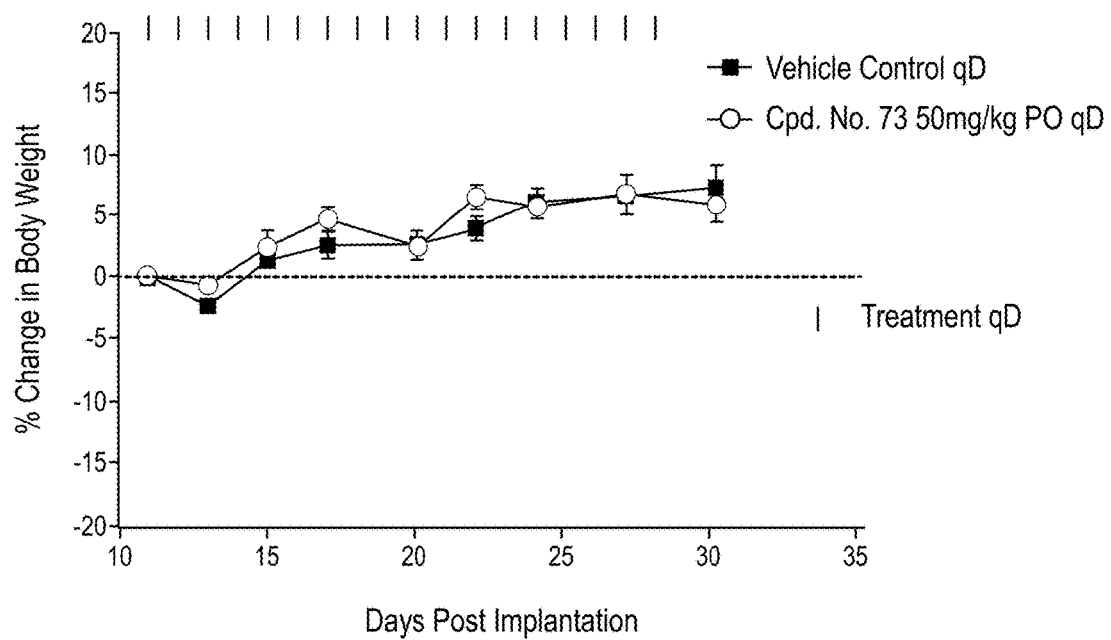
FIG. 6 is a line graph showing the animal weight following administration of BET inhibitors in MV4; 11 tumor-bearing SCID mice.
Figure 7:
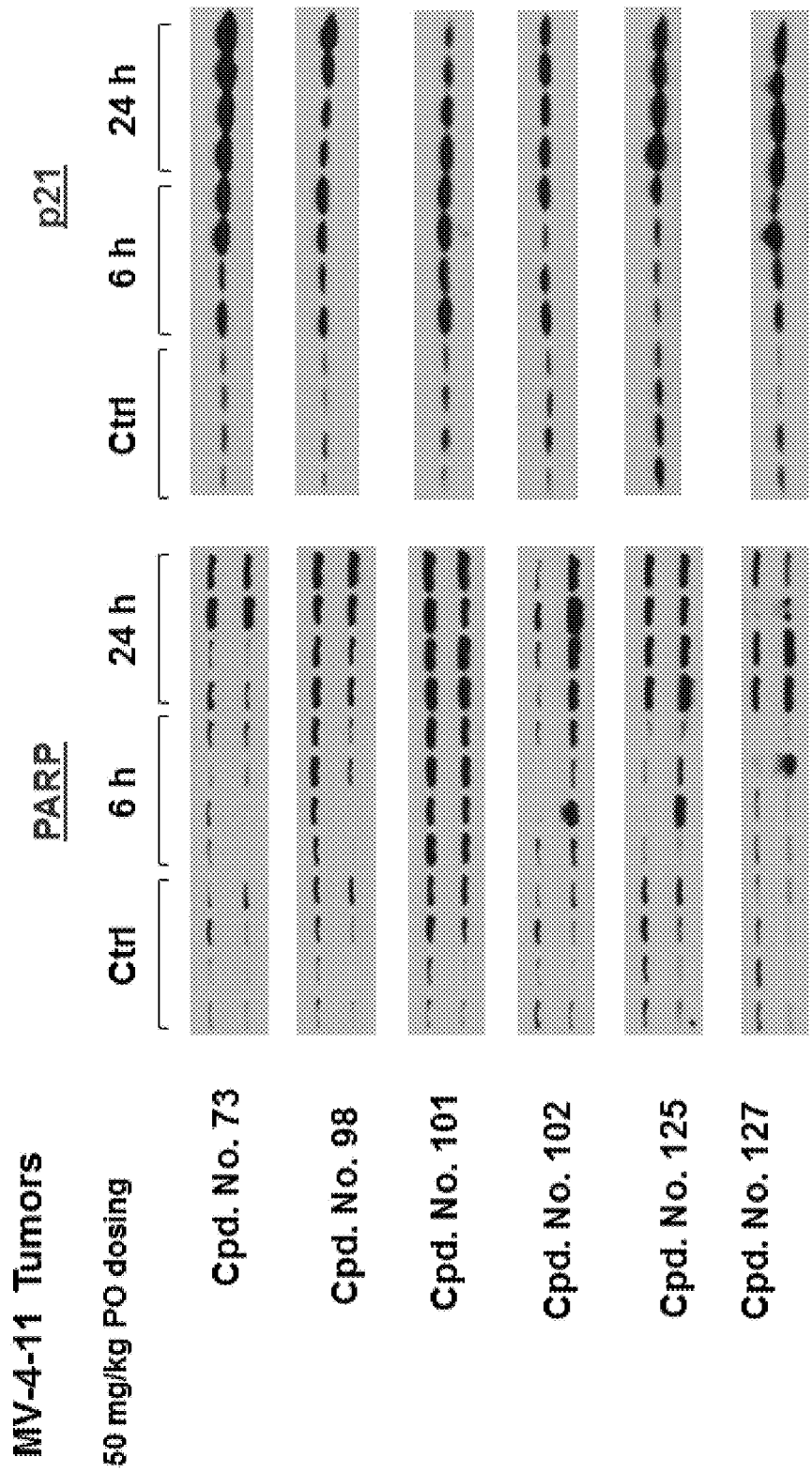
FIG. 7 is an illustration showing two western blot analyses of p21 activation and apoptosis induced by BET inhibitors in MV-4; 11 xenograft tumors in SCID mice. MV4-11 xenografts were treated with drugs at 50 mg/kg for 6 and 24 hours. Resected xenograft tumor tissues were grinded into powder in liquid nitrogen and lysed in lysis buffer [1% CHAPS, 150 mM NaCl, 20 mM Tris-HCl, 1 mM EDTA, 1 mM EGTA, and COMPLETE proteinase inhibitor (Roche)] for 2 freeze-thaw (−80° C. to room temperature) cycles then another 30 minutes on ice. Protein concentrations were determined using the Bio-Rad Protein Assay Dye reagent. Whole tumor lysates (20 µg) were separated on a 4-20% Novex gels (Invitrogen). The separated proteins were transferred to a PVDF membrane (BIO-RAD) and the PVDF membrane was then blotted with 5% Blotting-Grade Blocker (BIO-RAD) for 1 hour at room temperature. The primary antibodies used were: p21Waf1/Cip1 (12D1) Rabbit mAb [Cell Signaling technology (CST), Cat#2947] and PARP (46D11) Rabbit mAb [CST #9532]. The secondary antibody used was horseradish peroxidase conjugated goat anti-rabbit (Thermo Scientific Cat#31460). The BIO-RAD Clarity Western ECL Substrates (BIO-RAD) and HyBlot CL film (Denville) were used for signal development and detection using a SRX-101A tabletop processor (Konica Minolta).
Figure 8:
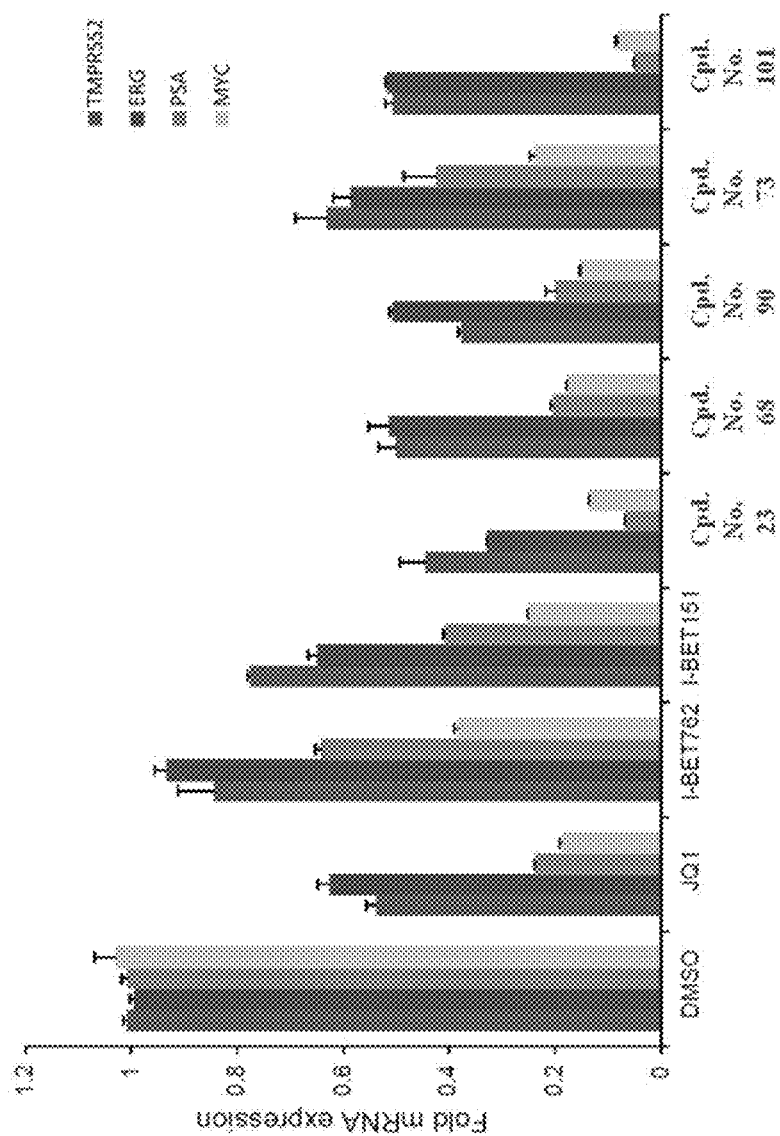
FIG. 8 is a bar graph showing AR target (PSA, ERG) and MYC (positive control) expression as measured by QRT-PCR analysis in VCaP cells treated with DMSO or 0.5 µM of the indicated BET Bromodomain inhibitor for 24 hours.
Figure 9:
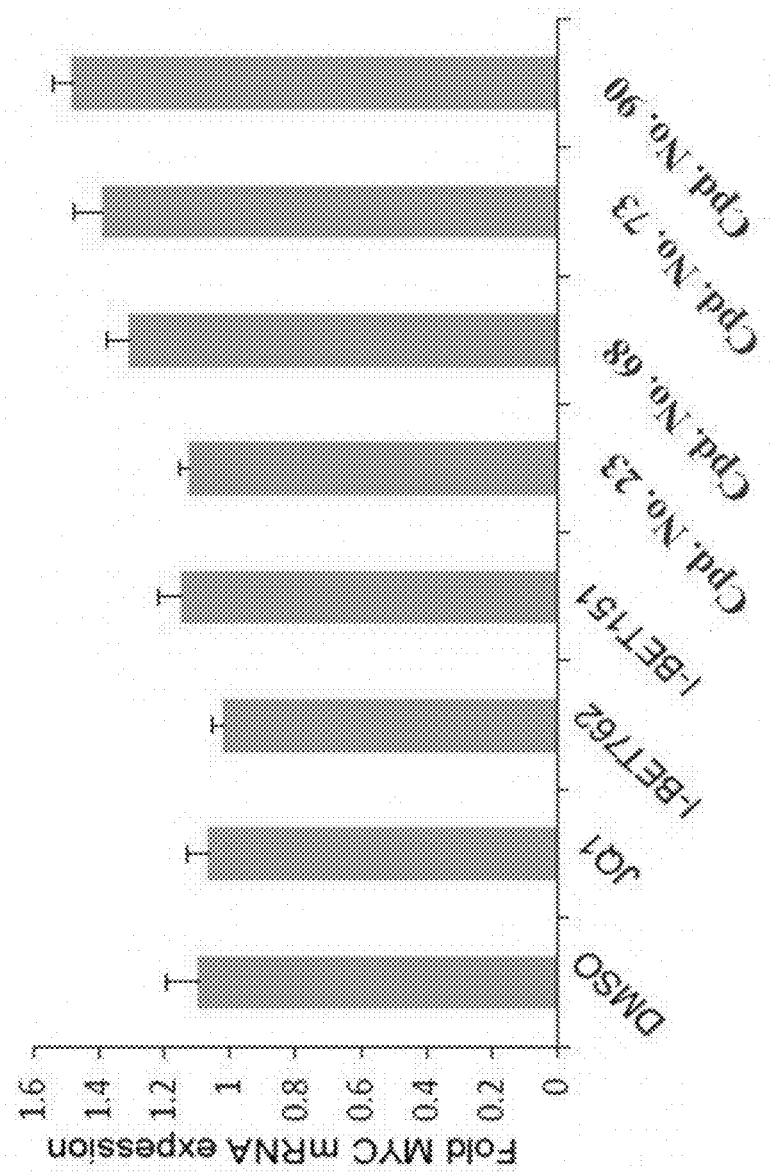
FIG. 9 is a bar graph showing MYC mRNA expression as measured by QRT-PCR analysis in AR negative DU145 cells treated with DMSO or 0.5 µM of the indicated BET Bromodomain inhibitor for 24 hours.
Figure 10:
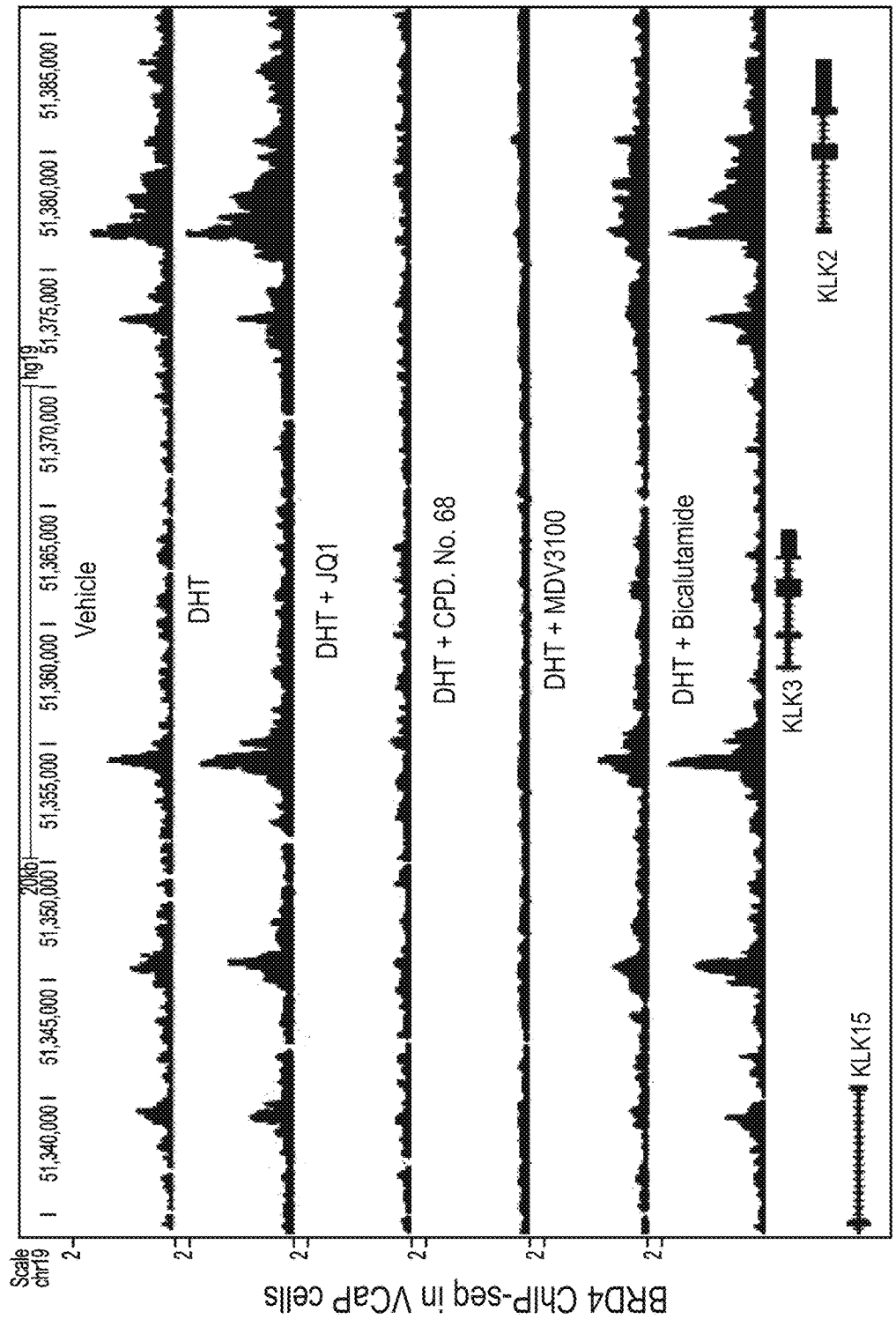
FIG. 10 is an illustration showing BRD4 de-recruitment from KLK3 (PSA) loci by BET inhibitors as measured by ChIP-seq. Starved VCaP cells were treated with 0.5 uM JQ1 or Cpd. No. 68 for 5 hrs prior to 12 hrs DHT stimulation, followed by BRD4 ChIP-seq. Anti-androgens MDV3100 (10 uM) and Bicaluatmide (25 uM) were used for comparative purpose. Figure depicts genome browser view of BRD4 binding events on AR regulated KLK3 loci. The y-axis denotes reads per million per base pair (rpm/bp). The x-axis denotes the genomic position with a scale bar on top right.
Figure 11:
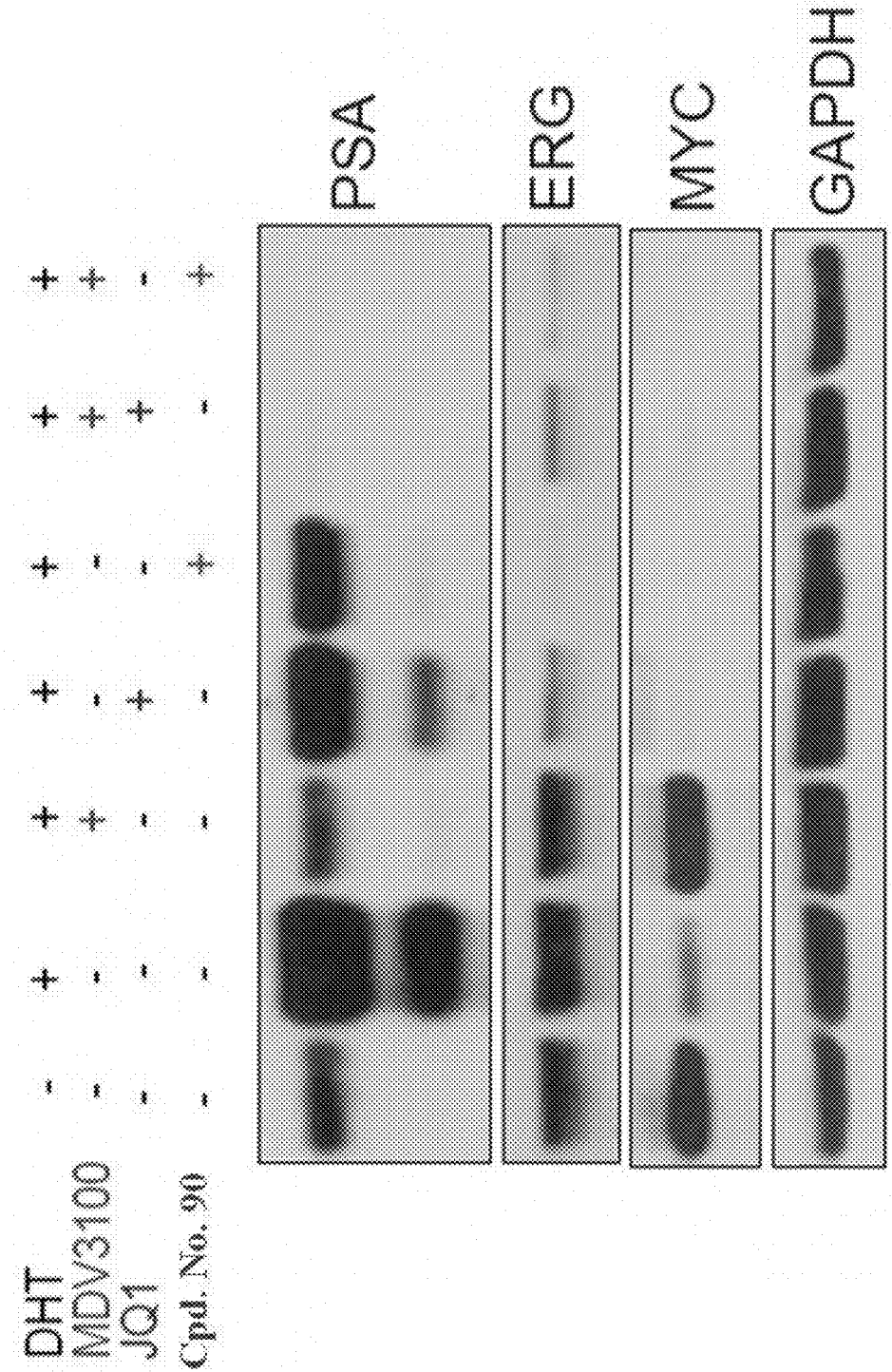
FIG. 11 is an illustration showing immunoblot analysis of PSA, ERG, and MYC proteins in starved VCaP cells pre-treated with vehicle, MDV3100 (10 µM), JQ1 (0.5 uM) or CD-225 alone or in combination as indicated for 4 hrs followed by DHT (10 nM) for 20 hrs. GAPDH was used as loading control.
Figure 12:
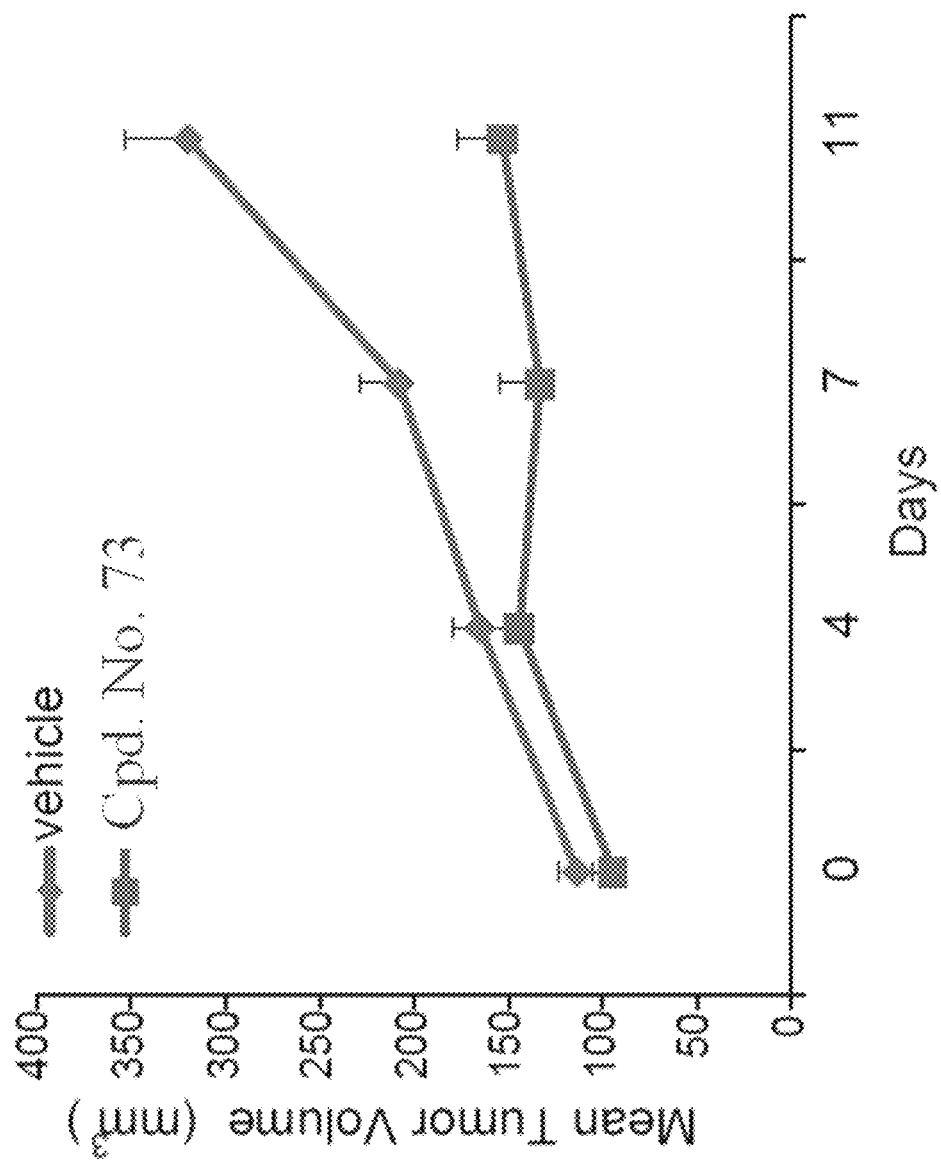
FIG. 12 is a line graph showing in vivo anti-tumor activity of Cpd. No. 73 in a VCaP prostate cancer mouse xenograph model. VCaP cells were implanted subcutaneously in mice and grown until tumors reached the size of approximately 100 mm$^3$. Xenografted mice were randomized and then received vehicle or 40 mg/kg Cpd. No. 73 by oral gavage for 5 days/week. Mean tumor volume±SEM is shown.
Figure 13:
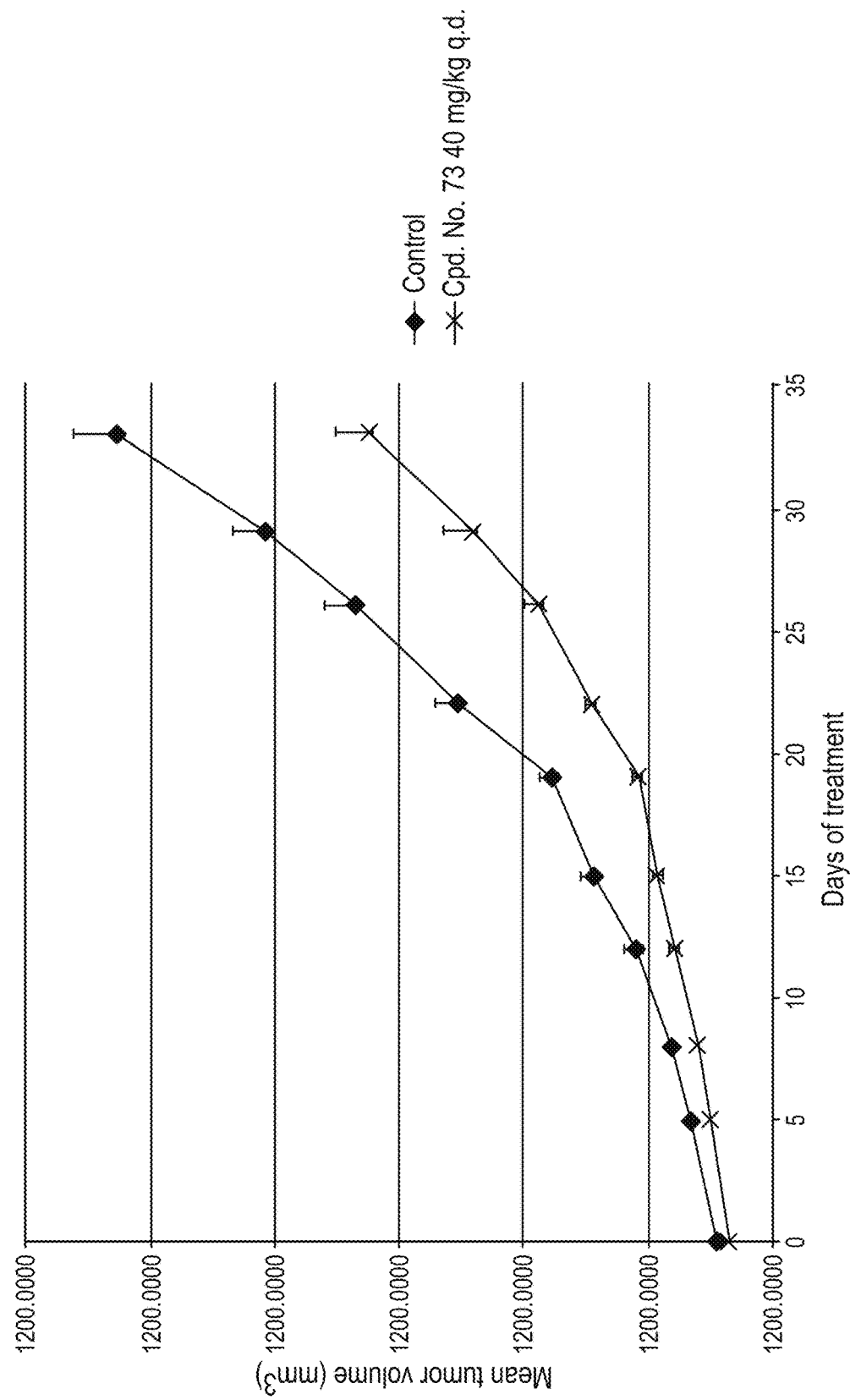
FIG. 13 is a line graph showing in vivo anti-tumor activity of Cpd. No. 73 in a VCaP prostate cancer mouse xenograph model. VCaP cells were implanted subcutaneously in mice and grown until tumors reached the size of approximately 100 mm$^3$. Xenografted mice were randomized and then received vehicle or 40 mg/kg Cpd. No. 73 by oral gavage for 13 days. Treatment was stopped from day 13 onwards and the animals were observed for tumor growth. Mean tumor volume±SEM is shown.

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

The term "BET bromodomain" as used herein means one or more of BRD2, BRD3, BRD4, and BRD-t.

The term "a disease or condition wherein inhibition of BET bromodomains provides a benefit" pertains to a condition in which at least one of BRD2, BRD3, BRD4, and BRD-t, and/or an action of at least one of BRD2, BRD3, BRD4, and BRD-t, is important or necessary, e.g., for the onset, progress, expression of that disease or condition, or a disease or a condition which is known to be treated by a BET bromodomain inhibitor. Examples of such conditions include, but are not limited to, a cancer, a chronic autoimmune disease, an inflammatory disease, a proliferative disease, sepsis, and a viral infection. One of ordinary skill in the art is readily able to determine whether a compound treats a disease or condition mediated by a BET bromodomain for any particular cell type, for example, by assays which conveniently can be used to assess the activity of particular compounds.

The term "second therapeutic agent" refers to a therapeutic agent different from a BET bromodomain inhibitor of structural formula (I) and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, a compound of structural formula (I) is a potent inhibitor of BET bromodomains and can be used in treating diseases and conditions wherein inhibition of BET bromodomains provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the invention to an individual in need of such treatment.

Within the meaning of the invention, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the invention, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce BET bromodomain signaling in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a BET bromodomain inhibitor of structural formula (I) can be administered at the same time or sequentially in any order at different points in time as a second therapeutic agent. A present BET bromodomain inhibitor and the second therapeutic agent can be administered separately, in any appropriate form and by any suitable route. When a present BET bromodomain inhibitor and the second therapeutic agent are not administered concurrently, it is understood that they can be administered in any order to a subject in need thereof. For example, a present BET bromodomain inhibitor can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a BET bromodomain inhibitor of structural formula (I) and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at 1 minute to 24 hours apart.

The use of the terms "a", "an", "the", and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

Research has established that targeting BET bromodomains using small molecule inhibitors is a viable cancer therapeutic strategy. The prior discovery of BET bromodomain inhibitors and early data have demonstrated that non-peptide, small molecule inhibitors of BET bromodomains have great therapeutic potential for the treatment of many diseases and conditions in which BET bromodomains have a role.

The present invention is directed to a new class of potent and specific inhibitors of BET bromodomains. The present compounds bind to BET bromodomains and function as potent antagonists of BET bromodomains. BET bromodomain inhibitors of the present invention therefore are useful in the treatment of a variety of diseases and conditions, including cancers and autoimmune diseases, in subjects in need of such treatment. Also provided are methods of treating a subject having unwanted proliferative cells comprising administering a therapeutically effective amount of a present compound to a subject in need of such treatment. Also provided are methods of preventing the proliferation of unwanted proliferating cells, such as cancers, in a subject comprising the step of administering a therapeutically effective amount of a compound of structural formula (I) to a subject at risk of developing a condition characterized by unwanted proliferating cells. In some embodiments, the compounds of structural formula (I) reduce the proliferation of unwanted cells by inducing apoptosis in those cells.

In one aspect, the present invention is drawn to the following particular embodiments:

Embodiment I

A compound having a structural formula (I):

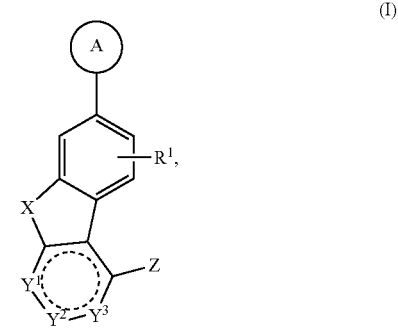

wherein

X is N(R$^a$), O, or S;

Y$^1$ and Y$^3$, independently, are CH or N;

Y$^2$ is CH, CR$^a$, N, or null;

Z is H,

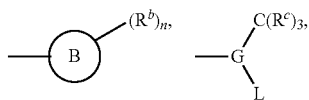

halo, OH, or null;

A is an unsubstituted or substituted 5-membered heterocyclic ring;

B is aryl, CH(R$^a$)-aryl, C$_{3-10}$cycloalkyl, CH(R$^a$)—C$_{3-10}$cycloalkyl, heteroaryl, CH(R$^a$)-heteroaryl, C$_{3-10}$heterocycloalkyl, or CH(R$^a$)—C$_{3-10}$heterocycloalkyl, each unsubstituted or substituted;

G is N, O, or S;

L is null, H, or C(R$^d$)$_3$;

R$^1$ is H, halo, OH, OR$^a$, or N(R$^a$)$_2$;

R$^a$, independently, is H, C$_{1-3}$alkyl, or benzyl;

R$^b$, independently, is C$_{1-6}$alkyl, halo, aryl, unsubstituted or substituted CH$_2$-aryl, unsubstituted or substituted C$_{3-10}$cycloalkyl, unsubstituted or substituted CH$_2$—C$_{3-10}$cycloalkyl, heteroaryl, unsubstituted or substituted CH$_2$-heteroaryl, unsubstituted or substituted C$_{3-10}$heterocycloalkyl, or unsubstituted or substituted CH$_2$—C$_{3-10}$heterocycloalkyl, or CHO;

n is an integer 0, 1, 2, or 3;

R$^c$ and R$^d$, each independently, are hydrogen, C$_{1-6}$alkyl, unsubstituted or substituted aryl, unsubstituted or substituted CH$_2$-aryl, unsubstituted or substituted C$_{3-10}$cycloalkyl, unsubstituted or substituted CH$_2$—C$_{3-10}$cycloalkyl, heteroaryl, unsubstituted or substituted CH$_2$-heteroaryl, unsubstituted or substituted C$_{3-10}$heterocycloalkyl, or unsubstituted or substituted CH$_2$—C$_{3-10}$heterocycloalkyl;

or a pharmaceutically acceptable salt, hydrate, or solvate thereof.

Embodiment II

The compound of Embodiment I, wherein ring A is an optionally substituted heteroaryl ring.

Embodiment III

The compound of Embodiment I, wherein ring A is optionally substituted:

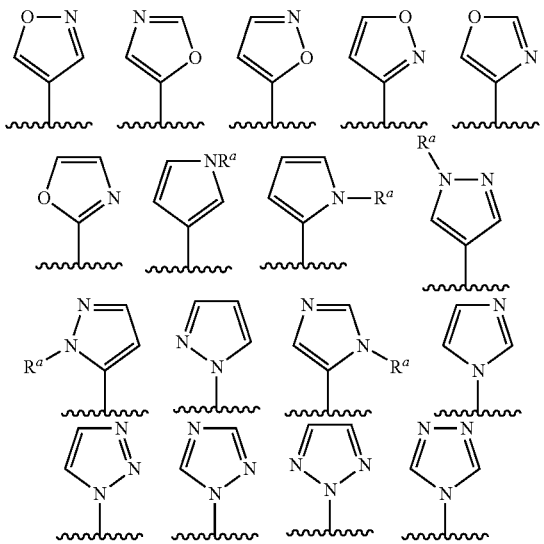

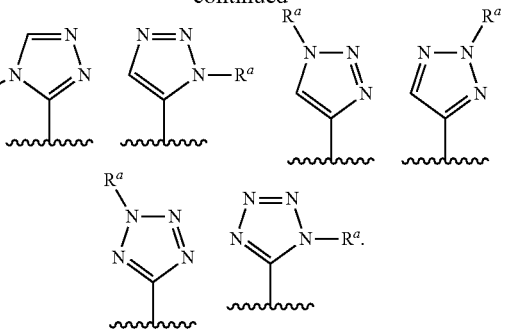

Embodiment IV

The compound of Embodiment I, wherein ring A is optionally substituted

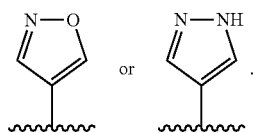

Embodiment V

The compound of Embodiment I wherein ring A is

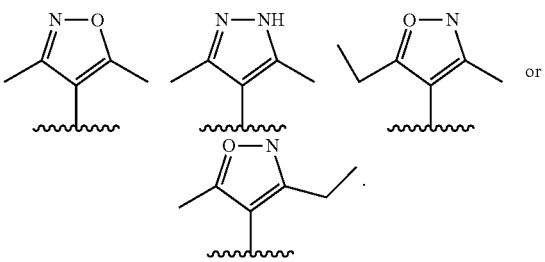

Embodiment VI

The compound of Embodiments I through V wherein R$^1$ is H or —OCH$_3$.

Embodiment VII

The compound of any of Embodiments I through VI wherein the ring system

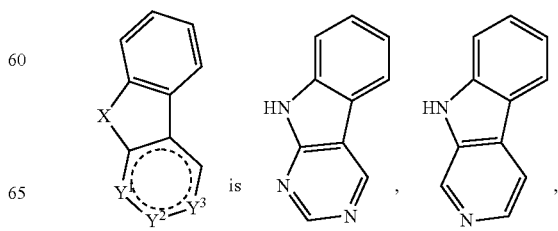

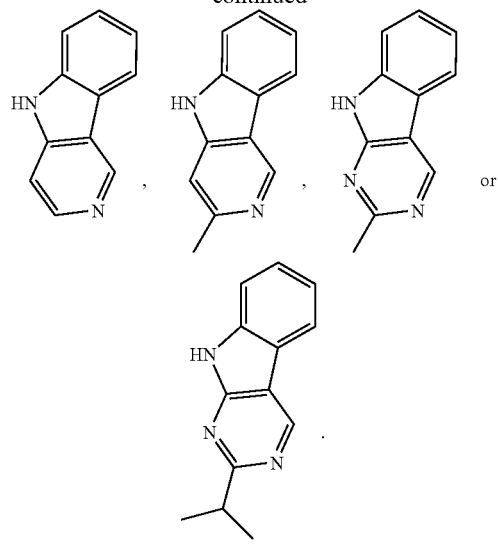
Embodiment VIII
The compound of Embodiments I through VII wherein Z is
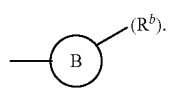
Embodiment IX
The compound of Embodiment VIII wherein the B ring, substituted or unsubstituted, is selected from the group consisting of
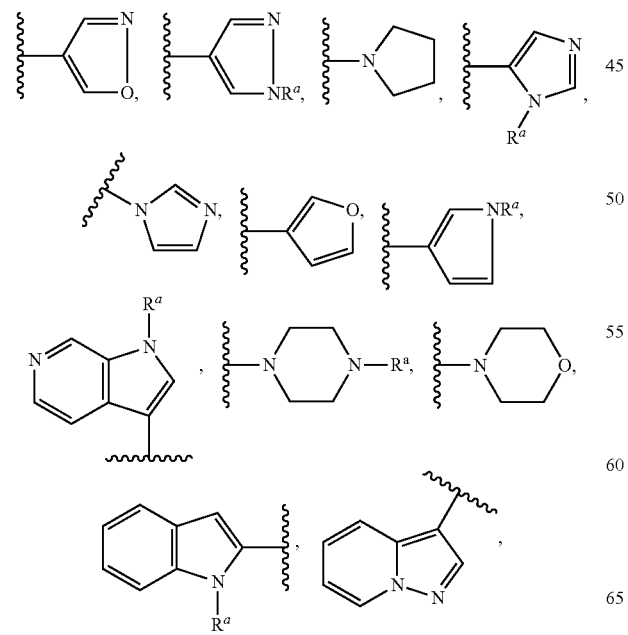
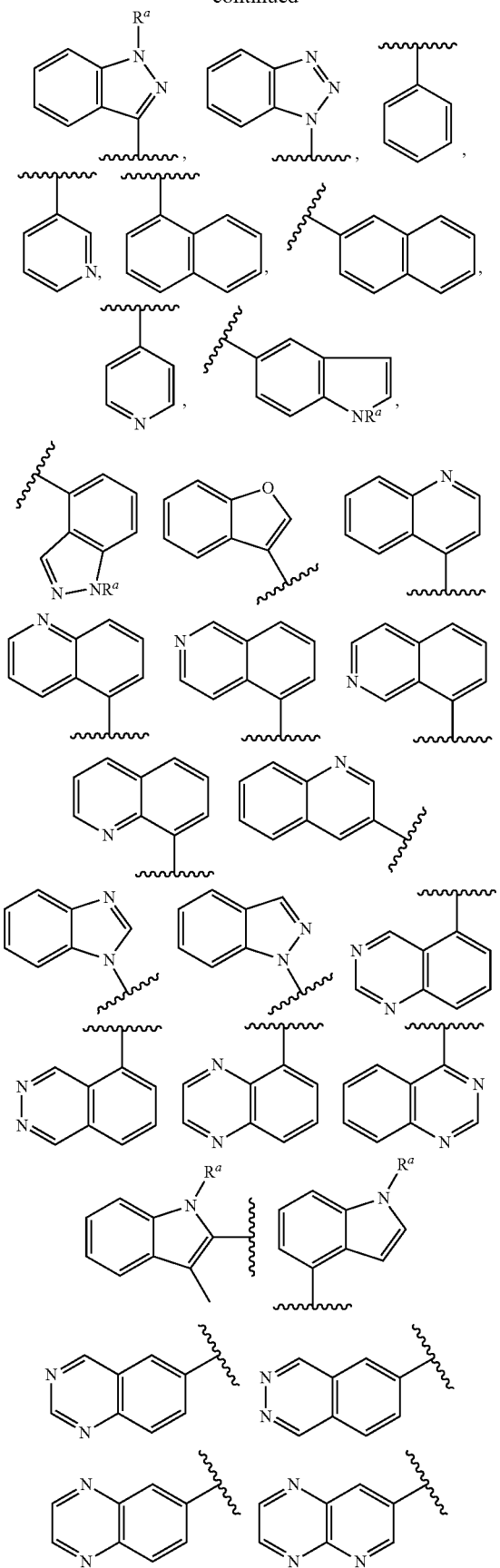

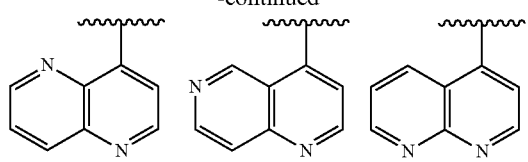
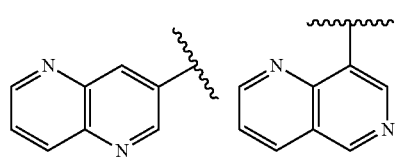
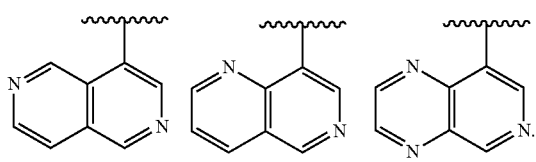
Embodiment X
The compound of Embodiment IX, wherein the B ring is substituted with one to three of methyl, phenyl, fluoro, pyridinyl, chloro, isopropyl, cyclopropyl, and ethyl.
Embodiment XI
A compound having the structure set forth as follows:
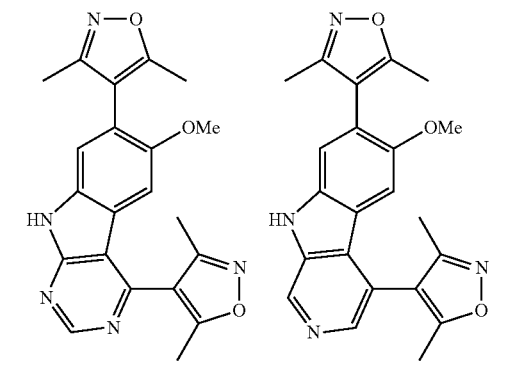
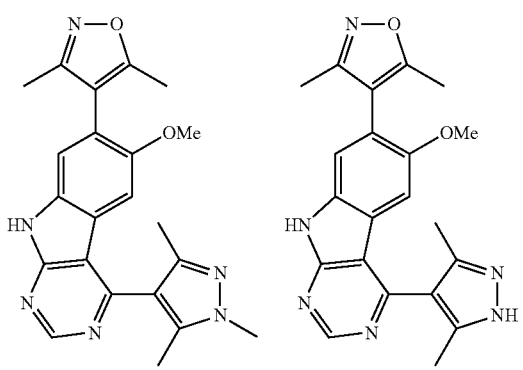
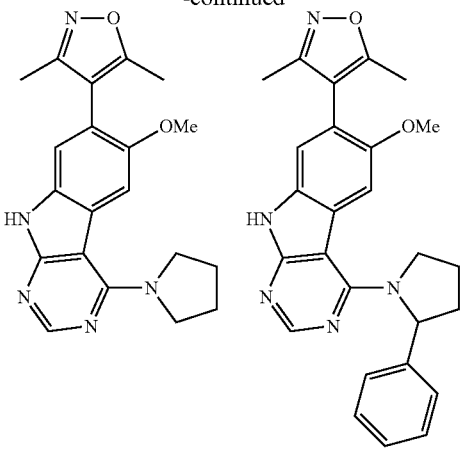
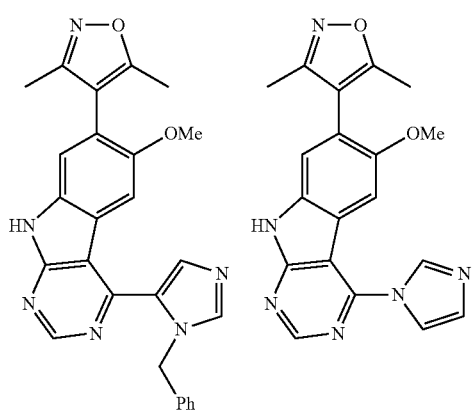
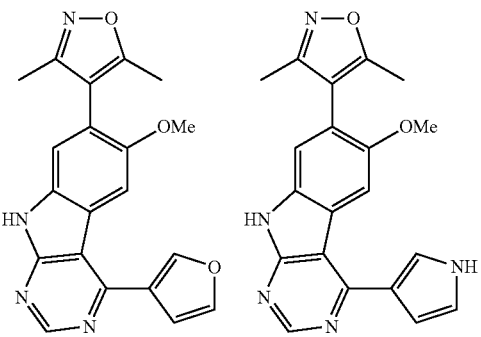
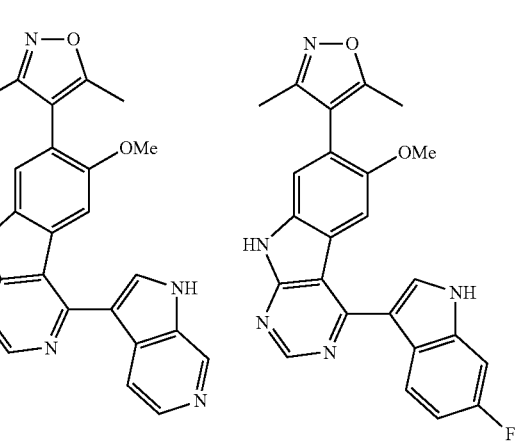

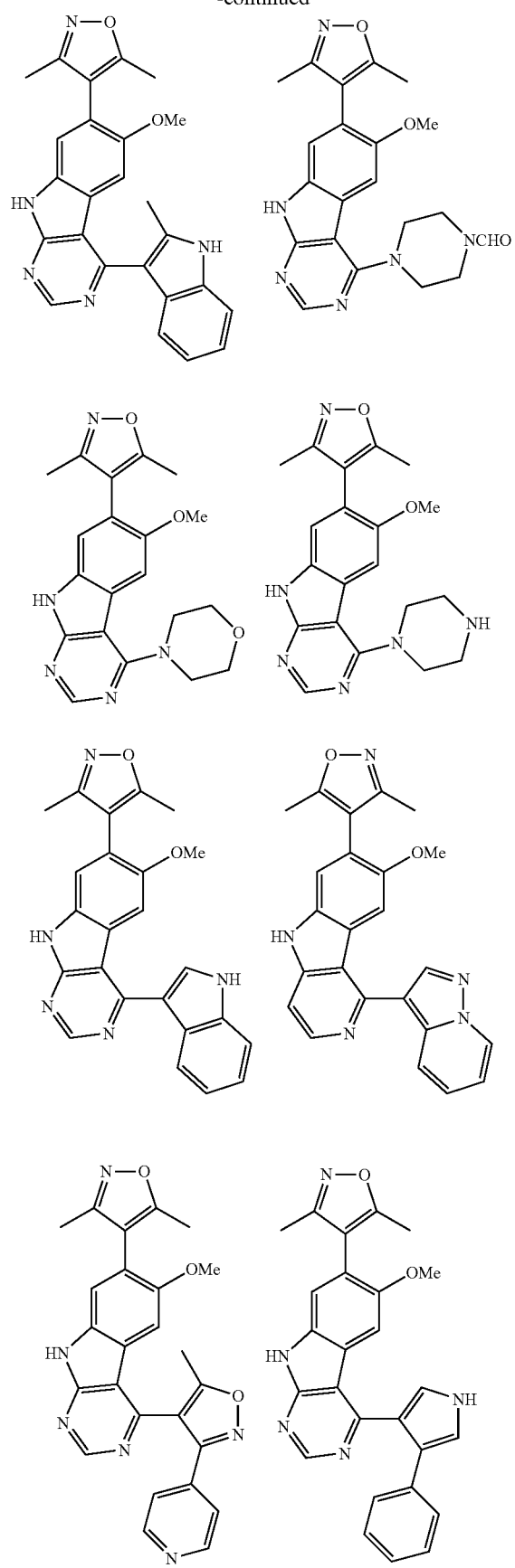
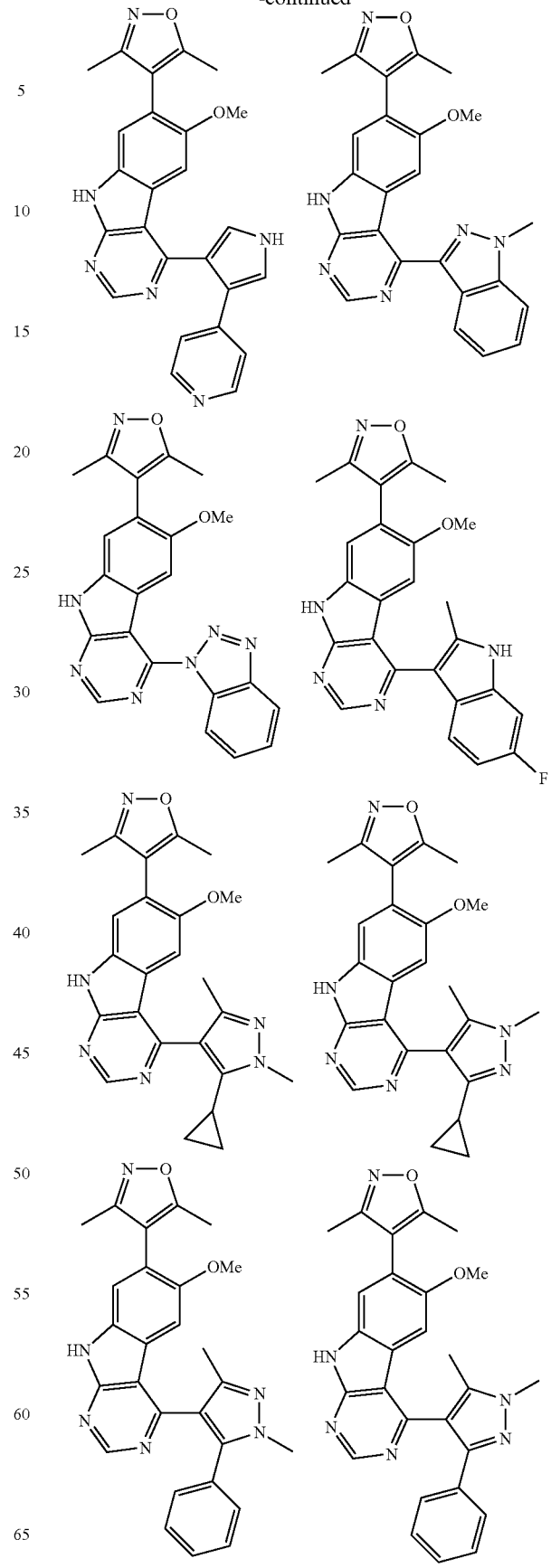

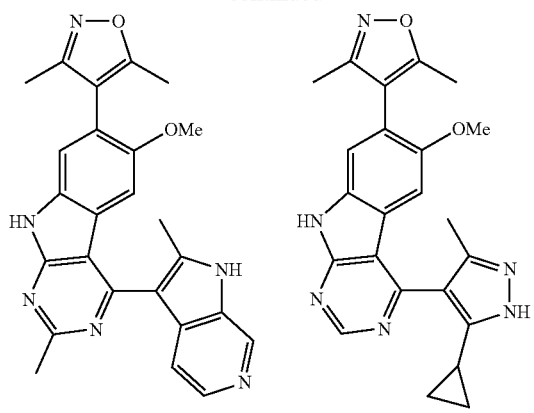
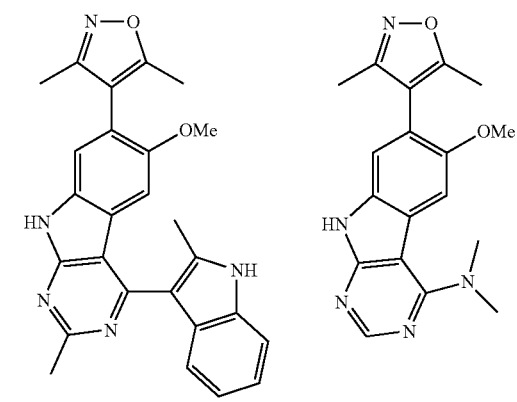
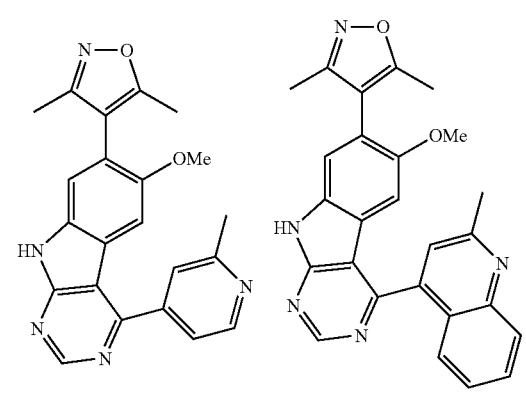
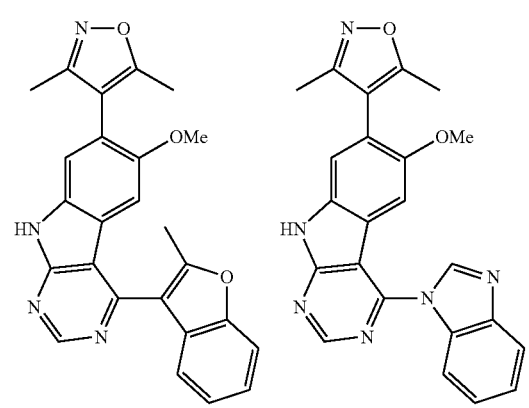
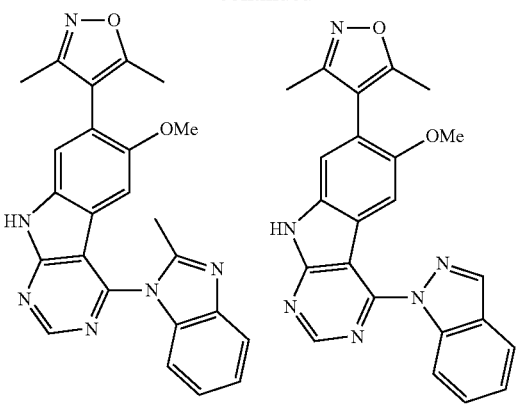
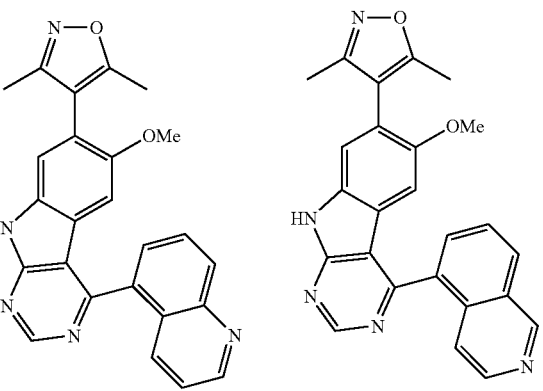
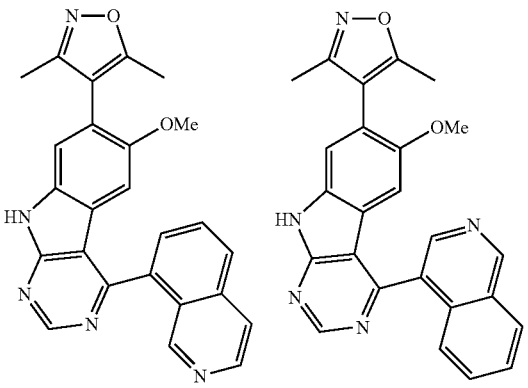
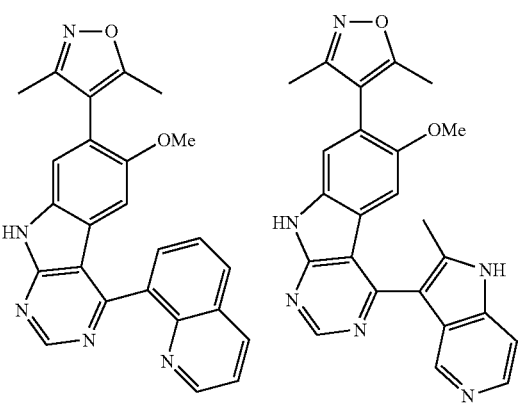

-continued
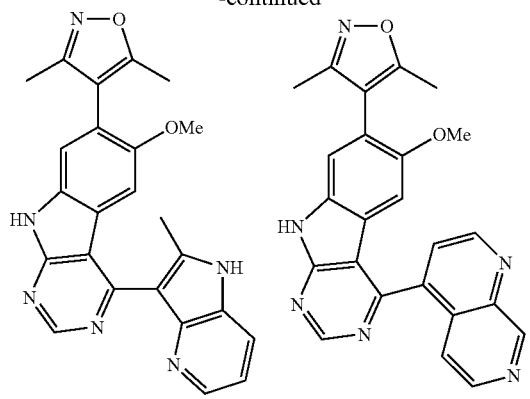
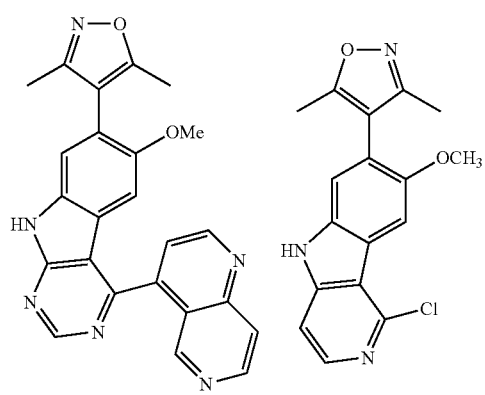
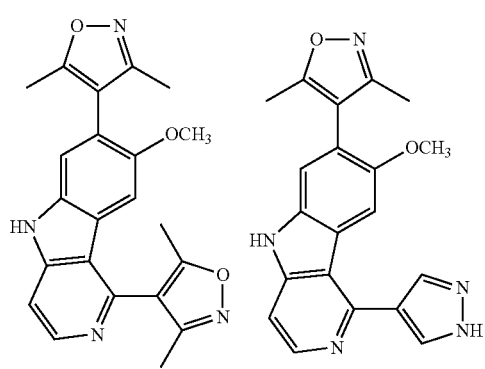
-continued
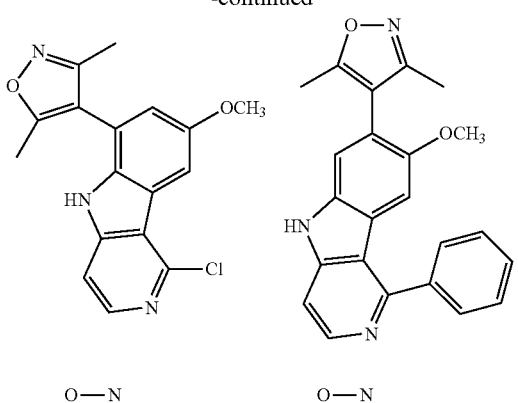
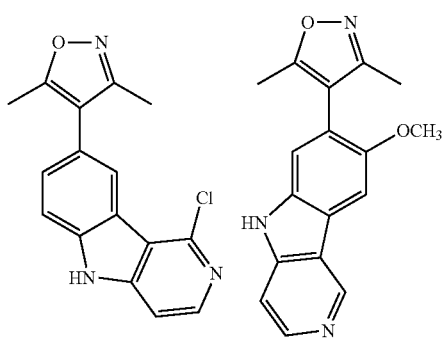
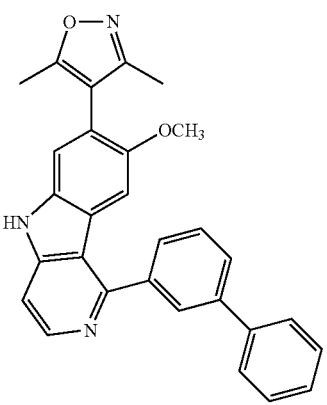

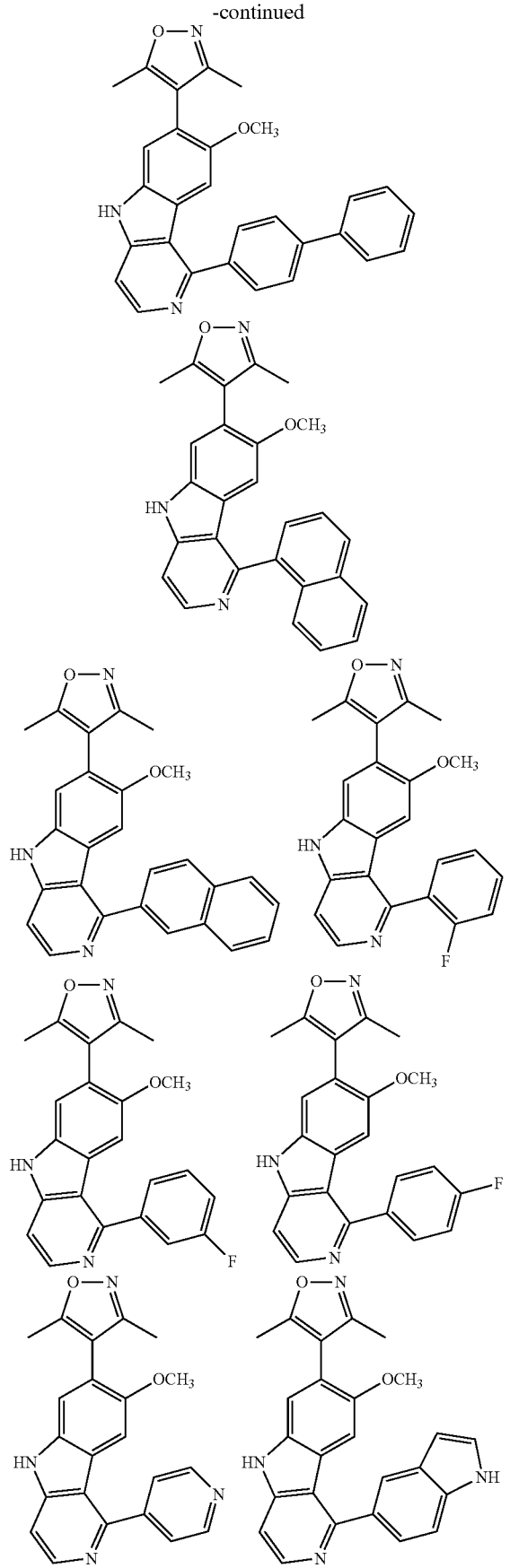
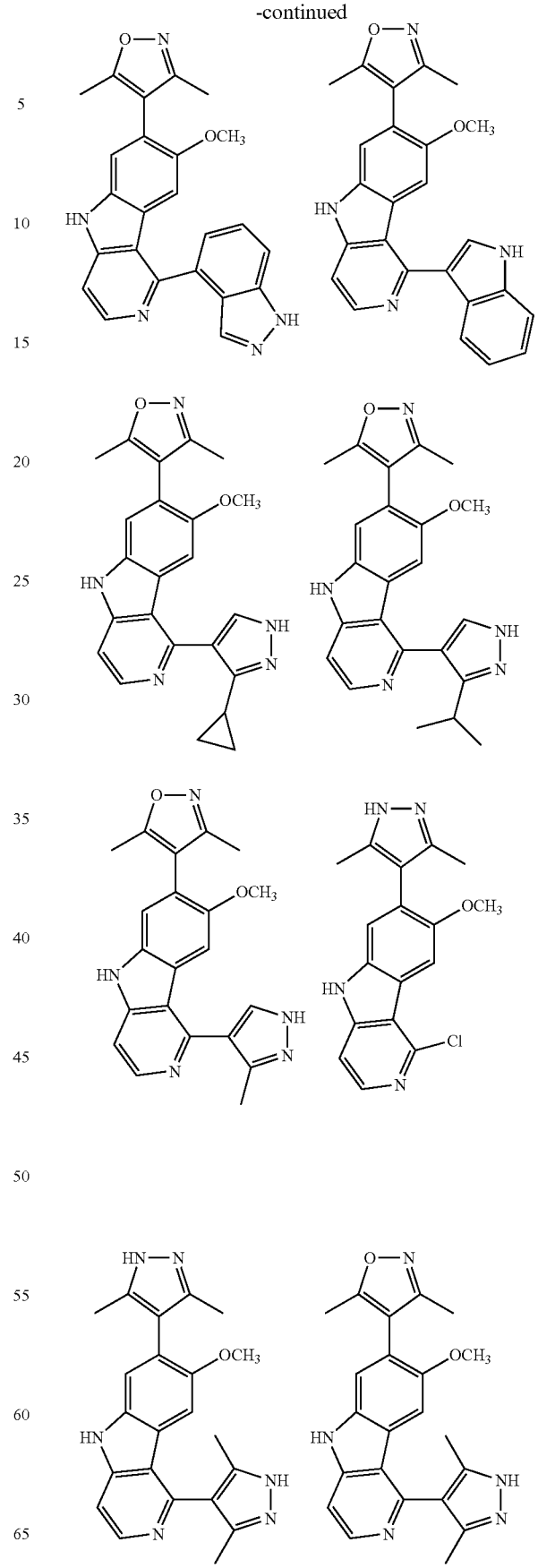

-continued

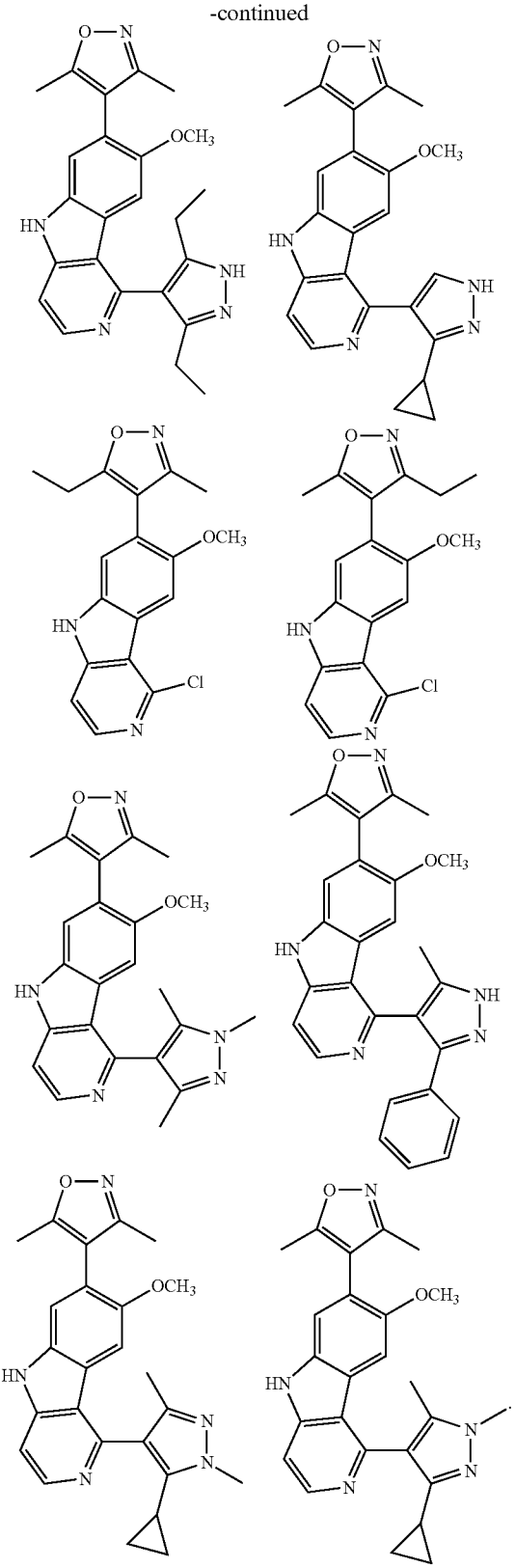

Embodiment XII

A composition comprising (a) compound of Embodiment I, (b) a second therapeutic agent useful in the treatment of a disease or condition wherein inhibition of BET bromodomain protein provides a benefit, and (c) an optional excipient and/or pharmaceutically acceptable carrier.

Embodiment XIII

The composition of Embodiment XII, wherein the second therapeutic agent comprises a chemotherapeutic agent useful in the treatment of cancer.

Embodiment XIV

A pharmaceutical composition comprising a compound of Embodiment I and a pharmaceutically acceptable carrier or vehicle.

Embodiment XV

A method of treating a disease or condition wherein inhibition of BET bromodomain protein provides a benefit comprising administering a therapeutically effective amount of a compound of Embodiment I to an individual in need thereof.

Embodiment XVI

The method of Embodiment XV further comprising administering a therapeutically effective amount of a second therapeutic agent useful in the treatment of the disease or condition.

Embodiment XVII

The method of Embodiment XVI, wherein the compound of Embodiment I and the second therapeutic agent are administered simultaneously.

Embodiment XVIII

The method of Embodiment XVI, wherein the compound of Embodiment I and the second therapeutic agent are administered separately.

Embodiment XIX

The method of Embodiment XV, wherein the disease or condition is a cancer, a chronic autoimmune disorder, an inflammatory condition, a proliferative disorder, sepsis, or a viral infection.

Embodiment XX

The method of Embodiment XVI, wherein the disease is a cancer and the second therapeutic agent is one or more of surgery, a chemotherapeutic agent, and radiation.

Embodiment XXI

The method of Embodiment XVI, wherein the disease is a cancer and the second therapeutic agent is selected from the agents disclosed in the specification.

Embodiment XXII

The method of Embodiment XVI, wherein the disease is a cancer and the second therapeutic agent comprises radiation disclosed in the specification.

Embodiment XXIII

The method of Embodiment XIX, wherein the cancer is selected from a cancer disclosed in the specification.

Embodiment XXIV

The method of Embodiment XVI, wherein the compound of Embodiment I and the second therapeutic agent are administered from a single composition.

Embodiment XXV

The method of Embodiment XVI, wherein the compound of Embodiment I and the second therapeutic agent are administered from separate compositions.

Embodiment XXVI

The method of Embodiment XVIII, wherein the compound of Embodiment I is administered prior to the second therapeutic agent.

Embodiment XXVII

The method of Embodiment XVIII, wherein the compound of Embodiment I is administered after the second therapeutic agent.

Embodiment XXVIII

The method of Embodiment XIX, wherein the proliferative disorder is selected from a disorder disclosed in the specification.

Embodiment XXIX

The method of Embodiment XIX, wherein the autoimmune disorder or inflammatory is disorder is selected from a disorder disclosed in the specification.

Embodiment XXX

The method of Embodiment XIX, wherein the viral infection is selected from the infection disclosed in the specification

Embodiment XXXI

A method of inhibiting activity of a BET bromodomain protein, or a mutant thereof, in a biological sample comprising contacting the biological sample with a compound according to any one of Embodiments I-XI or a composition according to Embodiment XIV.

Embodiment XXXII

The use of a compound according to any one of Embodiments I-XI in the manufacture of a medicament for the treatment of a disease or a condition for which a BET bromodomain inhibitor is indicated.

Embodiment XXXIII

The compound of Embodiment I, wherein $Y^2$ is CH, $CR^a$, or N, and Z is H,

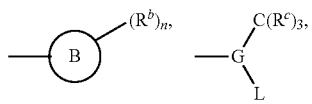

halo, or OH.

Embodiment XXXIV

The compound of Embodiment I, wherein ring A is an unsubstituted or substituted 5-membered heteroaryl ring.

Embodiment XXXV

The compound of Embodiments I through VII wherein Z is

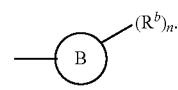

In another aspect, the present invention is directed to BET bromodomain inhibitors having a structural formula (I):

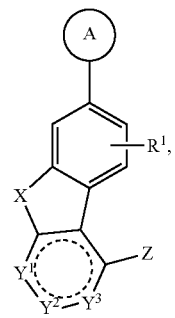

(I)

wherein
X is $N(R^{a1})$, O, or S;
$Y^1$ and $Y^3$, independently, are CH or N;
$Y^2$ is $CR^2$, N, or null;
Z is H,

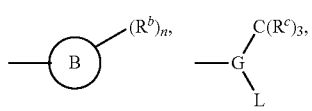

halo, or OH;
A is an unsubstituted or substituted 5-membered heterocyclic ring;
B is aryl, $CH(R^{a2})$-aryl, $C_{3-10}$cycloalkyl, $CH(R^{a2})$—$C_{3-10}$cycloalkyl, heteroaryl, $CH(R^{a2})$-heteroaryl, $C_{3-10}$heterocycloalkyl, or $CH(R^{a2})$—$C_{3-10}$heterocycloalkyl, each unsubstituted or substituted;
G is N, O, or S;
L is null, H, or $C(R^d)_3$;
$R^1$ is H, halo, OH, $OR^{a3}$, $R^{a3}$, or $N(R^{a3})_2$;
$R^{a1}$, $R^{a2}$, $R^{a3}$, $R^{a4}$, and $R^{a5}$ each independently, is H, $C_{1-3}$alkyl, phenyl, or benzyl;

$R^2$, independently, is H, $C_{1-3}$alkyl, phenyl, $(CH_2)_{1-3}C_{4-7}$heterocycloalkyl, $C_{4-7}$heterocycloalkyl, $CO_2H$, $CO_2(C_{1-3}$alkyl), $NH_2$, $NH(C_{1-3}$alkyl), $N(C_{1-3}$alkyl)$_2$, $(CH_2)_{1-3}NMe_2$, $(CH_2)_{1-3}OH$, $CH(Me)OH$, $C(Me)_2NH_2$, $C(Me)_2OH$, phenyl, benzyl, —C(=O)OR$^{a4}$, —C(=O)N(R$^{a4}$)$_2$,

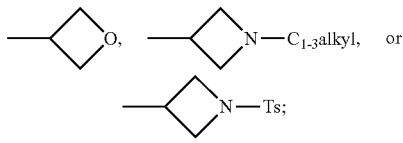

$R^b$, independently, is $C_{1-6}$alkyl, halo, aryl, unsubstituted or substituted $CH_2$-aryl, unsubstituted or substituted $C_{3-10}$cycloalkyl, unsubstituted or substituted $CH_2$—$C_{3-10}$cycloalkyl, heteroaryl, unsubstituted or substituted $CH_2$-heteroaryl, unsubstituted or substituted $C_{3-10}$heterocycloalkyl, unsubstituted or substituted $CH_2$—$C_{3-10}$heterocycloalkyl, $CF_3$, $CN$, $OR^{a5}$, $N(R^{a5})_2$, $N(CH_3)C(=O)(C_{1-3}$alkyl), $NH(CH_2)_{2-3}N(C_{2-3}$alkyl)$_2$, $C_{3-10}$heterocycloalkyl, $O(CH_2)_{2-3}N(C_{1-3}$alkyl)$_2$, $O(CH_2)_{2-3}$—$C_{3-10}$heterocycloalkyl, oxo(=O), or CHO;

n is an integer 0, 1, 2, or 3;

$R^c$ and $R^d$, each independently, are hydrogen, $C_{1-6}$alkyl, unsubstituted or substituted aryl, unsubstituted or substituted $CH_2$-aryl, unsubstituted or substituted $C_{3-10}$cycloalkyl, unsubstituted or substituted $CH_2$—$C_{3-10}$cycloalkyl, heteroaryl, unsubstituted or substituted $CH_2$-heteroaryl, unsubstituted or substituted $C_{3-10}$heterocycloalkyl, or unsubstituted or substituted $CH_2$—$C_{3-10}$heterocycloalkyl;

or a pharmaceutically acceptable salt, hydrate, or solvate thereof.

The compounds of structural formula (I) inhibit BET bromodomains and are useful in the treatment of a variety of diseases and conditions. In particular, the compounds of structural formula (I) are used in methods of treating a disease or condition wherein inhibition of BET bromodomains provides a benefit, for example, cancers and proliferative diseases. The method comprises administering a therapeutically effective amount of a compound of structural formula (I) to an individual in need thereof. The present methods also encompass administering a second therapeutic agent to the individual in addition to the compound of structural formula (I). The second therapeutic agent is selected from drugs known as useful in treating the disease or condition afflicting the individual in need thereof, e.g., a chemotherapeutic agent and/or radiation known as useful in treating a particular cancer.

As used herein, the term "alkyl" refers to straight chained and branched saturated $C_{1-10}$ hydrocarbon groups, including but not limited to methyl, ethyl, n-propyl, i-propyl, n-butyl, sec-butyl, t-butyl, n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, and 2-ethybutyl. The term $C_n$ means the alkyl group has "n" carbon atoms. The term "alkylene" refers to an alkyl group having a substituent. An alkyl, e.g., methyl, or alkylene, e.g., —$CH_2$—, group can be substituted with one or more, and typically one to three, of independently selected halo, trifluoromethyl, trifluoromethoxy, hydroxy, alkoxy, nitro, cyano, alkylamino, or amino groups, for example.

As used herein, the term "halo" is defined as fluoro, chloro, bromo, and iodo.

The term "hydroxy" is defined as —OH.

The term "alkoxy" is defined as —OR, wherein R is alkyl.

The term "amino" is defined as —$NH_2$, and the term "alkylamino" is defined as —$NR_2$, wherein at least one R is alkyl and the second R is alkyl or hydrogen.

The term "carbamoyl" is defined as —C(=O)$NR_2$.

The term "carboxy" is defined as —C(=O)OH or a salt thereof.

The term "nitro" is defined as —$NO_2$.

The term "cyano" is defined as —CN.

The term "trifluoromethyl" is defined as —$CF_3$.

The term "trifluoromethoxy" is defined as —$OCF_3$.

The term "Ts" means tosylate

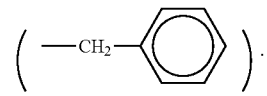

The term "Bn" means benzyl

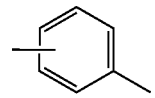

As used herein, groups such as

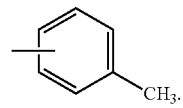

is an abbreviation for

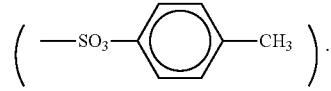

As used herein, the term "aryl" refers to a monocyclic or polycyclic aromatic group, preferably a monocyclic or bicyclic aromatic group. Examples of aryl groups include, but are not limited to, phenyl, naphthyl, fluorenyl, azulenyl, anthryl, phenanthryl, pyrenyl, biphenyl, and terphenyl. Aryl also refers to bicyclic and tricyclic carbon rings, where one ring is aromatic and the others are saturated, partially unsaturated, or aromatic, for example, dihydronaphthyl, indenyl, indanyl, or tetrahydronaphthyl (tetralinyl). Unless otherwise indicated, an aryl group can be unsubstituted or substituted with one or more, and in particular one to four, groups independently selected from, for example, halo, alkyl, alkenyl, —$OCF_3$, —$NO_2$, —CN, —NC, —OH, alkoxy, amino, alkylamino, —$CO_2H$, —$CO_2$alkyl, —OCOalkyl, aryl, and heteroaryl.

As used herein, the term "heterocyclic" refers to a heteroaryl and heterocycloalkyl ring systems.

As used herein, the term "heteroaryl" refers to a monocyclic or bicyclic ring system containing one or two aromatic rings and containing at least one nitrogen, oxygen, or sulfur atom in an aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl group has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quiazolinyl, thiadiazolopyrimidyl, and thienopyridyl. Unless otherwise indicated, a heteroaryl group can be unsubstituted or substituted with one or more, and in particular one to four, substituents selected from, for example, halo, alkyl, alkenyl, —OCF$_3$, —NO$_2$, —CN, —NC, —OH, alkoxy, amino, alkylamino, —CO$_2$H, —CO$_2$alkyl, —OCOalkyl, aryl, and heteroaryl.

As used herein, the term "cycloalkyl" means a monocyclic aliphatic ring containing three to eight carbon atoms, including cyclopropyl, cyclobutyl, cyclopentyl, cyclohexyl, cycloheptyl, and cyclooctyl, optionally substituted with one or more, and typically one to three, of independently selected halo, trifluoromethyl, trifluoromethoxy, hydroxy, alkoxy, nitro, cyano, alkylamino, or amino groups, for example.

As used herein, the term "heterocycloalkyl" means a monocyclic or a bicyclic aliphatic ring containing 4 to 12 total atoms, of which one to five of the atoms are independently selected from nitrogen, oxygen, and sulfur and the remaining atoms are carbon. Nonlimiting examples of heterocycloalkyl groups are azetidinyl, pyrrolidinyl, piperidinyl, piperazinyl, dihydropyrrolyl, morpholinyl, thiomorpholinyl, dihydropyridinyl, oxacycloheptyl, dioxacycloheptyl, thiacycloheptyl, diazacycloheptyl, each optionally substituted with one or more, and typically one to three, of independently selected halo, C$_{1-6}$ alkyl, C$_{1-6}$ alkoxy, cyano, amino, carbamoyl, nitro, carboxy, C$_{2-7}$ alkenyl, C$_{2-7}$ alkynyl, or the like on an atom of the ring.

The term "alkenyl" is defined identically as "alkyl," except for containing a carbon-carbon double bond, e.g., ethenyl, propenyl, and butenyl. The term "alkynyl" is defined identically as "alkyl," except the group contains a carbon-carbon triple bond.

As used herein, the term "C$_{1-6}$hydroxyalkyl" refers to straight chained and branched saturated C$_{1-6}$ hydrocarbon groups substituted with one, two, three, or four hydroxy groups. In one embodiment, the C$_{1-6}$hydroxyalkyl is substituted with one hydroxy group. In one embodiment, the C$_{1-6}$hydroxyalkyl is substituted with two hydroxy groups. Examples of C$_{1-6}$hydroxyalkyl groups include, but are not limited to, —C(CH$_3$)$_2$OH, —C(H)(CH$_3$)$_3$CH$_2$OH, —CH$_2$CH$_2$CH$_2$CH$_2$OH, and —CH$_2$CH$_2$CH(OH)CH$_2$OH.

As used herein, the term "hydroxyC$_{3-10}$heterocycloalkyl" refers to a heterocycloalkyl group as defined above substituted with one or two hydroxy groups. In one embodiment, the hydroxyC$_{3-10}$heterocycloalkyl is substituted with one hydroxy group. Examples of hydroxyC$_{3-10}$heterocycloalkyl groups include, but are not limited to, piperidin-4-ol and pyrrolidin-3-ol.

As used herein, the term "hydroxycycloalkyl" refers to a cycloalkyl group as defined above substituted with one or two hydroxy groups. In one embodiment, the hydroxycycloalkyl is substituted with one hydroxy group.

The term "pharmaceutically acceptable anion" as used herein refers to an anion associated with a quaternary pyridinium of the present disclosure that is acceptable for administration to a patient, e.g., a mammal, e.g., a human. In one embodiment, the pharmaceutically acceptable anion is the anion of a pharmaceutically acceptable inorganic acid, e.g., hydrochloric, perchloric, sulfuric, phosphoric, hydrobromic, hydroiodic or nitric acid and the like. In one embodiment, the pharmaceutically acceptable anion is the anion of a pharmaceutically acceptable organic acid, e.g., a mono or polyvalent organic acid, e.g., citric, fumaric, maleic, malic, ascorbic, succinic, tartaric, benzoic, acetic, phenylacetic, methanesulfonic, ethansulfonic, benzenesulfonic or p-toluenesulfonic acid and the like.

In accordance with the present invention, ring A is a five-membered heterocyclic ring, either heteroaryl or heterocycloalkyl, containing one to four heteroatoms, i.e., independently are nitrogen, oxygen, or sulfur. In various embodiments, ring A is substituted with one to three groups, independently selected from the group consisting of alkyl, cycloalkyl, haloalkyl, and halocycloalkyl, for example, methyl, ethyl, isopropyl, trifluoromethyl, cyclopropyl, or cyclobutyl.

Nonlimiting examples of A rings include, but are not limited to

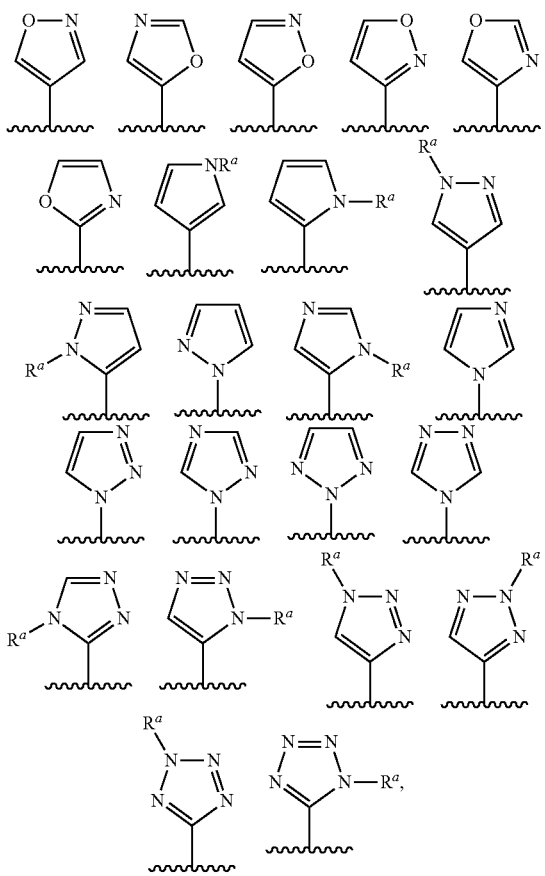

wherein R$^a$ is H, C$_{1-3}$alkyl, cyclopropyl, cyclobutyl, phenyl, or benzyl, and each optionally substituted with one to three substituents.

In some preferred embodiments, the A ring is:

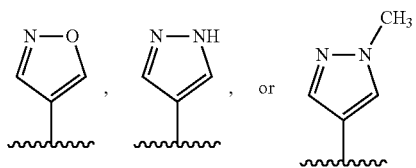

optionally substituted with one or more methyl and/or ethyl groups.

In some specific embodiments, the A ring is:

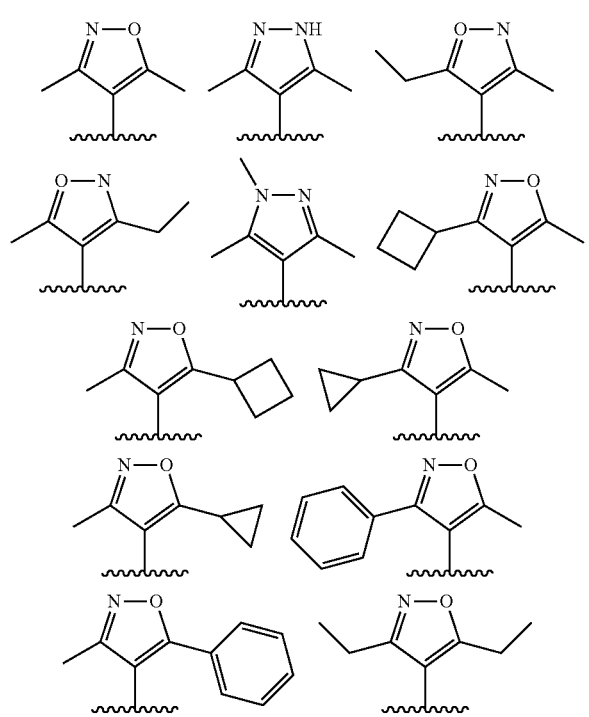

In some embodiments X is —NH, —NC$_6$H$_5$, —NCH$_3$, or —NCH$_2$C$_6$H$_5$.

In some embodiments Y$^1$ and Y$^3$ are N and N, CH and CH, or CH and N.

In some embodiments, Y$^2$ is CH, N, CCH$_3$, CCH(CH$_3$)$_2$,

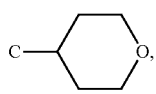

C—CO$_2$H, C—CO$_2$CH$_3$,

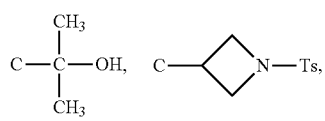

CCH$_2$OH, CCH$_2$NH$_2$, CCH$_2$N(CH$_3$)$_2$,

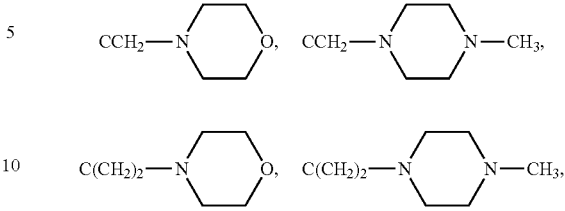

C(CH$_2$)$_2$N(CH$_3$)$_2$, C(CH$_2$)$_2$OH,

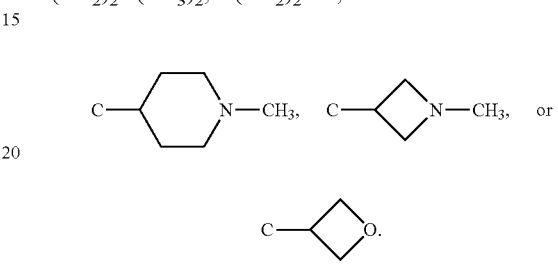

In some preferred embodiments R$^1$ is H or —OCH$_3$.

In various embodiments, the ring system is

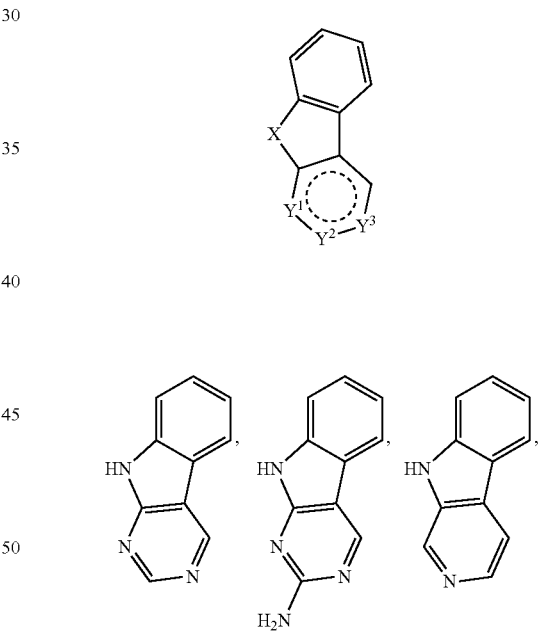

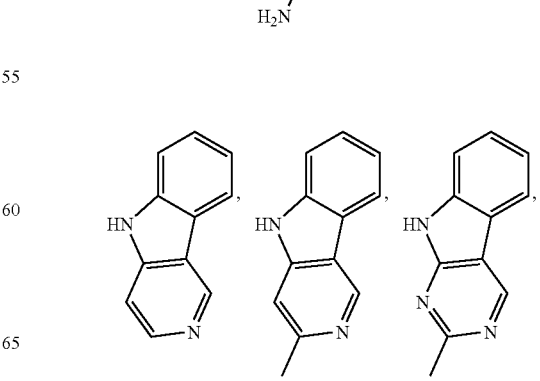

-continued
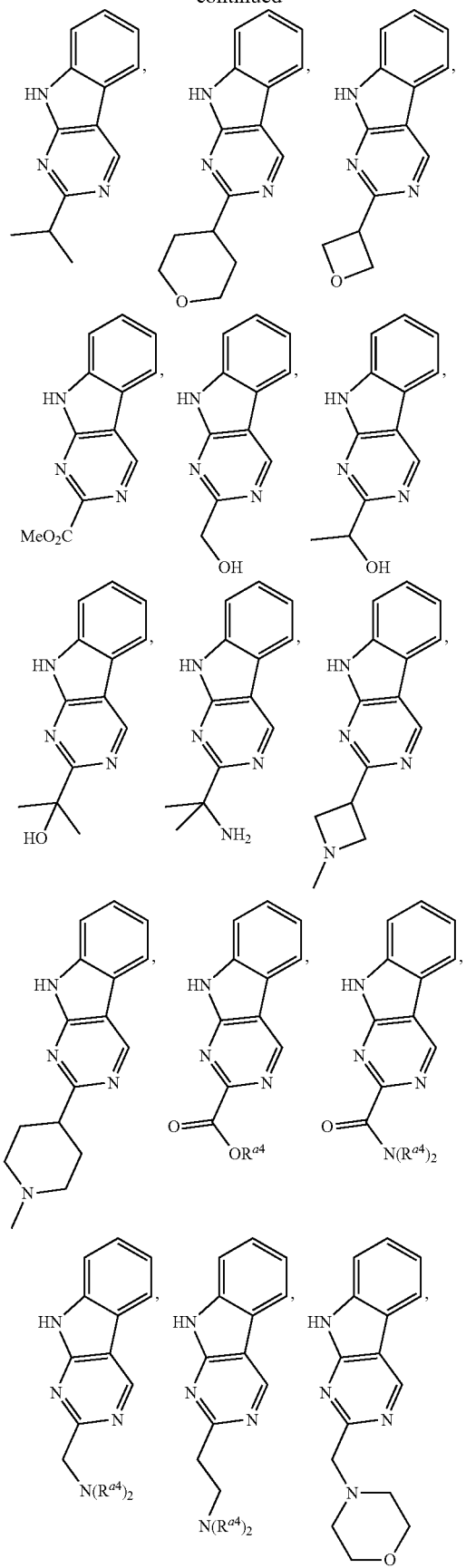
-continued
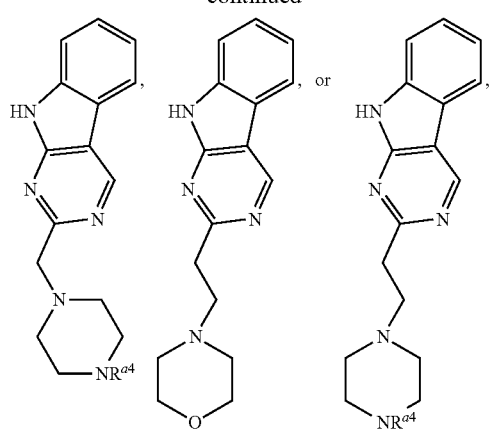
wherein $R^{a4}$ independently, is H, $C_{1-3}$alkyl, phenyl, or benzyl.
In various embodiments, Z is
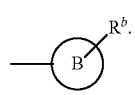
Nonlimiting examples of the B ring include
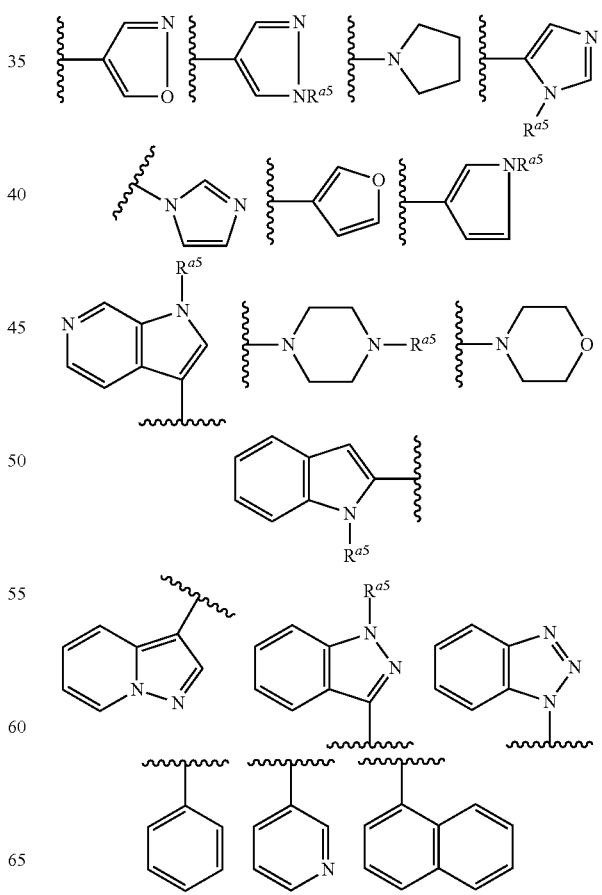

-continued
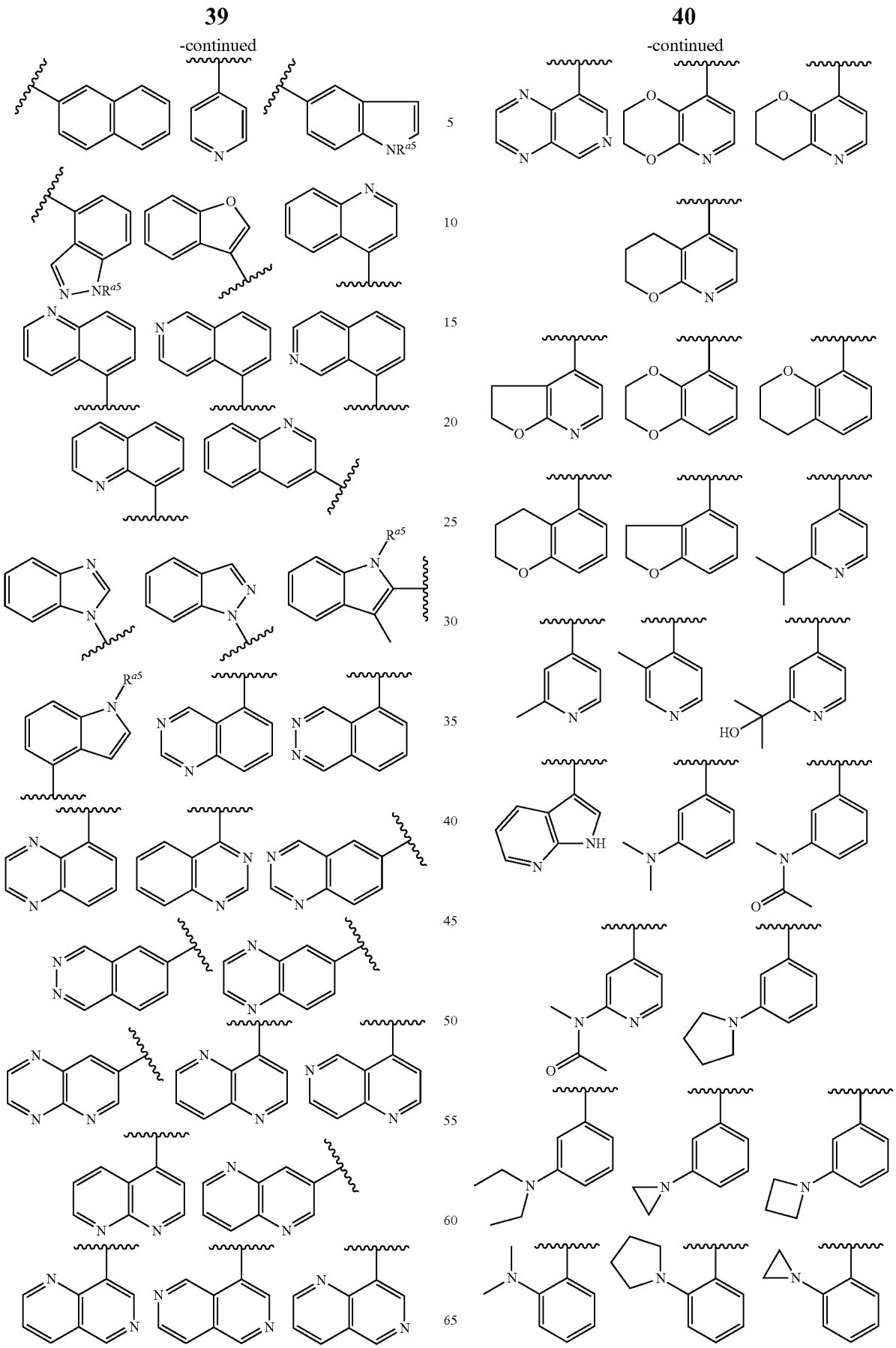

-continued
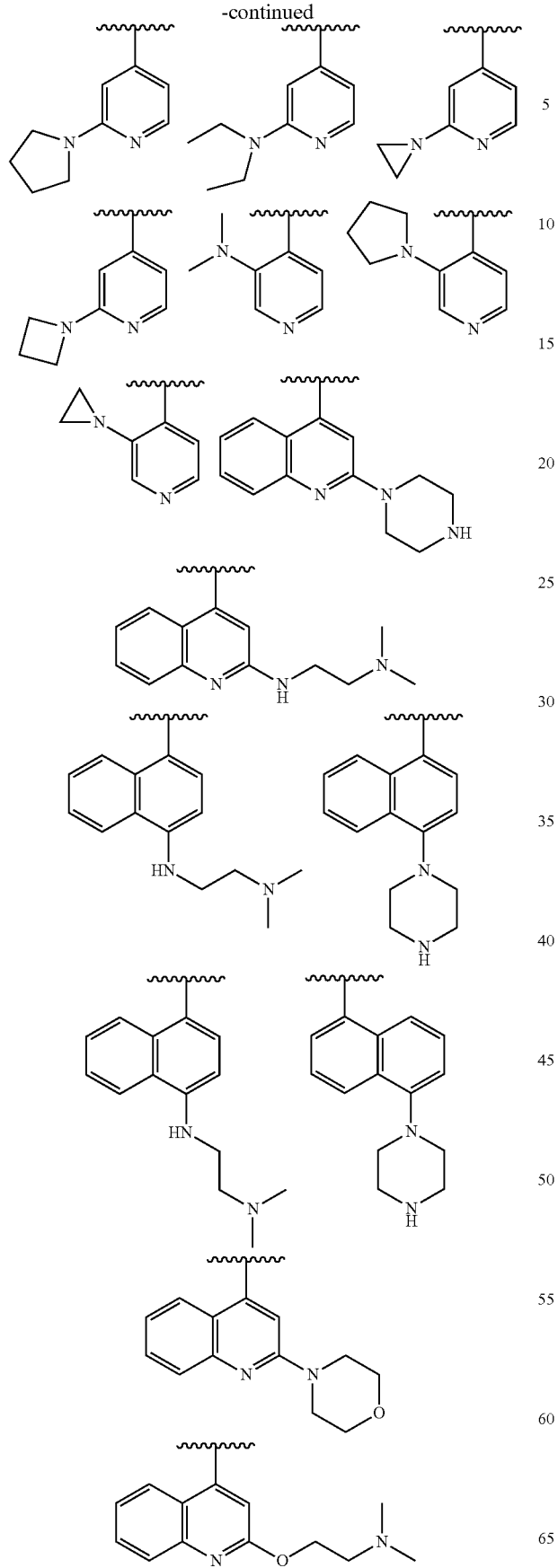
-continued
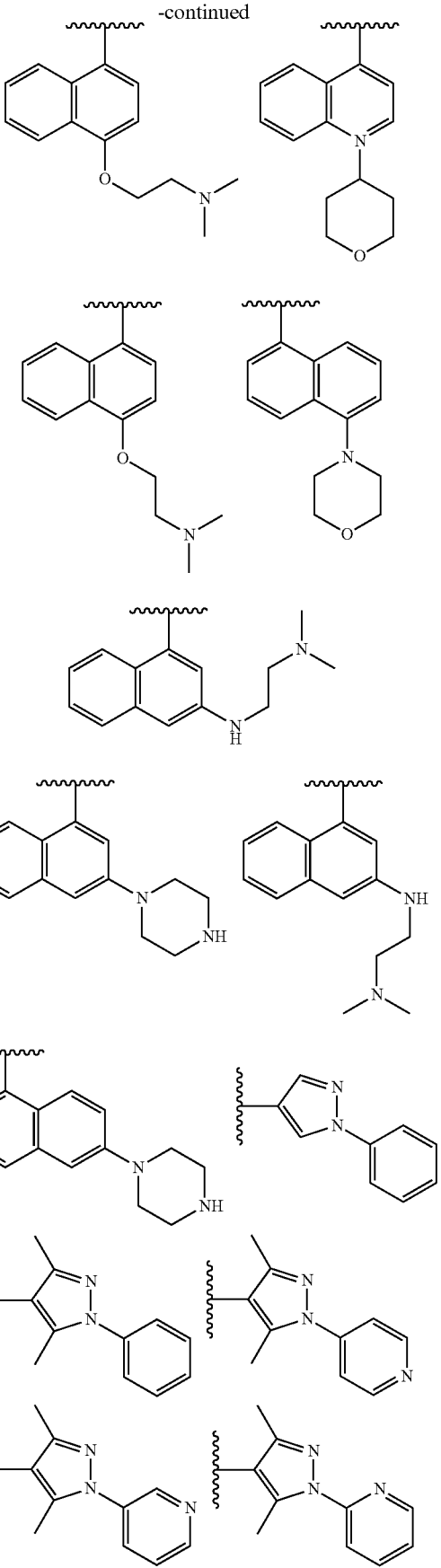

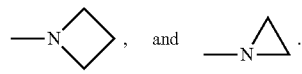

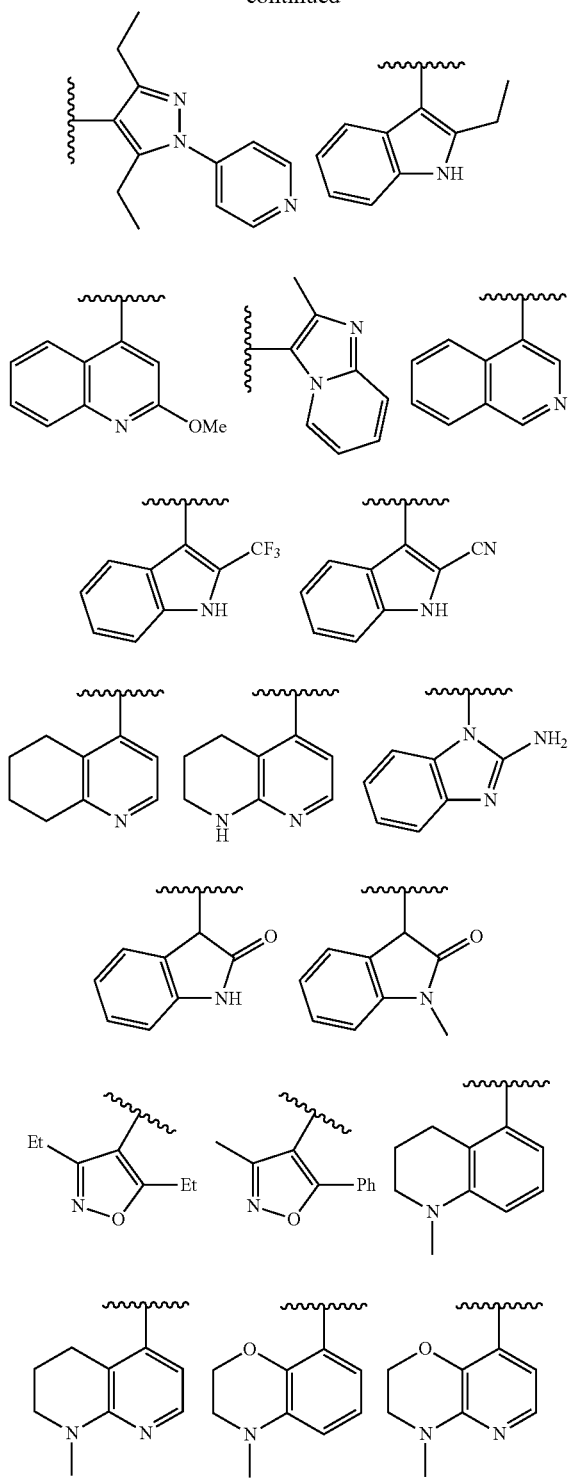

wherein R$^{a5}$ is H, C$_{1-3}$alkyl, phenyl, benzyl.

Various substituents on the carbon atoms of the B ring include, but are not limited to, one to three of methyl, phenyl, benzyl, CHO, CF$_3$, OCH$_3$, fluoro, pyridinyl, chloro, isopropyl, cyclopropyl, ethyl, C(CH$_3$)OH, NH$_2$, N(CH$_3$)$_2$, N(C$_2$H$_5$)$_2$, NH(CH$_2$)$_2$N(CH$_3$)$_2$, N(CH$_3$)C(=O)CH$_3$, oxo (=O), OH, OCH(CH$_3$)$_2$, O(CH$_2$)$_2$N(CH$_3$)$_2$, pyrrolyl, piperdinyl, piperizinyl, morpholino, In other embodiments, Z is N(CH$_3$)$_2$, H, OH, or chloro.

Additionally, salts, hydrates, and solvates of the present compounds also are included in the present invention and can be used in the methods disclosed herein. The present invention further includes all possible stereoisomers and geometric isomers of the compounds of structural formula (I). The present invention includes both racemic compounds and optically active isomers. When a compound of structural formula (I) is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of the compounds of structural formula (I) are possible, the present invention is intended to include all tautomeric forms of the compounds.

Compounds of the invention can exist as salts. Pharmaceutically acceptable salts of the compounds of the invention often are preferred in the methods of the invention. As used herein, the term "pharmaceutically acceptable salts" refers to salts or zwitterionic forms of the compounds of structural formula (I). Salts of compounds of formula (I) can be prepared during the final isolation and purification of the compounds or separately by reacting the compound with an acid having a suitable cation. The pharmaceutically acceptable salts of compounds of structural formula (I) can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present invention appearing herein is intended to include compounds of structural formula (I) as well as pharmaceutically acceptable salts, hydrates, or solvates thereof.

Specific compounds of the present invention include, but are not limited to, compounds having the structure set forth below.

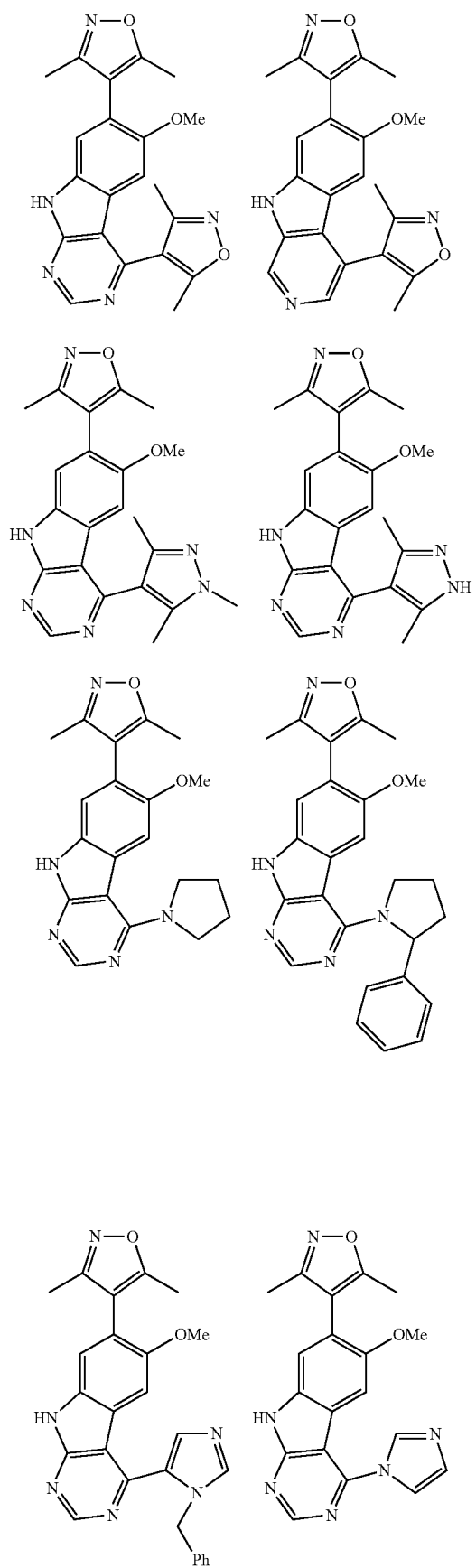
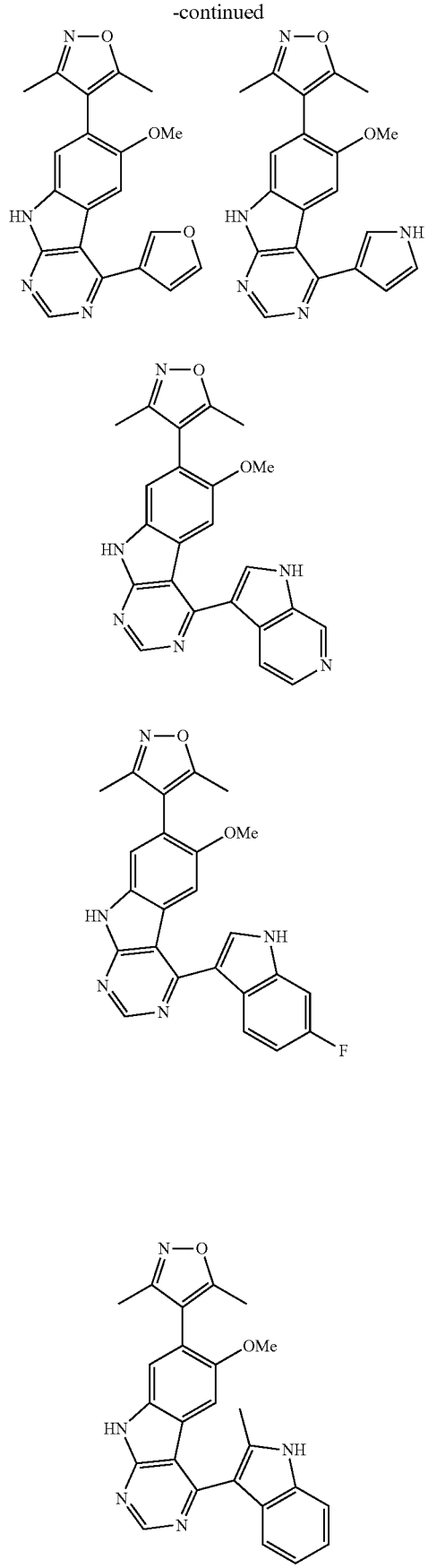

-continued
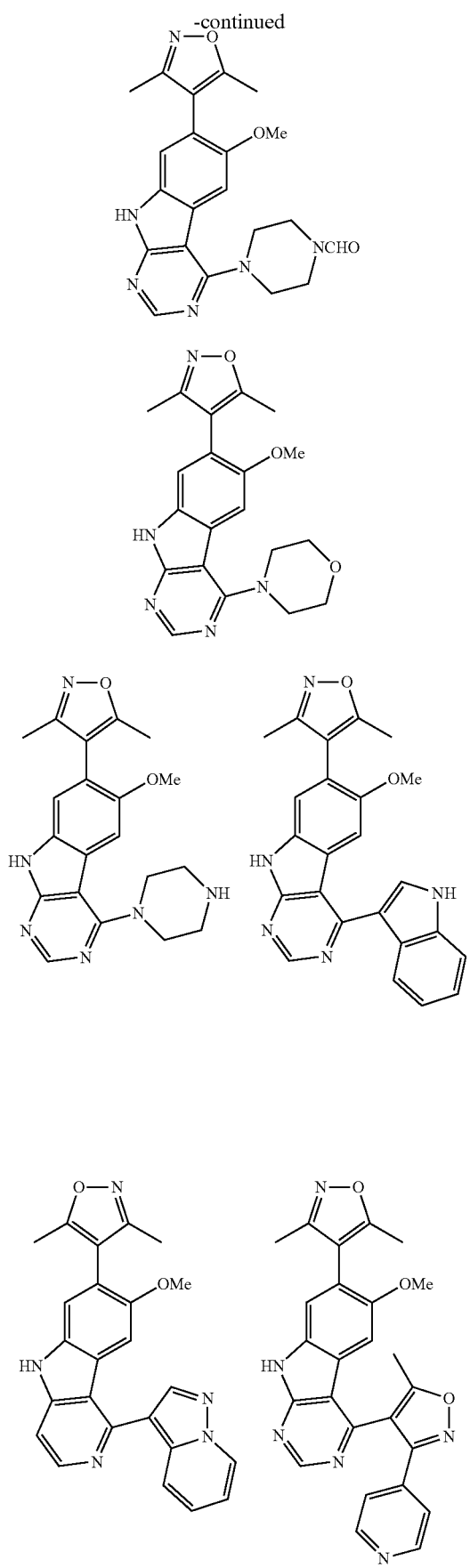
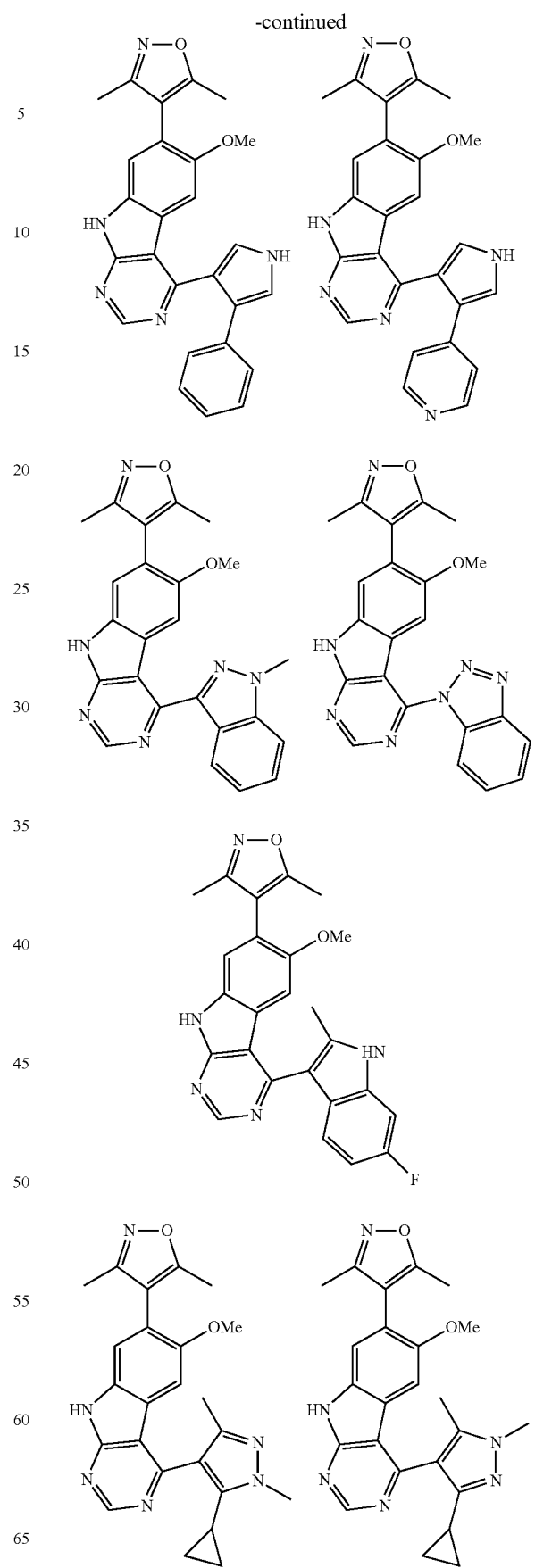

-continued
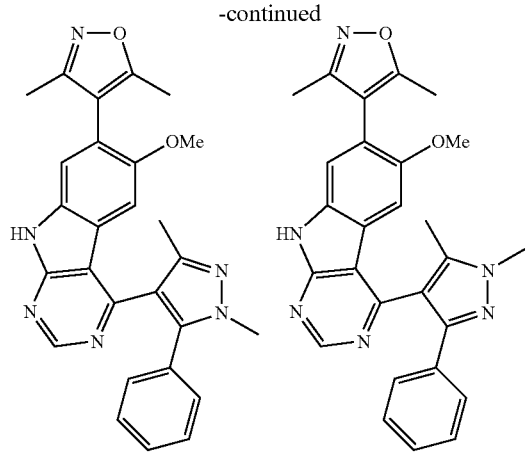
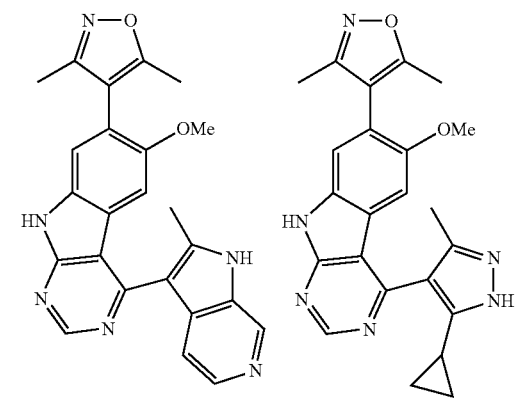
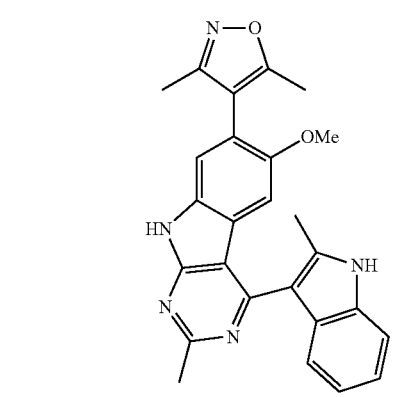
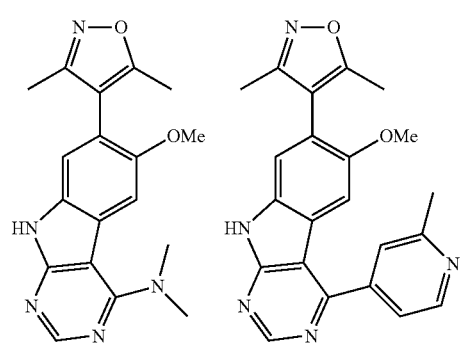
-continued
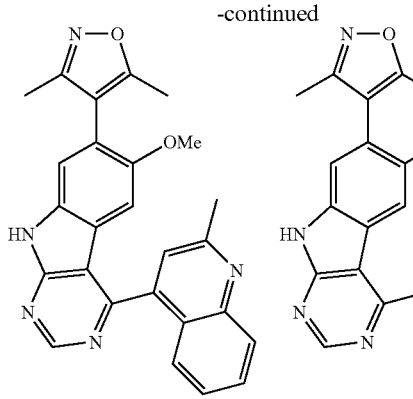
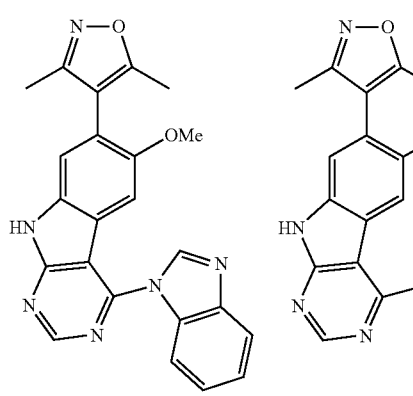
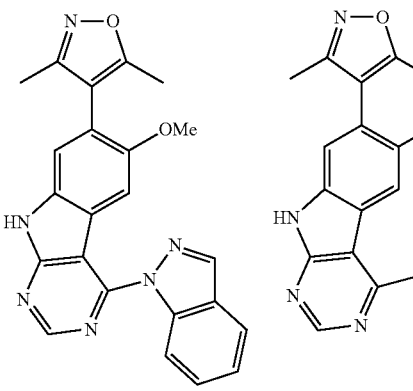
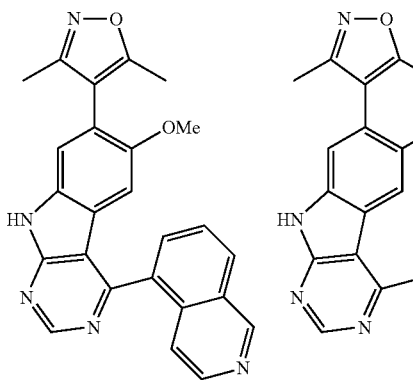

-continued
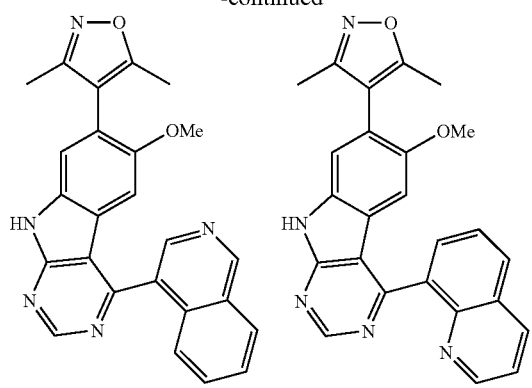
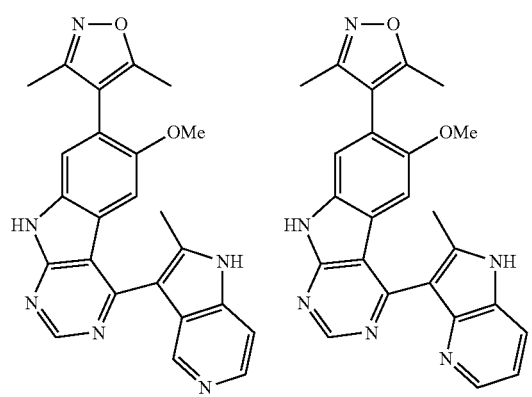
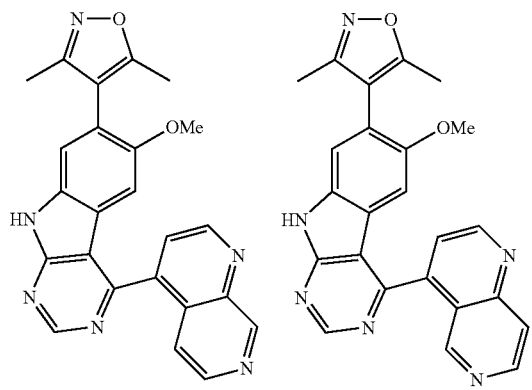
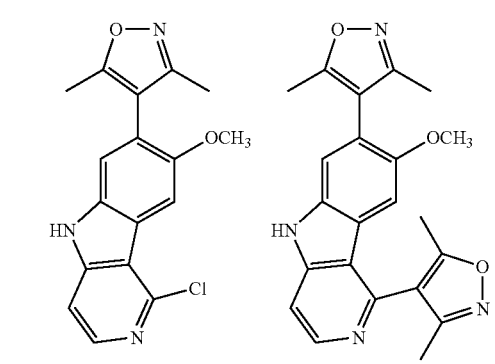
-continued
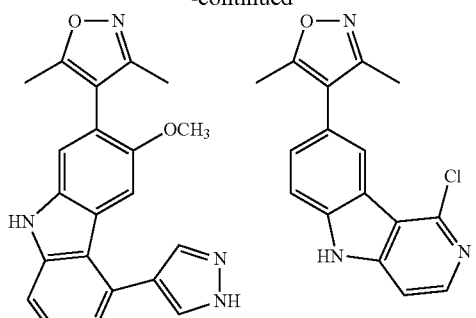
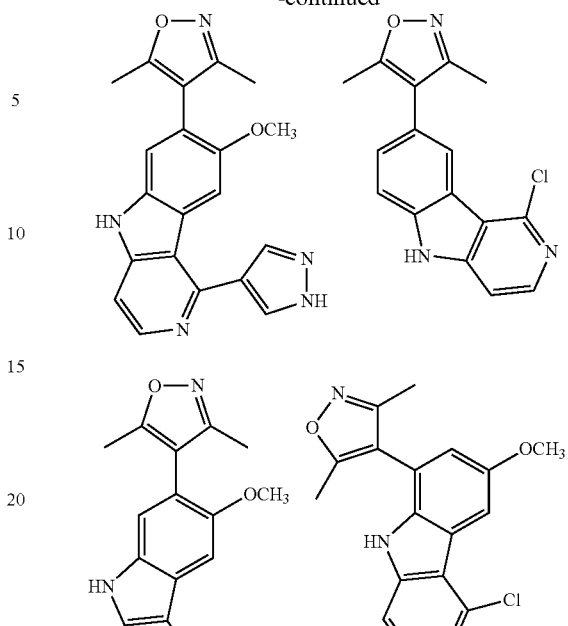
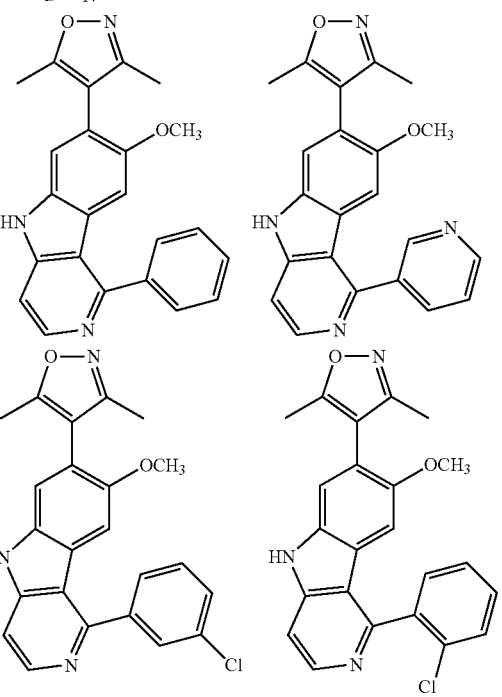
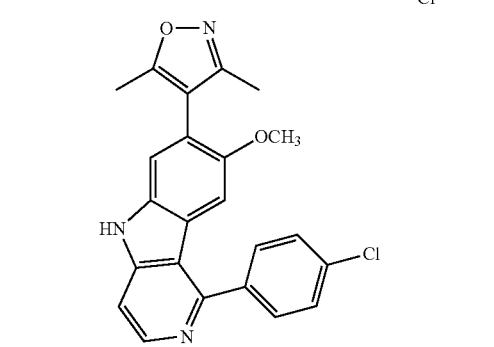

-continued
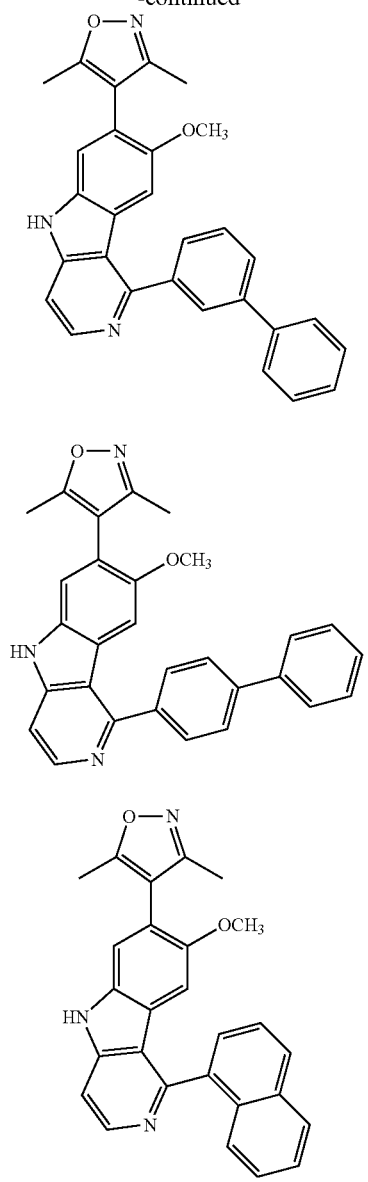
-continued
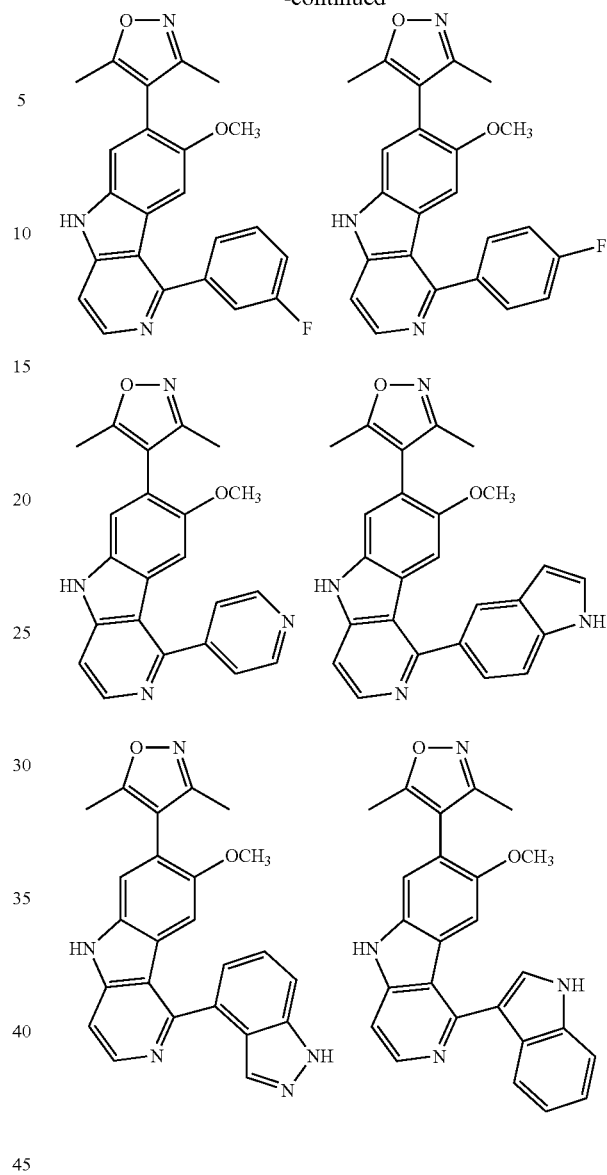
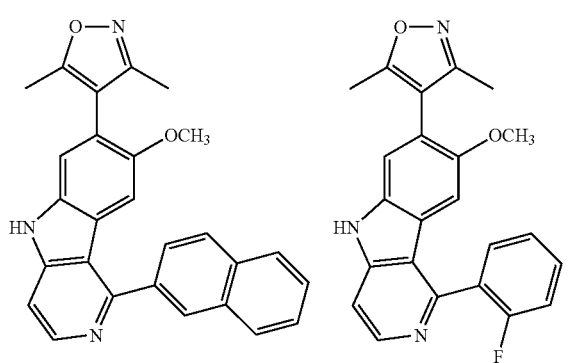
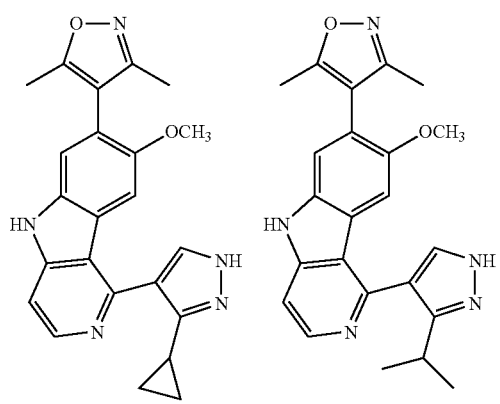

-continued
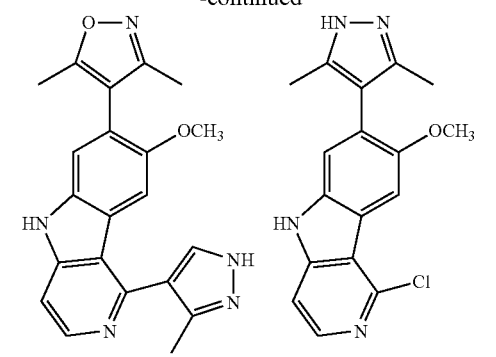
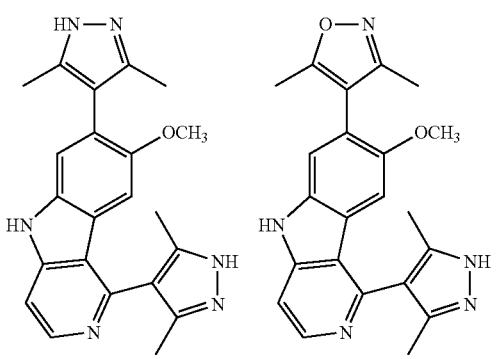
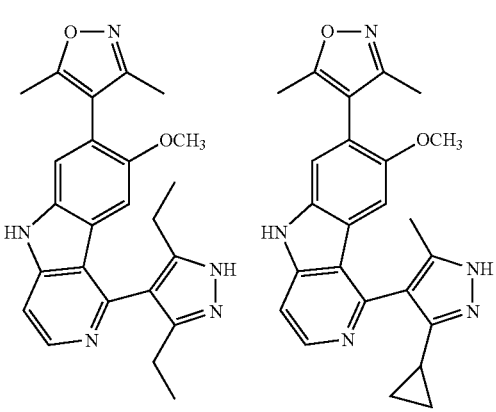
-continued
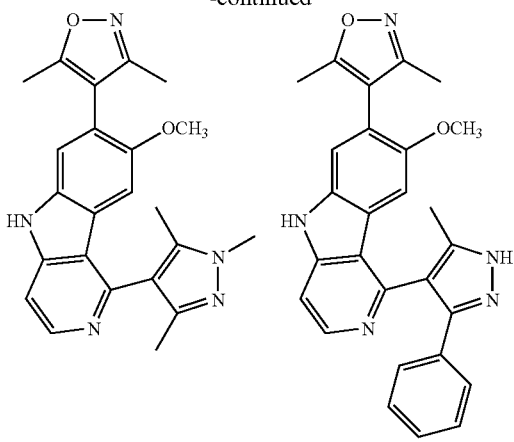
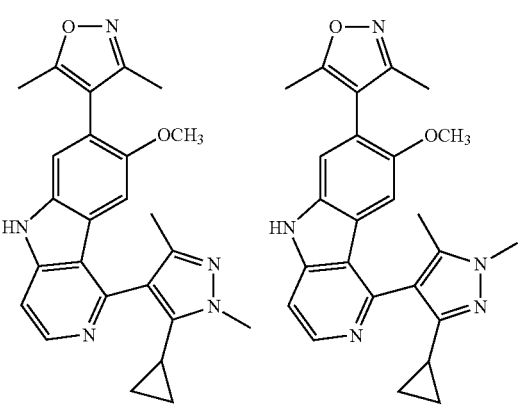
Additional compounds of the present invention include, but are not limited to, compounds having the structure set forth below:
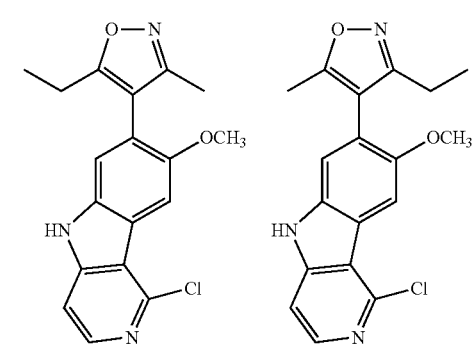
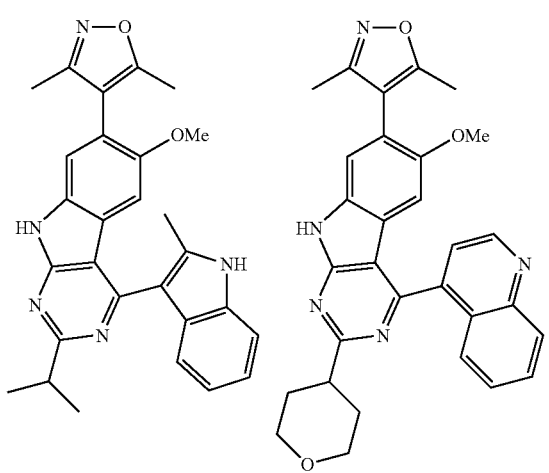

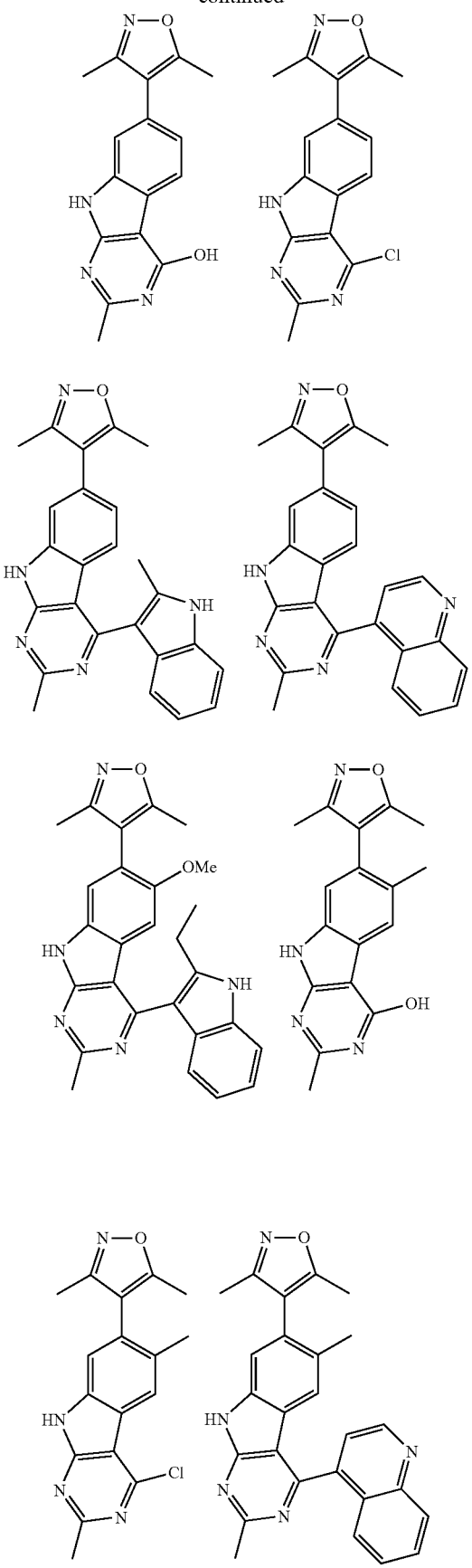
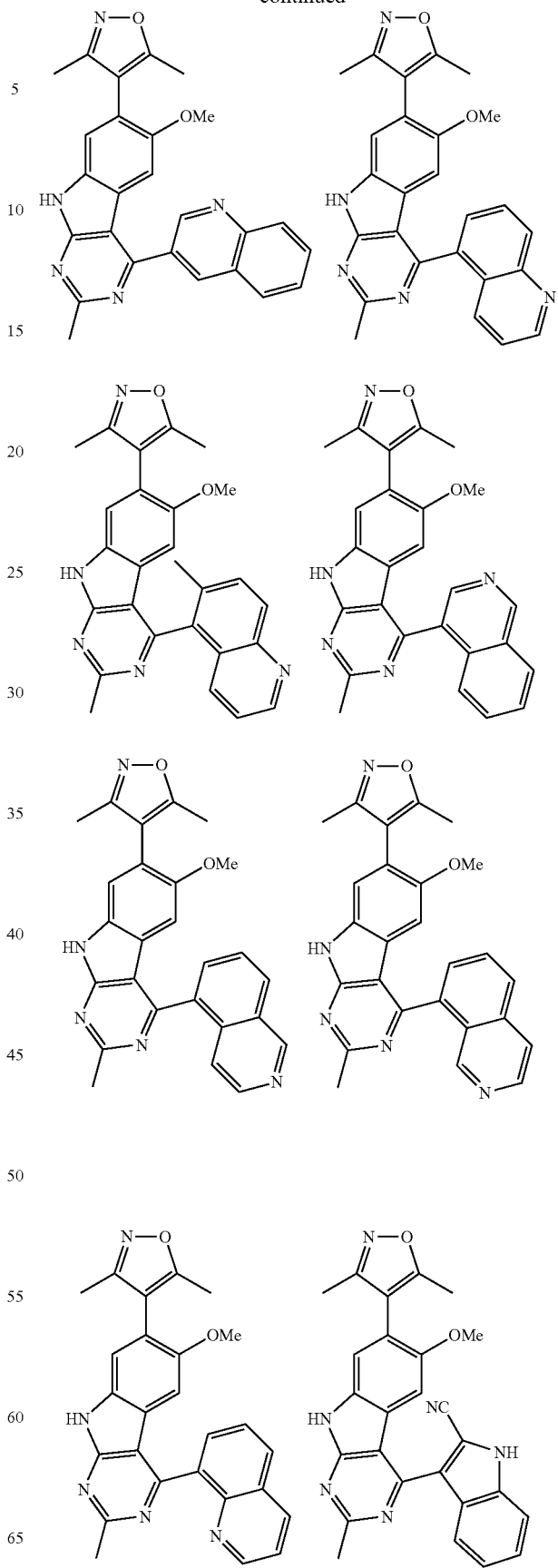

-continued
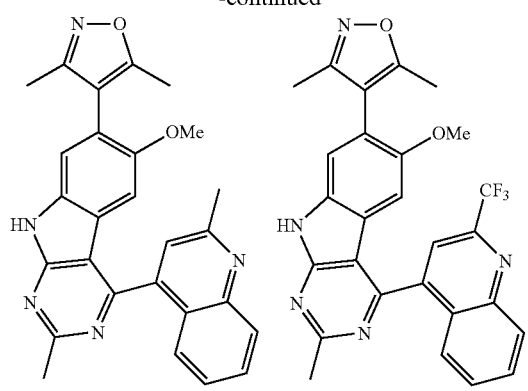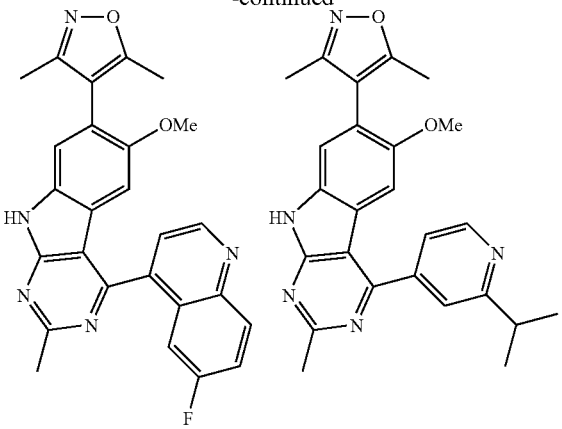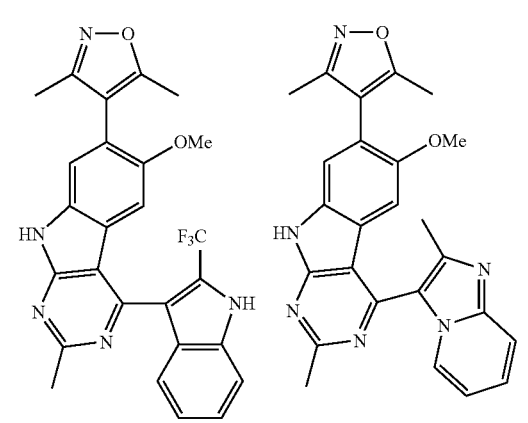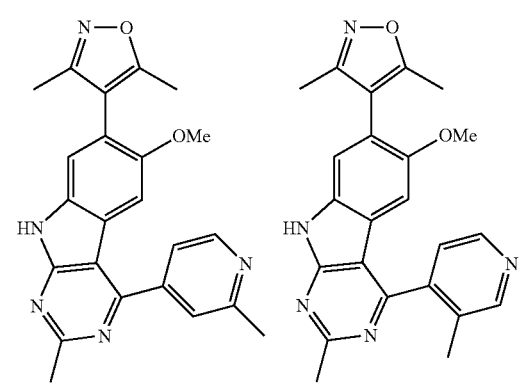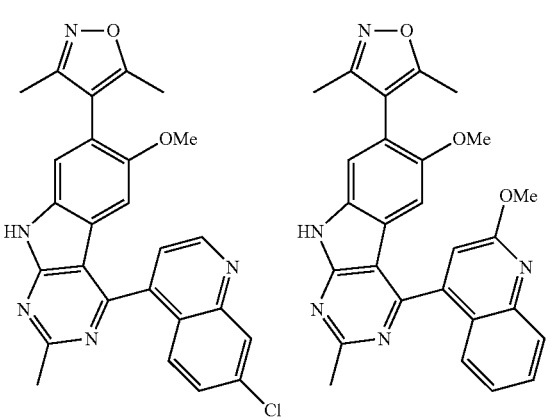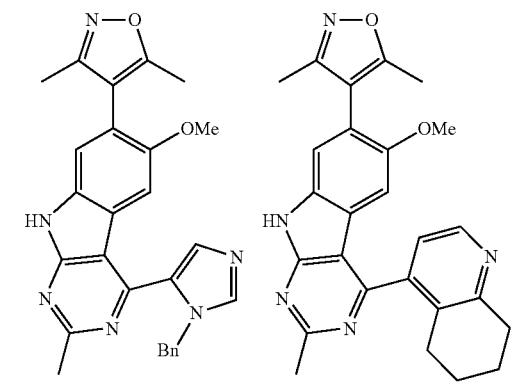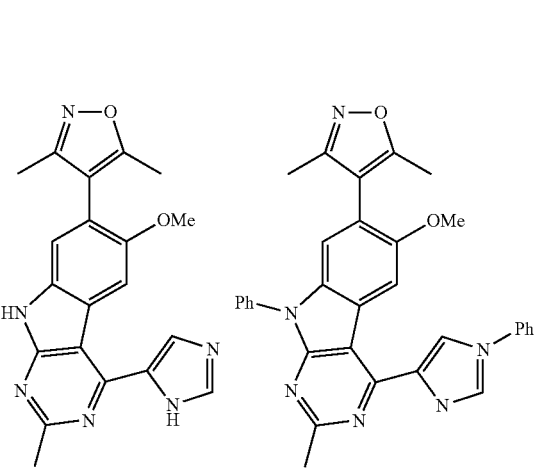

-continued
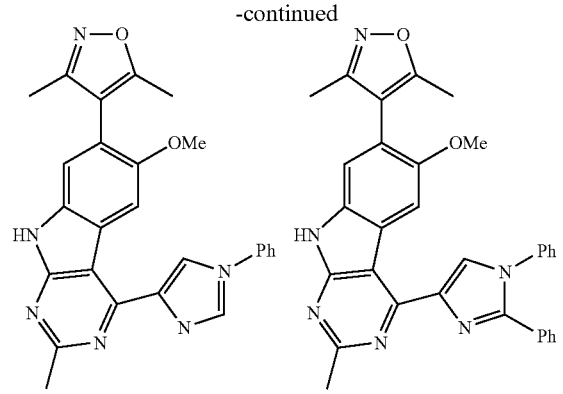
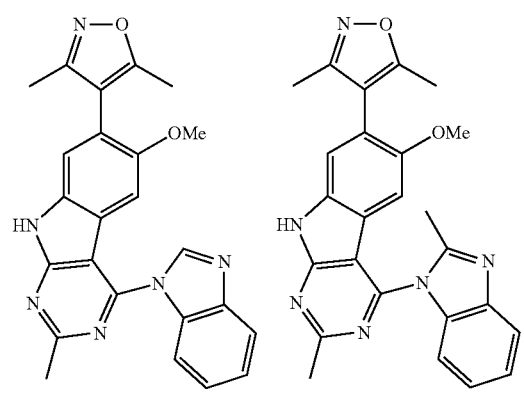
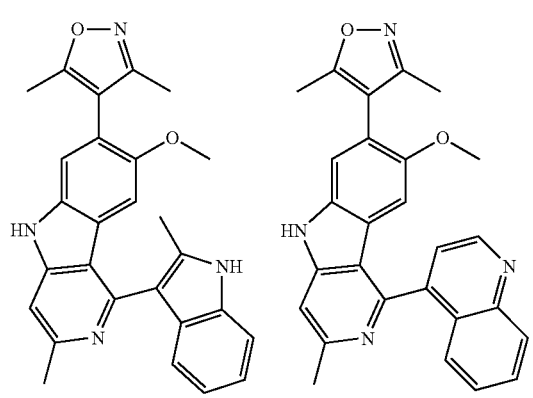
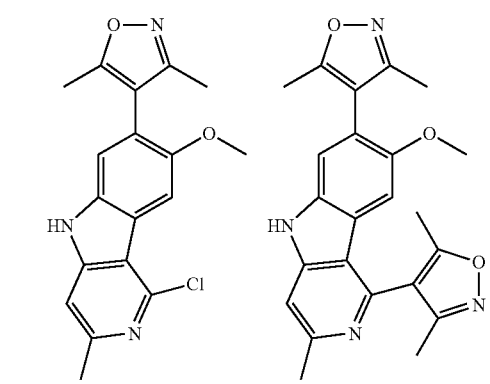
-continued
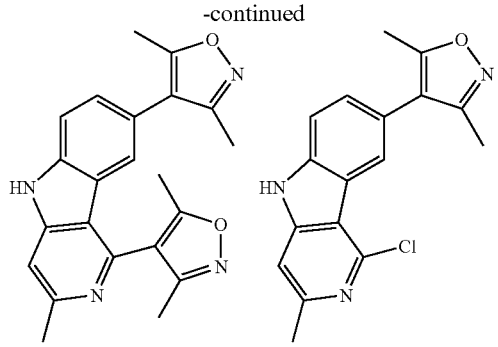
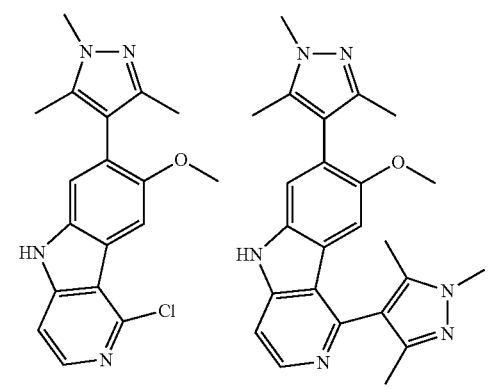
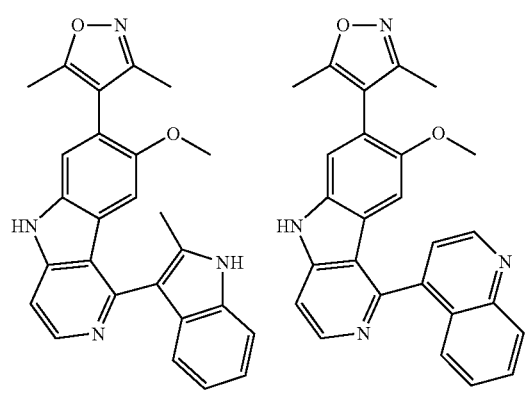
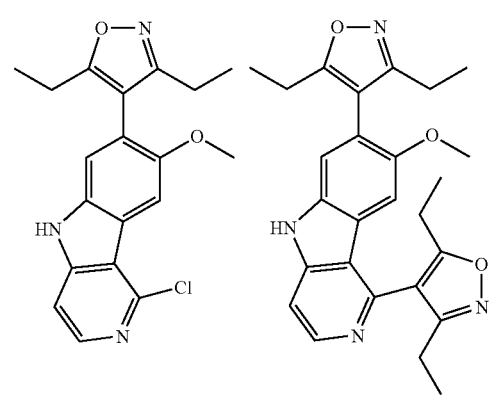

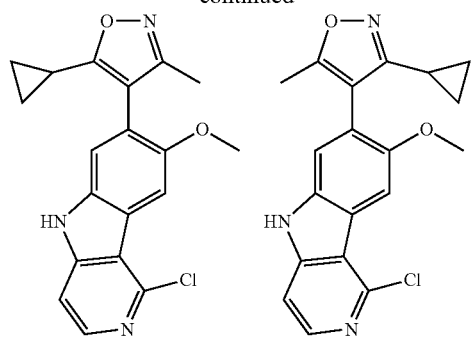
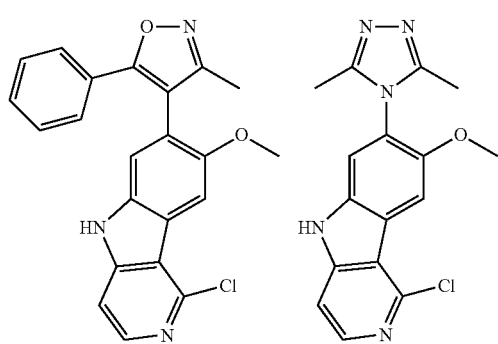
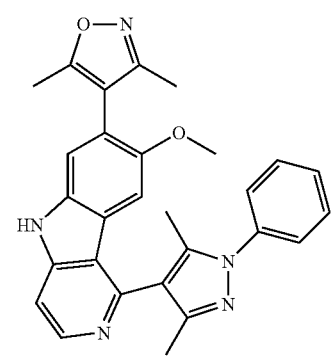
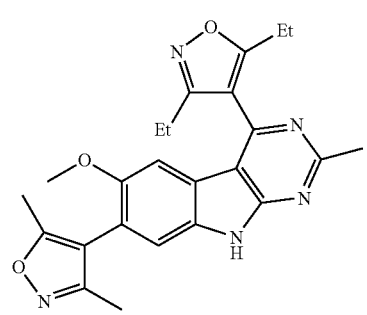
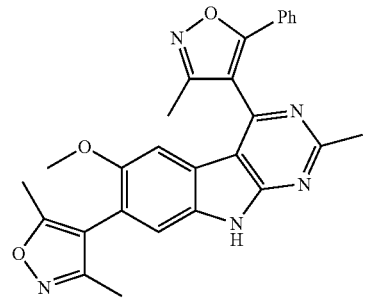
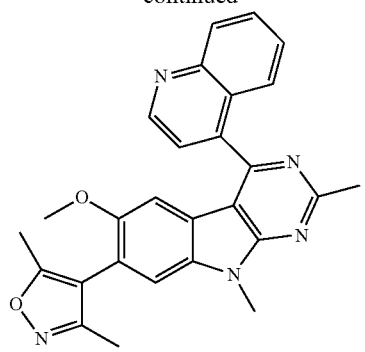
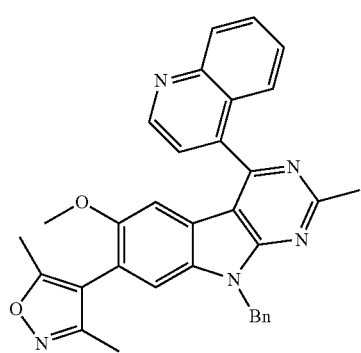
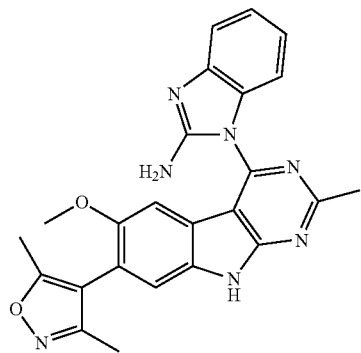
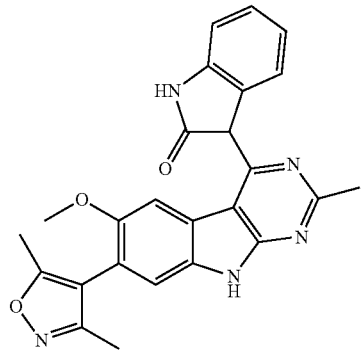

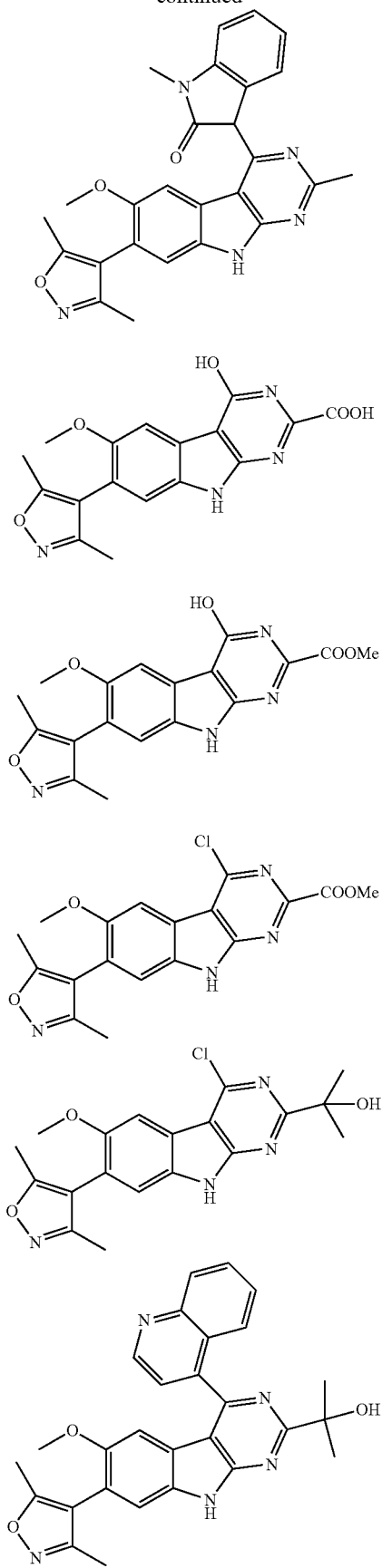
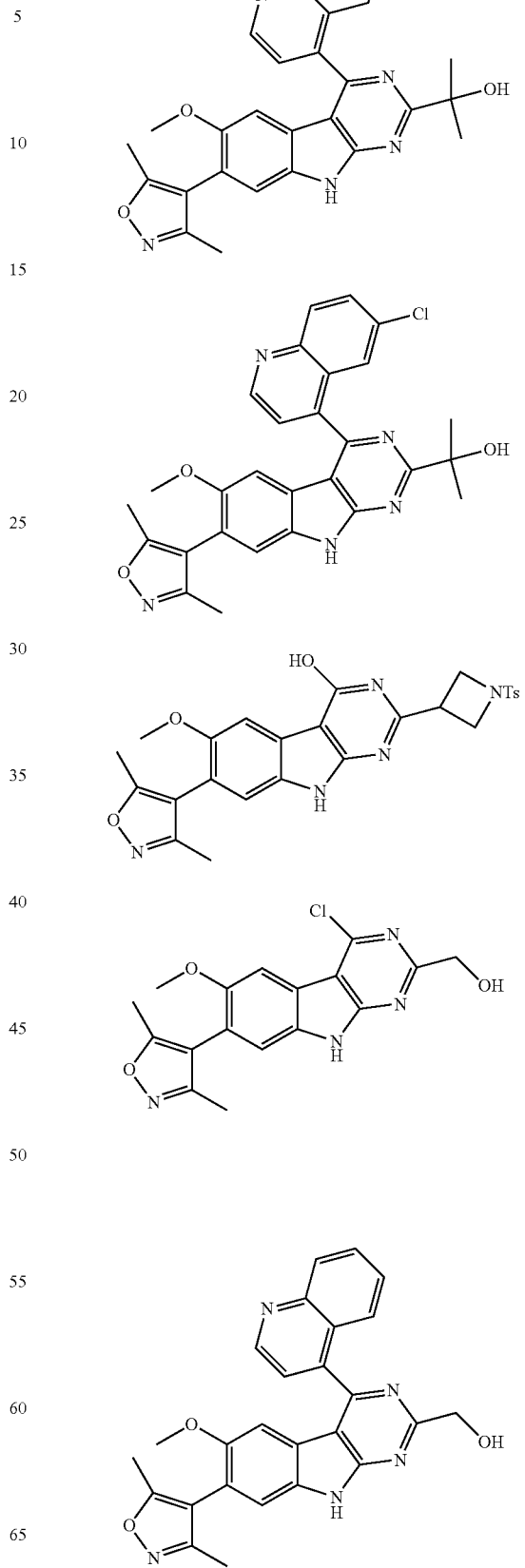

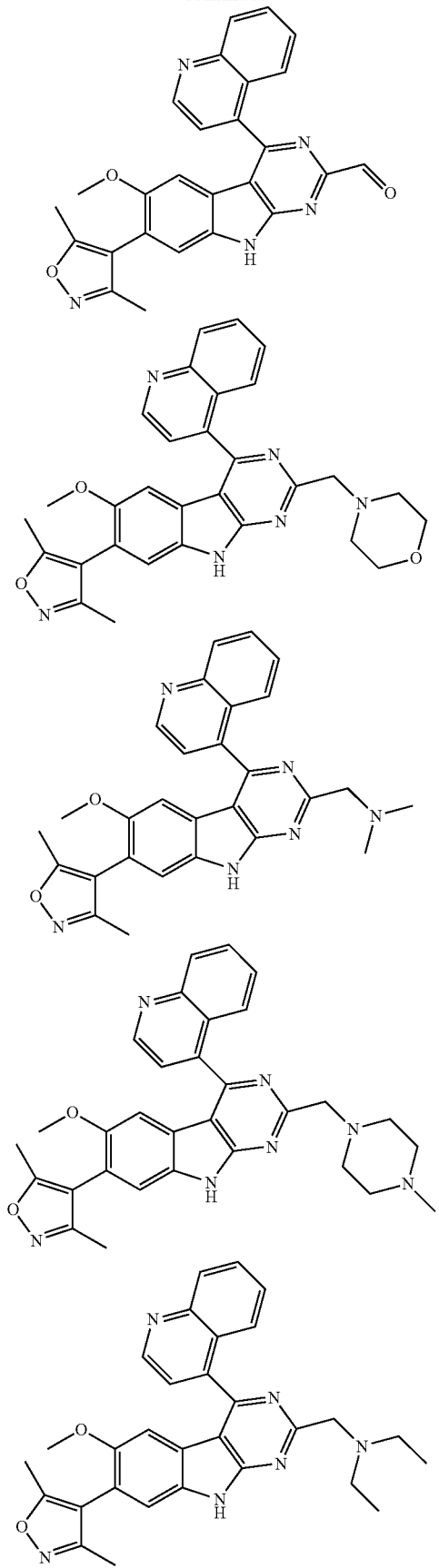
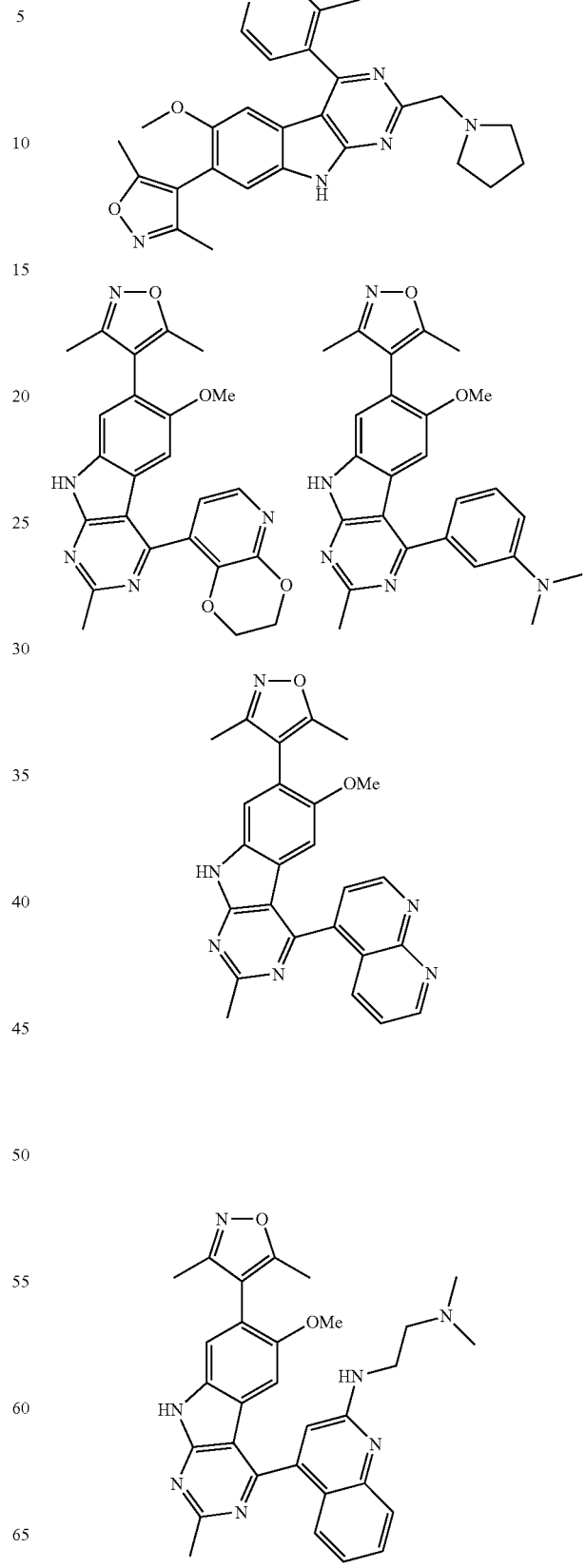

-continued
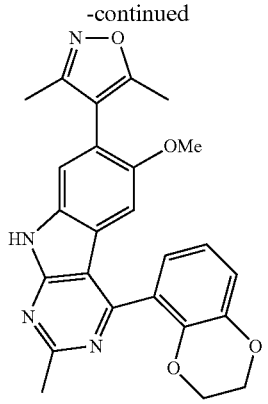
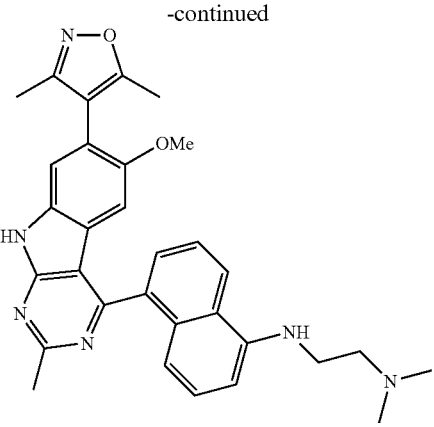
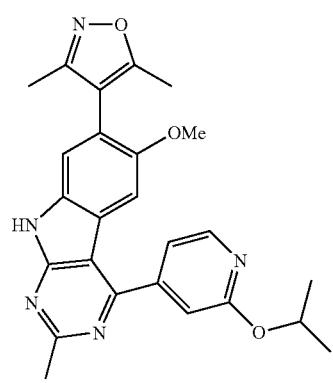
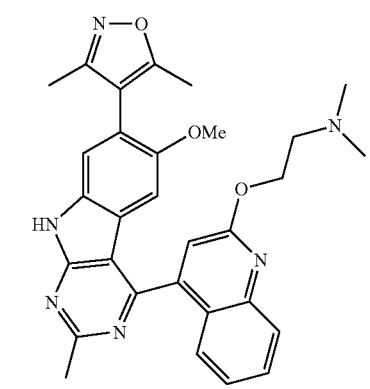
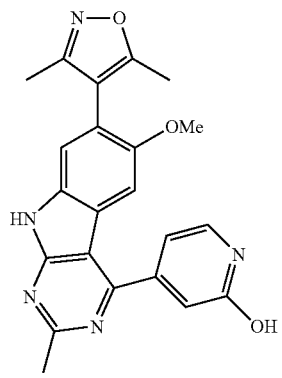
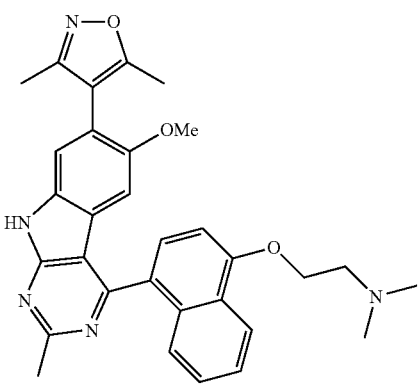
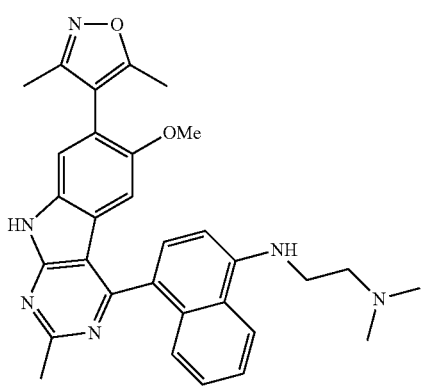
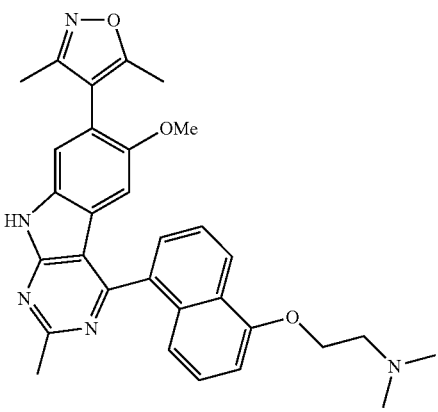

-continued
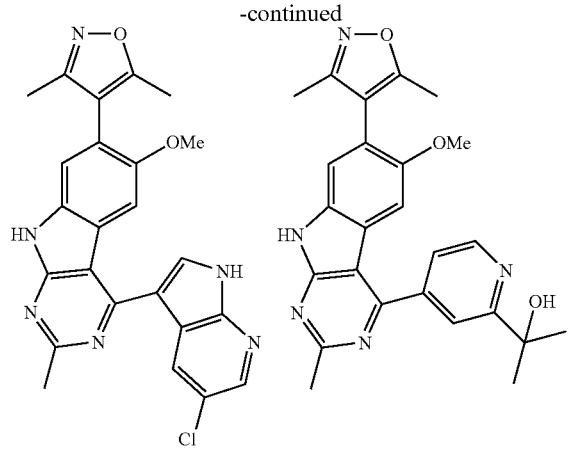
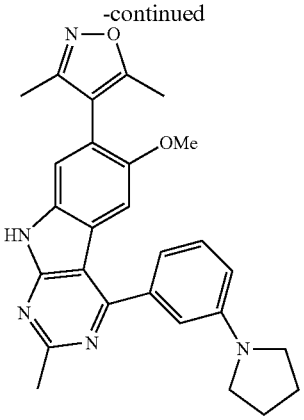
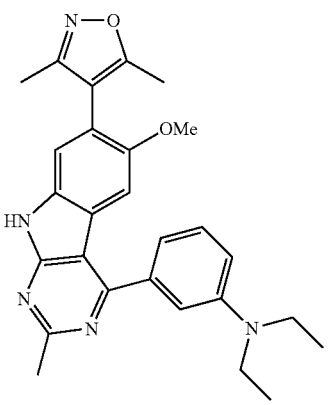
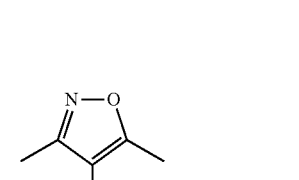
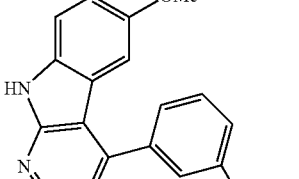

-continued
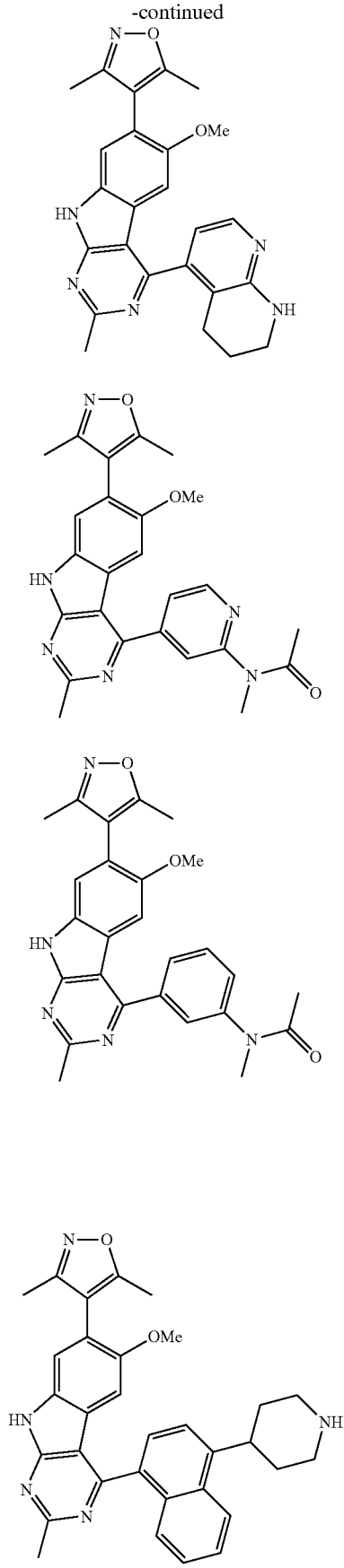
-continued
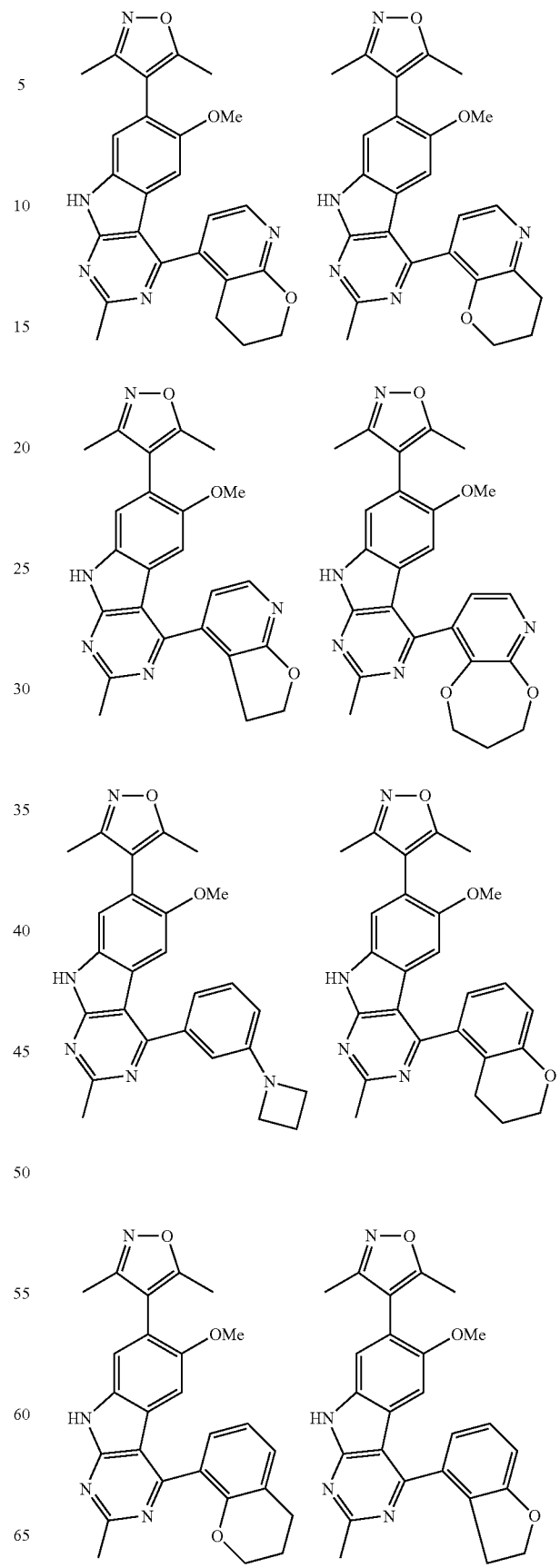

75
-continued
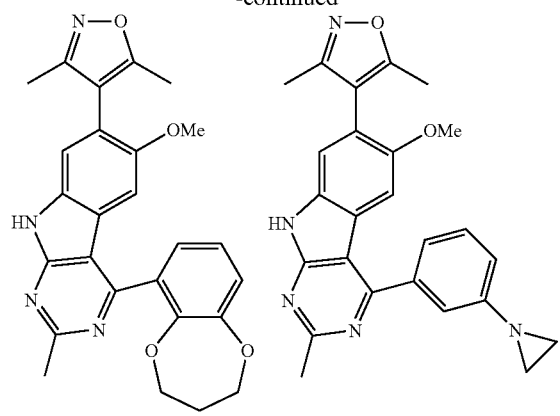
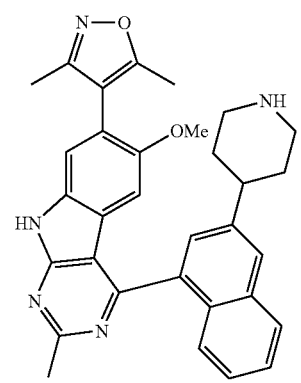
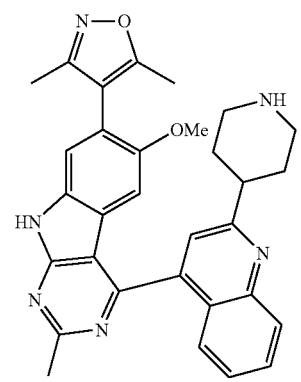
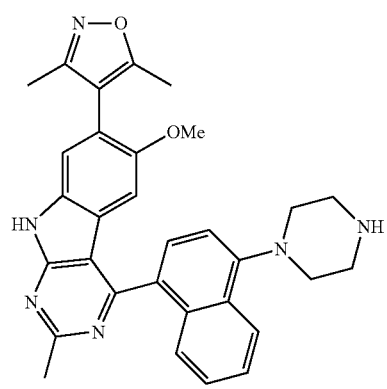
76
-continued
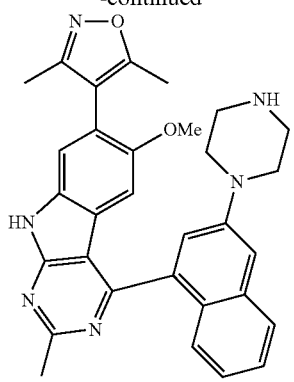
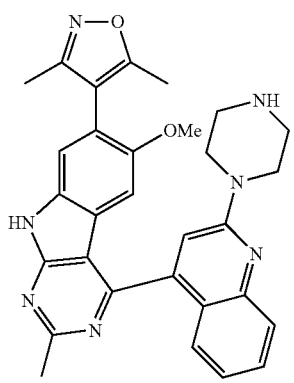
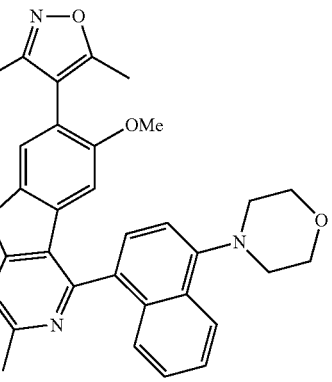
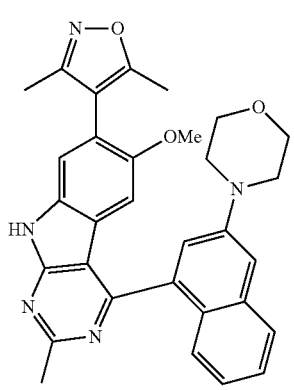

-continued
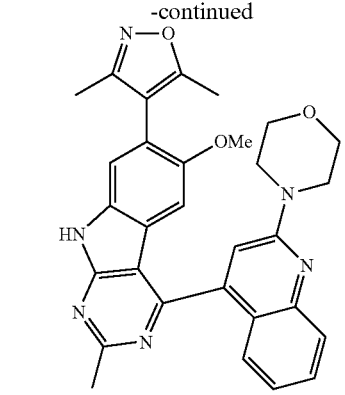
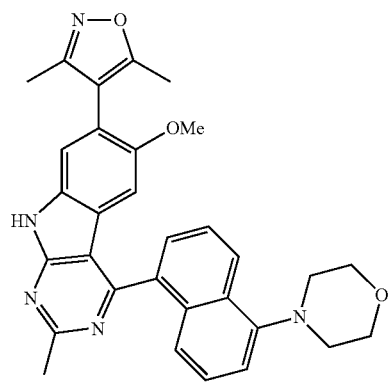
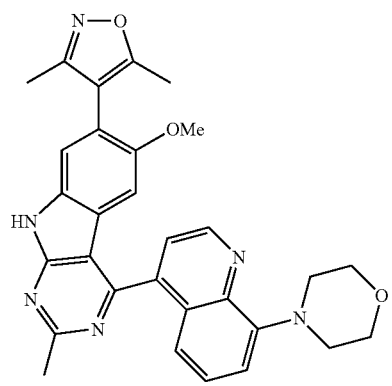
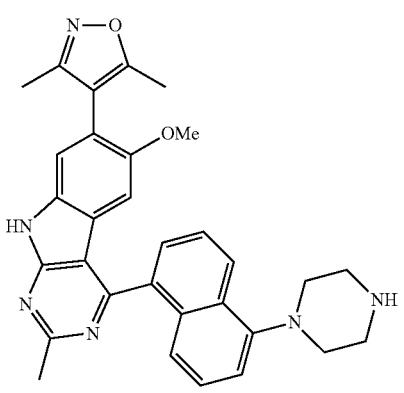
-continued
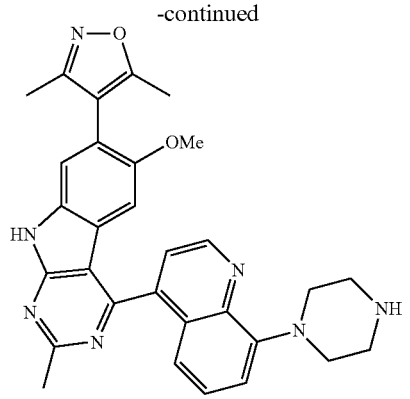
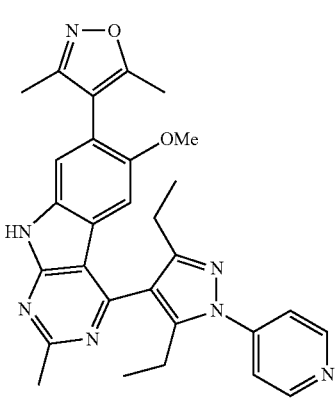
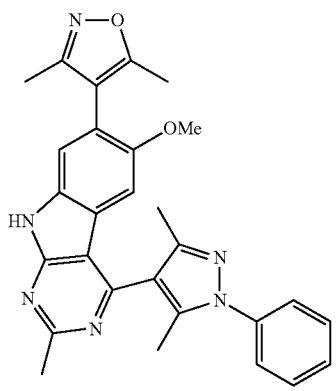
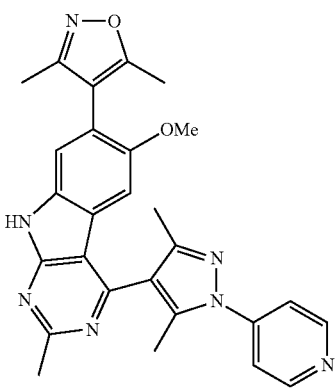

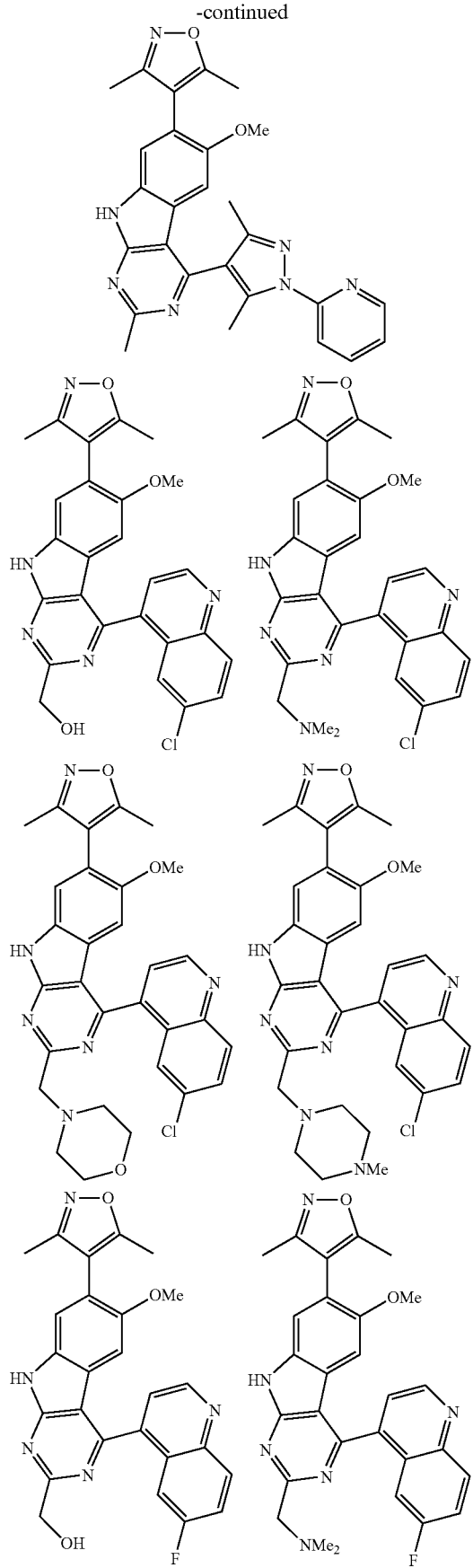
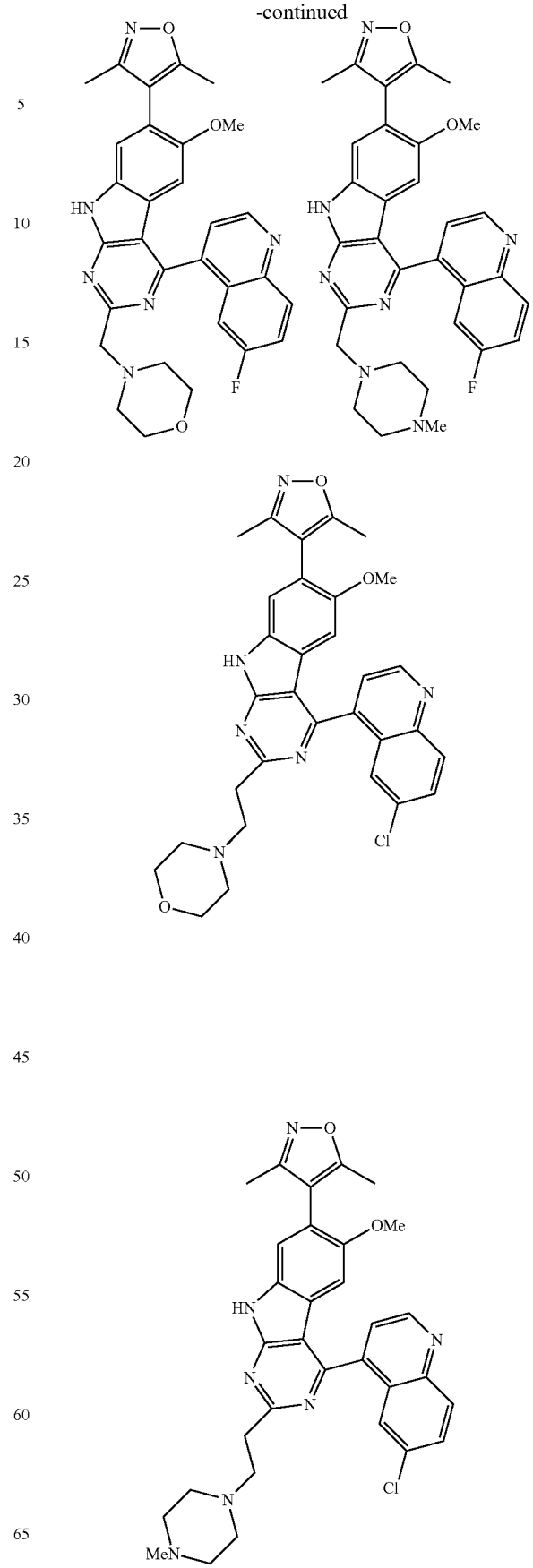

81
-continued
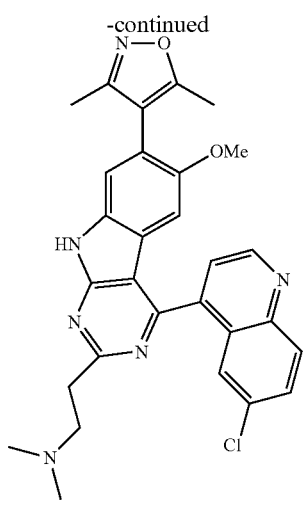
82
-continued
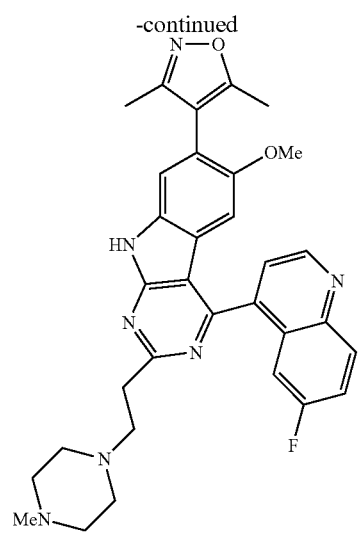
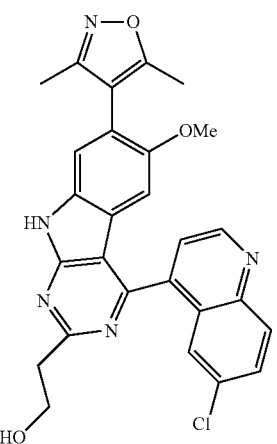
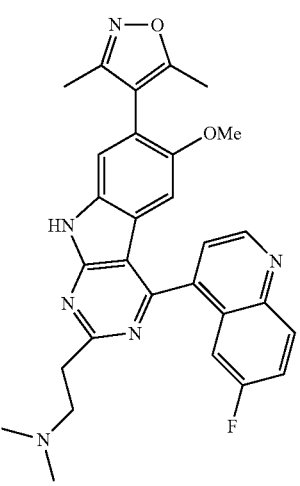
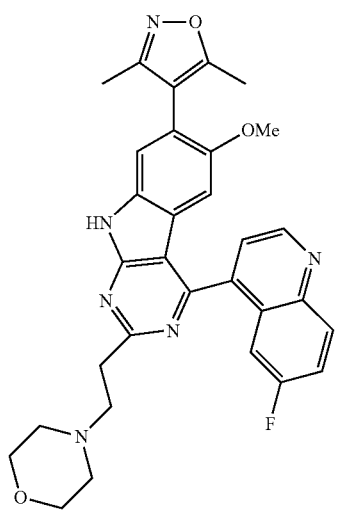
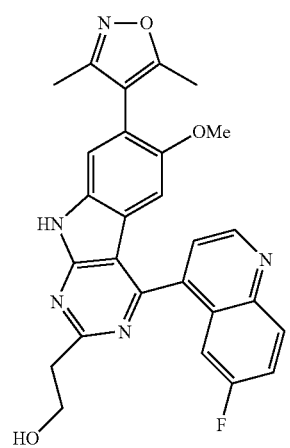

83
-continued
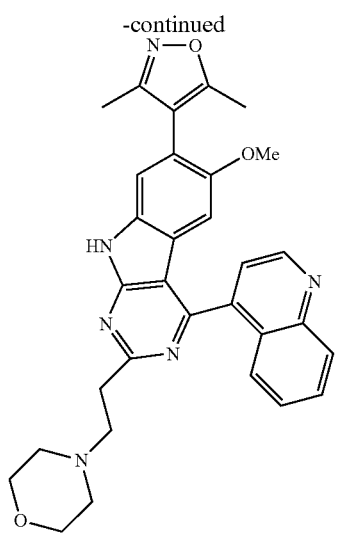
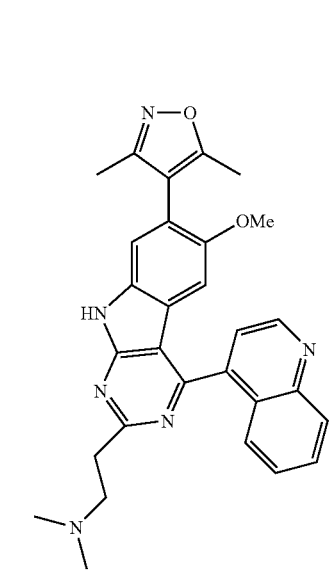
84
-continued
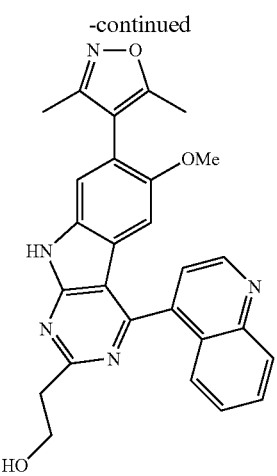
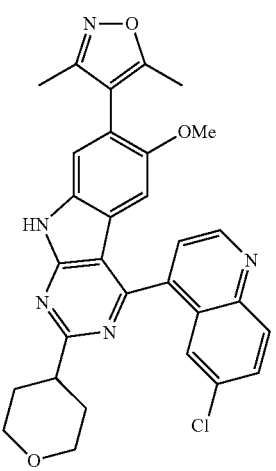

85

-continued

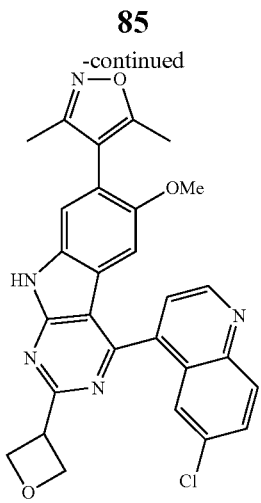

Additional compounds of the present invention include, but are not limited to, compounds having the structure set forth below:

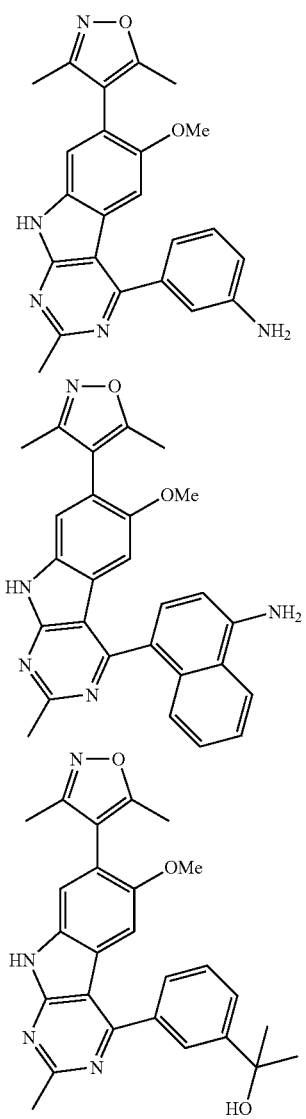

86

-continued

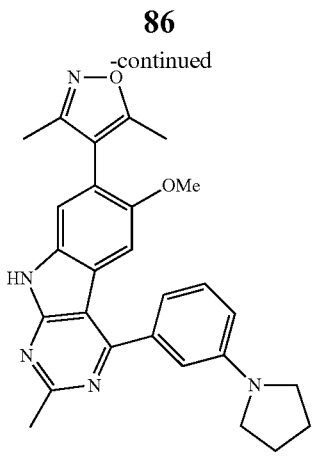

In one embodiment, the present invention provides compounds having Formula (II):

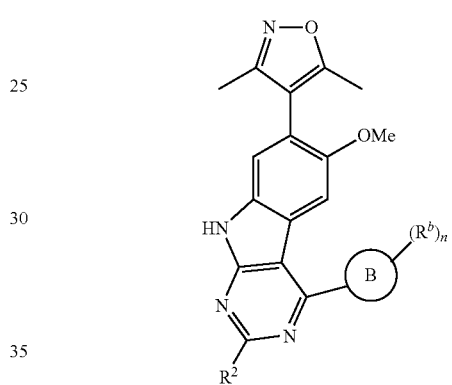

II wherein $R^2$ is H, $C_{1-3}$alkyl, phenyl, $(CH_2)_{1-3}$ $C_{4-7}$heterocycloalkyl, $C_{4-7}$heterocycloalkyl, $CO_2H$, $CO_2(C_{1-3}$alkyl), $NH_2$, $NH(C_{1-3}$alkyl), $N(C_{1-3}$alkyl)$_2$, $(CH_2)_{1-3}NMe_2$, $(CH_2)_{1-3}OH$, $CH(Me)OH$, $C(Me)_2NH_2$, $C(Me)_2OH$, phenyl, benzyl, —C(=O)O$R^{a4}$, —C(=O)N($R^{a4}$)$_2$,

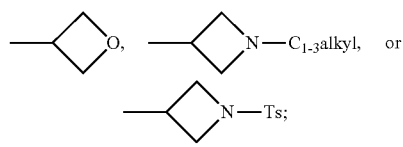

B is aryl, CH($R^{a2}$)-aryl, $C_{3-10}$cycloalkyl, CH($R^{a2}$)—$C_{3-10}$cycloalkyl, heteroaryl, CH($R^{a2}$)-heteroaryl, $C_{3-10}$heterocycloalkyl, or CH($R^2$)—$C_{3-10}$heterocycloalkyl, each unsubstituted or substituted; and $R^b$ is $C_{1-6}$alkyl, halo, aryl, unsubstituted or substituted CH$_2$-aryl, unsubstituted or substituted $C_{3-10}$cycloalkyl, unsubstituted or substituted CH$_2$—$C_{3-10}$cycloalkyl, heteroaryl, unsubstituted or substituted CH$_2$-heteroaryl, unsubstituted or substituted $C_{3-10}$heterocycloalkyl, unsubstituted or substituted CH$_2$—$C_{3-10}$heterocycloalkyl, CF$_3$, CN, O$R^{a5}$, N($R^{a5}$)$_2$, N(CH$_3$)C(=O)(C$_{1-3}$alkyl), NH(CH$_2$)$_{2-3}$N(C$_{1-3}$ alkyl)$_2$, $C_{3-10}$heterocycloalkyl, O(CH$_2$)$_{2-3}$N(C$_{1-3}$ alkyl)$_2$, O(CH$_2$)$_{2-3}$—$C_{3-10}$heterocycloalkyl, oxo(=O), or CHO; and n is 0, 1, 2, or 3;

or a pharmaceutically acceptable salt, hydrate, or solvate thereof.

In another embodiment, the present invention provides compounds having Formula (II), wherein B is heteroaryl and n is 0, or a pharmaceutically acceptable salt, hydrate, or solvate thereof. In another embodiment, B is:

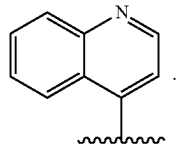

In another embodiment, the present invention provides compounds having Formula (II), wherein B is heteroaryl and n is 1, or a pharmaceutically acceptable salt, hydrate, or solvate thereof. In another embodiment, B is:

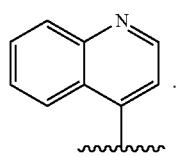 [SMILES: *c1ccnc2ccccc12]

In another embodiment, the present invention provides a compound selected from the group consisting of:

Cpd. No. 73

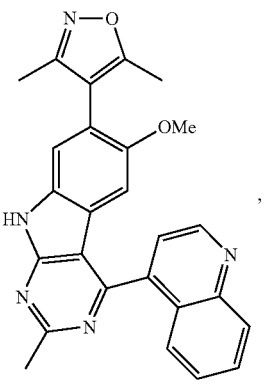

Cpd. No. 101

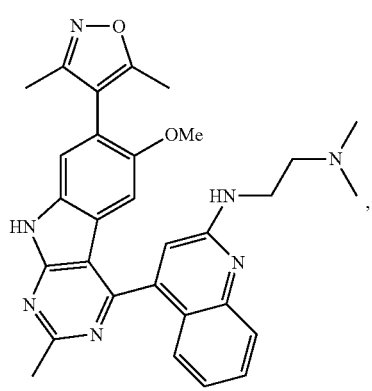

-continued

Cpd. No. 125

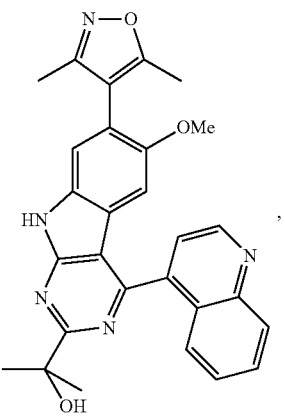

Cpd. No. 130

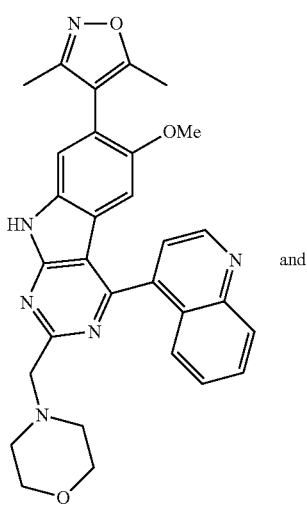

and

Cpd. No. 132

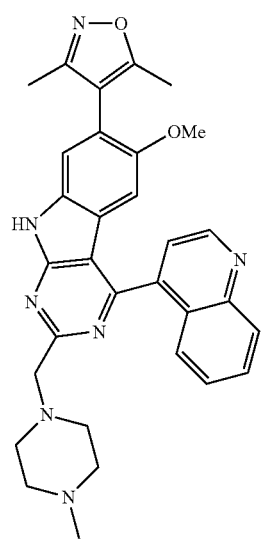

or a pharmaceutically acceptable salt, hydrate, or solvate thereof.

The present invention provides BET bromodomain inhibitors, as exemplified by compounds of structural formula (I), for the treatment of a variety of diseases and conditions wherein inhibition of BET brodomains has a beneficial effect. In one embodiment, the present invention relates to a method of treating an individual suffering from a disease or condition wherein inhibition of the BET bromodomains provides a benefit comprising administering a therapeutically effective amount of a compound of structural formula (I) to an individual in need thereof.

The method of the present invention can be accomplished by administering a compound of structural formula (I) as the neat compound or as a pharmaceutical composition. Administration of a pharmaceutical composition, or neat compound of structural formula (I), can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a compound of structural formula (I) and, optionally, a second therapeutic agent useful in the treatment of diseases and conditions wherein inhibition of BET bromodomains provides a benefit, packaged separately or together, and an insert having instructions for using these active agents.

In many embodiments, a compound of structural formula (I) is administered in conjunction with a second therapeutic agent useful in the treatment of a disease or condition wherein inhibition of BET bromodomains provides a benefit. The second therapeutic agent is different from the compound of structural formula (I). A compound of structural formula (I) and the second therapeutic agent can be administered simultaneously or sequentially to achieve the desired effect. In addition, the compound of structural formula (I) and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A compound of structural formula (I) and the second therapeutic agent can be administered together as a single-unit dose or separately as multi-unit doses, wherein the compound of structural formula (I) is administered before the second therapeutic agent or vice versa. One or more dose of the compound of structural formula (I) and/or one or more dose of the second therapeutic agent can be administered. The compounds of structural formula (I) therefore can be used in conjunction with one or more second therapeutic agents, for example, but not limited to, anticancer agents.

Diseases and conditions treatable by a method of the present invention include, but are not limited to, cancer and other proliferative disorders, inflammatory diseases, sepsis, autoimmune disease, and viral infection. In one embodiment, a human patient is treated with a compound of structural formula (I) and an optional pharmaceutically acceptable carrier, adjuvant, or vehicle, wherein the compound is administered in an amount sufficient to inhibit BET bromodomain activity in the patient.

In one embodiment, the disease to be treated by a compound and method of the present invention is cancer. Examples of treatable cancers include, but are not limited to, adrenal cancer, acinic cell carcinoma, acoustic neuroma, acral lentigious melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In another embodiment, the present invention provides a method of treating a benign proliferative disorder, such as, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

The compounds and methods of the present invention also treat infectious and noninfectious inflammatory events and autoimmune and other inflammatory diseases by administration of an effective amount of a present compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendictitis, pancreatitis, cholocystitus, agammaglobulinemia, psoriasis, allergy, Crohn's disease, irrtiable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, athersclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves' disease.

In other embodiments, the present invention provides a method of treating systemic inflammatory response syndromes, such as LPS-induced endotoxic shock and/or bacteria-induced sepsis by administration of an effective amount of a present compound to a mammal, in particular a human in need of such treatment.

The invention further provides a method for treating viral infections and diseases. Examples of viral infections and diseases treated using the compounds and methods described herein include episome-based DNA viruses including, but not limited to, human papillomavirus, Herpesvirus, Epstein-Barr virus, human immunodeficiency virus, hepatis B virus, and hepatitis C virus.

In another embodiment, a therapeutic method of modulating protein methylation, gene expression, cell proliferation, cell differentiation and/or apoptosis in vivo in diseases mentioned above, in particular cancer, inflammatory disease, and/or viral disease is provided by administering a therapeutically effective amount of one or more BET inhibitor of structural formula (I) to a subject in need of such therapy.

The invention further provides a method of regulating endogenous or heterologous promoter activity by contacting a cell with a provided compound.

In the present methods, a therapeutically effective amount of one or more compound (I), typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A compound of structural formula (I) can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a compound of structural formula (I) is administered in an effective amount to achieve its intended purpose. The exact formulation, route of administration, and dosage is determined by an individual physician in view of the diagnosed condition or disease. Dosage amount and interval can be adjusted individually to provide levels of a compound of structural formula (I) that is sufficient to maintain therapeutic effects.

Toxicity and therapeutic efficacy of the compounds of structural formula (I) can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a compound of structural formula (I) required for use in therapy varies with the nature of the condition being treated, the length of time that activity is desired, and the age and the condition of the patient, and ultimately is determined by the attendant physician. Dosage amounts and intervals can be adjusted individually to provide plasma levels of the BET bromodomain inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a present BET bromodomain inhibitor can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3);

five daily doses, with two days rest, and another five daily doses (5/2/5); or, any dose regimen determined to be appropriate for the circumstance.

A compound of structural formula (I) used in a method of the present invention can be administered in an amount of about 0.005 to about 500 milligrams per dose, about 0.05 to about 250 milligrams per dose, or about 0.5 to about 100 milligrams per dose. For example, a compound of structural formula (I) can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing a BET bromodomain inhibitor of structural formula (I), or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, 10 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 jag/kg, 800 jag/kg, 825 jag/kg, 850 jag/kg, 875 jag/kg, 900 jag/kg, 925 jag/kg, 950 jag/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

As stated above, a BET brodomomain inhibitor of structural formula (I) can be administered in combination with a second therapeutically active agent. In some embodiments, the second therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

In another embodiment, chemotherapeutic agents or other anti-proliferative agents can be combined with a present BET bromodomain inhibitor to treat proliferative diseases and cancer. Examples of therapies and anticancer agents that can be used in combination with compounds of structural formula (I) include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effect (e.g., an antiemetic), and any other approved chemotherapeutic drug.

Examples of antiproliferative compounds include, but are not limited to, an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Nonlimiting exemplary aromatase inhibitors include, but are not limited to, steroids, such as atamestane, exemestane, and formestane, and non-steroids, such as aminoglutethimide, roglethimide, pyridoglutethimide, trilostane, testolactone, ketokonazole, vorozole, fadrozole, anastrozole, and letrozole.

Nonlimiting anti-estrogens include, but are not limited to, tamoxifen, fulvestrant, raloxifene, and raloxifene hydrochloride. Anti-androgens include, but are not limited to, bicalutamide. Gonadorelin agonists include, but are not limited to, abarelix, goserelin, and goserelin acetate.

Exemplary topoisomerase I inhibitors include, but are not limited to, topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophillotoxines, such as etoposide and teniposide.

Microtubule active agents include microtubule stabilizing, microtubule destabilizing compounds, and microtublin polymerization inhibitors including, but not limited to, taxanes, such as paclitaxel and docetaxel; vinca alkaloids, such as vinblastine, vinblastine sulfate, vincristine, and vincristine sulfate, and vinorelbine; discodermolides; cochicine and epothilones and derivatives thereof.

Exemplary nonlimiting alkylating agents include cyclophosphamide, ifosfamide, melphalan, and nitrosoureas, such as carmustine and lomustine.

Exemplary nonlimiting cyclooxygenase inhibitors include Cox-2 inhibitors, 5-alkyl substituted 2-arylaminophenylacetic acid and derivatives, such as celecoxib, rofecoxib, etoricoxib, valdecoxib, or a 5-alkyl-2-arylaminophenylacetic acid, such as lumiracoxib.

Exemplary nonlimiting matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Exemplary nonlimiting mTOR inhibitors include compounds that inhibit the mammalian target of rapamycin (mTOR) and possess antiproliferative activity such as sirolimus, everolimus, CCI-779, and ABT578.

Exemplary nonlimiting antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Exemplary nonlimiting platin compounds include carboplatin, cis-platin, cisplatinum, and oxaliplatin.

Exemplary nonlimiting methionine aminopeptidase inhibitors include bengamide or a derivative thereof and PPI-2458.

Exemplary nonlimiting bisphosphonates include etridonic acid, clodronic acid, tiludronic acid, pamidronic acid, alendronic acid, ibandronic acid, risedronic acid, and zoledronic acid.

Exemplary nonlimiting antiproliferative antibodies include trastuzumab, trastuzumab-DM1, cetuximab, bevacizumab, rituximab, PR064553, and 2C4. The term "antibody" is meant to include intact monoclonal antibodies, polyclonal antibodies, multispecific antibodies formed from at least two intact antibodies, and antibody fragments, so long as they exhibit the desired biological activity.

Exemplary nonlimiting heparanase inhibitors include compounds that target, decrease, or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras, for example, a farnesyl transferase inhibitor, such as L-744832, DK8G557, tipifarnib, and lonafarnib.

Exemplary nonlimiting telomerase inhibitors include compounds that target, decrease, or inhibit the activity of telomerase, such as compounds that inhibit the telomerase receptor, such as telomestatin.

Exemplary nonlimiting proteasome inhibitors include compounds that target, decrease, or inhibit the activity of the proteasome including, but not limited to, bortezomid.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, I-β-D-arabinofuransylcytosine (ara-c), and bisulfan; and ALK inhibitors, which are compounds which target, decrease, or inhibit anaplastic lymphoma kinase.

Exemplary nonlimiting Flt-3 inhibitors include PKC412, midostaurin, a staurosporine derivative, SU11248, and MLN518.

Exemplary nonlimiting HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino, 17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing, or inhibiting the activity of the platelet-derived growth factor-receptors (PDGFR), such as a compound that targets, decreases, or inhibits the activity of PDGFR, such as an N-phenyl-2-pyrimidine-amine derivatives, such as imatinib, SU1O1, SU6668, and GFB-111; b) a compound targeting, decreasing, or inhibiting the activity of the fibroblast growth factor-receptors (FGFR); c) a compound targeting, decreasing, or inhibiting the activity of the insulin-like growth factor receptor I (IGF-IR), such as a compound that targets, decreases, or inhibits the activity of IGF-IR; d) a compound targeting, decreasing, or inhibiting the activity of the Trk receptor tyrosine kinase family, or ephrin B4 inhibitors; e) a compound targeting, decreasing, or inhibiting the activity of the Ax1 receptor tyrosine kinase family; f) a compound targeting, decreasing, or inhibiting the activity of the Ret receptor tyrosine kinase; g) a compound targeting, decreasing, or inhibiting the activity of the Kit/SCFR receptor tyrosine kinase, such as imatinib; h) a compound targeting, decreasing, or inhibiting the activity of the c-Kit receptor tyrosine kinases, such as imatinib; i) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, incorporated herein by reference, such as midostaurin; examples of further compounds include UCN-01, safingol, BAY 43-9006, bryostatin 1, perifosine; ilmofosine; RO 318220 and RO 320432; GO 6976; 1sis 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) a compound targeting, decreasing, or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, getfitinib, erlotinib, OSI-774, C1-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing, or inhibiting the activity of the c-Met receptor.

Exemplary compounds that target, decrease, or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with a present BET bromodomain inhibitor, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl) phthalazine or a pharmaceutically acceptable salt thereof, 1-(4-chloroanilino)-4-(4-pyridylmethyl)phthalazine succinate, angiostatin, endostain, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-a-epihydrocotisol, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

Other examples of second therapeutic agents, one or more of which a present BET bromodomain inhibitor also can be combined, include, but are not limited to: a treatment for Alzheimer's Disease, such as donepezil and rivastigmine; a treatment for Parkinson's Disease, such as L-DOPA/carbidopa, entacapone, ropinrole, pramipexole, bromocriptine, pergolide, trihexephendyl, and amantadine; an agent for treating multiple sclerosis (MS) such as beta interferon (e.g., AVONEX® and REBIF®), glatiramer acetate, and mitoxantrone; a treatment for asthma, such as albuterol and montelukast; an agent for treating schizophrenia, such as zyprexa, risperdal, seroquel, and haloperidol; an anti-inflammatory agent, such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor, such as an acetylcholinesterase inhibitor, an MAO inhibitor, an interferon, an anti-convulsant, an ion channel blocker, riluzole, or an anti-Parkinson's agent; an agent for treating cardiovascular disease, such as a beta-blocker, an ACE inhibitor, a diuretic, a nitrate, a calcium channel blocker, or a statin; an agent for treating liver disease, such as a corticosteroid, cholestyramine, an interferon, and an anti-viral agent; an agent for treating blood disorders, such as a corticosteroid, an anti-leukemic agent, or a growth factor; or an agent for treating immunodeficiency disorders, such as gamma globulin.

The above-mentioned second therapeutically active agents, one or more of which can be used in combination with a BET bromodomain inhibitor of structural formula (I), are prepared and administered as described in the art.

The compounds of the present invention typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of compounds of structural formula (I).

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the compound of structural formula (I) is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a compound of structural formula (I). When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a compound of structural formula (I).

When a therapeutically effective amount of a compound of structural formula (I) is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of structural formula (I) can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the compound of structural formula (I) to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A compound of structural formula (I) can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a compound of structural formula (I) can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A compound of structural formula (I) also can be formulated in rectal compositions, such as suppositories or retention enemas, e.g., containing conventional suppository bases. In addition to the formulations described previously, the compound of structural formula (I) also can be formulated as a depot preparation. Such long-acting formulations can be administered by implantation (for example, subcutaneously or intramuscularly) or by intramuscular injection. Thus, for example, the compounds of structural formula (I) can be formulated with suitable polymeric or hydrophobic materials (for example, as an emulsion in an acceptable oil) or ion exchange resins.

In particular, the compounds of structural formula (I) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The compounds of structural formula (I) also can be injected parenterally, for example, intravenously, intramuscularly, subcutaneously, or intracoronarily. For parenteral administration, the present BET bromodomain inhibitors are best used in the form of a sterile aqueous solution which can contain other substances, for example, salts or monosaccharides, such as mannitol or glucose, to make the solution isotonic with blood.

As an additional embodiment, the present invention includes kits which comprise one or more compounds or compositions packaged in a manner that facilitates their use to practice methods of the invention. In one simple embodiment, the kit includes a compound or composition described herein as useful for practice of a method (e.g., a composition comprising a compound of structural formula (I) and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration.

Prior BET bromodomain inhibitors possessed properties that hindered their development as therapeutic agents. In accordance with an important feature of the present invention, compounds of structural formula (I) were synthesized and evaluated as inhibitors for BET bromodomains. For example, compounds of the present invention typically have a bonding affinity ($IC_{50}$) to BET bromodomains of less than 100 μM, less than 50 μM, less than 25 μM, and less than 5 μM.

Synthesis of Compounds

Compounds of the present invention and were prepared as follows. The following synthetic schemes are representative of the reactions used to synthesize compounds of structural formula (I). Modifications and alternate schemes to prepare BET bromodomain inhibitors of the invention are readily within the capabilities of persons skilled in the art.

Solvents and reagents were obtained commercially and used without further purification. Chemical shifts (δ) of NMR spectra are reported as δ values (ppm) downfield relative to an internal standard, with multiplicities reported in the usual manner.

Unless otherwise stated all temperatures are in degrees Celsius.

In the synthetic methods, the examples, and throughout the specification, the abbreviations have the following meanings

| | |
|---|---|
| DMF | dimethylformamide |
| min | minutes |
| $CH_2Cl_2$/DCM | methylene chloride |
| MeOH | methanol |
| $Na_2SO_4$ | sodium sulfate |
| AcOH | acetic acid |
| MS | mass spectrometry |
| $Na_2CO_3$ | sodium carbonate |
| $Br_2$ | bromine |
| h | hours |
| $CH_3I$/MeI | methyl iodide |
| $CHCl_3$ | chloroform |
| $N_2$ | nitrogen gas |
| $H_2N-NH_2$ | hydrazine |
| $H_2$ | hydrogen gas |
| $POCl_3$ | phosphorous oxytrichloride |
| EtOAc | ethyl acetate |
| KOAc | potassium acetate |
| NaOAc | sodium acetate |
| $Na_2SO_3$ | sodium sulfite |
| $Na_2SO_4$ | sodium sulfate |
| $NaHCO_3$ | sodium bicarbonate |
| HCl | hydrochloric acid |
| g | gram |
| mol | mole |
| mmol | millimole |
| mL | milliliter |
| KOH | potassium hydroxide |
| $NH_2OH\cdot HCl$ | hydroxylamine hydrochloride |
| $CD_3OD$/MeOD | deuterated methanol |
| M | molar |
| N | normal |
| RT/rt | room temperature |
| DME | 1,2-dimethoxyethane |
| NMR | nuclear magnetic resonance spectrometry |
| THF | tetrahydrofuran |
| $NEt_3$ | triethylamine |
| $CDCl_3$ | deuterated chloroform |
| Hz | Hertz |
| Ar | aryl |
| $H_2O$ | water |
| EtOH | ethanol |
| DMAP | 4-dimethylaminopyridine |
| $K_2CO_3$ | potassium carbonate |
| NIS | N-iodosuccinimide |
| NBS | N-bromosuccinimide |
| NaH | sodium hydride |
| Zn | zinc |
| $NH_4Cl$ | ammonium chloride |
| $Pd(dppf)Cl_2$ | [1,1'-bis(diphenylphosphino)ferrocene]dichloro palladium (II) |
| $CF_3CO_2H$/TFA | trifluoroacetic acid |
| $EtN(iPr)_2$/DIPEA | diisopropylethylamine |
| $PyHBr_3$ | pyridinium tribromide |
| $NH_3$ | ammonia |
| Pd/C | palladium on carbon |
| $(PPh_3)_4Pd$/$Pd(PPh_3)_4$ | tetrakis(triphenylphosphine)palladium(0) |
| n-BuLi | n-butyl lithium |
| PCC | pyridinium chlorochromate |
| $Et_2O$ | diethyl ether |
| $(PhO)_2PO-N_3$ (DPPA) | diphenyl phosphorazidate |
| CuI | cupric iodide |
| $HCO_2NH_4$ | ammonium formate |
| $H_2N-CHO$ | formamide |

All final compounds are in trifluoroacetate salt form. The cations are not drawn in the following structures.

1. Synthesis of General Intermediates: RX3 or RX103

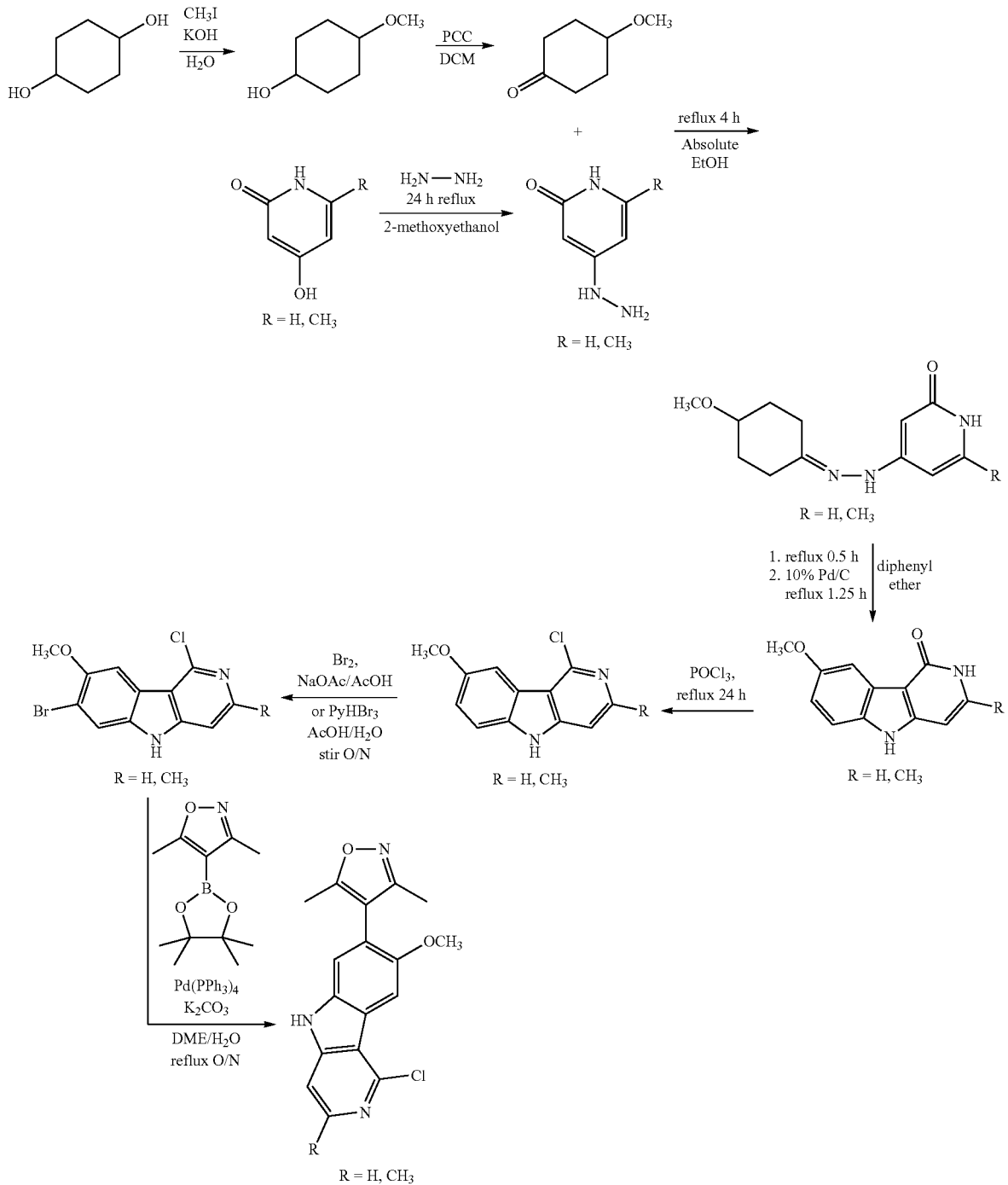

4-methoxycyclohexanol.

An aqueous solution (20 mL) of 1,4-cyclohexanediol (17.5 g, 150 mmol) and KOH (9.3 g, 170 mmol) was heated to reflux for one hour. After cooling to room temperature, water was removed under reduced pressure, then $CH_3I$ (32.0 g, 230 mmol) was added. After 24 hours stirring at room temperature, the reaction mixture was quenched with 100 mL water, and extracted with $CHCl_3$ (100 mL×3). The combined organic fraction was dried, then purified in flash column chromatography (washed out at ethyl acetate: hexane=1:1) to give 7.14 g (36%) pale yellow liquid as the titled compound (Known compound, ACS Registry No. 18068-06-9).

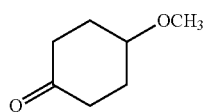

4-methoxycyclohexanone

4-Methoxycyclohexanol (41.9 g, 322 mmol) was dissolved in DCM (360 mL), and added slowly into a pyridinium chlorochromate (138.8 g, 644 mmol) DCM solution (720 mL). The resulting mixture was stirred for 4 hours under $N_2$ protection. Pyridinium chlorochromate as filtered with H type silica gel, and the filtrate was concentrated and purified with flash column (eluent EtOAc:Hexane=1:1) to give 38.4 g (93%) tilted compound as a pale yellow oil. $^1$HNMR (300 MHz, CDCl$_3$) δ 3.61 (t, 1H, J=2.4 Hz), 3.40 (s, 3H), 2.56 (m, 2H), 2.26 (m, 2H), 2.10 (m, 2H), 1.96 (m, 2H).

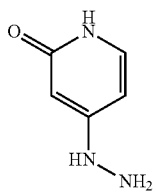

4-hydrazinylpyridin-2(1H)-one

4-Hydrazinylpyridin-2(1H)-one (4.97 g, 44.7 mmol) was added slowly into a 2-methoxyethanol solution of (100 mL) $H_2N-NH_2$ (9.19 g, 290 mmol). The mixture was heated to reflux for 24 hours, after which the solvent was removed and 4.57 g (81.6%) titled compound was given through recrystallization in ethanol. 1HNMR (300 MHz, D2O) δ 7.67 (s, 1H), 7.24 (d, 2H, J=7.2 Hz), 630 (s, 1H), 6.04 (d, 2H, J=7.2 Hz), 5.73 (s, 1H), 3.62 (s, 2H).

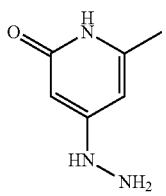

4-Hydrazinyl-6-methylpyridin-2(1H)-one

4-Hydroxy-6-methylpyridin-2(1H)-one (25 g, 200 mmol) and hydrazine monohydrate (65 g, 1299 mmol) mixture in 2-methoxyethanol (500 mL) was heated to reflux for 24 hours. After cooled to room temperature, the product was crystalized in ethanol (22.2 g, 79.8%). $^1$HNMR (300 MHz, DMSO-d$_6$) δ 10.22 (br, 1H), 7.40 (s, 1H), 5.41 (s, 1H), 5.24 (s, 1H), 4.04 (d, 2H, J=1.5 Hz), 1.99 (s, 3H).

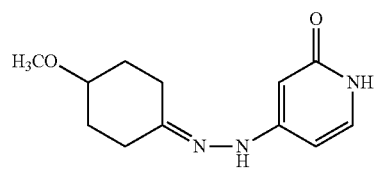 [SMILES: COC1CCC(=NNc2cc[nH]c(=O)c2)CC1]

4-(2-4-methoxycyclohexylidene)hydrazinyl)pyridine-2(1H)-one

4-Hydrazinylpyridin-2(1H)-one (2.07 g, 16.5 mmol) was suspended in 4-methoxycyclohexanone (2.33 g, 18.2 mmol) solution in absolute ethanol (100 mL). After being heated to reflux for 2 hours, the reaction mixture was concentrated to half of its original volume. The resulting precipitates were filtered and dried to give 3.02 g (77.0%) colorless solid. $^1$HNMR (300 MHz, DMSO-d$_6$) δ 10.50 (s, 1H), 9.28 (s, 1H), 7.07 (d, 1H, J=7.2 Hz), 6.01 (d, 1H, J=5.7 Hz), 5.67 (d, 1H, J=2.1 Hz), 3.45 (m, 1H), 3.28 (s, 3H), 2.35 (m, 2H), 2.20 (m, 2H), 1.86 (m, 2H), 1.62 (m, 2H).

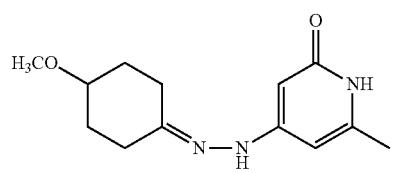 [SMILES: COC1CCC(=NNc2cc(C)[nH]c(=O)c2)CC1]

4-(2-(4-Methoxycyclohexylidene)hydrazinyl)-6-methylpyridin-2(1H)-one

4-Hydrazinyl-6-methylpyridin-2(1H)-one (16.33 g, 117 mmol) was suspended in an ethanol solution of 4-methoxycyclohexanone (16.5 g, 129 mmol). The mixture was heated to reflux for 2 hours, and concentrated to half of its volume. Filtered the precipitate and evaporated the filtrate to give colorless powder (30 g) which was used in next step without further purification. $^1$HNMR (300 MHz, DMSO-d$_6$) δ 6.12 (s, 1H), 5.90 (s, 1H), 3.40 (s, 3H), 2.48-3.40 (m, 2H), 2.28-2.41 (m, 2H), 2.22 (s, 3H), 1.88-2.03 (m, 2H), 1.71-1.78 (m, 2H).

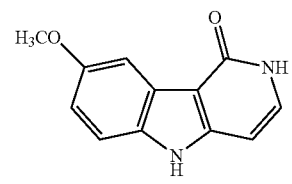 [SMILES: COc1ccc2[nH]c3cc[nH]c(=O)c3c2c1]

8-Methoxy-2,5-dihydro-1H-pyrido[4,3-b]indol-1-one 4-(2-(4-Methoxycyclohexylidene) hydrazinyl)pyridin-2 (1H)-one (20.1 g, 85.4 mmol) was suspended in 400 mL diphenyl ether. The mixture was heated to reflux under $N_2$ protection for 30 minutes. After cooling to room temperature, 10% Pd/C (6 g) was added and the mixture was heated to reflux again for 75 minutes. Then, hexane (800 mL) was added to the cooled mixture. The resulting precipitates were filtered and taken up into boiling AcOH (1100 mL), followed by filtering again to remove Pd—C. The filtrate was concentrated to give yellow solid, which was boiled in 8 mL ethanol. Then, the solid was filtered to give 9 g (50%) pale yellow solid as the titled compound. $^1$HNMR (300 MHz, DMSO-$d_6$) δ 11.54 (s, 1H), 11.03 (s, 1H), 7.60 (d, 1H, J=2.1 Hz), 7.37 (d, 1H, J=8.7 Hz), 7.25 (m, 1H), 6.90 (dd, 1H, $J_1$=2.7 Hz, $J_2$=8.7 Hz), 6.46 (d, 1H, J=7.2 Hz), 3.81 (s, 3H).

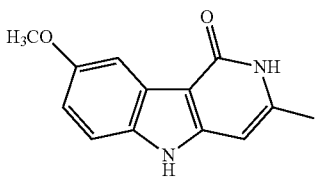 [SMILES: COc1ccc2[nH]c3cc(C)[nH]c(=O)c3c2c1]

8-Methoxy-3-methyl-5H-pyrido[4,3-b]indol-1-ol 4-(2-(4-methoxycyclohexylidene)hydrazinyl)-6-methyl-pyridin-2(1H)-one (1.99 g, 7.99 mmol) was refluxed in 60 mL diphenyl ether for 30 minutes, after cooled to room temperature, Pd—C (6.1 g, 0.57 mmol) was added and heat for additional 1.25 hours. Let it cooled, and precipitate with hexane (80 mL). The filter was taken up into hot AcOH (110 mL) and Pd—C was removed by filtration. Then evaporated AcOH and wash the crude product by having it boiled in MeOH (16 mL). The solid was collected and put into next step without further purification (1 g, 54.8%).

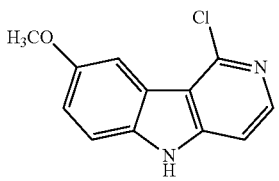 [SMILES: COc1ccc2[nH]c3ccnc(Cl)c3c2c1]

1-chloro-8-methoxy-5H-pyridol[4,3-b]indole

POCl$_3$ (20 mL) and 8-methoxy-5H-pyridol[4,3-b]indol-1-ol were refluxed for 24 hours followed by removal of POCl$_3$ under reduced pressure. The residue was refluxed with HCl for additional 1 hour. After cooling, the mixture was neutralized with ammonium hydroxide, the precipitate was filtered and purified with flash column chromatography (EtOAc:Hexane=1:1 as eluent) to give 0.44 g (64.5%) titled compound as a colorless powder. $^1$HNMR (300 MHz, MeOD-$d_4$) δ 8.26 (d, 1H, J=6.3 Hz), 7.94 (d, 1H, J=2.1 Hz), 7.61 (m, 2H), 7.31 (dd, 1H, $J_1$=2.1 Hz, $J_2$=8.7 Hz), 3.96 (s, 3H).

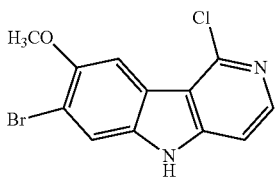 [SMILES: COc1cc2c(cc1Br)[nH]c1ccnc(Cl)c12]

7-bromo-1-chloro-8-methoxy-5H-pyrido[4,3-b]indole

1-Chloro-8-methoxy-5H-pyrido[4,3-b]indole (377 mg, 1.6 mmol) and NaOAc (197 mg, 2.4 mmol) were dissolved in AcOH (40 mL). Then bromine (389 mg, 2.4 mmol) was added dropwisely. After stirring at room temperature for overnight, the reaction was quenched with Na$_2$SO$_3$ solution. AcOH was then removed under reduced pressure and the resulting auqeous phase was extracted with EtOAc. The combined organic fraction was concentrated and purified with prep-HPLC to give 157 mg (31.1%) colorless powder. $^1$HNMR (300 MHz, MeOD-$d_4$) δ 8.21 (d, 1H, J=5.7 Hz), 8.00 (s, 1H), 7.84 (s, 1H), 7.50 (d, J=6.0 Hz), 4.03 (s, 3H).

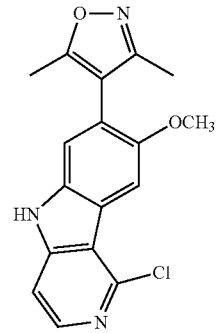

4-(1-chloro-8-methoxy-5H-pyrido[4,3-b]indol-7-yl)-3,5-dimethylisoxazole (RX3)

7-Bromo-1-chloro-8-methoxy-5H-pyrido[4,3-b]indole (157 mg, 0.5 mmol), 3,5-dimethylisoxazole-4-boronic acid pinacol ester (655 mg, 2.0 mmol), and K$_2$CO$_3$ (345 mg, 2.5 mmol) were dissolved in DME/H$_2$O (50 mL/25 mL) system. Then vacuumed, and refilled with N$_2$. After that, tetraki (triphenylphosphine)palladium (0) was added, followed by vacuuming and refilling with N$_2$. The reaction mixture was heated to reflux for overnight, when cooled to room temperature, it was extracted with EtOAc, and the combined organic fractions were concentrated before purification in prep-HPLC. 57 mg (34.6%) of the titled compound was obtained after being lyophilized for 24 hours as a pale yellow powder. $^1$HNMR (300 MHz, MeOD-$d_4$) δ 8.26 (d, 1H, J=6.0 Hz), 8.09 (s, 1H), 7.60 (d, 1H, J=6.3 Hz), 7.49 (s, 1H), 3.98 (s, 3H), 2.63 (s, 3H), 2.20 (s, 3H). ESIMS m/z [M+H]$^+$ calculated=328.77. found=328.83.

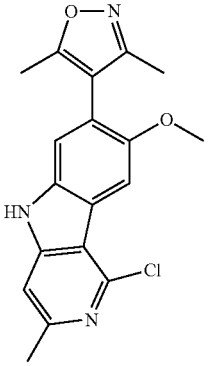

4-(1-chloro-8-methoxy-3-methyl-5H-pyrido[4,3-b]indol-7-yl)-3,5-dimethylisoxazole $^1$HNMR (300 MHz, MeOD-d$_4$) δ 8.03 (s, 1H), 7.44 (s, 1H), 7.42 (s, 1H), 3.97 (s, 3H), 2.69 (s, 3H), 2.36 (s, 3H), 2.19 (s, 3H). ESIMS m/z [M+H]$^+$ calcd.=342.80. found=342.58.

2. General Methods for Syntheses of Five-Membered Heterocyclic Containing Pinacol Boronates.

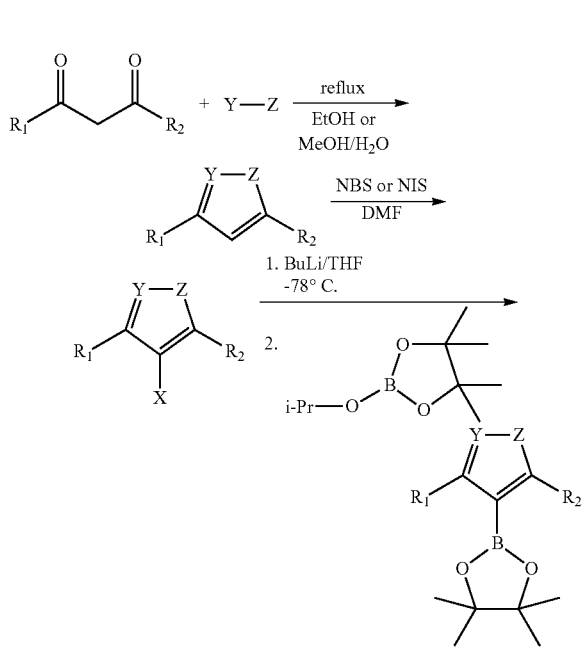

R$_1$, R$_2$ = methyl, ethyl, propyl, isopropyl, cyclopropyl, cyclobutyl, phenyl, other alkyl, heteroaryl, or aryl.
Y = N
Z = NH, O, N-alkyl
X = Br, I Example 1

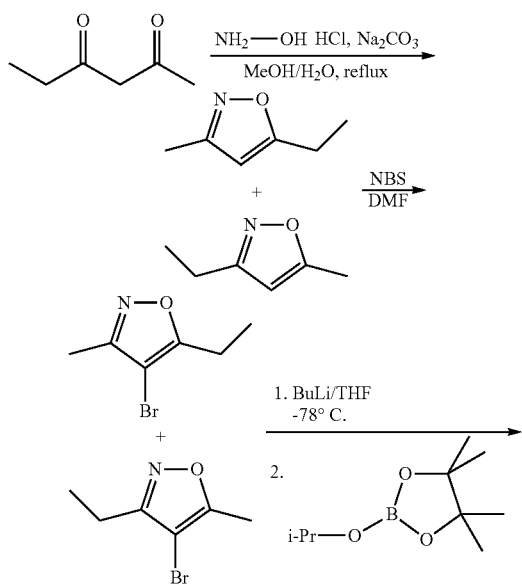

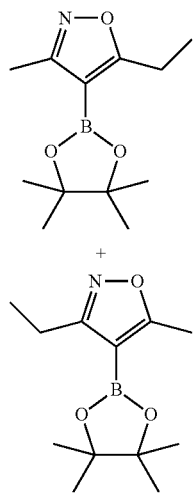

Example 2

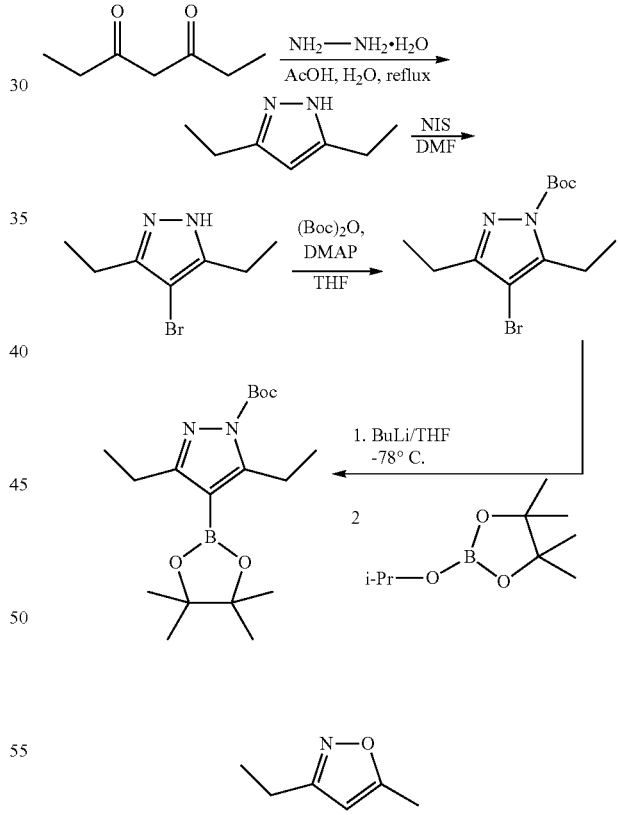

3-ethyl-5-methylisoxazole. NH$_2$OH·HCl (0.542 g, 7.8 mmol) was dissolved in MeOH/H$_2$O (10 mL/20 ml), followed by addition of a Na$_2$CO$_3$ (0.413 g, 3.9 mmol). When bubbles were absent, hexane-2,4-dione was added dropwisely. The mixture was heated at reflux overnight. After cooling to room temperature, the mixture was extracted with Et$_2$O (40 mL×2), and dried over Na$_2$SO$_4$ anhydrous. Removal of solvent to give 0.559 g (Yield: 57.3%) light yellow liquid. ¹HNMR (300 MHz, CDCl3), δ 5.82 (s, 1H), 2.74 (q, J=7.5 Hz, 2H), 2.28 (s, 3H), 1.28 (q, J=7.5 Hz, 3H).

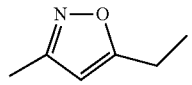

5-ethyl-3-methylisoxazole. ¹HNMR (300 MHz, CDCl₃), δ 5.85 (s, 1H), 2.66 (q, J=7.5 Hz, 2H), 2.40 (s, 3H), 1.28 (q, J=7.5 Hz, 3H).

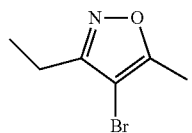

4-bromo-3-ethyl-5-methylisoxazole. A mixture of 3-ethyl-5-methylisoxazole (0.22 g, 2.01 mmol) and NBS (0.39 g, 2.21 mmol) in DMF (5 mL) was stirred at room temperature overnight. Then, the mixture was poured into ethyl acetate (20 mL) and extracted with water (20 mL×5). The combined organic phase was washed with saturated saline (20 mL), and dried over Na₂SO₄ anhydrous. The 4-bromo-3-ethyl-5-methylisoxazole was purified with silica gel flash column (washed out at ethyl acetate:hexanes=1:30) to give 0.338 g (Yield: 84.7%) light yellow liquid. ¹HNMR (300 MHz, CDCl₃), δ 2.77 (q, J=7.5 Hz, 2H), 2.28 (s, 3H), 130 (t, J=7.5 Hz, 3H).

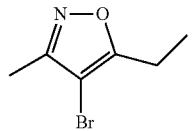

4-bromo-5-ethyl-3-methylisoxazole. ¹HNMR (300 MHz, CDCl₃), δ 2.67 (q, J=7.5 Hz, 2H), 2.41 (s, 3H), 1.30 (J=7.5 Hz 3H.

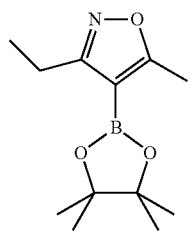 [SMILES: CCc1noc(C)c1B1OC(C)(C)C(C)(C)O1]

3-ethyl-5-methyl-4-(4,4,5,5-tetramethyl-1,3,2-dioxaborolan-2-yl)isoxazole. Synthesis was performed using the general methods for syntheses of pinacol boronates. ¹HNMR (300 MHz, CDCl₃), δ 2.93 (q, J=7.5 Hz, 2H), 2.35 (s, 3H), 1.32 (s, 12H), 1.26 (m, 3H).

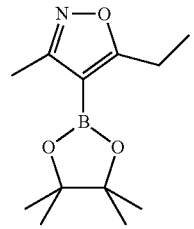 [SMILES: CCc1onc(C)c1B1OC(C)(C)C(C)(C)O1]

5-ethyl-3-methyl-4-(4,4,5,5-tetramethyl-1,3,2-dioxaborolan-2-yl)isoxazole. ¹HNMR (300 MHz, CDCl₃), δ 2.77 (q, J=7.5 Hz, 2H), 2.53 (s, 3H), 1.32 (s, 12H), 1.26 (m, 3H).

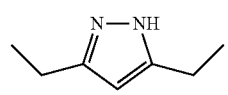

3,5-diethyl-1H-pyrazole. A mixture of heptane-3,5-dione (1.128 g, 8.8 mmol) and hydrazine hydrate (0.44 g, 8.9 mmol) was heated to reflux for 1 hour. Then, the mixture was extracted with ethyl acetate and dried over Na₂SO₄ anhydrous. Removal of solvent gave 0.96 g (Yield: 87.8%) bright yellow oil. ¹HNMR (300 MHz, CDCl3), δ 5.89 (s, 1H), 2.67 (q, J=7.5 Hz, 6H).

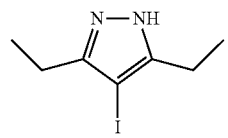

3,5-diethyl-4-iodo-1H-pyrazole. ¹HNMR (300 MHz, CDCl₃), δ 2.65 (q, J=7.5 Hz, 4H), 1.27 (t, J=7.5 Hz, 6H).

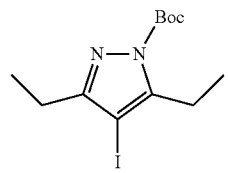 [SMILES: CCc1nn(C(=O)OC(C)(C)C)c(CC)c1I]

tert-butyl 3,5-diethyl-4-iodo-1H-pyrazole-1-carboxylate. A mixture of 3,5-diethyl-4-iodo-1H-pyrazole and (Boc)₂O was dissolved in THF and stirred at room temperature for 1 hour. The product then was purified with silica gel column (ethyl acetate:hexanes=1:3). ¹HNMR (300 MHz, CDCl₃), δ 3.01 (q, J=7.5 Hz, 2H), 2.65 (q, J=7.5 Hz, 2H), 1.66 (s, 9H), 1.28 (t, J=7.5 Hz, 3H), 1.18 (t, J=7.5 Hz, 3H).

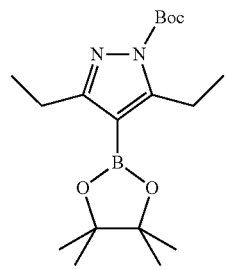 [SMILES: CCc1nn(C(=O)OC(C)(C)C)c(CC)c1B1OC(C)(C)C(C)(C)O1]

tert-butyl 3,5-diethyl-4-(4,4,5,5-tetramethyl-1,3,2-dioxaborolan-2-yl)-1H-pyrazole-1-carboxylate. ¹HNMR (300 MHz, CDCl₃), δ 3.15 (q, J=7.5 Hz, 2H), 2.74 (q, J=7.5 Hz, 2H), 1.61 (s, 9H), 1.27 (s, 12H), 1.17 (m, 6H).

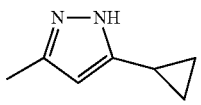

5-cyclopropyl-3-methyl-1H-pyrazole. ¹HNMR (300 MHz, CDCl₃) δ 9.01 (br, 1H), 5.72 (s, 1H), 2.27 (s, 3H), 1.90 (m, 1H), 0.92 (m, 2H), 0.70 (m, 2H).

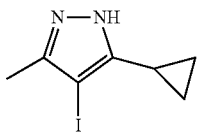

5-cyclopropyl-4-iodo-3-methyl-1H-pyrazole. ¹HNMR (300 MHz, CDCl₃) δ 2.23 (s, 3H), 1.83 (m, 1H), 0.95 (m, 2H), 0.80 (m, 2H)

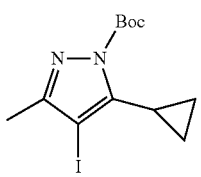 [SMILES: Cc1nn(C(=O)OC(C)(C)C)c(C2CC2)c1I]

tert-butyl 5-cyclopropyl-4-iodo-3-methyl-1H-pyrazole-1-carboxylate. ¹HNMR (300 MHz, CDCl₃), δ 2.52 (s, 3H), 1.82 (m, 1H), 1.61 (s, 9H), 0.98 (m, 2H), 0.90 (m, 2H).

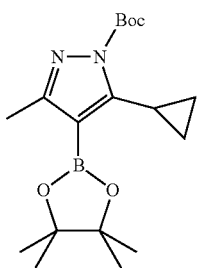 [SMILES: Cc1nn(C(=O)OC(C)(C)C)c(C2CC2)c1B1OC(C)(C)C(C)(C)O1]

tert-butyl 5-cyclopropyl-3-methyl-4-(4,4,5,5-tetramethyl-1,3,2-dioxaborolan-2-yl)-1H-pyrazole-1-carboxylate. ¹HNMR (300 MHz, CDCl₃), δ 2.65 (s, 3H), 2.28 (m, 1H), 1.62 (s, 9H), 1.33 (s, 12H), 0.99 (m, 2H, 0.88 (m, 2H).

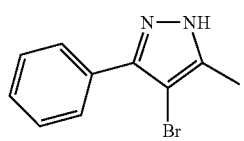

4-bromo-5-methyl-3-phenyl-1H-pyrazole. ¹HNMR (300 MHz, CDCl₃), δ 10.05 (br, 1H), 7.80 (m, 2H), 7.46 (m, 3H), 2.36 (s, 3H).

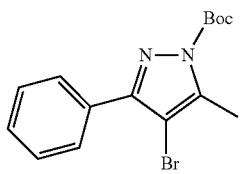 [SMILES: Cc1c(Br)c(-c2ccccc2)nn1C(=O)OC(C)(C)C]

tert-butyl 4-bromo-5-methyl-3-phenyl-1H-pyrazole-1-carboxylate. ¹HNMR (300 MHz, CDCl₃), δ 7.94 (m, 2H), 7.45 (m, 3H), 2.62 (s, 3H), 1.69 (s, 9H).

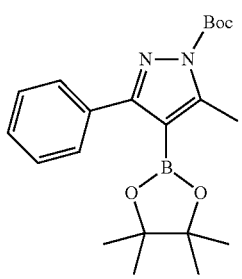 [SMILES: Cc1c(B2OC(C)(C)C(C)(C)O2)c(-c2ccccc2)nn1C(=O)OC(C)(C)C]

tert-butyl 3,5-dimethyl-4-(4,4,5,5-tetramethyl-1,3,2-dioxaborolan-2-yl)-1H-pyrazole-1-carboxylate. ¹HNMR (300 MHz, CDCl₃), δ 7.81 (m, 2H), 7.37 (m, 3H), 2.76 (s, 3H), 1.67 (s, 9H), 1.32 (s, 12H).

3. Synthesis of Final Compounds from the General Intermediates:

3.1 Reduction:

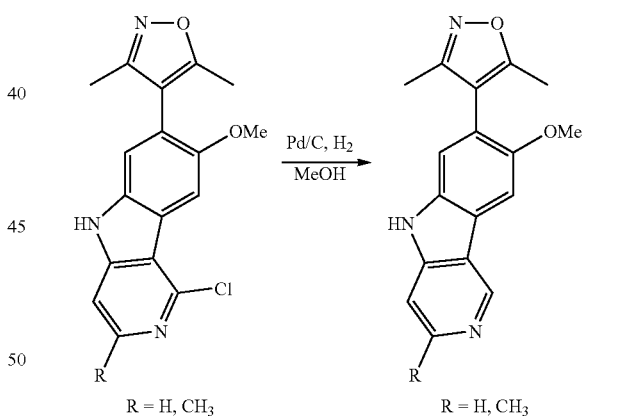

R = H, CH₃                R = H, CH₃

RX7

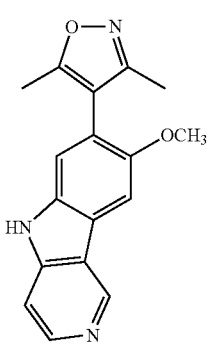

4-(8-methoxy-5H-pyrido[4,3-b]indol-7-yl)-3,5-dimethyl-isoxazole. 10% Pd—C (5 mg) was suspended in an MeOH solution of 4-(1-chloro-8-methoxy-5H-pyrido[4,3-b]indol-7-yl)-3,5-dimethylisoxazole (15 mg, 0.046 mmol). The reaction proceeded for 26 hours under a H$_2$ balloon at room temperature. Pd—C was filtered and the filtrate was purified in semi-prep HPLC to give 4 mg (30%) colorless powder after being lyophilized for 24 hours. $^1$HNMR (300 MHz, MeOD-d$_4$) δ 9.61 (s, 1H), 8.54 (d, 1H, J=6.9 Hz), 8.11 (s, 1H), 7.97 (s, 1H), 4.00 (s, 3H), 2.36 (s, 3H), 2.19 (s, 3H). ESIMS m/z [M+H]$^+$ calculated=294.33. found=294.75.

3.2 General Method for Suzuki Coupling:

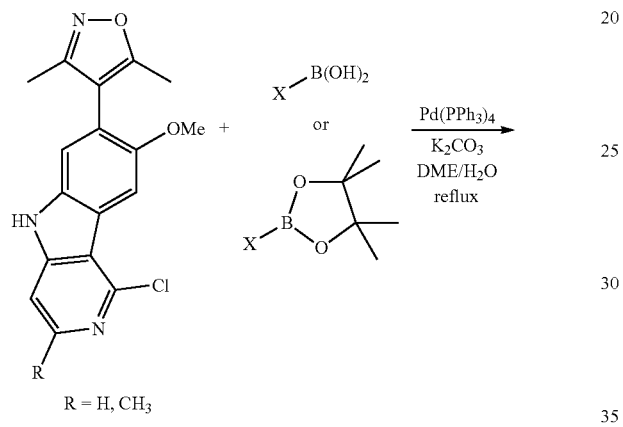

R = H, CH$_3$

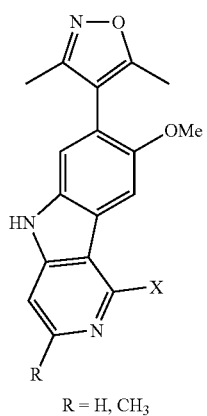

R = H, CH$_3$

RX3 (20 mg, 0.06 mmol), the boronic acid or boronic acid pinacol ester (4 equivalent), and K$_2$CO$_3$ (41.5 mg, 0.3 mmol) was stirred in 15 mL H$_2$O/DME (1:2). The mixture was vacuumed and Pd(PPh$_3$)$_4$ was added before heating to reflux under N$_2$ protection. After reflux overnight, the reaction was cooled to room temperature, and extracted with ethyl acetate. After removing the organic phase, the residue was purified using RP-HPLC and a colorless powder was obtained after overnight lyophilization.

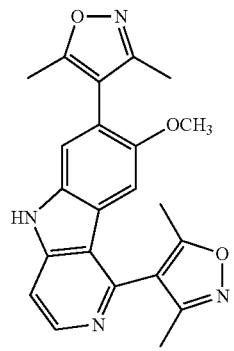

Cpd. No. 1

4,4'-(8-methoxy-5H-pyrido[4,3-b]indole-1,7-diyl)bis(3,5-dimethylisoxazole). $^1$HNMR (300 MHz, MeOD-d$_4$) δ 8.63 (d, 1H, J=6.6 Hz), 8.04 (d, 1H, J=6.6 Hz), 7.67 (s, 1H), 7.02 (s, 1H), 3.78 (s, 3H), 2.52 (s, 3H), 2.34 (s, 3H), 2.28 (s, 3H), 2.17 (s, 3H). ESIMS m/z [M+H]$^+$ calculated=389.43. found=389.50.

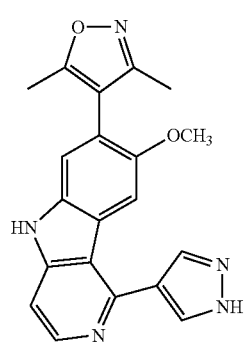

Cpd. No. 2

4-(8-methoxy-1-(1H-pyrazol-4-yl)-5H-pyrido[4,3-b]indol-7-yl)-3,5-dimethylisoxazole. $^1$HNMR (300 MHz, MeOD-d$_4$) δ 8.48 (s, 2H), 8.45 (d, 1H, J=6.9 Hz), 7.89 (d, 1H, J=6.9 Hz), 7.63 (s, 1H), 7.61 (s, 1H), 3.82 (s, 3H), 2.35 (s, 3H), 2.17 (s, 3H). ESIMS m/z [M+H]$^+$ calculated=360.39. found=361.17.

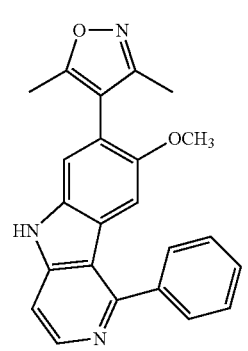

Cpd. No. 3

4-(8-methoxy-1-phenyl-5H-pyrido[4,3-b]indol-7-yl)-3,5-dimethylisoxazole. $^1$HNMR (300 MHz, MeOD-d$_4$) δ 8.53 (d, 1H, J=6.9 Hz), 7.98 (m, 3H), 7.86 (m, 3H), 7.61 (s, 1H), 7.17 (s, 1H), 3.63 (s, 3H), 2.33 (s, 3H), 2.15 (s, 3H). ESIMS m/z [M+H]$^+$ calculated=370.42. found=370.42.

Cpd. No. 4

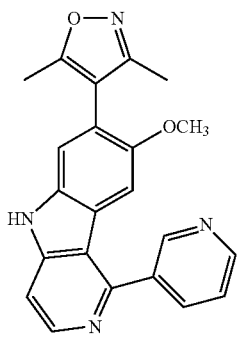

4-(8-methoxy-1-(pyridin-3-yl)-5H-pyrido[4,3-b]indol-7-yl)-3,5-dimethylisoxazole. $^1$HNMR (300 MHz, MeOD-d$_4$) δ 9.21 (br, 1H), 9.06 (br, 1H), 8.61 (d, 1H, J=6.9 Hz), 8.49 (d, 1H, J=7.8 Hz), 8.03 (d, 1H, J=6.6 Hz), 7.93 (br, 1H), 7.65 (s, 1H), 7.07 (s, 1H), 3.67 (s, 3H), 2.33 (s, 3H), 2.15 (s, 3H). ESIMS m/z [M+H]$^+$ calculated=371.41. found=371.75.

Cpd. No. 5

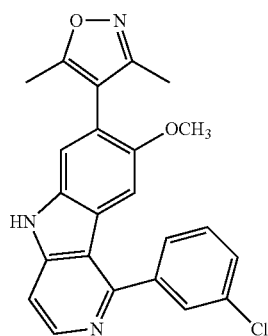

4-(1-(3-chlorophenyl)-8-methoxy-5H-pyrido[4,3-b]indol-7-yl)-3,5-dimethylisoxazole. $^1$HNMR (300 MHz, MeOD-d$_4$) δ 8.56 (d, 1H, J=6.9 Hz), 8.09 (d, 1H, J=1.2 Hz), 8.02 (d, 1H, J=6.9 Hz), 7.85-7.93 (m, 3H), 7.65 (s, 1H), 7.20 (s, 1H), 3.69 (s, 3H), 2.34 (s, 3H), 2.16 (s, 3H). ESIMS m/z [M+H]$^+$ calculated=404.87. found=405.00.

Cpd. No. 6

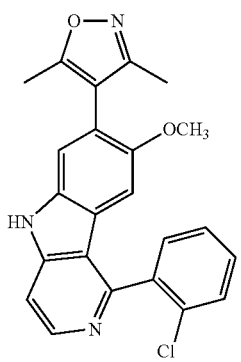

4-(1-(2-chlorophenyl)-8-methoxy-5H-pyrido[4,3-b]indol-7-yl)-3,5-dimethylisoxazole. $^1$HNMR (300 MHz, MeOD-d$_4$) δ 8.62 (d, 1H, J=6.9 Hz), 8.04 (d, 1H, J=6.6 Hz), 7.89 (m, 3H), 7.80 (m, 1H), 7.63 (s, 1H), 6.64 (s, 1H), 3.56 (s, 3H), 2.32 (s, 3H), 2.14 (s, 3H). ESIMS m/z [M+H]$^+$ calculated=404.87. found=404.92.

Cpd. No. 7

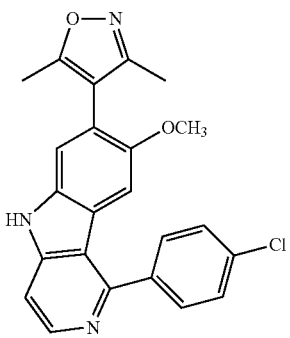

4-(1-(4-chlorophenyl)-8-methoxy-5H-pyrido[4,3-b]indol-7-yl)-3,5-dimethylisoxazole. $^1$HNMR (300 MHz, MeOD-d$_4$) δ 8.54 (d, 1H, J=6.9 Hz), 8.00 (d, 2H, J=8.7 Hz), 7.98 (d, 1H, J=6.6 Hz), 7.88 (d, 2H, J=8.7 Hz), 7.62 (s, 1H), 7.19 (s, 1H), 3.69 (s, 3H), 2.33 (s, 3H), 2.16 (s, 3H). ESIMS m/z [M+H]$^+$ calculated=404.87. found=405.33.

Cpd. No. 8

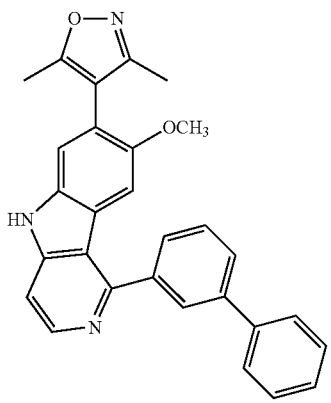

4-(1-([1,1'-biphenyl]-3-yl)-8-methoxy-5H-pyrido[4,3-b]indol-7-yl)-3,5-dimethylisoxazole. $^1$HNMR (300 MHz, MeOD-d$_4$) δ 8.56 (d, 1H, J=6.9 Hz), 8.29 (s, 1H), 8.15 (m, 1H), 7.98 (m, 3H), 7.81 (d, 2H, J=7.2 Hz), 7.62 (s, 1H), 7.50 (m, 3H), 7.26 (s, 1H), 3.50 (s, 3H), 2.32 (s, 3H), 2.14 (s, 3H). ESIMS m/z [M+H]$^+$ calculated=446.52. found=446.75.

Cpd. No. 9

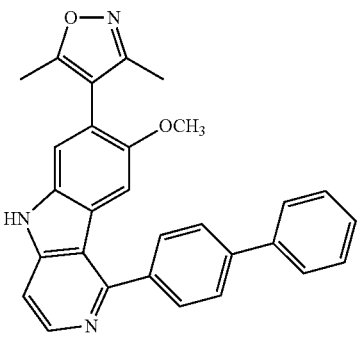

4-(1-([1,1'-biphenyl]-4-yl)-8-methoxy-5H-pyrido[4,3-b]indol-7-yl)-3,5-dimethylisoxazole. ¹HNMR (300 MHz, MeOD-d₄) δ 8.55 (d, 1H, J=6.9 Hz), 8.13 (d, 2H, J=8.7 Hz), 8.08 (d, 2H, J=8.4 Hz), 7.99 (d, 1H, J=6.6 Hz), 7.83 (dd, 2H, J₁=7.8 Hz, J₂=1.2 Hz), 7.63 (s, 1H), 7.48-7.59 (m, 3H), 7.31 (s, 1H), 3.66 (s, 3H), 2.34 (s, 3H), 2.16 (s, 3H). ESIMS m/z [M+H]⁺ calculated=446.52. found=446.92.

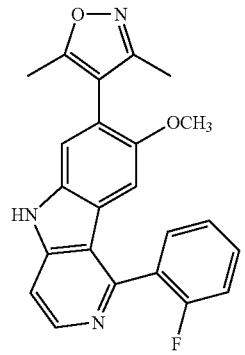

Cpd. No. 12

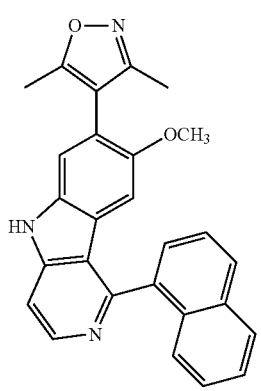

Cpd. No. 10

4-(8-methoxy-1-(naphthalen-1-yl)-5H-pyrido[4,3-b]indol-7-yl)-3,5-dimethylisoxazole. ¹HNMR (300 MHz, MeOD-d₄) δ 8.65 (d, 1H, J=6.9 Hz), 8.40 (d, 1H, J=8.1 Hz), 8.22 (d, 1H, J=8.4 Hz), 8.09 (d, 1H, J=6.9 Hz), 7.93 (m, 2H), 7.70 (m, 1H), 7.59 (s, 1H), 7.54 (m, 1H), 6.10 (s, 1H), 3.11 (s, 3H), 2.27 (s, 1H), 2.07 (s, 1H). ESIMS m/z [M+H]⁺ calculated=420.48. found=420.75.

4-(1-(2-fluorophenyl)-8-methoxy-5H-pyrido[4,3-b]indol-7-yl)-3,5-dimethylisoxazole. ¹HNMR (300 MHz, MeOD-d₄) δ 8.61 (d, 1H, J=6.6 Hz), 8.03 (d, 1H, J=6.9 Hz), 7.94 (m, 2H), 7.66 (m, 3H), 6.96 (s, 1H), 3.62 (s, 3H), 2.33 (s, 3H), 2.15 (s, 3H). ESIMS m/z [M+H]⁺ calculated=388.41. found=388.75.


Cpd. No. 13

4-(1-(3-fluorophenyl)-8-methoxy-5H-pyrido[4,3-b]indol-7-yl)-3,5-dimethylisoxazole. ¹HNMR (300 MHz, MeOD-d₄) δ 8.55 (d, 1H, J=6.9 Hz), 8.00 (d, 1H, J=6.9 Hz), 7.85 (m, 3H), 7.67 (m, 1H), 7.63 (s, 1H), 7.18 (s, 1H), 3.67 (s, 3H), 2.34 (s, 3H), 2.16 (s, 3H). ESIMS m/z [M+H]⁺ calculated=388.41. found=388.50.

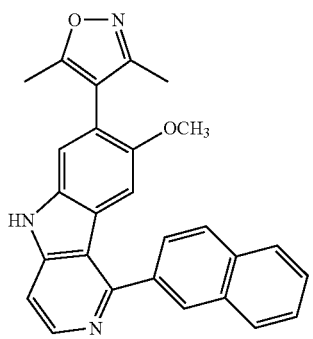

Cpd. No. 11

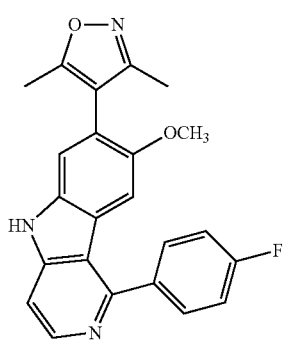

Cpd. No. 14

4-(8-methoxy-1-(naphthalen-2-yl)-5H-pyrido[4,3-b]indol-7-yl)-3,5-dimethylisoxazole. ¹HNMR (300 MHz, MeOD-d₄) δ 8.57 (d, 1H, J=6.9 Hz), 8.36 (d, 1H, J=8.4 Hz), 8.17 (dd, 2H, J=6.9 Hz, J₂=1.5 Hz), 8.04 (dd, 1H, J=8.4 Hz, J₂=1.8 Hz), 8.00 (d, 1H, J=6.6 Hz), 7.75 (m, 2H), 7.63 (s, 1H), 7.26 (s, 1H), 3.48 (s, 3H), 2.32 (s, 3H), 2.14 (s, 3H). ESIMS m/z [M+H]⁺ calculated=420.48. found=420.92.

4-(1-(4-fluorophenyl)-8-methoxy-5H-pyrido[4,3-b]indol-7-yl)-3,5-dimethylisoxazole. ¹HNMR (300 MHz, MeOD-d₄) δ 8.53 (d, 1H, J=6.9 Hz), 8.05 (m, 2H), 7.98 (d, 1H, J=6.6 Hz), 7.61 (m, 2H), 7.62 (s, 1H), 7.18 (s, 1H), 3.68 (s, 3H), 2.33 (s, 3H), 2.16 (s, 3H). ESIMS m/z [M+H]⁺ calculated=388.41. found=389.08.

Cpd. No. 15

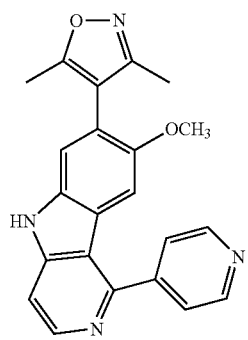

4-(8-methoxy-1-(pyridin-4-yl)-5H-pyrido[4,3-b]indol-7-yl)-3,5-dimethylisoxazole. $^1$HNMR (300 MHz, MeOD-d$_4$) δ 9.07 (d, 2H, J=5.7 Hz), 8.62 (d, 1H, J=6.9 Hz), 8.06 (m, 3H), 7.65 (s, 1H), 7.12 (s, 1H), 3.67 (s, 3H), 2.33 (s, 3H), 2.15 (s, 3H). ESIMS m/z [M+H]$^+$ calculated=371.41. found=372.25.

Cpd. No. 16

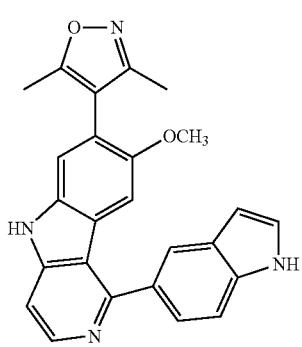

4-(1-(1H-indol-5-yl)-8-methoxy-5H-pyrido[4,3-b]indol-7-yl)-3,5-dimethylisoxazole. $^1$HNMR (300 MHz, MeOD-d$_4$) δ 8.47 (d, 1H, J=6.6 Hz), 8.25 (d, 1H, J=1.5 Hz), 7.91 (d, 1H, J=6.6 Hz), 7.84 (d, 1H, J=8.4 Hz), 7.70 (dd, 1H, J$_1$=8.4 Hz, J$_2$=1.8 Hz), 7.60 (s, 1H), 7.53 (d, 1H, J=3.0 Hz), 7.42 (s, 1H), 6.76 (d, 1H, J=3.3 Hz), 3.56 (s, 3H), 2.33 (s, 3H), 2.15 (s, 3H). ESIMS m/z [M+H]$^+$ calculated=409.46. found=409.67.

Cpd. No. 17

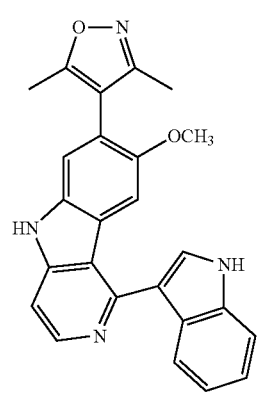

4-(1-(1H-indol-3-yl)-8-methoxy-5H-pyrido[4,3-b]indol-7-yl)-3,5-dimethylisoxazole. $^1$HNMR (300 MHz, MeOD-d$_4$) δ 8.46 (d, 1H, J=6.9 Hz), 8.13 (s, 1H), 7.89 (d, 1H, J=6.6 Hz), 7.72 (d, 1H, J=8.7 Hz), 7.59 (s, 1H), 7.40 (m, 2H), 7.25 (m, 1H), 7.01 (s, 1H), 3.30 (s, 3H), 2.33 (s, 3H), 2.14 (s, 3H). ESIMS m/z [M+H]$^+$ calculated=409.46. found=409.67.

Cpd. No. 18

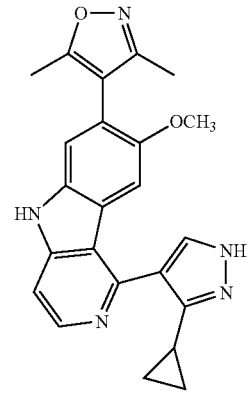

4-(1-(3-cyclopropyl-1H-pyrazol-4-yl)-8-methoxy-5H-pyrido[4,3-b]indol-7-yl)-3,5-dimethylisoxazole. $^1$HNMR (300 MHz, MeOD-d$_4$) δ 8.51 (d, 1H, J=6.9 Hz), 8.17 (s, 1H), 7.94 (d, 1H, J=6.9 Hz), 7.62 (s, 1H), 7.31 (s, 1H), 3.78 (s, 3H), 2.34 (s, 3H), 2.17 (s, 3H), 0.93 (m, 5H). ESIMS m/z [M+H]$^+$ calculated=400.45. found=400.67.

Cpd. No. 19

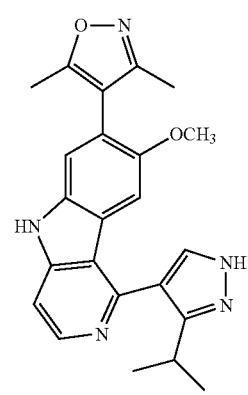

4-(1-(3-isopropyl-1H-pyrazol-4-yl)-8-methoxy-5H-pyrido[4,3-b]indol-7-yl)-3,5-dimethylisoxazole. $^1$HNMR (300 MHz, MeOD-d$_4$) δ 8.52 (d, 1H, J=6.6 Hz), 8.11 (s, 1H), 7.96 (d, 1H, J=6.9 Hz), 7.62 (s, 1H), 7.01 (s, 1H), 3.70 (s, 3H), 2.34 (s, 3H), 2.16 (s, 3H), 1.34-1.22 (m, 7H). ESIMS m/z [M+H]$^+$ calculated=402.47. found=402.92.

Cpd. No. 20

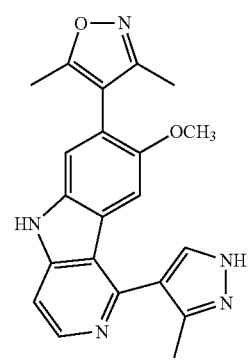

4-(8-methoxy-1-(3-methyl-1H-pyrazol-4-yl)-5H-pyrido[4,3-b]indol-7-yl)-3,5-dimethylisoxazole. ¹HNMR (300 MHz, MeOD-d₄) δ 8.50 (d, 1H, J=6.9 Hz), 8.22 (s, 1H), 7.93 (d, 1H, J=6.6 Hz), 7.62 (s, 1H), 7.23 (s, 1H), 3.76 (s, 3H), 2.40 (s, 3H), 2.34 (s, 3H), 2.17 (s, 3H). ESIMS m/z [M+H]⁺ calculated=374.42. found=374.25.

Cpd. No. 21

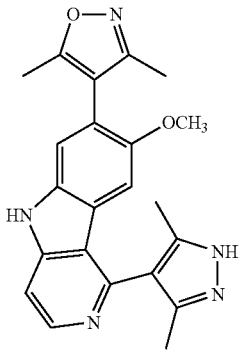

4-(1-(3,5-dimethyl-1H-pyrazol-4-yl)-8-methoxy-5H-pyrido[4,3-b]indol-7-yl)-3,5-dimethylisoxazole. ¹HNMR (300 MHz, MeOD-d₄) δ 8.54 (d, 1H, J=6.9 Hz), 7.95 (d, 1H, J=6.9 Hz), 7.63 (s, 1H), 7.02 (s, 1H), 3.74 (s, 3H), 2.34 (s, 3H), 2.29 (s, 6H), 2.16 (s, 3H). ESIMS m/z [M+H]⁺ calculated=388.44. found=388.42.

Cpd. No. 22

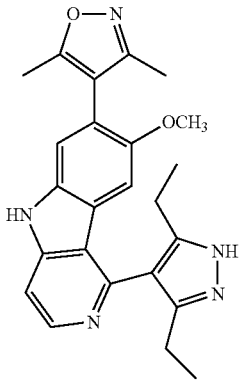

4-(1-(3,5-diethyl-1H-pyrazol-4-yl)-8-methoxy-5H-pyrido[4,3-b]indol-7-yl)-3,5-dimethylisoxazole. ¹HNMR (300 MHz, MeOD-d₄) δ 8.55 (d, 1H, J=6.9 Hz), 7.97 (d, 1H, J=6.9 Hz), 7.64 (s, 1H), 6.92 (s, 1H), 3.70 (s, 3H), 2.65 (m, 4H), 2.34 (s, 3H), 2.16 (s, 3H), 1.10 (t, 6H, J=7.5 Hz). ESIMS m/z [M+H]⁺ calculated=416.50. found=416.42.

Cpd. No. 23

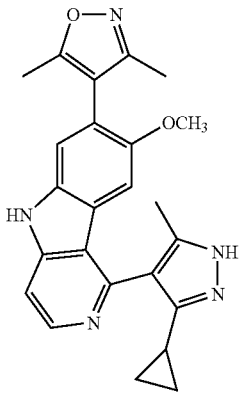

4-(1-(3-cyclopropyl-5-methyl-1H-pyrazol-4-yl)-8-methoxy-5H-pyrido[4,3-b]indol-7-yl)-3,5-dimethylisoxazole. ¹HNMR (300 MHz, MeOD-d₄) δ 8.55 (d, 1H, J=6.9 Hz), 7.96 (d, 1H, J=6.6 Hz), 7.63 (s, 1H), 7.12 (s, 1H), 3.76 (s, 3H), 2.35 (s, 3H), 2.28 (s, 3H), 2.17 (s, 3H), 1.73 (m, 1H), 0.87 (m, 4H). ESIMS m/z [M+H]⁺ calculated=414.48. found=414.50.

Cpd. No. 24

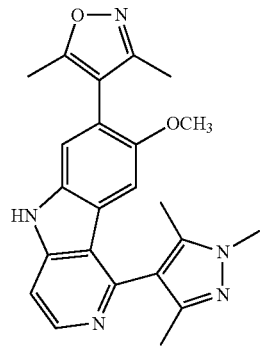

4-(8-methoxy-1-(1,3,5-trimethyl-1H-pyrazol-4-yl)-5H-pyrido[4,3-b]indol-7-yl)-3,5-dimethylisoxazole. ¹HNMR (300 MHz, MeOD-d₄) δ 8.54 (d, 1H, J=6.9 Hz), 7.95 (d, 1H, J=6.9 Hz), 7.63 (s, 1H), 7.04 (s, 1H), 3.97 (s, 3H), 3.75 (s, 3H), 2.34 (s, 3H), 2.32 (s, 3H), 2.21 (s, 3H), 2.16 (s, 3H). ESIMS m/z [M+H]⁺ calculated=402.47. found=402.75.

Cpd. No. 25

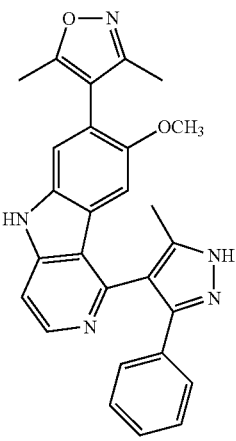

4-(8-methoxy-1-(5-methyl-3-phenyl-1H-pyrazol-4-yl)-5H-pyrido[4,3-b]indol-7-yl)-3,5-dimethylisoxazole. ¹HNMR (300 MHz, MeOD-d₄) δ 8.54 (d, 1H, J=6.9 Hz), 7.98 (d, 1H, J=6.9 Hz), 7.57 (s, 1H), 7.34 (m, 2H), 7.25 (m, 3H), 6.98 (s, 1H), 3.70 (s, 3H), 2.33 (s, 3H), 2.30 (s, 3H), 2.12 (s, 3H). ESIMS m/z [M+H]⁺ calculated=450.51. found=450.75.

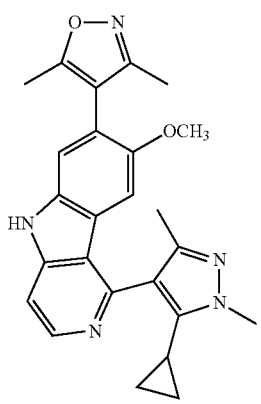

Cpd. No. 26

4-(1-(5-Cyclopropyl-1,3-dimethyl-1H-pyrazol-4-yl)-8-methoxy-5H-pyrido[4,3-b]indol-7-yl)-3,5-dimethylisoxazole. $^1$HNMR (300 MHz, MeOD-d$_4$) δ 8.56 (d, 1H, J=6.9 Hz), 7.97 (d, 1H, J=6.9 Hz), 7.64 (s, 1H), 6.98 (s, 1H), 4.08 (s, 3H), 3.74 (s, 3H), 2.34 (s, 3H), 2.17 (s, 3H), 2.16 (s, 3H), 1.99 (m, 1H), 0.83 (m, 2H), 0.38 (m, 1H), 0.14 (m, 1H). ESIMS m/z [M+H]$^+$ calculated=428.51. found=428.42.

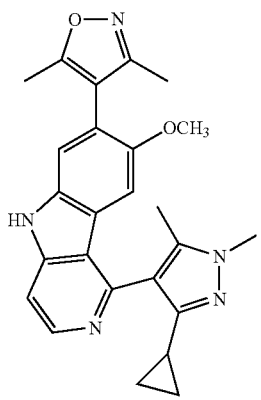

Cpd. No. 27

4-(1-(3-Cyclopropyl-1,5-dimethyl-1H-pyrazol-4-yl)-8-methoxy-5H-pyrido[4,3-b]indol-7-yl)-3,5-dimethylisoxazole. $^1$HNMR (300 MHz, MeOD-d$_4$) δ 8.55 (d, 1H, J=6.6 Hz), 7.95 (d, 1H, J=6.9 Hz), 7.63 (s, 1H), 7.20 (s, 1H), 3.93 (s, 3H), 3.78 (s, 3H), 2.35 (s, 3H), 2.30 (s, 3H), 2.17 (s, 3H), 1.63 (m, 1H), 0.97 (m, 1H), 0.85 (m, 3H). ESIMS m/z [M+H]$^+$ calculated=428.51. found=428.58.

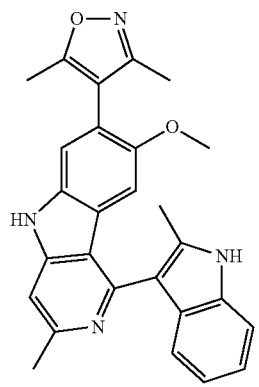

Cpd. No. 28

4-(8-Methoxy-3-methyl-1-(2-methyl-1H-indol-3-yl)-5H-pyrido[4,3-b]indol-7-yl)-3,5-dimethylisoxazole. $^1$HNMR (300 MHz, MeOD-d$_4$) δ 7.69 (s, 1H), 7.58 (d, 1H, J=8.4 Hz), 7.52 (s, 1H), 7.26-7.32 (m, 1H), 7.11-7.19 (m, 2H), 6.69 (s, 1H), 3.23 (s, 3H), 2.88 (s, 3H), 2.59 (s, 3H), 2.31 (s, 3H), 2.12 (s, 3H). ESIMS m/z [M+H]$^+$ calcd.=437.51. found=437.58.

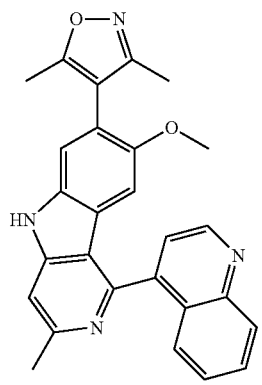

Cpd. No. 29

4-(8-Methoxy-3-methyl-1-(quinolin-4-yl)-5H-pyrido[4,3-b]indol-7-yl)-3,5-dimethylisoxazole. $^1$HNMR (300 MHz, MeOD-d$_4$) δ 9.31 (d, 1H, J=4.2 Hz), 8.39 (d, 1H, J=8.4 Hz), 8.04 (d, 1H, J=4.5 Hz), 7.98-8.02 (m, 1H), 7.94 (d, 1H, J=0.6 Hz), 7.69 (d, 2H, J=3.6 Hz), 7.57 (s, 1H), 6.05 (s, 1H), 3.14 (s, 3H), 2.95 (d, 1H, J=0.3 Hz), 2.26 (s, 3H), 2.07 (s, 3H). ESIMS m/z [M+H]$^+$ calcd.=435.50. found=435.67.

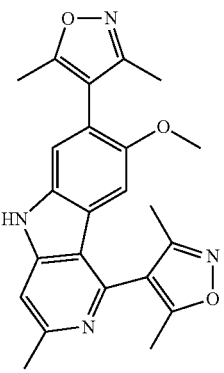

Cpd. No. 30

4,4'-(8-Methoxy-3-methyl-5H-pyrido[4,3-b]indole-1,7-diyl)bis(3,5-dimethylisoxazole). $^1$HNMR (300 MHz, MeOD-d$_4$) δ 7.81 (d, 1H, J=0.6 Hz), 7.60 (s, 1H), 6.96 (s, 1H), 3.77 (s, 3H), 2.89 (s, 3H), 2.52 (s, 3H), 2.34 (s, 3H), 2.81 (s, 3H), 2.16 (s, 3H). ESIMS m/z [M+H]$^+$ calcd.=403.45. found=403.67.

4. Synthesis of Final Compounds from the Other Intermediates.
4.1 Synthesis of Demethoxylated Compounds:

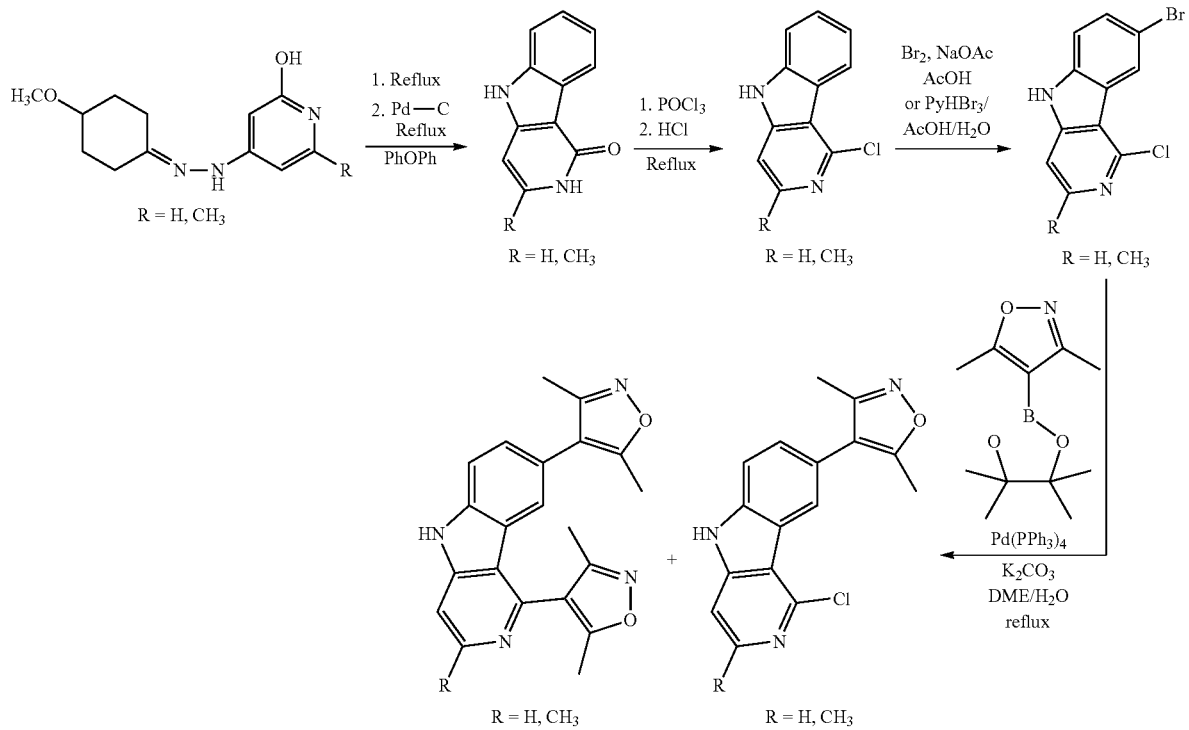

Synthetic methods are same to the reactions and conditions used in the synthesis of RX3.

RX6

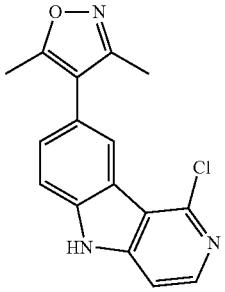

4-(1-Chloro-5H-pyrido[4,3-b]indol-8-yl)-3,5-dimethylisoxazole. ¹HNMR (300 MHz, MeOD-d₄) δ 8.40 (d, 1H, J=0.9 Hz), 8.31 (d, 1H, J=6.0 Hz), 7.77 (d, 1H, J=8.4 Hz), 7.62 (m, 2H), 2.49 (s, 1H), 2.33 (s, 1H). ESIMS m/z [M+H]⁺ calcd.=298.75. found=298.58.

Cpd. No. 31

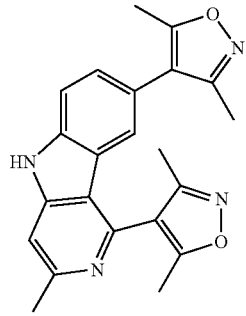

4,4'-(3-Methyl-5H-pyrido[4,3-b]indole-1,8-diyl)bis(3,5-dimethylisoxazole). ¹HNMR (300 MHz, MeOD-d₄) δ 7.87-7.89 (M, 2H), 7.71 (dd, 1H, J₁=8.4 Hz, J₂=1.5 Hz), 7.28 (d, 1H, J=0.6 Hz), 2.90 (s, 3H), 2.47 (s, 3H), 2.41 (s, 3H), 2.24 (s, 3H), 2.22 (s, 3H). ESIMS m/z [M+H]⁺ calcd.=373.43. found=373.67.

RX106

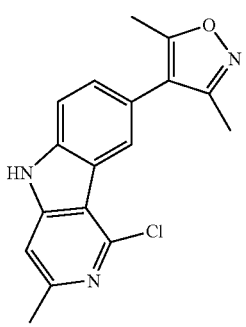

4-(1-Chloro-3-methyl-5H-pyrido[4,3-b]indol-8-yl)-3,5-dimethylisoxazole. ¹HNMR (300 MHz, MeOD-d₄) δ 8.34 (d, 1H, J=0.6 Hz), 7.75 (d, 1H, J=7.8 Hz), 7.60 (dd, 1H, J₁=5.4 Hz, J₂=1.8 Hz), 7.51 (s, 1H), 2.72 (s, 3H), 2.48 (s, 3H), 2.32 (s, 3H). ESIMS m/z [M+H]⁺ calcd.=312.77. found=313.17.

4.2 Synthesis of Final Compounds with 3,5-Dimethylisoxazole at a Different Position.

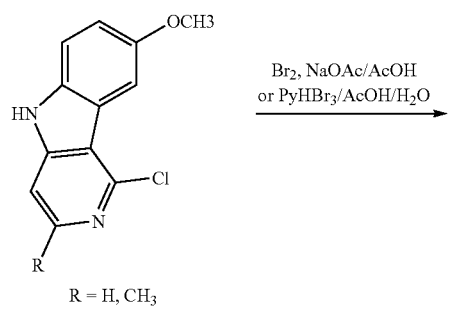

R = H, CH₃

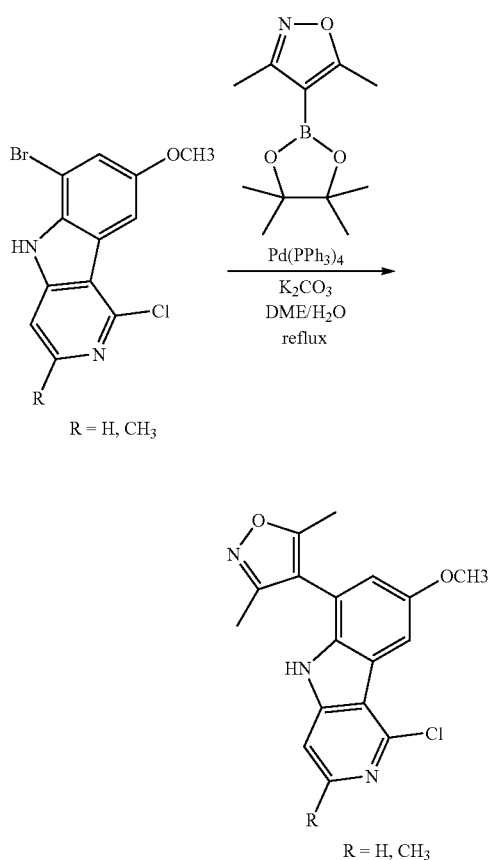

R = H, CH₃

Synthetic methods are same to the reactions and conditions used in the synthesis of RX3.

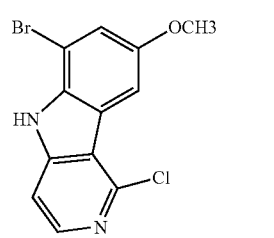

6-bromo-1-chloro-8-methoxy-5H-pyrido[4,3-b]indole. ¹HNMR (300 MHz, MeOD-$d_4$) δ 8.25 (d, J=6.0 Hz, 1H), 7.91 (d, J=2.4 Hz, 1H), 7.58 (d, J=6.0 Hz, 1H), 7.45 (d, J=2.1 Hz, 1H), 3.94 (s, 3H).

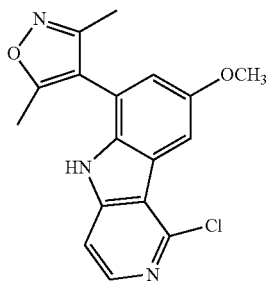

RX8

4-(8-methoxy-5H-pyrido[4,3-b]indol-6-yl)-3,5-dimethyl-isoxazole. ¹HNMR (300 MHz, MeOD-$d_4$) δ MR (300 MHz, J=6.0 Hz), 8.04 (d, 1H, J=2.4 Hz), 7.49 (d, 1H, J=6.0 Hz), 7.16 (d, 1H, J=2.4 Hz), 3.98 (s, 3H), 2.36 (s, 3H), 2.20 (s, 3H). ESIMS m/z [M+H]-calcd.=328.77. found=328.75.

4.3 Synthesis of Final Compounds Bearing Moieties in Addition to 3,5-dimethylisoxazole.

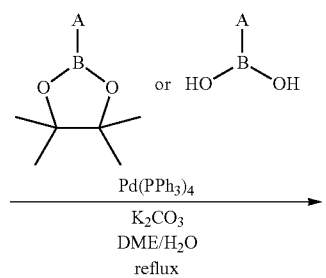

R = H, CH₃

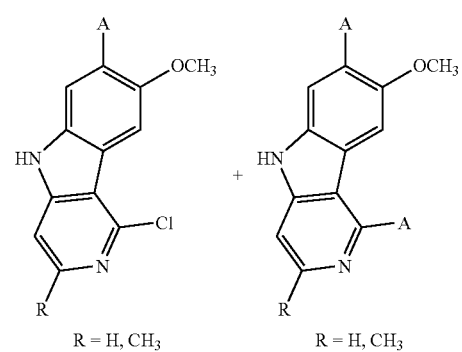

R = H, CH₃     R = H, CH₃

Synthesis is same to the above-disclosed general Suzuki Coupling method.

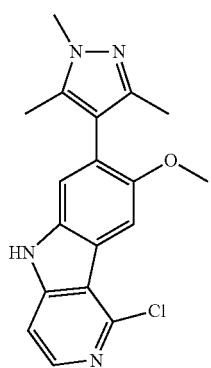

1-chloro-8-methoxy-7-(1,3,5-trimethyl-1H-pyrazol-4-yl)-5H-pyrido[4,3-b]indole. ¹HNMR (300 MHz, MeOD-d₄) δ 8.26 (d, 1H, J=6.0 Hz), 8.07 (s, 1H), 7.61 (d, 1H, J=6.3 Hz), 7.45 (s, 1H), 3.95 (s, 3H), 3.88 (s, 3H), 2.24 (s, 3H), 2.20 (s, 3H). ESIMS m/z [M+H]⁺ calcd.=341.81. found=342.33.

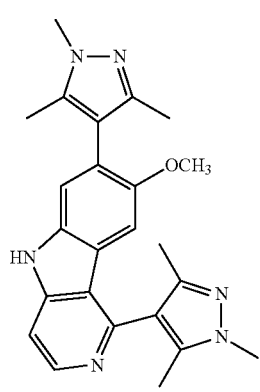

8-methoxy-1,7-bis(1,3,5-trimethyl-1H-pyrazol-4-yl)-5H-pyrido[4,3-b]indole. ¹HNMR (300 MHz, MeOD-d₄) δ 8.53 (d, 1H, J=6.6 Hz), 7.93 (d, 1H, J=6.6 Hz), 7.55 (s, 1H), 7.01 (s, 1H), 3.97 (s, 3H), 3.83 (s, 3H), 3.72 (s, 3H), 2.32 (s, 3H), 2.21 (s, 3H), 2.19 (s, 3H), 2.14 (s, 3H). ESIMS m/z [M+H]⁺ calcd.=415.51. found=415.58.

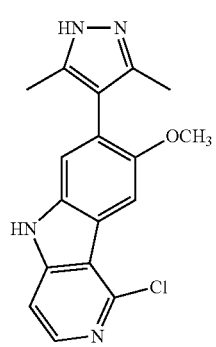

1-chloro-7-(3,5-dimethyl-1H-pyrazol-4-yl)-8-methoxy-5H-pyrido[4,3-b]indole. ¹HNMR (300 MHz, MeOD-d₄) δ 8.24 (d, 1H, J=6.0 Hz), 8.10 (s, 1H), 7.56 (d, 1H, J=6.0 Hz), 7.49 (s, 1H), 3.97 (s, 3H), 2.31 (s, 3H), 2.17 (s, 3H). ESIMS m/z [M+H]⁺ calcd.=327.79. found=327.92.

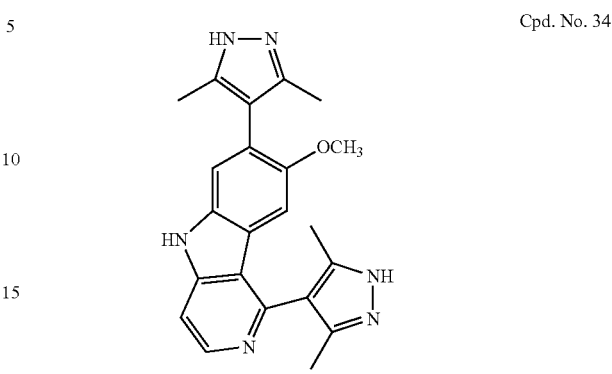

1,7-bis(3,5-dimethyl-1H-pyrazol-4-yl)-8-methoxy-5H-pyrido[4,3-b]indole. ¹HNMR (300 MHz, MeOD-d₄) δ 8.55 (d, 1H, J=6.6 Hz), 7.96 (d, 1H, J=6.9 Hz), 7.66 (s, 1H), 7.03 (s, 1H), 6.32 (s, 1H), 3.73 (s, 3H), 2.40-2.29 (m, 12H). ESIMS m/z [M+H]⁺ calcd.=387.46. found=387.50.

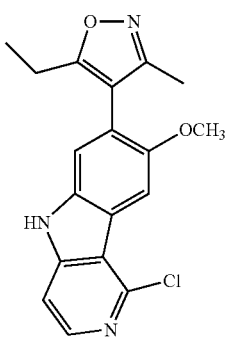

4-(1-chloro-8-methoxy-5H-pyrido[4,3-b]indol-7-yl)-5-ethyl-3-methylisoxazole. ¹HNMR (300 MHz, MeOD-d₄) δ 8.19 (d, 1H, J=5.7 Hz), 8.08 (s, 1H), 7.49 (d, 1H, J=5.7 Hz), 7.43 (s, 1H), 3.96 (s, 3H), 2.64 (q, 2H, J=7.5 Hz), 2.34 (s, 3H), 1.12 (t, 3H, J=7.5 Hz). ESIMS m/z [M+H]⁺ calcd.=342.80. found=342.67.

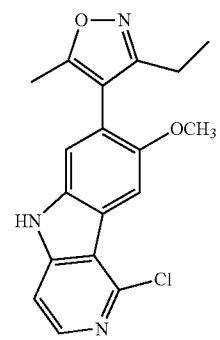

4-(1-chloro-8-methoxy-5H-pyrido[4,3-b]indol-7-yl)-3-ethyl-5-methylisoxazole. ¹HNMR (300 MHz, MeOD-d₄) δ 8.27 (d, 1H, J=6.3 Hz), 8.02 (s, 1H), 7.64 (d, 1H, J=6.3 Hz), 7.48 (s, 1H), 3.93 (s, 3H), 2.70 (q, 2H, J=7.5 Hz), 2.13 (s, 3H), 1.20 (t, 3H, J=7.5 Hz). ESIMS m/z [M+H]$^+$ calcd.=342.80. found=342.42.

5. Synthesis of General Intermediate Containing 9H-pyrimido[4,5-b]indole Core

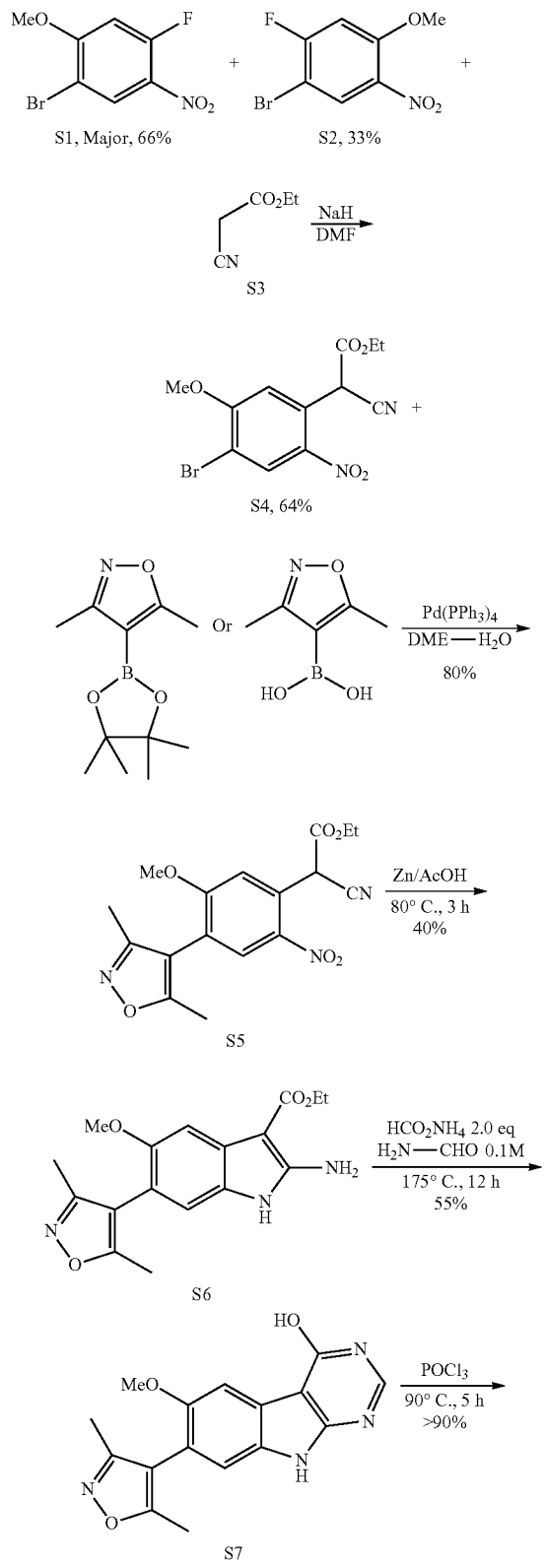

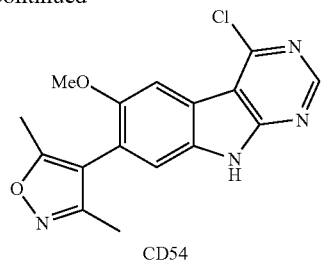

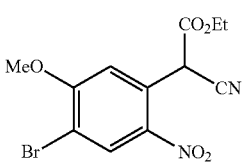

S3 (2.26 g, 20 mmol) was dissolved in anhydrous DMF (50 mL) and the solution was cooled to 0° C. NaH (1.2 g, 60% in mineral oil, 30 mmol) was added in small portions. The resulting reaction mixture was stirred for 0.5 h at 0° C. and an anhydrous DMF solution of known compounds S1 and S2 (20 mmol, ref. 2012, J. Med. Chem. 55, 449-464) was added. The resulting solution was stirred at 0° C. for 3 h before quenching with 1 N HCl. The aqueous layer was extracted with ethyl acetate and combined organic layers were washed with brine and dried over anhydrous Na$_2$SO$_4$. The volatile components were removed on a rotary evaporator and the residue was purified by flash column chromatogram. The desired product S4 was isolated as colorless oil with impurity of the other regioisomer (4.17 g, 64% yield). $^1$H NMR (300 MHz, CDCl$_3$): 8.41 (s, 1H), 7.11 (s, 1H), 5.60 (s, 1H), 4.24 (q, J=7.03 Hz, 2H), 4.01 (s, 3H), 1.25 (t, J=7.14 Hz, 3H).

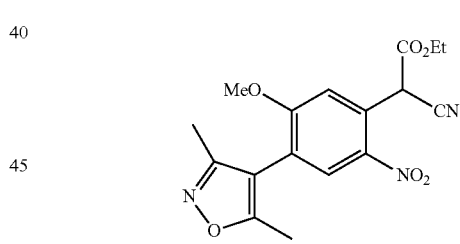

S4 (1.43 g, 4.2 mmol), 3,5-dimethyl-4-(4,4,5,5-tetramethyl-1,3,2-dioxaborolan-2-yl)isoxazole (2.34 g, 10.5 mmol), and K$_2$CO$_3$ (2.03 g, 14.7 mmol) were added to a round-bottom flask. DME (30 mL) and water (15 mL) were added at room temperature. The solution was degassed, then Pd(PPh$_3$)$_4$ (242 mg, 0.21 mmol) was added in one portion. The solution was again degassed, then heated at reflux for 14 h. The aqueous layer was extracted with ethyl acetate, the combined organic layers were washed with brine, then dried over anhydrous Na$_2$SO$_4$. The volatile components were removed on a rotary evaporator and the residue was purified by flash column chromatogram. The desired product S5 was isolated in >80% yield (1.47 g, contaminated with isomers and pinacol components). $^1$H NMR (CDCl$_3$, 300 MHz): 8.10 (s, 1H), 7.27 (s, 1H), 5.78 (s, 1H), 4.35 (q, J=7.12 Hz, 2H), 3.99 (s, 3H), 2.33 (s, 3H), 2.18 (s, 3H), 1.37 (t, J=7.14 Hz, 3H).

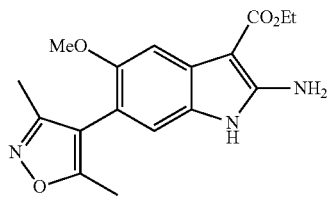

S6

To an AcOH (30 mL) solution of S5 (1.47 g) at 80° C., 0.8 g Zn powder was added in small portions. The mixture was stirred at 80° C. for 1 h, another 0.8 g Zn powder was added, and the reaction was kept at the same temperature for 2 h. The reaction was cooled, filtered, and washed with AcOH. The AcOH solution was combined and the volatile components were removed on a rotary evaporator. Purification by flash column chromatogram furnished the desired product S6 (0.55 g, ca, 40% yield). $^1$H NMR (CDCl$_3$, 300 MHz): 8.01 (br, s, 1H), 7.44 (s, 1H), 6.78 (s, 1H), 5.73 (br, s, 2H), 4.40 (q, J=7.08 Hz, 2H), 3.82 (s, 3H), 2.29 (s, 3H), 2.15 (s, 3H), 1.45 (t, J=7.08 Hz, 3H). ESI-MS calculated for C$_{17}$H$_{20}$N$_3$O$_4$ [M+H]$^+$: 330.15, Obtained: 330.25.

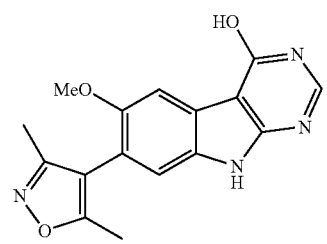

S7

S6 (0.45 g, 1.4 mmol), ammonium formate (1.06 g, 17 mmol), and formamide (16 mL) were heated at 175° C. for 12 h. The reaction was cooled to room temperature and water was added. Filtration of the mixture yielded S7 as a brown solid (0.24 g, 0.77 mmol, 55% yield). $^1$H NMR (DMSO-d6, 300 MHz): 8.09 (s, 1H), 7.57 (s, 1H), 7.24 (s, 1H), 3.81 (s, 3H), 3.30 (s, 1H), 2.62 (s, 3H), 2.06 (s, 3H), ESI-MS calculated for C$_{16}$H$_{15}$N$_4$O$_3$ [M+H]$^+$: 311.11, Obtained: 311.75.

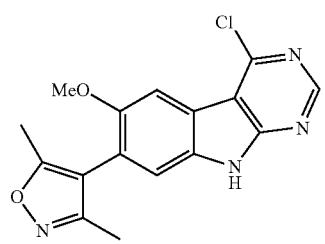

CD54

S7 (0.24 g, 0.77 mmol) was dissolved in POCl$_3$ (10 mL) and the mixture was heated at 90° C. for 5 h. The mixture was cooled to room temperature and the volatile components were removed on a rotary evaporator. Ethyl acetate (20 mL) was added at 0° C., followed by NaHCO$_3$ (20 mL) and water (20 mL). The mixture was filtered and the desired CD54 product was collected as a brown solid (0.17 g). The aqueous layer was extracted with ethyl acetate and the combined organic layers were washed with brine and dried over anhydrous Na$_2$SO$_4$. The volatile components were removed on a rotary evaporator affording a brown solid (80 mg, 90 purity of CD54). $^1$H NMR (DMSO-d6, 300 MHz): 8.74 (s, 1H), 7.84 (s, 1H), 7.45 (s, 1H), 3.89 (s, 3H), 3.31 (br, s, 1H), 2.29 (s, 3H), 2.09 (s, 3H) $^{13}$C NMR (DMSO-d6, 75 MHz): 167.84, 161.17. 155.84, 122.24, 120.26, 116.96, 115.15, 113.11, 105.80, 57.84, 13.36, 12.39 ESI-MS calculated for C$_{16}$H$_{14}$$^{35}$ClN$_4$O$_2$ [M+H]$^+$: 329.08, Obtained: 329.67.

Alternatively, S5 was also synthesized through a route showing below:

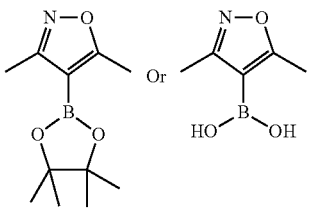

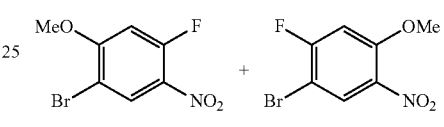

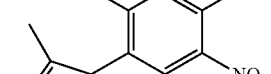

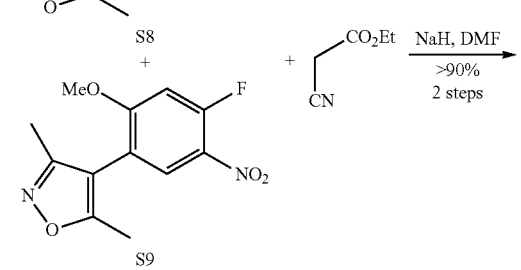

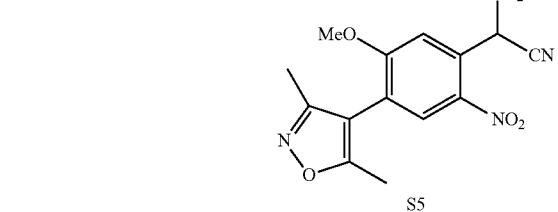

S5

A mixture of known compounds S1 and S2 (ref. 2012, J. Med. Chem. 55, 449-464) (3.0 g, 12 mmol), 3,5-dimethyl-4-(4,4,5,5-tetramethyl-1,3,2-dioxaborolan-2-yl)isoxazole (5.35 g, 24 mmol), and K$_2$CO$_3$ (5.0 g, 36 mmol) were added to a round-bottom flask. DME (50 mL) and water (30 mL) were added at room temperature. The solution was degassed before Pd(PPh$_3$)$_4$(700 mg, 0.6 mmol) was added in one portion. The solution was again degassed and then was heated at reflux for 14 h. The aqueous layer was extracted with ethyl acetate and combined organic layers were washed with brine and dried over anhydrous Na$_2$SO$_4$. The volatile components were removed on a rotary evaporator and the residue was purified by flash column chromatogram. The desired product S8 and S9 were isolated as a mixture in >80% yield (3.38 g). The major isomer is compound S9, $^1$H NMR (CDCl$_3$, 300 MHz): 8.03 (d, J=8.47 Hz, 1H), 6.93 (d, J=12.56 Hz, 1H), 4.00 (s, 3H), 2.40 (s, 3H), 2.24 (s, 3H).

S5 was synthesized by substitution of fluorine atom of S9 with ethyl 2-cyanoacetate using NaH as a base and DMF as solvent. The same reaction conditions to synthesize S5 from S4 was followed (>80% isolated yield).

6. General Methods for Syntheses of Pinacol Boronates

The syntheses of pinacol boronates using n-butyl lithium via a transmetalation intermediate is reported in the literature. The procedures reported in following publications were adopted: *Synthesis*, 2005, 20, 3581-3588, *Synlett*, 2006, 12, 1948-1952, and *J. Am. Chem. Soc,* 2011, 133, 15800-15802.

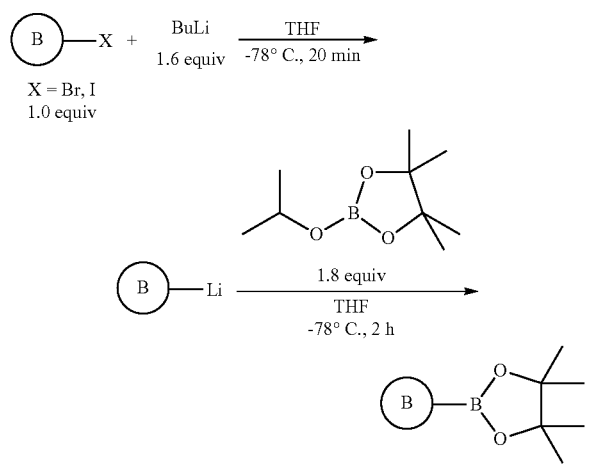

Four examples are illustrated below:

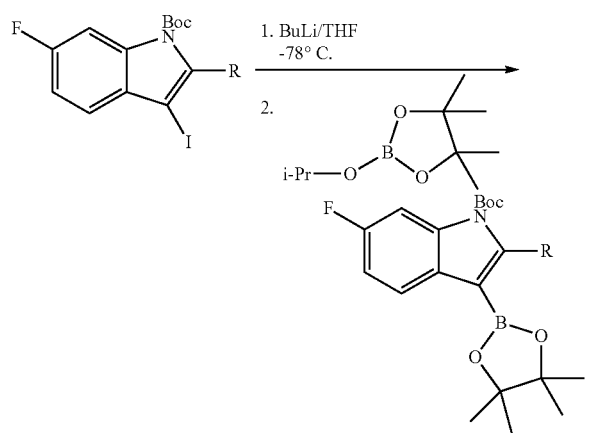

Synthesis of tert-butyl 6-fluoro-3-(4,4,5,5-tetramethyl-1,3,2-dioxaborolan-2-yl)-1H-indole-1-carboxylate (R=H). tert-Butyl 6-fluoro-3-iodo-1H-indole-1-carboxylate (541 mg, 1.5 mmol) was dissolved in anhydrous THF at −78° C. BuLi (2.5 M THF solution, 1.0 mL, 2.55 mmol) was added via a syringe and the reaction was stirred for 20 min. 2-Isopropoxy-4,4,5,5-tetramethyl-1,3,2-dioxaborolane (558 mg, 3.0 mmol) was added via a syringe at −78° C. and the reaction was stirred for 2 h before quenching with saturated aqueous NH$_4$Cl solution. The aqueous layer was extracted with ethyl acetate and the combined organic layers were washed with brine and dried over anhydrous Na$_2$SO$_4$. The volatile components were removed on a rotary evaporator the residue was purified by flash column chromatography (0.35 g, 67% yield). $^1$H NMR (CDCl$_3$, 300 MHz): 8.09 (dd, J=8.96, 4.66 Hz, 1H), 8.02 (s, 1H), 7.64 (dd, J=9.20, 2.57 Hz, 1H), 7.02 (dt, J=9.10, 2.60 Hz, 1H), 1.65 (s, 9H), 1.37 (s, 12H).

tert-Butyl 6-fluoro-2-methyl-3-(4,4,5,5-tetramethyl-1,3,2-dioxaborolan-2-yl)-1H-indole-1-carbo-xylate (R=Me, 82% yield)$^1$H NMR (CDCl$_3$, 300 MHz): 7.87 (dd, J=8.60, 5.84 Hz, 1H), 7.77 (dd, J=10.98, 2.41 Hz, 1H), 6.95 (dt, J=9.11, 2.42 Hz, 1H), 2.80 (s, 3H), 1.68 (s, 9H), 1.36 (s, 12H).

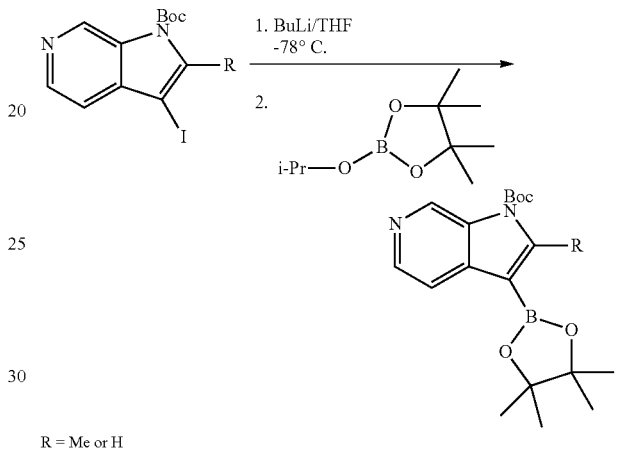

tert-butyl 3-(4,4,5,5-tetramethyl-1,3,2-dioxaborolan-2-yl)-1H-pyrrolo[2,3-c]pyridine-1-carboxylate (R=H, 57% yield). $^1$H NMR (CDCl$_3$, 300 MHz): 9.31 (s, 1H), 8.33 (d, J=5.34 Hz, 1H), 8.06 (s, 1H), 7.82 (dd, J=5.34, 0.97 Hz, 1H), 1.61 (s, 9H), 1.29 (s, 12H)

tert-Butyl 2-methyl-3-(4,4,5,5-tetramethyl-1,3,2-dioxaborolan-2-yl)-1H-pyrrolo[2,3-c]pyridine-1-carboxylate (R=Me, 89% yield). $^1$H NMR (CDCl$_3$, 300 MHz): 9.25 (d, J=0.99 Hz, 1H), 8.36 (d, J=5.26 Hz, 1H), 7.86 (dd, J=5.26, 0.99 Hz, 1H), 2.88 (s, 3H), 1.71 (s, 9H), 1.38 (s, 12H).

In some cases, boronic acid and/or its pinacol esters were synthesized through a transmetalation reaction promoted by i-PrMgCl and LiCl complex (Boymond, L. et. al. Angew. Chem. Int. Ed. 1998, 37, No. 12, 1701-1703 and Hawkins, V. et. al. Organic Process Research & Development 2008, 12, 1265-1268) following by adding the Grignard reagents into isopropyl pinacol borate or triisopropyl borate. For example, boronic acid pinacol ester CD164 was obtained through a synthetic route showing below. Carboxylic acid CD157 was synthesized following a previously reported method (Banno, H. et. al. WO 2010/090716 A1). Acid CD157 was converted into CD164 in two steps reaction following a previously reported method (Bethel, P. A. et. al. 2012, Tetrahedron, 68, 5434-5444).

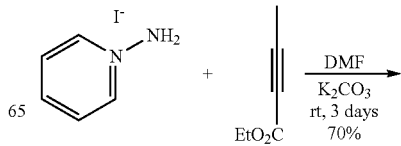

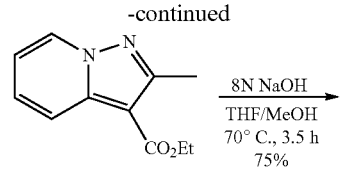

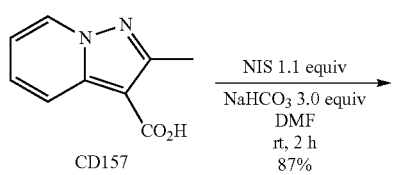

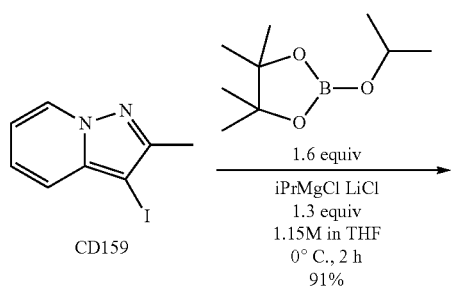

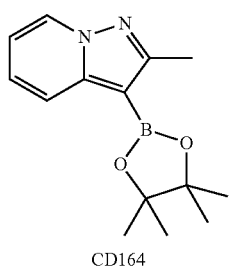

CD157, ¹H NMR (DMSO-d6, 300 MHz): 12.32 (br, CO₂H), 8.70 (d, J=6.91 Hz, 1H), 7.98 (d, J=8.85 Hz, 1H), 7.54-7.44 (m, 1H), 7.06-6.98 (m, 1H), 2.54 (s, 3H).

CD164, ¹H NMR (CDCl₃, 300 MHz): 8.39 (d, J=6.92 Hz, 1H), 8.84 (d, J=7.87 Hz, 1H), 7.15 (ddd, J=8.83, 6.77, 1.13 Hz, 1H), 6.72 (td, J=6.84, 1.39 Hz, 1H), 2.60 (s, 3H), 1.34 (s, 12H).

In some embodiments, the pinacol boronates prepared using this method were not sufficiently stable for flash column chromatography, and were used directly for next coupling step without further purification.

The syntheses of pinacol boronates can also been achieved via direct coupling of aryl halide and bis(pinacolato)diboron. The procedures reported in following literatures were adopted: *J. Org. Chem.* 1995, 7508-7510 and *Angew. Chem. Int. Ed.* 2007, 46, 5359-5363.

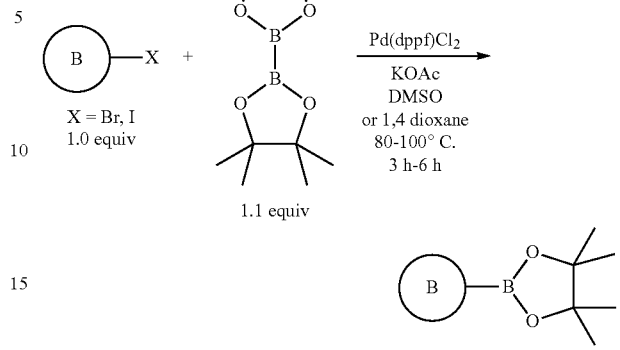

Three examples are illustrated as below:

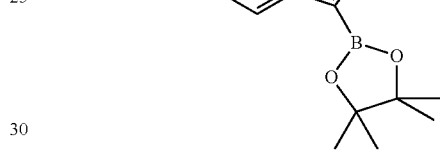

tert-Butyl 3-iodo-2-methyl-1H-indole-1-carboxylate (1.0 g 4.0 mmol) and bis(pinacolato)diboron were dissolved in dioxane. Et₃N was added via a syringe followed by Pd(dppf)Cl₂. The reaction mixture was refluxed for 3 h. The volatile components were removed on a rotary evaporator the residue was dissolved in ether. The mixture was filtered and ether solution was collected. The volatile components were removed on a rotary evaporator, and the residue was purified by flash column chromatography. tert-Butyl 2-methyl-3-(4,4,5,5-tetramethyl-1,3,2-dioxaborolan-2-yl)-1H-indole-1-carboxylate (>50% yield) was isolated with tert-butyl 2-methyl-1H-indole-1-carboxylate as impurity. Using the BuLi method, the desired product was isolated in 67% yield (>90% purity). ¹H NMR (CDCl₃, 300 MHz): 8.20-8.13 (m, 1H), 8.13-8.07 (m, 1H), 8.35-7.28 (m, 2H), 2.97 (s, 3H), 1.76 (s, 9H), 1.44 (s, 12H).

The synthesis method for tert-butyl 2-methyl-3-(4,4,5,5-tetramethyl-1,3,2-dioxaborolan-2-yl)-1H-indole-1-carboxylate is same as that for tert-Butyl 2-methyl-3-(4,4,5,5-tetramethyl-1,3,2-dioxaborolan-2-yl)-1H-indole-1-carboxylate. The yield was >50% yield. ¹H NMR (CDCl₃, 300 MHz): 7.90-7.80 (m, 1H), 7.45-7.35 (m, 1H), 7.25-7.10 (m, 2H), 2.66 (s, 3H), 1.38 (s, 9H).

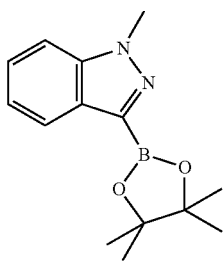

CD143

The synthesis method for CD143 is same as that for tert-Butyl 2-methyl-3-(4,4,5,5-tetramethyl-1,3,2-dioxaborolan-2-yl)-1H-indole-1-carboxylate. The isolated yield is 95% yield. $^1$H NMR (CDCl$_3$, 300 MHz): 8.49 (d, J=8.49 Hz, 1H), 7.50-7.38 (m, 2H), 7.28-7.18 (m, 1H), 4.17 (s, 3H), 1.25 (s, 12H).

7. Synthesis of Compounds from CD54

All final products were purified by reverse phase HPLC and the products were in the form of CF$_3$CO$_2$H salt (trifluoroacetic acid salt or TFA salt). In most cases, the counter anion was not shown in the showing structures, unless otherwise stated.

Some final products were synthesized via a Suzuki coupling as shown in scheme below. Suzuki coupling used CD54 as the aryl halide substrate, and commercially available or in-house made boronic acids or pinacol boronates used as the coupling partners. The reaction yields varied from 70% to 10%. Some pinacol boronates were also synthesized using general methods shown in previous schemes. One example of the Suzuki coupling procedure is illustrated in the synthesis of Cpd. No. 35.

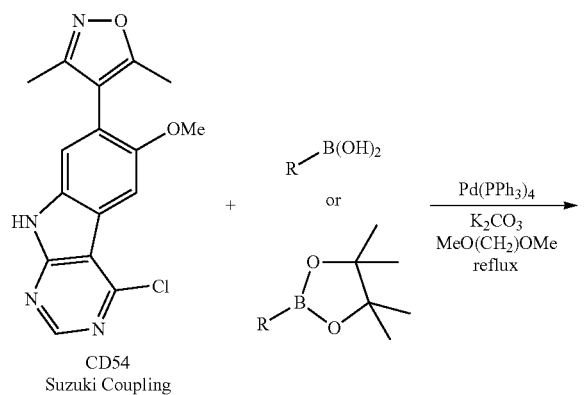

CD54
Suzuki Coupling

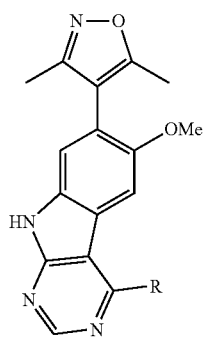

Method A: CD54 (33 mg, 0.1 mmol), 3,5-dimethyl-4-(4,4,5,5-tetramethyl-1,3,2-dioxaborolan-2-yl)isoxazole (66 mg, 0.3 mmol), and K$_2$CO$_3$ (70 mg, 0.5 mmol) were added to a round-bottom flask. DME (6 mL) and water (4 mL) were added at room temperature. The solution was degassed, then Pd(PPh$_3$)$_4$(10-15 mg, 0.008-0.012 mmol) was added in one portion. The solution was degassed again, then heated at reflux for 14 h. The aqueous layer was extracted with ethyl acetate and combined organic layers were washed with brine and dried over anhydrous Na$_2$SO$_4$. The volatile components were removed on a rotary evaporator and the residue was purified by reverse phase HPLC. The desired product Cpd. No. 35 TFA salt was isolated as a colorless solid (16 mg, 41%).

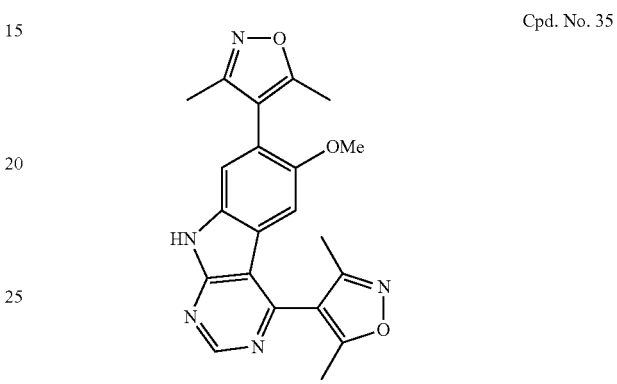

Cpd. No. 35

$^1$H NMR (MeOD-d4, 300 MHz): 9.15 (s, 1H), 7.58 (s, 1H), 7.08 (s, 1H), 3.79 (s, 3H), 2.51 (s, 3H), 2.32 (s, 3H), 2.31 (s, 3H), 2.15 (s, 3H). ESI-MS calculated for C$_{21}$H$_{20}$N$_5$O$_3$ [M+H]$^+$: 390.16, Obtained: 390.42

Various compounds of the invention were synthesized via a direct condensation of CD54 and an amine, alcohol, or thiol as shown below. The reaction yields varied from 60% to 5%. One example of the direct condensation procedure is illustrated in the synthesis of Cpd. No. 36.

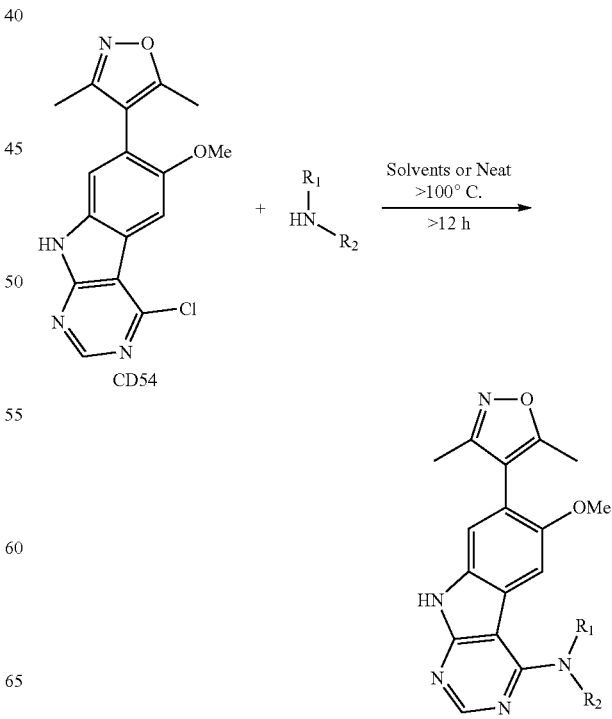

-continued

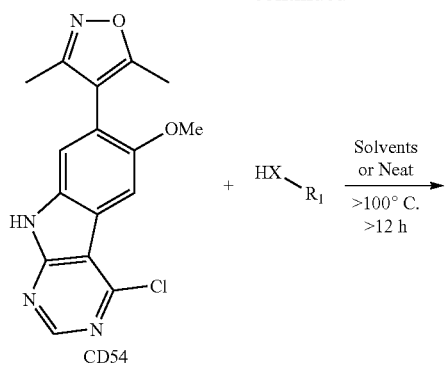

+ HX~R₁ →

Solvents or Neat
>100° C.
>12 h

CD54

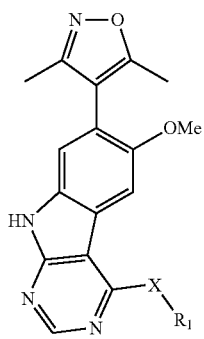

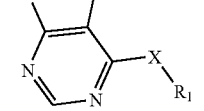

1. Solventes: DMF, NMP, DSMO
2. X = oxgen or sulfur

Method B: CD54 (80 mg, 0.3 mmol), (R)-1-(pyridin-2-yl)ethanamine (122 mg, 1 mmol), and EtN(i-Pr)₂ (0.3 mL, 1.5 mmol) were added to a round-bottomed flask. NMP (3 mL) was added at room temperature. The solution was heated at 140° C. for 14 h, then the reaction mixture was quenched by water (1 mL). The mixture was purified by reverse phase HPLC. The desired product Cpd. No. 36 TFA salt was isolated as a brown solid (16 mg, 20%).

Cpd. No. 36

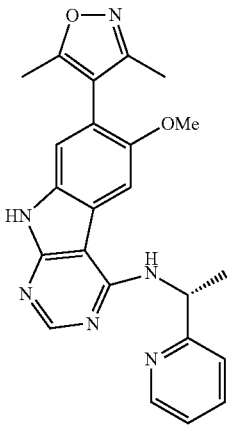

Cpd. No. 36: ¹H NMR (MeOD-d4, 300 MHz): 8.81 (d, J=5.58 Hz, 1H), 8.54 (s, 1H), 8.56-8.47 (m, 1H), 8.23-8.17 (m, 1H), 8.19 (s, 1H), 7.92 (t, J=6.39 Hz, 1H), 7.50 (s, 1H), 6.00 (q, J=7.11 Hz, 1H), 4.02 (s, 3H), 2.33 (s, 3H), 2.16 (s, 3H), 2.00 (d, J=7.11 Hz, 3H). ESI-MS calculated for C₂₃H₂₃N₆O₂ [M+H]⁺: 415.19, Obtained: 415.92.

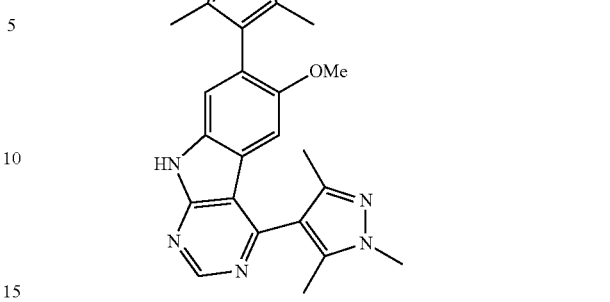

Method A-Suzuki coupling: 42% yield; ¹H NMR (MeOD-d4, 300 MHz): 9.20 (s, 1H), 7.65 (s, 1H), 7.16 (s, 1H), 3.97 (s, 3H), 3.81 (s, 3H), 2.40 (s, 3H), 2.35 (s, 3H), 2.29 (s, 3H), 2.17 (s, 3H). ESI-MS calculated for C₂₂H₂₃N₆O₂ [M+H]⁺: 403.19, Obtained: 403.50.

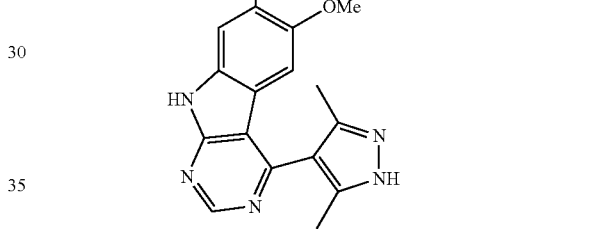

Method A—Suzuki coupling: 67% yield. ¹H NMR (MeOD-d4, 300 MHz): 9.17 (s, 1H), 7.62 (s, 1H), 7.12 (s, 1H), 3.77 (s, 3H), 2.34 (s, 6H), 2.32 (s, 3H), 2.15 (s, 3H), ESI-MS calculated for C₂₁H₂₁N₆O₂ [M+H]⁺: 389.17, Obtained: 389.83.

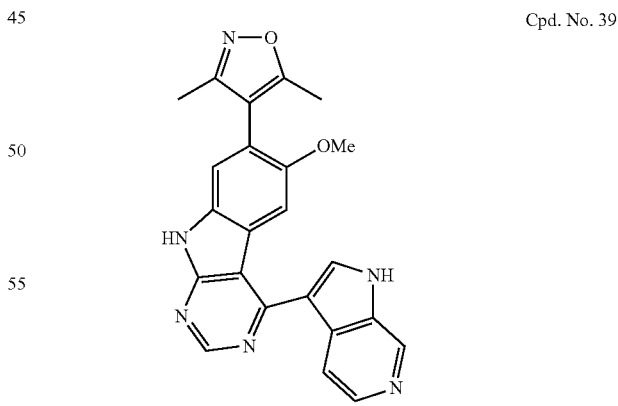

Method A-Suzuki coupling followed by treatment of trifluoroacetic acid (2 mL) for 15 min: 37% yield. ¹H NMR (MeOD-d4, 300 MHz): 9.40 (s, 1H), 9.16 (s, 1H), 9.09 (s, 1H), 8.46 (d, J=6.54 Hz, 1H), 8.25 (d, J=6.54 Hz, 1H), 7.58 (s, 1H), 7.19 (s, 1H), 3.58 (s, 3H), 2.32 (s, 3H), 2.14 (s, 3H), ESI-MS calculated for C₂₃H₁₉N₆O₂ [M+H]⁺: 411.16, Obtained: 411.42.

Cpd. No. 40

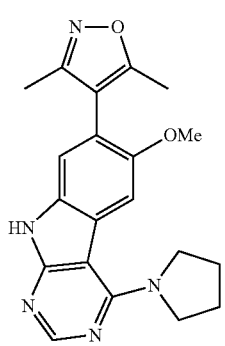

Method B-Direct Condensation: 11% yield. ¹H NMR (MeOD-d4, 300 MHz): 8.39 (s, 1H), 7.80 (s, 1H), 7.43 (s, 1H), 4.30-4.10 (m, 4H), 3.91 (s, 3H), 2.32 (s, 3H), 2.30-2.10 (m, 4H), 2.15 (s, 3H), ESI-MS calculated for $C_{20}H_{22}N_5O_2$ [M+H]⁺: 364.18, Obtained: 364.46.

Cpd. No. 41

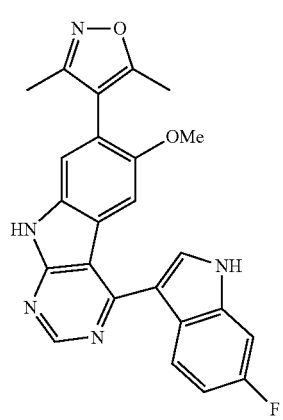

Method A-Suzuki coupling followed by treatment of trifluoroacetic acid (2 mL) for 15 min: 44% yield. ¹H NMR (MeOD-d4, 300 MHz): 9.10 (s, 1H), 8.38 (s, 1H), 7.80-7.70 (m, 1H), 7.62 (s, 1H), 7.30-7.10 (m, 3H), 3.52 (s, 3H), 2.35 (s, 3H), 2.16 (s, 3H), ESI-MS calculated for $C_{24}H_{19}FN_5O_2$ [M+H]⁺: 428.15, Obtained: 428.25.

Cpd. No. 42

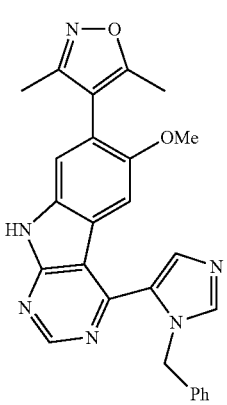

Method A-Suzuki coupling: 739% yield. ¹H NMR (MeOD-d4, 300 MHz): 9.36 (s, 1H), 9.06 (s, 1H), 8.38 (s, 1H), 7.42 (s, 1H), 7.25 (s, 1H), 5.78 (s, 2H), 3.78 (s, 3H), 2.34 (s, 3H), 2.17 (s, 3H), ESI-MS calculated for $C_{26}H_{23}N_6O_2$ [M+H]⁺: 451.19, Obtained: 451.25.

Cpd. No. 43

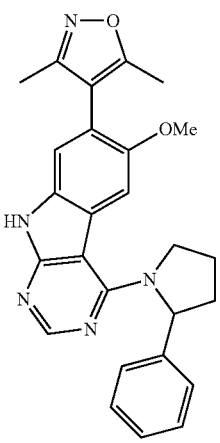

Method B-Direct Condensation: 39% yield. ¹H NMR (MeOD-d4, 300 MHz): 8.36 (s, 1H), 7.64 (s, 1H), 7.50-7.40 (m, 3H), 7.40-7.34 (m, 2H), 7.34-7.24 (m, 1H), 5.84 (t, J=6.13 Hz, 1H), 4.64-4.50 (m, 1H), 4.46-4.32 (m, 1H), 3.77 (s, 3H), 2.70-2.55 (m, 1H), 2.35-2.20 (m, 1H), 2.30 (s, 3H), 2.20-2.05 (m, 2H), 2.13 (s, 3H), ESI-MS calculated for $C_{26}H_{26}N_5O_2$ [M+H]⁺: 440.21, Obtained: 440.50.

Cpd. No. 44

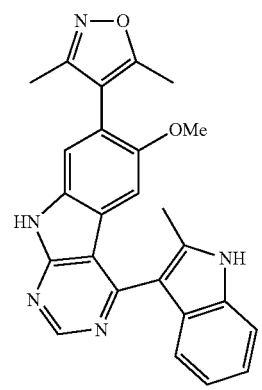

Method A-Suzuki coupling followed by treatment of trifluoroacetic acid (2 mL) for 15 min: 26% yield. ¹H NMR (MeOD-d4, 300 MHz): 9.12 (s, 1H), 7.61-7.58 (m, 1H), 7.58 (s, 1H), 7.37-7.15 (m, 3H), 6.82 (s, 1H), 3.32 (s, 3H), 2.67 (s, 3H), 2.31 (s, 3H), 2.12 (s, 3H), ESI-MS calculated for $C_{25}H_{22}N_5O_2$ [M+H]⁺: 424.18, Obtained: 424.42.

Cpd. No. 45

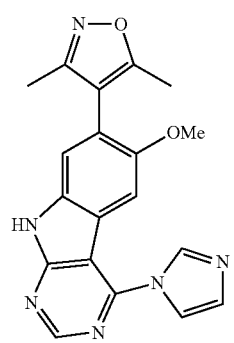

Method A-Suzuki coupling: 28% yield. ¹H NMR (MeOD-d4, 300 MHz): 9.73 (s, 1H), 8.95 (s, 1H), 8.46 (s, 1H), 7.93

(s, 1H), 7.53 (s, 1H), 7.47 (s, 1H), 3.85 (s, 3H), 2.33 (s, 3H), 2.15 (s, 3H), ESI-MS calculated for C₁₉H₁₇N₆O₂ [M+H]⁺: 361.14, Obtained: 361.33.

12 h. HPLC purification yield Cpd. No. 48 as TFA salt. ¹H NMR (MeOD-d4, 300 MHz): 8.55 (s, 1H), 8.19 (s, 1H), 7.46 (s, 1H), 7.41 (s, 1H), 4.10-3.90 (m, 4H), 3.97 (s, 3H), 3.90-3.80 (m, 2H), 3.80-3.70 (m, 2H), 2.33 (s, 3H), 2.16 (s, 3H). ESI-MS calculated for C₂₁H₂₃N₆O₃ [M+H]⁺: 407.18, Obtained: 407.33.

Cpd. No. 46

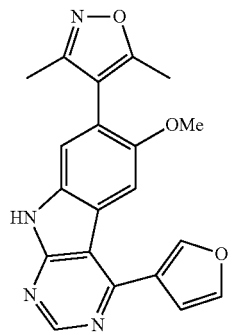

Cpd. No. 49

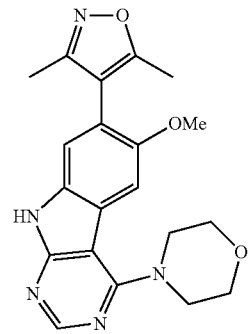

Method A-Suzuki coupling: 39% yield. ¹H NMR (MeOD-d4, 300 MHz): 9.10 (s, 1H), 8.61 (dd, J=1.52, 0.88 Hz, 1H), 8.04 (t, J=1.52 Hz, 1H), 7.78 (s, 1H), 7.59 (s, 1H), 7.28 (dd, J=1.91, 0.88 Hz, 1H), 3.86 (s, 3H), 2.33 (s, 3H), 2.16 (s, 3H), ESI-MS calculated for C₂₀H₁₇N₄O₃ [M+H]⁺: 361.13, Obtained: 361.33.

Method B-Direct Condensation: 45% yield. ¹H NMR (MeOD-d4, 300 MHz): 8.56 (s, 1H), 7.49 (s, 1H), 7.39 (s, 1H), 4.15-4.05 (m, 4H), 4.00-3.90 (m, 4H), 3.95 (s, 3H), 2.32 (s, 3H), 2.15 (s, 3H). ESI-MS calculated for C₂₀H₂₂N₅O₃ [M+H]⁺: 380.17, Obtained: 380.50.

Cpd. No. 47

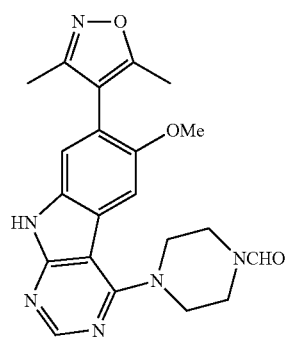

Cpd. No. 50

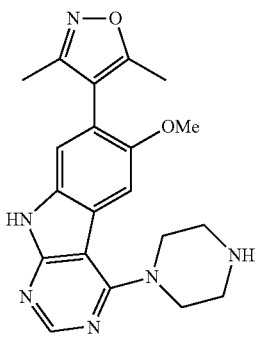

Method A-Suzuki coupling: 21% yield. ¹H NMR (MeOD-d4, 300 MHz): 8.95 (s, 1H), 8.08 (s, 1H), 7.93 (t, J=1.65 Hz, 1H), 7.57 (s, 1H), 7.23 (dd, J=2.91, 1.81 Hz, 1H), 7.03 (dd, J=2.91, 1.62 Hz, 1H), 3.87 (s, 3H), 2.34 (s, 3H), 2.17 (s, 3H), ESI-MS calculated for C₂₀H₁₈N₅O₂ [M+H]⁺: 360.15, Obtained: 360.25.

Method B-Direct Condensation: 42% yield. ¹H NMR (MeOD-d4, 300 MHz): 8.60 (s, 1H), 7.45 (s, 1H), 7.39 (s, 1H), 4.25-4.10 (m, 4H), 3.96 (s, 3H), 3.60-3.40 (m, 4H), 2.32 (s, 3H), 2.15 (s, 3H). ESI-MS calculated for C₂₀H₂₃N₆O₂ [M+H]⁺: 379.19, Obtained: 379.67.

Cpd. No. 48

Cpd. No. 51

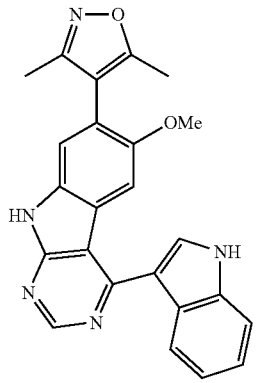

Method B-Direct Condensation: 42% yield. CD54, piperazine, and (iPr)₂NEt were heated up at 180° C. in DMF for Method A-Suzuki coupling followed by treatment of trifluoroacetic acid (2 mL) for 15 min: 40% yield. $^1$H NMR (MeOD-d4, 300 MHz): 9.06 (s, 1H), 8.27 (s, 1H), 7.71 (d, J=8.20 Hz, 1H), 7.57 (s, 1H), 7.50 (d, J=7.96 Hz, 1H), 7.41 (ddd, J=8.24, 7.21, 1.13 Hz, 1H), 7.29 (ddd, J=8.03, 7.08, 0.97 Hz, 1H), 7.15 (s, 1H), 3.42 (s, 1H), 2.32 (s, 1H), 2.13 (s, 1H), ESI-MS calculated for $C_{24}H_{20}N_5O_2$ [M+H]$^+$: 410.16, Obtained: 410.33.

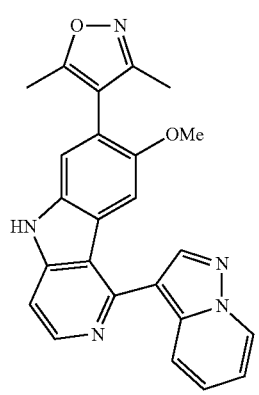

Cpd. No. 52

Method A-Suzuki coupling: 40% yield. $^1$H NMR (MeOD-d4, 300 MHz): 9.05 (s, 1H), 8.89 (d, J=7.00 Hz, 1H), 8.76 (s, 1H), 7.76 (d, J=7.85 Hz, 1H), 7.66-7.58 (m, 1H), 7.56 (s, 1H), 7.25 (dd, J=6.89, 6.92 Hz, 1H), 7.19 (s, 1H), 3.60 (s, 3H), 2.32 (s, 3H), 2.14 (s, 3H) ESI-MS calculated for $C_{24}H_{20}N_5O_2$ [M+H]$^+$: 410.16, Obtained: 410.12.

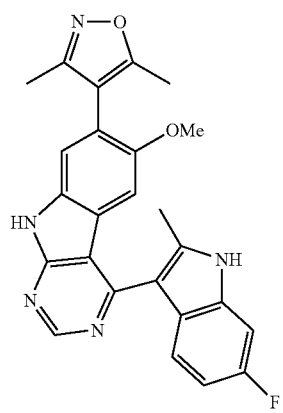

Cpd. No. 53

Method A-Suzuki coupling followed by treatment of trifluoroacetic acid (2 mL) for 15 min: 52% yield; $^1$H NMR (MeOD-d4, 300 MHz): 12.04 (NH), 9.16 (s, 1H), 7.62 (s, 1H), 7.34 (dd, J=9.33, 2.16 Hz, 1H), 7.27 (dd, J=8.74, 5.06 Hz, 1H), 7.01 (ddd, J=3.42 (s, 3H), 2.67 (s, 3H), 2.33 (s, 3H), 2.14 (s, 3H).

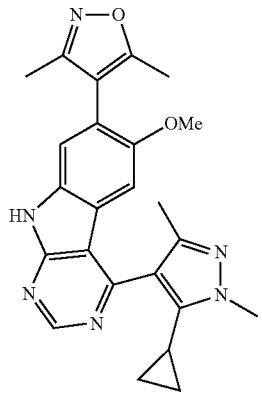

Cpd. No. 54

Method A-Suzuki coupling: 45% yield; $^1$H NMR (MeOD-d4, 300 MHz): 9.22 (s, 1H), 7.64 (s, 1H), 7.15 (s, 1H), 4.07 (s, 3H), 3.79 (s, 3H), 2.34 (s, 3H), 2.24 (s, 3H), 2.18 (s, 3H), 2.15-2.00 (m, 1H), 1.00-0.80 (m, 2H), 0.55-0.45 (m, 1H), 0.30-0.20 (m, 1H).

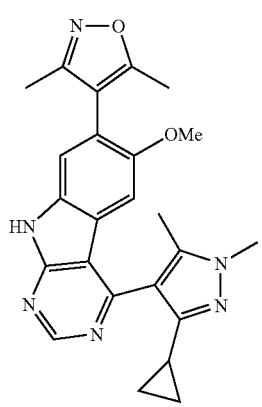

Cpd. No. 55

Method A-Suzuki coupling: 22% yield; $^1$H NMR (MeOD-d4, 300 MHz): 9.20 (s, 1H), 7.63 (s, 1H), 7.37 (s, 1H), 3.92 (s, 3H), 3.84 (s, 3H), 2.39 (s, 3H), 2.35 (s, 3H), 2.17 (s, 3H), 1.80-1.65 (m, 1H), 1.25-1.15 (m, 1H), 1.00-0.80 (m, 3H).

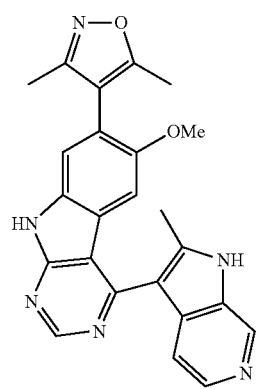

Cpd. No. 56

Method A-Suzuki coupling followed by treatment of trifluoroacetic acid (2 mL) for 15 min: 61% yield; $^1$H NMR (MeOD-d4, 300 MHz): 9.28 (s, 1H), 9.24 (s, 1H), 8.37 (d, J=6.53 Hz, 1H), 7.87 (d, J=6.53 Hz, 1H), 7.63 (s, 1H), 6.77 (s, 1H), 3.47 (s, 3H), 2.85 (s, 3H), 2.32 (s, 3H), 2.14 (s, 3H).

Cpd. No. 57

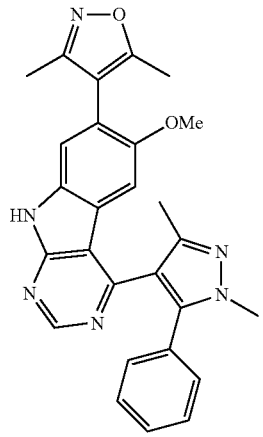

Cpd. No. 58

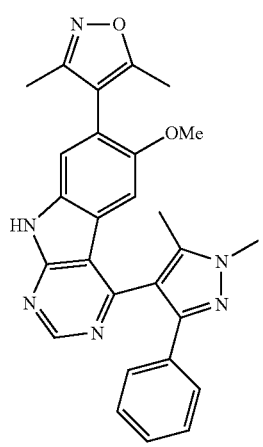

Method A-Suzuki coupling: 32% yield; Mixture of 2 isomers, ratio 1:1; ¹H NMR (MeOD-d4, 300 MHz): 9.17 (s, 1H), 9.06 (s, 1H), 7.56 (s, 1H), 7.51 (s, 1H), 7.50-7.40 (m, 1H), 7.40-7.30 (m, 6H), 7.25-7.15 (m, 3H), 7.15 (s, 1H), 7.00 (s, 1H), 4.06 (s, 3H), 4.00 (s, 3H), 3.82 (s, 3H), 3.68 (s, 3H), 2.41 (s, 3H), 2.32 (s, 3H), 2.31 (s, 3H), 2.26 (s, 3H), 2.13 (s, 3H), 2.07 (s, 3H).

Cpd. No. 59

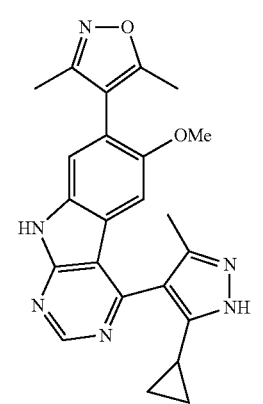

Method A-Suzuki coupling followed by treatment of trifluoroacetic acid (2 mL) for 15 min: 65% yield; ¹H NMR (MeOD-d4, 300 MHz): 9.13 (s, 1H), 7.58 (s, 1H), 7.30 (s, 1H), 3.83 (s, 3H), 2.38 (s, 3H), 2.37 (s, 3H), 2.19 (s, 3H), 1.90-1.70 (m, 1H), 1.10-1.00 (m, 1H), 1.00-0.80 (m, 3H).

Cpd. No. 60

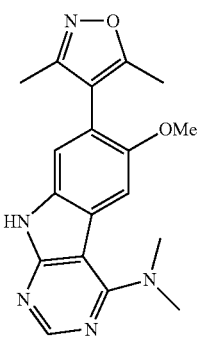

Method B-Direct condensation: 45% yield; ¹H NMR (MeOD-d4, 300 MHz): 8.49 (s, 1H), 7.65 (s, 1H), 7.49 (s, 1H), 3.96 (s, 3H), 3.64 (s, 6H), 2.34 (s, 3H), 2.18 (s, 3H).

Cpd. No. 61

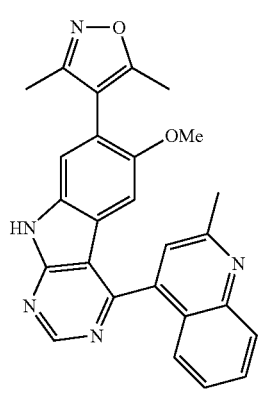

Method A-Suzuki coupling: 48% yield; ¹H NMR (MeOD-d4, 300 MHz): 9.17 (s, 1H), 8.37 (d, J=8.58 Hz, 1H), 8.27 (s, 1H), 8.17 (t, J=7.31 Hz, 1H), 8.03 (d, J=8.44 Hz, 1H), 7.82 (t, J=7.72 Hz, 1H), 7.49 (s, 1H), 6.43 (s, 1H), 3.30 (s, 3H), 3.12 (s, 3H), 2.27 (s, 3H), 2.08 (s, 3H).

Cpd. No. 62

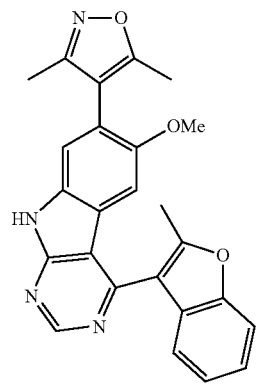

Method A-Suzuki coupling: 31% yield; ¹H NMR (MeOD-d4, 300 MHz): 9.22 (s, 1H), 7.73 (d, J=8.32 Hz, 1H), 7.60 (s, 1H), 7.55-7.45 (m, 1H), 7.40-7.30 (m, 2H), 6.85 (s, 1H), 3.37 (s, 3H), 2.68 (s, 3H), 2.30 (s, 3H), 2.12 (s, 3H).

Cpd. No. 63

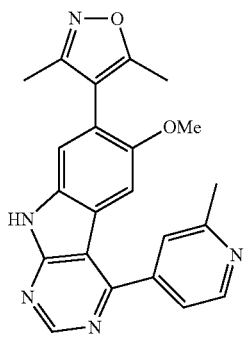

Method A-Suzuki coupling: 26% yield; ¹H NMR (MeOD-d4, 300 MHz): 9.08 (s, 1H), 9.00 (d, J=6.10 Hz, 1H), 8.54 (s, 1H), 8.46 (dd, J=6.10, 1.36 Hz, 1H), 7.51 (s, 1H), 7.45 (s, 1H), 3.79 (s, 3H), 2.96 (s, 3H), 2.32 (s, 3H), 2.15 (s, 3H).

Cpd. No. 64

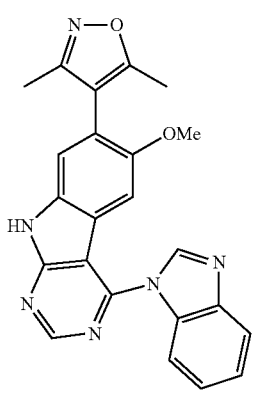

Method B-Direct condensation of CD54 and benzimidazole in anhydrous DMSO (4 mL) using EtN(i-Pr)₂ (0.1 mL) as base at 170° C. for 16 h. HPLC Isolated as TFA salt in 32% yield. ¹H NMR (MeOD-d4, 300 MHz): 9.45 (s, 1H), 9.01 (s, 1H), 8.00 (d, J=8.09 Hz, 1H), 7.67-7.51 (m, 3H), 7.51 (s, 1H), 6.78 (s, 1H), 3.44 (s, 3H), 2.31 (s, 3H), 2.12 (s, 3H). ESI-MS Calculated for $C_{23}H_{19}N_6O_2$ [M+H]⁺=411.16. Found: 411.75.

Cpd. No. 65

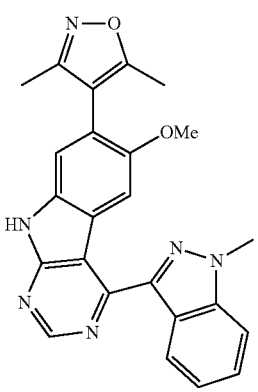

Optimized Suzuki coupling conditions previously reported (Jimenez, J.-M. et. al. 2013, J. Med. Chem. DIO: 10.1021/jm301465a) was followed to synthesize Cpd. No. 65. CD54 (34 mg, 0.1 mmol), 1-methyl-3-(4,4,5,5-tetramethyl-1,3,2-dioxaborolan-2-yl)-1H-indazole (CD143, 75 mg, 0.3 mmol), and Na₂CO₃ (50 mg) were mixed in round-bottom flask. To this flask, MeOH (4 mL), PhMe (4 mL), and water (1 mL) were added and the system was degassed and refilled with pure nitrogen. Pd(PPh₃)₄(20 mg) was then added. Again, the system was degassed and refilled with pure nitrogen. The mixture was heated at reflux for 12 h. The aqueous layer was extracted with ethyl acetate and the combined organic layers were washed with brine and dried over anhydrous Na₂SO₄. The volatile components were removed on a rotary evaporator and the residue was purified by reverse phase HPLC. The desired product Cpd. No. 65 was isolated as TFA salt in 23% yield. ¹H NMR (DMSO-d6, 300 MHz): 12.36 (s, 1H), 9.31 (s, 1H), 9.05 (s, 1H), 8.82 (d, J=8.18 Hz, 1H), 7.85 (d, J=8.48 Hz, 1H), 7.60-7.50 (m, 1H), 7.39 (s, 1H), 7.40-7.32 (m, 1H), 4.36 (s, 3H), 4.00 (s, 3H), 3.37 (s, NH), 2.32 (s, 3H), 2.13 (s, 3H). ESI-MS Calculated for $C_{24}H_{21}N_6O_2$ [M+H]⁺=425.17. Found: 425.83.

Cpd. No. 66

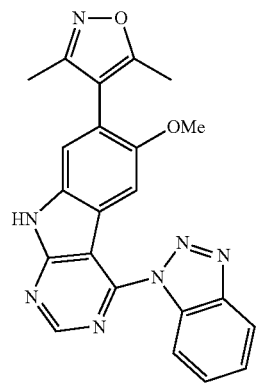

Coupling reaction of CD54 and benzotriazole catalyzed by Pd₂(dba)₃ [tris(dibenzylideneacetone)dipalladium(0)] and (±)-BINAP [(±)-1,1'-Binaphthalene-2,2'-diyl)bis(diphenylphosphine)] yielded Cpd. No. 66. A previously reported methods by Ueda, S. et. al (2012, J. Org. Chem. 77, 2543-2547) was adopted in this reaction with following modification: BINAP was used as phosphine ligand instead of the reported tBuXPhos (L3) or Me₄tBuXPhos (L1). CD54 (34 mg, 0.1 mmol), Benzotriazole (14 mg, 0.12 mmol), and K₃PO₄ (42 mg, 0.2 mmol) were added into a round-bottom flask. The round-bottom flask was degassed and refilled with pure nitrogen gas. In a second round-bottom flask, Pd₂(dba)₃ (9 mg, 0.01 mmol) and (±)-BINAP (15 mg, 0.024 mmol) were added. The round-bottom flask was degassed and refilled with pure nitrogen gas. To this flask, anhydrous toluene (10 mL) was added and the solution was heated at 120° C. for 3 min to generate the active catalyst. The active catalyst was transferred into the first flask and the reaction mixture was heat at reflux for 12 h. The mixture was then diluted with ethyl acetate and washed with water, brine. Organic lawyer was collected, the volatile components were removed on a rotary evaporator, and the residue was purified by reverse phase HPLC. The desired product Cpd. No. 64 was isolated as a TFA salt in 29% yield. ¹H NMR (DMSO-d6, 300 MHz): 12.88 (s, 1H), 9.04 (s, 1H), 8.61 (s, 1H), 8.26-8.18 (m, 2H), 7.68-7.60 (m, 2H), 7.48 (s, 1H), 3.87 (s, 3H), 3.30 (s, 3H), 3.15 (s, NH), 2.31 (s, 3H), 2.11 (s, 3H). ESI-MS Calculated for $C_{22}H_{18}N_7O_2$ [M+H]⁺=412.15. Found: 412.42.

8. Synthesis of General Intermediate Containing 9H-pyrido[3,4-b]indole Core and Compound Cpd. No. 67

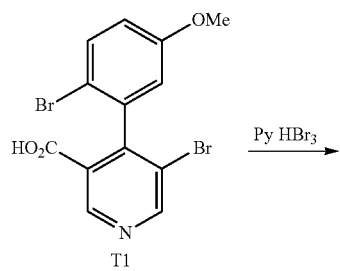

T1

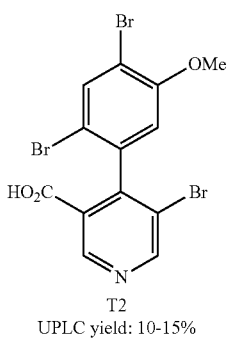

T2
UPLC yield: 10-15%

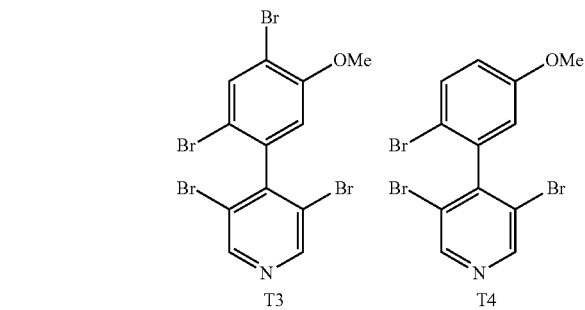

T3   T4

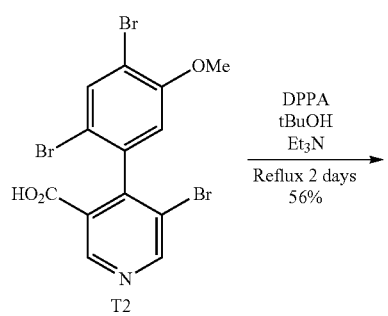

T2

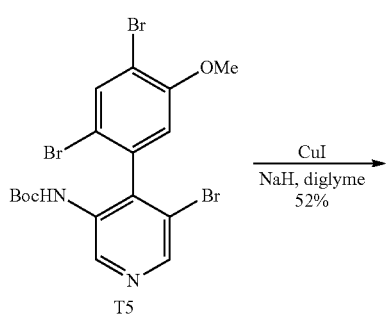

T5

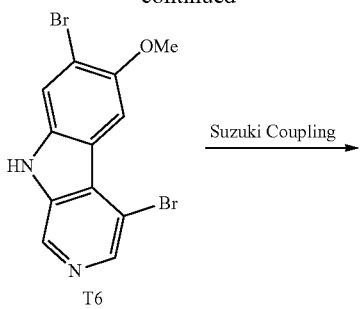

T6

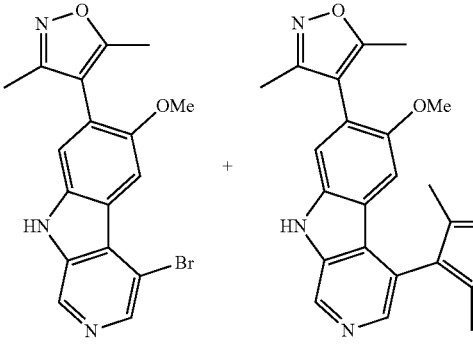

T7   Cpd. No. 67

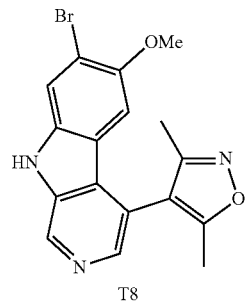

T8

A known acid T1 (1995, *Tetrahedron*, 51, 9531-9542.) was used as the substrate to synthesize T2. The acid T1 (193 mg, 0.5 mmol) was dissolved in AcOH—H$_2$O (6 mL-4 mL) at room temperature. PyHBr$_3$ (160 mg, 0.5 mmol) was added in one portion. The reaction was heated at 60° C. for 12 h, then another portion of PyHBr$_3$ (80 mg, 0.25 mmol) was added. The reaction was stirred at room temperature for 12 h. The reaction was quenched with 0.1 mL sat. Na$_2$SO$_3$ and the volatile components were removed on a rotary evaporator. MeOH was added, precipitate was removed by filtration, and the MeOH solution was collected. The volatile components were removed on a rotary evaporator and the residue was purified by reverse phase HPLC. The desired product T2 was obtained in 36 mg, 15% yield. Side products T3 and T4 were obtained in ca. 40% determined by UPLC based on conversion of starting materials.

T2

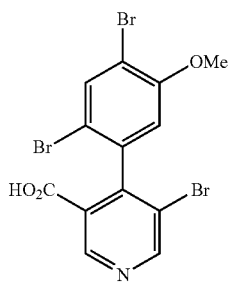

¹H NMR (CDCl₃, 300 MHz): 9.29 (s, 1H), 9.08 (s, 1H), 7.84 (s, 1H), 6.62 (s, 1H), 3.87 (s, 3H). ESI-MS calculated for $C_{13}H_9{}^{79}Br_3NO_3$ [M+H]⁺: 465.81, Obtained: 465.84.

T5

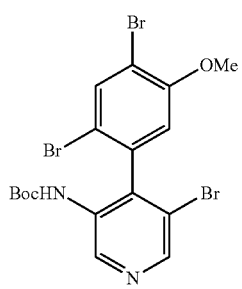

The acid T2 (113 mg, 0.24 mmol), Et₃N (excess, 0.5 mL), and t-BuOH (10 mL) were added in a round-bottom flask at room temperature. (PhO)₂PO—N₃ (DPPA, 124 mg, 0.45 mmol) was added in one portion, and the reaction was stirred at room temperature for 2 h, then heated at reflux for 30 h. The volatile components were removed on a rotary evaporator the residue was purified by flash column chromatography. The desired product T5 was isolated in 72 mg, 56% yield. ¹H NMR (CDCl₃, 300 MHz): 9.28 (s, 1H), 8.53 (s, 1H), 7.91 (s, 1H), 6.68 (s, 1H), 5.95 (s, 1H), 3.88 (s, 3H), 1.46 (s, 9H), ESI-MS calculated for $C_{17}H_{18}{}^{81}Br_2{}^{79}BrN_2O_3$ [M+H]⁺: 538.88, Obtained: 538.92.

T6

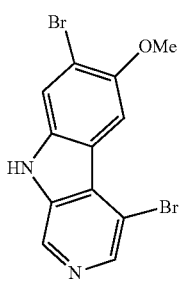

The substrate T5 (72 mg, 0.2 mmol), CuI (76 mg, 0.3 mmol), and NaH (40 mg, 0.4 mmol, 60% in mineral oil) were placed in an oven-dried round-bottom flask. Anhydrous diglyme (10 ml) was added via a syringe and the reaction mixture was heated at 120° C. for 14 h. The reaction mixture was quenched with 5% NH₃/H₂O. The aqueous layer was extracted with ethyl acetate, and combined organic layers were washed with brine and dried over anhydrous Na₂SO₄. The volatile components were removed on a rotary evaporator and the residue was purified by flash column chromatography. The desired product T6 was isolated in 22 mg, 52% yield. ¹H NMR (DMSO-d6, 300 MHz): 11.92 (NH, 1H), 8.89 (s, 1H), 8.41 (s, 1H), 8.10 (s, 1H), 7.94 (s, 1H), 3.94 (s, 3H). ¹³C NMR (DMSO-d6, 75 MHz): 155.70, 149.19, 138.98, 137.27, 135.70, 133.43, 119.53, 116.43, 113.92, 104.06, 94.54, 56.54. ESI-MS calculated for $C_{12}H_9{}^{79}Br_2N_2O$ [M+H]⁺: 356.91, Obtained: 357.58.

Cpd. No. 67

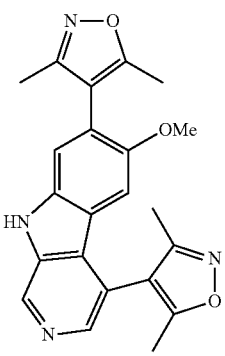

T6 (22 mg, 0.06 mmol), 3,5-dimethyl-4-(4,4,5,5-tetramethyl-1,3,2-dioxaborolan-2-yl)isoxazole (44 mg, 0.2 mmol), and K₂CO₃ (55 mg, 0.4 mmol) were placed in a round-bottom flask. DME (6 mL) and water (4 mL) were added, and the solution was degassed then Pd(PPh₃)₄(10 mg, 0.008 mmol) was added in one portion. The solution was degassed again, then heated at reflux for 14 h. The aqueous layer was extracted with ethyl acetate and the combined organic layers were washed with brine and dried over anhydrous Na₂SO₄. The volatile components were removed on a rotary evaporator and the residue was purified by reverse phase HPLC. The desired product Cpd. No. 67 TFA salt was isolated as a yellow-green solid (27 mg, TFA salt, >90% yield). ¹H NMR (MeOD-d4, 300 MHz): 9.26 (s, 1H), 8.45 (s, 1H), 7.71 (s, 1H), 7.03 (s, 1H), 3.74 (s, 3H), 2.41 (s, 3H), 2.33 (s, 3H), 2.19 (s, 3H), 2.15 (s, 3H). ESI-MS calculated for $C_{22}H_{21}N_4O_3$ [M+H]⁺: 389.16, Obtained: 389.42

9. Synthesis of General Intermediate Containing 5H-pyridazino[4,5-b]indole Core.

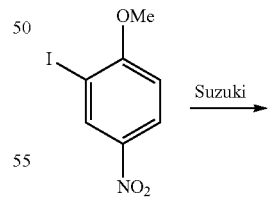

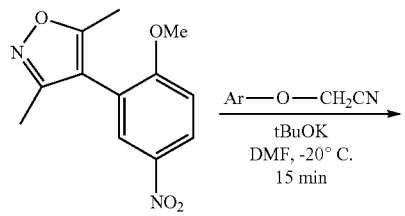

10. Synthesis of General Intermediate Containing 2-Methyl-9H-pyrimido[4,5-b]indole Core.
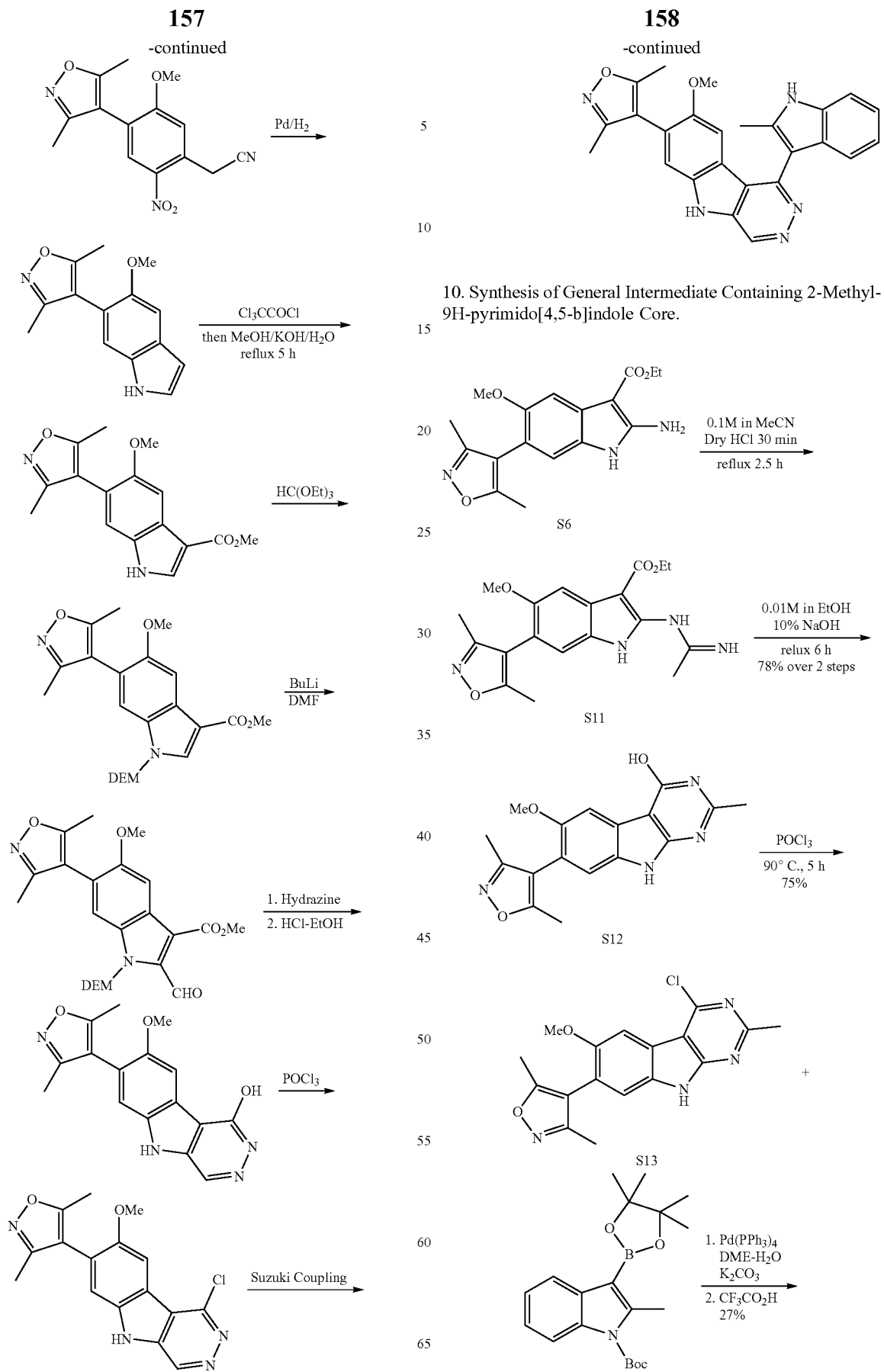

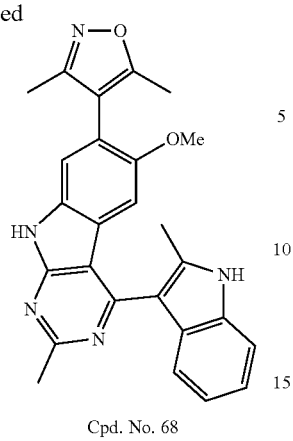

Cpd. No. 68

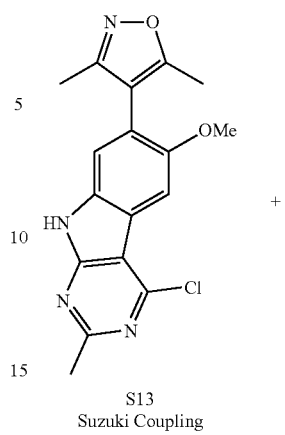

S13
Suzuki Coupling

To a round-bottom flask, S6 (0.37 g, 1.1 mmol) and MeCN (20 mL) were added at room temperature. Dry HCl was bubbled through MeCN for 30 min and the reaction mixture was warmed up to reflux (ca, 82° C.) for 2.5 h. The reaction was then cooled to room temperature and the volatile components were removed on a rotary evaporator. To this crude mixture, 10% NaOH aqueous solution (20 mL) and EtOH (50 mL) were added and the solution was heated at reflux for 6 h. The volatile components were then removed on a rotary evaporator and the aqueous residue was acidified with 2N HCl aqueous solution. The product S12 was allowed to precipitate at 0° C. Filtration of the mixture furnished pure S12 in 0.278 g (78% yield, 2 steps). $^1$H NMR (DMSO-d6, 300 MHz): 7.57 (s, 1H), 7.20 (s, 1H), 3.81 (s, 3H), 2.37 (s, 3H), 2.27 (s, 3H), 2.08 (s, 3H).

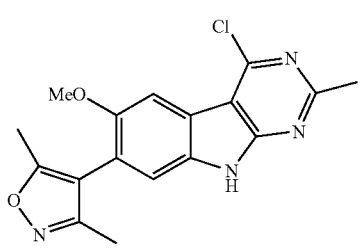

S13

To a round-bottom flask, S12 (0.278 g, 0.8 mmol) and POCl$_3$ (8 mL) were added. The mixture was heated at 90° C. for 6 h. The reaction mixture was cooled to room temperature and the volatile components were removed on a rotary evaporator. Water (20 mL) and ethyl acetate (20 mL) were added and the pH was adjusted to 8 using NaHCO$_3$ saturated aqueous solution. Filtration of the mixture furnished S13 as a brown solid in 0.208 g (75% yield). $^1$H NMR (DMSO-d6, 300 MHz): 7.81 (s, 1H), 7.43 (s, 1H), 3.89 (s, 3H), 2.69 (s, 3H), 2.31 (s, 3H), 2.11 (s, 3H).

Some final products were synthesized via a Suzuki coupling as shown in the scheme below. Suzuki coupling used S13 as the aryl halide substrate, and commercially available or in-house made boronic acids or pinacol boronates used as the coupling partners. The reaction yields varied from 70% to 10%. Some pinacol boronates were also synthesized using general methods shown in previous schemes. One example of the Suzuki coupling procedure is illustrated in the synthesis of Cpd. No. 68.

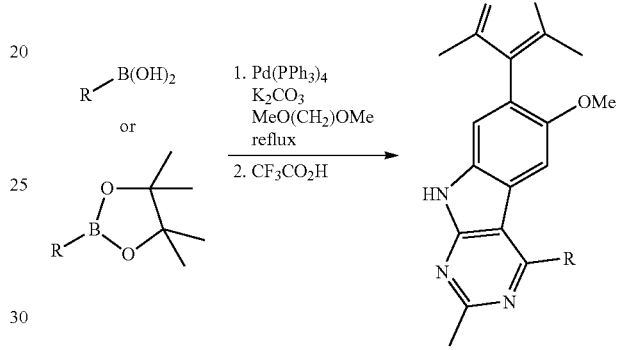

Method C:

S13 (34 mg, 0.1 mmol), tert-Butyl 2-methyl-3-(4,4,5,5-tetramethyl-1,3,2-dioxaborolan-2-yl)-1H-indole-1-carboxylate (100 mg, 0.3 mmol), and K$_2$CO$_3$ (70 mg, 0.4 mmol) were added to a round-bottom flask. DME (6 mL) and water (4 mL) were added at room temperature. The solution was degassed, then Pd(PPh$_3$)$_4$(20 mg, 0.017 mmol) was added in one portion. The solution was again degassed, following by heat-up at reflux for 14 h. The aqueous layer was extracted with ethyl acetate and combined organic layers were washed with brine and dried over anhydrous Na$_2$SO$_4$. The volatile components were removed on a rotary evaporator and the residue was treated with trifluoroacetic acid (2 mL) for 15 min at room temperature. Purification by reverse phase HPLC afforded desired product Cpd. No. 68 TFA salt was isolated as a colorless solid (12 mg, 27%).

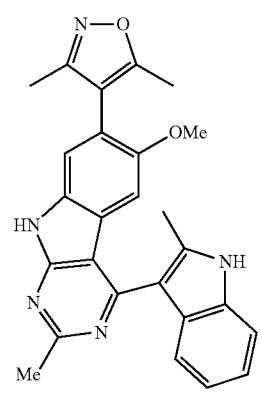

Cpd. No. 68

Cpd. No. 68: $^1$H NMR (MeOD-d4, 300 MHz): 11.94 (NH), 7.62 (d, J=8.13 Hz, 1H), 7.57 (s, 1H), 7.35 (ddd, J=8.17, 6.82, 1.30, 1H), 7.32-7.18 (m, 2H), 6.80 (s, 1H), 3.00 (s, 3H), 2.70 (s, 3H), 2.34 (s, 3H), 2.15 (s, 3H).

Cpd. No. 69

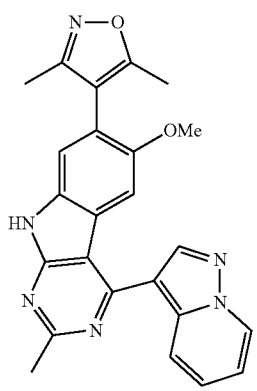

General Suzuki coupling reaction condition (Method C) was followed: 37% yield; $^1$H NMR (MeOD-d4, 300 MHz): 8.95 (d, J=7.00 Hz, 1H), 8.76 (s, 1H), 7.70-7.64 (m, 2H), 7.56 (s, 1H), 7.34-7.24 (m, 1H), 6.98 (s, 1H), 3.54 (s, 3H), 2.96 (s, 3H), 2.31 (s, 3H), 2.13 (s, 3H). ESI-MS Calculated for $C_{24}H_{21}N_6O_2$ [M+H]$^+$=425.17. Found: 425.42.

Cpd. No. 70

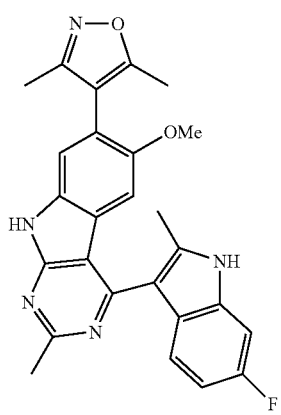

General Suzuki coupling reaction condition (Method C) was followed: 30% yield; $^1$H NMR (MeOD-d4, 300 MHz): 11.96 (s, NH), 7.54 (s, 1H), 7.40-7.20 (m, 2H), 7.10-6.90 (m, 1H), 6.77 (s, 1H), 3.38 (s, 3H), 2.96 (s, 3H), 2.63 (s, 3H), 2.30 (s, 3H), 2.11 (s, 3H). ESI-MS Calculated for $C_{26}H_{23}FN_5O_2$ [M+H]$^+$=456.18. Found: 456.33.

Cpd. No. 71

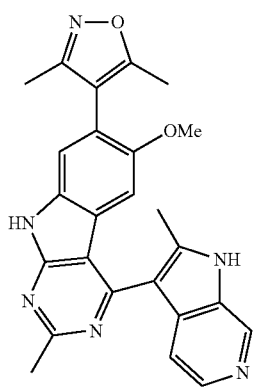

General Suzuki coupling reaction condition (Method C) was followed: 47% yield; $^1$H NMR (MeOD-d4, 300 MHz): 9.28 (s, 1H), 8.39 (d, J=6.53 Hz, 1H), 7.90 (d, J=6.50 Hz, 1H), 7.58 (s, 1H), 6.69 (s, 1H), 3.45 (s, 3H), 3.00 (s, 3H), 2.82 (s, 3H), 2.30 (s, 3H), 2.11 (s, 3H). ESI-MS Calculated for $C_{25}H_{23}N_6O_2$ [M+H]$^+$=439.19. Found: 439.58.

Cpd. No. 72

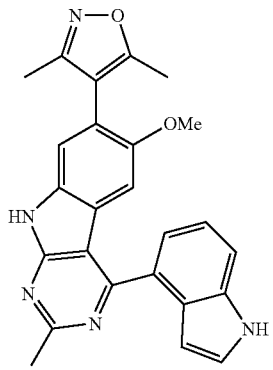

General Suzuki coupling reaction condition (Method C) was followed: 40% yield; $^1$H NMR (MeOD-d4, 300 MHz): 11.37 (s, NH), 7.89 (d, J=8.14 Hz, 1H), 7.64 (dd, J=7.34, 0.89 Hz, 1H), 7.56-7.43 (m, 2H), 7.52 (s, 1H), 6.73 (s, 1H), 6.31 (s, 1H), 3.37 (s, 3H), 2.98 (s, 3H), 2.29 (s, 3H), 2.10 (s, 3H). ESI-MS Calculated for $C_{25}H_{22}N_5O_2$ [M+H]$^+$=424.18. Found: 424.42.

Cpd. No. 73

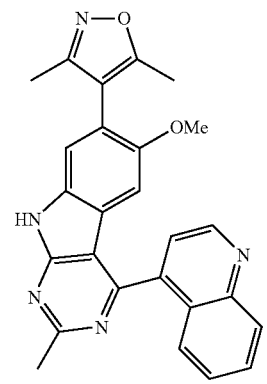

General Suzuki coupling reaction condition (Method C) was followed: 57% yield; $^1$H NMR (MeOD-d4, 300 MHz): 9.31 (d, J=4.59 Hz, 1H), 8.38 (d, J=8.50 Hz, 1H), 8.08 (d, J=4.63 Hz, 1H), 8.12-8.00 (m, 1H), 7.88 (d, J=7.76 Hz, 1H), 7.78-7.70 (m, 1H), 7.53 (s, 1H), 6.21 (s, 1H), 3.21 (s, 3H), 3.00 (s, 3H), 2.26 (s, 3H), 2.07 (s, 3H). ESI-MS Calculated for $C_{26}H_{22}N_5O_2$ [M+H]$^+$=436.18. Found: 436.50.

Cpd. No. 74

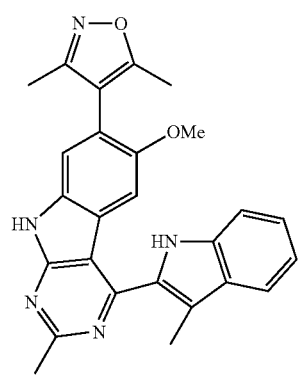

General Suzuki coupling reaction condition (Method C) was followed: 23% yield; $^1$H NMR (MeOD-d4, 300 MHz):

7.81 (d, J=8.10 Hz, 1H), 7.59 (d, J=8.10 Hz, 1H), 7.55 (s, 1H), 7.50-7.30 (m, 1H), 7.38 (s, 1H), 7.25 (t, J=8.10 Hz, 1H), 3.66 (s, 3H), 2.97 (s, 3H), 2.53 (s, 3H), 2.31 (s, 3H), 2.14 (s, 3H). ESI-MS Calculated for $C_{26}H_{24}N_5O_2$ [M+H]$^+$=438.19. Found: 438.67.

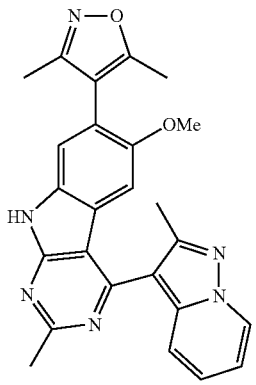

Cpd. No. 75

General Suzuki coupling reaction condition (Method C) was followed: 22% yield; $^1$H NMR (MeOD-d4, 300 MHz): 8.83 (s, J=6.97 Hz, 1H), 7.64-7.54 (m, 1H), 7.59 (s, 1H), 7.50 (d, J=8.82 Hz, 1H), 7.22 (td, J=6.81, 1.46 Hz, 1H), 6.74 (s, 1H), 3.50 (s, 3H), 2.99 (s, 3H), 2.65 (s, 3H), 2.33 (s, 3H), 2.14 (s, 3H). ESI-MS Calculated for $C_{25}H_{23}N_6O_2$ [M+H]$^+$=439.19. Found: 440.83.

S13 (30 mg), 3-quinoline boronic acid (60 mg), and $K_2CO_3$ (64 mg) were placed in a round-bottom flask. To this flask, 1,2-dimethoxyethane (DME, 6 mL) and water (4 mL) were added and the system was degassed to remove oxygen. Pd(PPh$_3$)$_4$ (20 mg) was added in one portion and the flask was degassed again. The mixture was heated at reflux for 12 h under nitrogen atmosphere. The reaction was then diluted with water and the aqueous layer was extracted with ethyl acetate (50 mL×2) and the combined organic layers were dried over anhydrous sodium sulfate. The solvent was removed in vacuum and the residue was purified by reverse phase preparative HPLC to yield the desired product Cpd. No. 76 in 22% yield as a salt of CF$_3$CO$_2$H.

The following compounds were prepared in following the same Suzuki coupling method [(Pd(PPh$_3$)$_4$ as catalyst and $K_2CO_3$ as base]. The boronic acids required for these syntheses are commercially available.

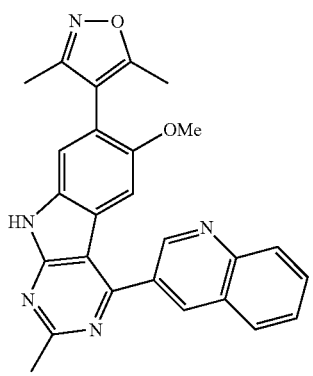

Cpd. No. 76

TFA salt $^1$H NMR (300 MHz, MeOD-d4): 9.47 (d, J=2.01 Hz, 1H), 9.21 (d, J=2.03 Hz, 1H), 8.29 (t, J=7.52 Hz, 2H), 8.08 (ddd, J=8.50, 6.99, 1.40 Hz, 1H), 7.88 (ddd, J=8.05, 7.14, 1.00 Hz, 1H), 7.57 (s, 1H), 7.29 (s, 1H), 3.60 (s, 3H), 3.00 (s, 3H), 2.31 (s, 3H), 2.13 (s, 3H). ESI-MS calculated for $C_{26}H_{22}N_5O_2$ [M+H]$^+$=436.18, Obtained: 436.83.

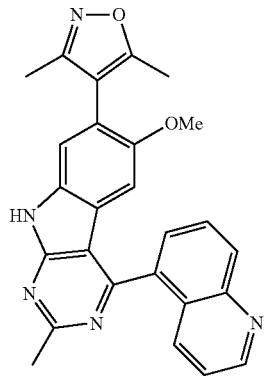

Cpd. No. 77

TFA salt yield: 27%. Suzuki coupling-Pd(PPh$_3$)$_4$—$K_2CO_3$ Method. $^1$H NMR (300 MHz, MeOD-d4): 9.15 (dd, J=4.39, 1.39 Hz, 1H), 8.61-8.53 (m, 1H), 8.41 (d, J=8.60 Hz, 1H), 8.25 (d, J=1.33 Hz, 1H), 8.24 (s, 1H), 7.72 (dd, J=7.74, 4.42 Hz, 1H), 7.57 (s, 1H), 6.30 (s, 1H), 3.28 (s, 3H), 3.03 (3H), 2.29 (s, 3H), 2.10 (s, 3H). ESI-MS calculated for $C_{26}H_{22}N_5O_2$ [M+H]$^+$=436.18, Obtained: 436.33.

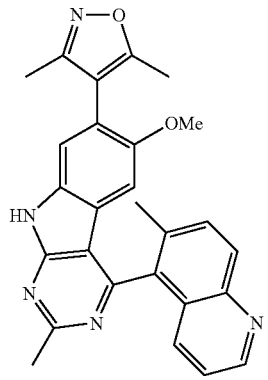

Cpd. No. 78

TFA salt yield: 36%. Suzuki coupling-Pd(PPh$_3$)$_4$—$K_2CO_3$ Method. $^1$H NMR (300 MHz, MeOD-d4): 9.08 (d, J=4.56 Hz, 1H), 8.46 (J=8.81 Hz, 1H), 8.22 (d, J=8.56 Hz, 1H), 8.17 (d, J=8.86 Hz, 1H), 7.69 (dd, J=8.63, 4.64 Hz, 1H), 7.55 (s, 1H), 6.14 (s, 1H), 3.28 (s, 3H), 3.01 (s, 3H), 2.47 (s, 3H), 2.25 (s, 3H), 2.06 (s, 3H). ESI-MS calculated for $C_{27}H_{24}N_5O_2$ [M+H]$^+$=450.19, Obtained: 450.50.

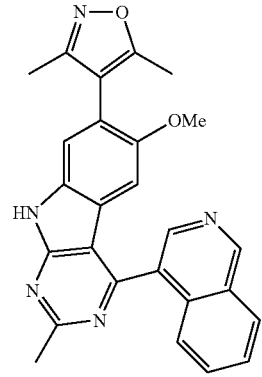

Cpd. No. 79

TFA salt yield: 54%. Suzuki coupling-Pd(PPh$_3$)$_4$—K$_2$CO$_3$ Method. $^1$H NMR (300 MHz, MeOD-d4): 9.78 (s, 1H), 8.98 (s, 1H), 8.53-8.46 (m, 1H), 8.04-7.92 (m, 2H), 7.90-7.82 (m, 1H), 7.55 (s, 1H), 6.23 (s, 1H), 3.20 (s, 3H), 3.01 (s, 3H), 2.26 (s, 3H), 2.07 (s, 3H). ESI-MS calculated for C$_{26}$H$_{22}$N$_5$O$_2$ [M+H]$^+$=436.18, Obtained: 436.50.

TFA salt yield: 35%. Suzuki coupling-Pd(PPh$_3$)$_4$—K$_2$CO$_3$ Method. $^1$H NMR (300 MHz, MeOD-d4): 9.54 (s, 1H), 8.74 (s, 1H), 8.61 (dd, J=7.75, 1.22 Hz, 1H), 8.52 (d, J=6.18 Hz, 1H), 8.47-8.35 (m, 2H), 7.54 (s, 1H), 6.42 (s, 1H), 3.32 (s, 3H), 2.99 (s, 3H), 2.26 (s, 3H), 2.08 (s, 3H). ESI-MS calculated for C$_{26}$H$_{22}$N$_5$O$_2$ [M+H]$^+$=436.18, Obtained: 436.56.

Cpd. No. 80

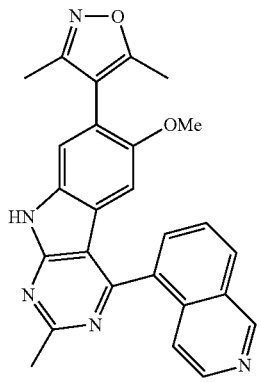

TFA salt yield: 29%. Suzuki coupling-Pd(PPh$_3$)$_4$—K$_2$CO$_3$ Method. $^1$H NMR (300 MHz, MeOD-d4): 9.85 (s, broad, 1H), 8.80 (d, J=8.32 Hz, 1H), 8.75-8.50 (broad, 1H), 8.56 (dd, J=7.24, 1.11 Hz), 8.26 (dd, J=8.29, 7.30 Hz, 1H), 8.04 (d, J=6.08 Hz, 1H), 6.32 (s, 1H), 3.29 (s, 3H), 3.00 (s, 3H), 2.27 (s, 3H), 2.08 (s, 3H). ESI-MS calculated for C26H22N5O2 [M+H]=436.18, Obtained: 436.68.

Cpd. No. 81

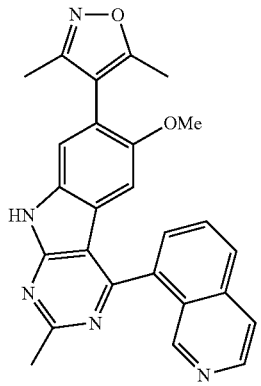

Cpd. No. 82

TFA salt yield: 18%. Suzuki coupling-Pd(PPh$_3$)$_4$—K$_2$CO$_3$ Method. $^1$H NMR (300 MHz, MeOD-d4): 8.89 (dd, J=4.28, 1.72 Hz, 1H), 8.65 (dd, J=8.41, 1.68 Hz, 1H), 8.47 (dd, J=8.28, 1.31 Hz, 1H), 8.37 (dd, J=7.18, 1.36 Hz, 1H), 8.02 (dd, J=8.20, 7.26 Hz, 1H), 7.74 (dd, J=8.38, 4.28 Hz, 1H), 7.54 (s, 1H), 6.43 (s, 1H), 3.33 (s, 3H), 2.99 (s, 3H), 2.27 (s, 3H), 2.08 (s, 3H). ESI-MS calculated for C$_{26}$H$_{22}$N$_5$O$_2$ [M+H]$^+$=436.18, Obtained: 436.83.

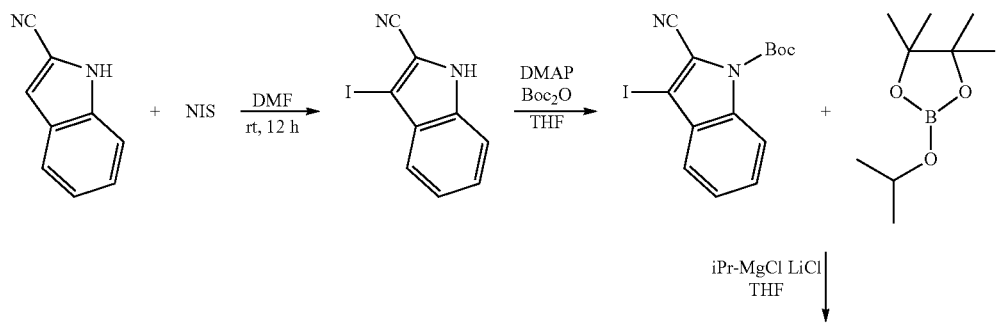

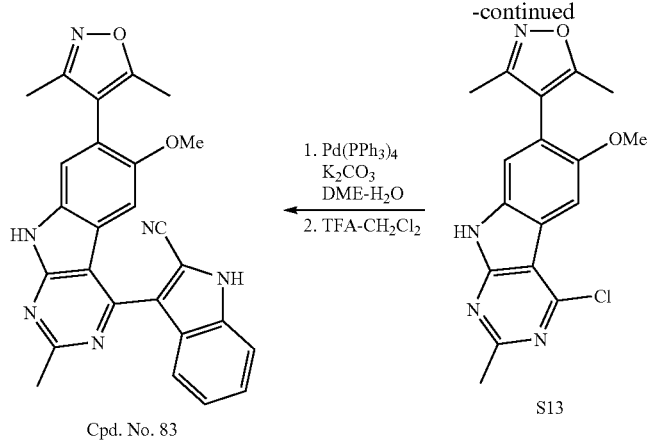

Cpd. No. 83

S13

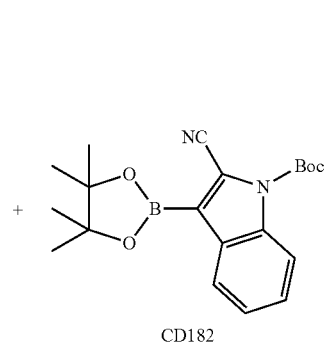

CD182

1H-Indole-2-carbonitrile (0.5 g) was dissolved in DMF (10 mL) at room temperature. The solution was cooled with a water-ice bath. N-Iodosuccinimide (NIS, 0.9 g) was added in small portions. The reaction was stirred at room temperature for 12 h before quenching with water. The aqueous layer was extracted with ethyl acetate (100 mL×3) and the combined organic layers were washed with water (40 mL×5) and dried over anhydrous sodium sulfate. The solvent was removed on a rotary evaporator. The residue was placed in a round-bottom flask and Boc$_2$O (3.1 g) and THF (20 mL) were added. DMAP (900 mg) was then added in small portions. The reaction was stirred at room temperature for 12 h. The solvent was removed on a rotary evaporator and the residue was purified by flash column chromatography to yield CD174 (1.52 g, 82% yield). $^1$H NMR (300 MHz, CDCl$_3$): 8.23 (d, J=8.52 Hz, 1H), 7.60-7.46 (m, 2H), 7.44-7.36 (m, 1H), 1.73 (s, 9H).

2-Isopropoxy-4,4,5,5-tetramethyl-1,3,2-dioxaborolane (0.6 g) and CD174 (0.7 g), and THF (10 m) were placed in a round-bottom flask. The solution was cooled with a water-ice bath. iPrMgCl—LiCl complex solution in THF (1.3 M, 1.60 mL) was added via a syringe. The reaction was stirred at room temperature for 3 h. The reaction mixture was quenched with statured aqueous NH$_4$Cl solution. The aqueous layer was extracted with ethyl acetate (100 mL×3) and the combined organic layers were washed with brine and dried over anhydrous sodium sulfate. The solvent was removed on a rotary evaporator and the residue was purified by flash column chromatography to yield CD182 (0.18 g). $^1$H NMR (300 MHz, CDCl$_3$): 8.19 (d, J=8.44 Hz, 1H), 8.05 (d, J=7.88 Hz, 1H), 7.47 (t, J=7.74 Hz, 1H), 7.34 (t, J=7.50 Hz, 1H), 1.73 (s, 9H), 1.41 (s, 12H).

Suzuki coupling of S13 and CD182 using Pd(PPh$_3$)$_4$—K$_2$CO$_3$ method and subsequent de-protection of Boc group in TFA-CH$_2$Cl$_2$ furnished Cpd. No. 90 in 2% yield after HPLC purification as a salt of CF$_3$CO$_2$H.

Cpd. No. 83

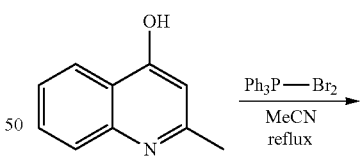

$^1$H NMR (300 MHz, MeOD-d4): 7.76 (dt, J=8.46, 0.79 Hz, 1H), 7.60 (ddd, J=8.40, 6.93, 1.11 Hz, 1H), 7.54 (dt, J=8.09, 0.95 Hz, 1H), 7.55 (s, 1H), 7.42-7.35 (m, 1H), 6.78 (s, 1H), 3.35 (s, 3H), 2.99 (s, 3H), 2.30 (s, 3H), 2.12 (s, 3H). ESI-MS calculated for C$_{26}$H$_{21}$N$_6$O$_2$ [M+H]$^+$=449.17, Obtained: 449.67

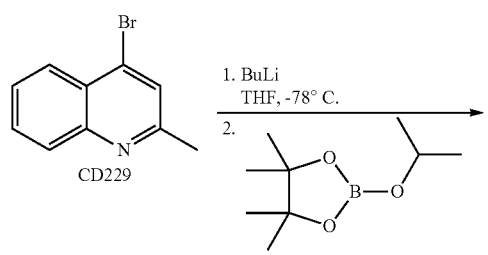

CD229

-continued

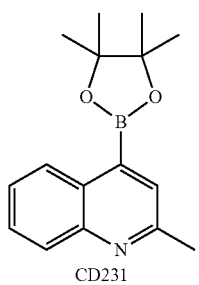

S13

CD231

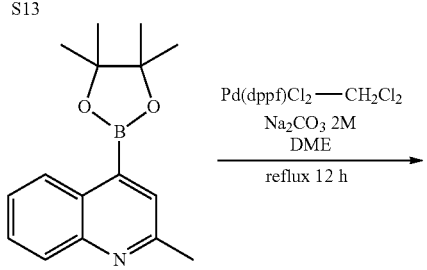

Cpd. No. 84

Ph₃P—Br₂ (prepared from 2.4 g Br₂ and 3.93 g PPh₃ in CH₂Cl₂, see reference J. Org. Chem. 1976, V 41, No. 20, p. 3279) was dissolved in MeCN. 2-Methyl-4-hydroxyquinoline (1.5 g) was added in one portion and the mixture was heated at reflux for 2 h. Solvent was removed and the residue was purified by flash column chromatography to furnish 4-bromo-2-methylquinoline CD229 in 0.60 g (41% yield). CD229 has also been prepared by reflux toluene solution of 2-methyl-4-hydroxyquinoline and POBr₃ for 4 h.

2-Isopropoxy-4,4,5,5-tetramethyl-1,3,2-dioxaborolane (5.20 g), 4-bromo-2-methylquinoline (2.23 g), and THF (40 mL) were placed in a round-bottom flask. The solution was cooled with a dry ice-ethanol bath at −78° C. BuLi (2.5 M THF solution, 7.2 mL) was added via a syringe. The reaction was stirred at −78° C. for 3 h before quenching with statured aqueous NH₄Cl solution. The aqueous layer was extracted with ethyl acetate (100 mL×3) and the combined organic layers were washed with brine and dried over anhydrous sodium sulfate. The solvent was removed on a rotary evaporator and the residue was purified by flash column chromatography to furnish 2-methylquinoline-4-boronic acid pinacol ester CD231 in 1.67 g (62% yield). ¹H NMR (300 MHz, CDCl₃): 8.58 (d, J=8.31 Hz, 1H), 8.02 (d, J=8.43 Hz, 1H), 7.66 (t, J=7.63 Hz, 1H), 7.51 (t, J=7.60 Hz, 1H), 7.26 (s, 1H), 2.74 (s, 3H), 1.43 (s, 12H). ESI-MS calculated for C₁₆H₂₁BNO₂ [M+H]⁺=270.17, observed: 270.83.

S13 (728 mg), 2-methylquinoline-4-boronic acid pinacol ester (1.67 g), 1,2-dimethoxyethane (60 mL), and Na₂CO₃ (20 mL, 2 M aqueous solution) were mixed in a round-bottom flask and the system was degassed to remove oxygen. Pd(dppf)Cl₂—CH₂Cl₂ complex (257 mg) was added on one portion and the system was degassed again. The mixture was heated at reflux for 12 h under nitrogen atmosphere. The reaction was then diluted with water and the aqueous layer was extracted with ethyl acetate (100 mL×3) and the combined organic layers were dried over anhydrous sodium sulfate. The solvent was removed in vacuum and the residue was purified by flash column chromatography to yield the desired product Cpd. No. 84 in 0.64 g (63% yield). Further purification was aided by a reverse phase HPLC to yield the corresponding products as a salt of CF₃CO₂H.

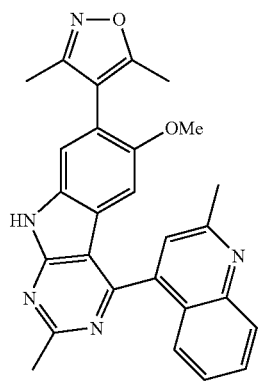

Cpd. No. 84

¹H NMR (300 MHz, MeOD-d4): 8.32 (d, J=8.47 Hz, 1H), 8.13 (s, 1H), 8.10 (ddd, J=8.44, 7.03, 1.26 Hz, 1H), 7.93 (d, J=7.86 Hz, 1H), 7.75 (t, J=7.71 Hz, 1H), 7.49 (s, 1H), 6.30 (s, 1H), 3.25 (s, 3H), 3.04 (s, 3H), 2.95 (s, 3H), 2.26 (s, 3H), 2.07 (s, 3H). ESI-MS calculated for C₂₇H₂₄N₅O₂ [M+H]⁺=450.19, Obtained: 450.42.

The following compounds were prepared using the same Suzuki coupling reaction conditions (sodium carbonate as base and (Pd(dppf)Cl₂—CH₂Cl₂ complex as catalyst) for the preparation of Cpd. No. 84. Their purification was performed on a reverse phase HPLC to yield the corresponding products as a salt of CF₃CO₂H.

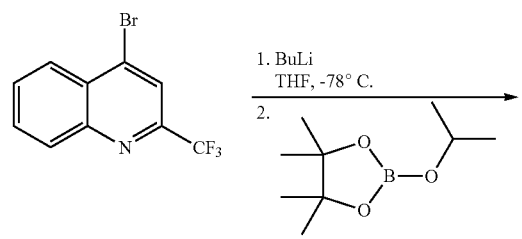

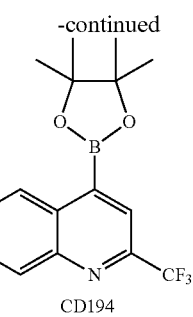

CD194

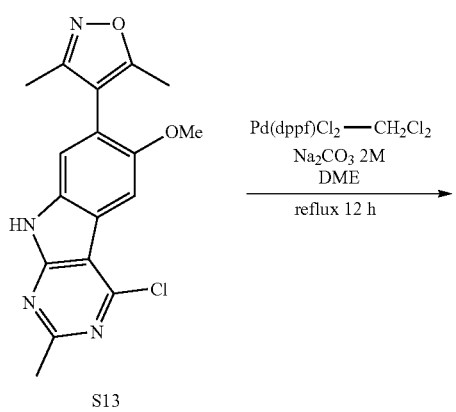

S13

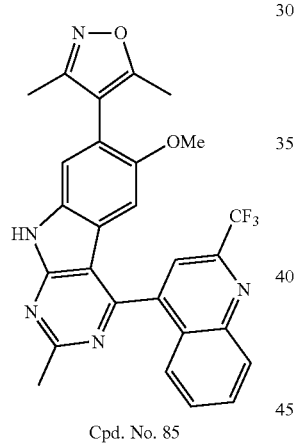

Cpd. No. 85

2-Trifluoromethyl-4-bromoquinoline (500 mg) was dissolved in anhydrous THF (15 mL). The solution was cooled to −78° C. in a dry ice-ethanol bath. BuLi (0.94 mL, 2.5 M in THF) was added dropwise and the mixture was stirred at −78° C. for 15 min. 2-Isopropoxy-4,4,5,5-tetramethyl-1,3,2-dioxaborolane (506 mg) was added via a syringe and the reaction mixture was stirred at −78° C. for 3 h before quenching with statured aqueous NH$_4$Cl solution. The aqueous layer was extracted with ethyl acetate (50 mL×3) and the combined organic layers were washed with brine and dried over anhydrous sodium sulfate. The solvent was removed on a rotary evaporator and the residue was purified by flash column chromatography to furnish 2-trifluoromethylquinoline 4-boronic acid pinacol ester CD194 in 0.35 g (60% yield). $^1$H NMR (300 MHz, CDCl$_3$): 8.74 (d, J=7.81 Hz, 1H), 8.22 (d, J=8.46 Hz, 1H), 7.80 (ddd, J=8.39, 6.85, 1.28 Hz, 1H), 7.69 (ddd, J=8.55, 7.04, 1.26 Hz, 1H), 1.45 (s, 12H).

Cpd. No. 85-TFA salt was prepared from Suzuki coupling of CD194 and S13 using Pd(dppf)Cl$_2$—CH$_2$Cl$_2$ complex —Na$_2$CO$_3$ (2 M) condition. 10% yield

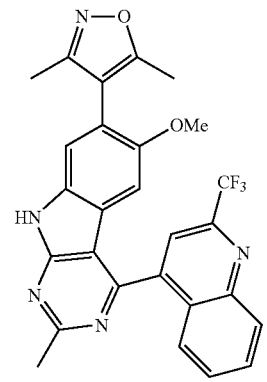

Cpd. No. 85

$^1$H NMR (300 MHz, MeOD-d4): 8.44 (d, J=8.61 Hz, 1H), 8.28 (s, 1H), 8.04 (t, J=7.71 Hz, 1H), 7.90 (d, J=8.19 Hz, 1H), 7.76 (t, J=8.03 Hz, 1H), 7.45 (s, 1H), 6.20 (s, 1H), 3.21 (s, 3H), 2.93 (s, 3H), 2.26 (s, 3H), 2.07 (s, 3H). ESI-MS calculated for C$_{27}$H$_{21}$F$_3$N$_5$O$_2$ [M+H]$^+$=504.16, Obtained: 504.58.

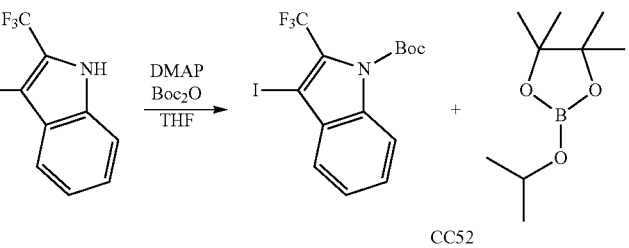

CC52 iPr-MgCl LiCl
THF

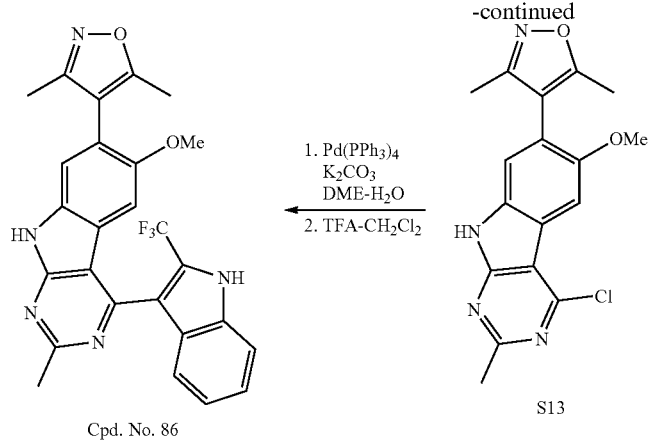

Cpd. No. 86

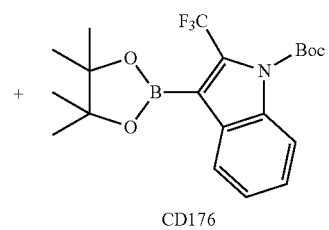

CD176

2-Trifluoromethyl-1H-indole (0.5 g) was dissolved in DMF (15 mL) at room temperature. The solution was cooled with a water-ice bath. N-Iodosuccinimide (NIS, 0.726 g) was added in small portions. The reaction was stirred at room temperature for 12 h before quenching with water. The aqueous layer was extracted with ethyl acetate (100 mL×3) and the combined organic layers were washed with water (40 mL×5) and dried over anhydrous sodium sulfate. The solvent was removed on a rotary evaporator. The residue was placed in a round-bottom flask and Boc$_2$O (1.18 g) and THF (20 mL) were added. DMAP (488 mg) was then added in small portions. The reaction was stirred at room temperature for 12 h. The solvent was removed on a rotary evaporator and the residue was purified by flash column chromatography to yield CC52 (1.52 g, 91% yield over two steps). $^1$H NMR (300 MHz, CDCl$_3$): 8.13 (d, J=7.94 Hz, 1H), 7.57 (d, J=7.94 Hz, 1H), 7.49 (t, J=7.49 Hz, 1H), 7.37 (t, J=7.53 Hz, 1H), 1.65 (s, 9H).

2-Isopropoxy-4,4,5,5-tetramethyl-1,3,2-dioxaborolane (690 g), CC52 (1.015 g), and THF (20 m) were placed in a round-bottom flask. The solution was cooled with an ice-water bath. iPrMgCl—LiCl (1.3 M THF solution, 2.50 mL) was added via a syringe. The reaction was stirred at 0° C. for 3 h. The reaction mixture was quenched with statured aqueous NH$_4$Cl solution. The aqueous layer was extracted with ethyl acetate (50 mL×3) and the combined organic layers were washed with brine and dried over anhydrous sodium sulfate. The solvent was removed on a rotary evaporator and the residue was purified by flash column chromatography to yield CD176 in 0.67 g (66% yield). $^1$H NMR (300 MHz, CDCl$_3$): 8.18 (d, J=8.45 Hz, 1H), 7.77 (d, J=7.81 Hz, 1H), 7.42 (t, J=7.81 Hz, 1H), 7.29 (t, J=7.55 Hz, 1H), 1.66 (s, 9H), 1.42 (s, 12H).

Cpd. 86-TFA salt was prepared from Suzuki coupling of CD176 and S13 using Pd(dppf)Cl$_2$—CH$_2$Cl$_2$ complex —Na$_2$CO$_3$ (2 M) condition. 5% yield.

Cpd. No. 86

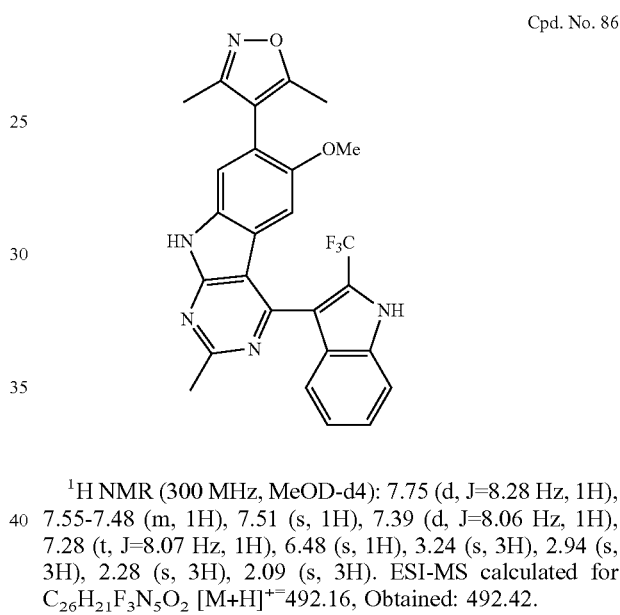

$^1$H NMR (300 MHz, MeOD-d4): 7.75 (d, J=8.28 Hz, 1H), 7.55-7.48 (m, 1H), 7.51 (s, 1H), 7.39 (d, J=8.06 Hz, 1H), 7.28 (t, J=8.07 Hz, 1H), 6.48 (s, 1H), 3.24 (s, 3H), 2.94 (s, 3H), 2.28 (s, 3H), 2.09 (s, 3H). ESI-MS calculated for C$_{26}$H$_{21}$F$_3$N$_5$O$_2$ [M+H]$^+$=492.16, Obtained: 492.42.

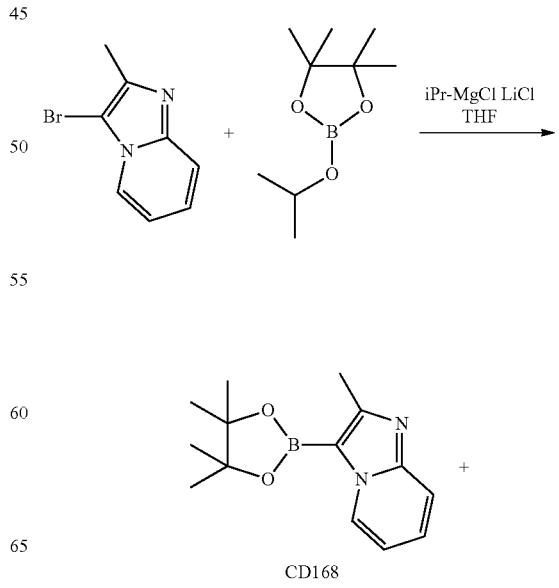

CD168

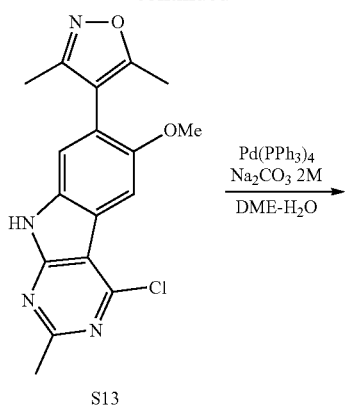

S13

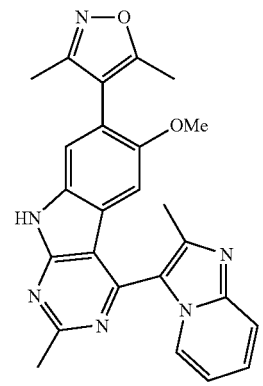

Cpd. No. 87

$^1$H NMR (300 MHz, MeOD-d4): 8.75 (d, J=6.78 Hz, 1H), 8.08 (dd, J=2.18, 1.05 Hz, 1H), 8.06 (d, J=1.04 Hz, 1H), 7.54-7.46 (m, 1H), 7.48 (s, 1H), 6.93 (s, 1H), 3.63 (s, 3H), 2.89 (s, 3H), 2.62 (s, 3H), 2.31 (s, 3H), 2.13 (s, 3H). ESI-MS calculated for $C_{25}H_{23}N_6O_2$ [M+H]$^+$=439.19, Obtained: 439.58.

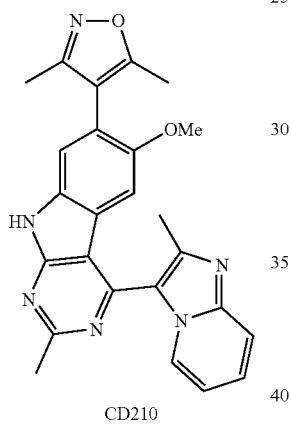

CD210

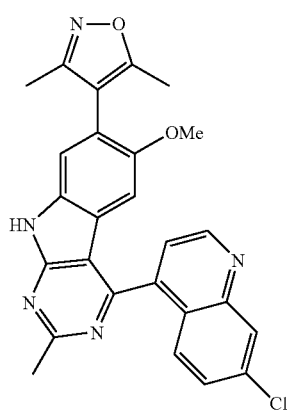

Cpd. No. 88

3-Bromo-2-methylimidazo[1,2-a]pyridine (2.11 g) and 2-isopropoxy-4,4,5,5-tetramethyl-1,3,2-dioxaborolane (2.98 g) were dissolved in anhydrous THF (40 mL) and the solution was cooled with an ice-water bath. iPrMgCl—LiCl (1.3 M in THF, 10 mL) was added via a syringe pump over 30 min. The reaction was stirred for 2.5 h before quenching with saturated aqueous NH$_4$Cl solution. The aqueous layer was extracted with ethyl acetate and the combined organic layers was washed with brine and dried over anhydrous sodium sulfate. The residue was purified by flash column chromatography to furnish the desired boronate CD168 in 1.25 g (48% yield). $^1$H NMR (300 MHz, CDCl$_3$): 8.81 (d, J=6.63 Hz, 1H), 7.54 (d, J=8.85 Hz, 1H), 7.25-7.16 (m, 1H), 6.78 (t, J=6.67 Hz, 1H), 2.63 (s, 3H), 1.37 (s, 12H).

Suzuki coupling of S13 and CD168 under Pd(dppf)Cl$_2$—CH$_2$Cl$_2$ complex —Na$_2$CO$_3$ (2M) furnished Cpd. No. 87-TFA salt in <7% yield.

TFA salt yield: 45%. Suzuki coupling-Pd(dppf)Cl$_2$—CH$_2$Cl$_2$ complex —Na$_2$CO$_3$ (2M). $^1$H NMR (300 MHz, MeOD-d4): 9.30 (d, J=4.44 Hz, 1H), 8.37 (d, J=2.01 Hz, 1H), 8.03 (d, J=4.44 Hz, 1H), 7.84 (d, J=9.00 Hz, 1H), 7.68 (dd, J=9.00, 2.07 Hz, 1H), 7.55 (s, 1H), 6.25 (s, 1H), 3.27 (s, 3H), 3.00 (s, 3H), 2.26 (s, 3H), 2.07 (s, 3H). ESI-MS calculated for $C_{26}H_{21}{}^{35}ClN_5O_2$ [M+H]$^+$=470.14, Obtained: 470.83.

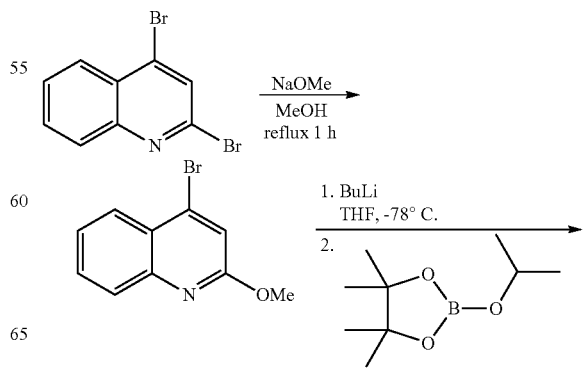

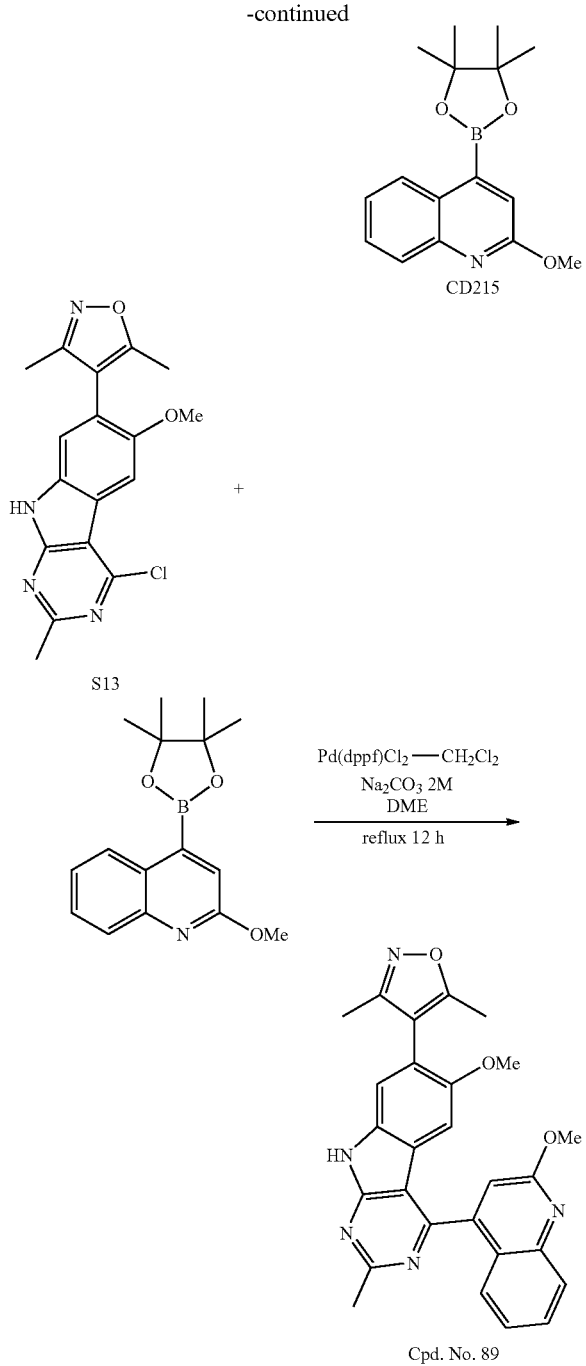

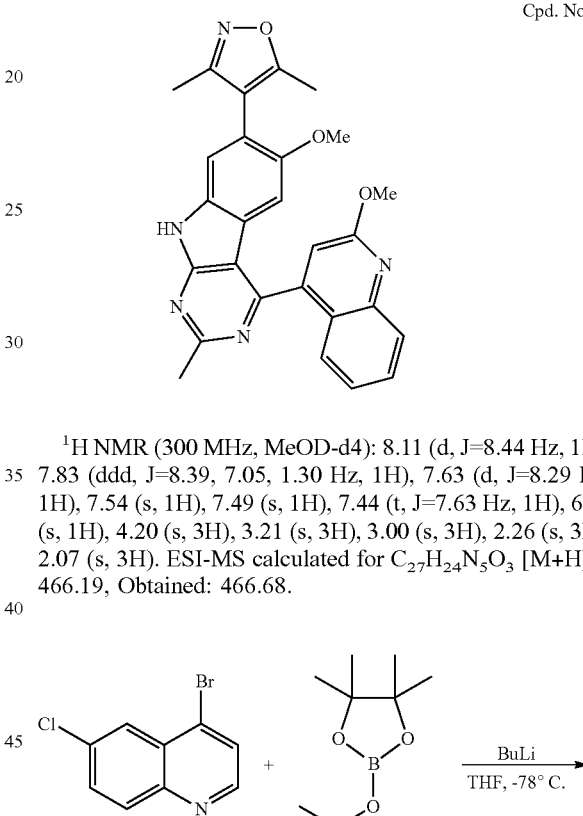

for 10 min before addition of 2-isopropoxy-4,4,5,5-tetramethyl-1,3,2-dioxaborolane (502 mg). The reaction was stirred for another 3 h before quenching with saturated aqueous NH₄Cl solution. The aqueous layer was extracted with ethyl acetate and the combined organic layers was washed with brine and dried over anhydrous sodium sulfate. The residue was purified by flash column chromatography to furnish the desired boronate CD215 in 0.35 g (82% yield). $^1$H NMR (300 MHz, CDCl$_3$): 8.52 (d, J=7.51 Hz, 1H), 7.86 (d, J=7.75 Hz, 1H), 7.60 (t, J=8.12 Hz, 1H), 7.41 (s, 1H), 7.40 (t, J=7.58 Hz, 1H), 4.07 (s, 3H), 1.40 (s, 12H).

Suzuki coupling of S13 and CD215 furnished Cpd. No. 89-TFA salt in 35% yield under Pd(dppf)Cl$_2$—CH$_2$Cl$_2$ complex —Na$_2$CO$_3$ (2M) condition.

$^1$H NMR (300 MHz, MeOD-d4): 8.11 (d, J=8.44 Hz, 1H), 7.83 (ddd, J=8.39, 7.05, 1.30 Hz, 1H), 7.63 (d, J=8.29 Hz, 1H), 7.54 (s, 1H), 7.49 (s, 1H), 7.44 (t, J=7.63 Hz, 1H), 6.27 (s, 1H), 4.20 (s, 3H), 3.21 (s, 3H), 3.00 (s, 3H), 2.26 (s, 3H), 2.07 (s, 3H). ESI-MS calculated for C$_{27}$H$_{24}$N$_5$O$_3$ [M+H]$^+$= 466.19, Obtained: 466.68.

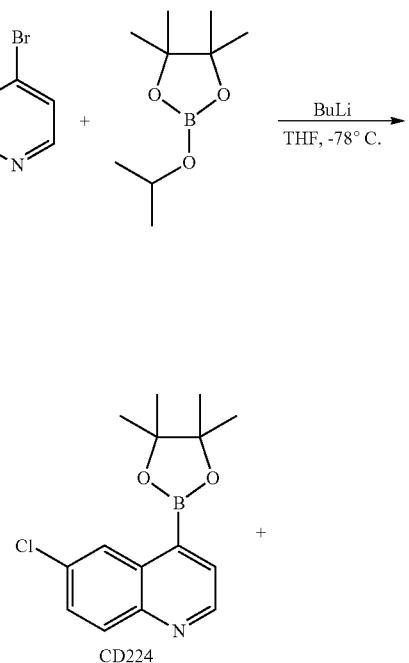

The preparation of 2-methoxy-4-bromoquinoline has been reported in patent WO 2010/030722 and the procedures in the literature were followed. 2,4-Dibromoquinoline (1.8 g) and sodium methoxide (25% in MeOH, 1.28 g) were dissolved in anhydrous MeOH (10 mL). The reaction was heated at reflux for 1 h. The reaction was cooled to room temperature and MeOH was removed on a rotary evaporator. The remaining residue was purified by flash column chromatography to furnish 2-methoxy-4-bromoquinolin in 0.715 g (48% yield).

2-Methoxy-4-bromoquinoline (357 mg) was dissolved in anhydrous THF (15 mL) and cooled down to −78° C. in a dry ice-ethanol bath. BuLi (2.5 M in THF, 1 mL) was slowly added via a syringe and the mixture was stirred at −78° C.

-continued

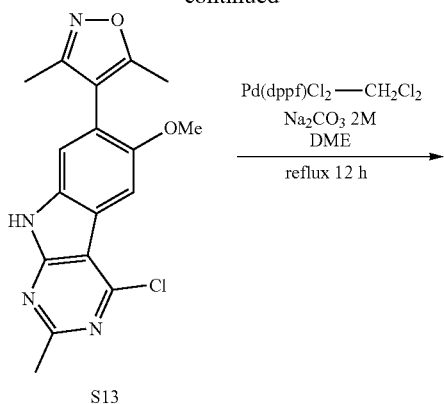

S13

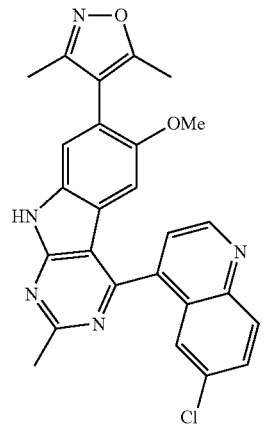

Cpd. No. 90

4-Bromo-6-chloro-quinoline (500 mg) and 2-isopropoxy-4,4,5,5-tetramethyl-1,3,2-dioxaborolane (1.04 g) were dissolved in anhydrous THF (20 mL) and the mixture was cooled to −78° C. in a dry ice-ethanol bath. BuLi (2.5 M in THF, 1.2 mL) was slowly added via a syringe and the reaction was stirred for another 3 h at −78° C. before quenching with saturated aqueous NH$_4$Cl solution. The aqueous layer was extracted with ethyl acetate and the combined organic layers was washed with brine and dried over anhydrous sodium sulfate. The residue was purified by flash column chromatography to furnish the desired 6-chloro-quinoline-4-boronic acid pinacol ester CD224 in 0.37 g (67% yield). $^1$H NMR (300 MHz, CDCl$_3$): 8.87 (d, J=4.08 Hz, 1H), 8.62 (d, J=2.14 Hz, 1H), 8.02 (d, J=8.98 Hz, 1H), 7.85 (d, J=4.08 Hz, 1H), 7.60 (dd, J=8.97, 2.15 Hz, 1H), 1.40 (s, 12H). ESI-MS calculated for C$_{15}$H$_{18}$B$^{35}$ClNO$_2$ [M+H]$^+$=290.11, observed: 290.56.

Suzuki coupling of S13 and CD224 furnished Cpd. No. 90-TFA salt in 44% yield under Pd(dppf)Cl$_2$—CH$_2$Cl$_2$ complex —Na$_2$CO$_3$ (2M) condition.

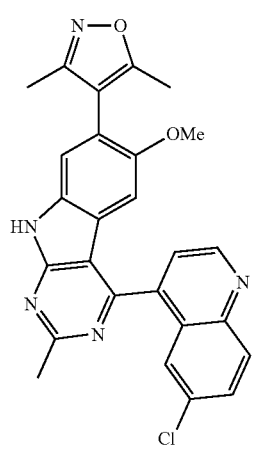

Cpd. No. 90

$^1$H NMR (300 MHz, MeOD-d4): 12.18 (s, broad, 1H), 9.26 (s, 1H), 8.35 (d, J=8.79 Hz, 1H), 7.97 (s, 1H), 7.82 (d, J=8.89 Hz, 1H), 7.76 (s, 1H), 7.26 (s, 1H), 6.24 (s, 1H), 3.46 (s, 3H), 2.96 (s, 3H), 2.25 (s, 3H), 2.09 (s, 3H). $^{13}$C NMR (75 MHz, MeOD-d4): 166.78, 160.20, 159.65, 155.43, 154.08, 150.63, 148.94, 144.89, 140.19, 135.71, 134.25, 132.90, 130.27, 125.55, 124.19, 123.11, 118.29, 116.30, 113.03, 112.29, 103.89, 55.47, 23.25, 11.72, 10.69. ESI-MS calculated for C$_{26}$H$_{21}$$^{35}$ClN$_5$O$_2$ [M+H]$^+$=470.14, Obtained: 470.60.

7-Fluroquinoline-4-boronic acid pinacol ester CD223 was prepared from 4-bromo-7-fluro-quinoline in 75% yield using the same method for preparation of CD224. $^1$H NMR (300 MHz, CDCl$_3$): 8.81 (d, J=4.20 Hz, 1H), 8.59 (dd, J=9.26, 6.29 Hz, 1H), 7.75 (d, J=4.19 Hz, 1H), 7.68 (dd, J=10.07, 2.62 Hz, 1H), 7.27 (ddd, J=8.82, 8.70, 2.55 Hz, 1H), 1.33 (s, 12H). $^{13}$C NMR (75 MHz, CDCl$_3$): 164.31, 161.00, 150.24, 148.68 (d, J$_{C-F}$=12.54 Hz), 130.76 (d, J$_{C-F}$=9.51 Hz), 128.20, 128.03 (d, J$_{C-F}$=1.95 Hz), 117.20 (d, J$_{C-F}$=24.54 Hz), 112.81 (d, J$_{C-F}$=20.13), 84.71, 24.93. ESI-MS calculated for C$_{15}$H$_{18}$BFNO$_2$ [M+H]$^+$=274.14, observed: 274.75.

Suzuki coupling of 7-fluroquinoline-4-boronic acid pinacol ester (CD223) and S13 furnished Cpd. No. 91-TFA salt in 31% under Pd(dppf)Cl$_2$—CH$_2$Cl$_2$ complex —Na$_2$CO$_3$ (2M) condition.

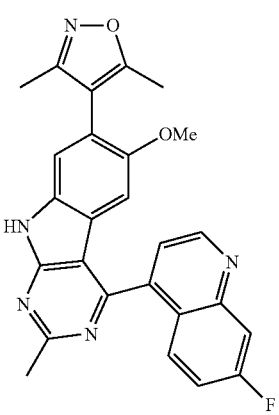

Cpd. No. 91

¹H NMR (300 MHz, MeOD-d4): 9.26 (d, J=4.46 Hz, 1H), 8.02-7.84 (m, 3H), 7.55-7.46 (m, 1H), 7.49 (s, 1H), 6.24 (s, 1H), 3.26 (s, 3H), 2.95 (s, 3H), 2.26 (s, 3H), 2.07 (s, 3H). ESI-MS calculated for C₂₆H₂₁FN₅O₂ [M+H]⁺=454.17, Obtained: 454.42.

6-Fluroquinoline-4-boronic acid pinacol ester CD234 was prepared from 4-bromo-6-fluro-quinoline in 85% yield using the same method for preparation of CD224. ¹H NMR (300 MHz, CDCl₃): 8.85 (d, J=4.09 Hz, 1H), 8.30 (dd, J=10.48, 2.69 Hz, 1H), 8.07 (dd, J=9.20, 5.71 Hz, 1H), 7.84 (d, J=4.02 Hz, 1H), 7.44 (ddd, J=9.46, 9.25, 2.76 Hz, 1H), 1.39 (s, 12H). ESI-MS calculated for C₁₅H₁₈BFNO₂ [M+H]⁺=274.14, observed: 274.67.

Suzuki coupling of 6-fluroquinoline-4-boronic acid pinacol ester (CD234) and S13 furnished Cpd. No. 92-TFA salt in 47% under Pd(dppf)Cl₂—CH₂Cl₂ complex —Na₂CO₃ (2M) condition.

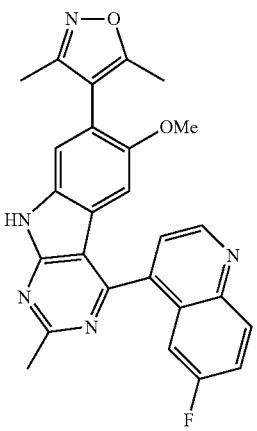

Cpd. No. 92

¹H NMR (300 MHz, MeOD-d4): 9.23 (d, J=4.44 Hz, 1H), 8.39 (dd, J=9.33, 5.33 Hz, 1H), 8.01 (d, J=4.42 Hz, 1H), 7.80 (ddd, J=9.25, 8.32, 2.78 Hz, 1H), 7.56-7.48 (m, 1H), 7.52 (s, 1H), 6.28 (s, 1H), 3.27 (s, 3H), 2.97 (s, 3H), 2.27 (s, 3H), 2.08 (s, 3H). ESI-MS calculated for C₂₆H₂₁FN₅O₂ [M+H]⁺= 454.17, Obtained: 454.44.

2-Isopropylpyridine-4-boronic acid pinacol ester CD263 was prepared from 4-bromo-2-isopropylpyridine in 30% yield using the same method for preparation of CD224. ¹H NMR (300 MHz, CDCl₃): 8.55 (d, J=5.62 Hz, 1H), 7.51 (s, 1H), 7.43 (d, J=5.60 Hz, 1H), 3.07 (septet, J=6.92 Hz, 1H), 1.35 (s, 12H), 1.31 (d, J=6.93 Hz, 6H).

Suzuki coupling of 2-isopropyridine-4-boronic acid pinacol ester (CD263) and S13 furnished Cpd. No. 93-TFA salt in 46% yield under Pd(dppf)Cl₂—CH₂Cl₂ complex —Na₂CO₃ (2M) condition.

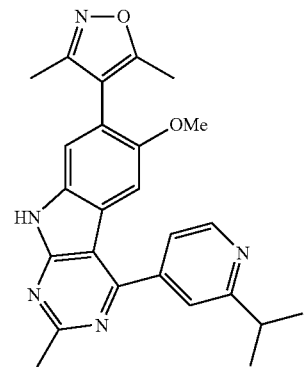

Cpd. No. 93

¹H NMR (300 MHz, MeOD-d4): 9.00 (d, J=5.61 Hz, 1H), 8.29 (d, J=0.90 Hz, 1H), 8.22 (dd, J=5.63, 1.65 Hz, 1H), 7.52 (s, 1H), 7.29 (s, 1H), 3.73 (s, 3H), 3.46 (septet, J=6.95 Hz, 1H), 2.92 (s, 3H), 2.31 (s, 3H), 2.14 (s, 3H), 1.51 (d, J=6.95 Hz, 6H). ¹³C NMR (75 MHz, MeOD-d4): 168.16, 167.57, 163.02, 161.14, 158.96, 155.20, 152.54, 149.33, 147.19, 135.98, 124.60, 124.52, 123.63, 120.32, 116.89, 114.70, 111.33, 105.43, 56.67, 36.31, 24.24, 22.55, 11.68, 10.81. ESI-MS calculated for C₂₅H₂₆N₅O₂ [M+H]⁺=428.21, Obtained: 428.75.

2-Methylpyridine-4-boronic acid pinacol ester is commercially available from Small Molecules Inc. It has also been prepared from following procedures: 4-Bromo-2-methylpyridine (1.0 g), Bis(pinacolato)diboron (1.4 g), potassium acetate (1.35 g), and anhydrous dioxane (30 mL) was mixed in a round-bottom flask. The system was degassed to remove oxygen and Pd(dppf)Cl₂ (35 mg) was added in one portion. The system was degassed again and heated at 100° C. for 12 h. The reaction was cooled to room temperature and black precipitate was removed by filtration. The solvent was removed on a rotary evaporator and the residue was purified by flash column to furnish 2-methylpyridine-4-boronic acid pinacol ester.

Suzuki coupling of 2-methylpyridine-4-boronic acid pinacol ester and S13 furnished Cpd. No. 94-TFA salt in 27% yield under Pd(dppf)Cl₂—CH₂Cl₂ complex —Na₂CO₃ (2M) condition.

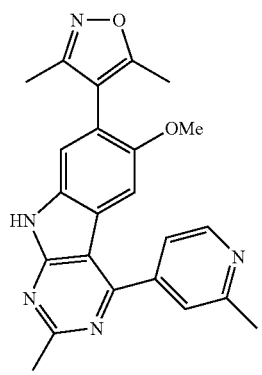

Cpd. No. 94

¹H NMR (300 MHz, MeOD-d4): 8.98 (d, J=5.85 Hz, 1H), 8.38 (s, 1H), 8.30 (d, J=5.62 Hz, 1H), 7.49 (s, 1H), 7.35 (s, 1H), 3.76 (s, 3H), 3.30 (s, 3H), 2.89 (s, 3H), 2.32 (s, 3H), 2.14 (s, 3H). ESI-MS calculated for C₂₃H₂₂N₅O₂ [M+H]⁺= 400.18, Obtained: 400.52.

3-Methylpyridine-4-boronic acid pinacol ester CD275 was prepared from 4-bromo-3-methyl pyridine using the same method for the preparation of 2-methylpyridine-4-boronic acid pinacol ester in 54% yield. ESI-MS calculated for $C_{12}H_{19}BNO_2$ [M+H]$^+$=220.15, Obtained: 220.72.

Suzuki coupling of 3-methylpyridine-4-boronic acid pinacol ester and S13 furnished Cpd. No. 95-TFA salt in 27% yield under Pd(dppf)Cl$_2$—CH$_2$Cl$_2$ complex —Na$_2$CO$_3$ (2M) condition.

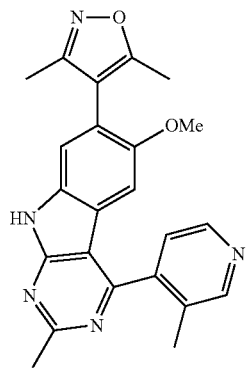

Cpd. No. 95

$^1$H NMR (300 MHz, MeOD-d4): 8.98 (s, 1H), 8.89 (d, J=5.25 Hz, 1H), 7.98 (d, J=5.32 Hz, 1H), 7.52 (s, 1H), 6.73 (s, 1H), 3.61 (s, 3H), 2.92 (s, 3H), 2.41 (s, 3H), 2.30 (s, 3H), 2.12 (s, 3H). ESI-MS calculated for $C_{23}H_{22}N_5O_2$ [M+H]$^+$= 400.18, Obtained: 400.58.

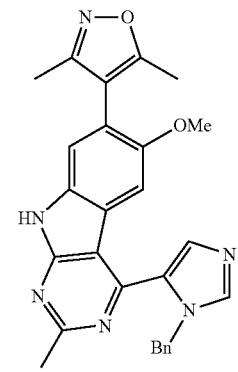

Cpd. No. 96

TFA salt yield: 29% Suzuki coupling-Pd(dppf)Cl$_2$—CH$_2$Cl$_2$ complex-Na$_2$CO$_3$ (2M). The boronic acid required is commercially available. $^1$H NMR (300 MHz, MeOD-d4): 9.41 (s, 1H), 8.35 (s, 1H), 7.38 (s, 1H), 7.12 (s, 1H), 7.02 (s, 5H), 5.72 (s, 2H), 3.75 (s, 3H), 2.84 (s, 3H), 2.30 (s, 3H), 2.14 (s, 3H). ESI-MS calculated for $C_{27}H_{25}N_6O_2$ [M+H]$^+$= 465.20, Obtained: 465.58.

The preparation of 4-nitro-5,6,7,8-tetrahydroquinoline-N-oxide has been previously reported in WO02076979 and the same procedure was followed.

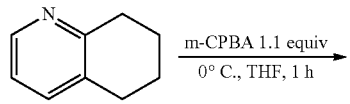

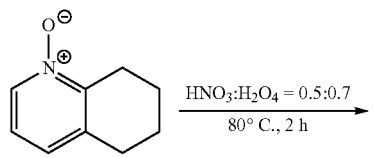

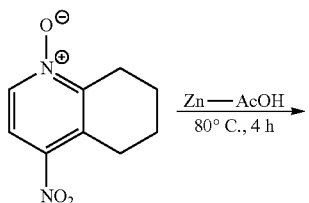

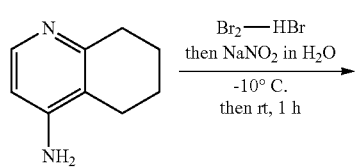

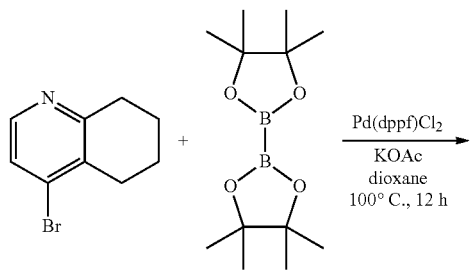

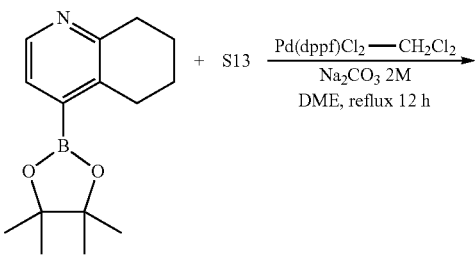

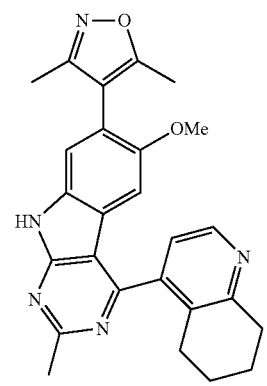

Cpd. No. 97

5,6,7,8-Tetrahydroquinoline (5.2 g) was dissolved in 100 mL anhydrous THF and the solution was cooled with ice-water bath. m-CPBA (10.8 g) was added in small portions and the mixture was stirred at 0° C. for 1 h. THF was then removed on a rotary evaporator and the residue was dissolved in $CH_2Cl_2$. The $CH_2Cl_2$ solution was washed with NaOH (2 N, 20 mL) and citric acid (10%, 40 mL) and dried over anhydrous sodium sulfate. The solvent was removed on a rotary evaporator and the residue of 5,6,7,8-tetrahydroquinoline-N-oxide was used for the next step without purification.

To a round bottom flask containing 5,6,7,8-tetrahydroquinoline-N-oxide was added a mixture of $HNO_3$—$H_2SO_4$ (10 mL (90%): 14 mL (98%)) at 0° C. The mixture was then heated at 80° C. for 2 h and was then poured onto ice cubes. The aqueous layer was extracted with $CH_2Cl_2$ to furnish 4-nitro-5,6,7,8-tetrahydroquinoline-N-oxide. The crude material was used without further purification.

The crude 4-nitro-5,6,7,8-tetrahydroquinoline-N-oxide was dissolved in acetic acid (40 mL) and zinc powder (20.8 g) was slowly added at room temperature and the mixture was heated at 80° C. for 4 h. The precipitate was removed by filtration and washed with acetic acid. The combined acetic acid solution was concentrated on a rotary evaporator and was neutralized by aqueous NaOH solution. The aqueous solution was extracted by chloroform (50 mL×8) and the combined organic phase was dried over anhydrous sodium sulfate. The solvent was removed on a rotary evaporator and the residue was purified by flash column chromatogram to furnish 4-amino-5,6,7,8-tetrahydroquinoline in 1.4 g (23% over three steps).

4-Amino-5,6,7,8-tetrahydroquinoline (1.4 g) was dissolved in 48% HBr (6.7 mL) and the solution was cooled to −10° C. To this solution, $Br_2$ was added via a syringe followed by slow addition of $NaNO_2$ (3.3 g) in 4 mL water and the reaction mixture was warm up to room temperature and stirred at room temperature for 1 h. The reaction mixture was then poured onto ice and the pH was adjusted=9 using aqueous sodium hydroxide solution. The aqueous layer was extracted with ethyl acetate and combined organic layer was dried over anhydrous sodium sulfate. Removal of solvent on a rotary evaporator and the remaining residue was purified by flash column chromatogram to furnish 4-bromo-5,6,7,8-tetrahydroquinoline in 1.00 g (47% yield).

4-Bromo-5,6,7,8-tetrahydroquinoline (0.5 g), bis(pinacolato)diboron (1 g), potassium acetate (735 mg), and anhydrous dioxane (20 mL) were placed in a round-bottom flask. The system was degassed to remove oxygen followed by the addition of $Pd(dffp)Cl_2$ (176 mg) in one portion. The system was degassed again and the reaction was heated at 100° C. for 12 h. The reaction was cooled to room temperature and black precipitate was removed by filtration. The solvent was removed on a rotary evaporator and the residue was purified by flash column chromatogram to furnish 5,6,7,8-tetrahydroquinoline-4-boronic acid pinacol ester CD292 in 0.18 g (28% yield). $^1$H NMR (300 MHz, $CDCl_3$): 8.32 (d, J=4.58 Hz, 1H), 7.36 (d, J=4.59 Hz, 1H), 2.98 (t, J=6.03 Hz, 2H), 2.92 (t, J=6.09 Hz, 2H), 1.90-1.72 (m, 4H), 1.33 (s, 12H). ESI-MS calculated for $C_{15}H_{23}BNO_2$ $[M+H]^+$=260.18, Obtained: 260.33.

Suzuki coupling of 5,6,7,8-tetrahydroquinoline-4-boronic acid pinacol ester and S13 furnished Cpd. No. 97-TFA salt in 33% yield under $Pd(dppf)Cl_2$—$CH_2Cl_2$ complex-$Na_2CO_3$ (2M) condition.

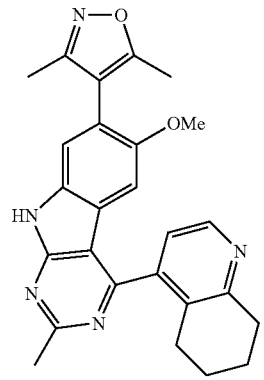

Cpd. No. 97

$^1$H NMR (300 MHz, MeOD-d4): 8.86 (d, J=5.76 Hz, 1H), 8.02 (d, J=5.76 Hz, 1H), 7.50 (s, 1H), 6.82 (s, 1H), 3.66 (s, 3H), 3.00-2.80 (m, 1H), 2.88 (s, 3H), 2.80-2.50 (m, 1H), 2.30 (s, 3H), 2.12 (s, 3H), 2.10-2.00 (m, 2H), 2.00-1.70 (m, 2H). $^{13}$C NMR (75 MHz, MeOD-d4): 168.13, 163.57, 161.14, 158.66, 157.33, 155.40, 151.94, 150.93, 142.17, 137.35, 135.78, 125.61, 123.39, 120.14, 116.89, 114.71, 111.32, 104.82, 56.69, 49.21, 30.02, 27.15, 24.65, 22.51, 22.21, 11.66, 10.78. ESI-MS calculated for $C_{26}H_{26}N_5O_2$ $[M+H]^+$=440.21, Obtained: 440.67

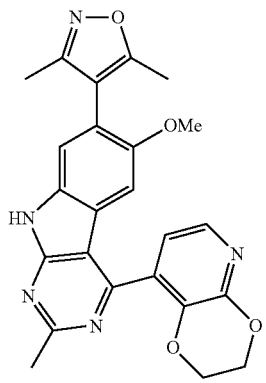

Cpd. No. 98

Cpd. No. 98 was synthesized from S13 and 8-(4,4,5,5-tetramethyl-1,3,2-dioxaborolan-2-yl)-2,3-dihydro-[1,4]dioxino[2,3-b]pyridine using Suzuki coupling condition [Pd $(dppf)Cl_2$—$CH_2Cl_2$ as catalyst and $Na_2CO_3$ 2 M in water as base]. HPLC purification yielded the Cpd. No. 98-TFA salt in 25% yield. $^1$H NMR (300 MHz, MeOD-d4): 8.12 (d, J=5.09 Hz, 1H), 7.56 (s, 1H), 7.45 (d, J=5.09 Hz, 1H), 7.15 (s, 1H), 4.65-4.55 (m, 2H), 4.44-4.35 (m, 2H), 3.72 (s, 3H), 2.97 (s, 3H), 2.31 (s, 3H), 2.13 (s, 3H). ESI-MS calculated for $C_{24}H_{22}N_5O_4$ $[M+H]^+$=444.17, Obtained: 444.46.

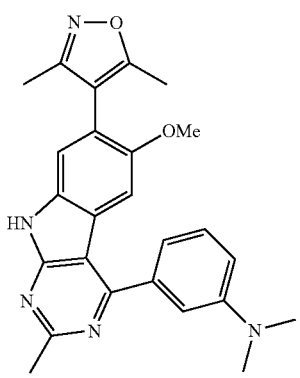

Cpd. No. 99

Cpd. No. 99 was synthesized from S13 and 3-(N,N-dimethylamino)phenylboronic acid using Suzuki coupling condition [Pd(dppf)Cl$_2$—CH$_2$Cl$_2$ as catalyst and Na$_2$CO$_3$ 2 M in water as base]. HPLC purification yielded the Cpd. No. 99-TFA salt in 50% yield. $^1$H NMR (300 MHz, MeOD-d4): 7.72-7.62 (m, 1H), 7.54 (s, 1H), 7.42 (s, 1H), 7.40-7.30 (m, 2H), 7.28 (dd, J=8.47, 2.05 Hz, 1H), 3.68 (s, 3H), 3.12 (s, 6H), 2.96 (s, 3H), 2.30 (s, 3H), 2.13 (s, 3H). ESI-MS calculated for C$_{25}$H$_{26}$N$_5$O$_2$ [M+H]$^+$=428.21, Obtained: 428.58.

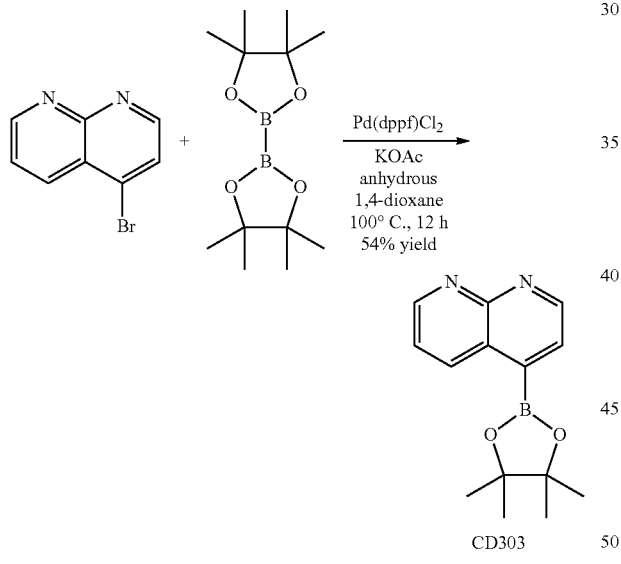

CD303

CD303, 4-(4,4,5,5-tetramethyl-1,3,2-dioxaborolan-2-yl)-1,8-naphthyridine, was synthesized following the method shown in the above scheme. 4-Bromo-1,8-naphthyridine (400 mg), bis(pinacolato)diboron (1.0 g), and KOAc (600 mg) were placed in a round-bottom flask equipped with a magnetic stirring bar. Anhydrous 1,4-dioxane (20 mL) was added and the mixture was degassed for 5 min to remove oxygen. Pd(dppf)Cl$_2$ (140 mg) was added and the system was again degassed and followed by refilling nitrogen. The mixture was heated at 100° C. for overnight (>12 h). The reaction was cooled to room temperature and filtered. The volatile components were removed on a rotary evaporator and the residue was purified in a preparative HPLC to yield CD303-TFA salt in 0.38 g. $^1$H NMR (300 MHz, MeOD-d4): 9.67 (d, J=8.48 Hz, 1H), 9.30 (t, J=5.11 Hz, 2H), 8.33 (d, J=4.36 Hz, 1H), 8.10 (dd, J=8.36, 4.89 Hz, 1H), 1.46 (s, 12H). ESI-MS calculated for C$_{14}$H$_{18}$BN$_2$O$_2$ [M+H]$^+$=257.15, obtained: 257.44.

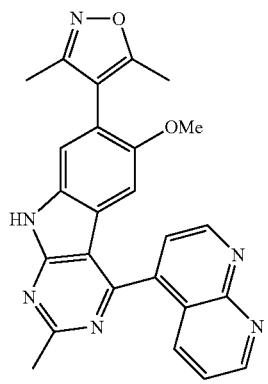

Cpd. No. 100

Cpd. No. 100 was synthesized from S13 and 4-(4,4,5,5-tetramethyl-1,3,2-dioxaborolan-2-yl)-1,8-naphthyridine-TFA salt using Suzuki coupling condition [Pd(dppf)Cl$_2$—CH$_2$Cl$_2$ as catalyst and Na$_2$CO$_3$ 2 M in water as base]. HPLC purification yielded the Cpd. No. 100-TFA salt in 5% yield. $^1$H NMR (300 MHz, MeOD-d4): 9.50 (d, J=4.40 Hz, 1H), 9.30 (d, J=4.29 Hz, 1H), 8.49 (dd, J=8.46, 1.76 Hz, 1H), 8.21 (d, J=4.48 Hz, 1H), 7.79 (dd, J=8.47, 4.38 Hz, 1H), 7.53 (s, 1H), 6.39 (s, 1H), 2.98 (s, 3H), 2.27 (s, 3H), 2.08 (s, 3H), 2.03 (s, 3H). ESI-MS calculated for C$_{25}$H$_{21}$N$_6$O$_2$ [M+H]$^+$=437.17, Obtained: 437.42.

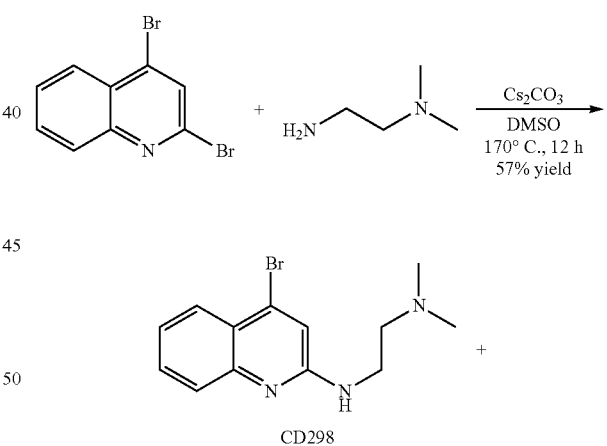

CD298

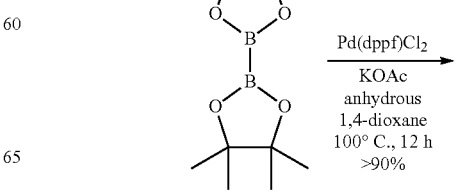

-continued

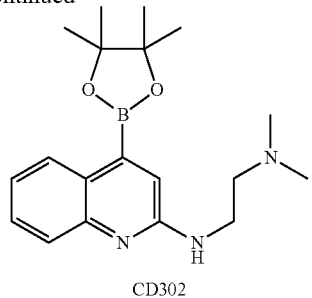

CD302

$N^1,N^1$-Dimethyl-$N^2$-(4-(4,4,5,5-tetramethyl-1,3,2-dioxaborolan-2-yl)quinolin-2-yl)ethane-1,2-diamine was synthesized following the method shown in the above scheme.

Step 1: synthesis of CD298. 2,4-Dibromoquinoline (572 mg), $N^1,N^1$-dimethylethane-1,2-diamine (240 mg), $Cs_2CO_3$ (652 mg), and DMSO (4 mL) were placed in a sealed tube. The mixture was heated at 170° C. for 12 h. The mixture was cooled to room temperature and purified on a reverse phase preparative HPLC. The desired product CD298-TFA salt was isolated in 0.47 g (57% yield). The 4-amination regioisomer was also isolated in ca. 40% yield. Free amine CD298 was also purified by flash column chromatography but in a compromised yield. The structure of CD298 was confirmed by comparing $^1$H NMR data of 2-bromo-N-methylquinolin-4-amine (Chemistry of heterocyclic compounds, vol 34, No. 7, 1998, page 837), 2-bromoquinolin-4-amine (J Med Chem 2009, 52, 926-931), and 4-bromoquinolin-2-amine (biochemistry, 2004, 43, 1440-1448). $^1$H NMR (300 MHz, CDCl$_3$, free amine): 7.93 (d, J=8.23 Hz, 1H), 7.65 (d, J=8.36 Hz, 1H), 7.54 (ddd, J=8.36, 6.96, 1.40 Hz, 1H), 7.25 (ddd, J=8.14, 6.91, 1.17 Hz, 1H), 6.98 (s, 1H), 5.40 (broad, 1H), 3.54 (dd, J=11.33, 5.25 Hz, 2H), 2.56 (t, J=5.81 Hz, 1H), 2.26 (s, 6H). ESI-MS calculated for $C_{13}H_{17}^{79}BrN_3$ [M+H]$^+$=294.06, obtained: 294.83.

Step 2: synthesis of CD302. CD302 [$N^1,N^1$-dimethyl-$N^2$-(4-(4,4,5,5-tetramethyl-1,3,2-dioxaborolan-2-yl)quinolin-2-yl)ethane-1,2-diamine] was synthesized from coupling of CD298 and bis(pinacolato)diboron using the same method for the preparation of CD303 [4-(4,4,5,5-tetramethyl-1,3,2-dioxaborolan-2-yl)-1,8-naphthyridine]. CD302 was obtained in 90% yield. $^1$H NMR (300 MHz, MeOD-d4): 8.53 (d, J=7.89 Hz, 1H), 7.91 (d, J=7.94 Hz, 1H), 7.75 (ddd, 8.43, 7.28, 1.26 Hz, 1H), 7.52 (ddd, J=8.39, 7.24, 1.11 Hz, 1H), 7.50 (s, 1H), 4.10 (t, J=6.18 Hz, 2H), 3.58 (t, J=6.18 Hz, 2H), 3.00 (s, 6H), 1.42 (s, 12ESI-MS calculated for $C_{19}H_{29}BN_3O_2$ [M+H]$^+$=342.24, obtained: 342.50

Cpd. No. 101

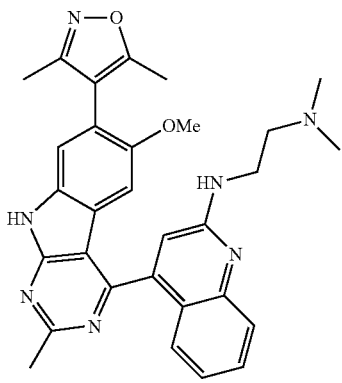

Cpd. No. 101 was synthesized from S13 and $N^1,N^1$-dimethyl-$N^2$-(4-(4,4,5,5-tetramethyl-1,3,2-dioxaborolan-2-yl)quinolin-2-yl)ethane-1,2-diamine using Suzuki coupling condition [Pd(dppf)Cl$_2$—CH$_2$Cl$_2$ as catalyst and Na$_2$CO$_3$ 2 M in water as base]. HPLC purification yielded the Cpd. No. 102-TFA salt in 37% yield. $^1$H NMR (300 MHz, MeOD-d4): 8.09 (d, J=8.35 Hz, 1H), 7.88 (t, J=7.31 Hz, 1H), 7.63 (d, J=7.62 Hz, 1H), 7.62 (s, 1H), 7.51 (s, 1H), 7.43 (t, J=7.62 Hz, 1H), 6.49 (s, 1H), 4.15 (t, J=6.05 Hz, 2H), 3.63 (t, J=6.15 Hz, 2H), 3.31 (s, 3H), 3.04 (s, 6H), 2.98 (s, 3H), 2.26 (s, 3H), 2.07 (s, 3H). ESI-MS calculated for $C_{30}H_{32}N_7O_2$ [M+H]$^+$= 522.26, Obtained: 522.50.

Cpd. No. 102

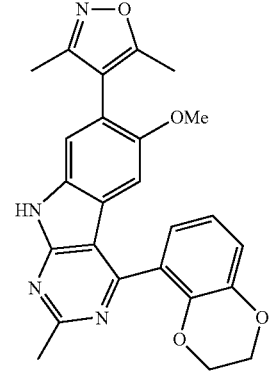

Cpd. No. 102 was synthesized from S13 and (2,3-dihydrobenzo[b][1,4]dioxin-5-yl)boronic acid using Suzuki coupling condition [Pd(dppf)Cl$_2$—CH$_2$Cl$_2$ as catalyst and Na$_2$CO$_3$ 2 M in water as base]. HPLC purification yielded the Cpd. No. 102-TFA salt in 28% yield. $^1$H NMR (300 MHz, MeOD-d4): 7.54 (s, 1H), 7.40-7.20 (m, 3H), 7.17 (s, 1H), 4.45-4.36 (m, 2H), 4.36-4.30 (m, 2H), 3.68 (s, 3H), 2.95 (s, 3H), 2.31 (s, 3H), 2.13 (s, 3H). ESI-MS calculated for $C_{25}H_{23}N_4O_4$ [M+H]$^+$=443.17, Obtained: 443.44.

Cpd. No. 103

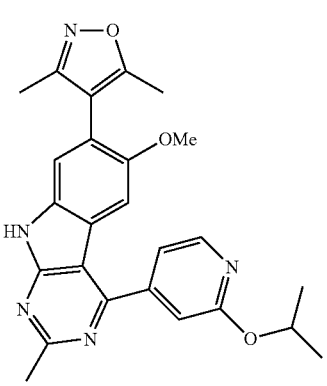

Cpd. No. 103 was synthesized from S13 and 2-isopropoxy-4-(4,4,5,5-tetramethyl-1,3,2-dioxaborolan-2-yl)pyridine using Suzuki coupling condition [Pd(dppf)Cl$_2$—CH$_2$Cl$_2$ as catalyst and Na$_2$CO$_3$ 2 M in water as base]. HPLC purification yielded the Cpd. No. 103-TFA salt in 43% yield. $^1$H NMR (300 MHz, MeOD-d4): 8.56 (d, J=5.20 Hz, 1H), 7.55 (s, 1H), 7.47 (dd, J=5.22, 1.40 Hz, 1H), 7.34 (d, J=3.55 Hz, 1H), 5.49 (septet, J=6.17 Hz, 1H), 3.73 (s, 3H), 2.95 (s, 3H), 2.31 (s, 3H), 2.14 (s, 3H), 1.41 (d, J=6.17 Hz, 6H). ESI-MS calculated for $C_{25}H_{26}N_5O_3$ [M+H]$^+$= 444.20, Obtained: 444.40.

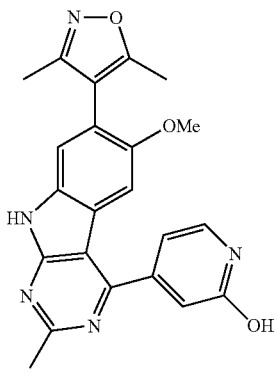

Cpd. No. 104

Suzuki coupling of S13 and 2-(tert-butoxy)-4-(4,4,5,5-tetramethyl-1,3,2-dioxaborolan-2-yl)pyridine [condition: Pd(dppf)Cl$_2$—CH$_2$Cl$_2$ as catalyst and Na$_2$CO$_3$ 2 M in water as base] afforded a mixture of Cpd. No. 104 and tert-Bu ether form of Cpd. No. 104. The mixture was treated with TFA followed by HPLC purification yielded the Cpd. No. 104-TFA salt as the major product. $^1$H NMR (300 MHz, MeOD-d4): 7.87 (d, J=6.71 Hz, 1H), 7.55 (s, 1H), 7.49 (s, 1H), 7.12 (s, 1H), 6.88 (dd, J=6.71, 1.69 Hz, 1H), 3.80 (s, 3H), 2.94 (s, 3H), 2.32 (s, 3H), 2.14 (s, 3H). ESI-MS calculated for C$_{22}$H$_{20}$N$_5$O$_3$ [M+H]$^+$=402.16, Obtained: 402.67.

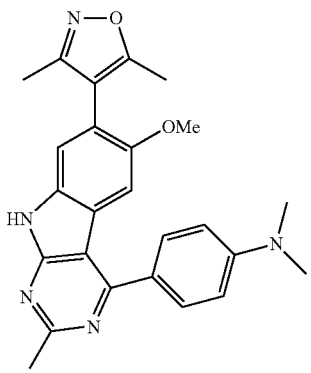

Cpd. No. 105

Cpd. No. 105 was synthesized from S13 and 4-(N,N-Dimethylamino)phenylboronic acid using Suzuki coupling condition [Pd(dppf)Cl$_2$—CH$_2$Cl$_2$ as catalyst and Na$_2$CO$_3$ 2 M in water as base]. HPLC purification yielded the Cpd. No. 105-TFA salt in 31% yield. $^1$H NMR (300 MHz, MeOD-d4): 7.94 (d, J=9.0 Hz, 2H), 7.64 (s, 1H), 7.51 (s, 1H), 7.08 (d, J=9.0 Hz, 2H), 3.77 (s, 3H), 3.17 (s, 3H), 2.91 (s, 3H), 2.32 (s, 3H), 2.14 (s, 3H). ESI-MS calculated for C$_{25}$H$_{26}$N$_5$O$_2$ [M+H]$^+$=428.21, Obtained: 428.42.

CD278 (25 mg, CF$_3$CO$_2$H salt) was dissolved in THF (15 mL). The solution was degassed to remove oxygen and 10% Pd on activated charcoal (20 mg) was added. A hydrogen balloon was applied to the reaction system and the reaction was stopped after 12 h. Pd-charcoal was filtered off and solvent was removed on a rotary evaporator. The residues were purified by reverse phase HPLC to yield the desired product Cpd. No. 106 in 17 mg (81% yield) as a salt of CF$_3$CO$_2$H.

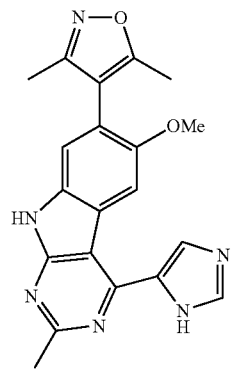

Cpd. No. 106

$^1$H NMR (300 MHz, MeOD-d4): 8.94 (s, 1H), 8.48 (s, 1H), 8.32 (s, 1H), 7.48 (s, 1H), 3.94 (s, 3H), 2.92 (s, 3H), 2.34 (s, 3H), 2.17 (s, 3H). ESI-MS calculated for C$_{20}$H$_{19}$N$_6$O$_2$ [M+H]=375.16, Obtained: 375.83.

CD281 (10 mg, CF$_3$CO$_2$H salt), iodobenzene (204 mg), Cs$_2$CO$_3$ (650 mg), proline (22 mg), CuI (40 mg), and DMF (5 mL) were placed in a round-bottom flask. The mixture was degassed to remove oxygen and then heated up at 120° C. for 12 h. The reaction mixture was quenched with water and the aqueous layer was extracted with ethyl acetate (50 mL×3). The combined organic layers were washed with brine and dried over anhydrous sodium sulfate. The solvent was removed on a rotary evaporator and the residue was purified by a phase HPLC. The desired product Cpd. No. 107 was obtained as TFA salt in 10 mg (19% yield).

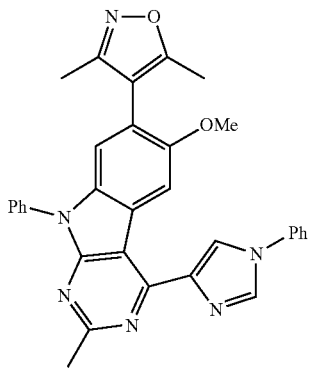

Cpd. No. 107

$^1$H NMR (300 MHz, MeOD-d4): 9.36 (s, 1H), 8.92 (s, 1H), 8.73 (s, 1H), 7.80-7.52 (m, 10H), 7.25 (s, 1H), 4.02 (s, 3H), 2.90 (s, 3H), 2.28 (s, 3H), 2.12 (s, 3H). ESI-MS calculated for C$_{32}$H$_{27}$N$_6$O$_2$ [M+H]$^+$=527.22, Obtained: 527.67.

CD281 (TFA salt, 15 mg), PhB(OH)$_2$ (36 mg), Cu(OAc)$_2$ (46 mg) and anhydrous molecular sieve 4 Å (250 mg) were placed in a round-bottom flask. Pyridine (0.05 mL) and CH$_2$Cl$_2$ (5 mL) was added via syringes. An oxygen balloon was applied to the reaction mixture and the reaction was stirred at room temperature for 2 days. The reaction was filtered through a pad of Celite® and the Celite® was washed with methanol. The organic layers were combined and the solvent was removed on a rotary evaporator. The remaining residue was purified by reverse phase HPLC to yield Cpd. No. 108 (4 mg, 22%), Cpd. No. 109 (2 mg, 12%), and Cpd. No. 107 (4 mg, 25%), with Cpd. Nos. 108 and 109 in the form of TFA-salt.

Cpd. No. 108

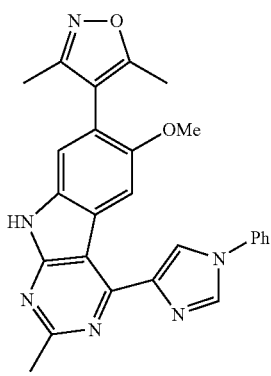

¹H NMR (300 MHz, MeOD-d4): 9.17 (s, 1H), 8.82 (s, 1H), 8.67 (s, 1H), 7.77 (d, J=8.05 Hz, 2H), 7.65 (t, J=7.76 Hz, 2H), 7.56 (d, J=7.33 Hz, 1H), 7.48 (s, 1H), 3.98 (s, 3H), 2.94 (s, 3H), 2.35 (s, 3H), 2.18 (s, 3H). ESI-MS calculated for $C_{26}H_{23}N_6O_2$ [M+H]$^+$=451.19, Obtained: 451.50.

Cpd. No. 109

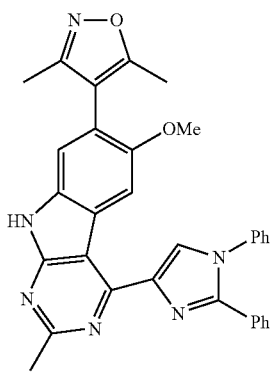

¹H NMR (300 MHz, MeOD-d4): 9.16 (s, 1H), 8.33 (s, 1H), 7.75-7.55 (m, 6H), 7.44 (s, 4H), 7.21 (s, 1H), 3.88 (s, 3H), 2.50 (s, 3H), 2.25 (s, 3H), 2.10 (s, 3H). ESI-MS calculated for $C_{32}H_{27}N_6O_2$ [M+H]$^+$=527.22, Obtained: 527.58.

S13 (34 mg), benzimidazole (24 mg), Cs$_2$CO$_3$ (190 mg), and DMSO (4 mL) were placed in a sealed tube equipped with a magnetic stirring bar. The reaction mixture was heated up at 170° C. for 12 h. The reaction mixture was diluted with water and the aqueous layer was extracted with ethyl acetate (50 mL×2). The combined organic layers were dried over anhydrous sodium sulfate and the solvent was removed on a rotary evaporator. The residue was purified by a reverse phase HPLC to yield Cpd. No. 110 as a salt of CF$_3$CO$_2$H (18 mg, 33% yield).

Cpd. No. 110

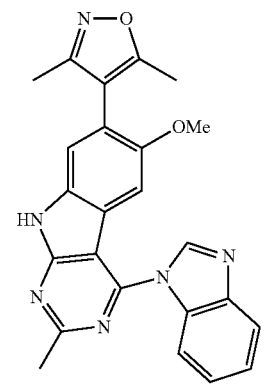

¹H NMR (300 MHz, MeOD-d4): 9.16 (s, 1H), 7.95 (d, J=7.91 Hz, 1H), 7.59-7.44 (m, 3H), 7.43 (s, 1H), 6.68 (s, 1H), 3.40 (s, 3H), 2.83 (s, 3H), 2.29 (s, 3H), 2.11 (s, 3H). ESI-MS calculated for $C_{24}H_{21}N_6O_2$ [M+H]$^+$=425.17, Obtained: 425.32.

Cpd. No. 111 was prepared from S13 and 2-methylbenzimidazole in 5% yield as a salt of CF$_3$CO$_2$H using the same condensation method for the preparation of Cpd. No. 110.

Cpd. No. 111

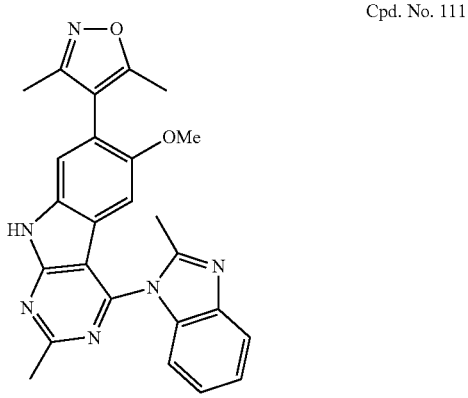 [SMILES: COc1cc2c(cc1-c1c(C)noc1C)[nH]c1nc(C)nc(-n3cnc4ccccc43)c12]

TFA salt ¹H NMR (300 MHz, MeOD-d4): 7.89 (d, J=8.20 Hz, 1H), 7.52 (t, J=7.82 Hz, 1H), 7.44 (s, 1H), 7.39 (t, J=7.82 Hz, 1H), 7.18 (d, J=8.57 Hz, 1H), 6.23 (s, 1H), 3.25 (s, 3H), 2.88 (s, 3H), 2.78 (s, 3H), 2.28 (s, 3H), 2.09 (s, 3H). ESI-MS calculated for $C_{25}H_{23}N_6O_2$ [M+H]$^+$=439.19, Obtained: 439.40.

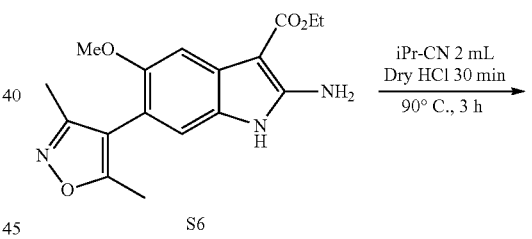

S6

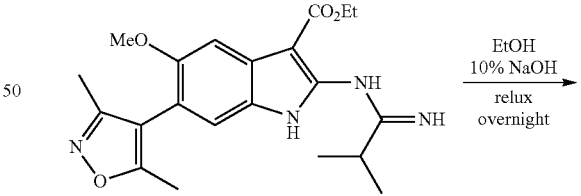

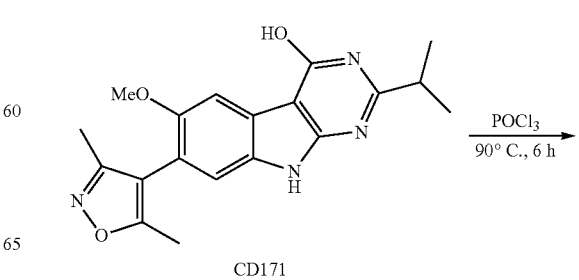

CD171

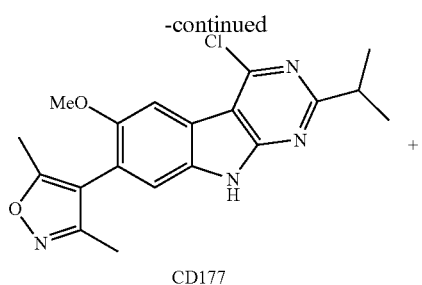

CD177

1. Pd(PPh$_3$)$_4$
   K$_2$CO$_3$
   DME-H$_2$O
   reflux
   overnight
2. TFA-CH$_2$Cl$_2$

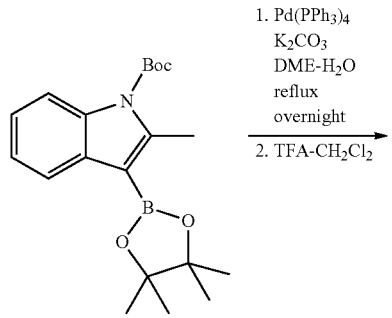

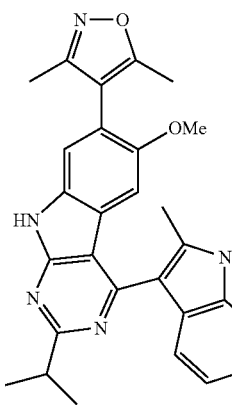

Cpd. No. 112

S6 (400 mg) was dissolved in isobutyronitrile (2 mL). HCl gas was bubbled into the solution for 40 min and the solution was heated at 90° C. for 3 h. The solvent was concentrated in vacuum and the residue was dissolved in ethanol (40 mL). NaOH (10%, 30 mL) was added to the ethanol solution and the mixture was heated at reflux for overnight. The solution was cooled to room temperature and concentrated in vacuum. Ethyl acetate (20 mL) was added followed by aqueous HCl solution to set pH=4-5. The precipitate was collected by filtration and the residue was washed with diethyl ether to furnish CD171 in 0.26 g. $^1$H NMR (300 MHz, DMSO-d6): 12.05 (s, 1H), 12.00 (s, 1H), 7.54 (s, 1H), 7.18 (s, 1H), 3.81 (s, 3H), 2.97 (septet, J=6.75 Hz, 1H), 2.26 (s, 3H), 2.06 (s, 3H), 1.25 (d, J=6.80 Hz, 6H).

CD171 (0.26 g) was mixed with phosphorus(V) oxychloride (5 mL) and heated at 90° C. for 6 h. The mixture was concentrated in vacuum and neutralized with excess aqueous NaHCO$_3$ saturated solution. Ethyl acetate (30 mL) was added and the precipitate was collected by filtration. The solid residue was washed with diethyl ether to furnish CD177 in 120 mg (43% yield). $^1$H NMR (300 MHz, DMSO-d6): 12.52 (s, 1H), 7.79 (s, 1H), 7.38 (s, 1H), 3.88 (s, 3H), 3.19 (septet, J=6.88 Hz, 1H), 2.28 (s, 3H), 2.09 (s, 3H), 1.33 (d, J=6.88 Hz, 6H).

Suzuki coupling of tert-butyl 2-methyl-3-(4,4,5,5-tetramethyl-1,3,2-dioxaborolan-2-yl)-1H-indole-1-carboxylate and CD177 and deprotection of Boc group in TFA-CH$_2$Cl$_2$ provided Cpd. No. 112 in 36% yield as a salt of CF$_3$CO$_2$H using Pd(PPh$_3$)$_4$—K$_2$CO$_3$ condition.

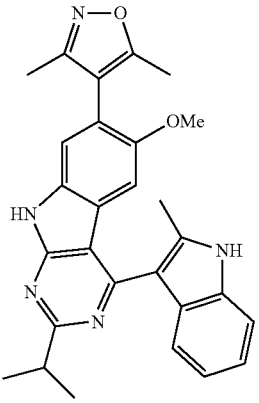

Cpd. No. 112

$^1$H NMR (300 MHz, MeOD-d4): 11.91 (s, 1H), 7.59 (d, J=8.10 Hz, 1H), 7.53 (s, 1H), 7.31 (ddd, J=8.16, 6.70, 1.33 Hz, 1H), 7.28-7.14 (m, 2H), 6.76 (s, 1H), 3.50 (septet, J=6.77 Hz, 1H), 3.00 (s, 3H), 2.66 (s, 3H), 2.30 (s, 3H), 2.11 (s, 3H), 1.56 (d, J=6.77 Hz, 3H), 1.55 (d, J=6.76 Hz, 3H). ESI-MS calculated for C$_{28}$H$_{28}$N$_5$O$_2$ [M+H]$^+$=466.22, Obtained: 466.58

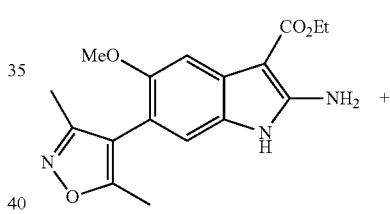

S6

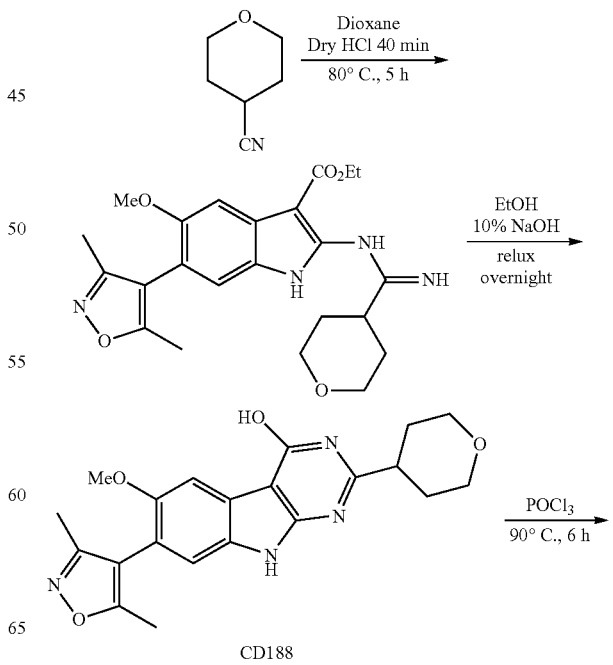

CD188

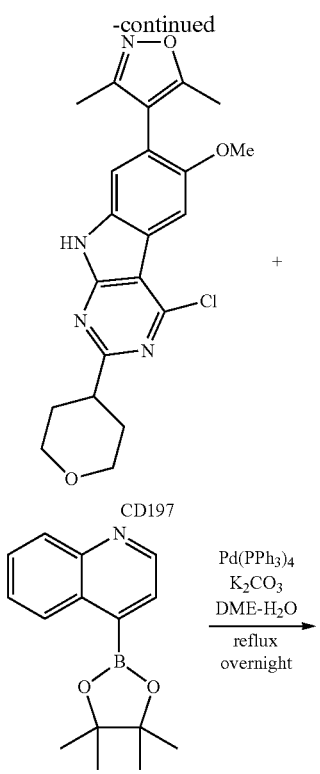

CD197

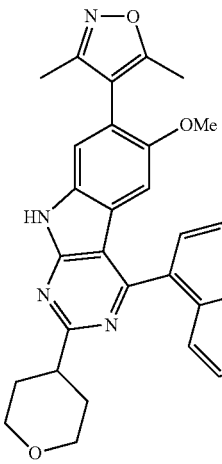

Cpd. No. 113 added and the precipitate was collected by filtration. The solid residue was washed with diethyl ether to furnish CD197 in 80 mg (63% yield).

Suzuki coupling of quinoline-4-boronic acid pinacol ester and CD197 furnished Cpd. No. 113-TFA salt in 8% yield using Pd(PPh₃)₄—K₂CO₃ condition.

Cpd. No. 113

$^1$H NMR (300 MHz, MeOD-d4): 9.31 (d, J=4.76 Hz, 1H), 8.36 (d, J=8.27 Hz, 1H), 8.10 (d, J=4.75 Hz, 1H), 8.05 (ddd, J=8.44, 6.91, 1.31 Hz, 1H), 7.92 (d, J=7.91 Hz, 1H), 7.79-7.70 (m, 1H), 7.48 (s, 1H), 6.29 (s, 1H), 4.12 (d, J=14.04 Hz, 2H), 3.64 (td, J=11.48, 2.27 Hz, 2H), 3.50-3.30 (m, 1H), 3.24 (s, 3H), 2.27 (s, 3H), 2.25-2.14 (m, 2H), 2.14-2.03 (m, 2H), 2.08 (s, 3H). ESI-MS calculated for C₃₀H₂₈N₅O₃ [M+H]⁺=506.22, Obtained: 506.33.

S6 (300 mg), tetrahydropyranyl-4-carbonitrile (330 mg), and dioxane (10 mL) were placed in a round-bottom flask. HCl gas was bubbled into the solution for 40 min and the solution was heated at 80° C. for 5 h. The solvent was concentrated in vacuum and the residue was dissolved in ethanol (30 mL). NaOH (10%, 30 mL) was added to the ethanol solution and the mixture was heated at reflux for 12 h. The solution was cooled to room temperature and concentrated in vacuum. Ethyl acetate (20 mL) was added followed by addition of aqueous HCl solution to set pH=4-5. The precipitate was collected by filtration and the residue was washed with diethyl ether to furnish CD188 in 0.12 g (33% yield). ESI-MS calculated for C₂₁H₂₃N₄O₄ [M+H]⁺= 395.17, Obtained: 395.58.

CD188 (0.12 g) was mixed with phosphorus(V) oxychloride (10 mL) and heated at 90° C. for 6 h. The mixture was concentrated in vacuum and neutralized with excess aqueous NaHCO₃ saturated solution. Ethyl acetate (20 mL) was

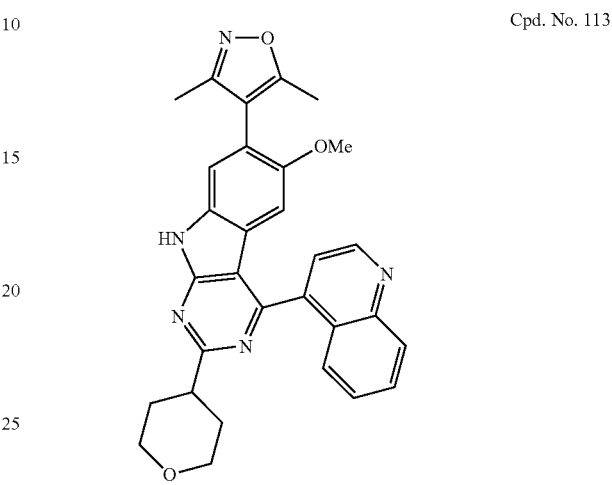

H-1

H-2

HK-06-203

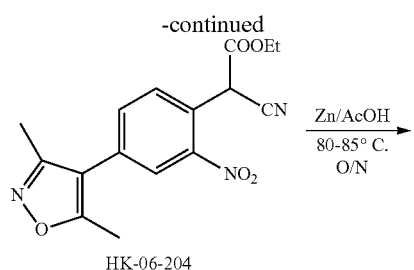

HK-06-204

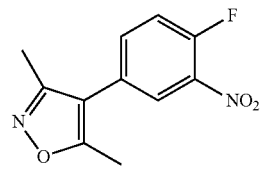

HK-06-203

To a mixture of 3,5-dimethyl-4-(4,4,5,5-tetramethyl-1,3,2-dioxaborolan-2-yl)isoxazole (H1) (12.2 g, 54.6 mmol, 2 equiv), 4-bromo-1-fluoro-2-nitrobenzene (H2) (6 g, 27.3 mmol, 1 equiv) and $K_2CO_3$ (11.3 g, 81.9 mmol, 3.0 equiv), 1,2-dimethoxyethane (60 mL) and water (40 mL) were added at room temperature. The mixture was purged with nitrogen before Pd(PPh$_3$)$_4$(1.6 g, 1.4 mmol, 0.05 equiv) was added in one portion. The reaction mixture was purged with nitrogen and refluxed at 90° C. overnight. The aqueous layer was extracted with ethyl acetate and combined organic layers were washed with brine, dried over anhydrous $Na_2SO_4$ and concentrated. The residue was purified over flash column chromatography furnishing 5.5 g (23.1 mmol) of the intermediate HK-06-203 as a bright yellow solid (85% yield). $^1$H NMR (CDCl$_3$, 300 MHz): 7.94 (dd, J=2.3 Hz, J=7.0 Hz, 1H), 7.57-7.50 (m, 1H), 7.39 (dd, J=8.7 Hz, J=10.4 Hz 1H), 2.42 (s, 3H), 2.27 (s, 3H).

HK-06-204

To a suspension of NaH (1.8 g, 60% in mineral oil, 46 mmol, 2.0 equiv) in dry DMF (40 mL), ethyl cyanoacetate (3.9 g, 34.5 mmol, 1.5 equiv) was added dropwise at 0° C. and the reaction was stirred at room temperature for 30 min. The mixture was cooled to 0° C., anhydrous DMF solution (20 mL) of HK-06-203 (5.45 g, 23 mmol, 1.0 equiv) was added via a syringe. The reaction mixture was allowed to warm up to room temperature and was stirred overnight. Ethyl acetate (50 ml) and MeOH (20 ml) were added to the reaction mixture, and pH was adjusted to 2-3 with aqueous 2 N HCl. The volatile components were removed on a rotary evaporator and the residue was purified over a flash column chromatography furnishing 6.9 g (21 mmol) of the intermediate HK-06-204 as bright yellow oil (91% yield). $^1$H NMR (CDCl$_3$, 300 MHz): 8.12 (d, J=1.6 Hz, 1H), 7.86 (d, J=8.0 Hz, 1H), 7.66 (dd, J=1.6 Hz, J=8.0 Hz, 1H), 5.69 (s, 1H), 4.34 (q, J=7.1 Hz, 2H), 2.48 (s, 3H), 2.32 (s, 3H), 1.35 (t, J=7.1 Hz, 3H).

HK-06-205

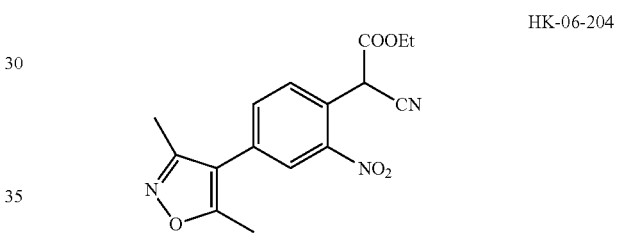

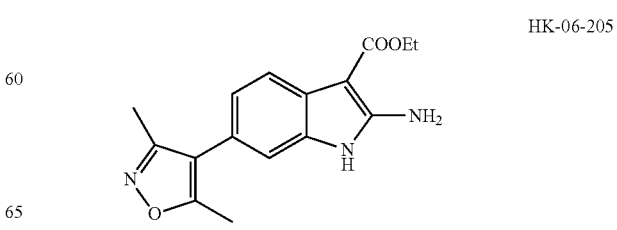

Cpd. No. 114

Acetic acid (23 mL) solution of HK-06-204 (2.5 g, 7.5 mmol, 1.0 equiv) at 85° C., zinc powder (1.21 g, 18.6 mmol, 2.5 equiv) was added in small portions. The mixture was stirred at 85° C. for 1 h, another 0.73 g zinc powder (11.2 mmol, 1.5 equiv) was added, and the reaction was stirred at the same temperature overnight. The reaction was cooled down and filtered, and the filtrate was concentrated. The residue was then taken into ethyl acetate and the pH was neutralized with saturated aqueous $NaHCO_3$ followed by extraction with ethyl acetate. The organic layers were combined, dried over anhydrous $Na_2SO_4$, concentrated and the remaining residue was purified over a flash column chromatography yielding 0.96 g (3.2 mmol) of the intermediate HK-06-205 as a brown solid (43% yield). $^1$H NMR ($CDCl_3$, 300 MHz): 9.16 (s, 1H), 7.83 (d, J=8.0 Hz, 1H), 7.97 (dd, J=1.3 Hz, J=8.0 Hz, 1H), 6.92-6.90 (m, 1H), 5.98 (s, 2H), 4.39 (q, J=7.1 Hz, 2H), 2.36 (s, 3H), 2.22 (s, 3H), 1.44 (t, J=7.1 Hz, 3H).

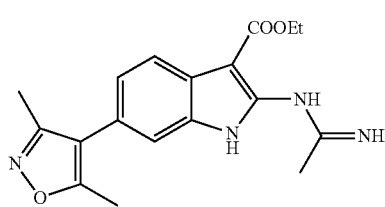

HK-06-208

Intermediate HK-06-205 (2.92 g, 9.8 mmol) was dissolved in MeCN (30 mL) at room temperature. Dry HCl was bubbled through the mixture for 30 min and the reaction mixture was refluxed at 85° C. for 3 h. The reaction was then cooled to room temperature and the volatile components were removed on a rotary evaporator. The dark brown solid crude HK-06-208 was used for the next step without further purification.

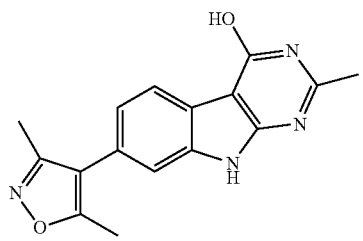

HK-06-209

The crude mixture HK-06-208 was dissolved in EtOH (80 mL). 10% NaOH aqueous solution (40 mL) was added followed by refluxing overnight. The volatile components were then removed on a rotary evaporator and the aqueous residue was acidified with 2N HCl aqueous solution. The brown precipitate was collected by filtration and washed with water and diethyl ether yielding 2.06 g intermediate HK-06-209 as brown solid (72% yield over 2 steps).

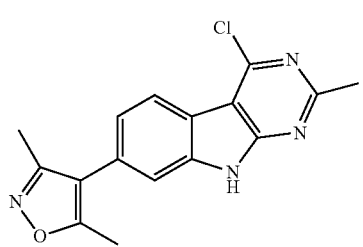

HK-06-211

Intermediate HK-06-209 (2 g, 6.8 mmol) was mixed with $POCl_3$ (20 mL) and the mixture was heated at 90° C. for 6 h. The reaction mixture was cooled to room temperature and the volatile components were removed on a rotary evaporator. Ethyl acetate (20 mL) was added and the pH was adjusted to 8 with excess saturated aqueous $NaHCO_3$ solution. Filtration of the mixture yielded 1.0 g intermediate HK-06-211 as a brown solid in (86% yield). $^1$H NMR (DMSO-$d_6$, 300 MHz): 12.63 (brs, 1H), 8.25 (d, J=8.1 Hz, 1H), 7.54 (d, J=0.8 Hz, 1H), 7.37 (dd, J=8.2 Hz, J=8.1 Hz, 1H), 2.68 (s, 3H), 2.46 (s, 3H), 2.27 (s, 3H).

Cpd. No. 114

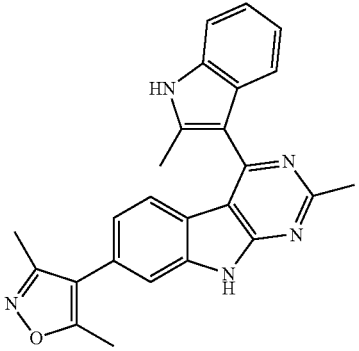

To a mixture of HK-06-211 (0.03 g, 0.1 mmol, 1.0 equiv), tert-butyl 2-methyl-3-(4,4,5,5-tetramethyl-1,3,2-dioxaborolan-2-yl)-1H-indole-1-carboxylate (0.1 g, 0.3 mmol, 3.0 equiv), and $K_2CO_3$ (0.07 g, 0.5 mmol, 5.0 equiv), DME (6 mL) and water (4 mL) were added at room temperature. The mixture was purged with nitrogen before $Pd(PPh_3)_4$ (0.02 g, 0.02 mmol, 0.02 equiv) was added in one portion. The reaction mixture was purged with nitrogen and refluxed at 90° C. for 9 h. The aqueous layer was extracted with ethyl acetate and combined organic layers were washed with brine, dried over anhydrous $Na_2SO_4$, and concentrated. The residue was taken into 1:1 mixture of $CH_2Cl_2$ and trifluoroacetic acid, stirred for 30 min at room temperature. The mixture was then concentrated and purified with preparative HPLC. The final compound then dissolved in $CH_3CN:H_2O$ (1:1) and lyophilized to yield 0.014 g (0.03 mmol) of the final compound Cpd. No. 114-$CF_3CO_2H$ salt as a bright yellow solid (85% yield). $^1$H NMR ($CD_3OD$, 300 MHz): 7.68-7.66 (m, 1H), 7.56 (d, J=8.7 Hz, 1H), 7.37-7.22 (m, 4H), 7.18-7.12 (m, 1H), 2.97 (s, 3H), 2.60 (s, 3H), 2.45 (s, 3H), 2.28 (s, 3H).

Cpd. No. 115 (TFA salt) was prepared from HK-06-211 using Suzuki coupling condition [$Pd(PPh_3)_4$—$K_2CO_3$ method] (12% yield)

Cpd. No. 115

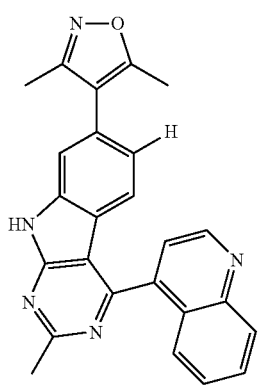

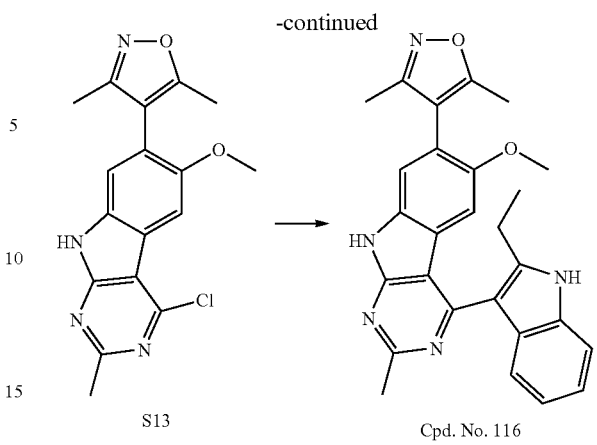

¹H NMR (300 MHz, MeOD-d4): 9.32 (d, J=4.60 Hz, 1H), 8.86 (d, J=8.59 Hz, 1H), 8.09 (d, J=4.63 Hz, 1H), 8.10-8.02 (m, 1H), 7.86 (d, J=8.45 Hz, 1H), 7.77-7.70 (m, 1H), 7.66 (d, J=0.78 Hz, 1H), 7.10 (dd, J=8.24, 1.46 Hz, 1H), 6.91 (d, J=8.22 Hz, 1H), 3.00 (s, 3H), 2.42 (s, 3H), 2.25 (s, 3H). ESI-MS calculated for $C_{25}H_{20}N_5O$ $[M+H]^+$=406.17, Obtained: 406.25

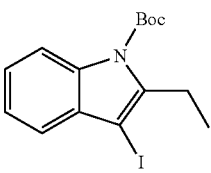

HK-06-231

A mixture of 2-ethyl-1H-indole (H-11, 0.5 g, 3.4 mmol, 1 equiv) and N-iodosuccinimide (0.93 g, 4.13 mmol, 1.2 equiv) was stirred in anhydrous DMF at room temperature overnight. The reaction mixture was diluted with excess of ethyl acetate, washed with $H_2O$ and brine. The organic phase was dried over anhydrous $Na_2SO_4$ and concentrated. The remaining crude HK-06-230 was mixed with di-tert-butyl dicarbonate (1.5 g, 6.9 mmol) in anhydrous THF. To this mixture portions of DMAP (0.42 g, 3.44 mmol) was added. The reaction was stirred at room temperature for 3 h at ambient atmosphere. Then the mixture was concentrated and the remaining residue was purified over flash chromatography yielding 0.6 g (1.6 mmol) of intermediate HK-06-231 (47% yield over 2 steps). ¹H NMR (CDCl₃, 300 MHz): 8.09-8.04 (m, 1H), 7.39-7.23 (m, 3H), 3.18 (q, J=7.4 Hz, 2H), 1.69 (s, 9H), 1.23 (t, J=7.4 Hz, 3H).

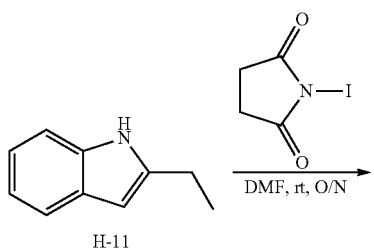

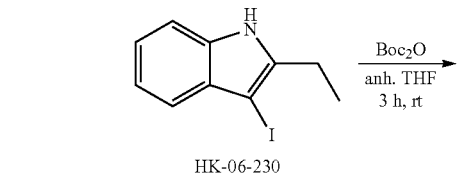

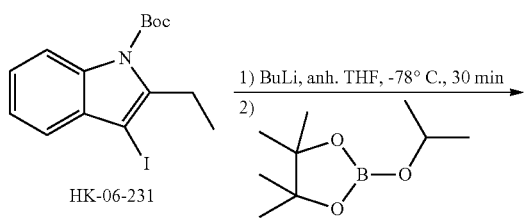

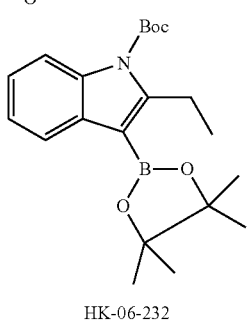

HK-06-232

To a solution of intermediate HK-06-231 (0.6 g, 1.6 mmol) in anhydrous THF at −78° C., n-BuLi (2.9 mmol, 1.8 equiv) was added dropwise. The reaction mixture was stirred at −78° C. for 30 min. Then to this mixture 2-isopropoxy-4,4,5,5-tetramethyl-1,3,2-dioxaborolane (0.6 g, 2 equiv) was added and the reaction was stirred for 2 h at −78° C. The reaction mixture was quenched with aqueous ammonium chloride solution and extracted to ethyl acetate. The organic phase was dried over anhydrous Na₂SO₄ and concentrated. The remaining crude was purified over flash chromatography yielding 0.39 g (1.04 mmol) of intermediate HK-06-232 (65% yield). ¹H NMR (CDCl₃, 300 MHz): 8.09-7.95 (m, 2H), 7.26-7.17 (m, 2H), 3.37 (q, J=7.3 Hz, 2H), 1.68 (s, 9H), 1.36 (s, 12H), 1.24 (t, J=7.4 Hz, 3H).

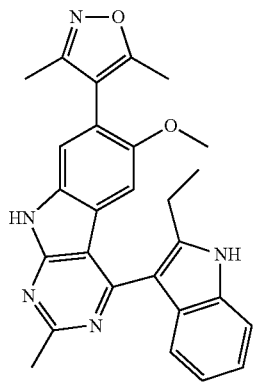

Cpd. No. 116

To a mixture of S13 (0.03 g, 0.1 mmol, 1.0 equiv), HK-06-232 (0.11 g, 0.3 mmol, 3.0 equiv) and K₂CO₃ (0.07 g, 0.5 mmol, 5.0 equiv), DME (6 mL) and water (4 mL) were added at room temperature. The mixture was purged with nitrogen before Pd(PPh₃)₄ (0.02 g, 0.02 mmol, 0.02 equiv) was added in one portion. The reaction mixture was purged with nitrogen and refluxed at 90° C. for overnight. The aqueous layer was extracted with ethyl acetate and combined organic layers were washed with brine, dried over anhydrous Na₂SO₄ and concentrated. The residue was taken into 1:1 mixture of CH₂Cl₂ and trifluoroacetic acid, stirred for 30 min at room temperature. The mixture was then concentrated and purified with preparative HPLC. The final compound then dissolved in CH₃CN:H₂O (1:1) and lyophilized to yield 0.018 g (0.03 mmol) of the final compound Cpd. No. 116 (TFA salt) as a bright yellow solid (30% yield). ¹H NMR (CD₃OD, 300 MHz): 7.64-7.59 (m, 1H), 7.53 (s, 1H), 7.35-7.25 (m, 2H), 7.22-7.15 (m, 1H), 6.74 (s, 1H), 3.32 (s, 3H), 3.06 (dq, J=3.6 Hz, J=7.6 Hz, 2H), 2.96 (s, 3H), 2.30 (s, 3H), 2.11 (s, 3H), 1.33 (t, J=7.6 Hz, 3H).

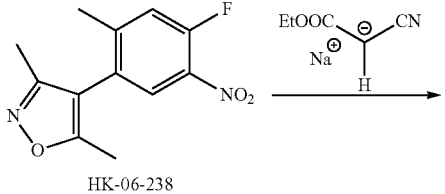

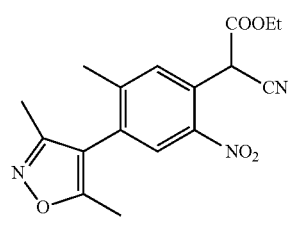
HK-06-237

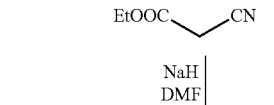
HK-06-238

HK-06-245

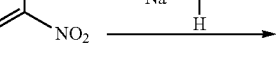
HK-06-248

HK-06-249

HK-06-250

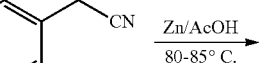
HK-06-255

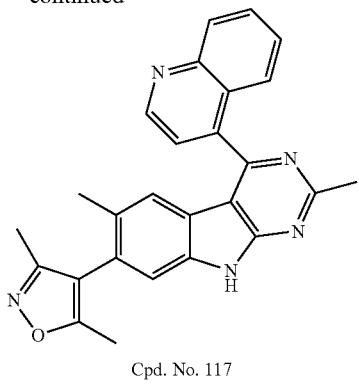

Cpd. No. 117

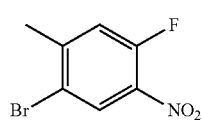

HK-06-237

4.5 g (23.8 mmol) of 1-bromo-4-fluoro-2-methylbenzene was added to a mixture of 1.5 ml conc. $H_2SO_4$ and 1.5 ml fuming nitric acid at 0° C. and the reaction was stirred at the same temperature for 1 h. The reaction mixture was poured into ice-water and extracted to $CH_2Cl_2$. Combined organic layers were dried over anhydrous $Na_2SO_4$ and concentrated. The remaining residue was purified over flash chromatography yielding intermediate 1-bromo-4-fluoro-2-methyl-5-nitrobenzene (HK-06-237) as bright yellow liquid (80% yield). $^1$H NMR (CDCl$_3$, 300 MHz): 8.26 (d, J=7.1 Hz, 1H), 7.20 (d, J=11.4 Hz, 1H), 2.48 (s, 3H).

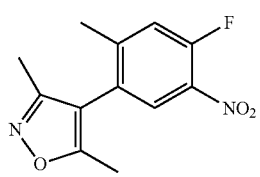

HK-06-238

To a mixture of 3,5-dimethyl-4-(4,4,5,5-tetramethyl-1,3,2-dioxaborolan-2-yl)isoxazole (0.89 g, 4 mmol, 2 equiv), 1-bromo-4-fluoro-2-methyl-5-nitrobenzene (0.47 g, 2 mmol, 1 equiv), and $K_2CO_3$ (0.83 g, 6 mmol, 3.0 equiv), DME (24 mL) and water (16 mL) were added at room temperature. The mixture was purged with nitrogen before Pd(PPh$_3$)$_4$ (0.12 g, 0.1 mmol, 0.05 equiv) was added in one portion. The reaction mixture was purged with nitrogen and refluxed at 90° C. overnight. The aqueous layer was extracted with ethyl acetate and combined organic layers were washed with brine, dried over anhydrous $Na_2SO_4$ and concentrated. The residue was purified over flash chromatography yielding 0.3 g (1.2 mmol) of the intermediate HK-06-238 as a bright yellow solid (60% yield). $^1$H NMR (CDCl$_3$, 300 MHz): $^1$H NMR (CDCl$_3$, 300 MHz): 7.85 (d, J=7.5 Hz, 1H), 7.26 (d, J=11.5 Hz, 1H), 2.27 (s, 3H), 2.23 (s, 3H), 2.11 (s, 3H).

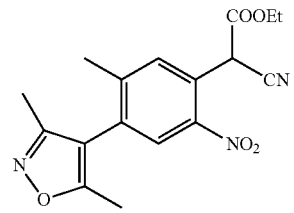

HK-06-245

To a suspension of NaH (0.09 g, 60% in mineral oil, 2.2 mmol, 2.0 equiv) in dry DMF (3 mL), ethyl cyanoacetate (0.19 g, 1.65 mmol, 1.5 equiv) was added dropwise at 0° C. and the reaction was stirred at room temperature for 30 min. The mixture was cooled to 0° C., anhydrous DMF solution (2 mL) of HK-06-238 (0.28 g, 1.1 mmol, 1.0 equiv) was added via a syringe. The reaction mixture was allowed to warm up to room temperature and was stirred overnight. Ethyl acetate (10 ml) and MeOH (5 ml) were added to the reaction mixture, and pH was adjusted to 2-3 with 2 N HCl aqueous solution. The volatile components were removed on a rotary evaporator and the residue was purified over flash chromatography yielding 0.34 g (1 mmol) of the intermediate HK-06-245 (90% yield). $^1$H NMR (CDCl$_3$, 300 MHz): 8.01 (s, 1H), 7.70 (s, 1H), 5.69 (s, 1H), 4.35 (q, J=7.1 Hz, 2H), 2.34-2.26 (m, 6H), 2.14 (d, J=8.2 Hz, 3H), 1.37 (t, J=7.1 Hz, 3H).

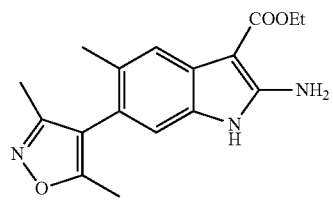

HK-06-248

Acetic acid (6 mL) solution of HK-06-245 (0.32 g, 1.06 mmol, 1.0 equiv) at 80° C., zinc powder (0.17 g, 2.7 mmol, 2.5 equiv) was added in small portions. The mixture was stirred at 85° C. for 1 h, another 0.10 g zinc powder (1.6 mmol, 1.5 equiv) was added, and the reaction was stirred at the same temperature for 3 h. The reaction was cooled down and filtered, thereafter, the filtrate was concentrated. The residue was then taken into ethyl acetate and the pH was neutralized with saturated NaHCO$_3$ followed by extraction with ethyl acetate. The organic layers were combined, dried over anhydrous Na$_2$SO$_4$, concentrated and the remaining residue was purified over flash chromatography yielding 0.12 g (0.38 mmol) of the intermediate HK-06-248 (43% yield).

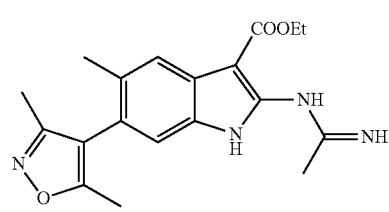

HK-06-249

Intermediate HK-06-248 (0.8 g, 2.5 mmol) was dissolved in MeCN (20 mL) at room temperature. Dry HCl was bubbled through the mixture for 30 min and the reaction mixture was refluxed at 85° C. for 3 h. The reaction was then cooled to room temperature and the volatile components were removed on a rotary evaporator. The brown solid crude (HK-06-249) was used for the next step without further purification.

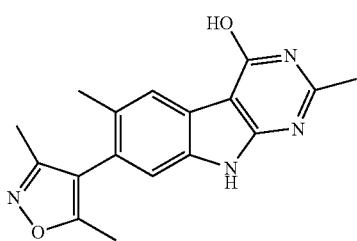
HK-06-250

The crude mixture HK-06-249 was dissolved in EtOH (20 mL) and 10% NaOH aqueous solution (10 mL) was added followed by refluxing overnight. The volatile components were then removed on a rotary evaporator and the aqueous residue was acidified with 2N HCl aqueous solution. The brown precipitate was filtered, washed with water and diethyl ether yielding intermediate HK-06-250 as a bright brown solid (0.63 g, 81% yield over 2 steps). $^1$H NMR (DMSO-$d_6$, 300 MHz): 12.13 (s, 1H), 11.95 (s, 1H), 7.89 (s, 1H), 7.17 (s, 1H), 2.41 (s, 3H), 2.21 (s, 3H), 2.17 (s, 3H), 2.02 (s, 3H).

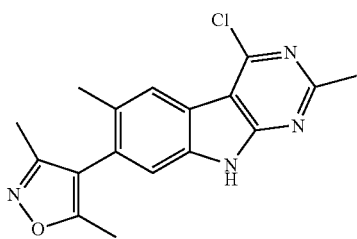
HK-06-255

Intermediate HK-06-250 (0.31 g, 1 mmol) was mixed with POCl$_3$ (3.5 mL) and the mixture was heated at 90° C. for 6.5 h. The reaction mixture was cooled to room temperature and the volatile components were removed on a rotary evaporator. Ethyl acetate (5 mL) was added and the pH was adjusted to 8 with excess saturated aqueous NaHCO$_3$ solution. Filtration of the mixture yielded 0.33 g intermediate HK-06-255 as brown solid in (99% yield). $^1$H NMR (DMSO-$d_6$, 300 MHz): 12.53 (s, 1H), 8.17 (s, 1H), 7.36 (s, 1H), 2.68 (s, 3H), 2.24 (s, 3H), 2.24 (s, 3H), 2.04 (s, 3H).

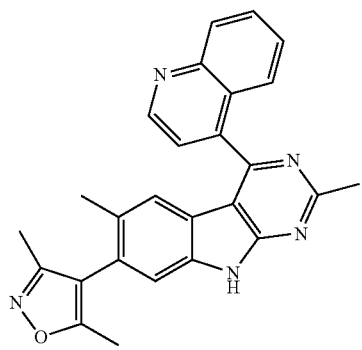
Cpd. No. 117

To a mixture of HK-06-255 (0.03 g, 0.1 mmol, 1.0 equiv), 4-(4,4,5,5-tetramethyl-1,3,2-dioxaborolan-2-yl)quinolone (0.05 g, 0.3 mmol, 3.0 equiv), and K$_2$CO$_3$ (0.07 g, 0.5 mmol, 5.0 equiv), DME (6 mL) and water (4 mL) were added at room temperature. The mixture was purged with nitrogen before Pd(PPh$_3$)$_4$(0.02 g, 0.02 mmol, 0.02 equiv) was added in one portion. The reaction mixture was purged with nitrogen and refluxed at 90° C. for overnight. The aqueous layer was extracted with ethyl acetate and combined organic layers were washed with brine, dried over anhydrous Na$_2$SO$_4$ and concentrated. The residue was then purified with preparative HPLC. The final compound dissolved in CH$_3$CN:H$_2$O (1:1) and lyophilized to yield 0.01 g (0.02 mmol) of the final compound Cpd. No. 117 (TFA salt) as a bright yellow solid (17% yield). ESI-MS calculated for C$_{26}$H$_{22}$N$_5$O [M+H]$^+$=420.18, Obtained: 420.42.

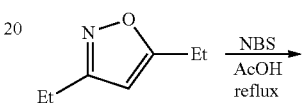

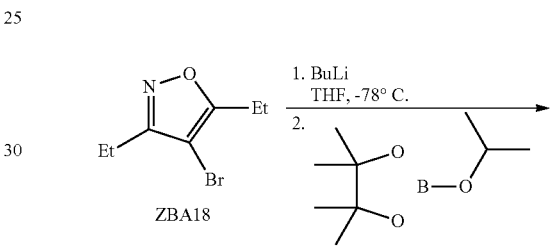
ZBA18

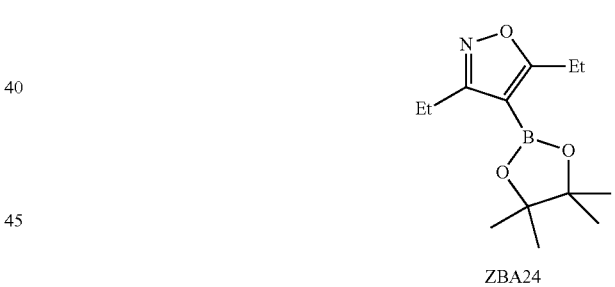
ZBA24

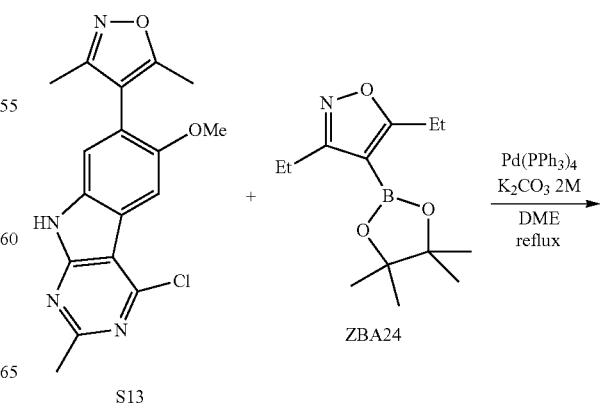
S13

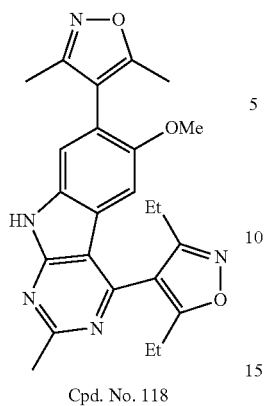

Cpd. No. 118

3,5-diethylisoxazole (125 mg) was dissolved in anhydrous AcOH (15 mL). NBS (178 mg) was added and the mixture was heated at reflux for 2 h before quenching with statured aqueous Na$_2$S$_2$O$_3$ solution. The aqueous layer was extracted with ethyl acetate (50 mL×3) and the combined organic layers were washed with brine and dried over anhydrous sodium sulfate. The solvent was removed on a rotary evaporator and the residue was purified by flash column chromatography to furnish ZBA18 in 183 mg (90% yield). ESI-MS calculated for C$_7$H$_{10}$BrNO [M+H]$^+$=204.00, Obtained: 204.23.

ZBA18 (312 mg) was dissolved in anhydrous THF (15 mL). The solution was cooled to −78° C. in a dry ice-ethanol bath. BuLi (0.94 mL, 2.5 M in THF) was added dropwise and the mixture was stirred at −78° C. for 15 min. 2-Isopropoxy-4,4,5,5-tetramethyl-1,3,2-dioxaborolane (506 mg) was added via a syringe and the reaction mixture was stirred at −78° C. for 3 h before quenching with statured aqueous NH$_4$Cl solution. The aqueous layer was extracted with ethyl acetate (50 mL×3) and the combined organic layers were washed with brine and dried over anhydrous sodium sulfate. The solvent was removed on a rotary evaporator and the residue was purified by flash column chromatography to furnish 2-trifluoromethylquinoline 4-boronic acid pinacol ester ZBA24 in 310 mg (80% yield).

Cpd. No. 118-TFA salt was prepared from Suzuki coupling of ZBA24 and S13 using Pd(PPh$_3$)$_4$—K$_2$CO$_3$ (2 M) condition. 40% yield. $^1$H NMR (300 MHz, MeOD-d4) δ 7.61 (s, 1H), 7.00 (s, 1H), 3.78 (s, 3H), 2.97 (s, 3H), 2.95-2.81 (m, 2H), 2.73 (q, J=7.5 Hz, 2H), 2.34 (s, 3H), 2.16 (s, 3H), 1.27 (t, J=7.6 Hz, 3H), 1.19 (t, J=7.5 Hz, 3H).

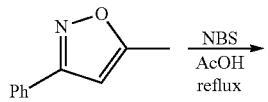

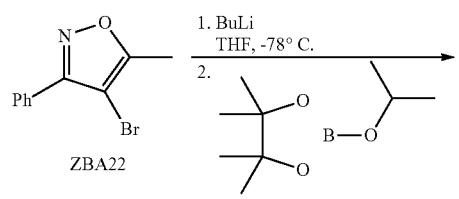

ZBA22

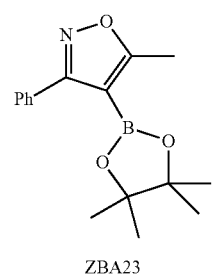

ZBA23

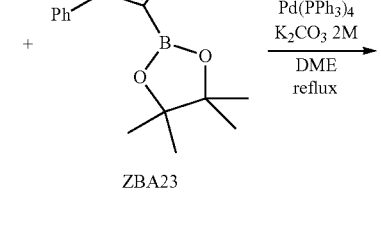

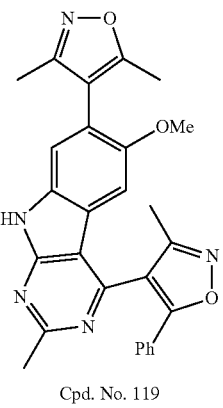

Cpd. No. 119

5-Ethyl-3-phenylisoxazole (173 mg) was dissolved in anhydrous AcOH (15 mL). NBS (178 mg) was added and the mixture was heated at reflux for 2 h before quenching with statured aqueous Na$_2$S$_2$O$_3$ solution. The aqueous layer was extracted with ethyl acetate (50 mL×3) and the combined organic layers were washed with brine and dried over anhydrous sodium sulfate. The solvent was removed on a rotary evaporator and the residue was purified by flash column chromatography to furnish ZBA22 in 226 mg (90% yield). ESI-MS calculated for C11H11BrNO [M+H]$^+$= 252.00, Obtained: 252.43.

ZBA22 (350 mg) was dissolved in anhydrous THF (15 mL). The solution was cooled to −78° C. in a dry ice-ethanol bath. BuLi (0.94 mL, 2.5 M in THF) was added dropwise and the mixture was stirred at −78° C. for 15 min. 2-Isopropoxy-4,4,5,5-tetramethyl-1,3,2-dioxaborolane (506 mg) was added via a syringe and the reaction mixture was stirred at −78° C. for 3 h before quenching with saturated aqueous NH$_4$Cl solution. The aqueous layer was extracted with ethyl acetate (50 mL×3) and the combined organic layers were washed with brine and dried over anhydrous sodium sulfate. The solvent was removed on a rotary evaporator and the residue was purified by flash column chromatography to furnish 2-trifluoromethylquinoline 4-boronic acid pinacol ester ZBA23 in 291 mg (70% yield).

Cpd. No. 119-TFA salt was prepared from Suzuki coupling of ZBA23 and S13 using Pd(PPh$_3$)$_4$—K$_2$CO$_3$ (2 M) condition. 40% yield. $^1$H NMR (300 MHz, MeOD-d4) δ 7.71-7.57 (m, 2H), 7.52-7.29 (m, 4H), 6.86 (s, 1H), 3.60 (s, 3H), 2.94 (s, 3H), 2.34 (s, 3H), 2.28 (s, 3H), 2.09 (s, 3H).

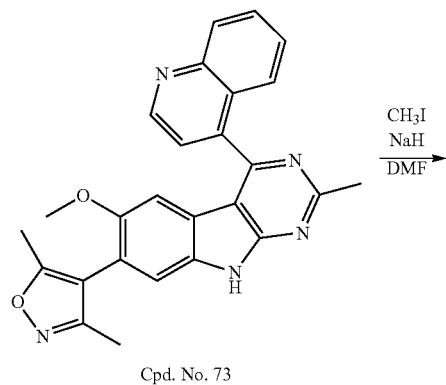

Cpd. No. 73

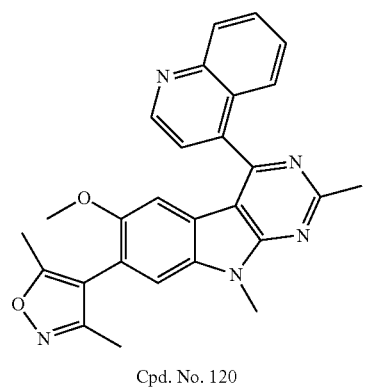

Cpd. No. 120

Cpd. No. 120: To a solution of Cpd. No. 73 (43.5 mg) in DMF, NaH (4 mg) and CH$_3$I (20 mg) were added. The mixture was stirred at room temperature for 0.5 h. Then water was added and the aqueous layer extracted with EtOAc. The combined EtOAc extracts were washed with H$_2$O, dried over Na$_2$SO$_4$, and concentrated under reduced pressure to afford Cpd. No. 120 (35 mg) after HPLC purification. $^1$H NMR (300 MHz, MeOD-d4) δ 9.17 (d, J=4.4 Hz, 1H), 8.29 (d, J=8.5 Hz, 1H), 7.91 (ddd, J=8.4, 6.9, 1.4 Hz, 1H), 7.83 (d, J=4.4 Hz, 1H), 7.74 (d, J=8.1 Hz, 1H), 7.59 (ddd, J=8.2, 6.9, 1.1 Hz, 1H), 7.53 (s, 1H), 6.21 (s, 1H), 4.03 (s, 3H), 3.20 (s, 3H), 2.92 (s, 3H), 2.28 (s, 3H), 2.09 (s, 3H).

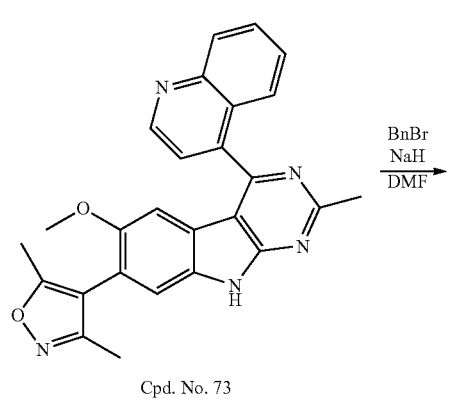

Cpd. No. 73

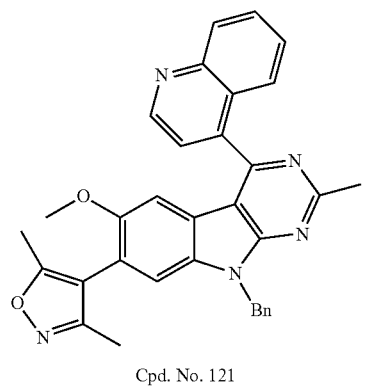

Cpd. No. 121

Cpd. No. 121: this compound was prepared from Cpd. No. 73 and BnBr using the same preparation method as Cpd. No. 120. $^1$H NMR (300 MHz, MeOD-d4) δ 9.18 (d, J=4.4 Hz, 1H), 8.29 (d, J=8.5 Hz, 1H), 7.95-7.83 (m, 2H), 7.79 (d, J=8.4 Hz, 1H), 7.60 (ddd, J=8.3, 6.9, 1.2 Hz, 1H), 7.40-7.23 (m, 6H), 6.22 (s, 1H), 5.80 (s, 2H), 3.18 (s, 3H), 2.95 (s, 3H), 2.10 (s, 3H), 1.95 (s, 3H).

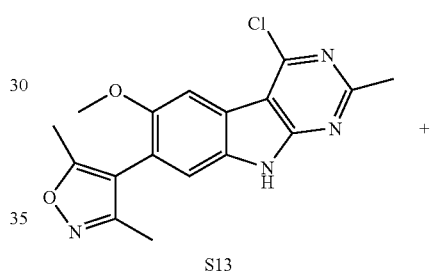

S13

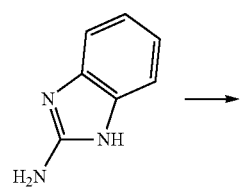

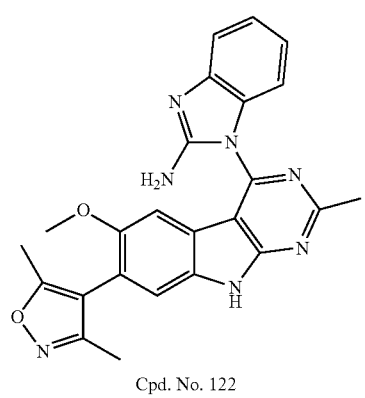

Cpd. No. 122

To a solution of S13 (40 mg) and 2-amino-1H-benzimidazole (40 mg) in DMSO (4 mL), $Cs_2CO_3$ (60 mg) was added. The mixture was stirred at 100° C. for 12 h. Then water was added the aqueous layer extracted with EtOAc. The combined EtOAc extracts were washed with $H_2O$, dried over $Na_2SO_4$, and concentrated under reduced pressure to afford Cpd. No. 122-TFA salt (20 mg) after HPLC purification. $^1H$ NMR (300 MHz, MeOD) δ 7.65 (d, J=8.0 Hz, 1H), 7.56-7.41 (m, 2H), 7.32 (t, J=7.8 Hz, 1H), 7.09 (d, J=8.1 Hz, 1H), 6.62 (s, 1H), 3.41 (s, 3H), 2.89 (s, 3H), 2.30 (s, 3H), 2.12 (s, 3H).

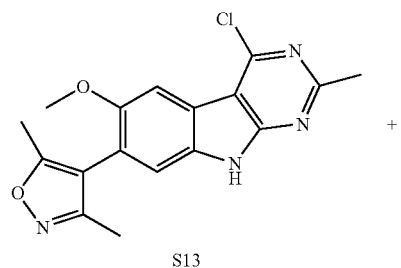

S13

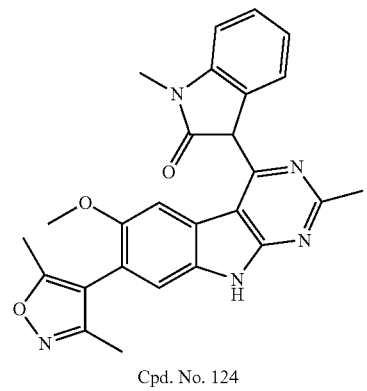

Cpd. No. 124

Cpd. No. 124: this compound was prepared from S13 and N-methyl oxindole using the same method as Cpd. No. 123. ESI-MS calculated for $C_{26}H_{24}N_5O_3$ $[M+H]^+$=454.18, Obtained: 454.34.

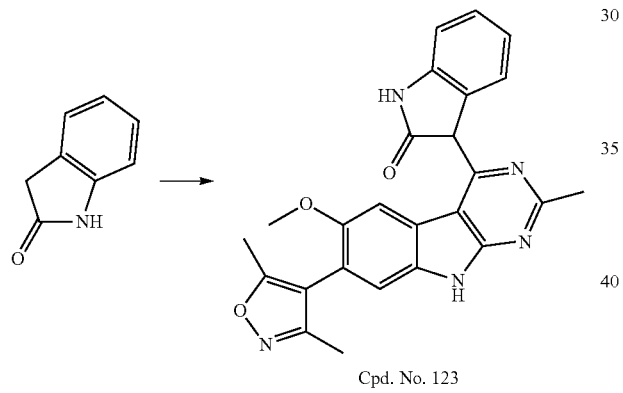

Cpd. No. 123

To a solution of S13 (40 mg) and oxindole (40 mg) in THF (6 mL), $K_2CO_3$ (60 mg), $Pd_2(dba)_3$ (17 mg), and xPhos (70 mg) were added. The mixture was stirred at 100° C. for 24 h. Then water was added and the aqueous layer was extracted with EtOAc. The combined EtOAc extracts were washed with $H_2O$, dried over $Na_2SO_4$, and concentrated under reduced pressure to afford Cpd. No. 123(4 mg) after HPLC purification. ESI-MS calculated for $C_{25}H_{22}N_5O_3$ $[M+H]^+$=440.17, Obtained: 440.32.

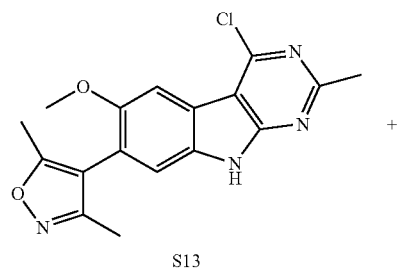

S13

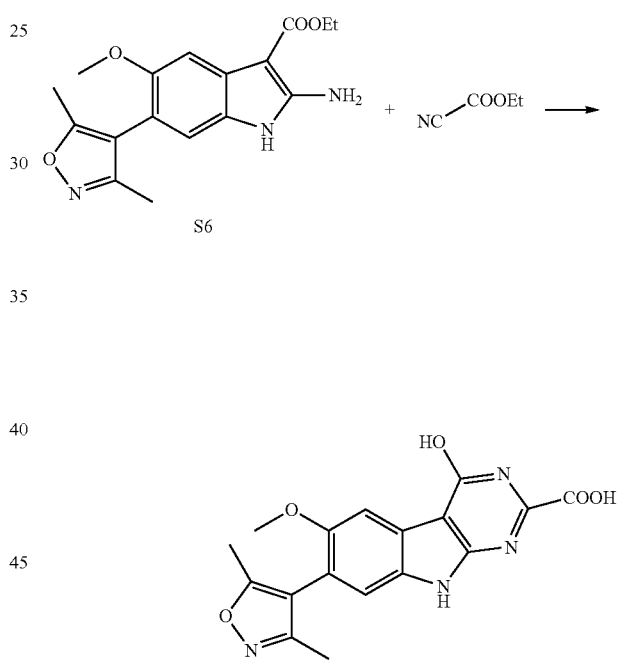

S6

ZBA89

To a round-bottom flask, S6 (0.37 g, 1.1 mmol) and ethyl cyanoformate (3 mL) were added at room temperature. Hydrogen chloride solution in dioxane was added and the reaction mixture was warmed up to reflux (82° C.) for 2.5 h. The reaction was then cooled to room temperature and the volatile components were removed on a rotary evaporator. To this crude mixture, 10% NaOH aqueous solution (20 mL) and EtOH (50 mL) were added and the solution was heated at reflux for 6 h. The volatile components were then removed on a rotary evaporator and the aqueous residue was acidified with 2N HCl aqueous solution. The product ZBA89 was allowed to precipitate at 0° C. Filtration of the mixture furnished pure ZBA89 as a solid in 0.31 g (80% yield, 2 steps). ESI-MS calculated for $C_{17}H_{15}N_4O_5$ $[M+H]^+$= 355.10, Obtained: 355.45.

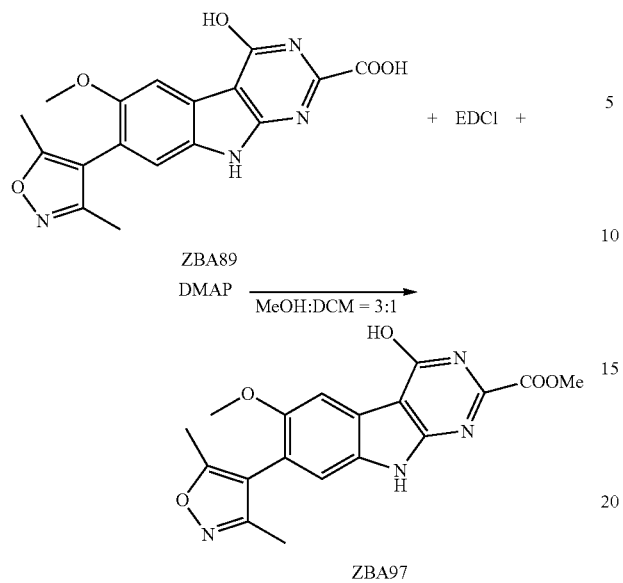

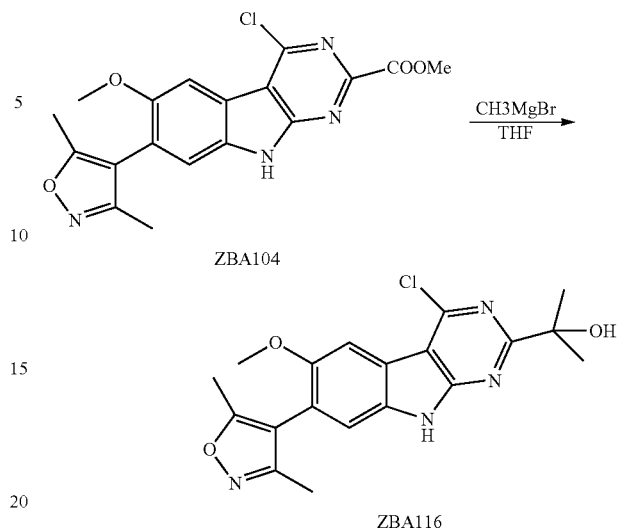

To a round-bottom flask, EDCI (0.7 g) and DMAP (0.1 g) were added to a solution of ZBA89 (0.2 g) in MeOH (100 mL) and DCM (30 mL) at room temperature. The mixture was stirred for 2 days and the volatile components were removed on a rotary evaporator. Then ethyl acetate (40 mL) was added. The product ZBA97 was allowed to precipitate. Filtration of the mixture furnished pure ZBA97 as a solid in 0.12 g (60% yield). $^1$H NMR (300 MHz, MeOD-d4) δ 7.86 (s, 1H), 7.39 (s, 1H), 4.07 (s, 3H), 3.93 (s, 3H), 2.34 (s, 3H), 2.17 (s, 3H).

CH$_3$MgBr solution (0.13 mL, 3 M in Et$_2$O) was added to a solution of ZBA104 (40 mg) in THF at room temperature. The mixture was stirred for 2 h and aq. NH$_4$Cl solution was added. The aqueous layer was extracted with EtOAc. The combined EtOAc extracts were washed with H$_2$O, dried over Na$_2$SO$_4$, and concentrated under reduced pressure to afford ZBA116 (37 mg). $^1$H NMR (300 MHz, MeOD-d4) δ 7.93 (s, 1H), 7.45 (s, 1H), 3.96 (s, 3H), 2.36 (s, 3H), 2.19 (s, 3H), 1.67 (s, 6H).

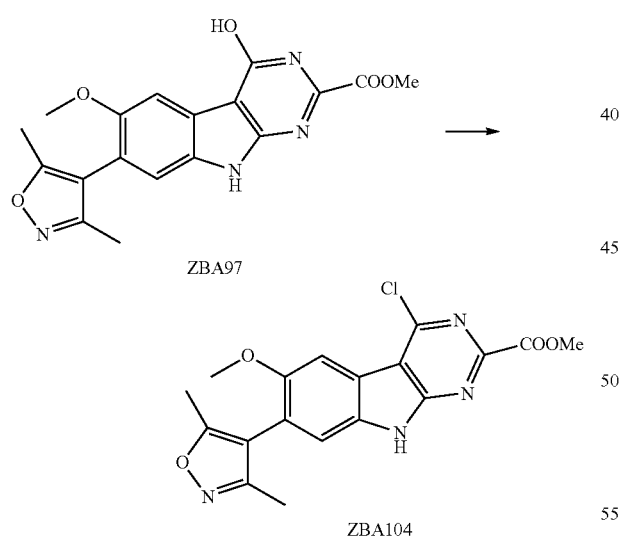

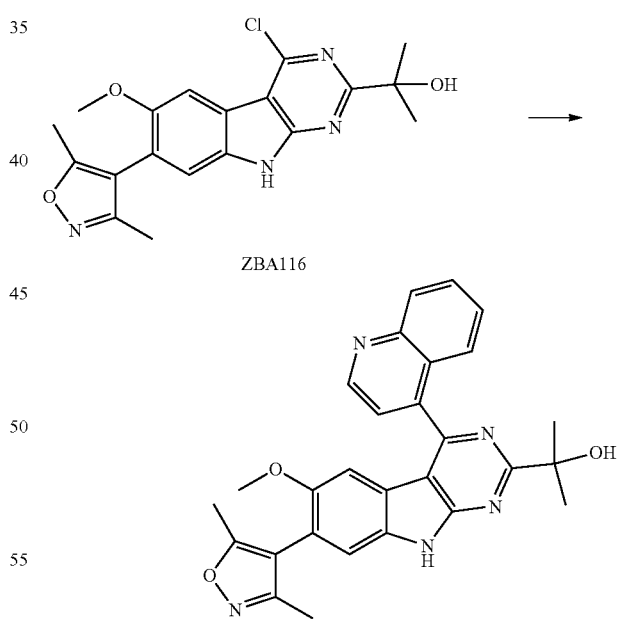

Cpd. No. 125

To a round-bottom flask, ZBA97 (0.278 g) and POCl$_3$ (8 mL) were added. The mixture was heated at 90° C. for 6 h. The reaction mixture was cooled to room temperature and the volatile components were removed on a rotary evaporator. Water (20 mL) and ethyl acetate (20 mL) were added and the pH was adjusted to 8 using NaHCO$_3$ saturated aqueous solution. Filtration of the mixture furnished ZBA104 as a brown solid in 0.208 g. $^1$H NMR (300 MHz, MeOD-d4) δ 8.02 (s, 1H), 7.55 (s, 1H), 4.07 (s, 3H), 3.99 (s, 3H), 2.37 (s, 3H), 2.20 (s, 3H).

Cpd. No. 125-TFA salt was prepared from Suzuki coupling of ZBA116 and quinolin-4-ylboronic acid using Pd(PPh$_3$)$_4$—K$_2$CO$_3$ (2 M) condition. 40% yield. $^1$H NMR (300 MHz, MeOD-d4) δ 9.33 (d, J=4.8 Hz, 1H), 8.39 (d, J=8.6 Hz, 1H), 8.21-8.03 (m, 2H), 7.94 (d, J=8.4 Hz, 1H), 7.85-7.71 (m, 1H), 7.52 (s, 1H), 6.29 (s, 1H), 3.26 (s, 3H), 2.29 (s, 3H), 2.10 (s, 3H), 1.81 (s, 6H).

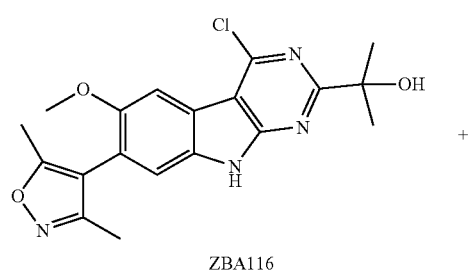

ZBA116

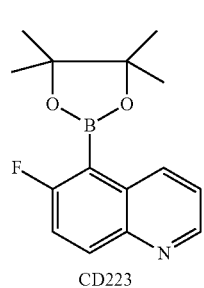

CD223

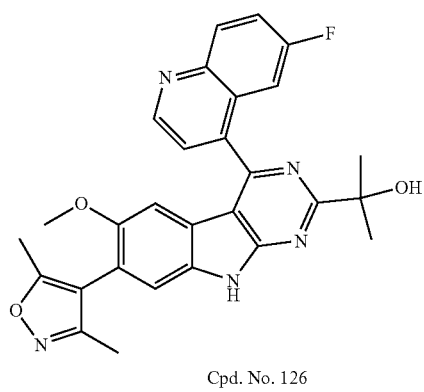

Cpd. No. 126

Cpd. No. 126-TFA salt was prepared from Suzuki coupling of ZBA116 and CD223 using Pd(PPh₃)₄—K₂CO₃ (2 M) condition. 40% yield. ¹H NMR (300 MHz, MeOD) δ 9.29 (d, J=4.6 Hz, 1H), 8.44 (dd, J=9.3, 5.3 Hz, 1H), 8.11 (d, J=4.5 Hz, 1H), 7.91-7.82 (m, 1H), 7.61 (dd, J=9.4, 2.7 Hz, 1H), 7.58 (s, 1H), 6.30 (s, 1H), 3.30 (s, 3H), 2.29 (s, 3H), 2.10 (s, 3H), 1.84 (s, 6H). ESI-MS calculated for C₂₈H₂₅FN₅O₃ [M+H]⁺=498.19, Obtained: 498.54.

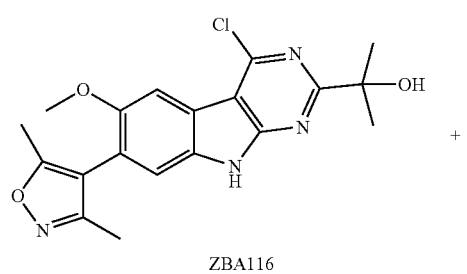

ZBA116

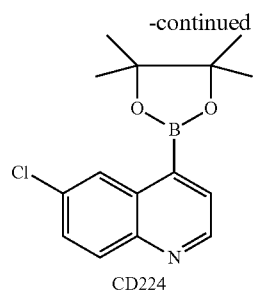

CD224

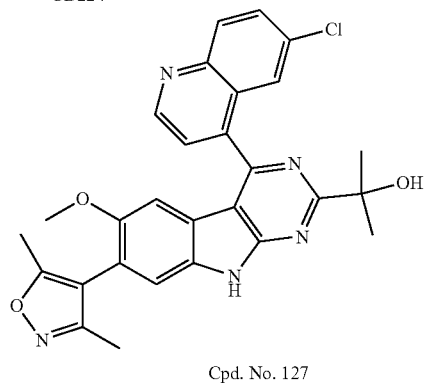

Cpd. No. 127

Cpd. No. 127-TFA salt was prepared from Suzuki coupling of ZBA116 and CD224 using Pd(PPh₃)₄—K₂CO₃ (2 M) condition. 40% yield. ¹H NMR (300 MHz, MeOD) δ 9.28 (t, J=7.9 Hz, 1H), 8.36 (d, J=8.8 Hz, 1H), 8.10 (d, J=4.5 Hz, 1H), 8.02-7.90 (m, 2H), 7.57 (s, 1H), 6.32 (s, 1H), 3.30 (s, 2H), 2.28 (s, 3H), 2.09 (s, 3H), 1.84 (s, 6H). ESI-MS calculated for C₂₈H₂₅ClN₅O₃ [M+H]⁺=514.16, Obtained: 514.36.

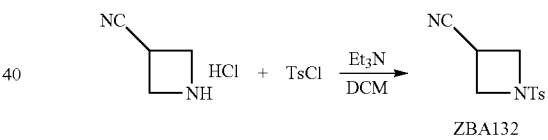

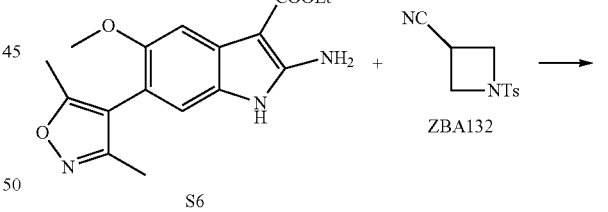

S6

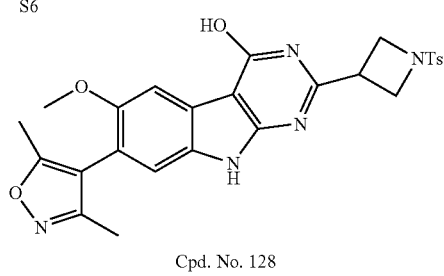

Cpd. No. 128

Azetidine-3-carbonitrile (1.8 g) was dissolved in DCM (50 ml). TsCl (3.1 g) and Et₃N (6.3 mL) were added and the mixture was stirred for 3 h. Aq. Brine was added and the aqueous layer was extracted with DCM. The combined DCM extracts were washed with H₂O, dried over Na₂SO₄, and concentrated under reduced pressure to afford ZBA132 (1.9 g) after flash column chromatography.

To a round-bottom flask, S6 (0.37 g, 1.1 mmol) and ZBA132 (2 g) were added at room temperature. Hydrogen chloride solution in dioxane (40 mL) was added and the reaction mixture was warmed up to reflux (82° C.) for 2.5 h. The reaction was then cooled to room temperature and the volatile components were removed on a rotary evaporator. To this crude mixture, 10% NaOH aqueous solution (20 mL) and EtOH (50 mL) were added and the solution was heated at reflux for 6 h. The volatile components were then removed on a rotary evaporator and the aqueous residue was acidified with 2N HCl aqueous solution. Water was removed on a rotary evaporator and the product Cpd. No. 128 (40 mg) was obtained after HPLC purification. ESI-MS calculated for $C_{26}H_{26}N_5O_5S$ $[M+H]^+$=520.16, Obtained: 520.55.

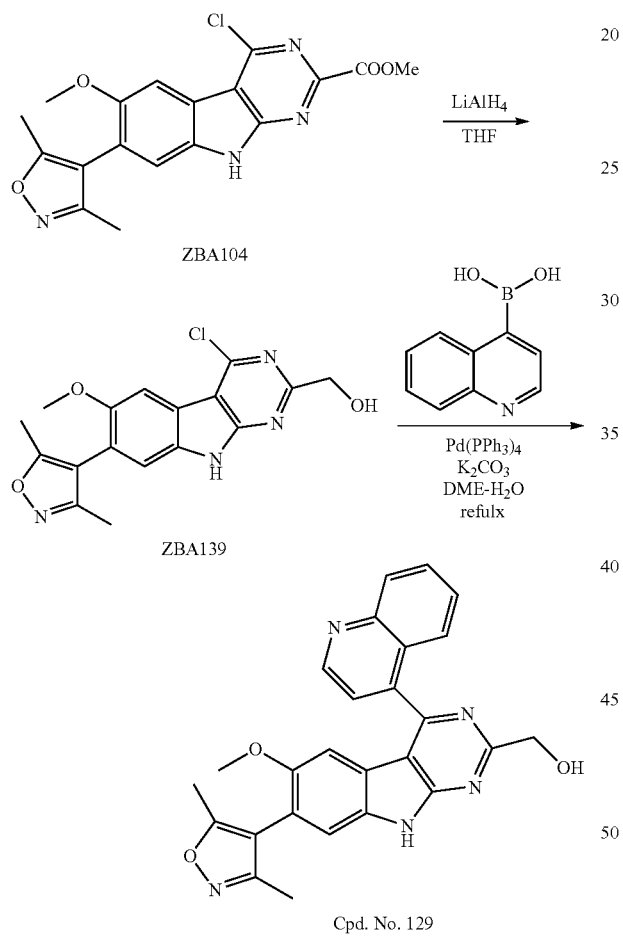

To a round-bottom flask, ZBA104 (0.038 g, 0.1 mmol) was dissolved in THF (7 mL) at room temperature. LiAlH$_4$ (7.6 mg, 0.2 mmol) was added and the reaction mixture was stirred for 2.5 h. Then water and Ethyl acetate was slowly added. The aqueous layer was extracted with EtOAc. The combined EtOAc extracts were washed with H$_2$O, dried over Na$_2$SO$_4$, and concentrated under reduced pressure to afford ZBA139 (27 mg). ESI-MS calculated for $C_{17}H_{15}ClN_4O_3$ $[M+H]^+$=359.09, Obtained: 359.43.

Cpd. No. 129-TFA salt was prepared from Suzuki coupling of ZBA139 and quinolin-4-ylboronic acid using Pd(PPh$_3$)$_4$—K$_2$CO$_3$ (2 M) condition. 38% yield. $^1$H NMR (300 MHz, MeOD) δ 9.49 (d, J=5.0 Hz, 1H), 8.50 (d, J=8.5 Hz, 1H), 8.36 (d, J=5.0 Hz, 1H), 8.16 (t, J=7.7 Hz, 1H), 8.07 (d, J=8.4 Hz, 1H), 7.85 (t, J=7.6 Hz, 1H), 7.58 (s, 1H), 6.36 (s, 1H), 5.13 (s, 2H), 3.30 (s, 3H), 2.27 (s, 3H), 2.08 (s, 3H). ESI-MS calculated for $C_{26}H_{22}N_5O_3$ $[M+H]^+$=452.17, Obtained: 452.57.

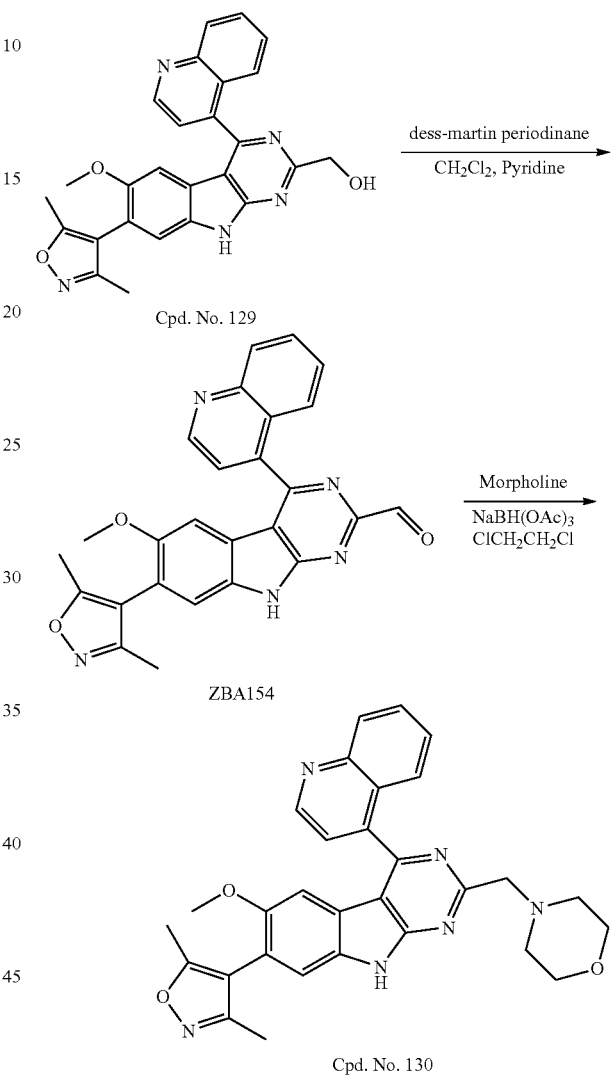

To a round-bottom flask, Cpd. No. 129 (0.045 g, 0.1 mmol) was dissolved in DCM (7 mL) and Pyridine (0.4 mL) at room temperature. Dess-martin periodinane (63.6 mg, 0.15 mmol) was added and the reaction mixture was stirred for 2.5 h. Then water and ethyl acetate was slowly added. The aqueous layer was extracted with EtOAc. The combined EtOAc extracts were washed with H$_2$O, dried over Na$_2$SO$_4$, and concentrated under reduced pressure to afford the aldehyde intermediate ZBA154. The intermediate ZBA154, morpholine (0.3 mL) and NaBH(OAc)$_3$ (90 mg, 0.4 mmol) was dissolved in ClCH$_2$CH$_2$Cl (10 mL) and the mixture was stirred overnight. Then water and Ethyl acetate was slowly added. The aqueous layer was extracted with EtOAc. The combined EtOAc extracts were washed with H$_2$O, dried over Na$_2$SO$_4$, and concentrated under reduced pressure to afford Cpd. No. 130 (24 mg) after HPLC purification. $^1$H NMR (300 MHz, MeOD) δ 9.33 (d, J=4.9 Hz, 1H), 8.39 (d, J=8.5 Hz, 1H), 8.13 (d, J=4.9 Hz, 1H), 8.08 (ddd, J=8.5, 6.9, 1.3 Hz, 1H), 8.00-7.93 (m, 1H), 7.75 (ddd, J=8.3, 6.9, 1.1 Hz, 1H), 7.49 (s, 1H), 6.37 (s, 1H), 4.87 (s, 2H), 4.04 (brs, 4H), 3.66 (brs, 4H), 3.27 (s, 3H), 2.28 (s, 3H), 2.09 (s, 3H). ESI-MS calculated for $C_{30}H_{29}N_6O_3$ $[M+H]^+$=521.23, Obtained: 521.67.

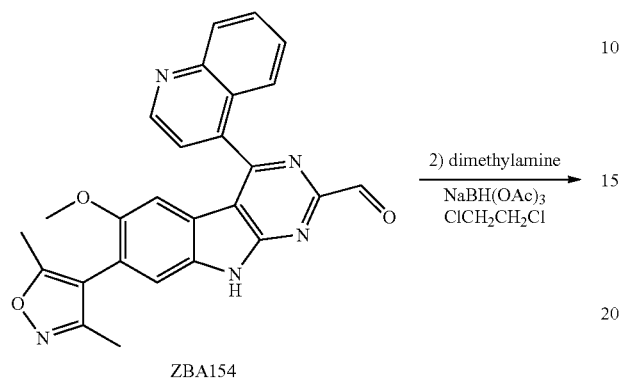

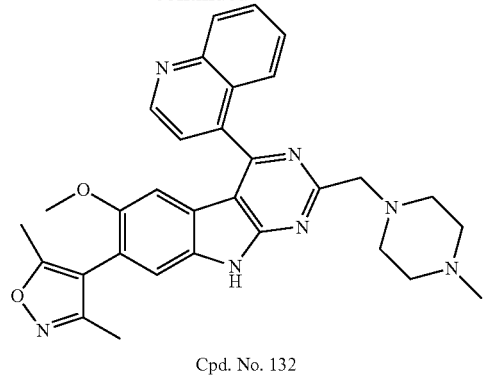

Cpd. No. 132

Cpd. No. 132-TFA salt was prepared from reductive amination of ZBA154 and 1-methylpiperazine using NaBH(OAc)$_3$ condition. 50% yield. $^1$H NMR (300 MHz, MeOD) δ 9.32 (d, J=4.8 Hz, 1H), 8.38 (d, J=8.6 Hz, 1H), 8.16-8.01 (m, 2H), 7.93 (d, J=8.2 Hz, 1H), 7.81-7.68 (m, 1H), 7.49 (s, 1H), 6.32 (s, 1H), 4.44 (s, 2H), 3.58-3.32 (m, 8H), 3.26 (s, 3H), 2.95 (s, 3H), 2.28 (s, 3H), 2.10 (s, 3H). ESI-MS calculated for $C_{31}H_{32}N_7O_2$ $[M+H]^+$=534.26, Obtained: 534.55.

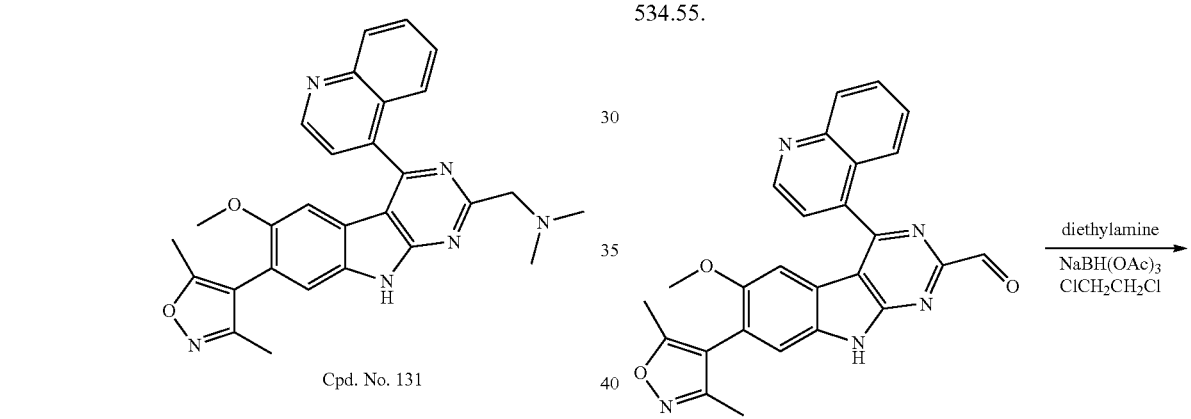

Cpd. No. 131

Cpd. No. 131-TFA salt was prepared from reductive amination of ZBA154 and dimethylamine using NaBH(OAc)$_3$ condition. 50% yield. $^1$H NMR (300 MHz, MeOD) δ 9.40 (d, J=5.0 Hz, 1H), 8.44 (d, J=8.5 Hz, 1H), 8.24 (d, J=5.0 Hz, 1H), 8.19-8.10 (m, 1H), 8.04 (d, J=8.3 Hz, 1H), 7.81 (t, J=7.4 Hz, 1H), 7.50 (s, 1H), 6.40 (s, 1H), 4.83 (s, 2H), 3.28 (s, 3H), 3.16 (s, 6H), 2.28 (s, 3H), 2.09 (s, 3H). ESI-MS calculated for $C_{28}H_{27}N_6O_2$ $[M+H]^+$=479.21, Obtained: 479.44.

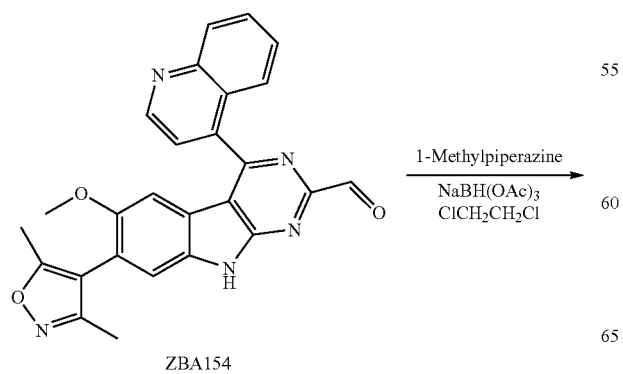

Cpd. No. 133

Cpd. No. 133-TFA salt was prepared from reductive amination of ZBA154 and diethylamine using NaBH(OAc)$_3$ condition. 50% yield. $^1$H NMR (300 MHz, MeOD) δ 9.35 (d, J=4.9 Hz, 1H), 8.40 (d, J=8.5 Hz, 1H), 8.15 (d, J=4.9 Hz, 1H), 8.09 (ddd, J=8.5, 6.9, 1.3 Hz, 1H), 7.99 (d, J=7.9 Hz, 1H), 7.76 (ddd, J=8.3, 6.9, 1.1 Hz, 1H), 7.50 (s, 1H), 6.39 (s, 1H), 4.83 (s, 2H), 3.65-3.40 (m, 4H), 3.28 (s, 3H), 2.28 (s, 3H), 2.09 (s, 3H), 1.47 (t, J=7.2 Hz, 6H). ESI-MS calculated for $C_{30}H_{31}N_6O_2$ $[M+H]^+$=507.25, Obtained: 507.44.

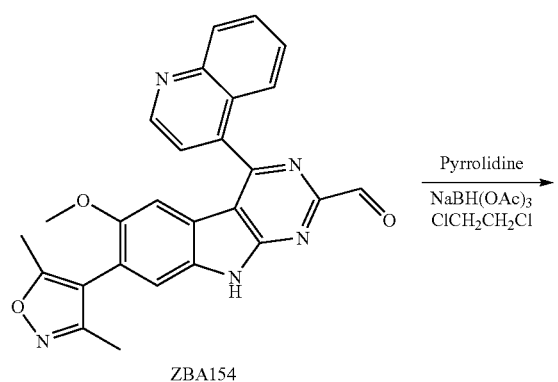

ZBA154

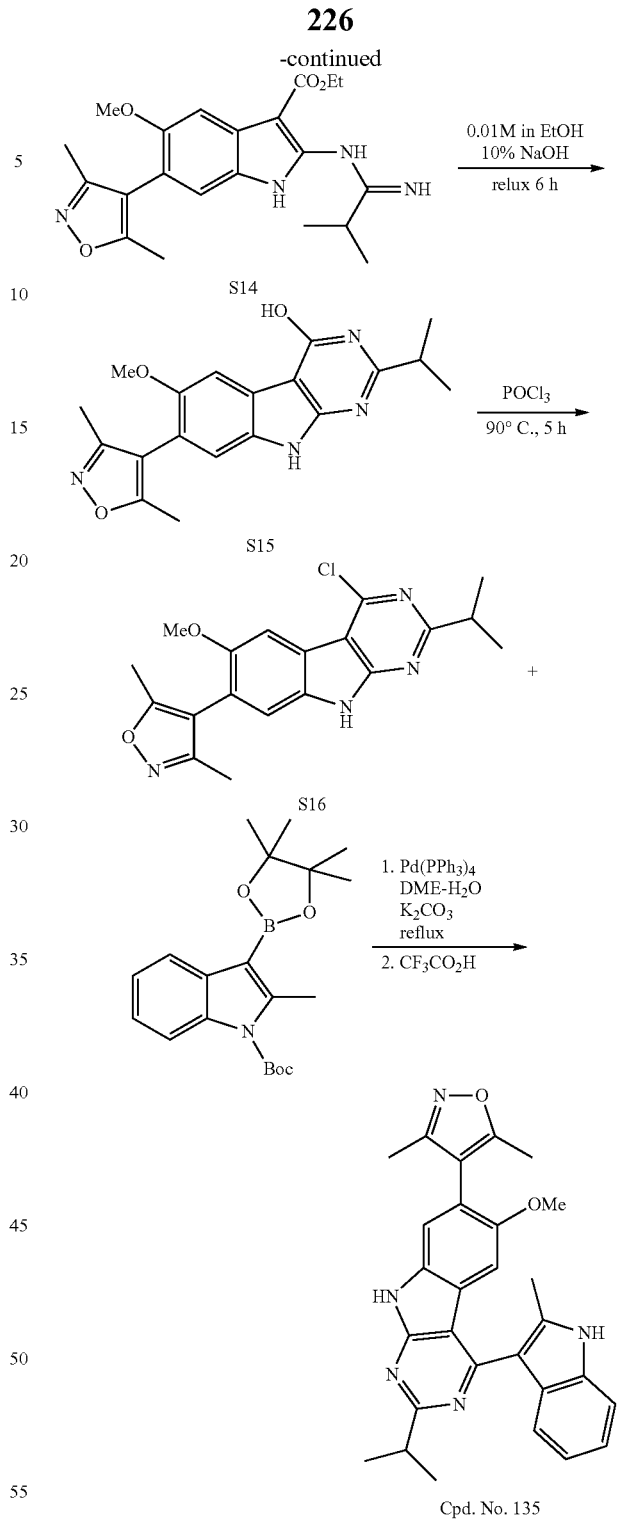

Cpd. No. 134

Cpd. No. 134-TFA salt was prepared from reductive amination of ZBA154 and pyrrolidine using NaBH(OAc)$_3$ condition. 53% yield. $^1$H NMR (300 MHz, MeOD) δ 9.31 (d, J=4.8 Hz, 1H), 8.38 (d, J=8.5 Hz, 1H), 8.14-8.01 (m, 2H), 7.94 (d, J=7.9 Hz, 1H), 7.77-7.70 (m, 1H), 7.48 (s, 1H), 6.35 (s, 1H), 4.91 (s, 2H), 4.05-3.85 (m, 2H), 3.51-3.31 (m, 2H), 3.26 (s, 3H), 2.39-2.00 (m, 10H). ESI-MS calculated for C$_{30}$H$_{29}$N$_6$O$_2$ [M+H]$^+$=505.23, Obtained: 505.43.

The same reaction conditions for the synthesis of S13 can be used to synthesize S16 (scheme below). Reflux S6 with isobutyronitrile in the presence of dry HCl will afford compound 14, which will readily cyclized into S15 upon treatment of base (NaOH-water-EtOH) at 120° C. Treatment of S15 with POCl$_3$ will afford S16, a key intermediate can undergo direct condensation/coupling reaction with amine and Suzuki coupling reaction with aromatic pinacol boronate or vinyl pinacol boronate. An example of Suzuki coupling of S16 and tert-Butyl 2-methyl-3-(4,4,5,5-tetramethyl-1,3,2-dioxaborolan-2-yl)-1H-indol-1-carboxylate is depicted in the following scheme to give Cpd. No. 135.

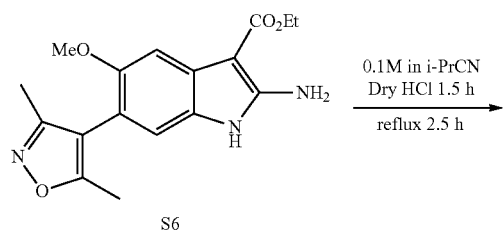

S6

The same reaction conditions for the synthesis of S13 can be used to synthesize S20 (scheme below). A similar method to synthesis of 4-chloro-9H-pyrimido[4,5-b]indol-2-amine from ethyl 2-amino-1H-indole-3-carboxylate has been reported by H. D. Hollisin Showalter and coworkers in Journal of Medicinal Chemistry (J. Med. Chem. 1999, 42, 5464-5474). Reflux S6 with cyanamide in the presence of concentrated HCl in 1,4-dioxane will afford intermediate S18, which will readily cyclized into S19 upon treatment of base (NaOH-water-EtOH) at relux. Treatment of S19 with POCl₃ at 90° C. will afford S20.

S20 is a key intermediate that can undergo direct condensation/coupling reaction with amine and Suzuki coupling reaction with aromatic pinacol boronate or vinyl pinacol boronate. An example of Suzuki coupling of S20 and commercially available quinolin-4-ylboronic acid was depicted in the following scheme.

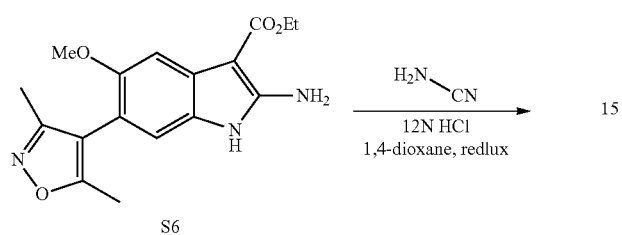

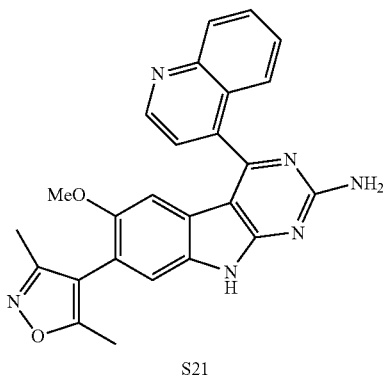

Standard reductive amine of S21 and a variety of aldehydes in the presence of NaBH(OAc)₃ and acetic acid in 1,2-dichloroethane will give the corresponding product S22.

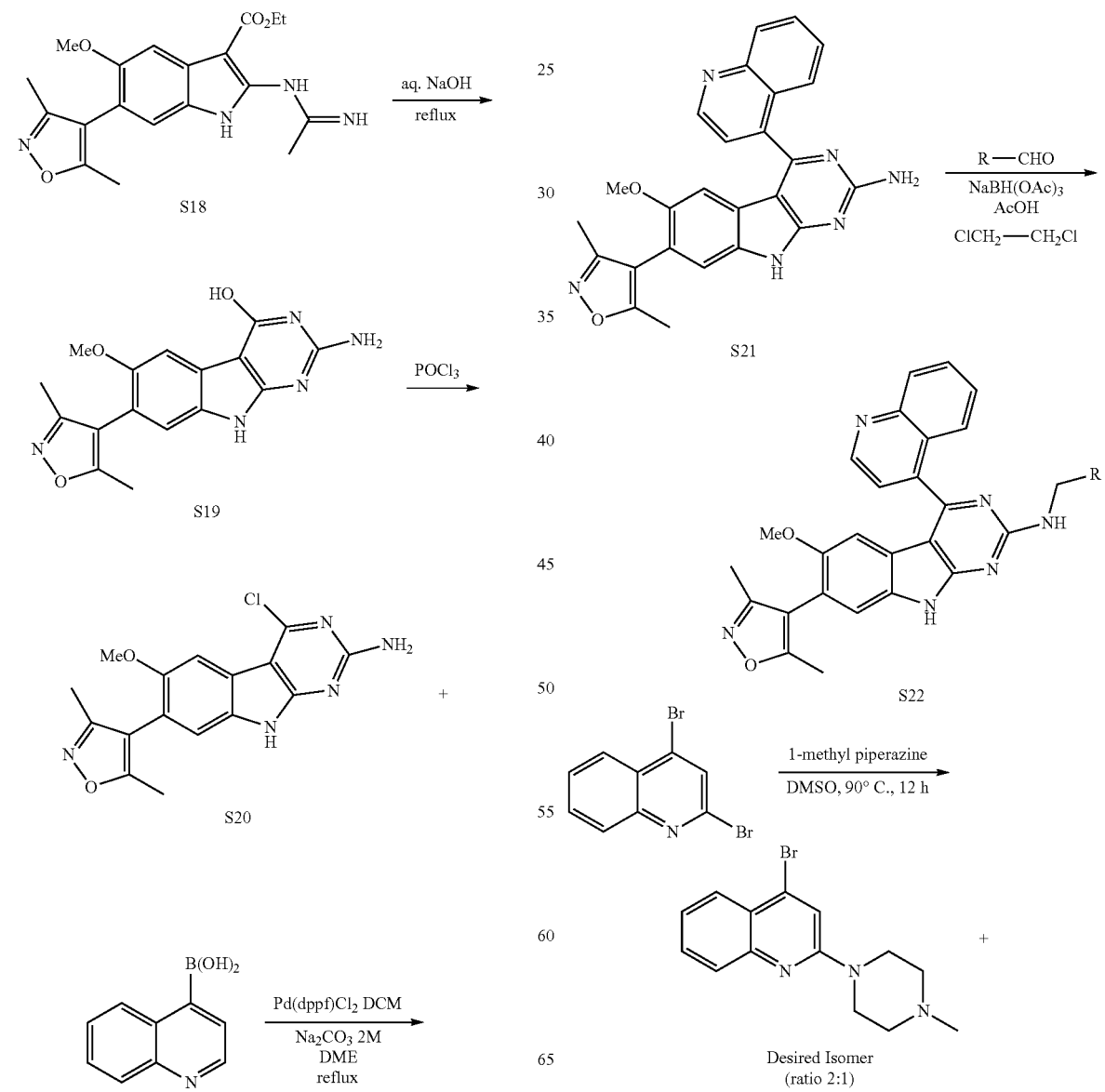

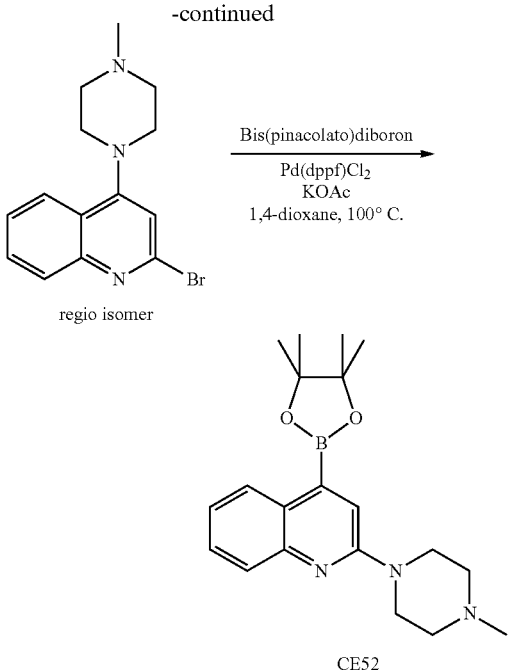

regio isomer

CE52

4-Bromo-2-(4-methylpiperazin-1-yl)quinoline (CE46)

2,4-Dibromoquinoline (572 mg, 2.0 mmol) and 1-methylpiperazine (200 mg, 2.0 mmol) were dissolved in anhydrous DMSO (6 mL). The solution was heated at 90° C. for 16 h. The reaction was quenched with water. The aqueous layer was extracted with ethyl acetate and the combined organic layers were washed with brine, dry over anhydrous sodium sulfate, and concentrated on a rotary evaporator. The residue was purified by flash column chromatography to yield 4-bromo-2-(4-methylpiperazin-1-yl)quinoline and its region isomer 2-bromo-4-(4-methylpiperazin-1-yl)quinoline in 0.50 g (ratio 2:1). The mixture of two isomers was used for synthesis of CE52 without further purification. 1H NMR (CDCl3, 300 MHz): 7.94 (d, J=8.19 Hz, 1H), 7.65 (d, J=8.14 Hz, 1H), 7.62-7.54 (m, 1H), 7.33 (ddd, J=8.11, 6.79, 1.16 Hz, 1H), 7.26 (s, 1H), 4.10-3.90 (m, 4H), 3.30-3.05 (m, 4H), 2.57 (s, 3H).

2-(4-Methylpiperazin-1-yl)-4-(4,4,5,5-tetramethyl-1,3,2-dioxaborolan-2-yl)quinoline (CE52)

4-Bromo-2-(4-methylpiperazin-1-yl)quinoline and its region isomer (0.50 g, 1.6 mmol, 1.0 equiv.), bis(pinacolato)diboron (812 mg, 3.2 mmol, 2.0 equiv.), and potassium acetate (640 mg, 6.4 mmol, 4.0 equiv.) were added to a round-bottom flask. Anhydrous 1,4-dixoane (10 mL) was added and the system was degassed and refilled nitrogen. Pd(dppf)Cl$_2$ (112 mg, 0.16 mmol, 0.1 equiv.) was added and the system was degassed again followed by heating at 100° C. for 16 h. The reaction mixture was cooled to room temperature and diluted by CH$_2$Cl$_2$. The solution was filtered through a pad of celite and the volatile components were removed on a rotary evaporator. The residue was purified by flash column chromatography. The title compound was isolated in 130 mg (mixture of isomers). ESI-MS calculated for C$_{20}$H$_{29}$BN$_3$O$_2$ [M+H]$^+$=354.24; Observed: 354.58.

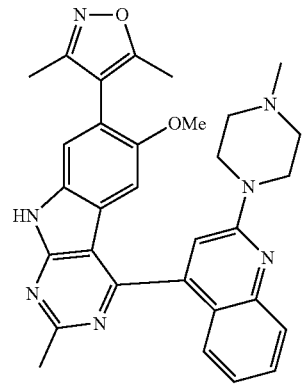

Cpd. No. 136

4-(6-Methoxy-2-methyl-4-(2-(4-methylpiperazin-1-yl)quinolin-4-yl)-9H-pyrimido[4,5-b]indol-7-yl)-3,5-dimethylisoxazole Suzuki coupling of 4-(4-chloro-6-methoxy-2-methyl-9H-pyrimido[4,5-b]indol-7-yl)-3,5-dimethylisoxazole (S13, 45 mg) and 2-(4-methylpiperazin-1-yl)-4-(4,4,5,5-tetramethyl-1,3,2-dioxaborolan-2-yl)quinoline (CE52, 130 mg) using condition Method 42 afforded the title compound as a salt of CF$_3$CO$_2$H (26 mg, 34% yield). $^1$H NMR (MeOD-d4, 300 MHz): 8.00 (d, J=8.39 Hz, 1H), 7.81 (s, 1H), 7.85-7.75 (m, 1H), 7.60-7.54 (m, 1H), 7.54 (s, 1H), 7.35 (t, J=7.27 Hz, 1H), 6.26 (s, 1H), 3.80-3.30 (m, 8H), 3.20 (s, 3H), 3.02 (s, 3H), 3.00 (s, 3H), 2.26 (s, 3H), 2.07 (s, 3H). ESI-MS calculated for C$_{31}$H$_{32}$N$_7$O$_2$ [M+H]$^+$=534.26; Observed: 534.42.

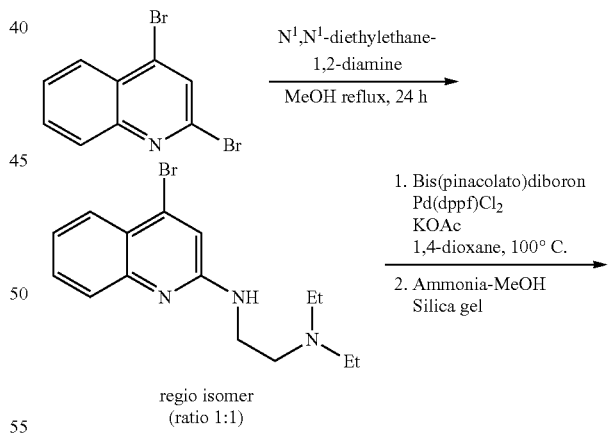

regio isomer
(ratio 1:1)

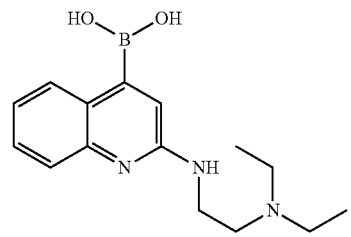

CE55

$N^1$-(4-bromoquinolin-2-yl)-$N^2$,$N^2$-diethylethane-1,2-diamine (CE49)

2,4-Dibromoquinoline (861 mg, 3.0 mmol) and $N^1$,$N^1$-diethylethane-1,2-diamine (348 mg, 3.0 mmol) were dissolved in anhydrous DMSO (6 mL). The solution was heated at 90° C. for 16 h. The reaction was quenched with water. The pH value of the reaction mixture was adjusted be less than 1 using $CF_3CO_2H$ and the mixture was purified on reverse phase HPLC to yield $N^1$-(4-bromoquinolin-2-yl)-$N^2$,$N^2$-diethylethane-1,2-diamine as a salt of TFA in 0.30 g (33% yield). The ratio for two region isomer is ca. 1:1 determined by analytical UPLC. $^1$H NMR (MeOD-d4, 300 MHz): 8.08 (d, J=8.20 Hz, 1H), 8.00-7.80 (m, 1H), 7.82 (t, J=7.58 Hz, 1H), 7.57 (t, J=8.12 Hz, 2H), 4.06 (t, J=6.35 Hz, 2H), 3.56 (t, J=6.35 Hz, 2H), 3.35 (q, J=7.39 Hz, 4H), 1.36 (t, J=7.39 Hz, 6H). ESI-MS calculated for $C_{15}H_{21}{}^{79}BrN_3$ [M+H]$^+$=322.09; Observed: 322.58.

(2-((2-(Diethylamino)ethyl)amino)quinolin-4-yl)boronic acid (CE55)

$N^1$-(4-bromoquinolin-2-yl)-$N^2$,$N^2$-diethylethane-1,2-diamine (0.30 g, 1.0 mmol, 1.0 equiv.), bis(pinacolato)diboron (500 mg, 2.0 mmol, 2.0 equiv.), and potassium acetate (400 mg, 4 mmol, 4.0 equiv.) were added to a round-bottom flask. Anhydrous 1,4-dixoane (10 mL) was added and the system was degassed and refilled with nitrogen. Pd(dppf)Cl$_2$ (70 mg, 0.1 mmol, 0.1 equiv.) was added and the system was degassed again followed by heating at 100° C. for 16 h. The reaction mixture was cooled to room temperature and diluted by CH$_2$Cl$_2$. The solution was filtered through a pad of celite and the volatile components were removed on a rotary evaporator. The residue was purified by flash column chromatography using MeOH—NH$_3$ as eluent. The title compound was obtained in 140 mg (38% yield). $^1$H NMR (MeOD-d4, 300 MHz): 7.98 (d, J=8.04 Hz, 1H), 7.74 (ddd, J=8.43, 7.20, 1.26 Hz, 1H), 7.96-7.84 (m, 1H), 7.50 (ddd, J=8.43, 7.31, 1.10 Hz, 1H), 7.30-7.20 (m, 1H), 4.08 (t, J=6.57 Hz, 2H), 3.56 (t, J=6.57 Hz, 2H), 3.35 (q, J=7.29, 4H), 1.36 (t, J=7.29 Hz, 6H).

Cpd. No. 137

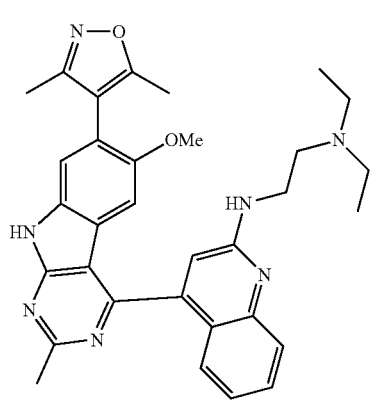

$N^1$-(4-(7-(3,5-Dimethylisoxazol-4-yl)-6-methoxy-2-methyl-9H-pyrimido[4,5-b]indol-4-yl)quinolin-2-yl)-$N^2$,$N^2$-diethylethane-1,2-diamine Suzuki coupling of S13 (70 mg) and (2-((2-(diethylamino)ethyl)amino)quinolin-4-yl)boronic acid (CE55, 130 mg) using condition Method 42 afforded the title compound (50 mg, 38% yield). $^1$H NMR (MeOD-d4, 300 MHz): 8.09 (d, J=8.41 Hz, 1H), 7.88 (t, J=7.75 Hz, 1H), 7.63 (d, J=8.05 Hz, 2H), 7.52 (s, 1H), 7.43 (t, J=7.67 Hz, 1H), 6.49 (s, 1H), 4.15 (t, J=6.29 Hz, 2H), 3.62 (t, J=6.41 Hz, 2H), 3.40 (q, J=7.20 Hz, 1H), 3.31 (s, 3H), 2.99 (s, 3H), 2.26 (s, 3H), 2.07 (s, 3H), 1.39 (t, J=7.3 Hz, 6H). ESI-MS calculated for $C_{32}H_{36}N_7O_2$ [M+H]$^+$=550.29; Observed: 550.25.

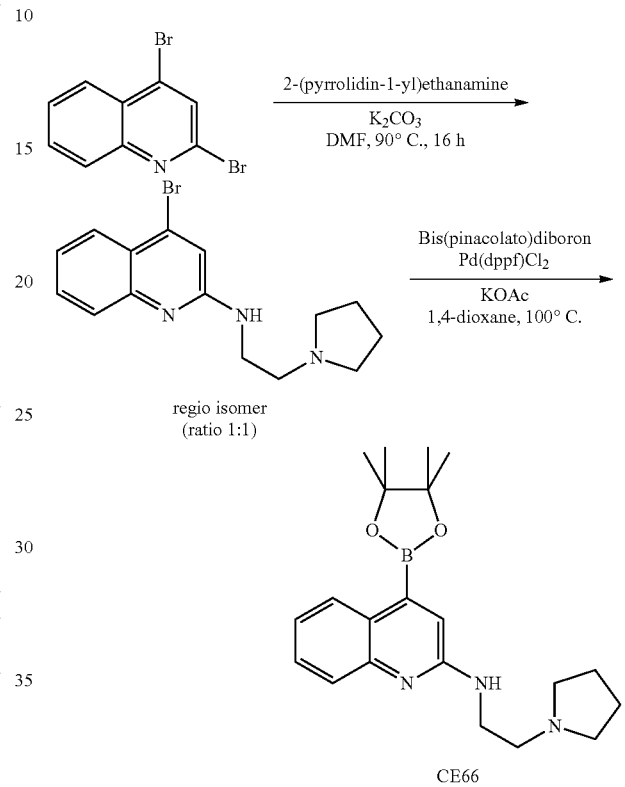

4-Bromo-N-(2-(pyrrolidin-1-yl)ethyl)quinolin-2-amine (CE62)

2,4-Dibromoquinoline (861 mg, 3.0 mmol), 2-(pyrrolidin-1-yl)ethanamine (342 mg, 3.0 mmol), and K$_2$CO$_3$ (414 mg, 3.0 mmol) were mixed in anhydrous DMF (6 mL). The solution was heated at 90° C. for 16 h. The pH value of the reaction mixture was adjusted be less than 1 using CF$_3$CO$_2$H and the mixture was purified on reverse phase HPLC to yield 4-bromo-N-(2-(pyrrolidin-1-yl)ethyl)quinolin-2-amine as a salt of TFA in 0.48 g (37% yield). The ratio for two region isomer is ca. 1:1 determined by analytical UPLC. $^1$H NMR (MeOD-d4, 300 MHz): 7.96 (d, J=8.22 Hz, 1H), 7.80-7.70 (m, 2H), 7.60-7.45 (m, 2H), 4.05 (t, J=Hz, 2H), 3.90-3.60 (m, 2H), 3.63 (t, J=6.08 Hz, 2H), 3.30-3.10 (m, 2H), 2.30-2.00 (m, 4H). ESI-MS calculated for $C_{15}H_{19}{}^{79}BrN_3$ [M+H]$^+$=320.08; Observed: 320.36.

N-(2-(Pyrrolidin-1-yl)ethyl)-4-(4,4,5,5-tetramethyl-1,3,2-dioxaborolan-2-yl)quinolin-2-amine (CE66)

4-Bromo-N-(2-(pyrrolidin-1-yl)ethyl)quinolin-2-amine (0.48 g, 1.11 mmol), bis(pinacolato)-diboron (762 mg, 3.0 mmol), and potassium acetate (600 mg, 6 mmol) were added to a round-bottom flask. Anhydrous 1,4-dixoane (10 mL) was added and the system was degassed and refilled with nitrogen. Pd(dppf)Cl$_2$ (0.105 mg, 0.15 mmol) was added and the system was degassed again followed by heating at 100° C. for 16 h. The reaction mixture was cooled to room temperature and diluted by CH$_2$Cl$_2$. The solution was filtered through a pad of celite and the volatile components were removed on a rotary evaporator. The residue was purified on reverse phase HPLC to yield the title compound as a salt of TFA in 320 mg (44% yield). $^1$H NMR (MeOD-d4, 300 MHz): 8.50 (d, J=8.12 Hz, 1H), 8.00-7.80 (m, 1H), 7.72 (t, J=7.63 Hz, 1H), 7.48 (t, J=8.07 Hz, 1H), 7.47 (s, 1H), 4.09 (t, J=5.86 Hz, 2H), 3.64 (t, J=6.03 Hz, 2H), 3.90-3.65 (m, 2H), 3.30-3.10 (m, 2H), 2.30-2.00 (m, 4H), 1.42 (s, 12H). ESI-MS calculated for C$_{21}$H$_{31}$BN$_3$O$_2$ [M+H]$^+$= 368.25; Observed: 368.33.

Cpd. No. 138

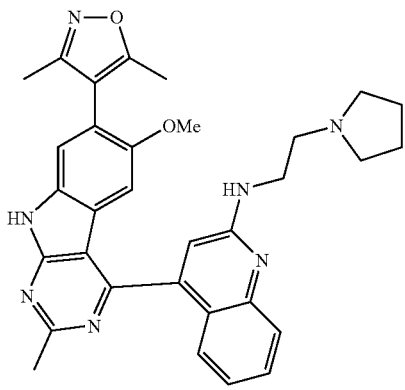

4-(7-(3,5-Dimethylisoxazol-4-yl)-6-methoxy-2-methyl-9H-pyrimido[4,5-b]indol-4-yl)-N-(2-(pyrrolidin-1-yl)ethyl)quinolin-2-amine Suzuki coupling of S13 (136 mg, 0.4 mmol) and N-(2-(pyrrolidin-1-yl)ethyl)-4-(4,4,5,5-tetramethyl-1,3,2-dioxaborolan-2-yl)quinolin-2-amine (CE66, 320 mg, 0.66 mmol) using condition Method 42 afforded the title compound as a salt of CF$_3$CO$_2$H (80 mg, 30% yield). $^1$H NMR (MeOD-d4, 300 MHz): 8.13 (d, J=8.38 Hz, 1H), 7.92 (t, J=7.25 Hz, 1H), 7.67 (d, J=7.39 Hz, 2H), 7.54 (s, 1H), 7.47 (t, J=7.69 Hz, 1H), 6.52 (s, 1H), 4.16 (t, J=6.11 Hz, 2H), 3.71 (t, J=6.22 Hz, 2H), 3.80-3.60 (m, 2H), 3.40-3.20 (m, 2H), 3.01 (s, 3H), 2.29 (s, 3H), 2.30-2.10 (m, 4H), 2.10 (s, 3H). ESI-MS calculated for C$_{32}$H$_{34}$N$_7$O$_2$ [M+H]$^+$=548.28; Observed: 548.88.

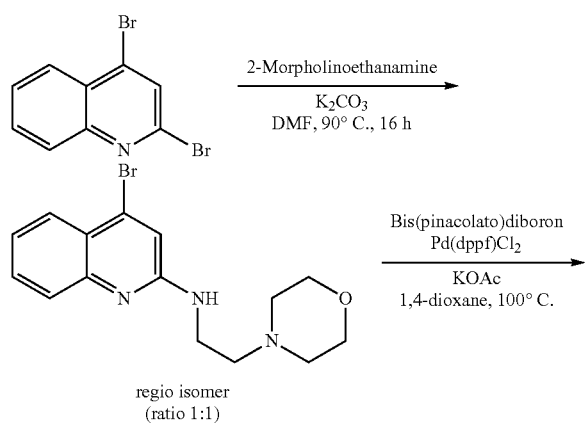

regio isomer
(ratio 1:1)

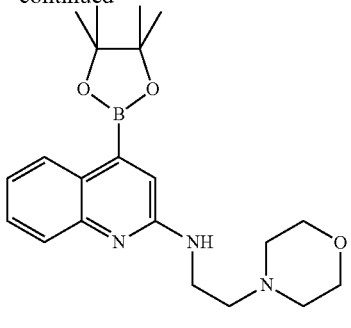

CE71

4-Bromo-N-(2-morpholinoethyl)quinolin-2-amine (CE60)

2,4-Dibromoquinoline (861 mg, 3.0 mmol), 2-morpholinoethanamine (390 mg, 3.0 mmol), and K$_2$CO$_3$ (414 mg, 3.0 mmol) were mixed in anhydrous DMF (6 mL). The solution was heated at 90° C. for 16 h. The pH value of the reaction mixture was adjusted be less than 1 using CF$_3$CO$_2$H and the mixture was purified on reverse phase HPLC to yield 4-bromo-N-(2-morpholinoethyl)quinolin-2-amine as a salt of TFA in 0.545 g (1.2 mmol, 40% yield). The ratio for two region isomer is ca. 1:1 determined by analytical UPLC. $^1$H NMR (MeOD-d4, 300 MHz): 8.06 (d, J=8.22 Hz, 1H), 7.90-7.70 (m, 2H), 7.70-7.50 (m, 2H), 4.09 (t, J=6.17 Hz, 2H), 4.00-3.85 (m, 4H), 3.60 (t, J=6.17 Hz, 2H), 3.50-3.30 (m, 4H). ESI-MS calculated for C$_{15}$H$_{19}$$^{79}$BrN$_3$O [M+H]$^+$= 336.07; Observed: 336.16.

N-(2-Morpholinoethyl)-4-(4,4,5,5-tetramethyl-1,3,2-dioxaborolan-2-yl)quinolin-2-amine (CE71)

4-Bromo-N-(2-morpholinoethyl)quinolin-2-amine (0.54 g, 1.2 mmol), bis(pinacolato)diboron (838 mg, 3.3 mmol), and potassium acetate (640 mg, 6.4 mmol) were added to a round-bottom flask. Anhydrous 1,4-dixoane (10 mL) was added and the system was degassed and refilled with nitrogen. Pd(dppf)Cl$_2$ (112 mg, 0.16 mmol) was added and the system was degassed again followed by heating at 100° C. for 16 h. The reaction mixture was cooled to room temperature and diluted by CH$_2$Cl$_2$. The solution was filtered through a pad of celite and the volatile components were removed on a rotary evaporator. The residue was purified on reverse phase flash column chromatography to yield the title compound as a salt of TFA in 460 mg (77% yield). $^1$H NMR (MeOD-d4, 300 MHz): 8.49 (d, J=8.11 Hz, 1H), 7.91 (d, J=7.73 Hz, 1H), 7.71 (t, J=7.76 Hz, 1H), 7.48 (t, J=7.53 Hz, 1H), 7.45 (s, 1H), 4.14 (t, J=5.91 Hz, 2H), 4.00-3.80 (m, 4H), 3.61 (t, J=5.91 Hz, 2H), 3.50-3.30 (m, 4H), 1.42 (s, 12H). ESI-MS calculated for C$_{21}$H$_{31}$BN$_3$O$_3$ [M+H]$^+$= 384.25; Observed: 384.50.

Cpd. No. 139

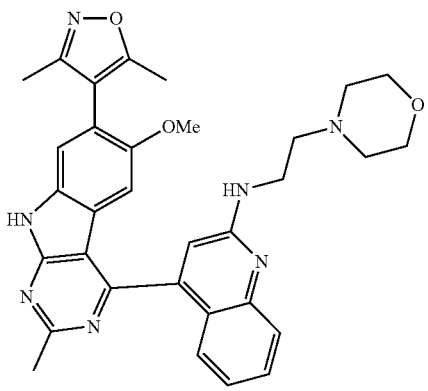

4-(7-(3,5-Dimethylisoxazol-4-yl)-6-methoxy-2-methyl-9H-pyrimido[4,5-b]indol-4-yl)-N-(2-morpholinoethyl)quinolin-2-amine Suzuki coupling of S13 (205 mg, 0.6 mmol) and N-(2-morpholinoethyl)-4-(4,4,5,5-tetramethyl-1,3,2-dioxaborolan-2-yl)quinolin-2-amine (CE71, 0.46 g, 0.93 mmol) using condition Method 42 afforded the title compound as a salt of $CF_3CO_2H$ (50 mg, 38% yield). $^1$H NMR (MeOD-d4, 300 MHz): 8.15 (d, J=7.91 Hz, 1H), 7.91 (t, J=7.79 Hz, 1H), 7.85-7.70 (m, 1H), 7.67 (d, J=7.85 Hz, 1H), 7.53 (s, 1H), 7.54 (t, J=7.71 Hz, 1H), 6.53 (s, 1H), 4.30-4.15 (m, 2H), 4.10-3.90 (m, 4H), 3.75-3.60 (m, 2H), 3.60-3.40 (m, 4H), 3.00 (s, 3H), 2.24 (s, 3H), 2.06 (s, 3H). ESI-MS calculated for $C_{32}H_{34}N_7O_3$ [M+H]$^+$=564.27; Observed: 564.67.

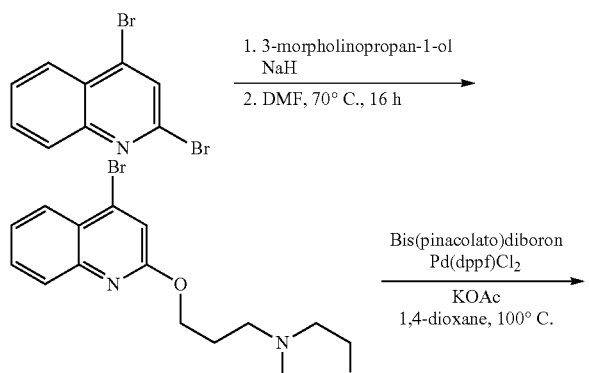

regio isomer
(ratio 1:1)

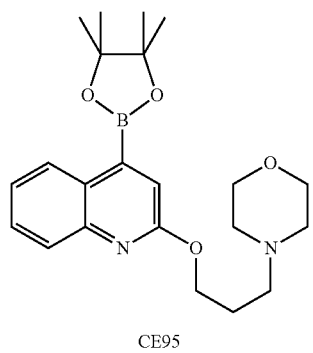

CE95

4-(3-((4-Bromoquinolin-2-yl)oxy)propyl)morpholine (CE90)

NaH (80 mg, 60% in mineral oil, 2.0 mmol) and anhydrous DMF (6 mL) were added to a round-bottom flask. To this flask, 3-morpholinopropan-1-ol (300 mg, 2.0 mmol) was added via a syringe and the mixture was stirred at room temperature for 20 min. 2,4-Dibromoquinoline (574 mg, 2.0 mmol) was added in one portion and the mixture was heated at 70° C. for 16 h. The reaction was quenched with water. The aqueous layer was extracted with ethyl acetate and the combined organic layers were washed with brine, dry over anhydrous sodium sulfate, and concentrated on a rotary evaporator. The residue was purified by flash column chromatography to yield 4-(3-((4-bromoquinolin-2-yl)oxy)propyl)morpholine in 0.168 g (0.48 mmol, 24% yield). The ratio for two region isomer is ca. 1:1 determined by analytical UPLC. $^1$H NMR (CDCl$_3$, 300 MHz): 8.11 (d, J=8.26 Hz, 1H), 7.84 (d, J=8.36 Hz, 1H), 7.69 (ddd, J=8.36, 7.11, 1.37 Hz, 1H), 7.49 (ddd, J=8.21, 6.86, 1.20 Hz, 1H), 7.28 (s, 1H), 4.56 (t, J=6.46 Hz, 2H), 3.84-3.72 (m, 4H), 2.58 (t, J=7.11 Hz, 2H), 2.58-2.50n (m, 4H), 2.12-2.02 (m, 2H).

4-(3-((4-(4,4,5,5-Tetramethyl-1,3,2-dioxaborolan-2-yl)quinolin-2-yl)oxy)propyl) morpholine (CE95)

4-(3-((4-Bromoquinolin-2-yl)oxy)propyl)morpholine in 0.168 g (0.48 mmol, 1.0 equiv.), bis(pinacolato)diboron (254 mg, 1.0 mmol, 2.0 equiv.), and potassium acetate (200 mg, 2.0 mmol, 4.0 equiv.) were added to a round-bottom flask. Anhydrous 1,4-dixoane (10 mL) was added and the system was degassed and refilled with nitrogen. Pd(dppf)Cl$_2$ (40 mg, 0.05 mmol, 0.1 equiv.) was added and the system was degassed again followed by heating at 100° C. for 16 h. The reaction mixture was cooled to room temperature and diluted by CH$_2$Cl$_2$. The solution was filtered through a pad of celite and the volatile components were removed on a rotary evaporator. The residue was purified by flash column chromatography to yield the title compound in 80 mg (42% yield). $^1$H NMR (CDCl$_3$, 300 MHz): 8.53 (dd, J=8.23, 1.02 Hz, 1H), 7.85 (dd, J=8.36, 0.70 Hz, 1H), 7.63 (ddd, J=8.36, 6.97, 1.44 Hz, 1H), 7.43 (ddd, J=8.20, 6.95, 1.29 Hz, 1H), 7.42 (s, 1H), 4.55 (t, J=6.32 Hz, 2H), 3.83-3.76 (m, 4H), 2.63 (t, J=7.36 Hz, 2H), 2.61-2.54 (m, 4H), 2.18-2.00 (m, 2H), 1.45 (s, 12H). ESI-MS calculated for $C_{22}H_{32}BN_2O_4$ [M+H]$^+$=399.25; Observed: 399.50.

Cpd. No. 140

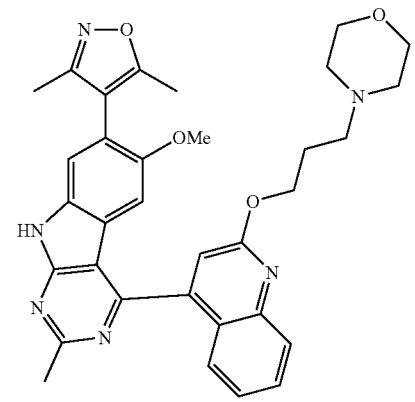

4-(3-((4-(7-(3,5-Dimethylisoxazol-4-yl)-6-methoxy-2-methyl-9H-pyrimido[4,5-b]indol-4-yl)quinolin-2-yl)oxy)propyl)morpholine Suzuki coupling of S13 (40 mg, 0.1 mmol) and 4-(3-((4-(4,4,5,5-tetramethyl-1,3,2-dioxaborolan-2-yl)quinolin-2-yl)oxy)propyl)morpholine (CE95, 80 mg) using condition Method 42 afforded the title compound as a salt of CF$_3$CO$_2$H (20 mg, 29% yield). $^1$H NMR (MeOD-d4, 300 MHz): 8.12 (d, J=8.46 Hz, 1H), 7.94-7.84 (m, 1H), 7.68 (d, J=8.31 Hz, 1H), 7.57 (s, 1H), 7.52 (s, 1H), 7.53-7.46 (m, 1H), 6.29 (s, 1H), 4.84-4.70 (m, 2H), 4.20-4.00 (m, 2H), 4.00-3.80 (m, 2H), 3.70-3.50 (m, 2H), 3.55-3.45 (m, 2H), 3.30-3.10 (m, 2H), 3.24 (s, 3H), 3.04 (s, 3H), 2.50-2.36 (m, 2H), 2.31 (s, 3H), 2.12 (s, 3H). ESI-MS calculated for C$_{33}$H$_{35}$N$_6$O$_4$ [M+H]$^+$=579.27; Observed: 579.33.

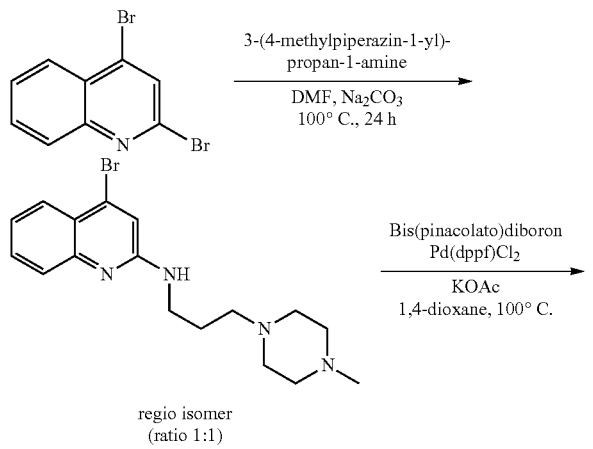

4-Bromo-N-(3-(4-methylpiperazin-1-yl)-propyl)quinolin-2-amine (CE86)

2,4-Dibromoquinoline (861 mg, 3.0 mmol), 3-(4-methylpiperazin-1-yl)-propan-1-amine (471 mg, 3.0 mmol), and Na$_2$CO$_3$ (315 mg, 3.0 mmol) were mixed in anhydrous DMF (6 mL). The solution was heated at 90° C. for 16 h. The pH value of the reaction mixture was adjusted be less than 1 using CF$_3$CO$_2$H and the mixture was purified on reverse phase HPLC to yield 4-bromo-N-(3-(4-methylpiperazin-1-yl)-propyl)quinolin-2-amine as a salt of TFA in 0.51 g (1.07 mmol, 36% yield). The ratio for two region isomer is ca. 1:1 determined by analytical UPLC. $^1$H NMR (MeOD-d4, 300 MHz): 8.00 (d, J=8.17 Hz, 1H), 7.96-7.82 (m, 1H), 7.77 (ddd, J=8.36, 7.16, 1.15 Hz, 1H), 7.52 (t, J=7.71 Hz, 1H), 7.50-7.40 (m, 1H), 3.70-3.60 (m, 10H), 3.50-3.30 (m, 2H), 3.00 (s, 3H), 2.36-2.16 (m, 2H). ESI-MS calculated for C$_{17}$H$_{24}$$^{79}$BrN$_4$ [M+H]$^+$=363.12; Observed: 363.56.

N-(3-(4-Methylpiperazin-1-yl)propyl)-4-(4,4,5,5-tetramethyl-1,3,2-dioxaborolan-2-yl)quinolin-2-amine (CE98)

4-Bromo-N-(3-(4-methylpiperazin-1-yl)-propyl)quinolin-2-amine (0.51 g, 1.07 mmol), bis(pinacolato)diboron (711 mg, 2.8 mmol), and potassium acetate (560 mg, 5.6 mmol) were added to a round-bottom flask. Anhydrous 1,4-dixoane (10 mL) was added and the system was degassed and refilled with nitrogen. Pd(dppf)Cl$_2$ (98 mg, 0.14 mmol) was added and the system was degassed again followed by heating at 100° C. for 16 h. The reaction mixture was cooled to room temperature and diluted by CH$_2$Cl$_2$. The solution was filtered through a pad of celite and the volatile components were removed on a rotary evaporator. The residue was purified on reverse phase HPLC to yield the title compound in 600 mg (>90% yield, with impurity). $^1$H NMR (MeOD-d4, 300 MHz): 8.54 (d, J=8.00 Hz, 1H), 8.00-7.80 (m, 1H), 7.75 (t, J=7.73 Hz, 1H), 7.57-7.46 (m, 1H), 7.51 (s, 1H), 3.86-3.66 (m, 10H), 3.52-3.42 (m, 2H), 3.04 (s, 3H), 2.38-2.22 (m, 2H), 1.46 (s, 12H). ESI-MS calculated for C$_{23}$H$_{36}$BN$_4$O$_2$ [M+H]$^+$=411.29; Observed: 411.50.

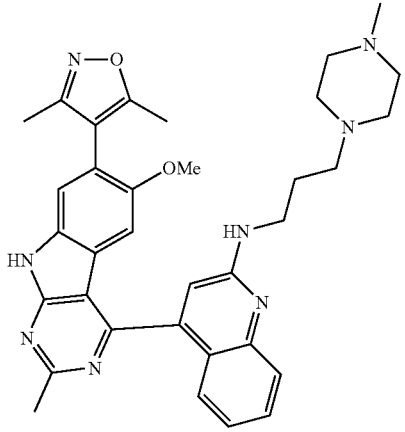

Cpd. No. 141

4-(7-(3,5-Dimethylisoxazol-4-yl)-6-methoxy-2-methyl-9H-pyrimido[4,5-b]indol-4-yl)-N-(3-(4-methylpiperazin-1-yl)propyl)quinolin-2-amine Suzuki coupling of S13 (205 mg, 0.6 mmol) and N-(3-(4-methylpiperazin-1-yl)propyl)-4-(4,4,5,5-tetramethyl-1,3,2-dioxaborolan-2-yl)quinolin-2-amine (CE98, 600 mg) using condition Method 42 afforded the title compound as a salt of CF$_3$CO$_2$H (156 mg, 37% yield). $^1$H NMR (MeOD-d4, 300 MHz): 8.30-8.10 (m, 1H), 7.92 (t, J=7.66 Hz, 1H), 7.67 (d, J=8.15 Hz, 1H), 7.75-7.60 (m, 1H), 7.55 (s, 1H), 7.47 (t, J=7.76 Hz, 1H), 6.55 (s, 1H), 4.00-3.80 (m, 2H), 3.80-3.60 (m, 8H), 3.55-3.40 (m, 2H), 3.31 (s, 3H), 2.97 (s, 3H), 2.96 (s, 3H), 2.46-2.28 (m, 2H), 1.76 (s, 3H). ESI-MS calculated for C$_{34}$H$_{39}$N$_8$O$_2$ [M+H]$^+$=591.32; Observed: 591.50.

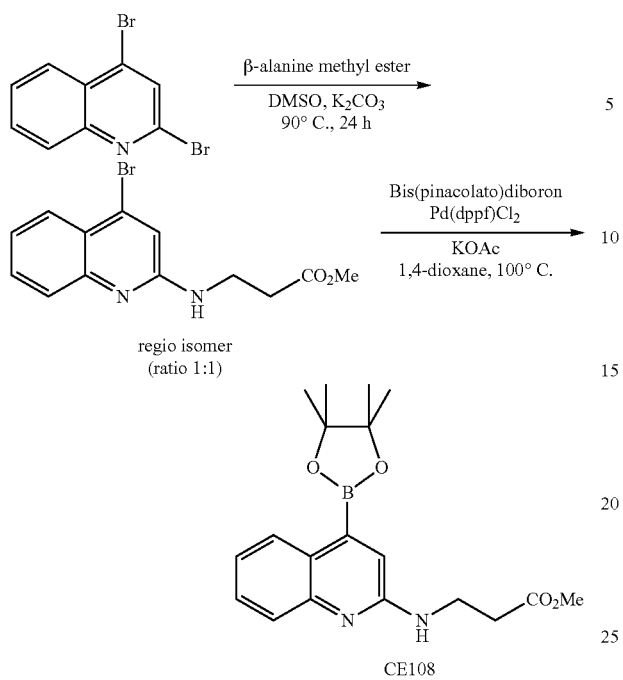

CE108

Methyl 3-((4-bromoquinolin-2-yl)amino)propanoate (CE101)

2,4-Dibromoquinoline (861 mg, 3.0 mmol), β-alanine methyl ester HCl salt (462 mg, 3.3 mmol), and K$_2$CO$_3$ (515 mg, 3.7 mmol) were mixed in anhydrous DMSO (6 mL). The solution was heated at 90° C. for 16 h. The reaction was quenched with water. The aqueous layer was extracted with ethyl acetate and the combined organic layers were washed with brine, dry over anhydrous sodium sulfate, and concentrated on a rotary evaporator. The residue was purified on flash column chromatography to yield methyl 3-((4-bromoquinolin-2-yl)amino)propanoate in 0.32 g (1.0 mmol, 33% yield). The ratio for two region isomers is ca. 1:1 determined by analytical UPLC. $^1$H NMR (CDCl$_3$, 300 MHz): 7.93 (dd, J=8.25, 0.95 Hz, 1H), 7.66 (dd, J=8.39, 0.69 Hz, 1H), 7.54 (ddd, J=8.36, 6.92, 1.41, 1H), 7.27 (ddd, J=8.18, 6.90, 1.25 Hz, 1H), 6.93 (s, 1H), 5.23 (t, J=5.44 Hz, 1H), 3.81 (q, J=6.12 Hz, 2H), 3.69 (s, 3H), 2.72 (t, J=6.07 Hz, 2H). ESI-MS calculated for C$_{13}$H$_{14}$$^{79}$BrN$_2$O$_2$ [M+H]$^+$=309.02; Observed: 309.42.

Methyl 3-((4-(4,4,5,5-tetramethyl-1,3,2-dioxaborolan-2-yl)quinolin-2-yl)amino) propanoate (CE108)

Methyl 3-((4-bromoquinolin-2-yl)amino)propanoate (0.42 g, 1.4 mmol), bis(pinacolato)diboron (711 mg, 2.8 mmol), and potassium acetate (560 mg, 5.6 mmol) were added to a round-bottom flask. Anhydrous 1,4-dixoane (10 mL) was added and the system was degassed and refilled with nitrogen. Pd(dppf)Cl$_2$ (98 mg, 0.14 mmol) was added and the system was degassed again followed by heating at 100° C. for 16 h. The reaction mixture was cooled to room temperature and diluted by CH$_2$Cl$_2$. The solution was filtered through a pad of celite and the volatile components were removed on a rotary evaporator. The residue was purified on reverse phase flash column chromatography to yield the title compound in 620 mg (with impurity). $^1$H NMR (MeOD-d4, 300 MHz): 8.34 (d, J=8.09 Hz, 1H), 7.85-7.70 (m, 1H), 7.70-7.55 (m, 1H), 7.45-7.30 (m, 2H), 3.90-3.70 (m, 2H), 3.68 (s, 3H), 2.90-2.70 (m, 2H), 1.39 (s, 12H). ESI-MS calculated for C$_{19}$H$_{26}$BN$_2$O$_4$ [M+H]$^+$= 357.20; Observed: 357.75.

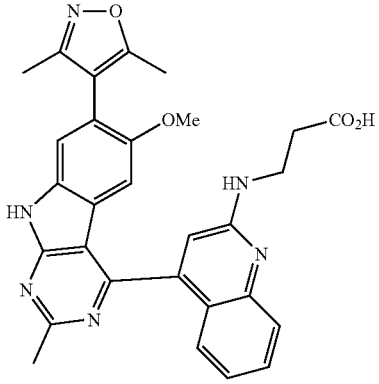

Cpd. No. 142

3-((4-(7-(3,5-Dimethylisoxazol-4-yl)-6-methoxy-2-methyl-9H-pyrimido[4,5-b]indol-4-yl)-quinolin-2-yl)amino)propanoic acid Suzuki coupling of S13 (180 mg, 0.5 mmol) and methyl 3-((4-(4,4,5,5-tetramethyl-1,3,2-dioxaborolan-2-yl)quinolin-2-yl)amino)propanoate (CE108, 620 mg, 1.32 mmol) using condition Method 42 afforded the title compound in 30 mg (9% yield). $^1$H NMR (MeOD-d4, 300 MHz): 8.11 (d, J=7.02 Hz, 1H), 7.90 (td, J=7.87, 1.00 Hz, 1H), 7.65 (d, J=7.78 Hz, 1H), 7.49 (s, 1H), 7.50-7.42 (m, 2H), 6.65 (s, 1H), 4.10-3.86 (m, 2H), 3.40 (s, 3H), 2.94 (s, 3H), 2.89 (t, J=5.66 Hz, 2H), 2.27 (s, 3H), 2.08 (s, 3H). ESI-MS calculated for C$_{29}$H$_{27}$N$_6$O$_4$ [M+H]$^+$=523.21; Observed: 523.33.

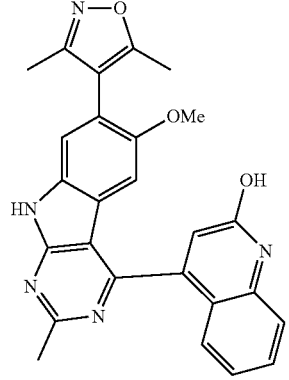

Cpd. No. 142A 4-(7-(3,5-Dimethylisoxazol-4-yl)-6-methoxy-2-methyl-9H-pyrimido[4,5-b]indol-4-yl)quinolin-2-ol (Cpd. No. 142A)

CD218 (470 mg, 1.0 mmol) was dissolved in THF (18 mL). HCl aq. solution (6 N, 30 mL) was added and the solution was heated at 75° C. for 16 h. HPLC purification yielded the title compound 370 mg (82% yield). $^1$H NMR (MeOD-d4, 300 MHz): 7.72 (t, J=7.73 Hz, 1H), 7.61 (d, J=7.94 Hz, 1H), 7.55 (s, 1H), 7.46 (d, J=7.73 Hz, 1H), 7.24 (t, J=7.59 Hz, 1H), 7.14 (s, 1H), 6.64 (s, 1H), 3.38 (s, 3H), 2.99 (s, 3H), 2.68 (s, 3H), 2.08 (s, 3H). ESI-MS calculated for $C_{26}H_{22}N_5O_3$ [M+H]$^+$=452.17; Observed: 452.92.

Cpd. No. 143

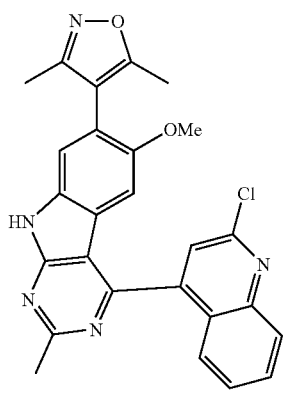

4-(4-(2-Chloroquinolin-4-yl)-6-methoxy-2-methyl-9H-pyrimido[4,5-b]indol-7-yl)-3,5-dimethylisoxazole (Cpd. No. 143)

4-(7-(3,5-Dimethylisoxazol-4-yl)-6-methoxy-2-methyl-9H-pyrimido[4,5-b]indol-4-yl)quinolin-2-ol (Cpd. No. 142, 370 mg) and POCl$_3$ (10 mL) was heated at 90° C. for 6 h. The volatile components were removed on a rotary evaporator and the residue was neutralized by NaHCO$_3$ saturated aq. solution. The aqueous layer was extracted with ethyl acetate and the combined organic layers were washed with brine, dry over anhydrous sodium sulfate, and concentrated on a rotary evaporator. The residue containing the title compound was used for the synthesize Cpd. No. 143 without further purification. ESI-MS calculated for $C_{26}H_{21}{}^{35}ClN_5O_2$ [M+H]$^+$=470.14; Observed: 470.94.

Cpd. No. 144

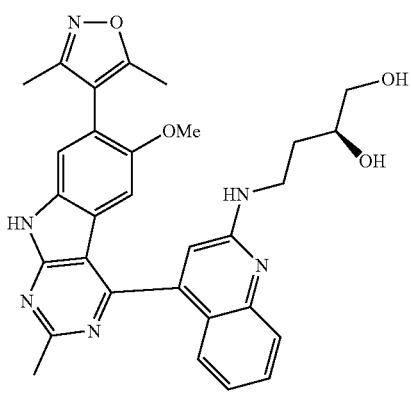

(2S)-4-((4-(7-(3,5-Dimethylisoxazol-4-yl)-6-methoxy-2-methyl-9H-pyrimido[4,5-b]indol-4-yl)quinolin-2-yl)amino)butane-1,2-diol 4-(4-(2-Chloroquinolin-4-yl)-6-methoxy-2-methyl-9H-pyrimido[4,5-b]indol-7-yl)-3,5-dimethylisoxazole (Cpd. No. 143, 100 mg, 0.2 mmol), (2S)-4-amino-1-(triphenylmethoxy)-2-butanol (200 mg, 0.58 mmol), K$_2$CO$_3$ (100 mg, 0.72 mmol), and DMSO (6 mL) were heated at 90° C. for 16 h. The reaction was quenched with water. The aqueous layer was extracted with ethyl acetate and the combined organic layers were washed with brine, dry over anhydrous sodium sulfate, and concentrated on a rotary evaporator. The residue was dissolved in CH$_2$Cl$_2$ and CF$_3$CO$_2$H was added. The mixture was stirred for 1 h followed by purification on preparative HPLC to yield the title compound in 10 mg (9% yield). $^1$H NMR (MeOD-d4, 300 MHz): 8.06 (d, J=7.44 Hz, 1H), 7.89 (t, J=7.56 Hz, 1H), 7.64 (d, J=7.98 Hz, 1H), 7.47 (s, 1H), 7.50-7.40 (m, 2H), 6.62 (s, 1H), 3.90-3.70 (m, 3H), 3.58 (d, J=4.11 Hz, 2H), 3.38 (s, 3H), 2.92 (s, 3H), 2.27 (s, 3H), 2.09 (s, 3H), 2.14-2.00 (m, 1H), 2.00-1.80 (m, 1H). ESI-MS calculated for $C_{30}H_{31}N_6O_4$ [M+H]$^+$=539.24; Observed: 539.83.

Cpd. No. 145

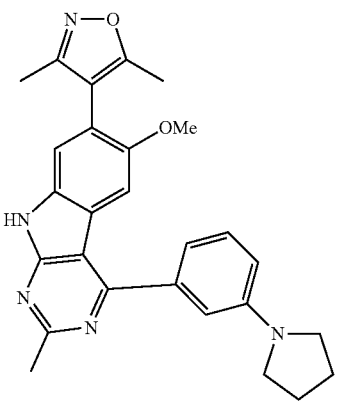

4-(6-Methoxy-2-methyl-4-(3-(pyrrolidin-1-yl)phenyl)-9H-pyrimido[4,5-b]indol-7-yl)-3,5-dimethylisoxazole Method 42: 4-(4-chloro-6-methoxy-2-methyl-9H-pyrimido[4,5-b]indol-7-yl)-3,5-dimethylisox-azole (S13, 40 mg, 0.1 mmol, 1.0 equiv.) and 3-(pyrrolidino)phenylboronic acid (70 mg, 0.3 mmol, 3.0 equiv.) were dissolved in 1,2-dimethoxyethane (4 mL). Sodium carbonate (2.0 M in water, 2 mL) was added. The system was degassed to remove oxygen and nitrogen was refilled. Pd(dppf)Cl$_2$—CH$_2$Cl$_2$ (20 mg, 0.024 mmol, 0.24 equiv.) were added and the system was degassed again and refilled with nitrogen. The reaction mixture was heated at reflux for 16 h. The reaction was quenched with water and extracted with ethyl acetate. The organic layers were combined and concentrated on a rotary evaporator. The residue was purified by reverse HPLC to afford the title compound as a salt of CF$_3$CO$_2$H (30 mg, 52% yield). $^1$H NMR (MeOD-d4, 300 MHz): 7.59 (t, J=7.94 Hz, 1H), 7.53 (s, 1H), 7.48 (s, 1H), 7.18 (d, J=7.75 Hz, 1H), 7.10 (s, 1H), 7.00 (dd, J=8.30, 1.98 Hz, 1H), 3.67 (s, 3H), 3.50-3.35 (m, 4H), 2.95 (s, 3H), 2.30 (s, 3H), 2.12 (s, 3H), 2.12-2.20 (m, 4H). ESI-MS calculated for $C_{27}H_{28}N_5O_2$ [M+H]$^+$=454.22; Observed: 454.68.

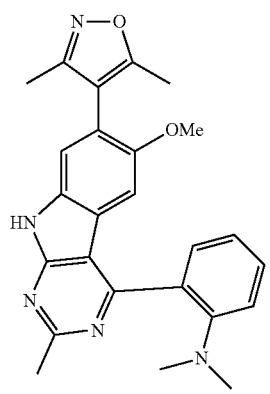

Cpd. No. 146

2-(7-(3,5-Dimethylisoxazol-4-yl)-6-methoxy-2-methyl-9H-pyrimido[4,5-b]indol-4-yl)-N,N-dimethylaniline Suzuki coupling of S13 and 3-(N,N-dimethylamino)phenylboronic acid, pinacol ester using condition Method 42 afforded the title compound as a salt of $CF_3CO_2H$ (34 mg, 65% yield). $^1$H NMR (MeOD-d4, 300 MHz): 7.78-7.66 (m, 2H), 7.54 (s, 1H), 7.46 (d, J=8.16 Hz, 1H), 7.29 (td, J=7.80, 0.91 Hz, 1H), 7.07 (s, 1H), 3.65 (s, 3H), 2.96 (s, 3H), 2.31 (s, 3H), 2.13 (s, 3H). ESI-MS calculated for $C_{25}H_{26}N_5O_2$ [M+H]$^+$=428.21; Observed: 428.58,

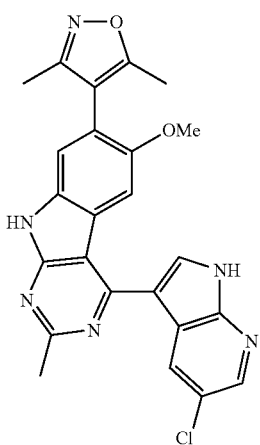

Cpd. No. 147

4-(4-(5-Chloro-1H-pyrrolo[2,3-b]pyridin-3-yl)-6-methoxy-2-methyl-9H-pyrimido[4,5-b]indol-7-yl)-3,5-dimethylisoxazole Suzuki coupling of S13 and 5-chloro-3-(4,4,5,5-tetramethyl-1,3,2-dioxaborolan-2-yl)-1H-pyrrolo[2,3-b]pyridine using condition Method 42 afforded the title compound as a salt of $CF_3CO_2H$ (10 mg, 10% yield). $^1$H NMR (MeOD-d4, 300 MHz): 8.47 (s, 1H), 7.98 (s, 1H), 7.55 (s, 1H), 7.03 (s, 1H), 3.50 (s, 3H), 2.95 (s, 3H), 2.31 (s, 3H), 2.13 (s, 3H). ESI-MS calculated for $C_{24}H_{20}^{35}ClN_6O_2$ [M+H]$^+$=459.13; Observed: 459.67,

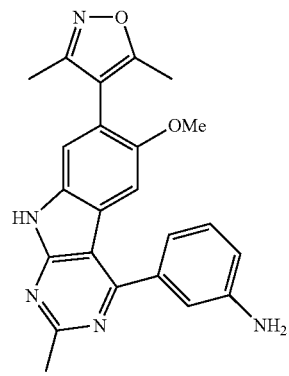

Cpd. No. 148

3-(7-(3,5-Dimethylisoxazol-4-yl)-6-methoxy-2-methyl-9H-pyrimido[4,5-b]indol-4-yl)aniline To a round-bottom flask, 4-(4-chloro-6-methoxy-2-methyl-9H-pyrimido[4,5-b]indol-7-yl)-3,5-dimethylisoxazole (S13, 347 mg, 1 mmol) and (3-Boc-aminophenyl)bronoic acid (711 mg, 3 mmol), 1,2-dimethoxyethane (20 mL), and $Na_2CO_3$ (2 M, 5 mL) were added. The system was degassed to remove oxygen and nitrogen was refilled. Pd(dppf)Cl$_2$—CH$_2$Cl$_2$ (81 mg, 0.1 mmol) was added and the system was degassed and refilled with nitrogen. The reaction mixture was heated at reflux for 16 h. The reaction was quenched with water and the aqueous layer was extracted with ethyl acetate. The organic layers were combined and the volatile components were removed on a rotary evaporator. The residue was dissolved in CH$_2$Cl$_2$ (4 mL) and $CF_3CO_2H$ (4 mL) was added. The reaction was stirred for 1 h before the volatile components were removed on a rotary evaporator. The remaining residue was purified by reverse HPLC to afford the title product as a salt of $CF_3CO_2H$ (80 mg, 16% yield). $^1$H NMR (MeOD-d4, 300 MHz): 7.74 (t, J=7.82 Hz, 1H), 7.70-7.60 (m, 2H), 7.55 (s, 1H), 7.47 (dd, J=8.04, 1.12 Hz, 1H), 7.36 (s, 1H), 3.72 (s, 3H), 2.96 (s, 3H), 2.30 (s, 3H), 2.12 (s, 3H). ESI-MS calculated for $C_{23}H_{22}N_5O_2$ [M+H]$^+$=400.18; Observed: 401.00.

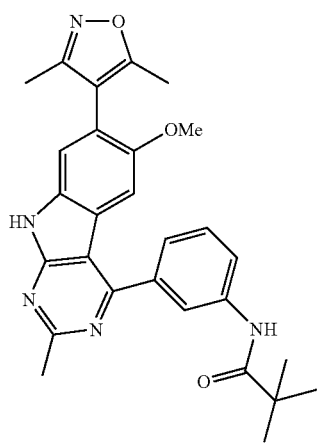

Cpd. No. 149

N-(3-(7-(3,5-Dimethylisoxazol-4-yl)-6-methoxy-2-methyl-9H-pyrimido[4,5-b]indol-4-yl)phenyl)pivalamide 3-(7-(3,5-Dimethylisoxazol-4-yl)-6-methoxy-2-methyl-9H-pyrimido[4,5-b]indol-4-yl)aniline (Cpd. No. 148, 40 mg) and pyridine (0.1 mL) were dissolved in anhydrous THF (5 mL). To this solution, trimethylacetic anhydride (60 mg, 0.3 mmol) was added via a syringe and the reaction mixture was stirred at ambient temperature for 16 h. The volatile components were removed on a rotary evaporator and the residue was purified by reverse HPLC to afford the title product as a salt of $CF_3CO_2H$ (38.2 mg, 64% yield). $^1$H NMR (MeOD-d4, 300 MHz): 9.52 (s, 1H), 8.61 (s, 1H), 7.84-7.68 (m, 3H), 7.54 (s, 1H), 7.51 (s, 1H), 3.70 (s, 3H), 3.52 (s, 3H), 2.96 (s, 3H), 2.32 (s, 3H), 2.14 (s, 3H), 1.32 (s, 9H). ESI-MS calculated for $C_{28}H_{30}N_5O_3$ [M+H]$^+$=484.23; Observed: 484.80.

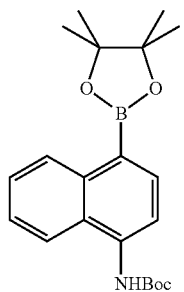

CE82

4-(Methoxycarbonyl)naphthalene-1-boronic acid, pinacol ester

1-Boc-amino-4-bromonaphthalene was synthesized following preceding procedures reported in PCT Int. Appl., 2003005999. 1-Boc-amino-4-bromonaphthalene (6.13 g, 19 mmol, 1.0 equiv.), bis(pinacolato)diboron (9.65 g, 38 mmol, 2.0 equiv.), and potassium acetate (5.6 g, 57 mmol, 3.0 equiv) were added to a round-bottom flask. Anhydrous 1,4-dixoane (60 mL) was added to the flask, which was degassed and refilled with nitrogen. Pd(dppf)Cl$_2$ (1.0 g, 1.9 mmol, 0.1 equiv.) was added and the flask was degassed again followed by heating at 100° C. for 16 h. The reaction mixture was cooled to room temperature and diluted by CH$_2$Cl$_2$. The solution was filtered through a pad of celite and the volatile components were removed on a rotary evaporator. The residue was purified by flash column chromatography. The title compound was isolated in 5.7 g (15.4 mmol, 81% yield). $^1$H NMR (MeOD-d4, 300 MHz): 8.81 (d, J=8.46 Hz, 1H), 8.06 (d, J=7.71 Hz, 1H), 7.97 (d, J=7.71 Hz, 1H), 7.83 (d, J=8.08 Hz, 1H), 7.56-7.40 (m, 2H), 7.13 (s, 1H), 1.53 (s, 9H), 1.38 (s, 12H). ESI-MS calculated for $C_{21}H_{28}BNNaO_4$ [M+Na]$^+$=392.20, Observed: 392.42.

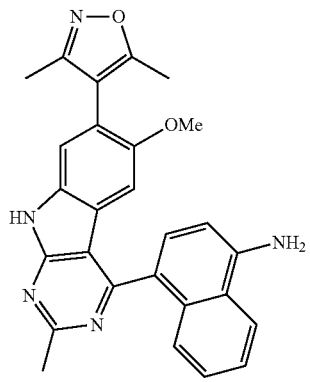

Cpd. No. 150

4-(7-(3,5-Dimethylisoxazol-4-yl)-6-methoxy-2-methyl-9H-pyrimido[4,5-b]indol-4-yl)naphthalen-1-amine (Cpd. No. 150)

Method 40: To a round-bottom flask, 4-(4-chloro-6-methoxy-2-methyl-9H-pyrimido[4,5-b]indol-7-yl)-3,5-dimethylisoxazole (S13, 5.4 g, 16 mmol, 1.0 equiv.) and 4-(methoxycarbonyl)naphthalene-1-boronic acid, pinacol ester (13.75 g, 37 mmol, 2.0 equiv.), 1,2-dimethoxyethane (150 mL), and Na$_2$CO$_3$ (2 M, 50 mL) were added. The system was degassed to remove oxygen and nitrogen was refilled. Pd(dppf)Cl$_2$—CH$_2$Cl$_2$ (1.3 g, 1.6 mmol, 0.1 equiv.) was added and the system was degassed and refilled with nitrogen. The reaction mixture was heated at reflux for 16 h. The reaction was quenched with water and the aqueous layer was extracted with ethyl acetate. The organic layers were combined and the volatile components were removed on a rotary evaporator. The residue was dissolved in CH$_2$Cl$_2$ (10 mL) and CF$_3$CO$_2$H (15 mL) were added. The solution was stirred at ambient temperature for 1 h. The volatile components were removed on a rotary evaporator and the residue was neutralized by NaHCO$_3$ saturated solution. The aqueous layer was extracted with ethyl acetate. The organic layers were combined and the volatile components were removed on a rotary evaporator. The residue was purified by flash column chromatography to yield the title compound in 2.23 g (31% yield over two steps). $^1$H NMR (MeOD-d4, 300 MHz): 8.30 (d, J=8.28 Hz, 1H), 7.80 (d, J=8.05 Hz, 1H), 7.65 (t, J=8.82 Hz, 1H), 7.58 (d, J=7.50 Hz, 1H), 7.54-7.46 (m, 1H), 7.50 (s, 1H), 7.05 (d, J=8.06 Hz, 1H), 6.33 (s, 1H), 3.20 (s, 3H), 2.97 (s, 3H), 2.26 (s, 3H), 2.07 (s, 3H). ESI-MS calculated for $C_{27}H_{24}N_5O_2$ [M+H]$^+$=450.19; Observed: 450.48.

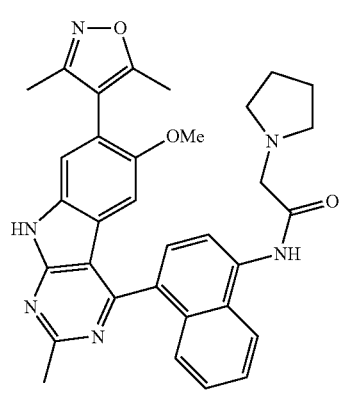

Cpd. No. 151

N-(4-(7-(3,5-Dimethylisoxazol-4-yl)-6-methoxy-2-methyl-9H-pyrimido[4,5-b]indol-4-yl)naphthalen-1-yl)-2-(pyrrolidin-1-yl)acetamide 4-(7-(3,5-Dimethylisoxazol-4-yl)-6-methoxy-2-methyl-9H-pyrimido[4,5-b]indol-4-yl)naphthalen-1-amine (Cpd. No. 150, 10 mg, 0.023 mmol) and NaHCO$_3$ (26 mg, 0.23 mmol) were dissolved in THF (4 mL). To this solution, chloroacetyl chloride (26 mg, 0.23 mmol) was added and the solution was stirred at ambient temperature for 16 h. To this solution, pyrrolidine (1 mL) was added and the reaction mixture was stirred for 12 h. The volatile components were removed on a rotary evaporator and the residue was purified by reverse HPLC affording the title compound as a salt of CF$_3$CO$_2$H (10 mg, 70% yield). $^1$H NMR (MeOD-d4, 300 MHz): 8.41 (d, J=7.89 Hz, 1H), 8.24 (d, J=7.90 Hz, 1H), 8.03 (d, J=7.87 Hz, 1H), 7.79 (t, J=7.78 Hz, 2H), 7.67-7.59 (m, 1H), 7.52 (s, 1H), 6.17 (s, 1H), 4.54 (s, 2H), 4.00-3.80 (m, 2H), 3.40-3.20 (m, 2H), 3.16 (s, 3H), 3.01 (s, 3H), 2.26 (s, 3H), 2.40-2.10 (m, 4H), 2.06 (s, 3H). ESI-MS calculated for C$_{33}$H$_{33}$N$_6$O$_3$ [M+H]$^+$=561.26; Observed: 561.67.

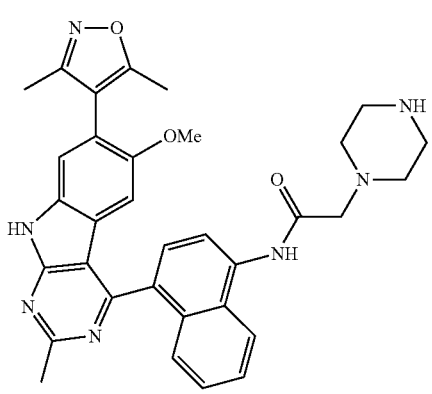

Cpd. No. 152

N-(4-(7-(3,5-Dimethylisoxazol-4-yl)-6-methoxy-2-methyl-9H-pyrimido[4,5-b]indol-4-yl)naphthalen-1-yl)-2-(piperazin-1-yl)acetamide 4-(7-(3,5-Dimethylisoxazol-4-yl)-6-methoxy-2-methyl-9H-pyrimido[4,5-b]indol-4-yl)naphthalen-1-amine (Cpd. No. 150, 45 mg, 0.1 mmol) and NaHCO$_3$ (160 mg, 2 mmol) were dissolved in anhydrous DMF (3 mL). To this solution, chloroacetyl chloride (113 mg, 1.0 mmol, 10. equiv.) was added and the solution was stirred for 16 h. The reaction mixture was diluted with water and the aqueous layer was extracted with ethyl acetate. The organic layers were combined and dried over anhydrous sodium sulfate. The volatile components were removed on a rotary evaporator. The remaining residue was dissolved in anhydrous DMF and piperazine (270 mg, 3 mmol) was added in one portion. The reaction was stirred at ambient temperature for 16 h before quenching with water. The aqueous layer was extracted with ethyl acetate and the organic layers were combined, the volatile components were removed on a rotary evaporator. The remaining residue was purified by reverse HPLC affording the title compound as a salt of CF$_3$CO$_2$H (50 mg, 74% yield). $^1$H NMR (MeOD-d4, 300 MHz): 8.33 (d, J=8.52 Hz, 1H), 8.20 (d, J=7.83 Hz, 1H), 8.04 (d, J=7.85 Hz, 1H), 7.83-7.75 (m, 2H), 7.67-7.58 (m, 1H), 7.54 (s, 1H), 6.21 (s, 1H), 3.86 (s, 2H), 3.57-3.43 (m, 4H), 3.33-3.22 (m, 4H), 3.17 (s, 3H), 3.01 (s, 3H), 2.26 (s, 3H), 2.06 (s, 3H). ESI-MS calculated for C$_{33}$H$_{34}$N$_7$O$_3$ [M+H]$^+$=576.27; Observed: 576.42.

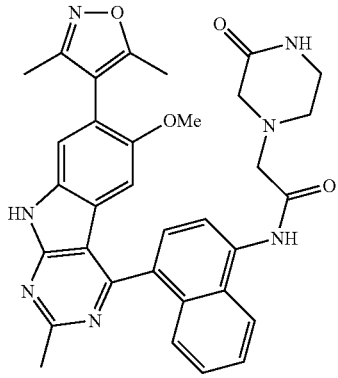

Cpd. No. 153

N-(4-(7-(3,5-Dimethylisoxazol-4-yl)-6-methoxy-2-methyl-9H-pyrimido[4,5-b]indol-4-yl)naphthalen-1-yl)-2-(3-oxopiperazin-1-yl)acetamide Method 149: 4-(7-(3,5-Dimethylisoxazol-4-yl)-6-methoxy-2-methyl-9H-pyrimido[4,5-b]indol-4-yl)naphthalen-1-amine (Cpd. No. 150, 80 mg, 0.2 mmol, 1.0 equiv.) and NaHCO$_3$ (200 mg, 2.3 mmol, 11 equiv.) were dissolved in anhydrous DMF (3 mL). To this solution, chloroacetyl chloride (113 mg, 1.0 mmol, 5.0 equiv.) was added and the solution was stirred for 16 h. The reaction mixture was diluted with water and the aqueous layer was extracted with ethyl acetate. The organic layers were combined and dried over anhydrous sodium sulfate. The volatile components were removed on a rotary evaporator. The remaining residue was dissolved in anhydrous DMF and 2-oxopiperazine (40 mg, 0.4 mmol, 2.0 equiv.) and EtN(i-Pr)$_2$ (0.2 mL) were added. The reaction was stirred at ambient temperature for 16 h before quenching with water. The aqueous layer was extracted with ethyl acetate and the organic layers were combined, the volatile components were removed on a rotary evaporator. The remaining residue was purified by reverse HPLC affording the title compound as a salt of CF$_3$CO$_2$H (46 mg, 34% yield). $^1$H NMR (MeOD-d4, 300 MHz): 8.41 (d, J=8.15 Hz, 1H), 8.26 (d, J=7.87 Hz, 1H), 8.05 (d, J=7.86 Hz, 1H), 7.79 (t, J=7.75 Hz, 2H), 7.67-7.60 (m, 1H), 7.54 (s, 1H), 6.18 (s, 1H), 4.46 (s, 2H), 4.06 (s, 2H), 3.68 (s, 4H), 3.16 (s, 3H), 3.02 (s, 3H), 2.25 (s, 3H), 2.06 (s, 3H). ESI-MS calculated for C$_{33}$H$_{32}$N$_7$O$_4$ [M+H]$^+$=590.25; Observed: 590.75.

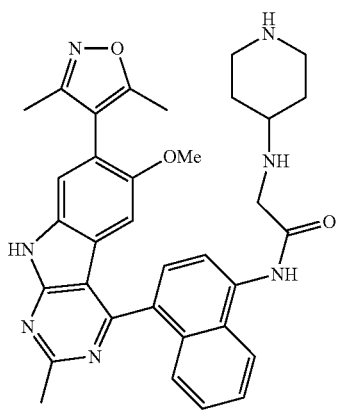

Cpd. No. 154

249

N-(4-(7-(3,5-Dimethylisoxazol-4-yl)-6-methoxy-2-methyl-9H-pyrimido[4,5-b]indol-4-yl)naphthalen-1-yl)-2-(piperidin-4-ylamino)acetamide Following protocol similar to Method 149, reaction of 4-(7-(3,5-dimethylisoxazol-4-yl)-6-methoxy-2-methyl-9H-pyrimido[4,5-b]indol-4-yl)naphthalen-1-amine (Cpd. No. 150), chloroacetyl chloride, and 4-amino-1-Boc piperidine afforded Boc protected title compound. Upon treatment of $CF_3CO_2H$ followed by reverse phase HPLC purification, the title compound was isolated in 39 mg (28% over two steps). $^1$H NMR (MeOD-d4, 300 MHz): 8.45 (d, J=8.32 Hz, 1H), 8.25 (d, J=7.87 Hz, 1H), 8.04 (d, J=7.88 Hz, 1H), 7.78 (t, J=7.96 Hz, 2H), 7.68-7.59 (m, 1H), 7.54 (s, 1H), 6.17 (s, 1H), 4.42 (s, 2H), 3.78-3.56 (m, 3H), 3.24-3.10 (m, 2H), 3.15 (s, 3H), 3.02 (s, 3H), 2.47 (d, J=12.26 Hz, 2H), 2.25 (s, 3H), 2.15-1.95 (m, 2H), 2.06 (s, 3H). ESI-MS calculated for $C_{34}H_{36}N_7O_3$ [M+H]$^+$=590.29; Observed: 590.58.

Cpd. No. 155

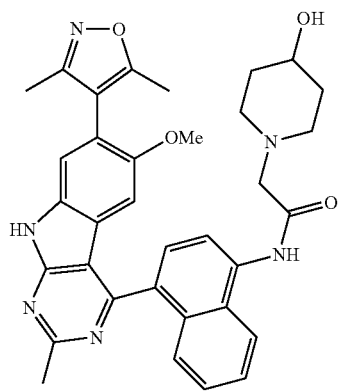

N-(4-(7-(3,5-Dimethylisoxazol-4-yl)-6-methoxy-2-methyl-9H-pyrimido[4,5-b]indol-4-yl)naphthalen-1-yl)-2-(4-hydroxypiperidin-1-yl)acetamide Following protocol similar to Method 149, reaction of 4-(7-(3,5-dimethylisoxazol-4-yl)-6-methoxy-2-methyl-9H-pyrimido[4,5-b]indol-4-yl)naphthalen-1-amine (Cpd. No. 150), chloroacetyl chloride, and 4-hydroxypiperidine afforded the title compound in 44 mg (32% yield). $^1$H NMR (MeOD-d4, 300 MHz): 8.42 (d, J=8.25 Hz, 1H), 8.26 (d, J=7.87 Hz, 1H), 8.05 (d, J=7.87 Hz, 1H), 7.79 (t, J=7.85 Hz, 2H), 7.67-7.60 (m, 1H), 7.54 (s, 1H), 6.18 (s, 1H), 4.45 (s, 2H), 4.20-1.00 (m, 0.5H), 3.90-3.70 (m, 1H), 3.70-3.50 (m, 2.5H), 3.16 (s, 3H), 3.02 (s, 3H), 2.30-2.10 (m, 2H), 2.25 (s, 3H), 2.10-1.80 (m, 2H), 2.06 (s, 3H). ESI-MS calculated for $C_{34}H_{35}N_6O_4$ [M+H]$^+$=591.27; Observed: 591.83.

Cpd. No. 156

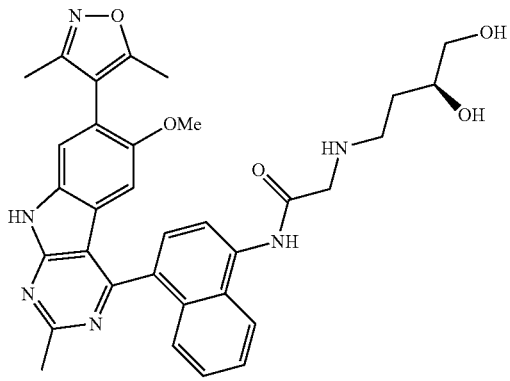

250

2-(((S)-3,4-Dihydroxybutyl)amino)-N-(4-(7-(3,5-dimethylisoxazol-4-yl)-6-methoxy-2-methyl-9H-pyrimido[4,5-b]indol-4-yl)naphthalen-1-yl)acetamide Following protocol similar to Method 149, reaction of 4-(7-(3,5-dimethylisoxazol-4-yl)-6-methoxy-2-methyl-9H-pyrimido[4,5-b]indol-4-yl)naphthalen-1-amine (Cpd. No. 150), chloroacetyl chloride, and (2S)-4-Amino-1-(triphenylmethoxy)-2-butanol afforded O-Trt protected title compound. Upon treatment of $CF_3CO_2H$ followed by reverse phase HPLC purification, the title compound was isolated in 16 mg (23% yield). $^1$H NMR (MeOD-d4, 300 MHz): 8.42 (d, J=8.30 Hz, 1H), 8.24 (d, J=7.84 Hz, 1H), 8.04 (d, J=7.84 Hz, 1H), 7.79 (t, J=7.87 Hz, 2H), 7.63 (t, J=7.33 Hz, 1H), 7.53 (s, 1H), 3.17 (s, 1H), 4.31 (s, 2H), 3.16 (s, 3H), 3.01 (s, 3H), 2.26 (s, 3H), 2.06 (s, 3H), 2.10-1.95 (m, 1H), 1.95-1.80 (m, 1H). ESI-MS calculated for $C_{33}H_{35}N_6O_5$ [M+H]$^+$=595.27; Observed: 595.92.

Cpd. No. 157

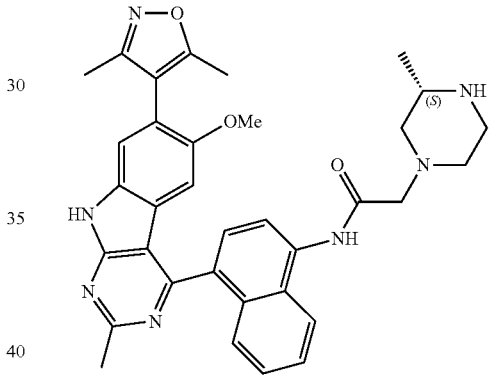

N-(4-(7-(3,5-Dimethylisoxazol-4-yl)-6-methoxy-2-methyl-9H-pyrimido[4,5-b]indol-4-yl)naphthalen-1-yl)-2-((S)-3-methylpiperazin-1-yl)acetamide Following protocol similar to Method 149, reaction of 4-(7-(3,5-dimethylisoxazol-4-yl)-6-methoxy-2-methyl-9H-pyrimido[4,5-b]indol-4-yl)naphthalen-1-amine (Cpd. No. 150), chloroacetyl chloride, and S-1-Boc-2-methylpiperazine afforded N-Boc protected title compound. Upon treatment of $CF_3CO_2H$ followed by reverse phase HPLC purification, the title compound was isolated in 187 mg (90% yield). $^1$H NMR (MeOD-d4, 300 MHz): 8.39 (d, J=8.19 Hz, 1H), 8.25 (d, J=7.85 Hz, 1H), 8.07 (d, J=7.85 Hz, 1H), 7.81 (t, J=7.77 Hz, 2H), 7.70-7.60 (m, 1H), 7.57 (s, 1H), 6.22 (s, 1H), 4.12 (s, 2H), 3.84-3.76 (m, 1H), 3.76-3.63 (m, 3H), 3.62-3.50 (m, 1H), 3.32-3.20 (m, 1H), 3.19 (s, 3H), 3.14-3.04 (m, 1H), 3.04 (s, 3H), 2.27 (s, 3H), 2.07 (s, 3H), 1.46 (d, J=6.56 Hz, 3H). ESI-MS calculated for $C_{34}H_{36}N_7O_3$ [M+H]$^+$=590.29; Observed: 590.67.

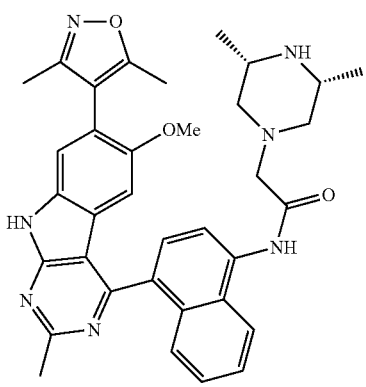

Cpd. No. 158

N-(4-(7-(3,5-Dimethylisoxazol-4-yl)-6-methoxy-2-methyl-9H-pyrimido[4,5-b]indol-4-yl)naphthalen-1-yl)-2-((3R,5S)-3, 5-dimethylpiperazin-1-yl)acetamide Following protocol similar to Method 149, reaction of 4-(7-(3,5-dimethylisoxazol-4-yl)-6-methoxy-2-methyl-9H-pyrimido[4,5-b]indol-4-yl)naphthalen-1-amine (Cpd. No. 150), chloroacetyl chloride, and 2,6-cis-dimethylpiperazine afforded the title compound in 60 mg (85% yield). $^1$H NMR (MeOD-d4, 300 MHz): 8.32 (d, J=8.21 Hz, 1H), 8.21 (d, J=7.86 Hz, 1H), 8.04 (d, J=7.86 Hz, 1H), 7.82-7.75 (m, 2H), 7.63 (ddd, J=8.20, 6.98, 1.08 Hz, 1H), 7.54 (s, 1H), 6.22 (s, 1H), 3.79 (s, 2H), 3.76-3.60 (m, 2H), 3.44 (d, J=13.00 Hz, 2H), 3.17 (s, 3H), 3.01 (s, 3H), 2.68 (ddd, J=12.95, 11.18, 1.62 Hz, 2H), 2.26 (s, 3H), 2.06 (s, 3H), 1.39 (d, J=6.52 Hz, 6H). ESI-MS calculated for $C_{35}H_{38}N_7O_3$ [M+H]$^+$=604.30; Observed: 604.58.

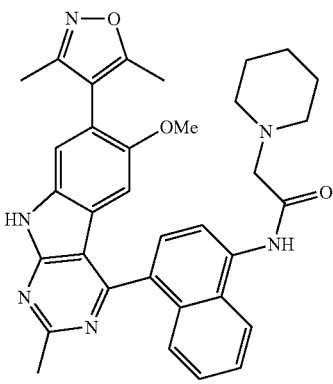

Cpd. No. 159

N-(4-(7-(3,5-Dimethylisoxazol-4-yl)-6-methoxy-2-methyl-9H-pyrimido[4,5-b]indol-4-yl)naphthalen-1-yl)-2-(piperidin-1-yl)acetamide Following protocol similar to Method 149, reaction of 4-(7-(3,5-dimethylisoxazol-4-yl)-6-methoxy-2-methyl-9H-pyrimido[4,5-b]indol-4-yl)naphthalen-1-amine (Cpd. No. 150), chloroacetyl chloride, and piperidine afforded the title compound in 47 mg (78% yield). $^1$H NMR (MeOD-d4, 300 MHz): 8.42 (d, J=8.24 Hz, 1H), 8.25 (d, J=7.89 Hz, 1H), 8.05 (d, J=7.87 Hz, 1H), 7.79 (t, J=7.90 Hz, 2H), 7.67-7.60 (m, 1H), 7.54 (s, 1H), 6.18 (s, 1H), 4.42 (s, 2H), 3.80-3.68 (m, 2H), 3.30-3.14 (m, 2H), 3.16 (s, 3H), 3.02 (s, 3H), 2.25 (s, 3H), 2.06 (s, 3H), 2.08-1.80 (m, 5H), 1.70-1.50 (m, 1H). ESI-MS calculated for $C_{34}H_{35}N_6O_3$ [M+H]$^+$=575.28; Observed: 575.48.

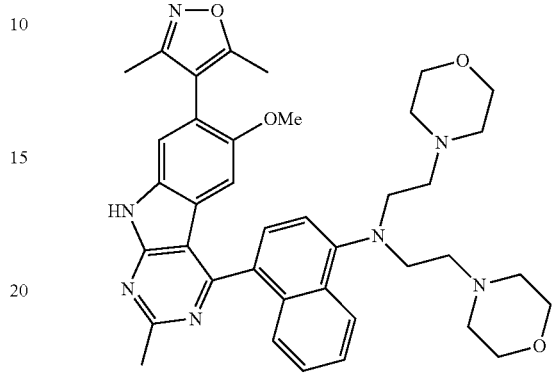

Cpd. No. 160

4-(7-(3,5-Dimethylisoxazol-4-yl)-6-methoxy-2-methyl-9H-pyrimido[4,5-b]indol-4-yl)-N,N-bis(2-morpholinoethyl)naphthalen-1-amine 4-(7-(3,5-Dimethylisoxazol-4-yl)-6-methoxy-2-methyl-9H-pyrimido[4,5-b]indol-4-yl)naphthalen-1-amine (Cpd. No. 150, 27 mg, 0.05 mmol) and 3-Morpholinopropanal-HCl (18 mg, 0.1 mmol) were dissolved in THF (5 mL). AcOH (0.1 mL) and NaBH(OAc)$_3$ (50 mg, 0.2 mmol) were added and the mixture was stirred for 16 h. The reaction was quenched with water and extracted with ethyl acetate. The organic layers were combined and removed on a rotary evaporator. The residue was purified by reverse HPLC affording the title compound as a salt of CF$_3$CO$_2$H (14 mg, 36% yield). $^1$H NMR (MeOD-d4, 300 MHz): 8.54 (d, J=8.28 Hz, 1H), 8.02 (d, J=7.79 Hz, 1H), 7.84-7.74 (m, 3H), 7.66-7.58 (m, 1H), 7.54 (s, 1H), 6.25 (s, 1H), 410-3.80 (m, 12H), 3.60-3.40 (m, 6H), 3.19 (s, 3H), 3.02 (s, 3H), 2.27 (s, 3H), 2.07 (s, 3H). ESI-MS calculated for $C_{39}H_{46}N_7O_4$ [M+H]$^+$=676.36; Observed: 676.75.

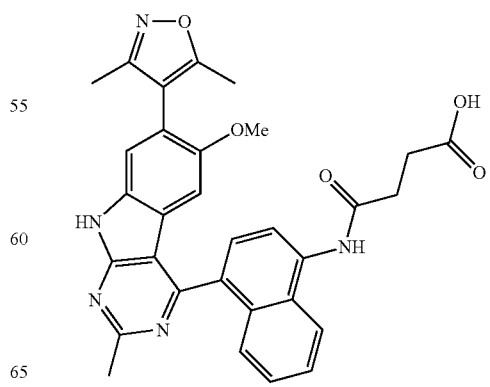

Cpd. No. 161

4-((4-(7-(3,5-Dimethylisoxazol-4-yl)-6-methoxy-2-methyl-9H-pyrimido[4,5-b]indol-4-yl)naphthalen-1-yl)amino)-4-oxobutanoic acid (Cpd. No. 161)

4-(7-(3,5-Dimethylisoxazol-4-yl)-6-methoxy-2-methyl-9H-pyrimido[4,5-b]indol-4-yl)naphthalen-1-amine (Cpd. No. 150, 120 mg, 0.3 mmol), succinic anhydride (60 mg, 0.6 mmol), and pyridine (2 mL) were dissolved in anhydrous DMF (5 mL) and the mixture was heated at 70° C. for 16 h. The reaction mixture was concentrated on a rotary evaporator and purified by reverse phase HPLC affording the title compound in 120 mg (60% yield). $^1$H NMR (MeOD-d4, 300 MHz): 8.42 (d, J=8.75 Hz, 1H), 8.10 (d, J=7.64 Hz, 1H), 8.00 (d, J=7.77 Hz, 1H), 7.80-7.70 (m, 2H), 7.65-7.56 (m, 1H), 1.53 (s, 1H), 6.20 (s, 1H), 3.17 (s, 3H), 3.01 (s, 3H), 2.93 (t, J=6.23 Hz, 2H), 2.79 (t, J=6.23 Hz, 2H), 2.25 (s, 3H), 2.06 (s, 3H). ESI-MS calculated for $C_{31}H_{28}N_5O_5$ [M+H]$^+$= 550.21; Observed: 550.50.

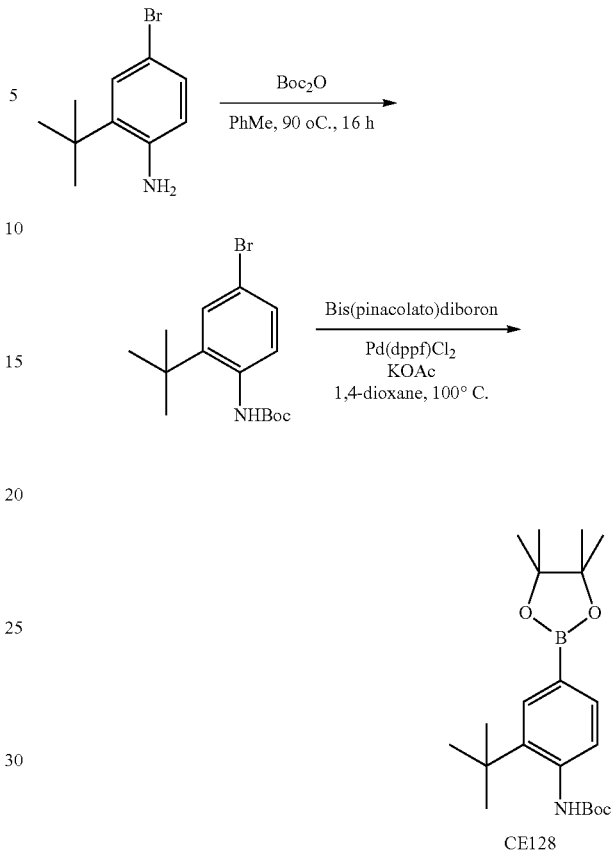

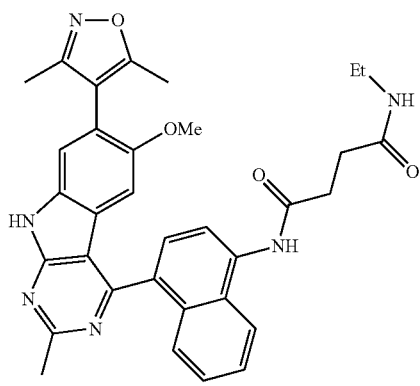

Cpd. No. 161A

N1-(4-(7-(3,5-Dimethylisoxazol-4-yl)-6-methoxy-2-methyl-9H-pyrimido[4,5-b]indol-4-yl)naphthalen-1-yl)-N4-ethylsuccinamide 4-((4-(7-(3,5-Dimethylisoxazol-4-yl)-6-methoxy-2-methyl-9H-pyrimido[4,5-b]indol-4-yl)naphthalen-1-yl)amino)-4-oxobutanoic acid (Cpd. No. 161, 60 mg, 0.1 mmol), EDCI·HCl (100 mg, 0.5 mmol), HOBt·H$_2$O (70 mg, 0.5 mmol), and anhydrous DMF (2.5 mL) were added to a round-bottom flask. EtNH$_2$ (2 M in THF, 1 mL) was added followed by addition of via a syringe and the reaction mixture was stirred for 16 h at ambient temperature. The reaction mixture was purified by reverse HPLC affording the title compound as a salt of CF$_3$CO$_2$H (22 mg, 33% yield). $^1$H NMR (MeOD-d4, 300 MHz): 8.42 (d, J=8.32 Hz, 1H), 8.14 (d, J=7.86 Hz, 1H), 7.99 (d, J=7.86 Hz, 1H), 7.76 (t, J=7.57 Hz, 2H), 7.64-7.56 (m, 1H), 7.52 (s, 1H), 6.21 (s, 1H), 3.25 (q, J=7.33 Hz, 2H), 3.17 (s, 3H), 3.01 (s, 3H), 2.93 (t, J=6.80 Hz, 2H), 2.68 (t, J=6.80 Hz, 2H), 2.26 (s, 3H), 2.06 (s, 3H), 1.14 (t, J=7.33 Hz, 3H). ESI-MS calculated for $C_{33}H_{33}N_6O_4$ [M+H]$^+$=577.26; Observed: 577.92.

tert-Butyl (2-(tert-butyl)-4-(4,4,5,5-tetramethyl-1,3,2-dioxaborolan-2-yl)phenyl)carbamate (CE128)

4-Bromo-2-(1,1-dimethylethyl)aniline (0.95 g, 4.2 mmol) and Boc anhydride (1.20 g, 5.46 mmol) were dissolved in anhydrous toluene (10 mL) and the solution was heated at 90° C. for 24 h. The mixture was purified by flash column chromatography to yield tert-butyl (4-bromo-2-(tert-butyl)phenyl)carbamate (2.42 g, contaminated with Boc$_2$O). tert-Butyl (4-bromo-2-(tert-butyl)phenyl)carbamate (2.42 g from previous step, view as 4.16 mmol), bis(pinacolato)diboron (2.13 g, 8.4 mmol, 2.0 equiv.), and potassium acetate (1.6 g, 16 mmol, 4.0 equiv.) were added to a round-bottom flask. Anhydrous 1,4-dixoane (20 mL) was added via a syringe and the flask was degassed and refilled with nitrogen. Pd(dppf)Cl$_2$ (322 mg, 0.46 mmol, 0.1 equiv.) was added and the system was degassed again followed by heating at 100° C. for 16 h. The reaction mixture was cooled to ambient temperature and diluted by CH$_2$Cl$_2$. The solution was filtered through a pad of celite and the volatile components were removed on a rotary evaporator. The residue was purified by flash column chromatography. The title compound was isolated in 2.0 g (contaminated with boronic acid pinacol ester). This material was used for preparation of Cpd. No. 162 without further purification. $^1$H NMR (MeOD-d4, 300 MHz): 7.77 (s, 1H), 7.70 (d, J=7.98 Hz, 1H), 7.63 (d, J=7.98 Hz, 1H), 6.54 (s, 1H), 1.49 (s, 9H), 1.42 (s, 9H), 1.32 (s, 12H). ESI-MS calculated for $C_{21}H_{34}BNNaO_4$ [M+Na]$^+$=398.25; Observed: 398.50.

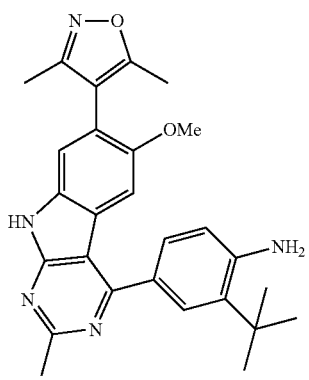

Cpd. No. 162

2-(tert-Butyl)-4-(7-(3,5-dimethylisoxazol-4-yl)-6-methoxy-2-methyl-9H-pyrimido[4,5-b]indol-4-yl)aniline (Cpd. No. 162)

Using same protocol similar to Method 40: Suzuki coupling of S13 (800 mg, 2.16 mmol) and tert-Butyl (2-(tert-butyl)-4-(4,4,5,5-tetramethyl-1,3,2-dioxaborolan-2-yl)phenyl)carbamate (CE128, 2.0 g) followed by CF$_3$CO$_2$H-promoted deprotection of Boc group yielded the title compound after flash column chromatography (510 mg, 52% yield). $^1$H NMR (MeOD-d4, 300 MHz): 7.75 (d, J=1.87 Hz, 1H), 7.51 (dd, J=8.21, 1.85 Hz, 1H), 7.45 (s, 1H), 7.26 (s, 1H), 6.87 (d, J=8.20 Hz, 1H), 3.63 (s, 3H), 2.69 (s, 3H), 2.25 (s, 3H), 2.01 (s, 3H), 1.41 (s, 9H). ESI-MS calculated for C$_{27}$H$_{30}$N$_5$O$_2$ [M+H]$^+$=456.24; Observed: 456.67.

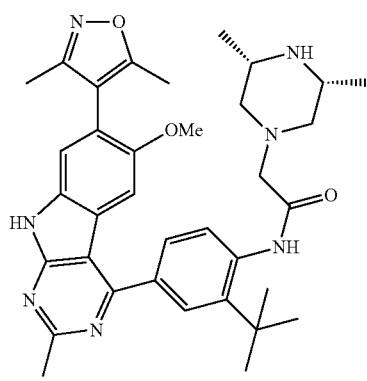

Cpd. No. 163

N-(2-(tert-Butyl)-4-(7-(3,5-dimethylisoxazol-4-yl)-6-methoxy-2-methyl-9H-pyrimido[4,5-b]indol-4-yl)phenyl)-2-((3R,5S)-3,5-dimethylpiperazin-1-yl)acetamide 42-(tert-Butyl)-4-(7-(3,5-dimethylisoxazol-4-yl)-6-methoxy-2-methyl-9H-pyrimido[4,5-b]indol-4-yl)aniline (Cpd. No. 162, 70 mg, 0.2 mmol, 1.0 equiv.) and NaHCO$_3$ (170 mg, 2.0 mmol, 10 equiv.) were dissolved in anhydrous THF (6 mL). To this solution, chloroacetyl chloride (120 mg, 1.0 mmol, 5.0 equiv.) was added and the solution was stirred for 16 h. The reaction mixture was diluted with water and the aqueous layer was extracted with ethyl acetate. The organic layers were combined and dried over anhydrous sodium sulfate. The volatile components were removed on a rotary evaporator. The remaining residue was dissolved in anhydrous DMF and 2,6-cis-dimethylpiperazine (66 mg, 0.6 mmol, 3.0 equiv.) and EtN(iPr$_2$) (0.2 mL) were added. The reaction was stirred at ambient temperature for 16 h before quenching with water. The aqueous layer was extracted with ethyl acetate and the organic layers were combined, the volatile components were removed on a rotary evaporator. The remaining residue was purified by reverse phase HPLC affording the title compound as a salt of CF$_3$CO$_2$H (86 mg, 60% yield). $^1$H NMR (MeOD-d4, 300 MHz): 8.10 (d, J=1.74 Hz, 1H), 8.05 (d, J=8.24 Hz, 1H), 7.93 (dd, J=8.24, 1.81 Hz, 1H), 7.57 (s, 1H), 7.35 (s, 1H), 3.97 (s, 2H), 3.71 (s, 3H), 3.64-3.50 (m, 2H), 3.40-3.32 (m, 2H), 2.97 (s, 3H), 2.64 (t, J=12.16 Hz, 2H), 2.31 (s, 3H), 2.13 (s, 3H), 1.55 (s, 9H), 1.38 (d, J=6.55 Hz, 6H). ESI-MS calculated for C$_{35}$H$_{44}$N$_7$O$_3$ [M+H]$^+$=610.35; Observed: 610.58.

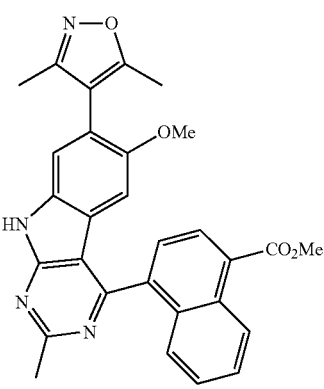

Cpd. No. 164

Methyl 4-(7-(3,5-dimethylisoxazol-4-yl)-6-methoxy-2-methyl-9H-pyrimido[4,5-b]indol-4-yl)-1-naphthoate (Cpd. No. 164)

4-(4-chloro-6-methoxy-2-methyl-9H-pyrimido[4,5-b]indol-7-yl)-3,5-dimethylisoxazole (S13, 1.71 g, 5.0 mmol, 1.0 equiv.) and methyl 4-(4,4,5,5-tetramethyl-1,3, 2-dioxaborolan-2-yl)-1-naphthoate (3.0 g, 10 mmol, 2.0 equiv.) were dissolved in 1,2-dimethoxyethane (60 mL). Sodium carbonate (2.0 M in water, 20 mL) was added. The system was degassed to remove oxygen and nitrogen was refilled. Pd(dppf)Cl$_2$—CH$_2$Cl$_2$ (408 mg, 0.5 mmol, 0.1 equiv.) was added and the flask was degassed again and refilled with nitrogen. The reaction mixture was heated at reflux for 16 h. The reaction was quenched with water and extracted with ethyl acetate. The organic layers were combined and removed on a rotary evaporator. The residue was purified by flash column chromatography to yield the title compound (1.04 g, 42% yield). $^1$H NMR (CDCl$_3$, 300 MHz): 11.73n (s, 1H), 9.09 (d, J=8.74 Hz, 1H), 8.39 (d, J=7.49 Hz, 1H), 7.84 (d, J=7.57 Hz, 2H), 7.72-7.65 (m, 1H), 7.53-7.46 (m 1H), 7.31 (s, 1H), 6.22 (s, 1H), 4.08 (s, 3H), 3.20 (s, 3H), 3.07 (s, 3H), 2.29 (s, 3H), 2.13 (s, 3H). ESI-MS calculated for C$_{29}$H$_{25}$N$_4$O$_4$ [M+H]$^+$=493.19; Observed: 493.50.

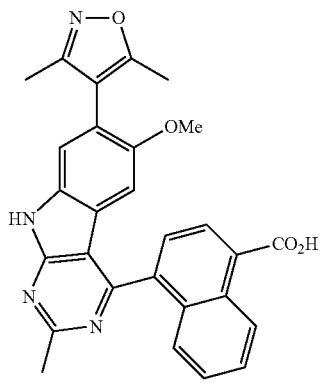

Cpd. No. 165

4-(7-(3,5-Dimethylisoxazol-4-yl)-6-methoxy-2-methyl-9H-pyrimido[4,5-b]indol-4-yl)-1-naphthoic acid (Cpd. No. 165)

Methyl 4-(7-(3,5-dimethylisoxazol-4-yl)-6-methoxy-2-methyl-9H-pyrimido[4,5-b]indol-4-yl)-1-naphthoate (Cpd. No. 164, 107 mg, 0.22 mmol) was dissolved in THF (5 mL) and water (5 mL). LiOH—H$_2$O (90 mg, 2.0 mmol, 10.0 equiv.) was added and solution was stirred for 16 h. The reaction mixture was extracted with ethyl acetate. Subsequently, the aqueous layer was neutralized to pH=2 and was extracted with ethyl acetate. The organic extracts of acidic aqueous solution were combined and concentrated on a rotary evaporator. The remaining residue was freeze-dried to yield the title compound in 100 mg (>90% yield). $^1$H NMR (MeOD-d4, 300 MHz): 9.13 (d, J=8.60 Hz, 1H), 8.47 (d, J=7.47 Hz, 1H), 8.07 (d, J=7.48 Hz, 1H), 7.84-7.74 (m, 2H), 7.61 (t, J=7.63), 7.55 (s, 1H), 6.13 (s, 1H), 3.16 (s, 3H), 3.03 (s, 3H), 2.24 (s, 3H), 2.04 (s, 3H). ESI-MS calculated for C$_{28}$H$_{23}$N$_4$O$_4$ [M+H]$^+$=479.17; Observed: 479.42.

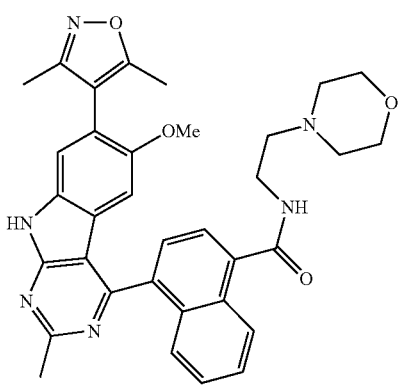

Cpd. No. 166

4-(7-(3,5-Dimethylisoxazol-4-yl)-6-methoxy-2-methyl-9H-pyrimido[4,5-b]indol-4-yl)-N-(2-morpholinoethyl)-1-naphthamide Method 64 (amide condensation): 4-(7-(3,5-Dimethylisoxazol-4-yl)-6-methoxy-2-methyl-9H-pyrimido[4,5-b]indol-4-yl)-1-naphthoic acid (Cpd. No. 165, 20 mg, 0.05 mmol), EDCI-HCl (100 mg, 0.5 mmol), and HOBt-H$_2$O (70 mg, 0.5 mmol) were added to a round-bottom flask. EtN(i-Pr)$_2$ (0.1 mL) was added followed by addition of DMF (2.5 mL). 2-Morpholinylethylamine (70 mg, 0.5 mmol) was added and the reaction mixture was stirred for 12 h. The reaction was quenched with NaHCO$_3$ saturated solution and the aqueous layer was extracted with ethyl acetate. The combined organic layers were concentrated on a rotary evaporator. The remaining residue was purified by reverse phase HPLC affording the title compound as a salt of CF$_3$CO$_2$H (20 mg, 69% yield). $^1$H NMR (MeOD-d4, 300 MHz): 8.55 (d, J=8.52 Hz, 1H), 8.10-8.02 (m, 2H), 7.84-7.74 (m, 2H), 7.68-7.60 (m, 1H), 7.54 (s, 1H), 6.15 (s, 1H), 4.20-4.00 (m, 2H), 4.00-3.60 (m, 8H), 3.97 (t, J=5.72 Hz, 2H), 3.57 (t, J=6.24 Hz, 2H), 3.17 (s, 3H), 3.02 (s, 3H), 2.26 (s, 3H), 2.06 (s, 3H). ESI-MS calculated for C$_{34}$H$_{35}$N$_6$O$_4$ [M+H]$^+$=591.27; Observed: 591.58.

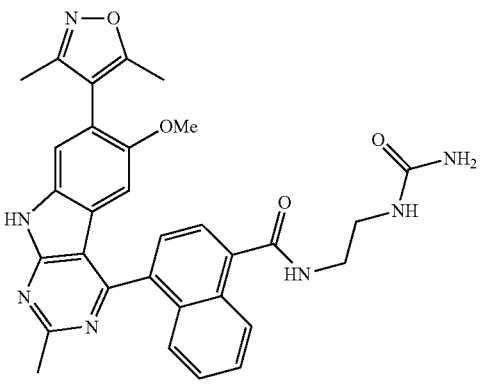

Cpd. No. 167

4-(7-(3,5-Dimethylisoxazol-4-yl)-6-methoxy-2-methyl-9H-pyrimido[4,5-b]indol-4-yl)-N-(2-ureidoethyl)-1-naphthamide Using amide condensation condition Method 64, reaction of 4-(7-(3,5-dimethylisoxazol-4-yl)-6-methoxy-2-methyl-9H-pyrimido[4,5-b]indol-4-yl)-1-naphthoic acid (Cpd. No. 165, 20 mg) and (2-Amino-ethyl)-urea-HCl (20 mg) afforded the title compound in 16 mg (57% yield). $^1$H NMR (MeOD-d4, 300 MHz): 8.49 (d, J=8.45 Hz, 1H), 8.03 (d, J=7.33 Hz, 1H), 7.97 (d, J=7.33 Hz, 1H), 7.82-7.73 (m, 2H), 7.65-7.58 (m, 1H), 7.53 (s, 1H), 6.17 (s, 1H), 3.63 (t, J=5.63 Hz, 2H), 3.47 (t, J=5.97 Hz, 1H), 3.19 (s, 3H), 3.01 (s, 3H), 2.26 (s, 3H), 2.06 (s, 3H). ESI-MS calculated for C$_{31}$H$_{30}$N$_7$O$_4$ [M+H]$^+$=564.24; Observed: 564.50.

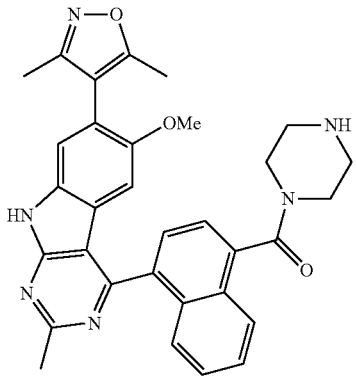

Cpd. No. 168

(4-(7-(3,5-Dimethylisoxazol-4-yl)-6-methoxy-2-methyl-9H-pyrimido[4,5-b]indol-4-yl)naphthalen-1-yl)(piperazin-1-yl)methanone Using amide condensation condition Method 64, reaction of 4-(7-(3,5-dimethylisoxazol-4-yl)-6-methoxy-2-methyl-9H-pyrimido[4,5-b]indol-4-yl)-1-naphthoic acid (Cpd. No. 165, 20 mg) and piperazine (63 mg) afforded the title compound in 8 mg (30% yield). $^1$H NMR (MeOD-d4, 300 MHz): 8.20-8.04 (m, 2H), 8.00-7.78 (m, 2H), 7.72-7.60 (m, 1H), 7.58-7.50 (m, 1H), 6.26-6.14 (m, 1H), 4.40-4.10 (m, 2H), 3.80-3.40 (m, 4H), 3.40-3.20 (m, 2H), 3.19 (s, 3H), 3.03 (s, 3H), 2.26 (s, 3H), 2.07 (s, 3H). ESI-MS calculated for $C_{32}H_{31}N_6O_3$ [M+H]$^+$=547.25; Observed: 547.67.

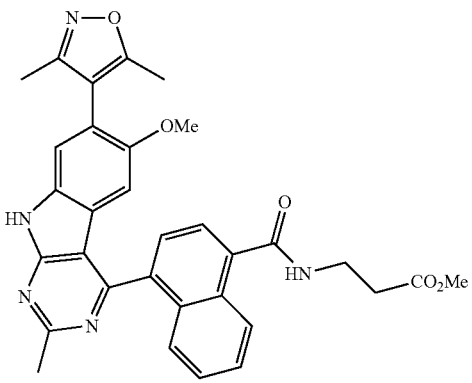

Cpd. No. 169

Methyl 3-(4-(7-(3,5-dimethylisoxazol-4-yl)-6-methoxy-2-methyl-9H-pyrimido[4,5-b]indol-4-yl)-1-naphthamido)propanoate Using amide condensation condition Method 64, reaction of 4-(7-(3,5-dimethylisoxazol-4-yl)-6-methoxy-2-methyl-9H-pyrimido[4,5-b]indol-4-yl)-1-naphthoic acid (Cpd. No. 165, 30 mg) and β-alanine methyl ester (28 mg) afforded the title compound. The crude was used in the next step without further purification.

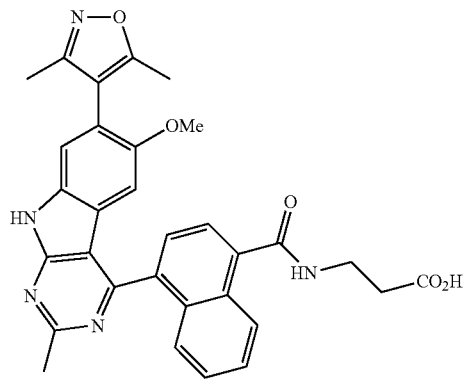

Cpd. No. 170

3-(4-(7-(3,5-Dimethylisoxazol-4-yl)-6-methoxy-2-methyl-9H-pyrimido[4,5-b]indol-4-yl)-1-naphthamido)propanoic acid Methyl 3-(4-(7-(3,5-dimethylisoxazol-4-yl)-6-methoxy-2-methyl-9H-pyrimido[4,5-b]indol-4-yl)-1-naphthamido)propanoate (Cpd. No. 169) was dissolved in THF—H$_2$O (1:1). LiOH—H$_2$O (10 equiv.) was added and the reaction was stirred at ambient temperature for 16 h. Volatile components were removed on a rotary evaporator and the residues was purified by on a reverse phase HPLC affording the title compound (22 mg, 34% yield). $^1$H NMR (MeOD-d4, 300 MHz): 8.46 (d, J=8.49 Hz, 1H), 8.02 (d, J=7.32 Hz, 1H), 7.92 (d, J=7.32 Hz, 1H), 7.83-7.72 (m, 2H), 7.65-7.57 (m, 1H), 7.52 (s, 1H), 6.15 (s, 1H), 3.80 (t, J=6.65 Hz, 2H), 3.18 (s, 3H), 3.01 (s, 3H), 2.78 (t, J=6.65 Hz, 2H), 2.26 (s, 3H), 2.06 (s, 3H). ESI-MS calculated for $C_{31}H_{28}N_5O_5$ [M+H]$^+$=550.21; Observed: 550.33.

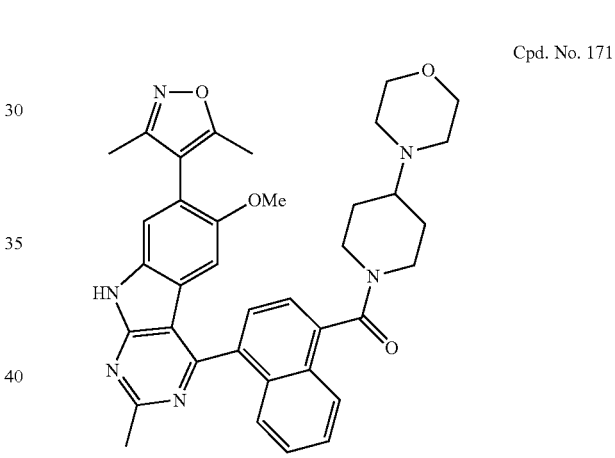

Cpd. No. 171

(4-(7-(3,5-Dimethylisoxazol-4-yl)-6-methoxy-2-methyl-9H-pyrimido[4,5-b]indol-4-yl)naphthalen-1-yl)(4-morpholinopiperidin-1-yl)methanone Using amide condensation condition Method 64, reaction of 4-(7-(3,5-dimethylisoxazol-4-yl)-6-methoxy-2-methyl-9H-pyrimido[4,5-b]indol-4-yl)-1-naphthoic acid (Cpd. No. 165, 40 mg) and 4-morpholinopiperidine (34 mg) afforded the title compound in 50 mg (78% yield). $^1$H NMR (MeOD-d4, 300 MHz): 8.22-8.02 (m, 2H), 8.00-7.78 (m, 3H), 7.72-7.62 (m, 1H), 7.60-7.56 (m, 1H), 6.26-6.16 (m, 1H), 5.20-5.06 (m, 1H), 4.40-4.00 (m, 2H), 4.00-3.55 (m, 2H), 3.54-3.45 (m, 4H), 3.40-3.00 (m, 4H), 3.22 (s, 3H), 3.05 (s, 3H), 2.60-2.40 (m, 1H), 2.28 (s, 3H), 2.20-1.80 (m, 2.5H), 2.08 (s, 3H), 1.70-1.50 (m, 0.5H). ESI-MS calculated for $C_{37}H_{39}N_6O_4$ [M+H]$^+$=631.30; Observed: 631.83.

Cpd. No. 172

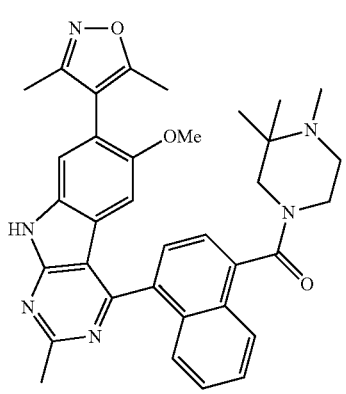

(4-(7-(3,5-Dimethylisoxazol-4-yl)-6-methoxy-2-methyl-9H-pyrimido[4,5-b]indol-4-yl)naphthalen-1-yl)(3,3,4-trimethylpiperazin-1-yl)methanone Using amide condensation condition Method 64, reaction of 4-(7-(3,5-dimethylisoxazol-4-yl)-6-methoxy-2-methyl-9H-pyrimido[4,5-b]indol-4-yl)-1-naphthoic acid (Cpd. No. 165, 20 mg) and 1,2,2-trimethylpiperidine (20 mg) afforded the title compound in 12 mg (40% yield). $^1$H NMR (MeOD-d4, 300 MHz): 8.20-8.00 (m, 2H), 8.00-7.80 (m, 3H), 7.70-7.60 (m, 1H), 7.60-7.50 (m, 1H), 6.40-6.10 (m, 1H), 3.80-3.40 (m, 4H), 3.40-3.10 (m, 2H), 3.02 (s, 3H), 2.90 (s, 3H), 2.26 (s, 3H), 2.07 (s, 3H), 1.70-1.50 (m, 3H), 1.40-1.00 (m, 3H). ESI-MS calculated for $C_{35}H_{37}N_6O_3$ [M+H]$^+$= 589.29; Observed: 589.83.

Cpd. No. 173

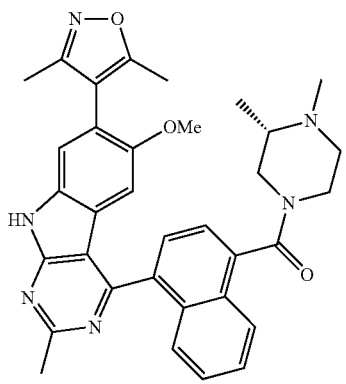

(4-(7-(3,5-Dimethylisoxazol-4-yl)-6-methoxy-2-methyl-9H-pyrimido[4,5-b]indol-4-yl)naphthalen-1-yl)((S)-3,4-dimethylpiperazin-1-yl)methanone Using amide condensation condition Method 64, reaction of 4-(7-(3,5-dimethylisoxazol-4-yl)-6-methoxy-2-methyl-9H-pyrimido[4,5-b]indol-4-yl)-1-naphthoic acid (Cpd. No. 165, 160 mg) and (S)-1,2-dimethyl-piperazine (224 mg) afforded the title compound in 150 mg (55% yield). $^1$H NMR (MeOD-d4, 300 MHz): 8.30-8.00 (m, 2H), 8.00-7.75 (m, 3H), 7.75-7.60 (m, 1H), 7.45 (s, 1H), 6.40-6.10 (m, 1H), 3.90-3.20 (m, 6H), 3.32 (s, 6H), 3.20 (s, 3H), 2.27 (s, 3H), 2.08 (s, 3H), 1.59 (d, J=6.30 Hz, 1.5H), 1.40-1.10 (m, 1.5H). ESI-MS calculated for $C_{34}H_{35}N_6O_3$ [M+H]$^+$=575.28; Observed: 575.83.

Cpd. No. 174

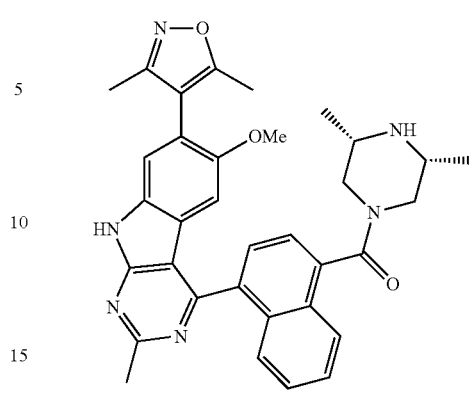

(4-(7-(3,5-Dimethylisoxazol-4-yl)-6-methoxy-2-methyl-9H-pyrimido[4,5-b]indol-4-yl)naphthalen-1-yl)((3R,5S)-3,5-dimethylpiperazin-1-yl)methanone Using amide condensation condition Method 64, reaction of 4-(7-(3,5-dimethylisoxazol-4-yl)-6-methoxy-2-methyl-9H-pyrimido[4,5-b]indol-4-yl)-1-naphthoic acid (Cpd. No. 165, 160 mg) and cis-2,6-dimethyl-piperazine (160 mg) afforded the title compound in 138 mg (52% yield). $^1$H NMR (MeOD-d4, 300 MHz): 8.30-8.00 (m, 2H), 8.00-7.70 (m, 3H), 7.70-7.60 (m, 1H), 7.60-7.50 (m, 1H), 6.50-6.10 (m, 1H), 5.20-5.00 (m, 1H), 3.80-3.20 (m, 4H), 3.19 (s, 3H), 3.03 (s, 3H), 2.26 (s, 3H), 2.06 (s, 3H), 1.56-1.46 (m, 3H), 1.24-1.10 (m, 3H). ESI-MS calculated for $C_{34}H_{35}N_6O_3$ [M+H]$^+$=575.28; Observed: 575.75.

Cpd. No. 175

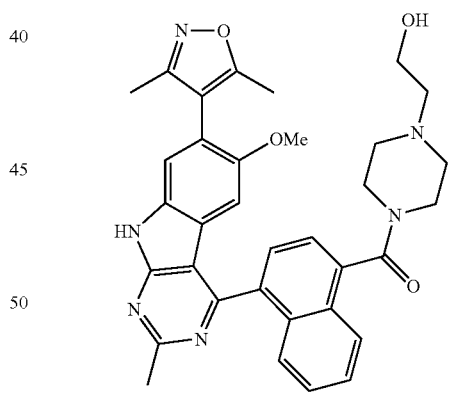

(4-(7-(3,5-Dimethylisoxazol-4-yl)-6-methoxy-2-methyl-9H-pyrimido[4,5-b]indol-4-yl)naphthalen-1-yl)(4-(2-hydroxyethyl)piperazin-1-yl)methanone Using amide condensation condition Method 64, reaction of 4-(7-(3,5-dimethylisoxazol-4-yl)-6-methoxy-2-methyl-9H-pyrimido[4,5-b]indol-4-yl)-1-naphthoic acid (Cpd. No. 165, 160 mg) and 1-(2-Hydroxyethyl)piperazine (140 mg) afforded the title compound in 172 mg (62% yield). $^1$H NMR (MeOD-d4, 300 MHz): 8.30-8.05 (m, 2H), 8.00-7.75 (m, 3H), 7.70-7.60 (m, 1H), 7.57 (s, 1H), 6.21 (s, 1H), 3.96

(t, J=4.39 Hz, 2H), 3.80-3.40 (m, 8H), 3.42 (t, J=4.39 Hz, 2H), 3.19 (s, 3H), 3.04 (s, 3H), 2.23 (s, 3H), 2.04 (s, 3H). ESI-MS calculated for $C_{34}H_{35}N_6O_4$ $[M+H]^+$=591.27; Observed: 591.50.

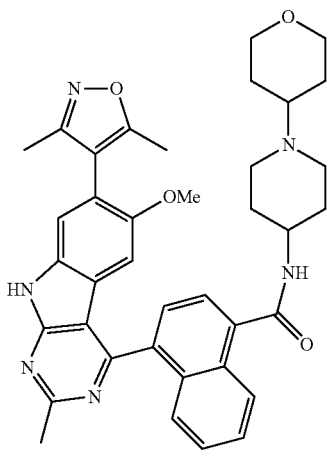

Cpd. No. 176

4-(7-(3,5-Dimethylisoxazol-4-yl)-6-methoxy-2-methyl-9H-pyrimido[4,5-b]indol-4-yl)-N-(1-(tetrahydro-2H-pyran-4-yl)piperidin-4-yl)-1-naphthamide Using amide condensation condition Method 64, reaction of 4-(7-(3,5-dimethylisoxazol-4-yl)-6-methoxy-2-methyl-9H-pyrimido[4,5-b]indol-4-yl)-1-naphthoic acid (Cpd. No. 165, 40 mg) and 1-(tetrahydro-2H-pyran-4-yl)-4-piperidinamine dihydrochloride (50 mg) afforded the title compound in 87 mg (>90% yield). $^1$H NMR (MeOD-d4, 300 MHz): 8.45 (d, J=8.46 Hz, 1H), 8.05 (d, J=7.20 Hz, 1H), 7.96 (d, J=7.34 Hz, 1H), 7.85-7.73 (m, 2H), 7.62 (ddd, J=8.23, 7.10, 1.03 Hz, 1H), 7.55 (s, 1H), 6.15 (s, 1H), 4.44-4.30 (m, 1H), 4.09 (dd, J=11.26, 3.87 Hz, 2H), 3.76 (d, J 12.35 Hz, 2H), 3.60-3.40 (m, 4H), 3.34-3.20 (m, 1H), 3.17 (s, 3H), 3.02 (s, 3H), 2.53-2.40 (m, 2H), 2.25 (s, 3H), 2.18-1.96 (m, 4H), 2.06 (s, 3H), 1.90-1.72 (m, 2H). ESI-MS calculated for $C_{38}H_{41}N_6O_4$ $[M+H]^+$=645.32; Observed: 645.58.

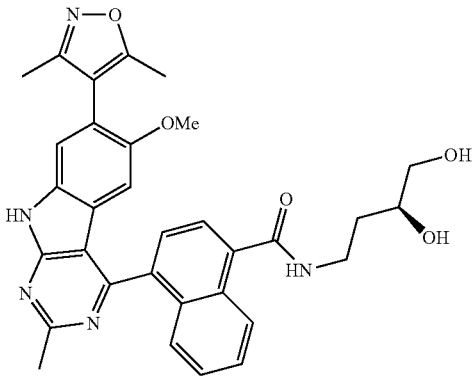

Cpd. No. 177

N—((S)-3,4-Dihydroxybutyl)-4-(7-(3,5-dimethylisoxazol-4-yl)-6-methoxy-2-methyl-9H-pyrimido[4,5-b]indol-4-yl)-1-naphthamide Method 77: 4-(7-(3,5-Dimethylisoxazol-4-yl)-6-methoxy-2-methyl-9H-pyrimido[4,5-b]indol-4-yl)-1-naphthoic acid (Cpd. No. 165, 20 mg, 0.05 mmol), EDCI-HCl (48 mg, 0.25 mmol), and HOBt-$H_2O$ (34 mg, 0.25 mmol) were added to a round-bottom flask. EtN(i-Pr)$_2$ (0.1 mL) was added followed by addition of DMF (2.5 mL) via syringes. (2S)-4-Amino-1-(triphenylmethoxy)-2-butanol (52 mg, 0.15 mmol) was added and the reaction mixture was stirred for 16 h. The reaction was quenched with NaHCO$_3$ saturated solution and the aqueous layer was extracted with ethyl acetate. The combined organic layers were concentrated on a rotary evaporator. The residue was dissolved in $CH_2Cl_2$ (4 mL) and $CF_3CO_2H$ (4 mL) was added and the mixture was stirred for 1 h before purification on a reverse phase HPLC affording the title compound as a salt of $CF_3CO_2H$ (19 mg, 68% yield). $^1$H NMR (MeOD-d4, 300 MHz): 8.46 (d, J=8.39 Hz, 1H), 8.04 (d, J=7.32 Hz, 1H), 7.95 (d, J=7.32 Hz, 1H), 7.84-7.74 (m, 2H), 7.66-7.58 (m, 1H), 7.54 (s, 1H), 6.17 (s, 1H), 3.86-3.75 (m, 1H), 3.75-3.66 (m, 2H), 3.56 (d, J=5.55 Hz, 2H), 3.19 (s, 3H), 3.02 (s, 3H), 2.26 (s, 3H), 2.06 (s, 3H), 2.10-1.90 (m, 1H), 1.90-1.70 (m, 1H). ESI-MS calculated for $C_{32}H_{32}N_5O_5$ $[M+H]^+$=566.24; Observed: 566.75.

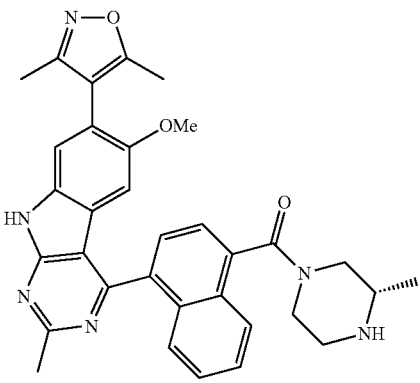

Cpd. No. 178

(4-(7-(3,5-Dimethylisoxazol-4-yl)-6-methoxy-2-methyl-9H-pyrimido[4,5-b]indol-4-yl)naphthalen-1-yl)((S)-3-methylpiperazin-1-yl)methanone Using amide condensation condition Method 77, reaction of 4-(7-(3,5-dimethylisoxazol-4-yl)-6-methoxy-2-methyl-9H-pyrimido[4,5-b]indol-4-yl)-1-naphthoic acid (Cpd. No. 165, 40 mg) and (S)-1-Boc-2-methyl-piperazine (60 mg) followed by $CF_3CO_2H$-promoted deprotection of Boc group afforded the title compound in 27 mg (41% yield). $^1$H NMR (MeOD-d4, 300 MHz): 8.28-8.00 (m, 2H), 8.00-7.74 (m, 2H), 7.70-7.60 (m, 1H), 7.53 (s, 1H), 6.40-6.10 (m, 1H), 3.80-3.40 (m, 4H), 3.40-3.10 (m, 3H), 3.19 (s, 3H), 3.02 (s, 3H), 2.26 (s, 3H), 2.07 (s, 3H), 1.51 (d, J=5.55 Hz, 1.5H), 1.16 (d, J=5.84 Hz, 1.5H). ESI-MS calculated for $C_{33}H_{33}N_6O_3$ $[M+H]^+$=561.26; Observed: 561.58.

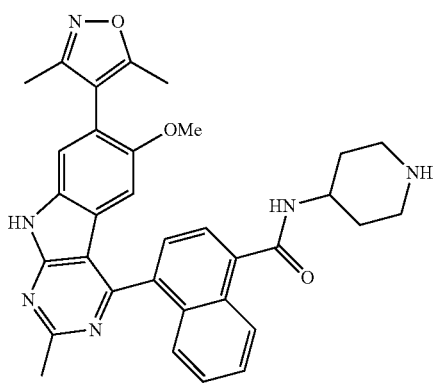

Cpd. No. 179

4-(7-(3,5-Dimethylisoxazol-4-yl)-6-methoxy-2-methyl-9H-pyrimido[4,5-b]indol-4-yl)-N-(piperidin-4-yl)-1-naphthamide Using amide condensation condition Method 77, reaction of 4-(7-(3,5-dimethylisoxazol-4-yl)-6-methoxy-2-methyl-9H-pyrimido[4,5-b]indol-4-yl)-1-naphthoic acid (Cpd. No. 165, 40 mg) and 1-Boc-4-amino-piperidine (60 mg) followed by $CF_3CO_2H$-promoted deprotection of Boc group afforded the title compound in 34 mg (51% yield). $^1$H NMR (MeOD-d4, 300 MHz): 9.15 (d, J=6.96 Hz, 1H), 8.44 (d, J=8.55 Hz, 1H), 8.04 (d, J=7.31 Hz, 1 h), 7.96 (d, J=7.31 Hz, 1H), 7.81 (d, J=8.28 Hz, 1H), 7.76 (d, J=8.42 Hz, 1H), 7.62 (t, J=7.63 Hz, 1H), 7.54 (s, 1H), 6.15 (s, 1H), 4.50-4.30 (m, 1H), 3.55 (d, J=12.83 Hz, 2H), 3.30-3.14 (m, 2H), 3.18 (s, 3H), 3.02 (s, 3H), 2.44-2.30 (m, 2H), 2.26 (s, 3H), 2.06 (s, 3H), 2.00-1.86 (m, 2H). ESI-MS calculated for $C_{33}H_{33}N_6O_3$ $[M+H]^+$=561.26; Observed: 561.58.

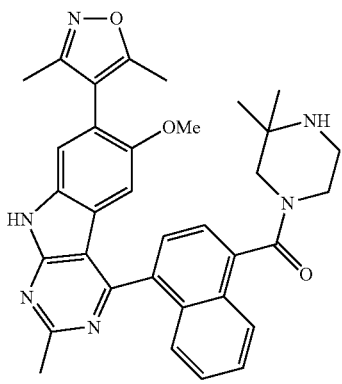

Cpd. No. 180

(4-(7-(3,5-Dimethylisoxazol-4-yl)-6-methoxy-2-methyl-9H-pyrimido[4,5-b]indol-4-yl)naphthalen-1-yl)(3,3-dimethylpiperazin-1-yl)methanone Using amide condensation condition Method 77, reaction of 4-(7-(3,5-dimethylisoxazol-4-yl)-6-methoxy-2-methyl-9H-pyrimido[4,5-b]indol-4-yl)-1-naphthoic acid (Cpd. No. 165, 160 mg) and 1-Boc-2,2-dimethylpiperidine (260 mg) followed by $CF_3CO_2H$-promoted deprotection of Boc group afforded the title compound in 150 mg (56% yield). $^1$H NMR (MeOD-d4, 300 MHz): 8.30-8.10 (m, 2H), 8.10-7.75 (m, 3H), 7.70-7.60 (m, 1H), 7.60-7.50 (m, 1H), 6.40-6.20 (m, 1H), 4.40-4.20 (m, 1.4H), 4.00-3.80 (m, 0.6H), 3.80-3.30 (m, 4H), 3.21 (s, 3H), 3.04 (s, 3H), 2.27 (s, 3H), 2.08 (s, 3H), 1.62 (d, J=3.58 Hz, 3H), 1.38 (s, 1.5H), 1.30-1.20 (m, 1.5H). ESI-MS calculated for $C_{34}H_{35}N_6O_3$ $[M+H]^+$=575.28; Observed: 575.75.

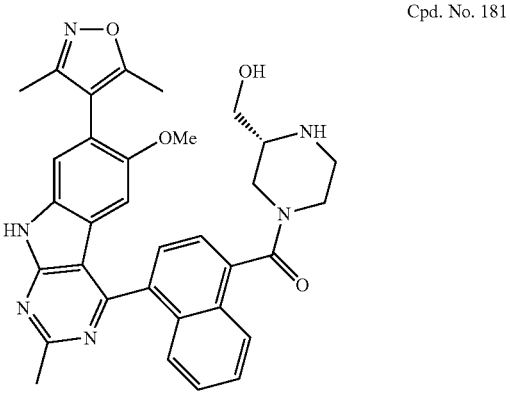 [SMILES: COc1cc2c(cc1-c1c(C)noc1C)[nH]c1nc(C)nc(-c3ccc(C(=O)N4CCN[C@@H](CO)C4)c4ccccc34)c12]

Cpd. No. 181

(4-(7-(3,5-Dimethylisoxazol-4-yl)-6-methoxy-2-methyl-9H-pyrimido[4,5-b]indol-4-yl)naphthalen-1-yl)((R)-3-(hydroxymethyl)piperazin-1-yl)methanone (Cpd. No. 181)

Using amide condensation condition Method 77, reaction of 4-(7-(3,5-dimethylisoxazol-4-yl)-6-methoxy-2-methyl-9H-pyrimido[4,5-b]indol-4-yl)-1-naphthoic acid (Cpd. No. 165, 100 mg) and (R)-1-Boc-2-hydroxymethylpiperazine (80 mg) followed by $CF_3CO_2H$-promoted deprotection of Boc group afforded the title compound in 92 mg (59% yield). $^1$H NMR (MeOD-d4, 300 MHz): 8.30-8.05 (m, 2H), 8.05-7.75 (m, 3H), 7.75-7.60 (m, 1H), 7.56 (s, 1H), 6.40-6.40 (m, 1H), 5.10-4.90 (m, 1H), 4.10-3.40 (m, 8H), 3.18 (s, 3H), 3.04 (s, 3H), 2.24 (s, 3H), 2.05 (s, 3H). ESI-MS calculated for $C_{33}H_{33}N_6O_4$ $[M+H]^+$=577.26; Observed: 577.83.

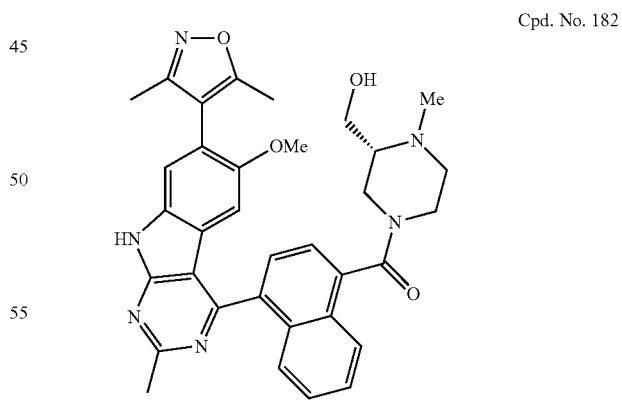

Cpd. No. 182

(4-(7-(3,5-Dimethylisoxazol-4-yl)-6-methoxy-2-methyl-9H-pyrimido[4,5-b]indol-4-yl)naphthalen-1-yl)((R)-3-(hydroxymethyl)-4-methylpiperazin-1-yl)methanone (Cpd. No. 182)

(4-(7-(3,5-Dimethylisoxazol-4-yl)-6-methoxy-2-methyl-9H-pyrimido[4,5-b]indol-4-yl)naphthalen-1-yl)((R)-3-(hydroxymethyl)piperazin-1-yl)methanone (Co, 20 mg), paraformaldehyde (30 mg), acetic acid (0.05 mL), and 1,2-dichloroethane (4 mL) were placed in a round-bottom flask. Sodium triacetoxyborohydride (400 mg) was added in one portion and the mixture was stirred at ambient temperature for 16 h. Water was added and the aqueous layer was extracted with ethyl acetate and $CH_2Cl_2$. The combined organic layers were concentrated on a rotary evaporator. The residue was purified on a reverse phase HPLC affording the title compound as a salt of $CF_3CO_2H$ (11 mg, 52% yield). $^1H$ NMR (MeOD-d4, 300 MHz): 8.30-8.00 (m, 2H), 8.00-7.75 (m, 3H), 7.75-7.60 (m, 1H), 7.53 (s, 1H), 6.50-6.10 (m, 1H), 5.10-4.90 (m, 1H), 4.30-3.20 (m, 8H), 3.19 (s, 3H), 3.04 (s, 3H), 3.02 (s, 3H), 2.26 (s, 3H), 2.07 (s, 3H). ESI-MS calculated for $C_{34}H_{35}N_6O_4$ $[M+H]^+$=591.27; Observed: 591.67.

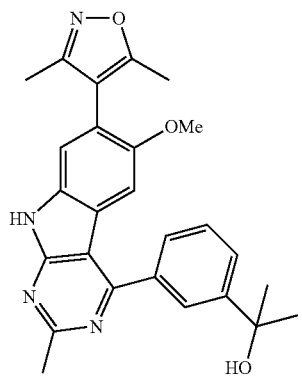

Cpd. No. 183

2-(3-(7-(3,5-Dimethylisoxazol-4-yl)-6-methoxy-2-methyl-9H-pyrimido[4,5-b]indol-4-yl)phenyl)propan-2-ol (free amine)

S13 (40 mg, 0.1 mmol, 1.0 equiv.) and 3-(2-hydroxy-2-propanyl)phenylboronic acid pinacol ester (90 mg, 0.3 mmol, 3.0 equiv.) were dissolved in 1,2-dimethoxyethane (4 mL). Sodium carbonate (2.0 M in water, 2 mL) was added. The system was degassed to remove oxygen and nitrogen was refilled. Pd(dppf)Cl$_2$—CH$_2$Cl$_2$ (20 mg, 0.024 mmol, 0.24 equiv.) were added and the system was degassed again and refilled with nitrogen. The reaction mixture was heated at reflux for 16 h. The reaction was quenched with water and extracted with ethyl acetate. The organic layers were combined and removed on a rotary evaporator. The residue was purified by reverse phase HPLC. The HPLC eluents containing the title compound was neutralized with ammonia solution and extracted with ethyl acetate to afford the title compound as free amine (10 mg, 22% yield). $^1H$ NMR (MeOD-d4, 300 MHz): 8.12 (s, 1H), 7.90-7.60 (m, 2H), 7.71 (t, J=7.66 Hz, 1H), 7.50 (s, 1H), 7.31 (s, 1H), 3.66 (s, 3H), 2.89 (s, 3H), 2.30 (s, 3H), 2.12 (s, 3H), 1.63 (s, 6H). ESI-MS calculated for $C_{26}H_{27}N_4O_3$ $[M+H]^+$=443.21; Observed: 443.72.

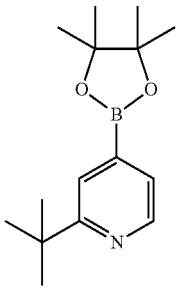

CE103

2-(tert-Butyl)-4-(4,4,5,5-tetramethyl-1,3,2-dioxaborolan-2-yl)pyridine (CE103)

4-Bromo-2-(tert-butyl)pyridine (1.0 g, 4.6 mmol, 1.0 equiv.) was dissolved in anhydrous THF (20 mL). The solution was cooled to −78° C. for 15 min before BuLi (3.7 mL, 2.5 M in THF, 9.2 mmol, 2.0 equiv.) was added via a syringe. The reaction solution was stirred at −78° C. for 30 min and 2-isopropoxy-4,4,5,5-tetramethyl-1,3,2-dioxaborolane (1.37 g, 7.36 mmol, 1.6 equiv.) was added via a syringe. The reaction was stirred at −78° C. for 3 h before quenching with saturated NH$_4$Cl aqueous solution. The aqueous layer was extracted with ethyl acetate and the combined organic layers were washed with brine, dried over anhydrous sodium sulfate, and concentrated on a rotary evaporator. The remaining residue was purified by flash column chromatography to yield the title compound in 70 mg (6% yield). $^1H$ NMR (CDCl$_3$, 300 MHz): 8.51 (d, J=4.68 Hz, 1H), 7.61 (s, 1H), 7.36 (d, J=4.68 Hz, 1H), 1.31 (s, 9H), 1.26 (s, 12H). $^{13}C$ NMR (CDCl$_3$, 75 MHz): 168.53, 148.06, 125.78, 124.07, 84.34, 37.42, 30.32, 24.90. ESI-MS calculated for $C_{15}H_{25}BNO_2$ $[M+H]^+$=262.20; Observed: 262.42.

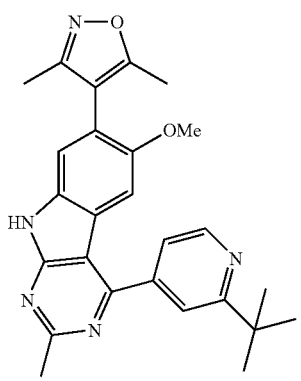

Cpd. No. 184

4-(4-(2-(tert-Butyl)pyridin-4-yl)-6-methoxy-2-methyl-9H-pyrimido[4,5-b]indol-7-yl)-3,5-dimethylisoxazole Suzuki coupling of S13 (273 mg, 0.80 mmol) and 2-(tert-butyl)-4-(4,4,5,5-tetramethyl-1,3,2-dioxaborolan-2-yl)pyridine (CE103, 440 mg, 1.68 mmol) using condition Method 42 followed by flash column chromatography afforded the title compound in 180 mg (51% yield). $^1H$ NMR (MeOD-d4, 300 MHz): 12.62 (s, 1H), 8.81 (d, J=4.84 Hz, 1H), 7.85 (s, 1H), 7.60 (d, J=4.65 Hz, 1H), 7.34 (s, 1H), 7.28 (s, 1H), 3.66

(s, 3H), 2.84 (s, 2H), 2.31 (s, 3H), 2.17 (s, 3H), 1.43 (s, 9H). ESI-MS calculated for $C_{26}H_{28}N_5O_2$ [M+H]$^+$=442.22; Observed: 442.50.

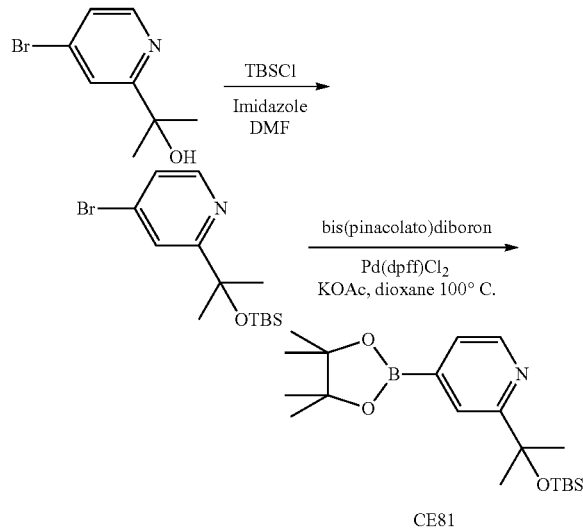

2-(2-((tert-Butyldimethylsilyl)oxy)propan-2-yl)-4-(4,4,5,5-tetramethyl-1,3,2-dioxaborolan-2-yl)pyridine (CE81)

2-(4-Bromopyridin-2-yl)propan-2-ol (0.57 g, 3.0 mmol), TBS-Cl (1.35 g, 9.0 mmol), and imidazole (816 mg, 12 mmol) were dissolved in anhydrous DMF (20 mL). The solution was heated at reflux for 3 days before quenching with water. The aqueous layer was extracted with ethyl acetate and the combined organic layers were washed with brine, dry over anhydrous sodium sulfate, and concentrated on a rotary evaporator. The residue was purified by flash column chromatography to yield 4-bromo-2-(2-((tert-butyldimethylsilyl)oxy)propan-2-yl)pyridine (0.46 g, 46% yield).

4-Bromo-2-(2-((tert-butyldimethylsilyl)oxy)propan-2-yl)pyridine (0.46 g, 1.4 mmol, 1.0 equiv.), bis(pinacolato)diboron (0.711 g, 2.8 mmol, 2.0 equiv.), and potassium acetate (0.549 g, 5.6 mmol, 4.0 equiv) were added to a round-bottom flask. Anhydrous 1,4-dixoane (15 mL) was added and the flask was degassed and refilled with nitrogen. Pd(dppf)Cl$_2$ (98 mg, 0.14 mmol, 0.1 equiv.) was added and the system was degassed again followed by heating at 100° C. for 16 h. The reaction mixture was cooled to ambient temperature and diluted by CH$_2$Cl$_2$. The solution was filtered through a pad of celite and the volatile components were removed on a rotary evaporator. The residue was purified by flash column chromatography to yield the title compound in 0.60 g (1.3 mmol, 90% yield). $^1$H NMR (CDCl$_3$, 300 MHz): 8.52 (d, J=4.74 Hz, 1H), 8.13 (t, J=0.98 Hz, 1H), 7.43 (dd, J=4.73, 1.08 Hz, 1H), 1.60 (s, 6H), 1.33 (s, 12H), 0.96 (s, 9H), 0.07 (s, 6H). ESI-MS calculated for $C_{20}H_{37}BNO_3Si$ [M+H]$^+$=378.26; Observed: 378.33.

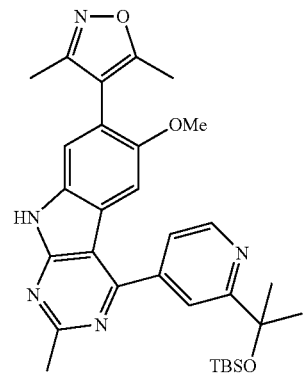

CE83

4-(4-(2-(2-((tert-Butyldimethylsilyl)oxy)propan-2-yl)pyridin-4-yl)-6-methoxy-2-methyl-9H-pyrimido[4,5-b]indol-7-yl)-3,5-dimethylisoxazole (CE83)

Suzuki coupling of S13 (240 mg, 0.7 mmol) and 2-(2-((tert-butyldimethylsilyl)oxy)propan-2-yl)-4-(4,4,5,5-tetramethyl-1,3,2-dioxaborolan-2-yl)pyridine (CE81, 0.62 g, 1.4 mmol) using condition Method 42 followed by flash column chromatography afforded the title compound in 0.337 mg (87% yield). $^1$H NMR (MeOD-d4 and CDCl$_3$, 300 MHz): 8.77 (d, J=4.99 Hz, 1H), 8.32 (s, 1H), 7.70 (dd, J=4.98, 1.48 Hz, 1H), 7.32 (s, 1H), 7.28 (s, 1H), 3.67 (s, 3H), 2.87 (s, 3H), 2.32 (s, 3H), 2.16 (s, 3H), 1.70 (s, 6H), 0.77 (s, 9H), 0.11 (s, 6H). ESI-MS calculated for C31H40N5O3Si [M+H]$^+$=558.29; Observed: 558.76.

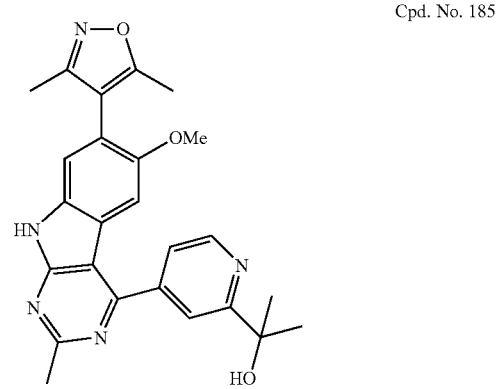 [SMILES: COc1cc2c(cc1-c1c(C)noc1C)[nH]c1nc(C)nc(-c3ccnc(C(C)(C)C#N)c3)c12]

Cpd. No. 185

2-(4-(7-(3,5-Dimethylisoxazol-4-yl)-6-methoxy-2-methyl-9H-pyrimido[4,5-b]indol-4-yl)pyridin-2-yl)propan-2-ol 4-(4-(2-(2-((tert-Butyldimethylsilyl)oxy)propan-2-yl)pyridin-4-yl)-6-methoxy-2-methyl-9H-pyrimido[4,5-b]indol-7-yl)-3,5-dimethylisoxazole (CE83, 0.337 g) was dissolved in 20 mL concentrated HCl and the mixture was stirred at room temperature for 24 h. The reaction mixture was purified by reverse phase HPLC affording the title compound as a salt of CF$_3$CO$_2$H (60 mg, 18% yield). $^1$H NMR (MeOD-d4, 300 MHz): 8.79 (d, J=5.06 Hz, 1H), 8.28 (s, 1H), 7.76 (dd, J=5.03, 1.57 Hz, 1H), 7.39 (s, 1H), 7.33 (s, 1H), 3.71 (s, 3H), 2.79 (s, 3H), 2.30 (s, 3H), 2.13 (s, 3H), 1.65 (s, 6H). ESI-MS calculated for $C_{25}H_{26}N_5O_3$ [M+H]$^+$= 444.20; Observed: 444.92.

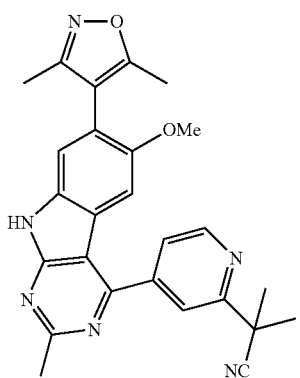

Cpd. No. 186

2-(4-(7-(3,5-Dimethylisoxazol-4-yl)-6-methoxy-2-methyl-9H-pyrimido[4,5-b]indol-4-yl)pyridin-2-yl)-2-methylpropanenitrile Suzuki coupling of S13 (342 mg, 1.0 mmol) and 2-methyl-2-[4-(tetramethyl-1,3, 2-dioxaborolan-2-yl)pyridin-2-yl]propanenitrile (0.5 g, 1.82 mmol) using condition Method 42 followed by reverse phase HPLC purification afforded the title compound as a salt of $CF_3CO_2H$ (227 mg, 41% yield). $^1$H NMR (MeOD-d4, 300 MHz): 9.06 (d, J=4.99 Hz, 1H), 8.25 (s, 1H), 8.00 (d, J=4.99, 1.47 Hz, 1H), 7.57 (s, 1H), 7.22 (s, 1H), 3.73 (s, 3H), 2.98 (s, 3H), 2.30 (s, 3H), 2.11 (s, 3H), 1.88 (s, 6H). ESI-MS calculated for $C_{26}H_{25}N_6O_2$ [M+H]$^+$=453.20; Observed: 453.67.

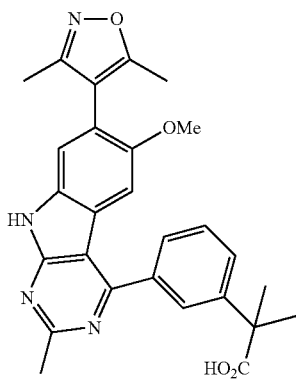

Cpd. No. 187

2-(3-(7-(3,5-Dimethylisoxazol-4-yl)-6-methoxy-2-methyl-9H-pyrimido[4,5-b]indol-4-yl)phenyl)-2-methylpropanoic acid (Cpd. No. 187)

Suzuki coupling of S13 (342 mg, 1.0 mmol) and 3-borono-a,a-dimethyl-benzeneacetic acid (0.42 g, 2.0 mmol) using condition Method 42 followed by reverse phase HPLC purification afforded the title compound as a salt of $CF_3CO_2H$ (88 mg, 15% yield). $^1$H NMR (MeOD-d4, 300 MHz): 8.02 (s, 1H), 7.93-7.77 (m, 2H), 7.57 (s, 1H), 7.22 (s, 1H), 3.68 (s, 3H), 2.97 (s, 3H), 2.30 (s, 3H), 2.11 (s, 3H), 1.68 (s, 6H). ESI-MS calculated for $C_{27}H_{27}N_4O_4$ [M+H]$^+$= 471.20; Observed: 471.67.

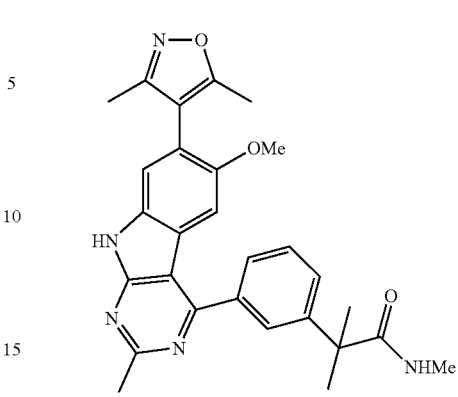

Cpd. No. 188

2-(3-(7-(3,5-Dimethylisoxazol-4-yl)-6-methoxy-2-methyl-9H-pyrimido[4,5-b]indol-4-yl)phenyl)-N,2-dimethylpropanamide 2-(3-(7-(3,5-Dimethylisoxazol-4-yl)-6-methoxy-2-methyl-9H-pyrimido[4,5-b]indol-4-yl)phenyl)-2-methylpropanoic acid (Cpd No. 187, 20 mg, 0.043 mmol), EDCI-HCl (60 mg, 0.3 mmol), and HOBt-H$_2$O (45 mg, 0.3 mmol) were added to a round-bottom flask. EtN(i-Pr)$_2$ (0.1 mL) was added followed by addition of DMF (3 mL). Methyl amine-HCl (14 mg, 0.2 mmol) was added and the reaction mixture was stirred for 16 h. The reaction mixture was purified by reverse phase HPLC affording the title compound as a salt of $CF_3CO_2H$ (17 mg, 67% yield). $^1$H NMR (MeOD-d4, 300 MHz): 7.97-7.88 (m, 2H), 7.88-7.76 (m, 2H), 7.55 (s, 1H), 7.27 (s, 1H), 3.70 (s, 3H), 2.97 (s, 3H), 2.73 (s, 3H), 2.31 (s, 3H), 2.13 (s, 3H), 1.67 (s, 6H). ESI-MS calculated for $C_{28}H_{30}N_5O_3$ [M+H]$^+$=484.23; Observed: 484.42.

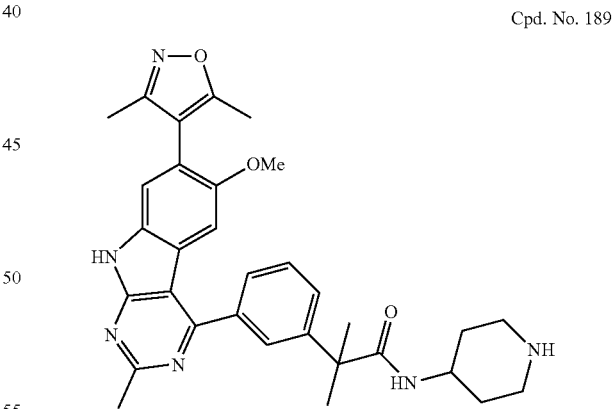

Cpd. No. 189

2-(3-(7-(3,5-Dimethylisoxazol-4-yl)-6-methoxy-2-methyl-9H-pyrimido[4,5-b]indol-4-yl)phenyl)-2-methyl-N-(piperidin-4-yl)propanamide 2-(3-(7-(3,5-Dimethylisoxazol-4-yl)-6-methoxy-2-methyl-9H-pyrimido[4,5-b]indol-4-yl)phenyl)-2-methylpropanoic acid (Cpd No. 187, 80 mg, 0.17 mmol), EDCI-HCl (191 mg, 1 mmol), and HOBt-H$_2$O (135 mg, 1 mmol) were added to a round-bottom flask. EtN(i-Pr)$_2$ (0.3 mL) was added followed by addition of DMF (5 mL). 4-Amino-1-

Boc-piperidine (80 mg, 0.4 mmol) was added and the reaction mixture was stirred for 16 h. The reaction was quenched with NaHCO$_3$ saturated and the aqueous layer was extracted with ethyl acetate. The combined organic layers were washed with 10% citric acid aqueous solution, brine, and concentrated on a rotary evaporator. The residue was dissolved in CH$_2$Cl$_2$ (4 mL) and CF$_3$CO$_2$H (4 mL) was added and the mixture was stirred for 1 h before purification on a reverse phase HPLC affording the title compound as a salt of CF$_3$CO$_2$H (47.6 mg, 42% yield). $^1$H NMR (MeOD-d4, 300 MHz): 7.98-7.90 (m, 2H), 7.84-7.76 (m, 2H), 7.56 (s, 1H), 7.28 (s, 1H), 4.10-3.90 (m, 1H), 3.70 (s, 3H), 3.40 (dt, J=12.64, 2.99 Hz, 2H), 3.04 (td, J=13.06, 2.82 Hz, 2H), 2.97 (s, 3H), 2.31 (s, 3H), 2.13 (s, 3H), 2.80-1.94 (m, 2H), 1.86-1.70 (m, 2H), 1.69 (s, 6H). ESI-MS calculated for C$_{32}$H$_{37}$N$_6$O$_3$ [M+H]$^+$=553.29; Observed: 553.58.

Cpd. No. 190

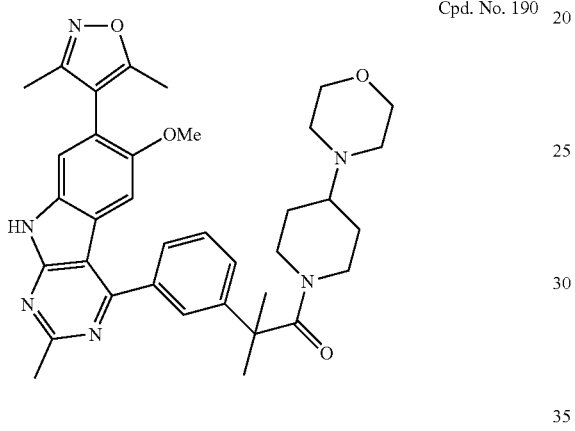

2-(3-(7-(3,5-Dimethylisoxazol-4-yl)-6-methoxy-2-methyl-9H-pyrimido[4,5-b]indol-4-yl)phenyl)-2-methyl-1-(4-morpholinopiperidin-1-yl)propan-1-one (Cpd. No. 190)

Example of general amide condensation method promoted by EDCI-HCl: Cpd No. 187 (40 mg, 0.1 mmol), HOBt (0.6 mmol) and EDCI-HCl (0.6 mmol) were placed in a round-bottom flask. To this flask, EtN(i-Pr)$_2$ (0.3 mL) and anhydrous DMF (3 mL) were added. 4-Morpholinopiperidine (50 mg, 0.3 mmol) was then added in one portion. The mixture was stirred at room temperature for 12 h before quenching with water. The mixture was purified on reverse phase HPLC to yield Cpd, No. 190 as a CF$_3$CO$_2$H salt in 11 mg (15%). $^1$H NMR (300 MHz, MeOD-d4): 8.04-7.96 (m, 1H), 7.90-7.82 (m, 2H), 7.74-7.66 (m, 1H), 7.57 (s, 1H), 7.23 (s, 1H), 4.00-3.85 (m, 2H), 3.80-3.60 (m, 2H), 3.68 (s, 3H), 3.40-3.20 (m, 2H), 3.10-2.90 (m, 2H), 2.97 (s, 3H), 2.75-2.60 (m, 2H), 2.32 (s, 3H), 2.14 (s, 3H), 2.10-1.80 (m, 2H), 1.67 (s, 6H), 1.50-1.20 (m, 2H). ESI-MS calculated for C$_{36}$H$_{43}$N$_6$O$_4$ [M+H]$^+$=623.33; observed: 623.58.

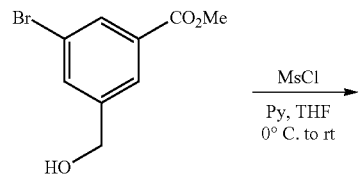

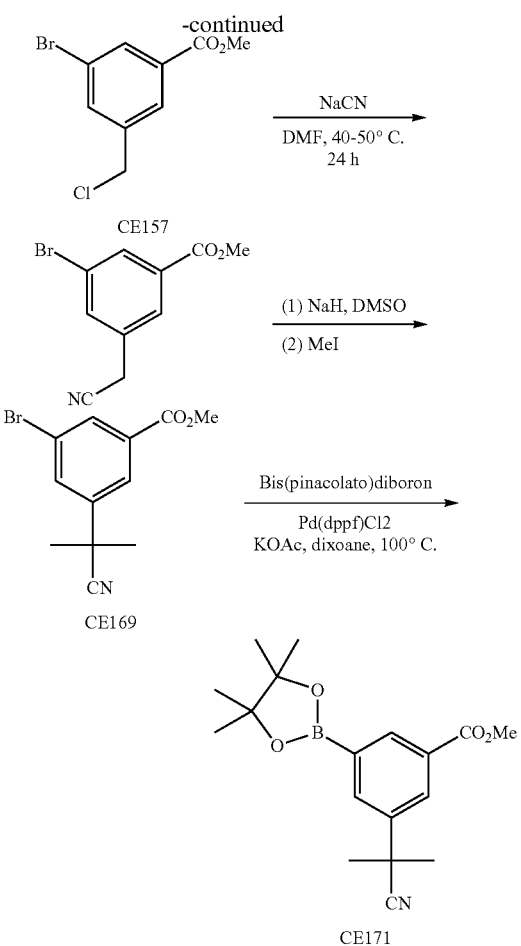

Methyl 3-bromo-5-(chloromethyl)benzoate (CE157)

Methyl 3-bromo-5-(hydroxymethyl)benzoate (2.45 g, prepared according to literature method, JACS, 2012, v134, 1673-1679), pyridine (3 mL) and anhydrous THF (50 mL) were mixed in a round-bottom flask, which was cooled with an ice-water bath. MeSO$_2$—Cl (1.55 mL) was added via a syringe and the reaction was warmed up to ambient temperature for 6 h. The mixture was quenched with water and the aqueous layer was extracted with ethyl acetate. The organic layers were combined, dried and the volatile components were removed on a rotary evaporator. The residue was purified by flash column chromatography to yield CD157 in 1.2 g (62% yield). $^1$H NMR (300 MHz, CDCl$_3$): 8.12 (t, J=1.62 Hz, 1H), 7.98 (t, J=1.48 Hz, 1H), 7.73 (t, J=1.75 Hz, 1H), 4.57 (s, 2H), 3.93 (s, 3H). Methyl 3-bromo-5-(cyanomethyl)benzoate (CE163)

CE157 (1.2 g) was dissolved in DMF (30 mL). NaCN (450 mg) was added and the reaction mixture was heated at 45° C. for 12 h. The mixture was quenched with water and the aqueous layer was extracted with ethyl acetate. The organic layers were combined, dried and the volatile components were removed on a rotary evaporator. The residue was purified by flash column chromatography to yield CE163 in 0.76 g (49% yield). $^1$H NMR (300 MHz, CDCl$_3$): 8.12 (s, 1H), 7.93 (s, 1H), 7.70 (s, 1H), 3.94 (s, 3H), 3.82 (s, 2H). ESI-MS calculated for C$_{10}$H$_9$$^{79}$BrNO$_2$ [M+H]$^+$=253.98; observed: 256.25.

Methyl 3-bromo-5-(2-cyanopropan-2-yl)benzoate (CE169)

CE163 (1.5 g) was dissolved in anhydrous DMSO (10 mL) and was cooled with an ice-water bath. NaH (960 mg, 60% in mineral oil) was added in small portions and the mixture was stirred for additional 20 min. MeI (1.94 mL) was added via a syringe and the mixture was warmed up to room temperature and stirred overnight. The mixture was quenched with water and the aqueous layer was extracted with ethyl acetate. The organic layers were combined, dried and the volatile components were removed on a rotary evaporator. The residue was purified by flash column chromatography to yield CE169 in 1.47 g (87% yield). $^1$H NMR (300 MHz, CDCl$_3$): 8.13 (dd, J=1.81, 1.40 Hz, 1H), 8.05 (s, J=1.82, 1.45 Hz, 1H), 7.82 (t, J=1.87 Hz, 1H), 3.964 (s, 3H), 1.75 (s, 6H). $^{13}$C NMR (75 MHz, CDCl$_3$): 165.40, 144.16, 133.01, 132.85, 132.36, 125.10, 123.64, 123.30, 52.86, 37.17, 29.16.

Methyl 3-(2-cyanopropan-2-yl)-5-(4,4,5,5-tetramethyl-1,3,2-dioxaborolan-2-yl)benzoate (CE171)

CE169 (1.47 g, 5.2 mmol), bis(pinacolato)diboron (2.54 g, 10 mmol), and potassium acetate (1.5 g, 15 mmol) were added to a round-bottom flask. Anhydrous 1,4-dixoane (20 mL) was added and the flask was degassed and refilled with nitrogen. Pd(dppf)Cl$_2$ (183 mg, 0.26 mmol) was added and the system was degassed again followed by heating at 100° C. for 16 h. The reaction mixture was cooled to ambient temperature and diluted by CH$_2$Cl$_2$. The solution was filtered through a pad of celite and the volatile components were removed on a rotary evaporator. The residue was purified by flash column chromatography to yield the title compound in 1.9 g (with impurity, >95% yield). $^1$H NMR (300 MHz, CDCl$_3$): 8.32 (s, 1H), 8.14 (s, 1H), 8.01 (s, 1H), 3.84 (s, 3H), 1.69 (s, 6H), 1.27 (s, 12H). $^{13}$C NMR (75 MHz, CDCl$_3$): 170.96, 166.51, 141.30, 135.65, 135.33, 130.32, 128.80, 124.08, 83.42, 52.19, 37.04, 29.05, 24.85. ESI-MS calculated for C$_{18}$H$_{24}$BNNaO$_4$ [M+H]$^+$=352.17; observed: 352.42.

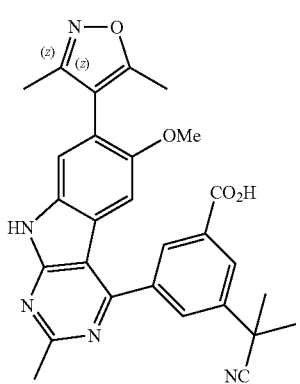

Cpd. No. 191

3-(2-Cyanopropan-2-yl)-5-(7-(3,5-dimethylisoxazol-4-yl)-6-methoxy-2-methyl-9H-pyrimido[4,5-b]indol-4-yl)benzoic acid (Cpd. No. 191)

To a round-bottom flask, 4-(4-chloro-6-methoxy-2-methyl-9H-pyrimido[4,5-b]indol-7-yl)-3,5-dimethylisoxazole (S13, 890 mg, 2.6 mmol) and CE171 (1.9 g, 5.2 mmol), 1,2-dimethoxyethane (20 mL), and Na$_2$CO$_3$ (2 M, 9 mL) were added. The system was degassed to remove oxygen and nitrogen was refilled. Pd(dppf)Cl$_2$—CH$_2$Cl$_2$ (106 mg, 0.13 mmol) was added and the system was degassed and refilled with nitrogen. The reaction mixture was heated at reflux for 16 h. The reaction was quenched with water and acidified to pH=2 followed by extraction with ethyl acetate. The organic layers were combined and the volatile components were removed on a rotary evaporator. The residue was dissolved in THF (10 mL) and water (10 mL). LiOH—H$_2$O (420 mg, 10 mmol) was added and the solution was stirred at ambient temperature for 24 h. The reaction mixture was extracted with diethyl ether followed by acidification to pH=2 and subsequent extraction with ethyl acetate. The organic layers were combined and the volatile components were removed on a rotary evaporator. The residue was purified by reverse phase HPLC to yield the title compound in 328 mg (25% yield over two steps). $^1$H NMR (300 MHz, MeOD-d4): 8.72 (t, J=1.57 Hz, 1H), 8.59 (t, J=1.52 Hz, 1H), 8.42 (t, J=1.53 Hz, 1H), 7.57 (s, 1H), 7.32 (s, 1H), 3.71 (s, 3H), 2.98 (s, 3H), 2.30 (s, 3H), 2.11 (s, 3H), 1.89 (s, 6H). ESI-MS calculated for C$_{28}$H$_{26}$N$_5$O$_4$ [M+H]$^+$= 496.20; observed: 496.25.

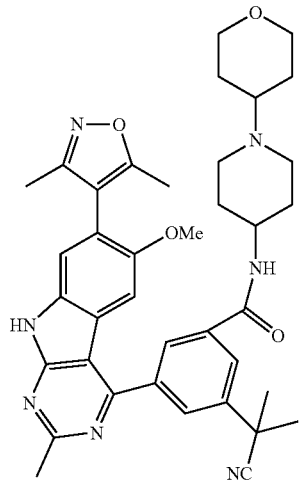

Cpd. No. 192

3-(2-Cyanopropan-2-yl)-5-(7-(3,5-dimethylisoxazol-4-yl)-6-methoxy-2-methyl-9H-pyrimido[4,5-b]indol-4-yl)-N-(1-(tetrahydro-2H-pyran-4-yl)piperidin-4-yl)benzamide (Cpd. No. 192)

Example of general amide condensation method promoted by EDCI-HCl: Cpd. No. 191 (30 mg), HOBt (84 mg, 0.6 mmol), and EDCI-HCl (120 mg, 0.6 mmol) were placed in a round-bottom flask. To this flask, EtN(i-Pr)$_2$ (0.3 mL) and anhydrous DMF (3 mL) were added. 1-(Tetrahydro-2H-pyran-4-yl)-4-piperidinamine dihydrochloride (60 mg, 0.3 mmol) was then added in one portion. The mixture was stirred at room temperature for 12 h before quenching with water. The mixture was purified on reverse phase HPLC to yield Cpd. No. 192 as a CF$_3$CO$_2$H salt in 33 mg (71% yield). $^1$H NMR (300 MHz, MeOD-d4): 8.57 (t, J=1.52 Hz, 1H), 8.43 (t, J=1.67 Hz, 1H), 8.36 (t, J=1.65 Hz, 1H), 7.57 (s, 1H), 7.27 (s, 1H), 4.30-4.15 (m, 1H), 4.15-4.00 (m, 2H), 3.78-3.66 (m, 2H), 3.70 (s, 3H), 3.54-3.36 (m, 3H), 3.26-3.12 (m, 2H), 2.98 (s, 3H), 2.40-2.28 (m, 2H), 2.31 (s, 3H), 2.13 (s, 3H), 2.10-1.90 (m, 4H), 1.90 (s, 6H), 1.90-1.70 (m, 2H). ESI-MS calculated for $C_{38}H_{44}N_7O_4$ $[M+H]^+$=662.35; observed: 662.58.

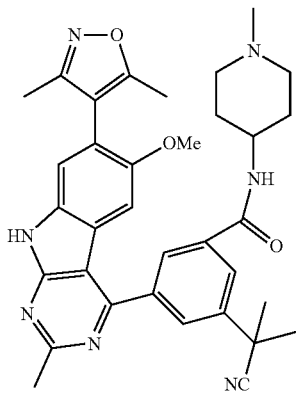

Cpd. No. 193

3-(2-Cyanopropan-2-yl)-5-(7-(3,5-dimethylisoxazol-4-yl)-6-methoxy-2-methyl-9H-pyrimido[4,5-b]indol-4-yl)-N-(1-methylpiperidin-4-yl)benzamide (Cpd. No. 193)

Example of general amide condensation method promoted by EDCI-HCl: Cpd. No. 191 (30 mg, 0.05 mmol), HOBt (60 mg, 0.4 mmol), and EDCI-HCl (80 mg, 0.4 mmol) were placed in a round-bottom flask. To this flask, EtN(i-Pr)$_2$ (0.2 mL) and anhydrous DMF (3 mL) were added. N-methylpiperidin-4-amine (23 mg, 0.2 mmol) was then added in one portion. The mixture was stirred at room temperature for 12 h before quenching with water. The mixture was purified on reverse phase HPLC to yield Cpd. No. 193 as a CF$_3$CO$_2$H salt in 40 mg (95% yield). $^1$H NMR (300 MHz, MeOD-d4): 8.57 (s, 1H), 8.43 (s, 1H), 8.37 (s, 1H), 7.57 (s, 1H), 7.27 (s, 1H), 4.30-4.16 (m, 1H), 3.70 (s, 3H), 3.68-3.56 (m, 2H), 3.26-3.10 (m, 2H), 2.98 (s, 3H), 2.90 (s, 3H), 2.34-2.20 (m, 2H), 2.31 (s, 3H), 2.12 (s, 3H), 2.08-1.92 (m, 2H), 1.90 (s, 6H). ESI-MS calculated for $C_{34}H_{38}N_7O_3$ $[M+H]^+$=592.30; observed: 592.58.

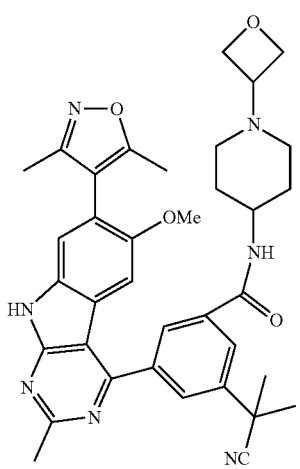

Cpd. No. 194

3-(2-Cyanopropan-2-yl)-5-(7-(3,5-dimethylisoxazol-4-yl)-6-methoxy-2-methyl-9H-pyrimido[4,5-b]indol-4-yl)-N-(1-(oxetan-3-yl)piperidin-4-yl)benzamide (Cpd. No. 194)

Example of general amide condensation method promoted by EDCI-HCl: Cpd. No. 191 (40 mg, 0.09 mmol), HOBt (70 mg, 0.5 mmol), and EDCI-HCl (100 mg, 0.5 mmol) were placed in a round-bottom flask. To this flask, EtN(i-Pr)$_2$ (0.3 mL) and anhydrous DMF (3 mL) were added. 1-oxetan-3-ylpiperidin-4-amine (70 mg, 0.3 mmol) was then added in one portion. The mixture was stirred at room temperature for 12 h before quenching with water. The mixture was purified on reverse phase HPLC to yield Cpd. No. 194 as a CF$_3$CO$_2$H salt in 37 mg (61% yield). $^1$H NMR (300 MHz, MeOD-d4): 8.57 (s, 1H), 8.44 (s, 1H), 8.36 (s, 1H), 7.57 (s, 1H), 7.26 (s, 1H), 4.90-4.80 (m, 4H), 4.50-4.36 (m, 1H), 4.34-4.20 (m, 1H), 3.70 (s, 3H), 3.66-3.46 (m, 2H), 3.18-2.96 (m, 2H), 2.98 (s, 3H), 2.38-2.22 (m, 2H), 2.31 (s, 3H), 2.16-1.96 (m, 2H), 2.12 (s, 3H), 1.90 (s, 6H). ESI-MS calculated for $C_{36}H_{40}N_7O_4$ $[M+H]^+$=634.31; observed: 634.50.

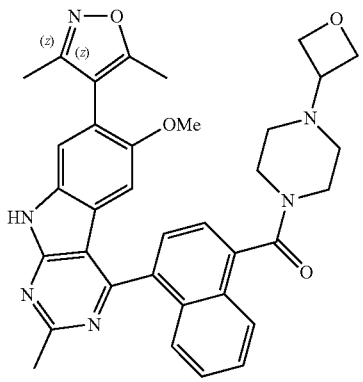

Cpd. No. 195

(4-(7-(3,5-Dimethylisoxazol-4-yl)-6-methoxy-2-methyl-9H-pyrimido[4,5-b]indol-4-yl)naphthalen-1-yl)(4-(oxetan-3-yl)piperazin-1-yl)methanone (Cpd. No. 195)

Cpd. No. 195 was prepared from Cpd. No. 165 (40 mg) and 1-oxetan-3-yl-piperazine (45 mg) using general amide condensation method promoted by EDCI-HCl. The reaction mixture was purified by reverse phase HPLC to yield Cpd. No. 195 as a CF$_3$CO$_2$H salt in 23 mg (38% yield). $^1$H NMR (300 MHz, MeOD-d4): 8.20-8.00 (m, 2H), 8.00-7.75 (m, 3H), 7.75-7.50 (m, 1H), 7.54 (s, 1H), 6.30-6.10 (m, 1H), 5.00-4.80 (m, 4H), 4.60-4.20 (m, 3H), 3.80-3.60 (m, 2H), 3.60-3.40 (m, 2H), 3.30-3.10 (m, 1H), 3.18 (s, 3H), 3.03 (s, 3H), 2.26 (s, 3H), 2.06 (s, 3H). ESI-MS calculated for $C_{35}H_{35}N_6O_4$ $[M+H]^+$=603.27; observed: 603.67.

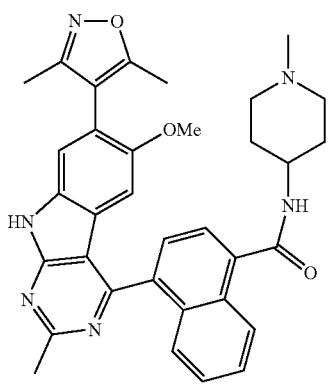

4-(7-(3,5-Dimethylisoxazol-4-yl)-6-methoxy-2-methyl-9H-pyrimido[4,5-b]indol-4-yl)-N-(1-methyl-piperidin-4-yl)-1-naphthamide (Cpd. No. 196)

Cpd. No. 196 was prepared from Cpd. No. 165 (48 mg) and N-methylpiperidin-4-amine (35 mg) using general amide condensation method promoted by EDCI-HCl. The reaction mixture was purified by reverse phase HPLC to yield Cpd. No. 196 as a CF$_3$CO$_2$H salt in 63 mg (91% yield). $^1$H NMR (300 MHz, MeOD-d4): 8.44 (d, J=8.48 Hz, 1H), 8.05 (d, J=7.12 Hz, 1H), 7.95 (d, J=7.33 Hz, 1H), 7.85-7.73 (m, 2H), 7.66-7.58 (m, 1H), 7.54 (s, 1H), 6.15 (s, 1H), 4.46-4.26 (m, 1H), 3.74-3.60 (m, 2H), 3.34-3.16 (m, 2H), 3.17 (s, 3H), 3.02 (s, 3H), 2.93 (s, 3H), 2.50-2.36 (m, 2H), 2.25 (s, 3H), 2.10-1.90 (m, 2H), 2.06 (s, 3H). ESI-MS calculated for C$_{34}$H$_{35}$N$_6$O$_3$ [M+H]$^+$=575.28; observed: 575.67.

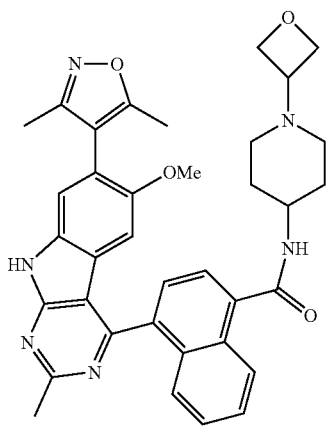

4-(7-(3,5-Dimethylisoxazol-4-yl)-6-methoxy-2-methyl-9H-pyrimido[4,5-b]indol-4-yl)-N-(1-(oxetan-3-yl)piperidin-4-yl)-1-naphthamide (Cpd. No. 197)

Cpd. No. 197 was prepared from Cpd. No. 165 (48 mg) and 1-oxetan-3-ylpiperidin-4-amine-2HCl (66 mg) using general amide condensation method promoted by EDCI-HCl. The reaction mixture was purified by reverse phase HPLC to yield Cpd. No. 197 as a CF$_3$CO$_2$H salt in 40 mg (54% yield). $^1$H NMR (300 MHz, MeOD-d4): 8.44 (d, J=8.48 Hz, 1H), 8.05 (d, J=7.33 Hz, 1H), 7.97 (d, J=7.31 Hz, 1H), 7.84-7.72 (m, 2H), 7.66-7.56 (m, 1H), 7.55 (s, 1H), 6.15 (s, 1H), 4.94-4.84 (m, 4H), 4.56-4.32 (m, 2H), 3.70-3.50 (m, 2H), 3.26-3.10 (m, 2H), 3.17 (s, 3H), 3.02 (s, 3H), 2.50-2.36 (m, 2H), 2.25 (s, 3H), 2.20-2.00 (m, 2H), 2.06 (s, 3H). ESI-MS calculated for C$_{36}$H$_{37}$N$_6$O$_4$ [M+H]$^+$=617.29; observed: 617.92.

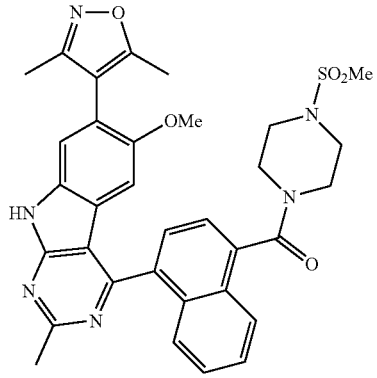

(4-(7-(3,5-Dimethylisoxazol-4-yl)-6-methoxy-2-methyl-9H-pyrimido[4,5-b]indol-4-yl)naphthalen-1-yl)(4-(methylsulfonyl)piperazin-1-yl)methanone (Cpd. No. 198)

Cpd No. 198 was prepared from Cpd. No. 165 (48 mg) and 1-methanesulfonyl-piperazine hydrochloride (48 mg) using general amide condensation method promoted by EDCI-HCl. The reaction mixture was purified by reverse phase HPLC to yield Cpd. No. 198 as a CF$_3$CO$_2$H salt in 54 mg (73% yield). $^1$H NMR (300 MHz, MeOD-d4): 8.18-8.04 (m, 2H), 7.94-7.76 (m, 3H), 7.72-7.60 (m, 1H), 7.56-7.52 (m, 1H), 6.24-6.20 (m, 1H), 4.20-4.00 (m, 2H), 3.60-3.38 (m, 4H), 3.30-3.10 (m, 2H), 3.20 (s, 3H), 3.02 (s, 3H), 2.91 (s, 3H), 2.26 (s, 3H), 2.07 (s, 3H). ESI-MS calculated for C$_{33}$H$_{33}$N$_6$O$_5$S [M+H]$^+$=625.22; observed: 625.80.

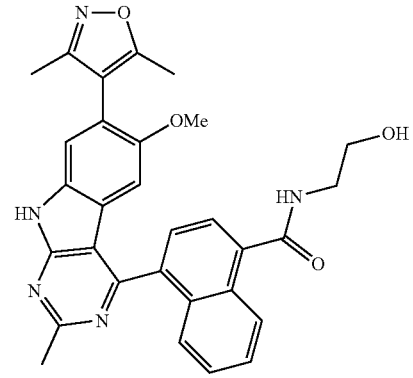

4-(7-(3,5-Dimethylisoxazol-4-yl)-6-methoxy-2-methyl-9H-pyrimido[4,5-b]indol-4-yl)-N-(2-hydroxyethyl)-1-naphthamide (Cpd No. 199)

Cpd. No. 199 was prepared from Cpd. No. 165 (47 mg) and 2-aminoethanol (20 mg) using general amide condensation method promoted by EDCI-HCl. The reaction mixture was purified by reverse phase HPLC to yield Cpd. No. 199 as a CF$_3$CO$_2$H salt in 22 mg (35% yield). $^1$H NMR (300 MHz, MeOD-d4): 8.49 (d, J=8.46 Hz, 1H), 8.04 (d, J=7.29 Hz, 1H), 7.98 (d, J=7.32 Hz, 1H), 7.84-7.74 (m, 2H), 7.67-7.58 (m, 1H), 7.54 (s, 1H), 6.18 (s, 1H), 3.90-3.84 (m, 2H), 3.73-3.63 (m, 2H), 3.19 (s, 3H), 3.02 (s, 3H), 2.26 (s, 3H), 2.06 (s, 3H). ESI-MS calculated for C$_{30}$H$_{28}$N$_5$O$_4$ [M+H]$^+$=522.21; observed: 522.50.

Cpd. No. 200

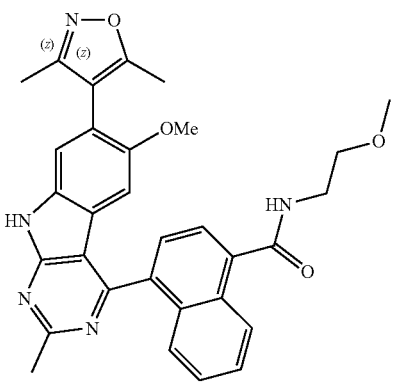

4-(7-(3,5-Dimethylisoxazol-4-yl)-6-methoxy-2-methyl-9H-pyrimido[4,5-b]indol-4-yl)-N-(2-methoxyethyl)-1-naphthamide (Cpd. No. 200)

Cpd. No. 200 was prepared from Cpd. No. 165 (40 mg) and 2-methoxyethylamine (24 mg) using general amide condensation method promoted by EDCI-HCl. The reaction mixture was purified by reverse phase HPLC to yield Cpd. No. 200 as a CF$_3$CO$_2$H salt in 32 mg (58% yield). $^1$H NMR (300 MHz, MeOD-d4): 8.47 (d, J=8.52 Hz, 1H), 8.05 (d, J=8.52 Hz, 1H), 7.94 (d, J=7.33 Hz, 1H), 7.84-7.72 (m, 2H), 7.68-7.58 (m, 1H), 7.54 (s, 1H), 6.17 (s, 1H), 3.78-3.65 (m, 4H), 3.46 (s, 3H), 3.19 (s, 3H), 3.02 (s, 3H), 2.25 (s, 3H), 2.06 (s, 3H). ESI-MS calculated for C$_{31}$H$_{30}$N$_5$O$_4$ [M+H]$^+$=536.23; observed: 536.25.

Cpd. No. 201

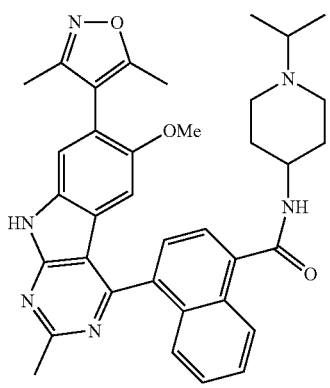

4-(7-(3,5-Dimethylisoxazol-4-yl)-6-methoxy-2-methyl-9H-pyrimido[4,5-b]indol-4-yl)-N-(1-isopropylpiperidin-4-yl)-1-naphthamide (Cpd. No. 201)

Cpd. No. 201 was prepared from Cpd. No. 165 (40 mg) and N-isopropylpiperidin-4-amine (42 mg) using general amide condensation method promoted by EDCI-HCl. The reaction mixture was purified by reverse phase HPLC to yield Cpd. No. 201 as a CF$_3$CO$_2$H salt in 22 mg (30% yield). $^1$H NMR (300 MHz, MeOD-d4): 9.18 (d, J=7.22 Hz, NH, 1H), 8.44 (d, J=8.54 Hz, 1H), 8.04 (d, J=7.30 Hz, 1H), 7.95 (d, J=7.30 Hz, 1H), 7.85-7.73 (m, 2H), 7.68-7.58 (m, 1H), 7.54 (s, 1H), 6.15 (s, 1H), 4.46-4.28 (m, 1H), 3.70-3.52 (m, 3H), 3.50-3.20 (m, 2H), 3.17 (s, 3H), 3.02 (s, 3H), 2.56-2.30 (m, 2H), 2.26 (s, 3H), 2.14-1.96 (m, 2H), 2.06 (s, 3H). ESI-MS calculated for C$_{36}$H$_{39}$N$_6$O$_3$ [M+H]$^+$=603.31; observed: 603.75.

Cpd. No. 202

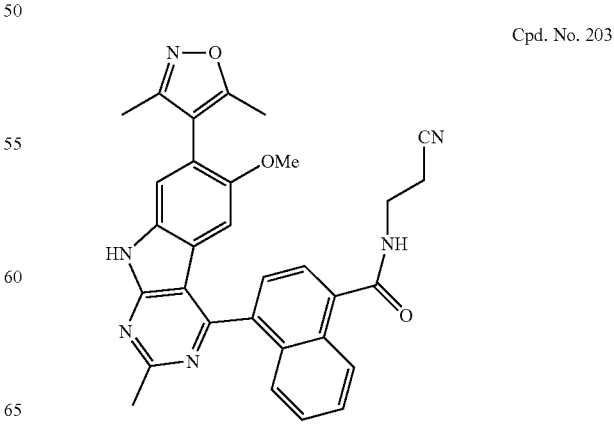

4-(7-(3,5-Dimethylisoxazol-4-yl)-6-methoxy-2-methyl-9H-pyrimido[4,5-b]indol-4-yl)-N-(2-(2-methoxyethoxy)ethyl)-1-naphthamide (Cpd. No. 202)

Cpd. No. 202 was prepared from Cpd. No. 165 (40 mg) and 2-(2-methoxyethoxy) ethanamine (40 mg) using general amide condensation method promoted by EDCI-HCl. The reaction mixture was purified by reverse phase HPLC to yield Cpd. No. 202 as a CF$_3$CO$_2$H salt in 27 mg (47% yield). $^1$H NMR (300 MHz, MeOD-d4): 8.48 (d, J=8.50 Hz, 1H), 8.05 (d, J=7.33 Hz, 1H), 7.96 (d, J=7.33 Hz, 1H), 7.84-7.73 (m, 2H), 7.66-7.58 (m, 1H), 7.54 (s, 1H), 6.17 (s, 1H), 3.82-3.68 (m, 6H), 3.64-3.56 (m, 2H), 3.36 (s, 3H), 3.19 (s, 3H), 3.02 (s, 3H), 2.26 (s, 3H), 2.06 (s, 3H). ESI-MS calculated for C$_{33}$H$_{34}$N$_5$O$_5$ [M+H]$^+$=580.26; observed: 580.58.

Cpd. No. 203

N-(2-Cyanoethyl)-4-(7-(3,5-dimethylisoxazol-4-yl)-6-methoxy-2-methyl-9H-pyrimido[4,5-b]indol-4-yl)-1-naphthamide (Cpd. No. 203)

Cpd. No. 203 was prepared from Cpd. No. 165 (40 mg) and aminoacetonitrile (21 mg) using general amide condensation method promoted by EDCI-HCl. The reaction mixture was purified by reverse phase HPLC to yield Cpd. No. 203 as a $CF_3CO_2H$ salt in 14 mg (25% yield). ESI-MS calculated for $C_{31}H_{27}N_6O_3$ $[M+H]^+=531.21$; observed: 531.42.

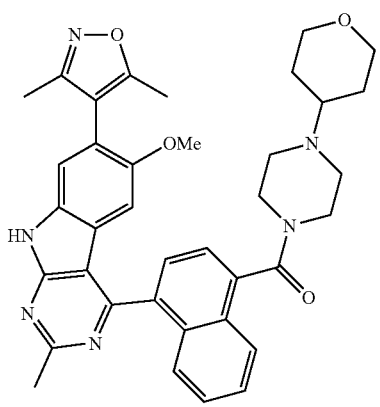

Cpd. No. 204

(4-(7-(3,5-Dimethylisoxazol-4-yl)-6-methoxy-2-methyl-9H-pyrimido[4,5-b]indol-4-yl)naphthalen-1-yl)(4-(tetrahydro-2H-pyran-4-yl)piperazin-1-yl)methanone (Cpd. No. 204)

Cpd. No. 204 was prepared from Cpd. No. 165 (40 mg) and 1-(tetrahydro-2H-pyran-4-yl)piperazine (72 mg) using general amide condensation method promoted by EDCI-HCl. The reaction mixture was purified by reverse phase HPLC to yield Cpd. No. 204 as a $CF_3CO_2H$ salt in 50 mg (79% yield). $^1$H NMR (300 MHz, MeOD-d4): 8.20-8.06 (m, 2H), 8.00-7.90 (m, 1H), 7.90-7.76 (m, 2H), 7.72-7.60 (m, 1H), 7.54 (s, 1H), 6.28-6.14 (m, 1H), 4.18-4.02 (m, 2H), 3.80-3.30 (m, 9H), 3.30 (s, 3H), 3.19 (s, 3H), 3.02 (s, 3H), 2.26 (s, 3H), 2.16-2.00 (m, 2H), 2.06 (s, 3H), 1.90-1.70 (m, 2H), 1.44-1.30 (m, 2H). ESI-MS calculated for $C_{37}H_{39}N_6O_4$ $[M+H]^+=631.30$; observed: 631.37.

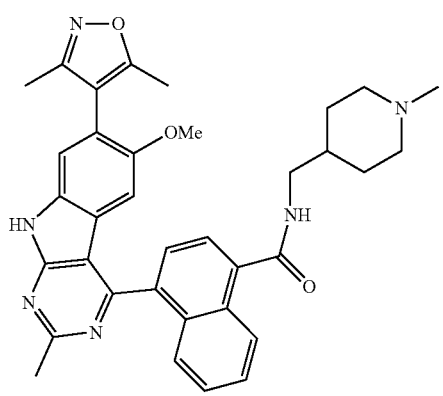

Cpd. No. 205

4-(7-(3,5-Dimethylisoxazol-4-yl)-6-methoxy-2-methyl-9H-pyrimido[4,5-b]indol-4-yl)-N-((1-methylpiperidin-4-yl)methyl)-1-naphthamide (Cpd. No. 205)

Cpd. No. 205 was prepared from Cpd. No. 165 (40 mg) and (1-methylpiperidin-4-yl)methanamine (39 mg) using general amide condensation method promoted by EDCI-HCl. The reaction mixture was purified by reverse phase HPLC to yield Cpd. No. 205 as a $CF_3CO_2H$ salt in 33 mg (56% yield). $^1$H NMR (300 MHz, MeOD-d4): 8.44 (d, J=8.50 Hz, 1H), 8.05 (d, J=7.32 Hz, 1H), 7.98 (d, J=7.33 Hz, 1H), 7.85-7.73 (m, 2H), 7.67-7.58 (m, 1H), 7.54 (s, 1H), 6.15 (s, 1H), 3.68-3.48 (m, 4H), 3.18 (s, 3H), 3.14-3.00 (m, 2H), 3.02 (s, 3H), 2.90 (s, 3H), 2.25 (s, 3H), 2.20-2.20 (m, 3H), 2.06 (s, 3H), 1.76-1.60 (m, 2H). ESI-MS calculated for $C_{35}H_{37}N_6O_3$ $[M+H]^+=589.29$; observed: 589.67.

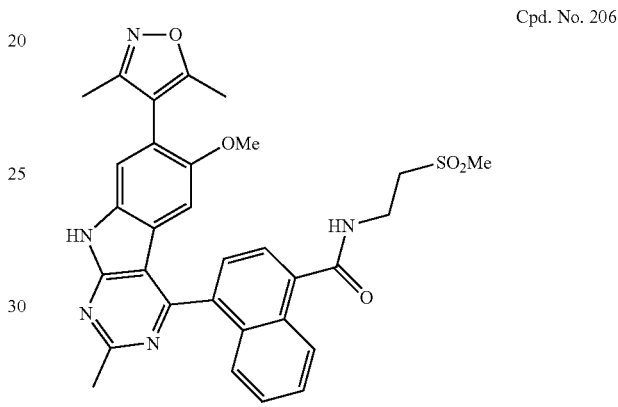

Cpd. No. 206

4-(7-(3,5-Dimethylisoxazol-4-yl)-6-methoxy-2-methyl-9H-pyrimido[4,5-b]indol-4-yl)-N-(2-(methylsulfonyl)ethyl)-1-naphthamide (Cpd. No. 206)

Cpd. No. 206 was prepared from Cpd. No. 165 (40 mg) and 2-aminoethylmethyl sulfone (48 mg) using general amide condensation method promoted by EDCI-HCl. The reaction mixture was purified by reverse phase HPLC to yield Cpd. No. 206 as a $CF_3CO_2H$ salt in 25 mg (42% yield). $^1$H NMR (300 MHz, MeOD-d4): 8.53 (d, J=8.49 Hz, 1H), 8.04 (d, J=7.35 Hz, 1H), 8.01 (d, J=7.35 Hz, 1H), 7.86-7.76 (m, 2H), 7.67-7.58 (m, 1H), 7.53 (s, 1H), 6.14 (s, 1H), 4.10-4.00 (m, 2H), 3.64-3.56 (m, 2H), 3.18 (s, 3H), 3.12, 3.01 (s, 3H), 2.26 (s, 3H), 2.06 (s, 3H). ESI-MS calculated for $C_{31}H_{30}N_5O_5S$ $[M+H]^+=584.20$; observed: 584.50.

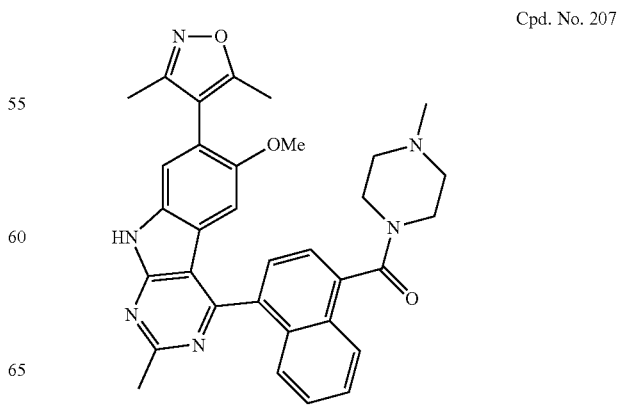

Cpd. No. 207

(4-(7-(3,5-Dimethylisoxazol-4-yl)-6-methoxy-2-methyl-9H-pyrimido[4,5-b]indol-4-yl)naphthalen-1-yl)(4-methylpiperazin-1-yl)methanone (Cpd. No. 207)

Cpd. No. 207 was prepared from Cpd. No. 165 (40 mg) and 1-methylpiperazine (30 mg) using general amide condensation method promoted by EDCI-HCl. The reaction mixture was purified by reverse phase HPLC to yield Cpd. No. 207 as a $CF_3CO_2H$ salt in 50 mg (86% yield). $^1H$ NMR (300 MHz, MeOD-d4): 8.30-8.05 (m, 2H), 8.00-7.80 (m, 3H), 7.70-7.60 (m, 1H), 7.54 (s, 1H), 6.26-6.14 (m, 1H), 3.80-3.50 (m, 4H), 3.50-3.00 (m, 4H), 3.19 (s, 3H), 3.03 (s, 3H), 2.99 (s, 3H), 2.26 (s, 3H), 2.07 (s, 3H). ESI-MS calculated for $C_{33}H_{33}N_6O_3$ $[M+H]^+=561.26$; observed: 561.50.

Cpd. No. 208

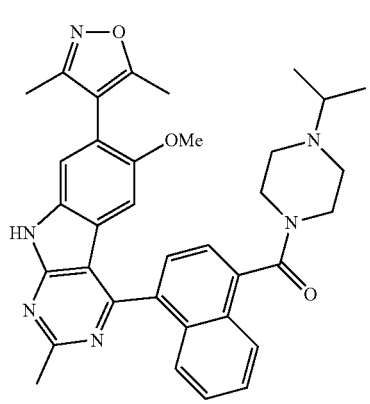

(4-(7-(3,5-Dimethylisoxazol-4-yl)-6-methoxy-2-methyl-9H-pyrimido[4,5-b]indol-4-yl)naphthalen-1-yl)(4-isopropylpiperazin-1-yl)methanone (Cpd. No. 208)

Cpd. No. 208 was prepared from Cpd. No. 165 (40 mg) and 1-isopropylpiperazine (40 mg) using general amide condensation method promoted by EDCI-HCl. The reaction mixture was purified by reverse phase HPLC to yield Cpd. No. 208 as a $CF_3CO_2H$ salt in 43 mg (73% yield). $^1H$ NMR (300 MHz, MeOD-d4): 8.30-8.00 (m, 2H), 8.00-7.75 (m, 3H), 7.75-7.60 (m, 1H), 7.60-7.50 (m, 1H), 6.20-6.10 (m, 1H), 3.80-3.00 (m, 9H), 3.19 (s, 3H), 3.02 (s, 3H), 2.26 (s, 3H), 2.07 (s, 3H), 1.42 (d, J=6.60 Hz, 6H). ESI-MS calculated for $C_{35}H_{37}N_6O_3$ $[M+H]^+=589.29$; Observed: 589.50.

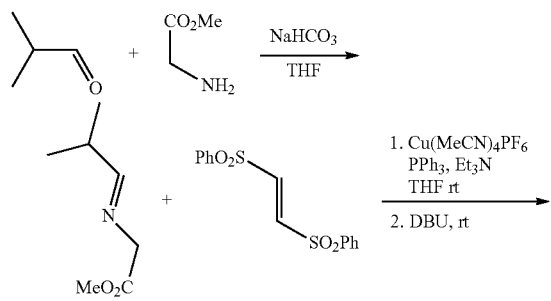

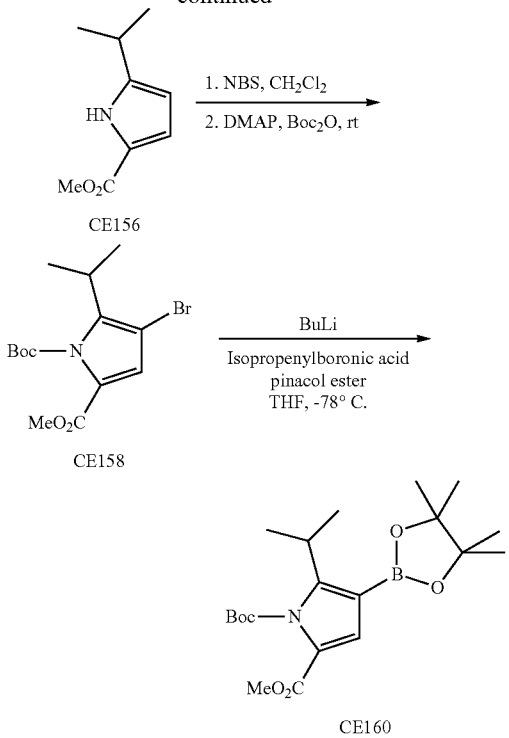

Methyl 5-isopropyl-1H-pyrrole-2-carboxylate (CE156)

Step 1: Isobutyl aldehyde (2.2 g, 30 mmol), L-glycine methyl ester (3.45 g, 30 mmol) and $NaHCO_3$ (3.36 g, 40 mmol) were mixture in a round-bottom flask followed by addition of anhydrous THF (100 mL). The reaction mixture was stirred at room temperature for overnight. The solid was filter off and the solution was concentrated on a rotary evaporator. The major of remaining residue (3.65 g) was imine and was used without further purification.

Step 2: $Ph_3P$ (340 mg, 1.3 mmol) and $Cu(MeCN)_4PF_6$ (483 mg, 1.3 mmol) were added to a dry round-bottom flask. Anhydrous THF (100 mL) was added followed by addition of $Et_3N$ (2.1 mL, 11.7 mmol). The imine obtained from step 1 (3.65 g, 25.5 mmol) was added as a THF solution and trans-1,2-Bis(phenylsulfonyl)ethylene (8.0 g, 26 mmol) was added in small portions. The system was degassed and refilled with nitrogen. The reaction mixture was stirred at room temperature overnight. DBU (7.8 mL, 52 mmol) was then added via s syringe and the mixture was stirred at room temperature for 4 h. The mixture was diluted with ethyl acetate and wash with 1N HCl to remove DBU. The organic layer was dried, concentrated on a rotary evaporator. The remaining residue was purified by flash column chromatography to yield CE156 in 1.52 g (35% yield). The method was previously reported by Angew. Chem. Int. Ed. 2007, 46, 9261-9264 and Chem. Eur. J. 2010, 16, 9864-9873. $^1H$ NMR (300 MHz, $CDCl_3$): 10.43 (s, 1H), 6.91 (s, 1H), 6.03 (s, 1H), 3.89 (s, 3H), 3.14-2.96 (m, 1H), 1.35 (d, J=6.87 Hz, 6H). $^{13}C$ NMR (75 MHz, $CDCl_3$): 162.47, 145.82, 120.67, 116.07, 105.81, 51.24, 27.46, 22.38. ESI-MS calculated for $C_9H_{14}NO_2$ $[M+H]^+=168.10$; observed: 168.33.

Methyl 4-bromo-5-isopropyl-1H-pyrrole-2-carboxylate

CE156 (1.52 g, 9.1 mmol) was dissolved in CH$_2$Cl$_2$ (20 mL) and cooled with an ice-water bath. NBS (1.62 g, 9.1 mmol) was added in small portions and the mixture was stirred at room temperature for 1 h. The volatile components were removed on a rotary evaporator and the residue was used without further purification. $^1$H NMR (300 MHz, CDCl$_3$): 6.83 (d, J=2.69 Hz, 1H), 3.83 (s, 3H), 3.24-3.06 (m, 1H), 1.27 (d, J=7.06 Hz, 6H).

1-tert-Butyl 2-methyl 4-bromo-5-isopropyl-1H-pyrrole-1,2-dicarboxylate (CE158)

Methyl 4-bromo-5-isopropyl-1H-pyrrole-2-carboxylate (1.52 g, previous crude) and Boc$_2$O (2.94 g, 15 mmol) were dissolved in anhydrous THF (20 mL). DMAP (1.1 g, 9 mmol) was added in small portions. The reaction was stirred at room temperature for overnight. The volatile components were removed on a rotary evaporator and the residue was purified by flash column chromatography to yield CE158 in 2.65 g (84% yield over two steps) $^1$H NMR (300 MHz, CDCl$_3$): 6.81 (s, 1H), 3.80 (s, 3H), 3.32-3.16 (m, 1H), 1.59 (s, 9H), 1.38 (d, J=7.16 Hz, 6H).

1-tert-Butyl 2-methyl 5-isopropyl-4-(4,4,5,5-tetramethyl-1,3,2-dioxaborolan-2-yl)-1H-pyrrole-1,2-dicarboxylate (CE160)

CE158 (2.65, 7.66 mmol) and 2-isopropoxy-4,4,5,5-tetramethyl-1,3,2-dioxaborolane (2.29 g, 12.3 mmol) were dissolved in anhydrous THF (20 mL). The solution was cooled to −78° C. for 15 min before BuLi (4.92 mL, 2.5 M in THF, 12.3 mmol) was added via a syringe. The reaction was stirred at −78° C. for 6 h before quenching with saturated NH$_4$Cl aqueous solution. The aqueous layer was extracted with ethyl acetate and the combined organic layers were washed with brine, dried over anhydrous sodium sulfate, and concentrated on a rotary evaporator. The remaining residue was purified by flash column chromatography to yield the title compound in 1.35 g (45% yield). $^1$H NMR (300 MHz, CDCl$_3$): 7.16 (s, 1H), 3.75 (s, 3H), 3.35-3.15 (m, 1H), 1.58 (s, 9H), 1.37 (d, J=7.05 Hz, 6H), 1.26 (s, 12H). $^{13}$C NMR (75 MHz, CDCl$_3$): 160.62, 153.65, 150.51, 125.56, 122.24, 85.45, 83.25, 51.40, 27.73, 27.46, 24.84, 21.75. ESI-MS calculated for C$_{20}$H$_{32}$BNNaO$_6$ [M+Na]$^+$=416.22; observed: 416.17.

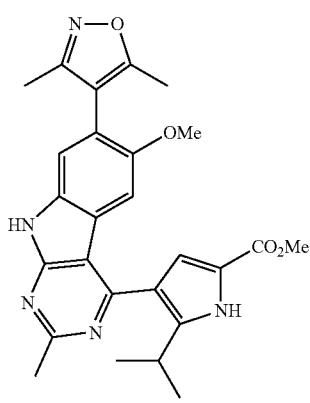

Cpd. No. 209

Methyl 4-(7-(3,5-dimethylisoxazol-4-yl)-6-methoxy-2-methyl-9H-pyrimido[4,5-b]indol-4-yl)-5-isopropyl-1H-pyrrole-2-carboxylate (Cpd. No. 209)

To a round-bottom flask, 4-(4-chloro-6-methoxy-2-methyl-9H-pyrimido[4,5-b]indol-7-yl)-3,5-dimethylisoxazole (S13, 342 mg, 0.8 mmol), CE160 (632 mg, 1.61 mmol), 1,2-dimethoxyethane (10 mL), and Na$_2$CO$_3$ (2 M, 4 mL) were added. The system was degassed to remove oxygen and nitrogen was refilled. Pd(dppf)Cl$_2$—CH$_2$Cl$_2$ (70 mg, 0.08 mmol) was added and the system was degassed and refilled with nitrogen. The reaction mixture was heated at reflux for 16 h. The aqueous layer was extracted with ethyl acetate and the organic layers were combined and the volatile components were removed on a rotary evaporator. The residue was purified by flash column chromatography to yield the title compound in 140 mg (40% yield). $^1$H NMR (300 MHz, MeOD-d4): 7.54 (s, 1H), 7.29 (s, 1H), 7.24 (s, 1H), 3.89 (s, 3H), 3.71 (s, 3H), 3.20-3.04 (m, 1H), 2.92 (s, 3H), 2.31 (s, 3H), 2.13 (s, 3H), 1.28 (d, J=6.88 Hz, 6H). ESI-MS calculated for C$_{26}$H$_{28}$N$_5$O$_4$ [M+H]$^+$=474.21; observed: 474.42.

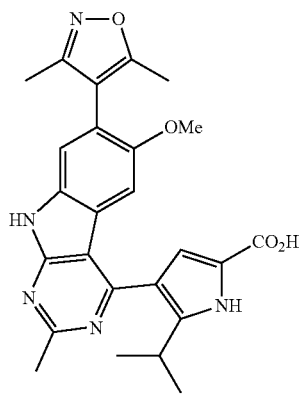

Cpd. No. 210

4-(7-(3,5-Dimethylisoxazol-4-yl)-6-methoxy-2-methyl-9H-pyrimido[4,5-b]indol-4-yl)-5-isopropyl-1H-pyrrole-2-carboxylic acid (Cpd. No. 210)

Cpd. No. 209 (140 mg, 0.30 mmol) was dissolved in THF—H$_2$O (10 mL, 3:2). LiOH—H$_2$O (120 mg) was added in one portion and the mixture was stirred at ambient temperature for overnight. The volatile components were removed on a rotary evaporator and the remaining residues were purified by reverse phase HPLC to yield the title compound as a salt of CF$_3$CO$_2$H in 40 mg (23% yield). $^1$H NMR (300 MHz, MeOD-d4): 7.55 (s, 1H), 7.29 (s, 1H), 7.28 (s, 1H), 3.73 (s, 3H), 3.20-3.04 (m, 1H), 2.93 (s, 3H), 2.31 (s, 3H), 2.13 (s, 3H), 1.29 (d, J=6.97 Hz, 6H). ESI-MS calculated for C$_{25}$H$_{26}$N$_5$O$_4$ [M+H]$^+$=460.20; observed: 460.50.

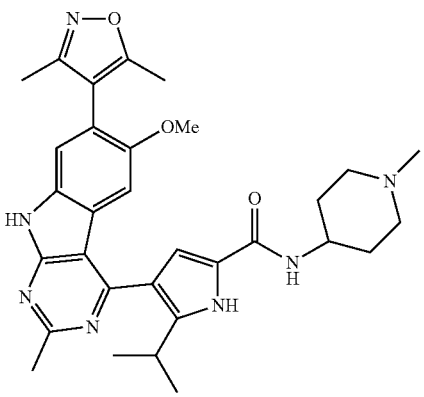

4-(7-(3,5-Dimethylisoxazol-4-yl)-6-methoxy-2-methyl-9H-pyrimido[4,5-b]indol-4-yl)-5-isopropyl-N-(1-methylpiperidin-4-yl)-1H-pyrrole-2-carboxamide (Cpd. No. 211)

Cpd. No. 211 was prepared from Cpd. No. 210 (15 mg) and N-methylpiperidin-4-amine (40 mg) using general amide condensation method promoted by EDCI-HCl. The reaction mixture was purified by reverse phase HPLC to yield Cpd. No. 211 as a $CF_3CO_2H$ salt in 11 mg (53% yield). $^1H$ NMR (300 MHz, MeOD-d4): 7.54 (s, 1H), 7.29 (s, 1H), 7.28 (s, 1H), 4.26-4.08 (m, 1H), 3.72 (s, 3H), 3.68-3.52 (m, 2H), 3.24-3.10 (m, 3H), 2.93 (s, 3H), 2.89 (s, 3H), 2.31 (s, 3H), 2.30-2.16 (m, 2H), 2.13 (s, 3H), 1.98-1.80 (m, 2H), 1.29 (d, J=6.96 Hz, 6H). ESI-MS calculated for $C_{31}H_{38}N_7O_3$ $[M+H]^+=556.30$; observed: 556.42.

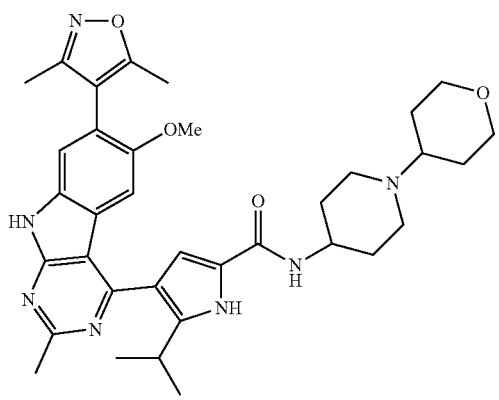

4-(7-(3,5-Dimethylisoxazol-4-yl)-6-methoxy-2-methyl-9H-pyrimido[4,5-b]indol-4-yl)-5-isopropyl-N-(1-(tetrahydro-2H-pyran-4-yl)piperidin-4-yl)-1H-pyrrole-2-carboxamide (Cpd. No. 212)

Cpd. No. 212 was prepared from Cpd. No. 210 (40 mg) and 1-(tetrahydro-2H-pyran-4-yl)-4-piperidinamine dihydrochloride (54 mg) using general amide condensation method promoted by EDCI-HCl. The reaction mixture was purified by reverse phase HPLC to yield Cpd. No. 212 as a $CF_3CO_2H$ salt in 47 mg (73% yield). $^1H$ NMR (300 MHz, MeOD-d4): 7.54 (s, 1H), 7.31 (s, 1H), 7.29 (s, 1H), 4.26-4.12 (m, 1H), 4.12-4.02 (m, 2H), 3.76-3.64 (m, 2H), 3.72 (s, 13H), 3.52-3.38 (m, 3H), 3.26-3.10 (m, 3H), 2.93 (s, 3H), 2.34-2.22 (m, 2H), 2.31 (s, 3H), 2.13 (s, 3H), 2.10-1.70 (m, 6H), 1.29 (d, J=6.97 Hz, 6H). ESI-MS calculated for $C_{35}H_{44}N_7O_4$ $[M+H]^+=626.35$; observed: 626.67.

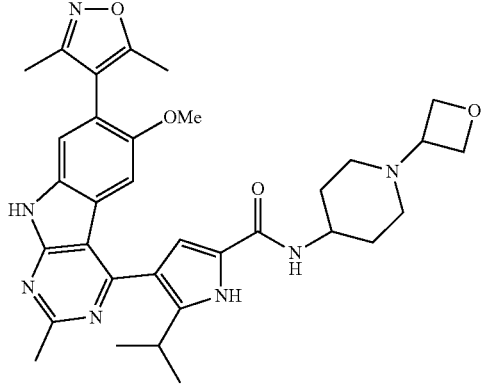

4-(7-(3,5-Dimethylisoxazol-4-yl)-6-methoxy-2-methyl-9H-pyrimido[4,5-b]indol-4-yl)-5-isopropyl-N-(1-(oxetan-3-yl)piperidin-4-yl)-1H-pyrrole-2-carboxamide (Cpd. No. 213)

Cpd. No. 213 was prepared from Cpd. No. 210 (40 mg) and 1-oxetan-3-ylpiperidin-4-amine (48 mg) using general amide condensation method promoted by EDCI-HCl. The reaction mixture was purified by reverse phase HPLC to yield Cpd. No. 213 as a $CF_3CO_2H$ salt in 42 mg (68% yield). $^1H$ NMR (300 MHz, MeOD-d4): 7.55 (s, 1H), 7.34 (s, 1H), 7.30 (s, 1H), 4.90-4.80 (m, 4H), 4.50-4.40 (m, 1H), 4.30-4.14 (m, 1H), 3.72 (s, 3H), 3.66-3.50 (m, 2H), 3.26-2.94 (m, 3H), 2.93 (s, 3H), 2.38-2.20 (m, 2H), 2.30 (s, 3H), 2.18-1.90 (m, 2H), 2.13 (s, 3H), 1.29 (d, J=6.95 Hz, 6H). ESI-MS calculated for $C_{33}H_{40}N_7O_4$ $[M+H]^+=598.31$; observed: 598.42.

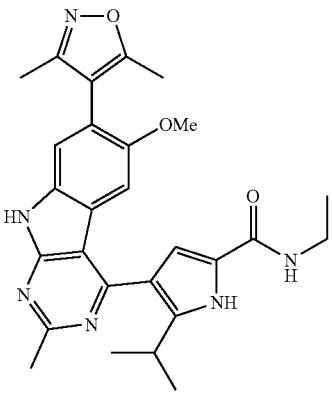

4-(7-(3,5-Dimethylisoxazol-4-yl)-6-methoxy-2-methyl-9H-pyrimido[4,5-b]indol-4-yl)-N-ethyl-5-isopropyl-1H-pyrrole-2-carboxamide (Cpd. No. 214)

Cpd. No. 214 was prepared from Cpd. No. 210 (46 mg) and ethylamine (2 M in THF, 0.3 mL) using general amide condensation method promoted by EDCI-HCl. The reaction mixture was purified by reverse phase HPLC to yield Cpd. No. 214 as a $CF_3CO_2H$ salt in 35 mg (58% yield). $^1H$ NMR (300 MHz, MeOD-d4): 7.54 (s, 1H), 7.31 (s, 1H), 7.21 (s, 1H), 3.73 (s, 3H), 3.41 (q, J=7.25 Hz, 2H), 3.22-3.08 (m, 1H), 2.93 (s, 3H), 2.31 (s, 3H), 2.13 (s, 3H), 1.29 (d, J=6.97 Hz, 6H), 1.22 (t, J=7.24 Hz, 3H). ESI-MS calculated for $C_{27}H_{31}N_6O_3$ $[M+H]^+$=487.25; observed: 487.25.

Cpd. No. 215

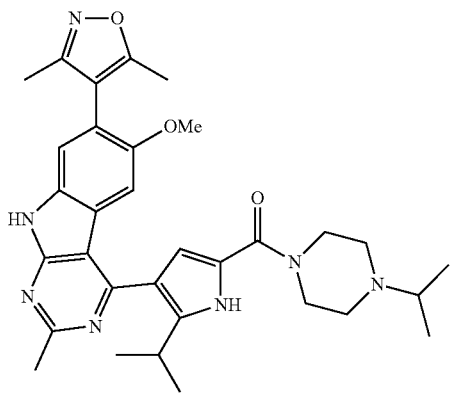

(4-(7-(3,5-Dimethylisoxazol-4-yl)-6-methoxy-2-methyl-9H-pyrimido[4,5-b]indol-4-yl)-5-isopropyl-1H-pyrrol-2-yl)(4-isopropylpiperazin-1-yl)methanone (Cpd. No. 215)

Cpd. No. 215 was prepared from Cpd. No. 210 (46 mg) and 1-isopropylpiperazine (40 mg) using general amide condensation method promoted by EDCI-HCl. The reaction mixture was purified by reverse phase HPLC to yield Cpd. No. 215 as a $CF_3CO_2H$ salt in 40 mg (59% yield). $^1H$ NMR (300 MHz, MeOD-d4): 7.55 (s, 1H), 7.20 (s, 1H), 7.05 (s, 1H), 3.80-3.00 (m, 9H), 3.10 (septet, J=7.02 Hz, 1H), 3.72 (s, 3H), 2.94 (s, 3H), 2.31 (s, 3H), 2.13 (s, 3H), 1.40 (d, J=6.57 Hz, 6H), 1.28 (d, J=6.90 Hz, 6H). ESI-MS calculated for $C_{32}H_{40}N_7O_3$ $[M+H]^+$=570.32; Observed: 570.58.

Cpd. No. 216

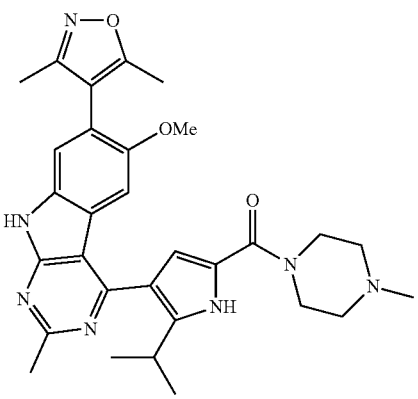

(4-(7-(3,5-Dimethylisoxazol-4-yl)-6-methoxy-2-methyl-9H-pyrimido[4,5-b]indol-4-yl)-5-isopropyl-1H-pyrrol-2-yl)(4-methylpiperazin-1-yl)methanone (Cpd. No. 216)

Cpd. No. 216 was prepared from Cpd. No. 210 (40 mg) and 1-methylpiperazine (30 mg) using general amide condensation method promoted by EDCI-HCl. The reaction mixture was purified by reverse phase HPLC to yield Cpd. No. 216 as a $CF_3CO_2H$ salt in 24 mg (43% yield). $^1H$ NMR (300 MHz, MeOD-d4): 7.55 (s, 3H), 7.20 (s, 1H), 7.03 (s, 1H), 3.72 (s, 3H), 3.70-3.00 (m, 8H), 3.10 (septet, J=6.96 Hz, 1H), 2.96 (s, 3H), 2.94 (s, 3H), 2.31 (s, 3H), 2.13 (s, 3H), 1.28 (d, J=6.97 Hz, 6H). ESI-MS calculated for $C_{30}H_{36}N_7O_3$ $[M+H]^+$=542.29; Observed: 542.42 tert-Butyldimethyl((4-(4,4,5,5-tetramethyl-1,3,2-dioxaborolan-2-yl)naphthalen-1-yl)methoxy)silane (CE187)

Step 1: (4-Bromonaphthalen-1-yl)methanol (10.06 g, 43 mmol) and TBS-Cl (8.46 g, 56 mmol) were dissolved in anhydrous THF (100 mL) and the mixture was cooled with an ice-water bath. Imidazole (4.42 g, 65 mmol) was added in small portions and the reaction was warmed up to ambient temperature overnight. Water was added and the aqueous layer was extracted with ethyl acetate. The combined organic layers were washed with brine, dried over anhydrous sodium sulfate, and concentrated on a rotary evaporator. The remaining residue was purified by flash column chromatography to yield ((4-bromonaphthalen-1-yl)methoxy)(tert-butyl)dimethylsilane in 13.82 g (91% yield).

Step 2: ((4-bromonaphthalen-1-yl)methoxy)(tert-butyl) dimethylsilane (13.82 g, 39.4 mmol) and 2-isopropoxy-4,4, 5,5-tetramethyl-1,3,2-dioxaborolane (11.16 g, 60 mmol) were dissolved in anhydrous THF (100 mL). The solution was cooled to −78° C. for 15 min before BuLi (24 mL, 2.5 M in THF, 60 mmol) was added via a syringe. The reaction was stirred at −78° C. for 6 h before quenching with saturated NH$_4$Cl aqueous solution. The aqueous layer was extracted with ethyl acetate and the combined organic layers were washed with brine, dried over anhydrous sodium sulfate, and concentrated on a rotary evaporator. The remaining residue was purified by flash column chromatography to yield the title compound in 12.46 g (79% yield). $^1$H NMR (300 MHz, CDCl$_3$): 8.80 (d, J=7.61 Hz, 1H), 8.07 (d, J=7.07 Hz, 1H), 7.96 (dd, J=7.89, 1.31 Hz, 1H), 7.60 d, J=7.11 Hz, 1H), 7.57-7.45 (m, 2H), 7.26 (s, 1H), 5.22 (s, 2H), 1.42 (s, 12H), 0.95 (s, 9H), 0.11 (s, 6H).

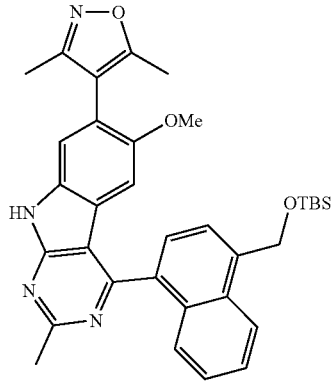

4-(4-(4-(((tert-Butyldimethylsilyl)oxy)methyl)naphthalen-1-yl)-6-methoxy-2-methyl-9H-pyrimido[4,5-b]indol-7-yl)-3,5-dimethylisoxazole (CE191)

To a round-bottom flask, 4-(4-chloro-6-methoxy-2-methyl-9H-pyrimido[4,5-b]indol-7-yl)-3,5-dimethylisoxazole (S13, 5.47 g, 16 mmol), CE187 (12.46 g, 31.3 mmol), 1,2-dimethoxyethane (100 mL), and Na$_2$CO$_3$ (2 M, 50 mL) were added. The system was degassed to remove oxygen and nitrogen was refilled. Pd(dppf)Cl$_2$—CH$_2$Cl$_2$ (1.30 mg, 1.6 mmol) was added and the system was degassed and refilled with nitrogen. The reaction mixture was heated at reflux for 16 h. The aqueous layer was extracted with ethyl acetate and the organic layers were combined and dried The volatile components were removed on a rotary evaporator. The remaining residue was purified by flash column chromatography to yield the title compound in 3.86 g (41% yield). $^1$H NMR (300 MHz, CDCl$_3$): 8.23 (d, J=8.45 Hz, 1H), 7.77 (d, J=7.28 Hz, 1H), 7.72-7.60 (m, 2H), 7.58-7.48 (m, 1H), 7.38-7.32 (m, 1H), 7.30 (s, 1H), 6.15 (s, 1H), 5.30 (q, J=13.39 Hz, 2H), 3.09 (s, 3H), 2.83 (s, 3H), 2.19 (s, 3H), 2.02 (s, 3H), 0.92 (s, 9H), 0.13 (s, 6H).

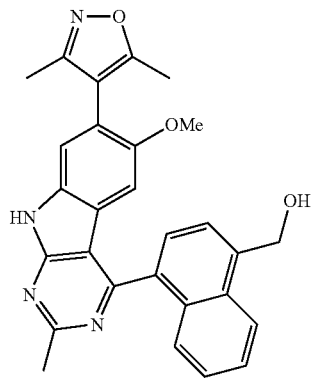

(4-(7-(3,5-Dimethylisoxazol-4-yl)-6-methoxy-2-methyl-9H-pyrimido[4,5-b]indol-4-yl)naphthalen-1-yl)methanol (CE192)

CE191 (1.9 g, 3.3 mmol) was dissolved in THF (20 mL) and TBAF (6 mL, 1.0 M in THF, 6 mmol) was added via a syringe. The reaction mixture was stirred at ambient temperature for overnight. The volatile components were removed on a rotary evaporator. The remaining residue was purified by flash column chromatography to yield the title compound in 1.2 g (78% yield). Further purification on reverse phase HPLC afforded the CE192 as a CF$_3$CO$_2$H salt. $^1$H NMR (300 MHz, MeOD-d4): 8.39 (d, J=8.50 Hz, 1H), 8.046-7.94 (m, 2H), 7.86-7.70 (m, 2H), 7.64-7.56 (m, 1H), 7.53 (s, 1H), 6.18 (s, 1H), 5.34 (d, J=14.15 Hz, 1H), 5.28 (d, J=14.11 Hz, 1H), 3.16 (s, 3H), 3.01 (s, 3H), 2.25 (s, 3H), 2.06 (s, 3H). ESI-MS calculated for C$_{28}$H$_{25}$N$_4$O$_3$ [M+H]$^+$=465.19; observed: 465.32.

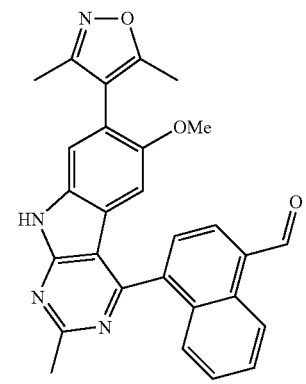

4-(7-(3,5-Dimethylisoxazol-4-yl)-6-methoxy-2-methyl-9H-pyrimido[4,5-b]indol-4-yl)-1-naphthaldehyde (CE194)

CE192 (1.2 g, 2.6 mmol) was dissolved in DMSO (20 mL). IBX (1.46 g, 5.2 mmol) was added in small portions and the mixture was stirred at room temperature for overnight before quenching with NaHCO$_3$. The aqueous layer was extracted with ethyl acetate and the organic layers were combined and dried. The volatile components were removed on a rotary evaporator. The remaining residue was purified by flash column chromatography to yield the title compound in 1.19 g (98% yield). $^1$H NMR (300 MHz, DMSO-d6): 12.29 (s, 1H), 10.56 (s, 1H), 9.34 (d, J=8.65 Hz, 1H), 8.42 (d, J=7.33 Hz, 1H), 8.01 (d, J=7.24 Hz, 1H), 7.85-7.75 (m, 2H), 7.60-7.53 (m, 1H), 7.33 (s, 1H), 6.12 (s, 1H), 3.11 (s, 3H), 2.79 (s, 3H), 2.21 (s, 3H), 1.99 (s, 3H). ESI-MS calculated for $C_{28}H_{23}N_4O_3$ [M+H]$^+$=463.18; observed: 463.67.

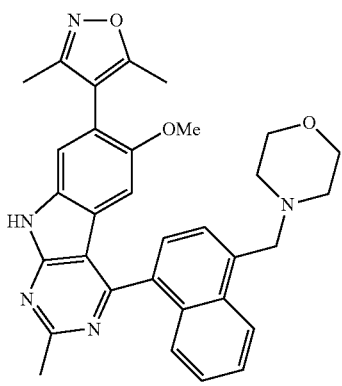

Cpd. No. 217

4-((4-(7-(3,5-Dimethylisoxazol-4-yl)-6-methoxy-2-methyl-9H-pyrimido[4,5-b]indol-4-yl)naphthalen-1-yl)methyl)morpholine (Cpd. No. 217)

CE194 (50 mg), morpholine (18 mg, 0.2 mmol), and acetic acid (0.1 mL) were dissolved in anhydrous THF (3 mL). NaBH(OAc)$_3$ (120 mg, 0.5 mmol) was added in one portion and the mixture was stirred at ambient temperature for overnight. The volatile components were removed on a rotary evaporator. The remaining residue was purified by reverse phase HPLC to yield the title compound Cpd. No. 217 as a CF$_3$CO$_2$H salt in 31 mg (47% yield). $^1$H NMR (300 MHz, MeOD-d4): 8.61 (d, J=8.55 Hz, 1H), 8.15 (d, J=7.41 Hz, 1H), 8.08 (d, J=7.41 Hz, 1H), 7.92-7.84 (m, 2H), 7.72-7.64 (m, 1H), 7.54 (s, 1H), 6.18 (s, 1H), 5.15 (d, J=13.59 Hz, 1H), 5.07 (d, J=13.59 Hz, 1H), 4.10-3.80 (m, 4H), 3.54-3.46 (m, 4H), 3.17 (s, 3H), 3.02 (s, 3H), 2.25 (s, 3H), 2.06 (s, 3H). ESI-MS calculated for $C_{32}H_{32}N_5O_3$ [M+H]$^+$=534.25; observed: 557.50.

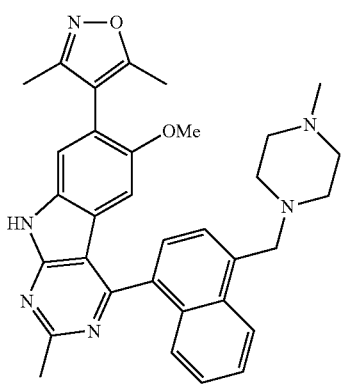

Cpd. No. 218

4-(6-Methoxy-2-methyl-4-(4-((4-methylpiperazin-1-yl)methyl)naphthalen-1-yl)-9H-pyrimido[4,5-b]indol-7-yl)-3,5-dimethylisoxazole (Cpd. No. 218)

CE194 (50 mg), 1-methylpiperazine (20 mg, 0.2 mmol), and acetic acid (0.1 mL) were dissolved in anhydrous THF (3 mL). NaBH(OAc)$_3$ (120 mg, 0.5 mmol) was added in one portion and the mixture was stirred at ambient temperature for overnight. The volatile components were removed on a rotary evaporator. The remaining residue was purified by reverse phase HPLC to yield the title compound Cpd. No. 218 as a CF$_3$CO$_2$H salt in 19 mg (29% yield). $^1$H NMR (300 MHz, MeOD-d4): 8.62 (d, J=8.35 Hz, 1H), 7.97 (d, J=7.29 Hz, 1H), 7.90 (d, J=7.36 Hz, 1H), 7.80-7.72 (m, 2H), 7.64-7.56 (m, 1H), 7.53 (s, 1H), 6.16 (s, 1H), 4.35 (s, 2H), 3.48-3.30 (m, 4H), 3.15 (s, 3H), 3.10-2.90 (m, 4H), 3.01 (s, 3H), 2.91 (s, 3H), 2.25 (s, 3H), 2.06 (s, 3H). ESI-MS calculated for $C_{33}H_{35}N_6O_2$ [M+H]$^+$=547.28; observed: 547.33.

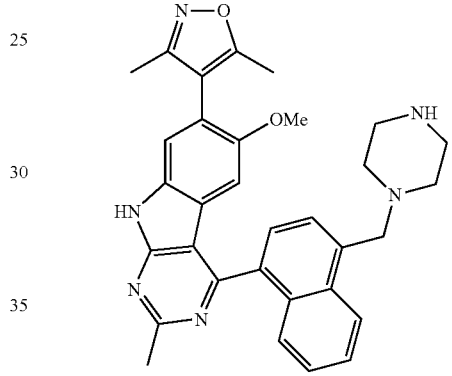

Cpd. No. 219

4-(6-Methoxy-2-methyl-4-(4-(piperazin-1-ylmethyl)naphthalen-1-yl)-9H-pyrimido[4,5-b]indol-7-yl)-3,5-dimethylisoxazole (Cpd. No. 219)

Step 1: CE194 (300 mg, 0.7 mmol), 1-Boc-piperazine (260 mg, 1.4 mmol), and acetic acid (0.2 mL) were dissolved in anhydrous THF (5 mL). NaBH(OAc)$_3$ (445 mg, 2.1 mmol) was added in one portion and the mixture was stirred at ambient temperature for overnight. The volatile components were removed on a rotary evaporator. The remaining residue was directly used for next step.

Step 2: The previous residue from step 1 was mixed with CH$_2$Cl$_2$ (5 mL) followed by addition of triethylsilane (0.1 mL) and CF$_3$CO$_2$H (5 mL). The mixture was stirred at ambient temperature for 2 h and the volatile components were removed on a rotary evaporator. The remaining residue was purified by reverse phase HPLC to yield the title compound Cpd. No. 219 as a CF$_3$CO$_2$H salt in 300 mg (80% yield over two steps). $^1$H NMR (300 MHz, MeOD-d4): 8.61 (d, J=8.25 Hz, 1H), 8.00 (d, J=7.31 Hz, 1H), 7.96 (d, J=7.31 Hz, 1H), 7.84-7.74 (m, 2H), 7.65-7.57 (m, 1H), 7.54 (s, 1H), 6.17 (s, 1H), 4.52 (s, 2H), 3.42-3.32 (m, 4H), 3.18-3.10 (m, 4H), 3.15 (s, 3H), 3.02 (s, 3H), 2.25 (s, 3H), 2.06 (s, 3H). ESI-MS calculated for $C_{32}H_{33}N_6O_2$ [M+H]$^+$=533.27; observed: 533.25.

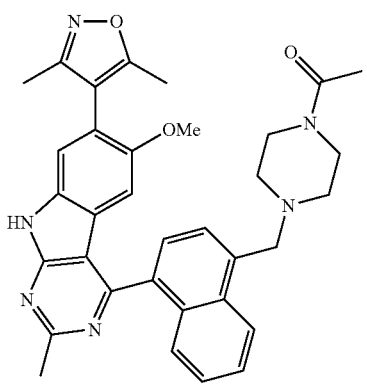

Cpd. No. 220

1-(4-((4-(7-(3,5-Dimethylisoxazol-4-yl)-6-methoxy-2-methyl-9H-pyrimido[4,5-b]indol-4-yl)naphthalen-1-yl)methyl)piperazin-1-yl)ethanone (Cpd. No. 220)

Cpd. No. 219(50 mg) was dissolved in anhydrous THF (3 mL). Acetic anhydride (0.05 mL, 0.2 mmol) was added via a syringe and the mixture was stirred at ambient temperature for 4 h. The volatile components were removed on a rotary evaporator. The remaining residue was purified by reverse phase HPLC to yield the title compound Cpd. No. 220 as a $CF_3CO_2H$ salt in 33 mg (48% yield). $^1H$ NMR (300 MHz, MeOD-d4): 8.59 (d, J=8.53 Hz, 1H), 8.15 (d, J=7.42 Hz, 1H), 8.09 (d, J=7.42 Hz, 1H), 7.92-7.82 (m, 2H), 7.72-7.64 (m, 1H), 7.55 (s, 1H), 6.19 (s, 1H), 5.15 (d, J=13.58 Hz, 1H), 5.08 (d, J=13.58 Hz, 1H), 3.96-3.82 (m, 4H), 3.60-3.50 (m, 2H), 3.50-3.40 (m, 2H), 3.18 (s, 3H), 3.02 (s, 3H), 2.25 (s, 3H), 2.17 (s, 3H), 2.06 (s, 3H). ESI-MS calculated for $C_{34}H_{35}N_6O_3$ $[M+H]^+$=575.28; observed: 575.42.

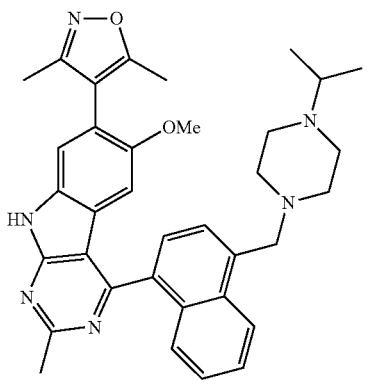

Cpd. No. 221

4-(4-(4-((4-Isopropylpiperazin-1-yl)methyl)naphthalen-1-yl)-6-methoxy-2-methyl-9H-pyrimido[4,5-b]indol-7-yl)-3,5-dimethylisoxazole (Cpd. No. 221)

CE194 (46 mg), 1-isopropylpiperazine (60 mg, 0.3 mmol), and acetic acid (0.1 mL) were dissolved in anhydrous THF (5 mL). $NaBH(OAc)_3$ (110 mg, 0.5 mmol) was added in one portion and the mixture was stirred at ambient temperature for overnight. The volatile components were removed on a rotary evaporator. The remaining residue was purified by reverse phase HPLC to yield the title compound Cpd. No. 221 as a $CF_3CO_2H$ salt in 55 mg (80% yield). $^1H$ NMR (300 MHz, MeOD-d4): 8.61 (d, J=8.19 Hz, 1H), 8.02-7.90 (m, 2H), 7.82-7.72 (m, 2H), 7.65-7.56 (m, 1H), 7.54 (s, 1H), 6.17 (s, 1H), 4.49 (d, J=13.44 Hz, 1H), 4.42 (d, J=13.44 Hz, 1H), 3.70-2.70 (m, 8H), 3.55 (septet, J=6.62 Hz, 1H), 3.16 (s, 3H), 3.02 (s, 3H), 2.25 (s, 3H), 2.06 (s, 3H), 1.38 (d, J=6.65 Hz, 6H). ESI-MS calculated for $C_{35}H_{39}N_6O_2$ $[M+H]^+$=575.31; Observed: 575.92

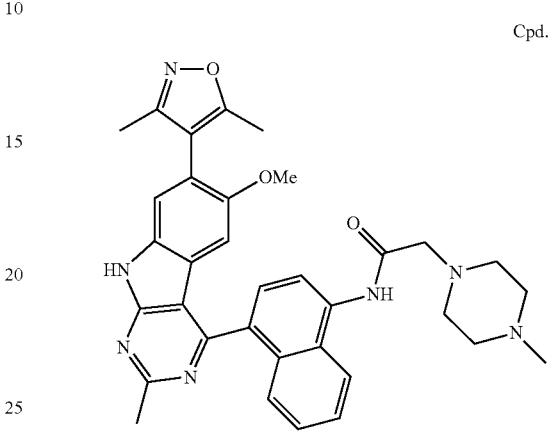

Cpd. No. 222

N-(4-(7-(3,5-Dimethylisoxazol-4-yl)-6-methoxy-2-methyl-9H-pyrimido[4,5-b]indol-4-yl)naphthalen-1-yl)-2-(4-methylpiperazin-1-yl)acetamide (Cpd. No. 222)

Following protocol similar to Method 149, reaction of 4-(7-(3,5-dimethylisoxazol-4-yl)-6-methoxy-2-methyl-9H-pyrimido[4,5-b]indol-4-yl)naphthalen-1-amine (Cpd. No. 150, 45 mg, 0.1 mmol) chloroacetyl chloride (113 mg, 1 mmol), and N-methylpiperidin-4-amine (40 mg, 0.4 mmol) afforded the title compound. Upon treatment of $CF_3CO_2H$ followed by reverse phase HPLC purification, the title compound was isolated in 39 mg as a $CF_3CO_2H$ salt (55% over two steps). $^1H$ NMR (300 MHz, MeOD-d4): 8.35 (d, J=8.69 Hz, 1H), 8.22 (d, J=7.83 Hz, 1H), 8.06 (d, J=7.85 Hz, 1H), 7.85-7.77 (m, 2H), 7.68-7.61 (m, 1H), 7.56 (s, 1H), 6.24 (s, 1H), 3.83 (s, 2H), 3.62-3.50 (m, 4H), 3.38-3.22 (m, 4H), 3.19 (s, 3H), 3.04 (s, 3H), 3.01 (s, 3H), 2.28 (s, 3H), 2.08 (s, 3H), ESI-MS calculated for $C_{34}H_{36}N_7O_3$ $[M+H]^+$= 590.29; observed: 590.50.

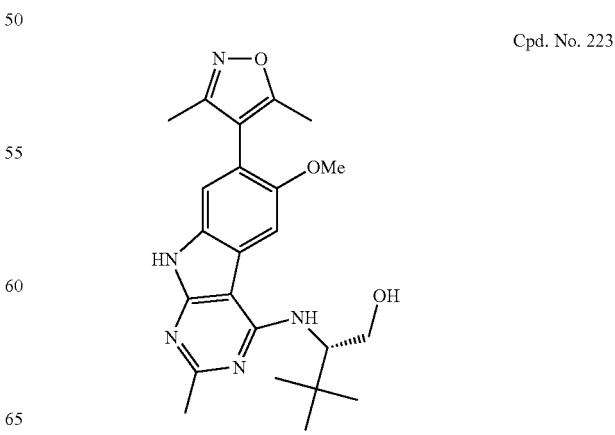

Cpd. No. 223

(2S)-2-((7-(3,5-Dimethylisoxazol-4-yl)-6-methoxy-2-methyl-9H-pyrimido[4,5-b]indol-4-yl)amino)-3,3-dimethylbutan-1-ol (Cpd. No. 223)

S13 (70 mg), L-tert Leucinol (44 mg), NaHCO$_3$ (32 mg) and anhydrous DMSO (3 mL) were heated at 150° C. for 16 h. The mixture was then purified by reverse phase HPLC to yield Cpd. No. 223 as a CF$_3$CO$_2$H salt in 9 mg (9% yield). $^1$H NMR (300 MHz, MeOD-d4): 7.88 (s, 1H), 7.45 (s, 1H), 4.70-4.55 (m, 1H), 4.04 (dd, J=12.02, 4.75 Hz, 1H), 4.00-3.93 (m, 1H), 3.96 (s, 3H), 2.72 (s, 3H), 2.32 (s, 3H), 2.16 (s, 3H), 1.12 (s, 9H). ESI-MS calculated for C$_{23}$H$_{30}$N$_5$O$_3$ [M+H]$^+$=424.23; observed: 424.60.

(2S)-2-((7-(3,5-Dimethylisoxazol-4-yl)-6-methoxy-2-methyl-9H-pyrimido[4,5-b]indol-4-yl)amino)-2-phenylethanol (Cpd. No. 225)

S13 (68 mg), L-phenyl glycinol (56 mg), NaHCO$_3$ (84 mg) and anhydrous DMSO (3 mL) were heated at 100° C. for 16 h. The mixture was then purified by reverse phase HPLC to yield Cpd. No. 225 as a CF$_3$CO$_2$H salt in 70 mg (62% yield). $^1$H NMR (300 MHz, MeOD-d4): 8.06 (s, 1H), 7.56-7.50 (m, 2H), 7.44 (s, 1H), 7.42-7.26 (m, 3H), 5.84 (dd, J=7.56, 4.87 Hz, 1H), 4.20 (dd, J=11.38, 7.77 Hz, 1H), 4.13 (dd, J=11.38, 4.87 Hz, 1H), 3.97 (s, 3H), 2.65 (s, 3H), 2.32 (s, 3H), 2.15 (s, 3H). ESI-MS calculated for C$_{25}$H$_{26}$N$_5$O$_3$ [M+H]$^+$=444.20; observed: 444.67.

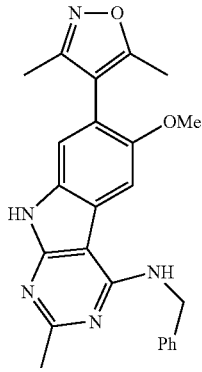

Cpd. No. 224

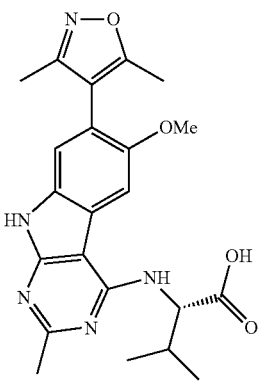

Cpd. No. 226

N-benzyl-7-(3,5-dimethylisoxazol-4-yl)-6-methoxy-2-methyl-9H-pyrimido[4,5-b]indol-4-amine (Cpd. No. 224)

S13 (68 mg), L-phenyl glycine (60 mg), NaHCO$_3$ (48 mg) and anhydrous DMSO (3 mL) were heated at 100° C. for 16 h. The mixture was then purified by reverse phase HPLC to yield Cpd. No. 224 as a CF$_3$CO$_2$H salt in 52 mg (50% yield). $^1$H NMR (300 MHz, MeOD-d4): 8.05 (s, 1H), 7.48-7.40 (m, 2H), 7.44 (s, 1H), 7.38-7.22 (m, 3H), 5.08 (s, 2H), 3.93 (s, 3H), 2.69 (s, 3H), 2.30 (s, 3H), 2.13 (s, 3H). ESI-MS calculated for C$_{24}$H$_{24}$N$_5$O$_2$ [M+H]$^+$=414.19; observed: 414.60.

(2S)-2-((7-(3,5-Dimethylisoxazol-4-yl)-6-methoxy-2-methyl-9H-pyrimido[4,5-b]indol-4-yl)amino)-3-methylbutanoic acid (Cpd. No. 226)

S13 (68 mg), valine (48 mg), NaHCO$_3$ (84 mg) and anhydrous DMSO (3 mL) were heated at 100° C. for 16 h. The mixture was then purified by reverse phase HPLC to yield Cpd. No. 226 as a CF$_3$CO$_2$H salt in 46 mg (43% yield). $^1$H NMR (300 MHz, MeOD-d4): 7.89 (s, 1H), 7.45 (s, 1H), 3.97 (s, 3H), 2.69 (s, 3H), 2.60-2.46 (m, 1H), 2.33 (s, 3H), 2.15 (s, 3H), 1.17 (t, J=6.95 Hz, 6H). ESI-MS calculated for C$_{22}$H$_{26}$N$_5$O$_4$ [M+H]$^+$=424.20; observed: 424.33.

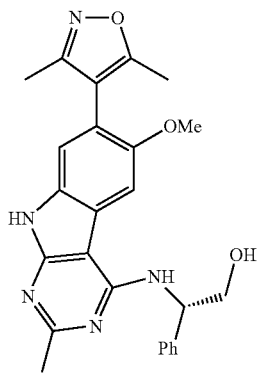

Cpd. No. 225

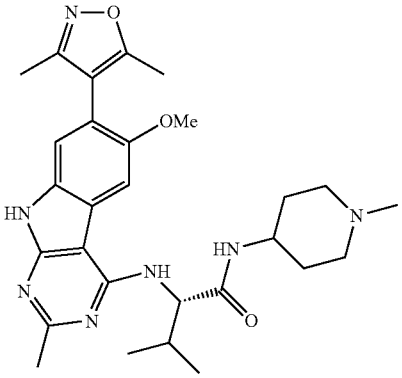

Cpd. No. 227

(2S)-2-((7-(3,5-Dimethylisoxazol-4-yl)-6-methoxy-2-methyl-9H-pyrimido[4,5-b]indol-4-yl)amino)-3-methyl-N-(1-methylpiperidin-4-yl)butanamide (Cpd. No. 227)

Cpd. No. 227 was prepared from Cpd. No. 226 (30 mg) and N-methylpiperidin-4-amine (33 mg) using general amide condensation method promoted by EDCI-HCl. The reaction mixture was purified by reverse phase HPLC to yield Cpd. No. 227 as a $CF_3CO_2H$ salt in 38 mg (85% yield). $^1$H NMR (300 MHz, MeOD-d4): 7.94 (s, 1H), 7.46 (s, 1H), 4.84 (d, J=8.65 Hz, 1H), 4.10-3.90 (m, 1H), 3.98 (s, 3H), 3.65-3.50 (m, 2H), 3.20-3.06 (m, 2H), 2.87 (s, 3H), 2.73 (s, 3H), 2.50-2.36 (m, 1H), 2.32 (s, 3H), 2.26-2.08 (m, 2H), 2.14 (s, 3H), 1.94-1.76 (m, 2H), 1.12 (t, J=6.11 Hz, 6H). ESI-MS calculated for $C_{28}H_{38}N_7O_3$ $[M+H]^+$=520.30; observed: 520.55.

Cpd. No. 228

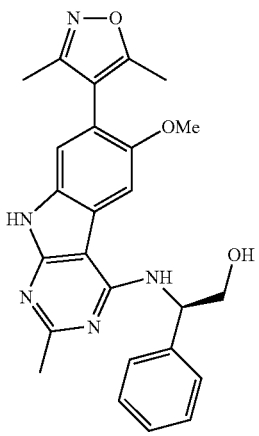

(2R)-2-((7-(3,5-Dimethylisoxazol-4-yl)-6-methoxy-2-methyl-9H-pyrimido[4,5-b]indol-4-yl)amino)-2-phenylethanol (Cpd. No. 228)

S13 (68 mg), D-phenylglycinol (56 mg), EtN(i-Pr)$_2$ (0.2 mL) and anhydrous DMSO (3 mL) were heated at 100° C. for 16 h. The mixture was then purified by reverse phase HPLC to yield Cpd. No. 228 as a $CF_3CO_2H$ salt in 35 mg (32% yield). $^1$H NMR (300 MHz, MeOD-d4): 8.06 (s, 1H), 7.57-7.50 (m, 2H), 7.44 (s, 1H), 7.43-7.25 (m, 3H), 5.83 (dd, J=7.55, 4.93 Hz, 1H), 4.20 (dd, J=11.38, 7.74 Hz, 1H), 4.13 (dd, J=11.38, 4.88 Hz, 1H), 3.97 (s, 3H), 2.66 (s, 3H), 2.32 (s, 3H), 2.15 (s, 3H). ESI-MS calculated for $C_{25}H_{26}N_5O_3$ $[M+H]^+$=444.20; observed: 444.25.

Cpd. No. 229

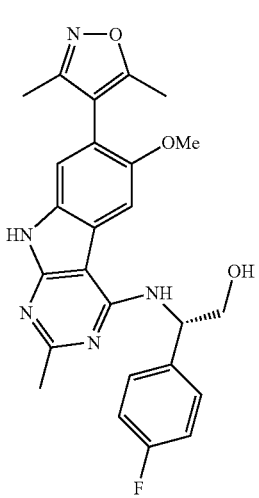

(2S)-2-((7-(3,5-Dimethylisoxazol-4-yl)-6-methoxy-2-methyl-9H-pyrimido[4,5-b]indol-4-yl)amino)-2-(4-fluorophenyl)ethanol (Cpd. No. 229)

S13 (70 mg), (S)-2-amino-2-(4-fluorophenyl)ethanol (60 mg), EtN(i-Pr)$_2$ (0.1 mL) and anhydrous DMSO (3 mL) were heated at 100° C. for 16 h. The mixture was then purified by reverse phase HPLC to yield Cpd. No. 229 as a $CF_3CO_2H$ salt in 9 mg (8% yield). $^1$H NMR (300 MHz, MeOD-d4): 8.06 (s, 1H), 7.60-7.54 (m, 1H), 7.44 (s, 1H), 7.15-7.07 (m, 1H), 5.82 (dd, J=7.37, 5.08 Hz, 1H), 4.17 (dd, J=11.35, 7.64 Hz, 1H), 4.10 (dd, J=11.35, 5.07 Hz, 1H), 3.98 (s, 3H), 2.66 (s, 3H), 2.32 (s, 3H), 2.15 (s, 3H). ESI-MS calculated for $C_{25}H_{25}FN_5O_3$ $[M+H]^+$=462.19; observed: 462.25.

Cpd. No. 230

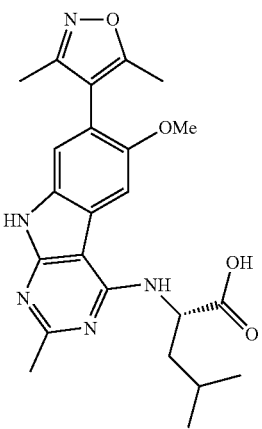

(2S)-2-((7-(3,5-Dimethylisoxazol-4-yl)-6-methoxy-2-methyl-9H-pyrimido[4,5-b]indol-4-yl)amino)-4-methylpentanoic acid (Cpd. No. 230)

S13 (70 mg), L-Leucine (52 mg), NaHCO$_3$ (84 mg) and anhydrous DMSO (3 mL) were heated at 100° C. for 16 h. The mixture was then purified by reverse phase HPLC to yield Cpd. No. 230 as a $CF_3CO_2H$ salt in 60 mg (54% yield). $^1$H NMR (300 MHz, MeOD-d4): 8.01 (s, 1H), 7.43 (s, 1H), 5.32 (dd, J=10.40, 4.58 Hz, 1H), 3.96 (s, 3H), 2.68 (s, 3H), 2.34 (s, 3H), 2.15 (s, 3H), 2.14-2.06 (m, 1H), 2.04-1.90 (m, 1H), 1.90-1.78 (m, 1H), 1.03 (t, J=6.93 Hz, 6H). ESI-MS calculated for $C_{23}H_{28}N_5O_4$ $[M+H]^+$=438.21; observed: 438.42.

Cpd. No. 231

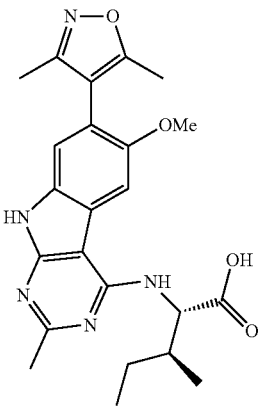

(2S,3S)-2-((7-(3,5-Dimethylisoxazol-4-yl)-6-methoxy-2-methyl-9H-pyrimido[4,5-b]indol-4-yl)amino)-3-methylpentanoic acid (Cpd. No. 231)

S13 (70 mg), L-Isoleucine (52 mg), NaHCO$_3$ (84 mg) and anhydrous DMSO (3 mL) were heated at 100° C. for 16 h. The mixture was then purified by reverse phase HPLC to yield Cpd. No. 231 as a CF$_3$CO$_2$H salt in 54 mg (49% yield). $^1$H NMR (300 MHz, MeOD-d4): 7.89 (s, 1H), 7.46 (s, 1H), 5.09 (d, J=6.64 Hz, 1H), 3.97 (s, 3H), 2.72 (s, 3H), 2.36-2.24 (m, 1H), 2.33 (s, 3H), 2.16 (s, 3H), 1.86-1.70 (m, 1H), 1.56-1.36 (m, 1H), 1.12 (d, J=6.84 Hz, 3H), 1.04 (t, J=7.37 Hz, 3H). ESI-MS calculated for C$_{23}$H$_{28}$N$_5$O$_4$ [M+H]$^+$=438.21; observed: 438.33.

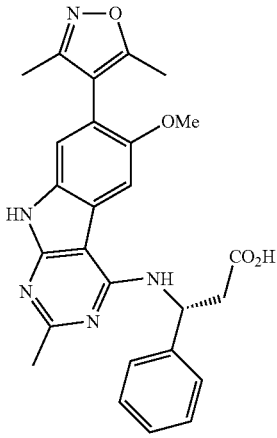

Cpd. No. 232

(3R)-3-((7-(3,5-Dimethylisoxazol-4-yl)-6-methoxy-2-methyl-9H-pyrimido[4,5-b]indol-4-yl)amino)-3-phenylpropanoic acid (Cpd. No. 232)

S13 (684 mg), (R)-3-amino-3-phenylpropionic acid (660 mg), NaHCO$_3$ (800 mg) and anhydrous DMSO (10 mL) were heated at 130° C. for 16 h. The mixture was then purified by reverse phase HPLC to yield Cpd. No. 232 as a CF$_3$CO$_2$H salt in 270 mg (23% yield). $^1$H NMR (300 MHz, MeOD-d4): 8.00 (s, 1H), 7.60-7.50 (m, 2H), 7.45 (s, 1H), 7.40-7.20 (m, 3H), 6.12 (t, J=5.74 Hz, 1H), 3.97 (s, 3H), 3.23 (d, J=5.81 Hz, 2H), 2.67 (s, 3H), 2.32 (s, 3H), 2.15 (s, 3H). ESI-MS calculated for C$_{26}$H$_{26}$N$_5$O$_4$ [M+H]$^+$=472.20; observed: 4752.25.

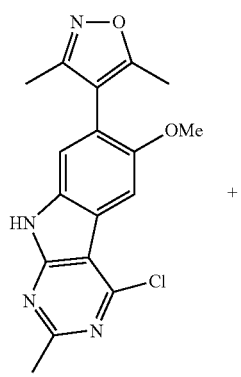

+

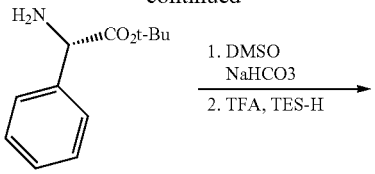

1. DMSO, NaHCO3
2. TFA, TES-H

(2S)-2-((7-(3,5-Dimethylisoxazol-4-yl)-6-methoxy-2-methyl-9H-pyrimido[4,5-b]indol-4-yl)amino)-2-phenylacetic acid (Cpd. No. 233)

Step 1: S13 (682 mg, 2.0 mmol), (S)-tert-butyl 2-amino-2-phenylacetate (1.0 g, 4.0 mmol), NaHCO$_3$ (800 mg, 8 mmol) and anhydrous DMSO (10 mL) were heated at 130° C. for 16 h. The mixture was then diluted with water and the aqueous layer was extracted with ethyl acetate. The organic layers were combined and dried, and the volatile components were removed on a rotary evaporator. The remaining residue was directly used for the next step.

Step 2: The previous residue from step 1 was mixed with CF$_3$CO$_2$H (10 mL) and water (0.5 mL) followed by addition of triethylsilane (1 mL). The mixture was stirred at ambient temperature for overnight and the volatile components were removed on a rotary evaporator. The remaining residue was purified by reverse phase HPLC to yield the title compound Cpd. No. 233 as a CF$_3$CO$_2$H salt in 87 mg (8% yield). $^1$H NMR (300 MHz, MeOD-d4): 7.95 (s, 1H), 7.66-7.60 (m, 2H), 7.46 (s, 1H), 7.45-7.33 (m, 3H), 6.23 (s, 1H), 3.95 (s, 3H), 2.69 (s, 3H), 2.32 (s, 3H), 2.15 (s, 3H). ESI-MS calculated for C$_{25}$H$_{24}$N$_5$O$_4$ [M+H]$^+$=458.18; observed: 458.25.

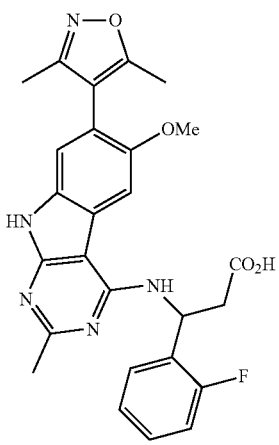

Cpd. No. 234

3-((7-(3,5-Dimethylisoxazol-4-yl)-6-methoxy-2-methyl-9H-pyrimido[4,5-b]indol-4-yl)amino)-3-(2-fluorophenyl)propanoic acid (Cpd. No. 234)

S13 (342 mg), (R)-3-amino-3-(2-fluoro-phenyl)-propionic acid (360 mg), NaHCO$_3$ (300 mg) and anhydrous DMSO (10 mL) were heated at 130° C. for 16 h. The mixture was then purified by reverse phase HPLC to yield Cpd. No. 234 as a CF$_3$CO$_2$H salt in 236 mg (39% yield). $^1$H NMR (300 MHz, MeOD-d4): racemic, 8.01 (s, 1H), 7.56-7.48 (m, 1H), 7.10-7.30 (m, 1H), 7.46 (s, 1H), 7.22-7.10 (m, 2H), 6.31 (t, J=5.93 Hz, 1H), 3.99 (s, 3H), 3.25-3.18 (m, 2H), 2.67 (s, 3H), 2.33 (s, 3H), 2.16 (s, 3H). ESI-MS calculated for C$_{26}$H$_{25}$FN$_5$O$_4$ [M+H]$^+$=490.19; observed: 490.62.

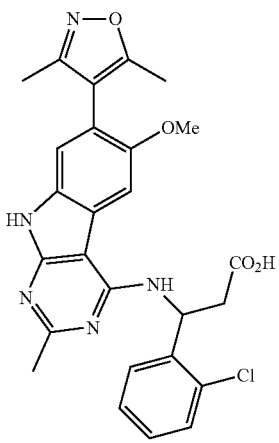

Cpd. No. 235

3-(2-Chlorophenyl)-3-((7-(3,5-dimethylisoxazol-4-yl)-6-methoxy-2-methyl-9H-pyrimido[4,5-b]indol-4-yl)amino)propanoic acid (Cpd. No. 235)

S13 (70 mg), (R)-3-amino-3-(2-chloro-phenyl)-propionic acid (80 mg), NaHCO$_3$ (84 mg) and anhydrous DMSO (3 mL) were heated at 130° C. for 16 h. The mixture was then purified by reverse phase HPLC to yield Cpd. No. 235 as a CF$_3$CO$_2$H salt in 39 mg (31% yield). $^1$H NMR (300 MHz, MeOD-d4): racemic, 8.04 (s, 1H), 7.62-7.54 (m, 1H), 7.50-7.46 (m, 1H), 7.46 (s, 1H), 7.34-7.24 (m, 2H), 6.37 (t, J=6.37 Hz, 1H), 4.00 (s, 3H), 3.24-3.17 (m, 2H), 2.64 (s, 3H), 2.33 (s, 3H), 2.16 (s, 3H). ESI-MS calculated for C$_{26}$H$_{25}$ClN$_5$O$_4$ [M+H]$^+$=506.16; observed: 506.67.

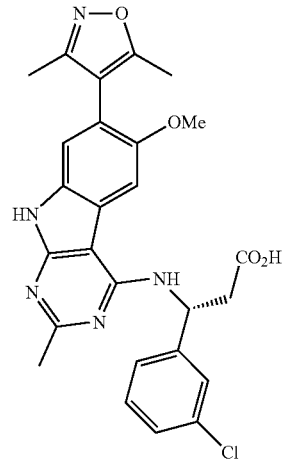

Cpd. No. 236

(3R)-3-(3-Chlorophenyl)-3-((7-(3,5-dimethylisoxazol-4-yl)-6-methoxy-2-methyl-9H-pyrimido[4,5-b]indol-4-yl)amino)propanoic acid (Cpd. No. 236)

S13 (68 mg), (R)-3-amino-3-(3-chlorophenyl)propanoic acid (80 mg), NaHCO$_3$ (100 mg) and anhydrous DMSO (3 mL) were heated at 130° C. for overnight. The mixture was then purified by reverse phase HPLC to yield Cpd. No. 236 as a CF$_3$CO$_2$H salt in 56 mg (55% yield). $^1$H NMR (300 MHz, MeOD-d4): 8.00 (s, 1H), 7.55 (s, 1H), 7.50-7.44 (m, 1H), 7.46 (s, 1H), 7.40-7.25 (m, 2H), 6.11 (t, J=6.09 Hz, 1H), 3.98 (s, 3H), 3.22 (d, J=6.15 Hz, 2H), 2.69 (s, 3H), 2.32 (s, 3H), 2.15 (s, 3H). ESI-MS calculated for C$_{26}$H$_{25}$$^{35}$ClN$_5$O$_4$ [M+H]$^+$=506.16; Observed: 506.58.

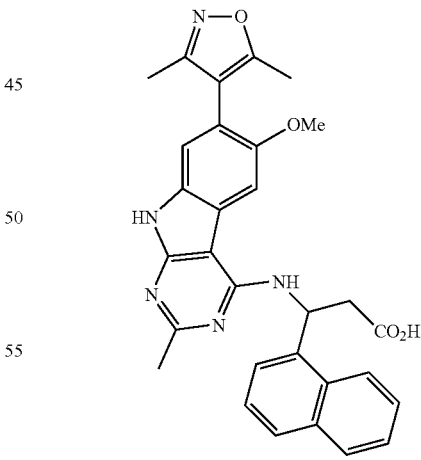

Cpd. No. 237

3-((7-(3,5-Dimethylisoxazol-4-yl)-6-methoxy-2-methyl-9H-pyrimido[4,5-b]indol-4-yl)amino)-3-(naphthalen-1-yl)propanoic acid (Cpd. No. 237)

S13 (68 mg), 3-amino-3-(naphthalen-1-yl)propanoic acid (86 mg), NaHCO$_3$ (100 mg) and anhydrous DMSO (3 mL)

were heated at 130° C. for overnight. The mixture was then purified by reverse phase HPLC to yield Cpd. No. 237 as a $CF_3CO_2H$ salt in 35 mg (28% yield). $^1$H NMR (300 MHz, MeOD-d4): 8.31 (d, 1H, J=8.4 Hz, 1H), 8.08 (s, 1H), 7.93 (d, 1H, J=7.6 Hz, 1H), 7.83 (d, 1H, J=8.3 Hz, 1H), 7.72-7.60 (m, 2H), 7.60-7.50 (m, 1H), 7.48-7.40 (m, 1H), 7.47 (s, 1H), 6.91 (t, J=5.80 Hz, 1H), 3.98 (s, 3H), 3.36-3.28 (m, 2H), 2.57 (s, 3H), 2.33 (s, 3H), 2.16 (s, 3H). ESI-MS calculated for $C_{30}H_{28}N_5O_4$ $[M+H]^+$=522.21; Observed: 522.33.

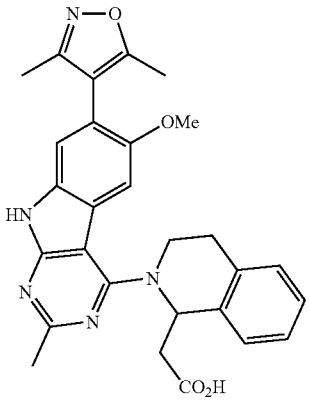

Cpd. No. 238

2-(2-(7-(3,5-Dimethylisoxazol-4-yl)-6-methoxy-2-methyl-9H-pyrimido[4,5-b]indol-4-yl)-1,2,3,4-tetra-hydroisoquinolin-1-yl)acetic acid (Cpd. No. 238)

S13 (68 mg), 2-(1,2,3,4-tetrahydroisoquinolin-1-yl)acetic acid (80 mg), $NaHCO_3$ (100 mg) and anhydrous DMSO (3 mL) were heated at 130° C. for overnight. The mixture was then purified by reverse phase HPLC to yield Cpd. No. 238 as a $CF_3CO_2H$ salt in 55 mg (45% yield). $^1$H NMR (300 MHz, MeOD-d4): 7.48-7.40 (m, 1H), 7.46 (s, 1H), 7.35-7.20 (m, 3H), 7.29 (s, 1H), 6.40-6.24 (m, 1H), 4.67 (dd, J=13.41, 5.22 Hz, 1H), 4.14 (td, J=12.65, 4.06 Hz, 1H), 3.70 (s, 3H), 3.30-2.94 (m, 4H), 2.73 (s, 3H), 2.30 (s, 3H), 2.13 (s, 3H). ESI-MS calculated for $C_{28}H_{28}N_5O_4$ $[M+H]^+$=498.21; Observed: 498.33

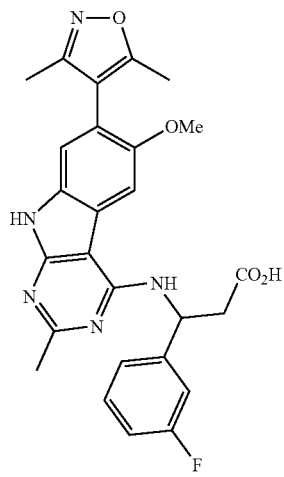

Cpd. No. 239

3-((7-(3,5-Dimethylisoxazol-4-yl)-6-methoxy-2-methyl-9H-pyrimido[4,5-b]indol-4-yl)amino)-3-(3-fluorophenyl)propanoic acid (Cpd. No. 239)

S13 (68 mg), 3-amino-3-(3-fluorophenyl)propanoic acid (80 mg), $NaHCO_3$ (100 mg) and anhydrous DMSO (3 mL) were heated at 130° C. for overnight. The mixture was then purified by reverse phase HPLC to yield Cpd. No. 239 as a $CF_3CO_2H$ salt in 48 mg (41% yield). $^1$H NMR (300 MHz, MeOD-d4): 8.00 (s, 1H), 7.46 (s, 1H), 7.42-7.24 (m, 3H), 7.10-6.96 (m, 1H), 6.13 (t, J=6.00 Hz, 1H), 3.97 (s, 3H), 3.23 (d, J=6.1 Hz, 1H) 2.68 (s, 3H), 2.32 (s, 3H), 2.15 (s, 3H). ESI-MS calculated for $C_{26}H_{25}FN_5O_4$ $[M+H]^+$=490.19; Observed: 490.17.

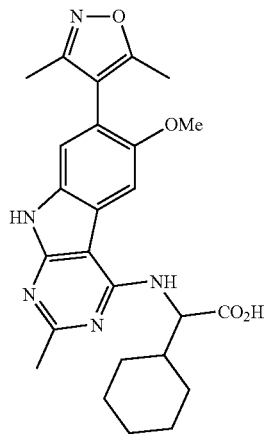

Cpd. No. 240

2-Cyclohexyl-2-((7-(3,5-dimethylisoxazol-4-yl)-6-methoxy-2-methyl-9H-pyrimido[4,5-b]indol-4-yl)amino)acetic acid (Cpd. No. 240)

S13 (68 mg), 2-amino-2-cyclohexylacetic acid (80 mg), $NaHCO_3$ (100 mg) and anhydrous DMSO (3 mL) were heated at 130° C. for overnight. The mixture was then purified by reverse phase HPLC to yield Cpd. No. 240 as a $CF_3CO_2H$ salt in 47 mg (41% yield). $^1$H NMR (300 MHz, MeOD-d4): 7.93 (s, 1H), 7.45 (s, 1H), 5.05 (d, J=7.32 Hz, 1H), 3.97 (s, 3H), 3.30 (s, 3H), 2.72 (s, 3H), 2.33 (s, 3H), 2.30-2.10 (m, 1H), 2.16 (s, 3H), 2.04-1.90 (m, 2H), 1.90-1.64 (m, 3H), 1.50-1.10 (m, 5H). ESI-MS calculated for $C_{25}H_{30}N_5O_4$ $[M+H]^+$=464.23; Observed: 464.33.

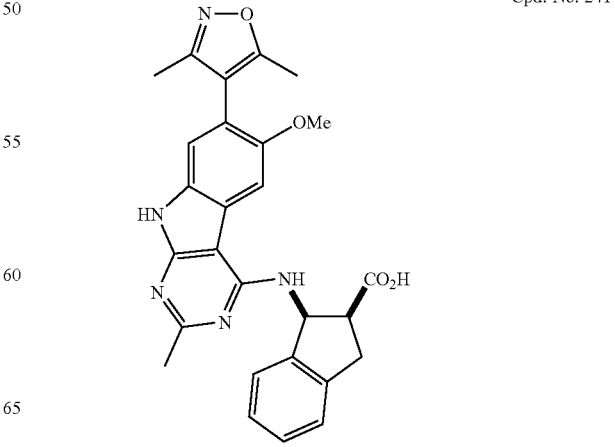

Cpd. No. 241 cis-1-((7-(3,5-Dimethylisoxazol-4-yl)-6-methoxy-2-methyl-9H-pyrimido[4,5-b]indol-4-yl)amino)-2,3-dihydro-1H-indene-2-carboxylic acid (Cpd. No. 241)

S13 (68 mg), cis-1-amino-2,3-dihydro-1H-indene-2-carboxylic acid (80 mg), NaHCO₃ (100 mg) and anhydrous DMSO (3 mL) were heated at 130° C. for overnight. The mixture was then purified by reverse phase HPLC to yield Cpd. No. 241 as a CF₃CO₂H salt in 47 mg (28% yield). ¹H NMR (300 MHz, MeOD-d4): 7.81 (s, 1H), 7.44 (s, 1H), 7.40-7.20 (m, 4H), 6.43 (d, J=7.68 Hz, 1H), 3.90-3.80 (m, 1H), 3.89 (s, 3H), 3.59 (dd, J=16.21, 4.90 Hz, 1H), 3.42-3.30 (m, 1H), 2.78 (s, 3H), 2.30 (s, 3H), 2.13 (s, 3H). ESI-MS calculated for $C_{27}H_{26}N_5O_4$ [M+H]⁺=484.20; Observed: 484.42.

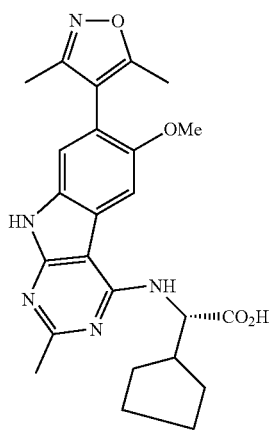

Cpd. No. 242

(2S)-2-Cyclopentyl-2-((7-(3,5-dimethylisoxazol-4-yl)-6-methoxy-2-methyl-9H-pyrimido[4,5-b]indol-4-yl)amino)acetic acid (Cpd. No. 242)

S13 (68 mg), (S)-2-amino-2-cyclopentylacetic acid (56 mg), NaHCO₃ (100 mg) and anhydrous DMSO (3 mL) were heated at 130° C. for overnight. The mixture was then purified by reverse phase HPLC to yield Cpd. No. 242 as a CF₃CO₂H salt in 47 mg (38% yield). ¹H NMR (300 MHz, MeOD-d4): 7.99 (s, 1H), 7.44 (s, 1H), 4.97 (d, J=9.56 Hz, 1H), 3.97 (s, 3H), 2.76-7.62 (m, 1H), 2.70 (s, 3H), 2.33 (s, 3H), 2.16 (s, 3H), 2.06-1.90 (m, 2H), 1.84-1.42 (m, 6H). ESI-MS calculated for $C_{24}H_{28}N_5O_4$ [M+H]⁺=450.21; Observed: 450.33.

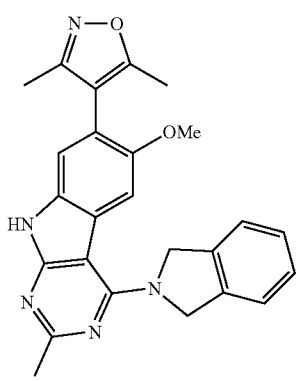

Cpd. No. 243

4-(4-(Isoindolin-2-yl)-6-methoxy-2-methyl-9H-pyrimido[4,5-b]indol-7-yl)-3,5-dimethyl-isoxazole (Cpd. No. 243)

S13 (68 mg), isoindoline (70 mg), NaHCO₃ (100 mg) and anhydrous DMSO (3 mL) were heated at 130° C. for overnight. The mixture was then purified by reverse phase HPLC to yield Cpd. No. 243 as a CF₃CO₂H salt in 5 mg (5% yield). ¹H NMR (300 MHz, MeOD-d4): 8.04 (s, 1H), 7.60-7.50 (m, 2H), 7.46 (s, 1H), 7.45-7.35 (m, 2H), 5.68 (s, 4H), 4.03 (s, 3H), 2.76 (s, 3H), 2.36 (s, 3H), 2.20 (s, 3H). ESI-MS calculated for $C_{25}H_{24}N_5O_2$ [M+H]⁺=426.19; Observed: 426.42.

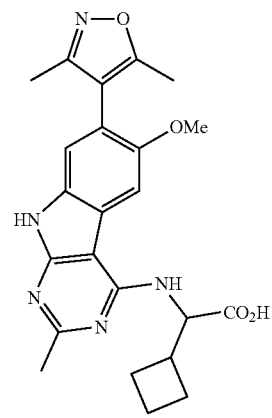

Cpd. No. 244

2-Cyclobutyl-2-((7-(3,5-dimethylisoxazol-4-yl)-6-methoxy-2-methyl-9H-pyrimido[4,5-b]indol-4-yl)amino)acetic acid (Cpd. No. 244)

S13 (68 mg), 2-amino-2-cyclobutylacetic acid (60 mg), NaHCO₃ (100 mg) and anhydrous DMSO (3 mL) were heated at 130° C. for overnight. The mixture was then purified by reverse phase HPLC to yield Cpd. No. 244 as a CF₃CO₂H salt in 32 mg (29% yield). ¹H NMR (300 MHz, MeOD-d4): 8.00 (s, 1H), 7.44 (s, 1H), 5.13 (d, J=10.19 Hz, 1H), 3.96 (s, 3H), 3.30-3.00 (m, 1H), 2.71 (s, 3H), 2.40-2.10 (m, 3H), 2.32 (s, 3H), 2.10-1.80 (m, 3H), 2.15 (s, 3H). ESI-MS calculated for $C_{23}H_{26}N_5O_4$ [M+H]=436.20; Observed: 436.58.

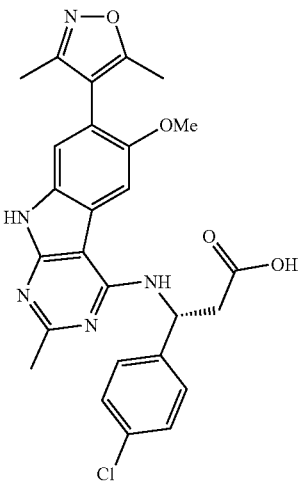

Cpd. No. 245

(3R)-3-(4-Chlorophenyl)-3-((7-(3,5-dimethylisoxazol-4-yl)-6-methoxy-2-methyl-9H-pyrimido[4,5-b]indol-4-yl)amino)propanoic acid (Cpd. No. 245)

S13 (68 mg), (R)-3-amino-3-(4-chlorophenyl)propanoic acid (80 mg), NaHCO$_3$ (100 mg) and anhydrous DMSO (3 mL) were heated at 130° C. for overnight. The mixture was then purified by reverse phase HPLC to yield Cpd. No. 245 as a CF$_3$CO$_2$H salt in 35 mg (29% yield). $^1$H NMR (300 MHz, MeOD-d4): δ3.00 (s, 1H), 7.51 (d, 1H, J=8.6 Hz), 7.46 (s, 1H), 7.36 (d, 1H, J=8.5 Hz), 6.11 (t, J=5.95 Hz, 1H), 3.97 (s, 3H), 3.22 (d, J=6.06 Hz, 2H), 2.68 (s, 3H), 2.31 (s, 3H), 2.14 (s, 3H). ESI-MS calculated for C$_{26}$H$_{25}$$^{35}$ClN$_5$O$_4$ [M+H]$^+$=506.16; Observed: 506.67.

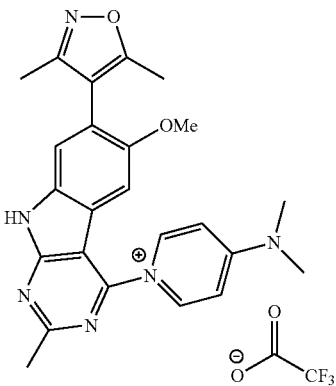

Cpd. No. 246

4-(Dimethyl amino)-1-(7-(3,5-dimethylisoxazol-4-yl)-6-methoxy-2-methyl-9H-pyrimido[4,5-b]indol-4-yl)pyridin-1-ium 2,2,2-trifluoroacetate (Cpd. No. 246)

S13 (70 mg), 3-methyl-4-phenyl-1H-pyrozol-5-amine (40 mg), EtN(i-Pr)$_2$ (0.2 mL), 4-dimethylaminopyridine (4 mg), and anhydrous DMSO (3 mL) were heated at 130° C. for overnight. The mixture was then purified by reverse phase HPLC to yield Cpd. No. 246 in 14 mg (78% yield). $^1$H NMR (300 MHz, MeOD-d4): 8.86 (d, J=8.02 Hz, 2H), 7.48 (s, 1H), 7.37 (d, J=8.02 Hz, 2H), 7.34 (s, 1H), 3.83 (s, 3H), 3.45 (s, 6H), 2.83 (s, 3H), 2.32 (s, 3H), 2.14 (s, 3H). ESI-MS calculated for C$_{24}$H$_{25}$N$_6$O$_2$ [M]=429.20; Observed: 429.42.

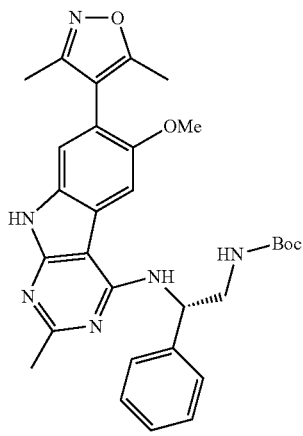

CE214 tert-Butyl ((2S)-2-((7-(3,5-dimethylisoxazol-4-yl)-6-methoxy-2-methyl-9H-pyrimido[4,5-b]indol-4-yl)amino)-2-phenyl ethyl)carbamate (CE214)

S13 (684 mg), amine (708 mg), NaHCO$_3$ (600 mg) and anhydrous DMSO (10 mL) were heated at 130° C. for 16 h. The mixture was diluted with water and the aqueous layer was extracted with ethyl acetate. The combined organic layers were washed with brine, dried and concentrated on a rotary evaporator. The remaining residue was then purified by flash column chromatography to yield CE214 in 320 mg (30% yield). $^1$H NMR (300 MHz, MeOD-d4): 7.90 (s, 1H), 7.48-7.40 (m, 2H), 7.38-7.20 (m, 4H), 5.62-5.50 (m, 1H), 5.26-5.10 (m, 1H), 3.90-3.74 (m, 1H), 3.58-3.46 (m, 1H), 2.58 (s, 3H), 2.34 (s, 3H), 2.21 (s, 3H), 1.38 (s, 9H). ESI-MS calculated for C$_{30}$H$_{35}$N$_6$O$_4$ [M+H]$^+$=543.27; observed: 543.33.

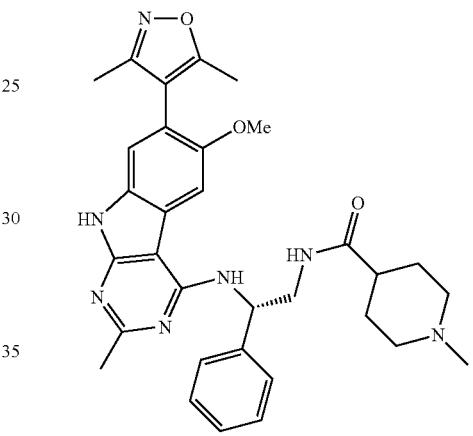

Cpd. No. 247

N-((2S)-2-((7-(3,5-Dimethylisoxazol-4-yl)-6-methoxy-2-methyl-9H-pyrimido[4,5-b]indol-4-yl)amino)-2-phenylethyl)-1-methylpiperidine-4-carboxamide (Cpd. No. 247)

Step 1: CE214 (120 mg, 0.22 mmol) was dissolved in CH$_2$Cl$_2$—CF$_3$CO$_2$H (10 mL 2:3) followed by addition of triethylsilane (0.1 mL). The reaction mixture was stirred at ambient temperature for 2 h. The volatile components were removed on a rotary evaporator and the remaining residue was used for next step without further purification.

Step 2: The previous crude residue from step 1, 1-methylpiperidine-4-carboxylic acid (90 mg, 0.6 mmol), EDCI-HCl (191 mg, 1 mmol) and HOBt (135 mg, 1 mmol) were dissolved in anhydrous DMF (3 mL) followed by addition of EtN(i-Pr)$_2$ (0.5 mL). The reaction mixture was stirred at ambient temperature for overnight and the mixture was then purified by reverse phase HPLC to yield the title compound as a salt of CF$_3$CO$_2$H in 80 mg (59% e yield). $^1$H NMR (300 MHz, MeOD-d4): 8.32 (s, 1H), 7.45 (s, 1H), 7.45-7.24 (m, 5H), 5.77 (dd, J=5.97, 3.71 Hz, 1H), 4.11 (s, 3H), 3.92-3.80 (m, 2H), 3.57-3.46 (m, 2H), 3.04-2.90 (m, 2H), 2.82 (s, 3H), 2.56-2.44 (m, 1H), 2.56 (s, 3H), 2.33 (s, 3H), 2.16 (s, 3H), 2.04-1.82 (m, 4H). ESI-MS calculated for C$_{32}$H$_{38}$N$_7$O$_3$ [M+H]$^+$=568.30; observed: 568.33.

313

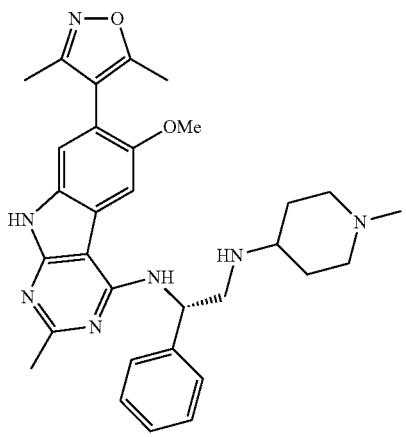

Cpd. No. 248

(1S)—N1-(7-(3,5-Dimethylisoxazol-4-yl)-6-methoxy-2-methyl-9H-pyrimido[4,5-b]indol-4-yl)-N2-(1-methylpiperidin-4-yl)-1-phenylethane-1,2-diamine (Cpd. No. 248)

Step 1: Cpd. No. 228 (70 mg, 0.158 mmol) was dissolved in DMSO (5 mL) followed by addition of IBX (200 mg). The mixture was stirred at ambient temperature for overnight. NaHCO$_3$ saturate solution was added and the aqueous layer was extracted with ethyl acetate. The combined organic layers were washed with brine, dried and concentrated on a rotary evaporator. The remaining residue containing (2S)-2-((7-(3,5-dimethylisoxazol-4-yl)-6-methoxy-2-methyl-9H-pyrimido[4,5-b]indol-4-yl)amino)-2-phenylacetaldehyde was used directly for the next step.

Step 2: the previous crude aldehyde residue from step 1, N-methylpiperidin-4-amine (60 mg) and acetic acid (0.2 mL) were dissolved in anhydrous THF (4 mL) followed by addition of NaBH(OAc)$_3$ (400 mg, 2 mmol). The reaction mixture was stirred at ambient temperature for overnight. The volatile components were removed on a rotary evaporator and the residue was purified on reverse phase HPLC to yield the title compound Cpd. No. 248 as a salt of CF$_3$CO$_2$H in 55 mg (53% yield). $^1$H NMR (300 MHz, MeOD-d4): 8.11 (s, 1H), 7.68-7.60 (m, 2H), 7.48-7.30 (m, 3H), 7.43 (s, 1H), 6.44 (dd, J=10.66, 3.07 Hz, 1H), 4.10 (t, J=11.86 Hz, 1H), 3.96 (s, 3H), 3.77 (dd, J=12.87, 3.43 Hz, 1H), 3.72-3.58 (m, 3H), 3.22-3.06 (m, 2H), 2.88 (s, 3H), 2.72 (s, 3H), 2.58-2.40 (m, 2H), 2.31 (s, 3H), 2.14 (s, 3H), 2.12-2.00 (m, 2H). ESI-MS calculated for C$_{31}$H$_{38}$N$_7$O$_2$ [M+H]$^+$=540.31; observed: 540.33.

314

7-(3,5-Dimethylisoxazol-4-yl)-6-methoxy-2-methyl-N—((S)-2-(4-methylpiperazin-1-yl)-1-phenylethyl)-9H-pyrimido[4,5-b]indol-4-amine (Cpd. No. 249)

Following the method for the preparation of Cpd. No. 248, 80 mg of (2S)-2-((7-(3,5-dimethylisoxazol-4-yl)-6-methoxy-2-methyl-9H-pyrimido[4,5-b]indol-4-yl)amino)-2-phenylacetaldehyde was prepared and placed in a round-bottom flask. 1-Methylpiperazine (60 mg, 0.6 mmol), acetic acid (0.1 mL), and NaBH(OAc)$_3$ (212 mg, 1.0 mmol) were subsequently added and the reaction mixture was stirred at ambient temperature for overnight. The volatile components were removed on a rotary evaporator and the residue was purified on reverse phase HPLC to yield the title compound Cpd. No. 249 as a salt of CF$_3$CO$_2$H in 22 mg (17% yield). CE222 was also isolated as a salt of CF$_3$CO$_2$H in 30 mg (37% yield). $^1$H NMR (300 MHz, MeOD-d4): 8.05 (s, 1H), 7.62-7.55 (m, 2H), 7.44 (s, 1H), 7.45-7.30 (m, 3H), 6.28 (dd, J=10.60, 4.35 Hz, 1H), 3.96 (s, 3H), 3.68 (dd, J=13.14, 10.70 Hz, 1H), 3.50-3.22 (m, 9H), 2.88 (s, 3H), 2.70 (s, 3H), 2.31 (s, 3H), 2.14 (s, 3H). ESI-MS calculated for C$_{30}$H$_{36}$N$_7$O$_2$ [M+H]$^+$=526.29; observed: 526.58.

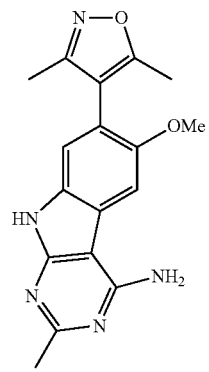

CE22

7-(3,5-Dimethylisoxazol-4-yl)-6-methoxy-2-methyl-9H-pyrimido[4,5-b]indol-4-amine (CE222)

$^1$H NMR (300 MHz, MeOD-d4): 8.00 (s, 1H), 7.41 (s, 1H), 3.95 (s, 3H), 2.69 (s, 3H), 2.32 (s, 3H), 2.15 (s, 3H). ESI-MS calculated for C$_{17}$H$_{18}$N$_5$O$_2$ [M+H]$^+$=324.15; observed: 324.25.

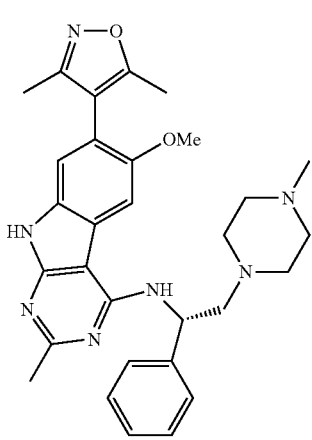

Cpd. No. 249

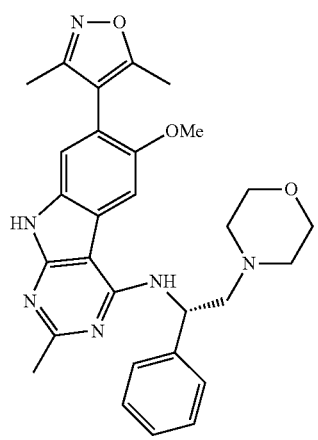

Cpd. No. 250

7-(3,5-Dimethylisoxazol-4-yl)-6-methoxy-2-methyl-N—((S)-2-morpholino-1-phenylethyl)-9H-pyrimido[4,5-b]indol-4-amine (Cpd. No. 250)

Following the method for the preparation of Cpd. No. 248, 80 mg of (2S)-2-((7-(3,5-dimethylisoxazol-4-yl)-6-methoxy-2-methyl-9H-pyrimido[4,5-b]indol-4-yl)amino)-2-phenylacetaldehyde was prepared and placed in a round-bottom flask. Morpholine (54 mg, 0.6 mmol), acetic acid (0.1 mL), and NaBH(OAc)$_3$ (212 mg, 0.5 mmol) were subsequently added and the reaction mixture was stirred at ambient temperature for overnight. The volatile components were removed on a rotary evaporator and the residue was purified on reverse phase HPLC to yield the title compound Cpd. No. 250 as a salt of CF$_3$CO$_2$H in 19 mg (15% yield). CE222 was also isolated as side product. $^1$H NMR (300 MHz, MeOD-d4): 8.06 (s, 1H), 7.64-7.53 (m, 2H), 7.50-7.35 (m, 3H), 7.43 (s, 1H), 6.66 (dd, J=11.63, 2.98 Hz, 1H), 4.17 (dd, J=13.25, 11.83 Hz, 1H), 3.98-3.83 (m, 5H), 3.96 (s, 3H), 3.80-3.55 (m, 2H), 3.55-3.40 (m, 2H), 2.73 (s, 3H), 2.31 (s, 3H), 2.14 (s, 3H). ESI-MS calculated for C$_{29}$H$_{33}$N$_6$O$_3$ [M+H]$^+$=513.26; observed: 513.17.

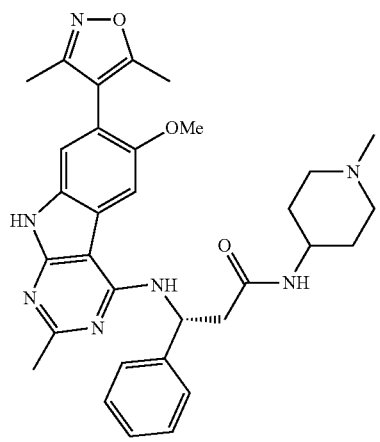

(3R)-3-((7-(3,5-Dimethylisoxazol-4-yl)-6-methoxy-2-methyl-9H-pyrimido[4,5-b]indol-4-yl)amino)-N-(1-methylpiperidin-4-yl)-3-phenylpropanamide (Cpd. No. 251)

Cpd. No. 251 was prepared from Cpd. No. 232 (46 mg) and N-methylpiperidin-4-amine (40 mg) using general amide condensation method promoted by EDCI-HCl. The reaction mixture was purified by reverse phase HPLC to yield Cpd. No. 251 as a CF$_3$CO$_2$H salt in 51 mg (75% yield). $^1$H NMR (300 MHz, MeOD-d4): 8.17 (s, 1H), 7.47 (s, 1H), 7.47-7.42 (m, 2H), 7.38-7.25 (m, 3H), 5.95 (t, J=4.72 Hz, 1H), 4.03 (s, 1H), 4.00-3.82 (m, 1H), 3.55-3.40 (m, 2H), 3.14-2.90 (m, 4H), 2.82 (s, 1H), 2.63 (s, 1H), 2.34 (s, 1H), 2.17 (s, 1H), 2.12-1.80 (m, 2H), 1.74-1.58 (m, 1H), 1.54-1.36 (m, 1H). ESI-MS calculated for C$_{32}$H$_{38}$N$_7$O$_3$ [M+H]$^+$=568.30; observed: 568.25.

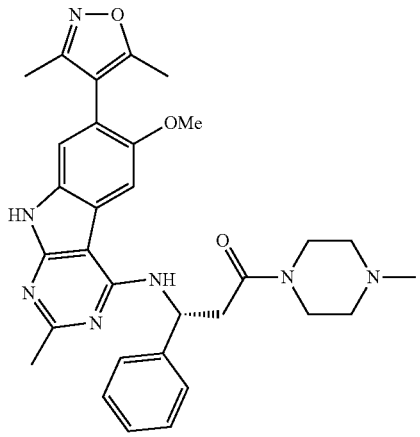

(3R)-3-((7-(3,5-Dimethylisoxazol-4-yl)-6-methoxy-2-methyl-9H-pyrimido[4,5-b]indol-4-yl)amino)-1-(4-methylpiperazin-1-yl)-3-phenylpropan-1-one (Cpd. No. 252)

Cpd. No. 252 was prepared from Cpd. No. 232 (40 mg) and 1-methylpiperazine (30 mg) using general amide condensation method promoted by EDCI-HCl. The reaction mixture was purified by reverse phase HPLC to yield Cpd. No. 252 as a CF$_3$CO$_2$H salt in 40 mg (70% yield). $^1$H NMR (300 MHz, MeOD-d4): 8.07 (s, 1H), 7.56-7.48 (m, 2H), 7.46 (s, 1H)), 7.46-7.26 (m, 3H), 6.09 (t, J=4.30 Hz, 1H), 4.80-4.60 (m, 1H), 4.20-4.00 (m, 1H), 4.01 (s, 3H), 3.58 (dd, J=15.73, 4.78 Hz, 1H), 3.53-2.60 (m, 8H), 2.46 (s, 3H), 2.32 (s, 3H), 2.15 (s, 3H). ESI-MS calculated for C$_{31}$H$_{36}$N$_7$O$_3$ [M+H]$^+$=554.29; observed: 554.33.

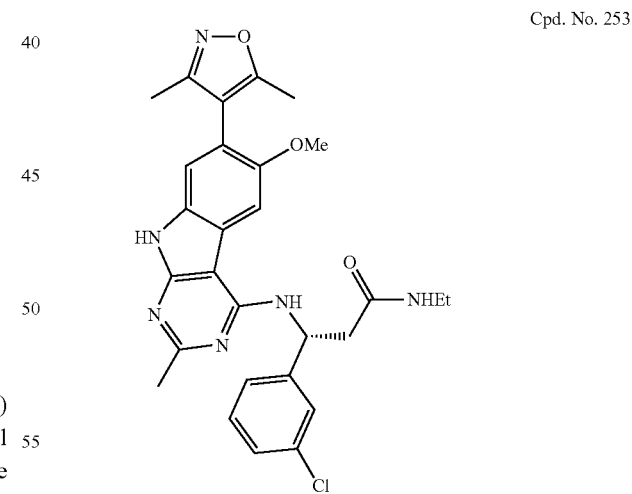

(3R)-3-(3-Chlorophenyl)-3-((7-(3,5-dimethylisoxazol-4-yl)-6-methoxy-2-methyl-9H-pyrimido[4,5-b]indol-4-yl)amino)-N-ethylpropanamide (Cpd. No. 253)

Cpd. No. 253 was prepared from Cpd. No. 236 (30 mg) and ethyl amine (0.4 mmol, 0.2 mL of 2M solution in THF) using general amide condensation method promoted by EDCI-HCl. The reaction mixture was purified by reverse phase HPLC to yield Cpd. No. 253 as a CF$_3$CO$_2$H salt in 33 mg (85% yield). $^1$H NMR (300 MHz, MeOD-d4): 8.19 (s, 1H), 7.49 (s, 2H), 7.45-7.20 (m, 3H), 5.92 (t, J=4.69 Hz, 1H), 4.06 (s, 3H), 3.30-3.10 (m, 2H), 3.10 (dd, J=14.69, 5.09 Hz, 1H), 2.91 (dd, J=14.69, 4.52 Hz, 1H), 2.66 (s, 3H), 2.36 (s, 3H), 2.19 (s, 3H), 1.02 (t, J=7.26 Hz, 3H). ESI-MS calculated for C$_{28}$H$_{30}$$^{35}$ClN$_6$O$_3$ [M+H]$^+$=533.21; Observed: 533.62.

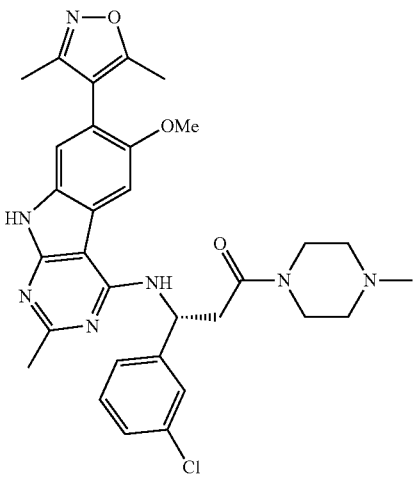

Cpd. No. 254

(3R)-3-(3-Chlorophenyl)-3-((7-(3,5-dimethylisoxazol-4-yl)-6-methoxy-2-methyl-9H-pyrimido[4,5-b]indol-4-yl)amino)-1-(4-methylpiperazin-1-yl)propan-1-one (Cpd. No. 254)

Cpd. No. 254 was prepared from Cpd. No. 236 (40 mg) and 1-methylpiperazine (30 mg) using general amide condensation method promoted by EDCI-HCl. The reaction mixture was purified by reverse phase HPLC to yield Cpd. No. 254 as a CF$_3$CO$_2$H salt in 41 mg (72% yield). $^1$H NMR (300 MHz, MeOD-d4): 8.02 (s, 1H), 7.60-7.56 (m, 1H), 7.50-7.28 (m, 3H), 7.46 (s, 1H), 6.11 (t, J=4.99 Hz, 1H), 4.00 (s, 3H), 3.70-2.80 (br, 8H), 3.56 (dd, J=16.14, 5.42 Hz, 1H), 3.24 (dd, J=16.14, 4.97 Hz, 1H), 2.67 (s, 3H), 2.32 (s, 3H), 2.15 (s, 3H). ESI-MS calculated for C$_{31}$H$_{35}$$^{35}$ClN$_7$O$_3$ [M+H]$^+$=588.25; Observed: 588.58.

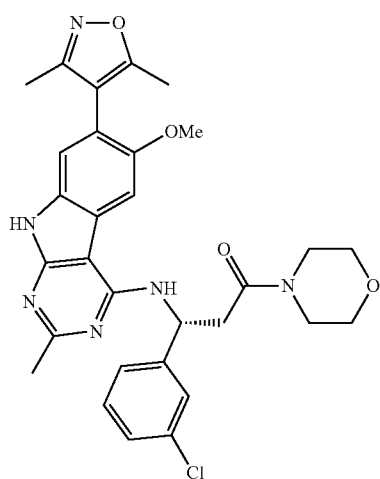

Cpd. No. 255

(3R)-3-(3-Chlorophenyl)-3-((7-(3,5-dimethylisoxazol-4-yl)-6-methoxy-2-methyl-9H-pyrimido[4,5-b]indol-4-yl)amino)-1-morpholinopropan-1-one (Cpd. No. 255)

Cpd. No. 255 was prepared from Cpd. No. 236 (40 mg) and morpholine (27 mg) using general amide condensation method promoted by EDCI-HCl. The reaction mixture was purified by reverse phase HPLC to yield Cpd. No. 255 as a CF$_3$CO$_2$H salt in 31 mg (56% yield). $^1$H NMR (300 MHz, MeOD-d4): 8.07 (s, 1H), 7.56-7.26 (m, 4H), 7.47 (s, 1H), 6.02 (t, J=4.73 Hz, 1H), 4.01 (s, 3H), 3.70-3.20 (m, 8H), 3.20-3.00 (m, 2H), 2.65 (s, 3H), 2.32 (s, 3H), 2.15 (s, 3H). ESI-MS calculated for C$_{30}$H$_{32}$$^{35}$ClN$_6$O$_4$ [M+H]$^+$=575.22; Observed: 575.62.

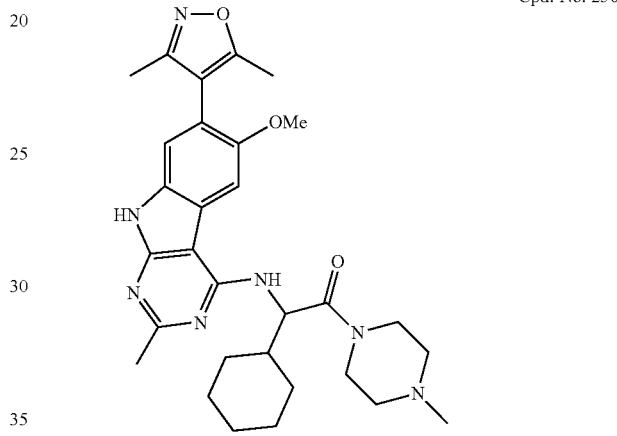

Cpd. No. 256

2-Cyclohexyl-2-((7-(3,5-dimethylisoxazol-4-yl)-6-methoxy-2-methyl-9H-pyrimido[4,5-b]indol-4-yl)amino)-1-(4-methylpiperazin-1-yl)ethanone (Cpd. No. 256)

Cpd. No. 256 was prepared from Cpd. No. 240 (36 mg) and 1-methylpiperazine (38 mg) using general amide condensation method promoted by EDCI-HCl. The reaction mixture was purified by reverse phase HPLC to yield Cpd. No. 256 as a CF$_3$CO$_2$H salt in 17 mg (33% yield). $^1$H NMR (300 MHz, MeOD-d4): 7.99 (s, 1H), 7.48 (s, 1H), 4.00 (s, 3H), 5.70-5.50 (m, 1H), 3.90-3.00 (m, 8H), 2.98 (s, 3H), 2.77 (s, 3H), 2.34 (s, 3H), 2.30-2.10 (m, 1H), 2.17 (s, 3H), 2.10-1.95 (m, 1H), 1.95-1.65 (m, 4H), 1.50-1.10 (m, 5H). ESI-MS calculated for C$_{30}$H$_{40}$N$_7$O$_3$ [M+H]$^+$=546.32; Observed: 546.42.

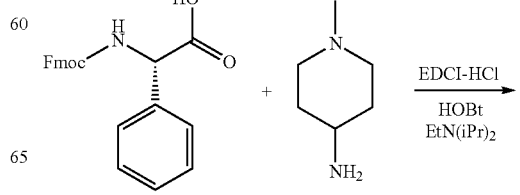

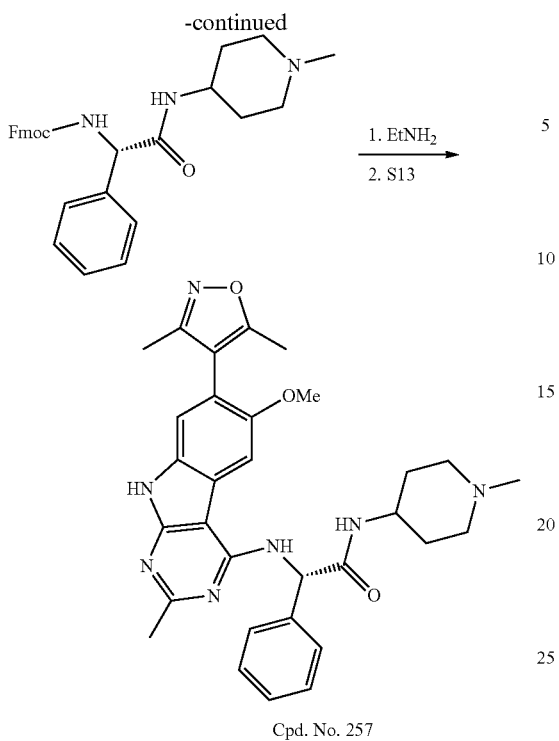

Cpd. No. 257

(2S)-2-((7-(3,5-Dimethylisoxazol-4-yl)-6-methoxy-2-methyl-9H-pyrimido[4,5-b]indol-4-yl)amino)-N-(1-methylpiperidin-4-yl)-2-phenylacetamide (Cpd. No. 257)

Step 1: Fmoc-L-phenylglycine (740 mg, 2.0 mmol), EDCI-HCl (600 mg, 3.0 mmol) and HOBt (405 mg, 3.0 mmol) were dissolved in dichloromethane (10 mL). EtN(i-Pr)$_2$ (0.5 mL) and N-methylpiperidin-4-amine (228 mg, 2.0 mmol) were sequentially added via syringes. The mixture was stirred at ambient temperature for 4 h. Water was added and the aqueous layer was extracted with ethyl acetate. The organic layers were combined, dried and concentrated on a rotary evaporator. The remaining residue was used directly for the next step.

Step 2: The previous residue from step 1 was dissolved in THF (10 mL). EtNH$_2$ (5 mL, 2.0 M in THF) was added via a syringe and the mixture was stirred for 12 h. The volatile components were removed on a rotary evaporator. The remaining residue was vacuumed for 1 day and used directly for the next step.

Step 3: The previous residue from step 2 was dissolved in anhydrous DMSO (6 mL). NaHCO$_3$ (200 mg) and S13 (400 mg, 1.17 mmol) were added and the mixture was heated at 130° C. for overnight. Water (2 mL) was added and the mixture was filtered. The solution was purified by reverse phase HPLC to yield the title compound Cpd. No. 257 as a salt of CF$_3$CO$_2$H in 55 mg (7% yield). $^1$H NMR (300 MHz, MeOD-d4): 7.87 (s, 1H), 7.68-7.60 (m, 2H), 7.54 (s, 1H), 7.54-7.34 (m, 3H), 6.13 (s, 1H), 4.12-4.00 (m, 1H), 3.95 (s, 3H), 3.64-3.48 (m, 2H), 3.26-3.00 (m, 3H), 2.86 (s, 3H), 2.70 (s, 3H), 2.31 (s, 3H), 2.30-2.00 (m, 3H), 2.14 (s, 3H), 1.96-1.66 (m, 2H). ESI-MS calculated for C$_{31}$H$_{36}$N$_7$O$_3$ [M+H]$^+$=554.29; observed: 554.17.

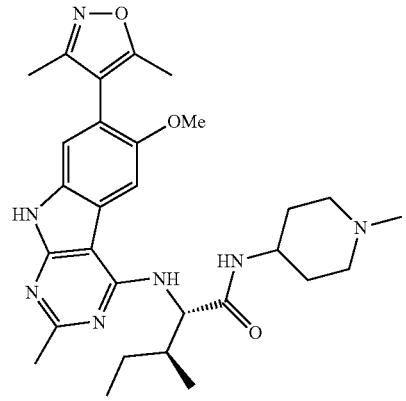

Cpd. No. 258

(2S,3S)-2-((7-(3,5-Dimethylisoxazol-4-yl)-6-methoxy-2-methyl-9H-pyrimido[4,5-b]indol-4-yl)amino)-3-methyl-N-(1-methylpiperidin-4-yl)pentanamide (Cpd. No. 258)

Cpd. No. 258 was prepared from Cpd. No. 231 (43 mg) and N-methylpiperidin-4-amine (36 mg) using general amide condensation method promoted by EDCI-HCl. The reaction mixture was purified by reverse phase HPLC to yield Cpd. No. 258 as a CF$_3$CO$_2$H salt in 15 mg (23% yield). ESI-MS calculated for C$_{29}$H$_{40}$N$_7$O$_3$ [M+H]$^+$=534.32; observed: 534.08.

4-(6-Methoxy-2-methyl-4-(4-((4-(methylsulfonyl)piperazin-1-yl)methyl)naphthalen-1-yl)-9H-pyrimido[4,5-b]indol-7-yl)-3,5-dimethylisoxazole (Cpd. No. 259)

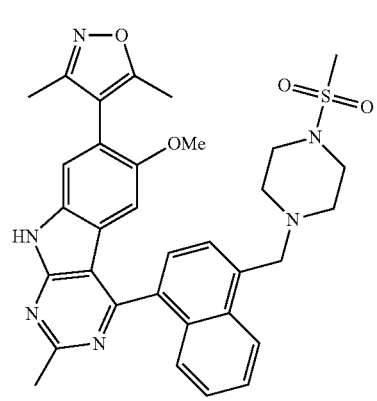

Cpd. No. 259

CE194 (46 mg), 1-(methylsulfonyl)piperazine (48 mg, 0.3 mmol), and acetic acid (0.1 mL) were dissolved in anhydrous THF (5 mL). NaBH(OAc)$_3$ (110 mg, 0.5 mmol) was added in one portion and the mixture was stirred at ambient temperature for overnight. The volatile components were removed on a rotary evaporator. The remaining residue was purified by reverse phase HPLC to yield the title compound Cpd. No. 259 as a CF$_3$CO$_2$H salt in 71 mg (98% yield). $^1$H NMR (300 MHz, MeOD-d4): 8.31 (d, J=8.47 Hz, 1H), 8.16 (d, J=7.40 Hz, 1H), 8.09 (d, J=7.38 Hz, 1H), 7.90-7.82 (m, 2H), 7.72-7.63 (m, 1H), 7.55 (s, 1H), 6.20 (s, 1H), 5.15 (d, J=13.60 Hz, 1H), 5.09 (d, J=13.74 Hz, 1H), 3.18 (s, 3H), 3.02 (s, 3H), 2.94 (s, 3H), 2.25 (s, 3H), 2.06 (s, 3H). ESI-MS calculated for $C_{33}H_{35}N_6O_4S$ [M+H]$^+$=611.24, Observed: 611.58.

4-(7-(3,5-Dimethylisoxazol-4-yl)-6-methoxy-2-methyl-9H-pyrimido[4,5-b]indol-4-yl)-5-isopropyl-N-methyl-1H-pyrrole-2-carboxamide (Cpd. No. 260)

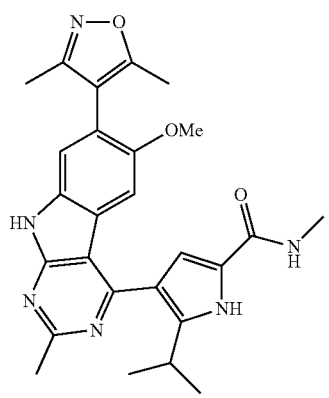

Cpd. No. 260

Cpd. No. 260 was prepared from Cpd. No. 210 (46 mg) and methyl amine-HCl (21 mg) using general amide condensation method promoted by EDCI-HCl. The reaction mixture was purified by reverse phase HPLC to yield Cpd. No. 260 as a $CF_3CO_2H$ salt in 38 mg (65% yield). $^1$H NMR (300 MHz, MeOD-d4): 7.54 (s, 1H), 7.29 (s, 1H), 7.16 (s, 1H), 3.72 (s, 3H), 3.14 (septet, J=6.99 Hz, 1H), 2.93 (s, 3H), 2.92 (s, 3H), 2.31 (s, 3H), 2.13 (s, 3H), 1.28 (d, J=6.97 Hz, 6H). ESI-MS calculated for $C_{26}H_{29}N_6O_3$ [M+H]$^+$=473.23, Observed: 473.44.

(4-(7-(3,5-Dimethylisoxazol-4-yl)-6-methoxy-2-methyl-9H-pyrimido[4,5-b]indol-4-yl)-5-isopropyl-1H-pyrrol-2-yl)(4-hydroxypiperidin-1-yl)methanone (Cpd. No. 261)

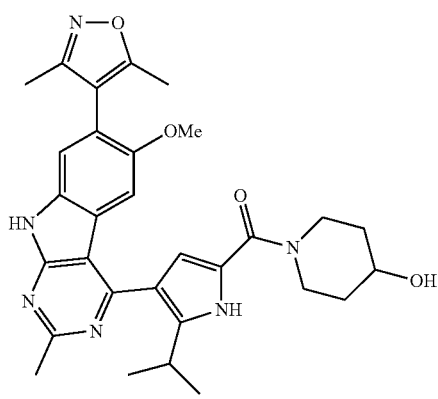

Cpd. No. 261

Cpd. No. 261 was prepared from Cpd. No. 210 (35 mg) and 4-hydroxylpiperidine (30 mg) using general amide condensation method promoted by EDCI-HCl. The reaction mixture was purified by reverse phase HPLC to yield Cpd. No. 261 as a $CF_3CO_2H$ salt in 22 mg (45% yield). $^1$H NMR (300 MHz, MeOD-d4): 7.54 (s, 1H), 7.25 (s, 1H), 6.93 (s, 1H), 4.30-4.18 (m, 2H), 4.00-3.88 (m, 1H), 3.73 (s, 3H), 3.60-3.40 (m, 2H), 3.11 (septet, J=6.98 Hz, 1H), 2.93 (s, 3H), 2.32 (s, 3H), 2.14 (s, 3H), 2.00-1.88 (m, 2H), 1.62-1.46 (m, 2H), 1.28 (d, J=6.98 Hz, 6H). ESI-MS calculated for $C_{30}H_{35}N_6O_4$ [M+H]$^+$=543.27, Observed: 543.92.

4-(7-(3,5-Dimethylisoxazol-4-yl)-6-methoxy-2-methyl-9H-pyrimido[4,5-b]indol-4-yl)-N-(4-hydroxycyclohexyl)-5-isopropyl-1H-pyrrole-2-carboxamide (Cpd. No. 262)

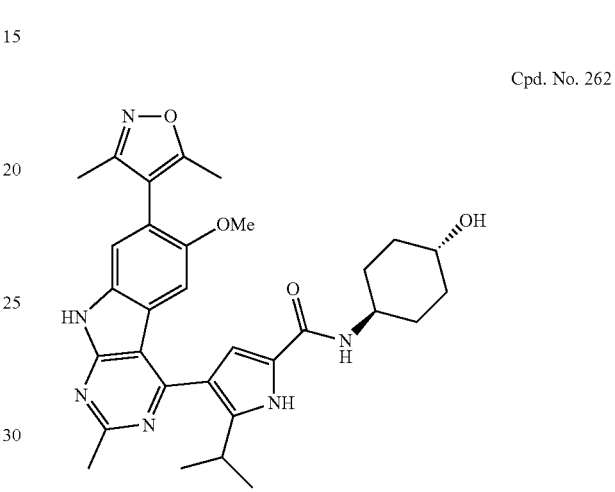

Cpd. No. 262

Cpd. No. 262 was prepared from Cpd. No. 210 (35 mg) and trans-4-aminohexanol (30 mg) using general amide condensation method promoted by EDCI-HCl. The reaction mixture was purified by reverse phase HPLC to yield Cpd. No. 262 as a $CF_3CO_2H$ salt in 28 mg (55% yield). $^1$H NMR (300 MHz, MeOD-d4): 7.54 (s, 1H), 7.31 (s, 1H), 7.26 (s, 1H), 3.94-3.80 (m, 1H), 3.72 (s, 3H), 3.60-3.48 (m, 1H), 3.16 (septet, J=6.97 Hz, 1H), 2.93 (s, 3H), 2.31 (s, 3H), 2.13 (s, 3H), 2.08-1.92 (m, 4H), 1.54-1.36 (m, 4H), 1.29 (d, J=6.96 Hz, 6H). ESI-MS calculated for $C_{31}H_{37}N_6O_4$ [M+H]$^+$=557.29, Observed: 557.33.

4-(7-(3,5-Dimethylisoxazol-4-yl)-6-methoxy-2-methyl-9H-pyrimido[4,5-b]indol-4-yl)-5-isopropyl-N-(oxetan-3-yl)-1H-pyrrole-2-carboxamide (Cpd. No. 263)

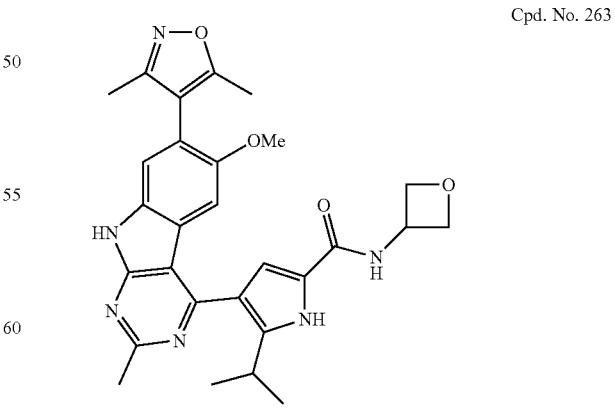

Cpd. No. 263

Cpd. No. 263 was prepared from Cpd. No. 210 (35 mg) and oxetan-3-amine (30 mg) using general amide condensation method promoted by EDCI-HCl. The reaction mixture was purified by reverse phase HPLC to yield Cpd. No.

263 as a CF₃CO₂H salt in 18 mg (38% yield). ¹H NMR (300 MHz, MeOD-d4): 7.80 (s, 1H), 7.56 (s, 1H), 7.11 (s, 1H), 5.15 (t, J=9.55 Hz, 1H), 5.01 (dd, J=9.18, 6.10 Hz, 1H), 4.75-4.65 (m, 1H), 3.87 (dd, J=11.97, 2.81 Hz, 1H), 3.76 (dd, J=11.97, 3.40 Hz, 1H), 3.71 (s, 3H), 3.20 (septet, J=7.01 Hz, 1H), 2.94 (s, 3H), 2.31 (s, 3H), 2.13 (s, 3H), 1.32 (d, J=6.98 Hz, 6H). ESI-MS calculated for $C_{28}H_{31}N_6O_4$ [M+H]⁺=515.24, Observed: 515.25.

4-(7-(3,5-Dimethylisoxazol-4-yl)-6-methoxy-2-methyl-9H-pyrimido[4,5-b]indol-4-yl)-N-((cis)-3-hydroxy-3-methylcyclobutyl)-5-isopropyl-1H-pyrrole-2-carboxamide (Cpd. No. 264)

Cpd. No. 264

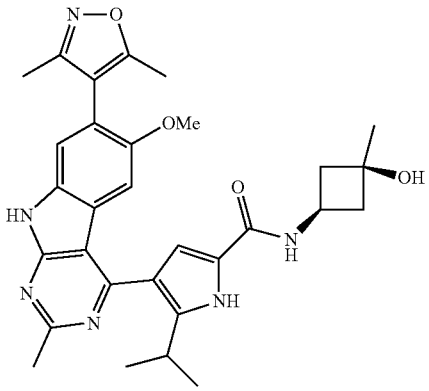

Cpd. No. 210 (35 mg) and (cis)-3-((tert-butyldimethylsilyl)oxy)-3-methylcyclobutanamine (35 mg) were coupled using general amide condensation method promoted by EDCI-HCl. The reaction mixture was treated with CF₃CO₂H (4 mL) and was stirred at room temperature for 2 hours. The mixture was purified by reverse phase HPLC to yield Cpd. No. 264 as a CF₃CO₂H salt in 42 mg (72% yield). ¹H NMR (300 MHz, MeOD-d4): 7.54 (s, 1H), 7.30 (s, 1H), 7.27 (s, 1H), 4.11 (quintet, J=8.30 Hz, 1H), 3.72 (s, 3H), 3.15 (septet, J=6.97 Hz, 1H), 2.93 (s, 3H), 2.56-2.42 (m, 2H), 2.31 (s, 3H), 2.20-2.08 (m, 2H), 2.13 (s, 3H), 1.39 (s, 3H), 1.29 (d, J=6.97 Hz, 6H). ESI-MS calculated for $C_{30}H_{35}N_6O_4$ [M+H]⁺=543.27, Observed: 543.50.

(4-(7-(3,5-Dimethylisoxazol-4-yl)-6-methoxy-2-methyl-9H-pyrimido[4,5-b]indol-4-yl)naphthalen-1-yl)(4-hydroxypiperidin-1-yl)methanone (Cpd. No. 265)

Cpd. No. 265

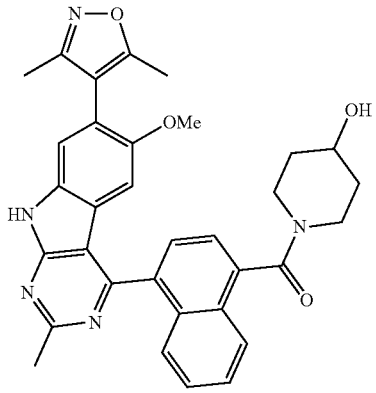

Cpd. No. 265 was prepared from the acid Cpd. No. 165 (48 mg) and 4-hydroxylpiperidine (30 mg) using general amide condensation method promoted by EDCI-HCl. The reaction mixture was purified by reverse phase HPLC to yield Cpd. No. 265 as a CF₃CO₂H salt in 60 mg (89% yield). ¹H NMR (300 MHz, MeOD-d4): 8.16-8.04 (m, 2H), 7.90-7.74 (m, 3H), 7.70-7.60 (m, 1H), 7.58-7.52 (m, 1H), 6.28-6.10 (m, 1H), 4.50-4.30 (m, 1H), 4.10-3.90 (m, 1H), 3.70-3.50 (m, 1H), 3.50-3.35 (m, 1H), 3.21 (s, 3H), 3.03 (s, 3H), 3.02 (s, 3H), 2.26 (s, 3H), 2.20-2.00 (m, 1H), 2.06 (s, 3H), 1.90-1.60 (m, 2H), 1.60-1.20 (m, 1H). ESI-MS calculated for $C_{33}H_{32}N_5O_4$ [M+H]⁺=562.25, Observed: 562.67.

4-(7-(3,5-Dimethylisoxazol-4-yl)-6-methoxy-2-methyl-9H-pyrimido[4,5-b]indol-4-yl)-N-(4-hydroxycyclohexyl)-1-naphthamide (Cpd. No. 266)

Cpd. No. 266

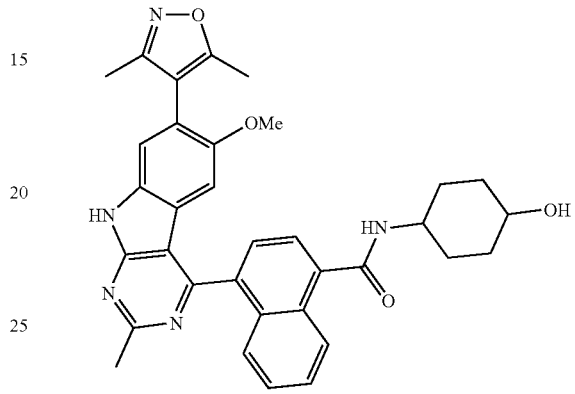

Cpd. No. 266 was prepared from the acid Cpd. No. 165 (48 mg) and trans-4-aminohexanol (40 mg) using general amide condensation method promoted by EDCI-HCl. The reaction mixture was purified by reverse phase HPLC to yield Cpd. No. 266 as a CF₃CO₂H salt in 37 mg (53% yield). ¹H NMR (300 MHz, MeOD-d4): 8.41 (d, J=8.44 Hz, 1H), 8.02 (d, J=7.33 Hz, 1H), 7.89 (d, J=7.28 Hz, 1H), 7.83-7.73 (m, 2H), 7.65-7.58 (m, 1H), 7.53 (s, 1H), 6.17 (s, 1H), 4.10-4.00 (m, 1H), 3.70-3.55 (m, 1H), 3.19 (s, 3H), 3.01 (s, 3H), 2.24-2.12 (m, 2H), 2.10-2.02 (m, 2H), 2.26 (s, 3H), 2.07 (s, 3H), 1.56-1.44 (m, 4H). ESI-MS calculated for $C_{34}H_{34}N_5O_4$ [M+H]⁺=576.26, Observed: 576.58.

(3R)-3-(3-Chlorophenyl)-3-((7-(3,5-dimethylisoxazol-4-yl)-6-methoxy-2-methyl-9H-pyrimido[4,5-b]indol-4-yl)amino)-1-(4-hydroxypiperidin-1-yl)propan-1-one (Cpd. No. 267)

Cpd. No. 267

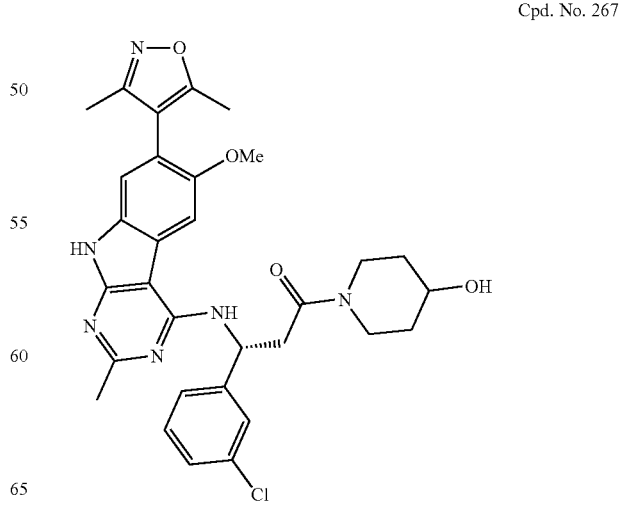

Cpd. No. 267 was prepared from the acid Cpd. No. 236 (40 mg) and 4-hydroxylpiperidine (30 mg) using general amide condensation method promoted by EDCI-HCl. The reaction mixture was purified by reverse phase HPLC to yield Cpd. No. 267 as a $CF_3CO_2H$ salt in 34 mg (60% yield). $^1$H NMR (300 MHz, MeOD-d4): 8.08 (s, 1H), 7.60-7.20 (m, 4H), 7.47 (s, 1H), 6.10-5.90 (m, 1H), 4.20-3.65 (m, 3H), 4.02 (s, 3H), 3.60-3.40 (m, 1H), 3.40-3.00 (m, 3H), 2.66 (s, 3H), 2.33 (s, 3H), 2.17 (s, 3H), 1.90-1.60 (m, 1.5H), 1.50-1.30 (m, 1.5H), 1.30-1.10 (m, 0.5H), 1.00-0.80 (m, 0.5H). ESI-MS calculated for $C_{31}H_{3435}ClN_6O_4$ [M+H]$^+$= 589.23, Observed: 589.58.

(3R)-3-(3-Chlorophenyl)-3-((7-(3,5-dimethylisoxazol-4-yl)-6-methoxy-2-methyl-9H-pyrimido[4,5-b]indol-4-yl)amino)-N-((trans)-4-hydroxycyclohexyl)propanamide (Cpd. No. 268)

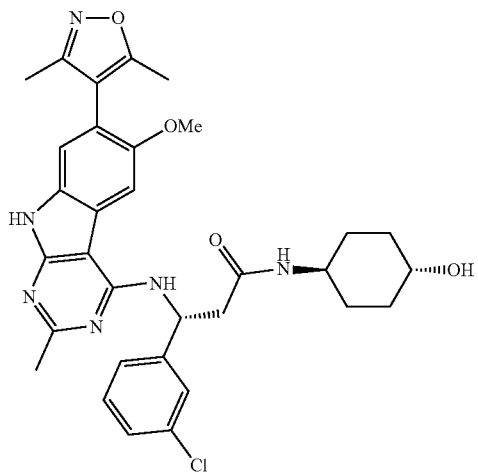

Cpd. No. 268

Cpd. No. 268 was prepared from the acid Cpd. No. 236 (40 mg) and 4-hydroxylpiperidine (33 mg) using general amide condensation method promoted by EDCI-HCl. The reaction mixture was purified by reverse phase HPLC to yield Cpd. No. 268 as a $CF_3CO_2H$ salt in 52 mg (90% yield). $^1$H NMR (300 MHz, MeOD-d4): 8.18 (s, 1H), 7.46 (s, 1H), 7.45 (s, 1H), 7.42-7.30 (m, 3H), 5.89 (t, J=4.70 Hz, 1H), 4.04 (s, 3H), 3.70-3.54 (m, 1H), 3.54-3.40 (m, 1H), 3.05 (dd, J=14.45, 5.15 Hz, 1H), 2.87 (dd, J=14.51, 4.50 Hz, 1H), 2.63 (s, 3H), 2.33 (s, 3H), 2.17 (s, 3H), 2.00-1.60 (m, 4H), 1.40-0.90 (m, 4H). ESI-MS calculated for $C_{32}H_{36}{}^{35}ClN_6O_4$ [M+H]$^+$=603.25, Observed: 603.58.

(3R)-3-((7-(3,5-Dimethylisoxazol-4-yl)-6-methoxy-2-methyl-9H-pyrimido[4,5-b]indol-4-yl)amino)-3-(3-methoxyphenyl)propanoic acid (Cpd. No. 269)

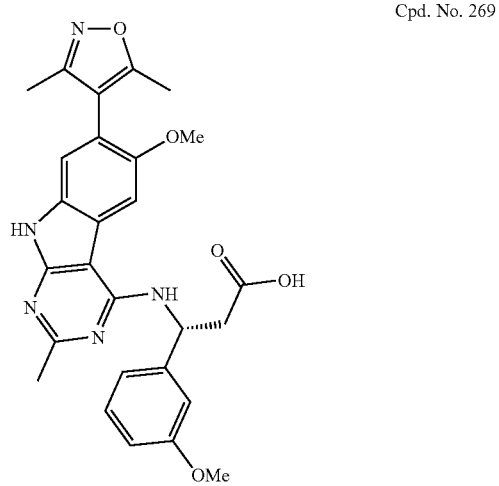 [SMILES: COc1cccc([C@@H](CC(=O)O)Nc2nc(C)nc3[nH]c4cc(-c5c(C)noc5C)c(OC)cc4c23)c1]

Cpd. No. 269

S13 (70 mg), (R)-3-amino-3-(3-methoxyphenyl)propanoic acid (80 mg), NaHCO$_3$ (100 mg) and anhydrous DMSO (3 mL) were heated at 130° C. for overnight. The mixture was then purified by reverse phase HPLC to yield Cpd. No. 269 as a $CF_3CO_2H$ salt in 39 mg (32% yield). $^1$H NMR (300 MHz, MeOD-d4): 8.00 (s, 1H), 7.46 (s, 1H), 7.32-7.22 (m, 1H), 7.12-7.04 (m, 2H), 6.88-6.82 (m, 1H), 6.08 (t, J=5.89 Hz, 1H), 3.97 (s, 3H), 3.77 (s, 3H), 3.21 (d, J=5.95 Hz, 2H), 2.68 (s, 3H), 2.13 (s, 3H), 2.15 (s, 3H). ESI-MS calculated for $C_{27}H_{28}N_5O_5$ [M+H]$^+$=502.21, Observed: 502.34.

(3R)-3-(3-Chlorophenyl)-3-((7-(3,5-dimethylisoxazol-4-yl)-6-methoxy-2-methyl-9H-pyrimido[4,5-b]indol-4-yl)amino)propan-1-ol (Cpd. No. 270)

Step 1: The acid Cpd. No. 236 (220 mg) was dissolved in MeOH (20 mL). Four drops of concentrated $H_2SO_4$ was added via a glass pipet. The reaction mixture was heated at reflux for overnight. The reaction solution was concentrated and treated with NaHCO$_3$ saturated solution and the aqueous layer was extracted with ethyl acetate. The combined organic layers were combined and dried over anhydrous sodium sulfate. The volatile components were removed on a rotary evaporator. The remaining residue was used for the next step without purification.

Step 2: The previous residue was dissolved in ethanol. Sodium borohydride (200 mg) was added at ambient temperature. The mixture was stirred at room temperature for overnight. NaHCO$_3$ saturated aqueous solution was added and the aqueous layer was extracted with ethyl acetate. The combined organic layers were combined and dried over anhydrous sodium sulfate. The volatile components were removed on a rotary evaporator. The remaining residue was purified on a reverse phase HPLC to yield Cpd. No. 270 in 52 mg (56% yield) as a $CF_3CO_2H$ salt.

Cpd. No. 270

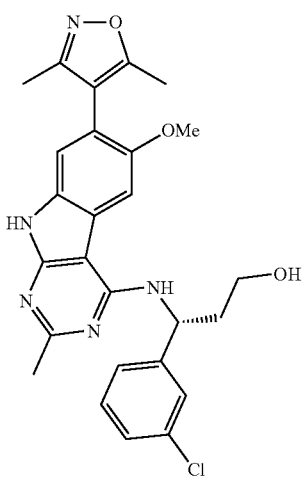

<sup>1</sup>H NMR (300 MHz, MeOD-d4): 7.90 (s, 1H), 7.52 (s, 1H), 7.49 (s, 1H), 7.50-7.20 (m, 3H), 5.87 (t, J=5.07 Hz, 1H), 3.97 (s, 3H), 3.94-3.84 (m, 1H), 3.84-3.72 (m, 1H), 2.64 (s, 3H), 2.60-2.42 (m, 1H), 2.34 (s, 3H), 2.30-2.14 (m, 1H), 2.17 (s, 3H). ESI-MS calculated for $C_{26}H_{2735}ClN_5O_3$ $[M+H]^+$=492.18, Observed: 492.62

4-(4-(1-Isopropyl-1H-pyrazol-5-yl)-6-methoxy-2-methyl-9H-pyrimido[4,5-b]indol-7-yl)-3,5-dimethylisoxazole (Cpd. No. 271)

Cpd. No. 271

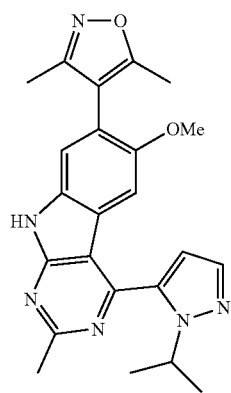

To a round-bottom flask, 4-(4-chloro-6-methoxy-2-methyl-9H-pyrimido[4,5-b]indol-7-yl)-3,5-dimethylisoxazole (S13, 1.09 g, 3.2 mmol), (1-isopropyl-1H-pyrazol-5-yl)boronic acid (1.0 g, 6.5 mmol), 1,2-dimethoxyethane (18 mL), and Na$_2$CO$_3$ (2 M in water, 6 mL) were added. The system was degassed to remove oxygen and nitrogen was refilled. Pd(dppf)Cl$_2$—CH$_2$Cl$_2$ (245 mg, 0.3 mmol) was added and the system was degassed and refilled with nitrogen. The reaction mixture was heated at reflux for overnight. The aqueous layer was extracted with ethyl acetate and the organic layers were combined and the volatile components were removed on a rotary evaporator. The residue was purified by flash column chromatography to yield the title compound in 277 mg (21% yield). The compound was further purified by reverse HPLC to yield Cpd. No. 271 as a CF$_3$CO$_2$H salt. <sup>1</sup>H NMR (300 MHz, MeOD-d4): 7.92 (d, J=1.52 Hz, 1H), 7.54 (s, 1H), 6.94 (d, J=1.81 Hz, 1H), 6.91 (s, 1H), 4.52 (septet, J=6.50 Hz, 1H), 3.69 (s, 3H), 2.94 (s, 3H), 2.31 (s, 3H), 2.13 (s, 3H), 1.46 (d, J=6.52 Hz, 6H). ESI-MS calculated for $C_{23}H_{25}N_6O_2$ $[M+H]^+$=417.20, Observed: 417.50.

2-(5-Bromo-2-methoxyphenyl)propan-2-ol (CE305)

CE305

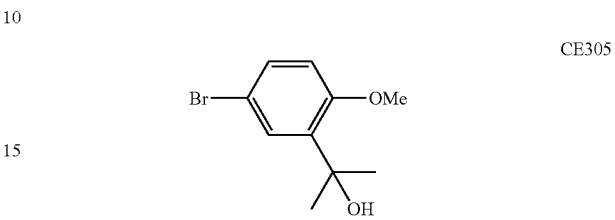

Methyl 5-bromo-2-methoxybenzoate (10 g, 40 mmol) was dissolved in anhydrous THF (60 mL), which was subsequently cooled with ice-water bath. MeMgBr (3.0 M in ether, 30 mL, 90 mmol) was added via a syringe at 0° C. and the reaction mixture was stirred for overnight. The reaction was quenched with saturated ammonium chloride. The aqueous layer was extracted with ethyl acetate and the organic layers were combined and the volatile components were removed on a rotary evaporator. The residue containing CE305 was used for the next step without further purification. <sup>1</sup>H NMR (300 MHz, CDCl$_3$): 7.77-7.67 (m, 2H), 7.45 (d, J=2.50 Hz, 1H), 7.28 (dd, J=8.70, 2.50 Hz, 1H), 6.74 (d, J=8.71 Hz, 1H), 3.90 (s, 1H), 3.82 (s, 3H), 1.55 (s, 6H).

2-(2-Methoxy-5-(4,4,5,5-tetramethyl-1,3,2-dioxaborolan-2-yl)phenyl)propan-2-ol (CE308)

CE308

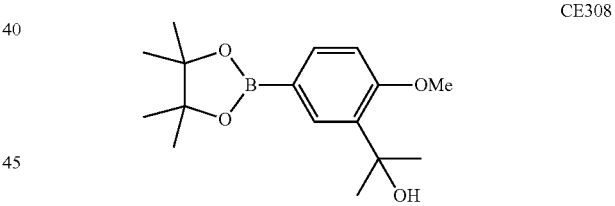

2-(5-Bromo-2-methoxyphenyl)propan-2-ol (1.0 g, 4.0 mmol), bis(pinacolato)diboron (2.03 g, 8.0 mmol) and potassium acetate (1.2 g, 12 mmol) were added to a round-bottom flask. Anhydrous 1,4-dixoane (20 mL) was added to the flask, which was degassed and refilled with nitrogen. Pd(dppf)Cl$_2$ (280 mg, 0.4 mmol) was added and the flask was degassed again followed by heating at 100° C. for overnight. The reaction mixture was cooled to room temperature and diluted by CH$_2$Cl$_2$. The solution was filtered through a pad of celite and the volatile components were removed on a rotary evaporator. The residue was purified by flash column chromatography. The title compound was isolated in 1.27 g contained with some impurity, which was used for the next step without further purification. <sup>1</sup>H NMR (300 MHz, CDCl$_3$): 6.92 (d, J=8.09 Hz, 1H), 3.93 (s, 3H), 1.63 (s, 6H), 1.33 (s, 12H). <sup>13</sup>C NMR (75 MHz, CDCl$_3$): 159.72, 135.75, 135.27, 132.41, 110.85, 83.84, 72.89, 55.52, 29.89, 25.06. ESI-MS calculated for $C_{16}H_{25}BNaO_4$ $[M+H]^+$= 315.17, Observed: 315.67.

2-(5-(7-(3,5-Dimethylisoxazol-4-yl)-6-methoxy-2-methyl-9H-pyrimido[4,5-b]indol-4-yl)-2-methoxyphenyl)propan-2-ol (Cpd. No. 272)

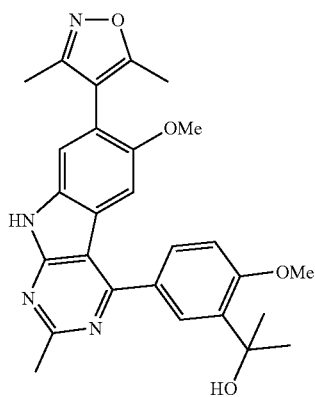

Cpd. No. 272

To a round-bottom flask, 4-(4-chloro-6-methoxy-2-methyl-9H-pyrimido[4,5-b]indol-7-yl)-3,5-dimethylisoxazole (S13, 680 mg, 2.0 mmol), CE308 (1.27 g, 4.3 mmol), 1,2-dimethoxyethane (18 mL), and $Na_2CO_3$ (2 M in water, 6 mL) were added. The system was degassed to remove oxygen and nitrogen was refilled. Pd(dppf)$Cl_2$—$CH_2Cl_2$ (163 mg, 0.2 mmol) was added and the system was degassed and refilled with nitrogen. The reaction mixture was heated at reflux for overnight. The aqueous layer was extracted with ethyl acetate and the organic layers were combined and the volatile components were removed on a rotary evaporator. The residue was purified by flash column chromatography to yield the title compound, which was further purified by reversed HPLC to yield Cpd. No. 272 in 221 mg (20%). $^1$H NMR (300 MHz, MeOD-d4): 8.14 (s, 1H), 8.82 (d, J=8.33 Hz, 1H), 7.21 (d, J=8.26 Hz, 1H), 7.44 (s, 1H), 7.32 (s, 1H), 3.99 (s, 3H), 3.71 (s, 3H), 2.78 (s, 3H), 2.31 (s, 3H), 2.14 (s, 3H), 1.66 (s, 6H). ESI-MS calculated for $C_{27}H_{29}N_4O_4$ [M+H]$^+$=473.22, Observed: 473.50.

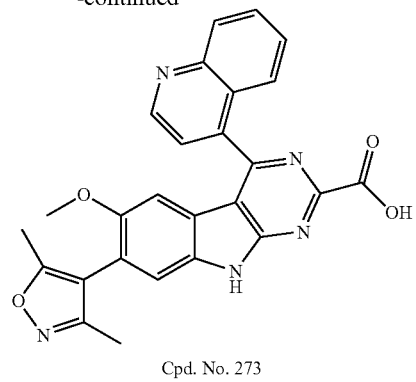

Cpd. No. 273

To a round-bottom flask, ZBA154 (0.19 g) was dissolved in THF (9 mL), t-BuOH (9 mL) and $H_2O$ (3 mL) at room temperature. $NaClO_2$ (303 mg), $NaH_2PO_4$ (505 mg) and 2-Methyl-2-butene (1.5 mL) was added and the reaction mixture was stirred overnight. Then water and ethyl acetate was slowly added. The aqueous layer was extracted with EtOAc. The combined EtOAc extracts were washed with $H_2O$, dried over $Na_2SO_4$, and concentrated under reduced pressure to afford Cpd. No. 273 (140 mg) after HPLC purification. ESI-MS calculated for $C_{26}H_{20}N_5O_4$ [M+H]$^+$= 466.15, Obtained: 466.65.

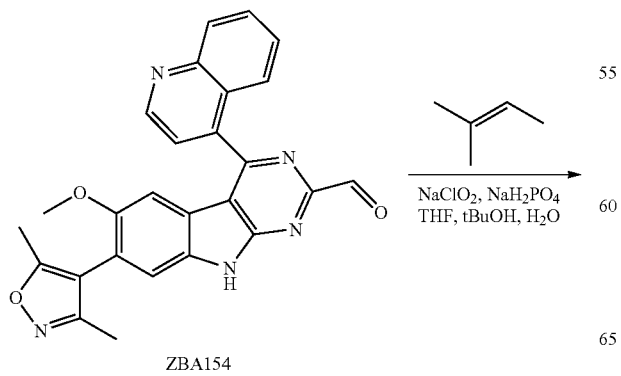

Cpd. No. 274

(amide condensation): ZBA191 (20 mg), HBTU (24 mg), HOBt·$H_2O$ (6 mg) and DMF (1 mL) were added to a round-bottom flask. EtN(i-Pr)$_2$ (0.05 mL) was added followed by addition of 1-methylpiperazine (10 mg) was added and the reaction mixture was stirred for 12 h. The reaction was quenched with NaHCO$_3$ saturated solution and the aqueous layer was extracted with ethyl acetate. The combined organic layers were concentrated on a rotary evaporator. The remaining residue was purified by reverse phase HPLC affording the Cpd. No. 274 as a salt of CF$_3$CO$_2$H (14 mg). ESI-MS calculated for C$_{31}$H$_{30}$N$_7$O$_3$ [M+H]$^+$=548.24, Obtained: 548.55. $^1$H NMR (300 MHz, MeOD) δ 9.37 (d, J=5.0 Hz, 1H), 8.40 (d, J=8.5 Hz, 1H), 8.23 (d, J=4.7 Hz, 1H), 8.12 (t, J=7.8 Hz, 1H), 8.03 (d, J=8.5 Hz, 1H), 7.84-7.72 (m, 1H), 7.50 (d, J=11.4 Hz, 1H), 6.40 (s, 1H), 4.47-4.20 (m, 1H), 3.86-3.30 (m, 8H), 3.28 (s, 3H), 2.99 (s, 3H), 2.29 (s, 3H), 2.08 (d, J=8.8 Hz, 3H).

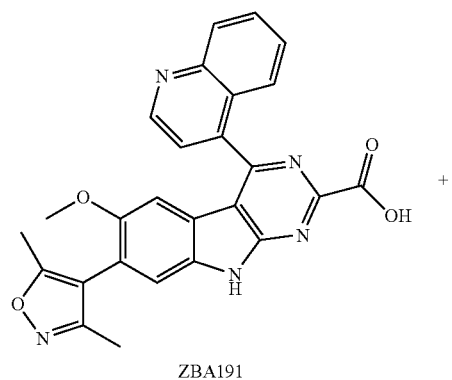

ZBA191

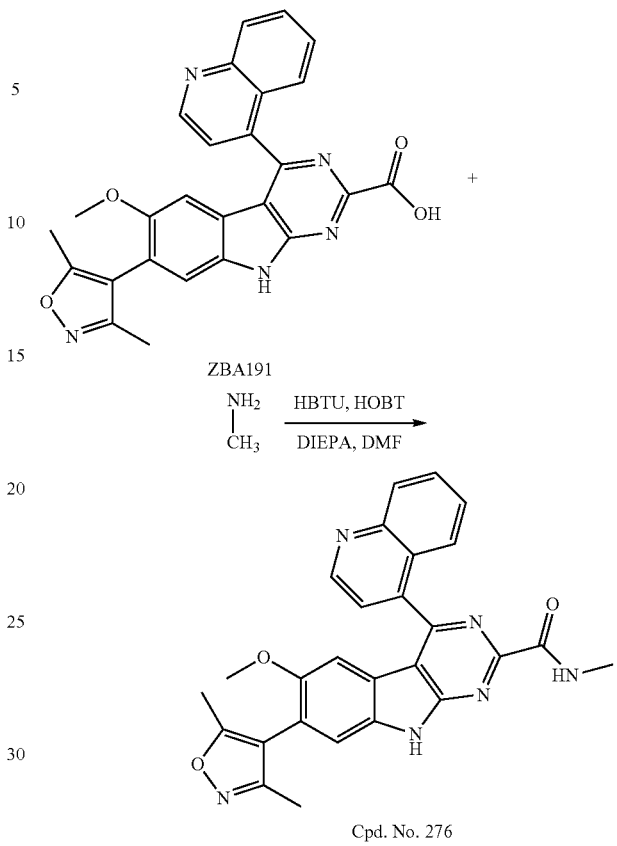

ZBA191

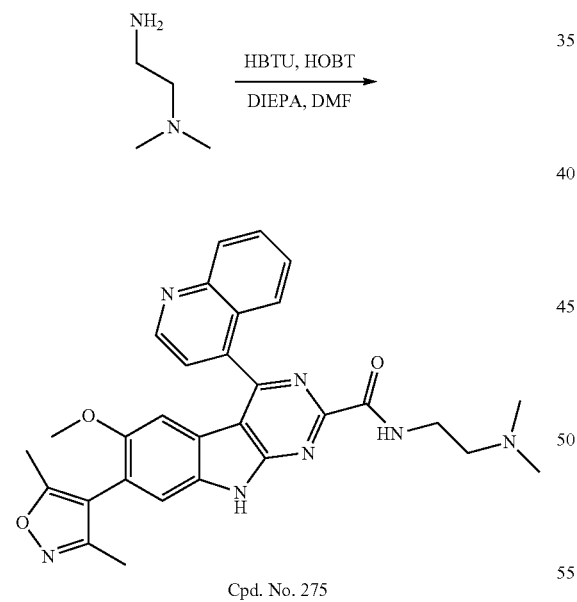

Cpd. No. 275

Cpd. No. 275-TFA salt was prepared from amide condensation of ZBA191 and N,N-dimethylethylenediamine using HBTU-HOBT condition. 60% yield. ESI-MS calculated for C$_{30}$H$_{30}$N$_7$O$_3$ [M+H]$^+$=536.24, Obtained: 536.77. $^1$H NMR (300 MHz, MeOD) δ 9.23 (d, J=4.7 Hz, 1H), 8.34 (d, J=8.5 Hz, 1H), 8.09-7.90 (m, 2H), 7.78 (d, J=8.0 Hz, 1H), 7.70-7.57 (m, 1H), 7.51 (s, 1H), 6.30 (s, 1H), 3.92 (t, J=5.6 Hz, 2H), 3.48 (d, J=5.2 Hz, 2H), 3.24 (s, 3H), 3.04 (s, 6H), 2.29 (s, 3H), 2.10 (s, 3H).

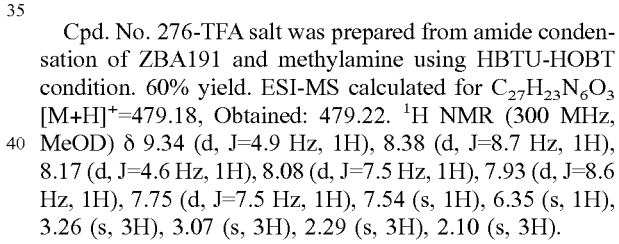

Cpd. No. 276

Cpd. No. 276-TFA salt was prepared from amide condensation of ZBA191 and methylamine using HBTU-HOBT condition. 60% yield. ESI-MS calculated for C$_{27}$H$_{23}$N$_6$O$_3$ [M+H]$^+$=479.18, Obtained: 479.22. $^1$H NMR (300 MHz, MeOD) δ 9.34 (d, J=4.9 Hz, 1H), 8.38 (d, J=8.7 Hz, 1H), 8.17 (d, J=4.6 Hz, 1H), 8.08 (d, J=7.5 Hz, 1H), 7.93 (d, J=8.6 Hz, 1H), 7.75 (d, J=7.5 Hz, 1H), 7.54 (s, 1H), 6.35 (s, 1H), 3.26 (s, 3H), 3.07 (s, 3H), 2.29 (s, 3H), 2.10 (s, 3H).

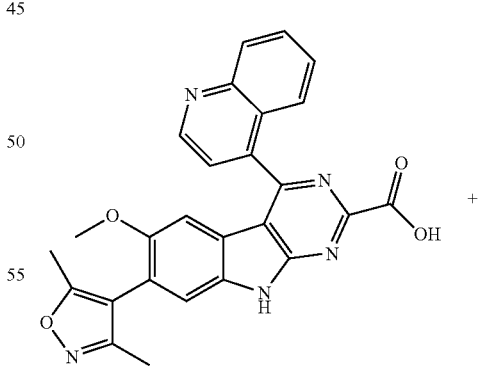

ZBA191

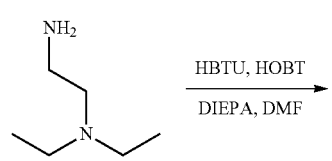

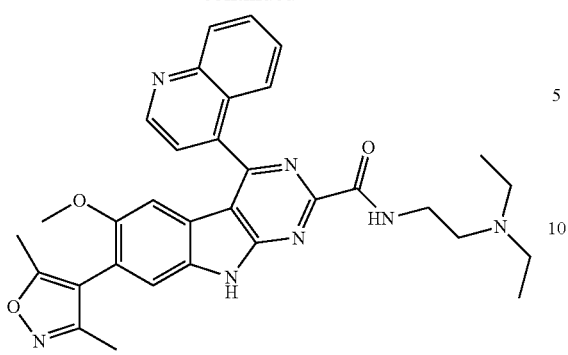

Cpd. No. 277

Cpd. No. 277-TFA salt was prepared from amide condensation of ZBA191 and N,N-diethylethylenediamine using HBTU-HOBT condition. 70% yield. ESI-MS calculated for $C_{32}H_{34}N_7O_3$ [M+H]$^+$=564.27, Obtained: 564.38. $^1$H NMR (300 MHz, MeOD) δ 9.36 (d, J=4.8 Hz, 1H), 8.40 (d, J=8.5 Hz, 1H), 8.17 (d, J=4.8 Hz, 1H), 8.08 (t, J=7.7 Hz, 1H), 7.91 (d, J=8.4 Hz, 1H), 7.74 (t, J=7.2 Hz, 1H), 7.55 (s, 1H), 6.36 (s, 1H), 3.96-3.37 (m, 8H), 3.26 (s, 3H), 2.29 (s, 3H), 2.10 (s, 3H), 1.38 (t, J=7.0 Hz, 6H).

Cpd. No. 278-TFA salt was prepared from amide condensation of ZBA191 and 1-(2-aminoethyl)pyrrolidine using HBTU-HOBT condition. 70% yield. ESI-MS calculated for $C_{32}H_{32}N_7O_3$ [M+H]$^+$=562.25, Obtained: 562.48. $^1$H NMR (300 MHz, MeOD) δ 9.25 (d, J=4.6 Hz, 1H), 8.35 (d, J=8.6 Hz, 1H), 8.04-7.94 (m, 2H), 7.80 (d, J=8.2 Hz, 1H), 7.64 (t, J=7.4 Hz, 1H), 7.51 (s, 1H), 6.30 (s, 1H), 3.96-3.79 (m, 4H), 3.51 (t, J=5.4 Hz, 2H), 3.26-3.12 (m, 5H), 2.29 (s, 3H), 2.24-1.95 (m, 7H).

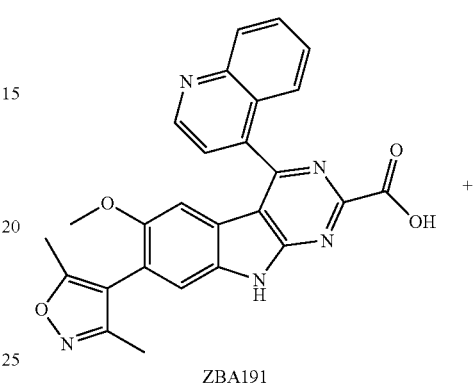

ZBA191

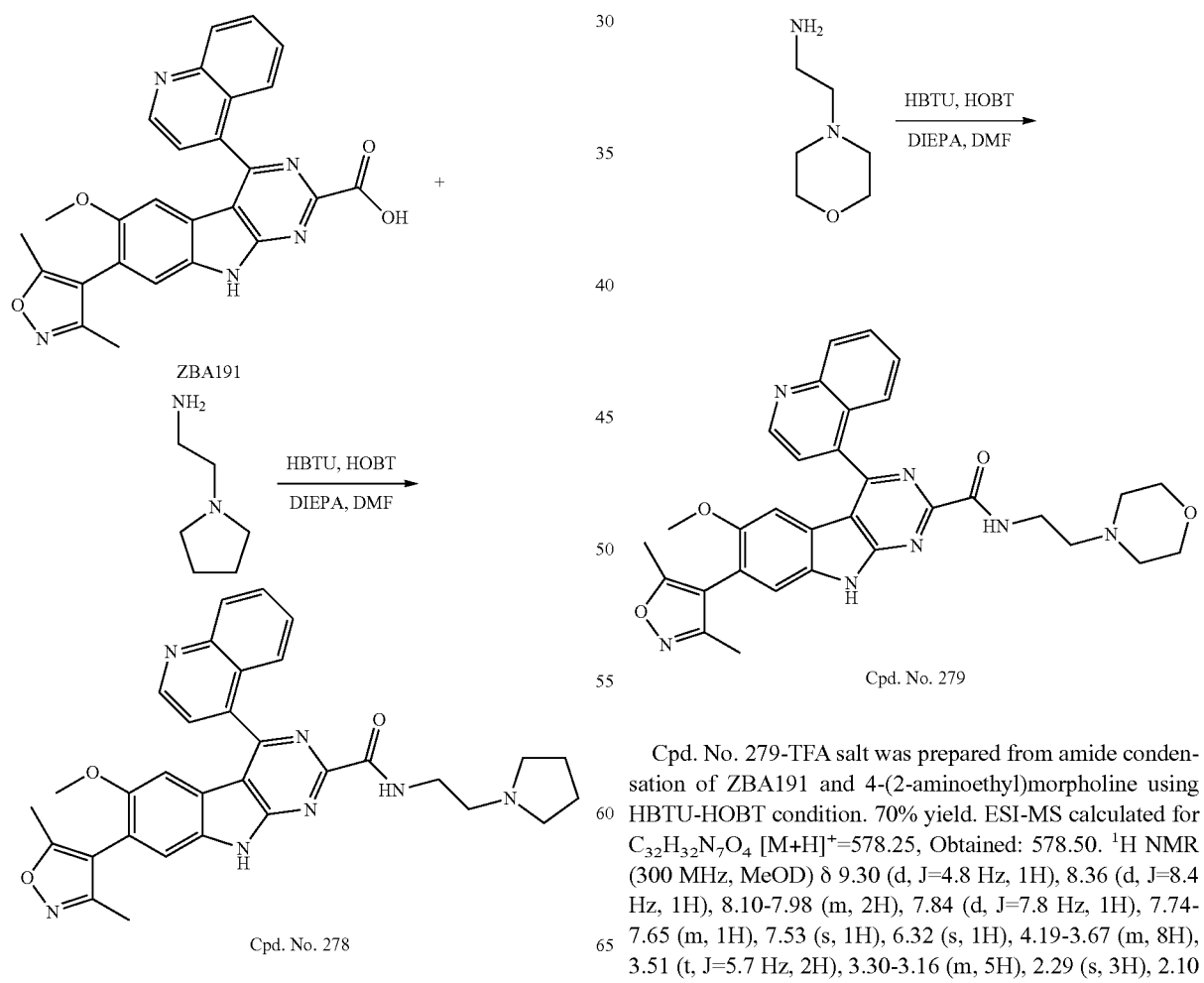

Cpd. No. 278

Cpd. No. 279

Cpd. No. 279-TFA salt was prepared from amide condensation of ZBA191 and 4-(2-aminoethyl)morpholine using HBTU-HOBT condition. 70% yield. ESI-MS calculated for $C_{32}H_{32}N_7O_4$ [M+H]$^+$=578.25, Obtained: 578.50. $^1$H NMR (300 MHz, MeOD) δ 9.30 (d, J=4.8 Hz, 1H), 8.36 (d, J=8.4 Hz, 1H), 8.10-7.98 (m, 2H), 7.84 (d, J=7.8 Hz, 1H), 7.74-7.65 (m, 1H), 7.53 (s, 1H), 6.32 (s, 1H), 4.19-3.67 (m, 8H), 3.51 (t, J=5.7 Hz, 2H), 3.30-3.16 (m, 5H), 2.29 (s, 3H), 2.10 (s, 3H).

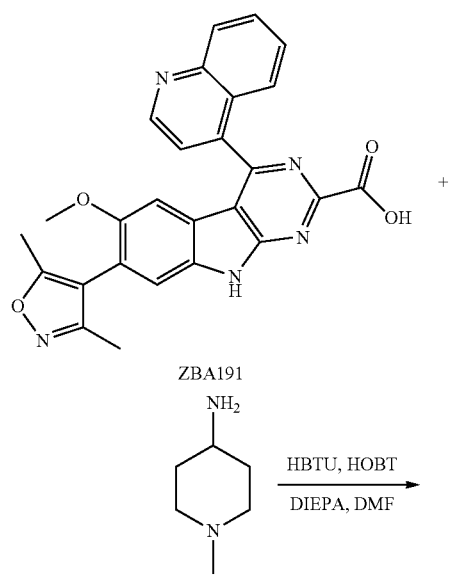

ZBA191

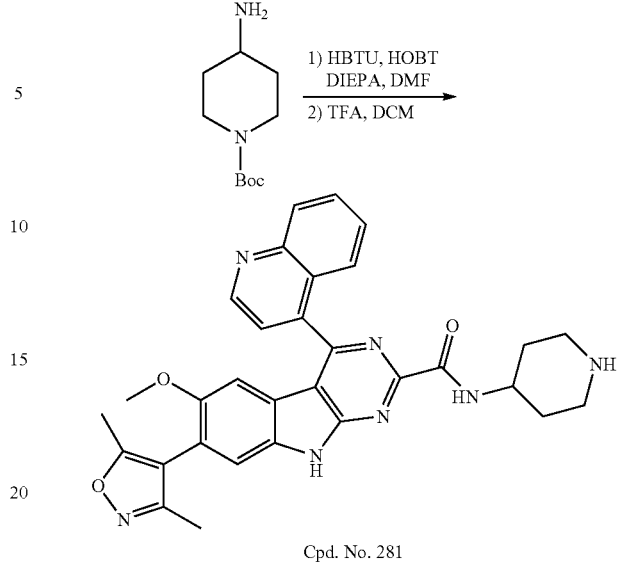

Cpd. No. 281

ZBA191 (20 mg), HBTU (24 mg), HOBt-H₂O (6 mg) and DMF (1 mL) were added to a round-bottom flask. EtN(i-Pr)₂ (0.05 mL) was added followed by addition of 4-Amino-1-Boc-piperidine (20 mg) was added and the reaction mixture was stirred for 12 h. The reaction was quenched with NaHCO₃ saturated solution and the aqueous layer was extracted with ethyl acetate. The combined organic layers were concentrated on a rotary evaporator. The remaining residue was dissolved in TFA (2 mL) and DCM (2 mL). The mixture was stirred for 3 hours and was concentrated on a rotary evaporator. The remaining residue was purified by reverse phase HPLC affording the Cpd. No. 281 as a salt of $CF_3CO_2H$ (13 mg). ESI-MS calculated for $C_{31}H_{30}N_7O_3$ [M+H]$^+$=548.24, Obtained: 548.44. $^1$H NMR (300 MHz, MeOD) δ 9.32 (d, J=4.8 Hz, 1H), 8.38 (d, J=8.5 Hz, 1H), 8.11 (d, J=4.8 Hz, 1H), 8.08-7.99 (m, 1H), 7.87 (d, J=8.0 Hz, 1H), 7.69 (dd, J=11.3, 4.1 Hz, 1H), 7.57 (s, 1H), 6.31 (s, 1H), 4.41-4.25 (m, 1H), 3.59-3.44 (m, 2H), 3.28-3.13 (m, 5H), 2.35-2.21 (m, 5H), 2.14-1.90 (m, 5H).

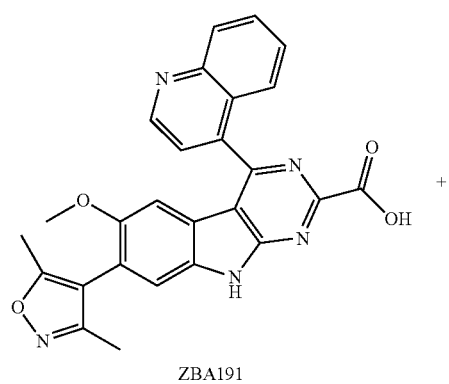

Cpd. No. 280

Cpd. No. 280-TFA salt was prepared from amide condensation of ZBA191 and 1-methyl-4-piperidinamine using HBTU-HOBT condition. 65% yield. ESI-MS calculated for $C_{32}H_{32}N_7O_3$ [M+H]$^+$=562.25, Obtained: 562.66. $^1$H NMR (300 MHz, MeOD) δ 9.38 (d, J=5.0 Hz, 1H), 8.40 (d, J=8.5 Hz, 1H), 8.20 (d, J=5.0 Hz, 1H), 8.09 (ddd, J=8.4, 7.0, 1.2 Hz, 1H), 7.92 (d, J=8.0 Hz, 1H), 7.75 (ddd, J=8.3, 6.9, 1.0 Hz, 1H), 7.57 (s, 1H), 6.35 (s, 1H), 4.32 (tt, J=11.4, 4.0 Hz, 1H), 3.64 (d, J=13.3 Hz, 2H), 3.30-3.16 (m, 5H), 2.93 (s, 3H), 2.37-2.25 (m, 5H), 2.17-1.98 (m, 5H).

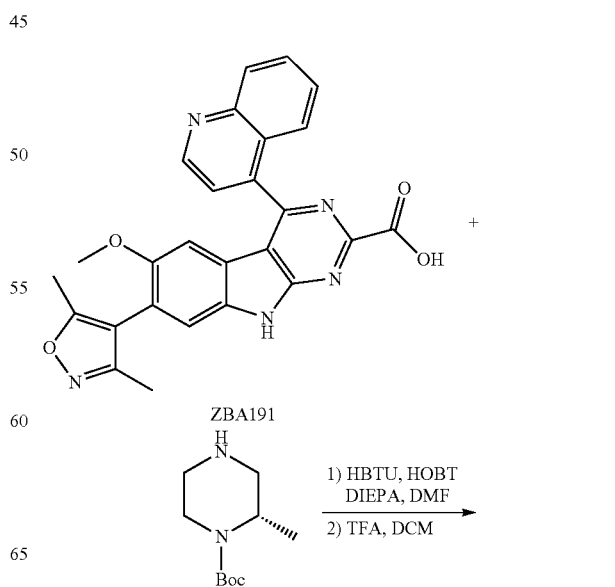

ZBA191

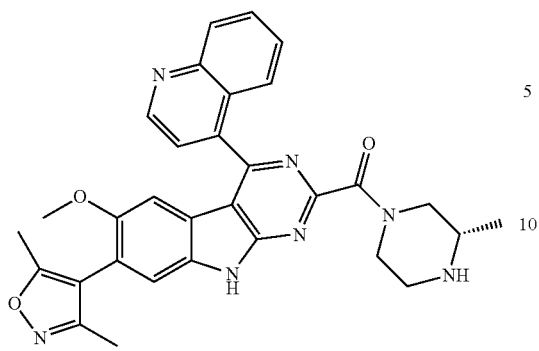

Cpd. No. 282

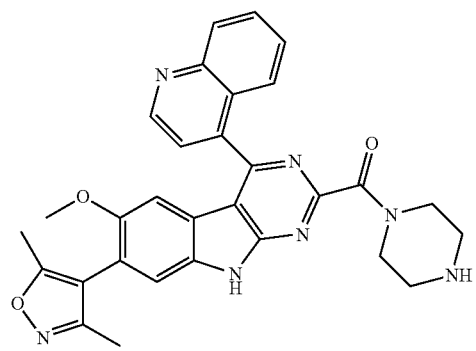

Cpd. No. 283

ZBA191 (20 mg), HBTU (24 mg), HOBt-H$_2$O (6 mg) and DMF (1 mL) were added to a round-bottom flask. EtN(i-Pr)$_2$ (0.05 mL) was added followed by addition of (S)-1-N-Boc-2-methylpiperazine (20 mg) was added and the reaction mixture was stirred for 12 h. The reaction was quenched with NaHCO$_3$ saturated solution and the aqueous layer was extracted with ethyl acetate. The combined organic layers were concentrated on a rotary evaporator. The remaining residue was dissolved in TFA (2 mL) and DCM (2 mL). The mixture was stirred for 3 hours and was concentrated on a rotary evaporator. The remaining residue was purified by reverse phase HPLC affording the Cpd. No. 282 as a salt of CF$_3$CO$_2$H (13 mg). ESI-MS calculated for C$_{31}$H$_{30}$N$_7$O$_3$ [M+H]$^+$=548.24, Obtained: 548.47.

ZBA191 (20 mg), HBTU (24 mg), HOBt-H$_2$O (6 mg) and DMF (1 mL) were added to a round-bottom flask. EtN(i-Pr)$_2$ (0.05 mL) was added followed by addition of 1-Boc-piperazine (18 mg) was added and the reaction mixture was stirred for 12 h. The reaction was quenched with NaHCO$_3$ saturated solution and the aqueous layer was extracted with ethyl acetate. The combined organic layers were concentrated on a rotary evaporator. The remaining residue was dissolved in TFA (2 mL) and DCM (2 mL). The mixture was stirred for 3 hours and was concentrated on a rotary evaporator. The remaining residue was purified by reverse phase HPLC affording the Cpd. No. 283 as a salt of CF$_3$CO$_2$H (12 mg). ESI-MS calculated for C$_{30}$H$_{28}$N$_7$O$_3$ [M+H]$^+$=534.22, Obtained: 534.44. $^1$H NMR (300 MHz, MeOD) δ 9.27 (d, J=4.7 Hz, 1H), 8.35 (d, J=8.5 Hz, 1H), 8.04-7.98 (m, 2H), 7.91 (d, J=7.7 Hz, 1H), 7.69 (ddd, J=8.3, 6.9, 1.1 Hz, 1H), 7.50 (s, 1H), 6.36 (s, 1H), 4.16-4.09 (m, 2H), 3.98-3.89 (m, 2H), 3.47-3.40 (m, 2H), 3.39-3.34 (m, 2H), 3.26 (s, 3H), 2.29 (s, 3H), 2.10 (s, 3H).

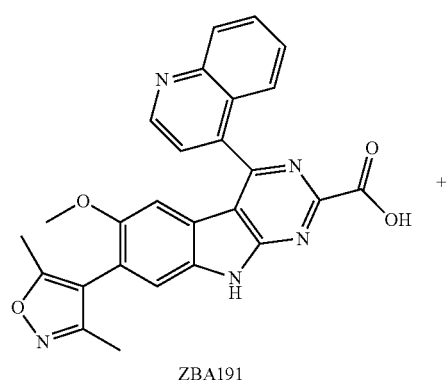

ZBA191

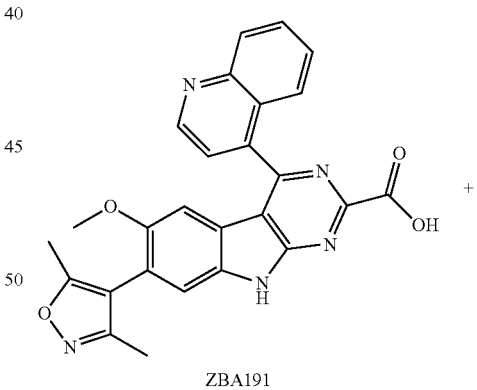

ZBA191

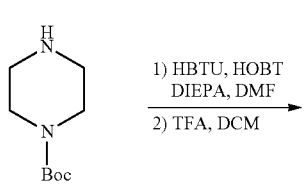

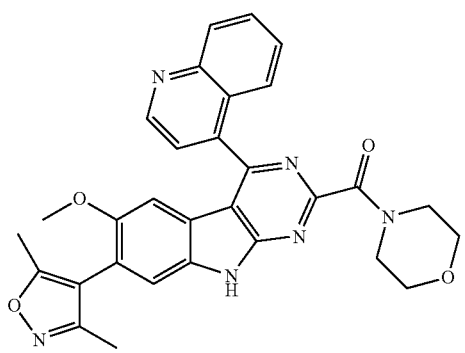

Cpd. No. 284

Cpd. No. 284-TFA salt was prepared from amide condensation of ZBA191 and morpholine using HBTU-HOBT condition. 75% yield. ESI-MS calculated for $C_{30}H_{27}N_6O_4$ [M+H]$^+$=535.20, Obtained: 535.44. $^1$H NMR (300 MHz, MeOD) δ 9.35 (d, J=5.0 Hz, 1H), 8.39 (d, J=8.5 Hz, 1H), 8.19 (d, J=5.0 Hz, 1H), 8.10 (ddd, J=8.5, 6.9, 1.3 Hz, 1H), 8.02 (d, J=7.9 Hz, 1H), 7.78 (ddd, J=8.3, 6.9, 1.0 Hz, 1H), 7.50 (s, 1H), 6.40 (s, 1H), 3.86 (dd, J=7.4, 2.6 Hz, 4H), 3.78-3.69 (m, 2H), 3.66-3.57 (m, 2H), 3.29 (s, 3H), 2.29 (s, 3H), 2.10 (s, 3H).

Cpd. No. 285-TFA salt was prepared from amide condensation of ZBA191 and 4-Hydroxypiperidine using HBTU-HOBT condition. 75% yield. ESI-MS calculated for $C_{31}H_{29}N_6O_4$ [M+H]$^+$=549.22, Obtained: 549.64. $^1$H NMR (300 MHz, MeOD) δ 9.39 (s, 1H), 8.41 (d, J=8.5 Hz, 1H), 8.28 (d, J=5.0 Hz, 1H), 8.15 (t, J=7.7 Hz, 1H), 8.09 (d, J=8.4 Hz, 1H), 7.82 (t, J=7.5 Hz, 1H), 7.50 (s, 1H), 6.45 (s, 1H), 4.35-4.15 (m, 1H), 4.03-3.68 (m, 2H), 3.55-3.35 (m, 2H), 3.31 (s, 3H), 2.29 (s, 3H), 2.10 (s, 3H), 2.07-1.87 (m, 2H), 1.72-1.55 (m, 2H).

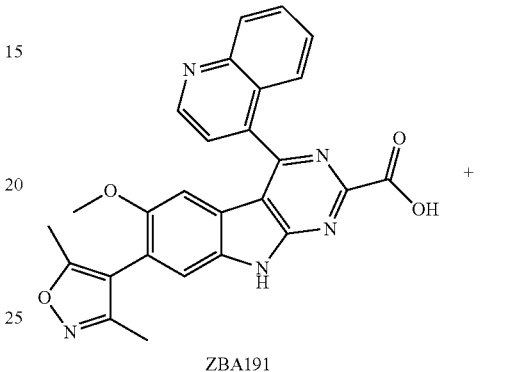

ZBA191

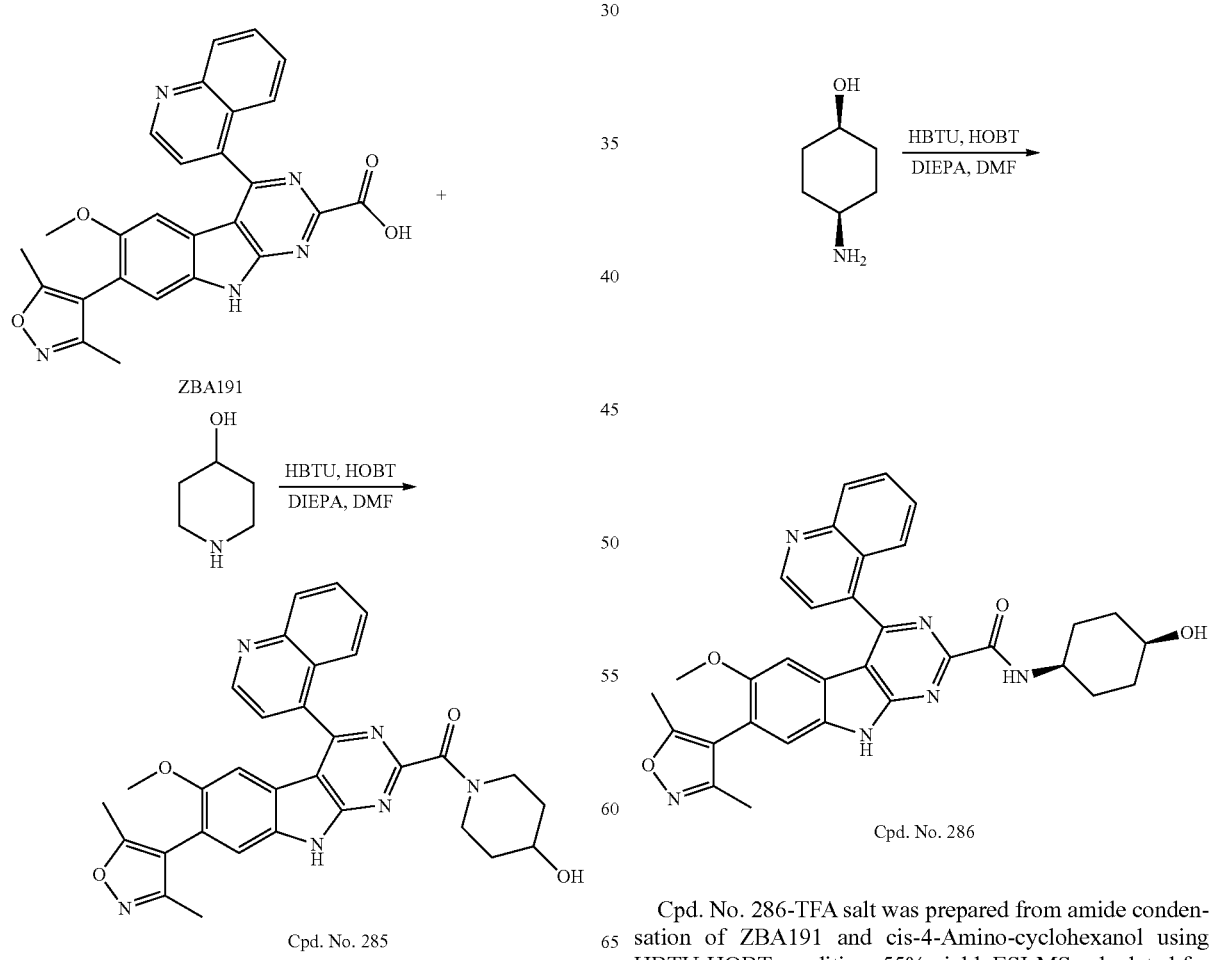

Cpd. No. 285

Cpd. No. 286

Cpd. No. 286-TFA salt was prepared from amide condensation of ZBA191 and cis-4-Amino-cyclohexanol using HBTU-HOBT condition. 55% yield. ESI-MS calculated for $C_{32}H_{31}N_6O_4$ [M+H]$^+$=563.24, Obtained: 563.45.

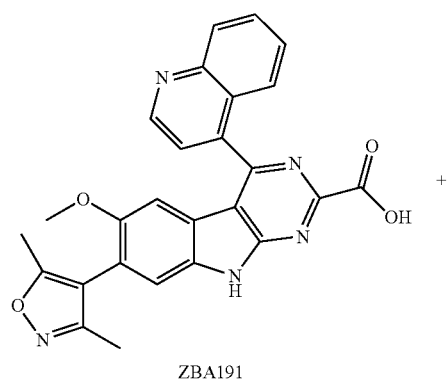

ZBA191

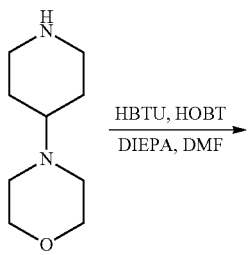

HBTU, HOBT
DIEPA, DMF →

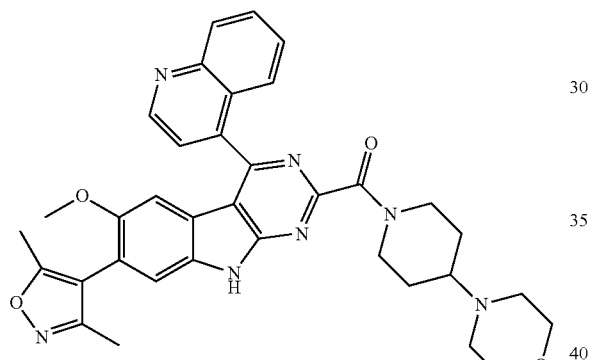

Cpd. No. 287

Cpd. No. 287-TFA salt was prepared from amide condensation of ZBA191 and 4-morpholinopiperidine using HBTU-HOBT condition. 67% yield. ESI-MS calculated for $C_{35}H_{36}N_7O_4$ [M+H]$^+$=618.28, Obtained: 618.66. $^1$H NMR (300 MHz, MeOD) δ 9.38 (d, J=5.1 Hz, 1H), 8.41 (d, J=8.5 Hz, 1H), 8.26 (d, J=5.1 Hz, 1H), 8.14 (dd, J=11.4, 4.1 Hz, 1H), 8.06 (d, J=8.5 Hz, 1H), 7.86-7.79 (m, 1H), 7.51 (s, 1H), 6.42 (s, 1H), 4.20-4.05 (m, 4H), 3.75 (t, J=12.1 Hz, 2H), 3.67-3.41 (m, 4H), 3.30 (s, 3H), 3.27-2.96 (m, 3H), 2.45-2.14 (m, 5H), 2.10 (s, 3H), 1.94-1.69 (m, 2H).

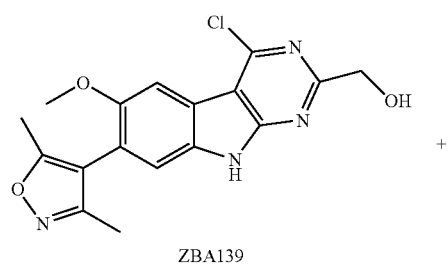

ZBA139

-continued

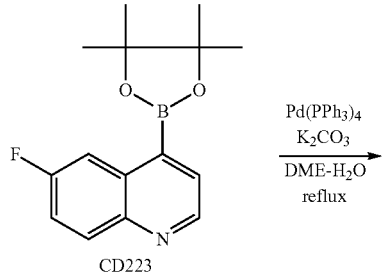

CD223

Pd(PPh$_3$)$_4$
K$_2$CO$_3$
DME-H$_2$O
reflux
→

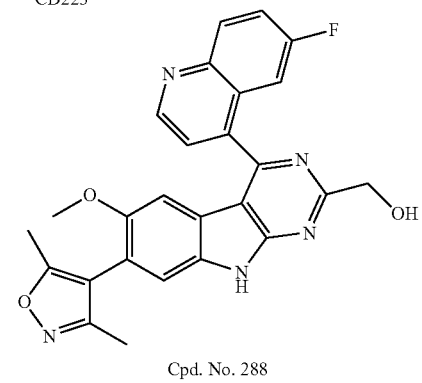

Cpd. No. 288

Cpd. No. 288-TFA salt was prepared from Suzuki coupling of ZBA139 and CD223 using Pd(PPh$_3$)$_4$—K$_2$CO$_3$ (2 M) condition. 35% yield. ESI-MS calculated for $C_{26}H_{21}FN_5O_3$ [M+H]$^+$=470.16, Obtained: 470.35. $^1$H NMR (300 MHz, MeOD) δ 9.30 (s, 1H), 8.43 (dd, J=9.2, 5.2 Hz, 1H), 8.10 (d, J=4.3 Hz, 1H), 7.86 (t, J=7.3 Hz, 1H), 7.65-7.55 (m, 2H), 6.31 (s, 1H), 5.12 (s, 2H), 3.99 (s, 3H), 2.29 (s, 3H), 2.10 (s, 3H).

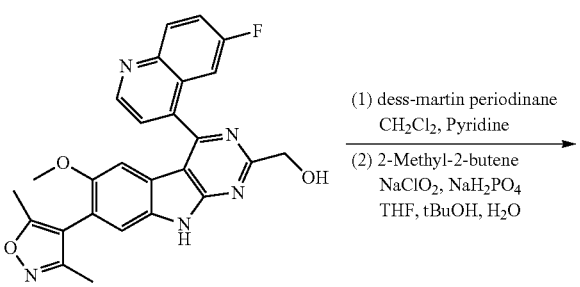

Cpd. No. 288

(1) dess-martin periodinane
CH$_2$Cl$_2$, Pyridine (2) 2-Methyl-2-butene
NaClO$_2$, NaH$_2$PO$_4$
THF, tBuOH, H$_2$O
→

Cpd. No. 289

To a round-bottom flask, Cpd. No. 288 (0.045 g, 0.1 mmol) was dissolved in DCM (7 mL) and Pyridine (0.4 mL) at room temperature. Dess-martin periodinane (63.6 mg, 0.15 mmol) was added and the reaction mixture was stirred for 2.5 h. Then water and ethyl acetate was slowly added. The aqueous layer was extracted with EtOAc. The combined EtOAc extracts were washed with $H_2O$, dried over $Na_2SO_4$, and concentrated under reduced pressure to afford the aldehyde intermediate which then was dissolved in THF (3 mL), t-BuOH (3 mL) and $H_2O$ (1 mL) at room temperature. $NaClO_2$ (75 mg), $NaH_2PO_4$ (125 mg) and 2-Methyl-2-butene (0.5 mL) was added and the reaction mixture was stirred overnight. Then water and ethyl acetate was slowly added. The aqueous layer was extracted with EtOAc. The combined EtOAc extracts were washed with $H_2O$, dried over $Na_2SO_4$, and concentrated under reduced pressure to afford Cpd. No. 289 (25 mg) after HPLC purification. ESI-MS calculated for $C_{26}H_{19}FN_5O_4$ $[M+H]^+=484.14$, Obtained: 484.33.

organic layers were concentrated on a rotary evaporator. The remaining residue was dissolved in TFA (2 mL) and DCM (2 mL). The mixture was stirred for 3 hours and was concentrated on a rotary evaporator. The remaining residue was purified by reverse phase HPLC affording the Cpd. No. 290 as a salt of $CF_3CO_2H$ (15 mg). ESI-MS calculated for $C_{30}H_{28}FN_6O_5$ $[M+H]^+=571.21$, Obtained: 571.64. $^1$H NMR (300 MHz, MeOD) δ 9.23 (d, J=4.6 Hz, 1H), 8.38 (dd, J=9.3, 5.2 Hz, 1H), 8.10 (d, J=4.6 Hz, 1H), 7.84-7.73 (m, 1H), 7.69-7.44 (m, 2H), 6.47 (s, 1H), 4.44-4.32 (m, 1H), 3.84-3.60 (m, 3H), 3.53 (d, J=5.5 Hz, 1H), 3.33 (s, 3H), 2.28 (s, 3H), 2.09 (s, 3H), 2.00-1.65 (m, 2H).

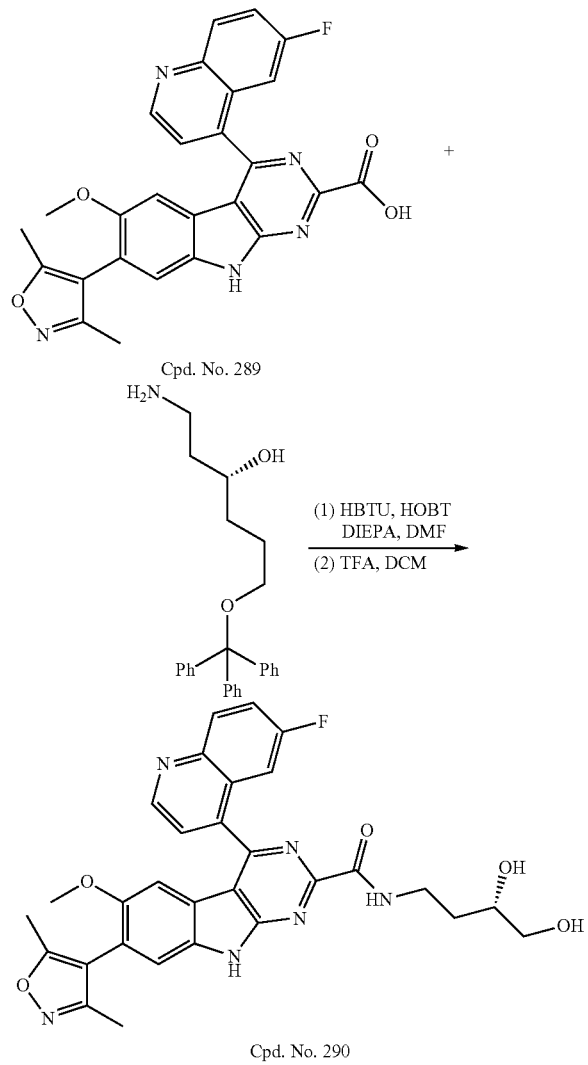

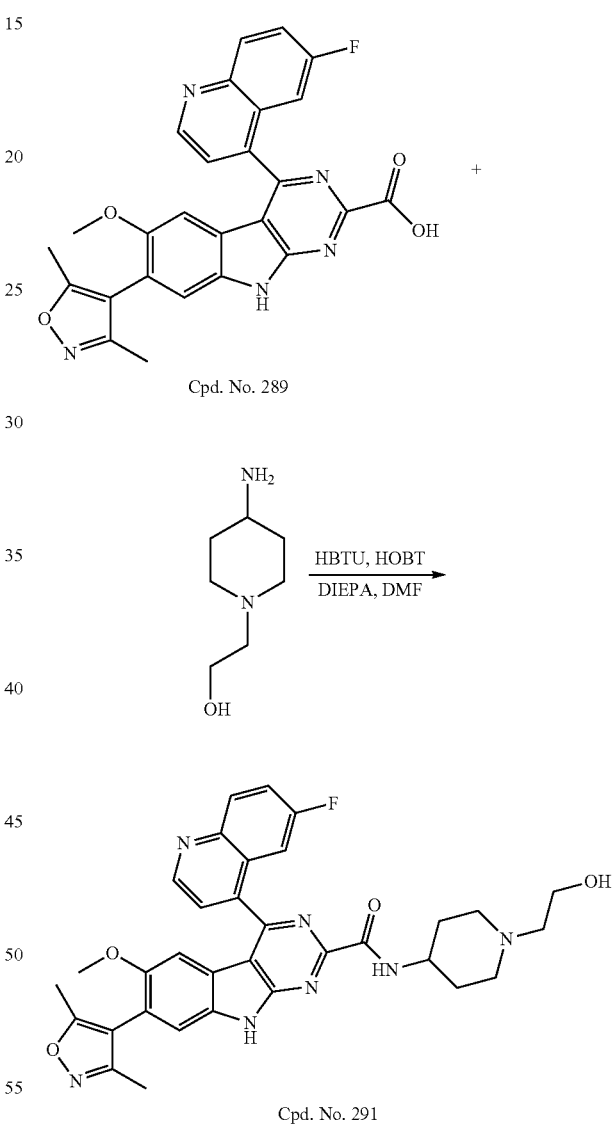

Cpd. No. 289 (20 mg), HBTU (24 mg), HOBt-$H_2O$ (6 mg) and DMF (1 mL) were added to a round-bottom flask. EtN(i-Pr)$_2$ (0.05 mL) was added followed by addition of (S)-4-amino-1-(trityloxy)butan-2-ol (28 mg) was added and the reaction mixture was stirred for 12 h. The reaction was quenched with $NaHCO_3$ saturated solution and the aqueous layer was extracted with ethyl acetate. The combined Cpd. No. 291-TFA salt was prepared from amide condensation of Cpd. No. 289 and 2-(4-aminopiperidin-1-yl)ethanol using HBTU-HOBT condition. 50% yield. ESI-MS calculated for $C_{33}H_{33}FN_7O_4$ $[M+H]^+=610.25$, Obtained: 610.44. $^1$H NMR (300 MHz, MeOD) δ 9.31 (d, J=5.1 Hz, 1H), 8.43 (dd, J=9.3, 5.0 Hz, 1H), 8.21 (d, J=5.0 Hz, 1H), 7.91-7.80 (m, 1H), 7.63-7.51 (m, 2H), 6.54 (s, 1H), 4.52-4.33 (m, 1H), 3.97-3.73 (m, 4H), 3.55-3.20 (m, 7H), 2.48-1.98 (m, 10H).

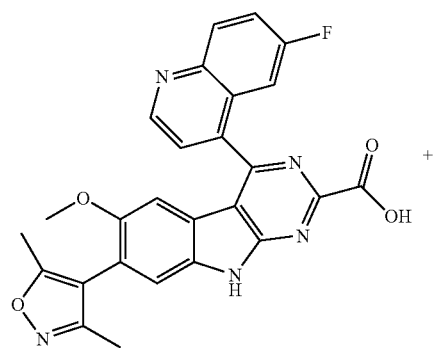

Cpd. No. 289

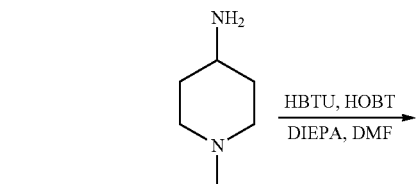

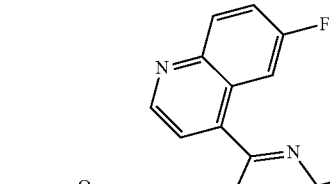

Cpd. No. 292

Cpd. No. 292-TFA salt was prepared from amide condensation of Cpd. No. 289 and 1-isopropyl-piperidin-4-ylamine using HBTU-HOBT condition. 70% yield. ESI-MS calculated for $C_{34}H_{35}FN_7O_3$ [M+H]$^+$=608.27, Obtained: 608.66. $^1$H NMR (300 MHz, MeOD) δ 9.23 (d, J=4.6 Hz, 1H), 8.38 (dd, J=9.3, 5.3 Hz, 1H), 8.05 (d, J=4.5 Hz, 1H), 7.79 (ddd, J=9.3, 8.2, 2.8 Hz, 1H), 7.59 (s, 1H), 7.48 (dd, J=9.6, 2.7 Hz, 1H), 6.42 (s, 1H), 4.45-4.25 (m, 1H), 3.67-3.17 (m, 8H), 2.42-2.30 (m, 2H), 2.30 (s, 3H), 2.16-1.97 (m, 5H), 1.41 (d, J=6.7 Hz, 6H).

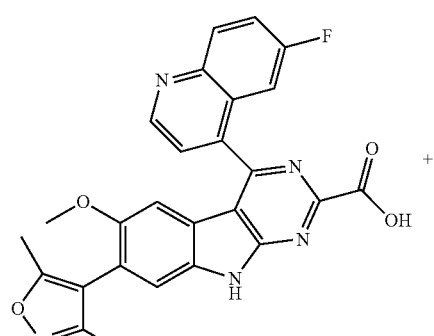

Cpd. No. 289

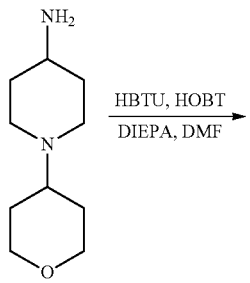

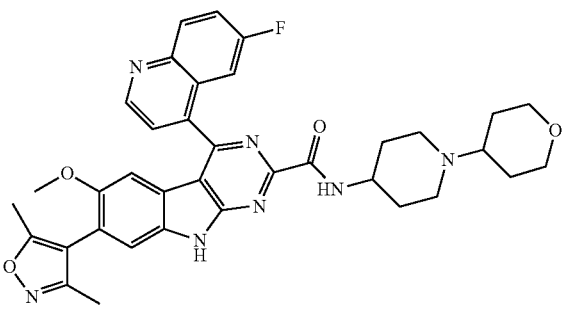

Cpd. No. 293

Cpd. No. 293-TFA salt was prepared from amide condensation of Cpd. No. 289 and 1-(tetrahydro-2H-pyran-4-yl)-4-piperidinamine using HBTU-HOBT condition. 70% yield. ESI-MS calculated for $C_{36}H_{37}FN_7O_4$ [M+H]$^+$=650.28, Obtained: 650.46. $^1$H NMR (300 MHz, MeOD) δ 9.26 (d, J=4.7 Hz, 1H), 8.39 (dd, J=9.4, 5.2 Hz, 1H), 8.10 (d, J=4.6 Hz, 1H), 7.82 (ddd, J=9.3, 8.2, 2.8 Hz, 1H), 7.60 (s, 1H), 7.51 (dd, J=9.5, 2.6 Hz, 1H), 6.44 (s, 1H), 4.40-4.23 (m, 1H), 4.14-4.04 (m, 2H), 3.83-3.40 (m, 5H), 3.33 (s, 3H), 3.24 (t, J=12.2 Hz, 2H), 2.42-2.32 (m, 2H), 2.30 (s, 3H), 2.17-2.03 (m, 7H), 1.90-1.70 (m, 2H).

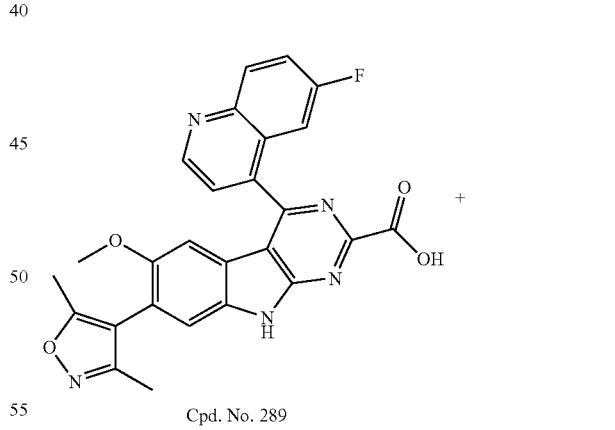

Cpd. No. 289

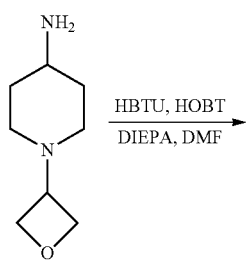

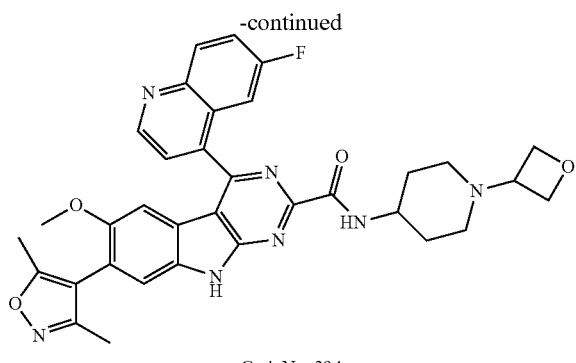

Cpd. No. 294

Cpd. No. 294-TFA salt was prepared from amide condensation of Cpd. No. 289 and 1-(oxetan-3-yl)piperidin-4-amine using HBTU-HOBT condition. 40% yield. ESI-MS calculated for $C_{34}H_{33}FN_7O_4$ [M+H]$^+$=622.25, Obtained: 622.45. $^1$H NMR (300 MHz, MeOD) δ 9.26 (d, J=4.7 Hz, 1H), 8.40 (dd, J=9.4, 5.2 Hz, 1H), 8.10 (d, J=4.7 Hz, 1H), 7.87-7.79 (m, 1H), 7.57 (s, 1H), 7.52 (dd, J=9.6, 2.7 Hz, 1H), 6.43 (s, 1H), 4.95-4.80 (m, 4H), 4.54-4.24 (m, 2H), 3.70-3.49 (m, 2H), 3.36 (s, 3H), 3.22-3.02 (m, 2H), 2.43-2.25 (m, 5H), 2.21-2.04 (m, 5H).

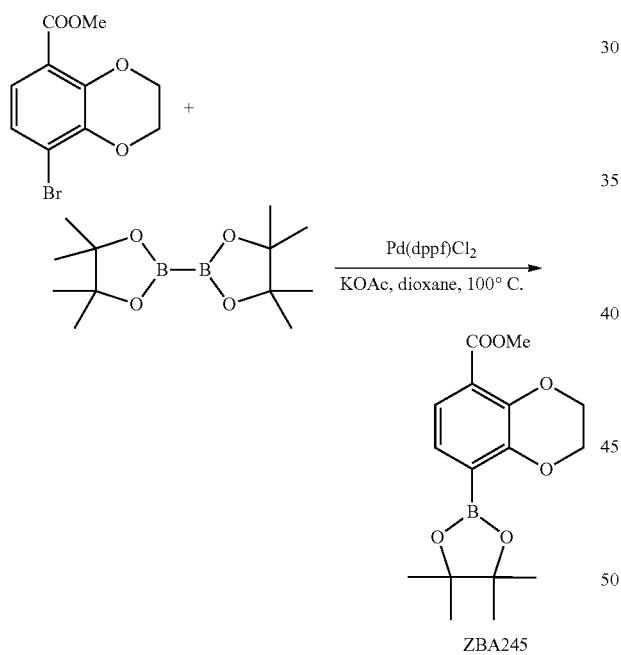

ZBA245 methyl 8-bromo-2,3-dihydrobenzo[b][1,4]dioxine-5-carboxylate (1.1 g, 4.16 mmol), bis(pinacolato)diboron (2.13 g, 8.4 mmol, 2.0 equiv.), and potassium acetate (1.6 g, 16 mmol, 4.0 equiv.) were added to a round-bottom flask. Anhydrous 1,4-dixoane (20 mL) was added via a syringe and the flask was degassed and refilled with nitrogen. Pd(dppf)Cl$_2$ (322 mg, 0.46 mmol, 0.1 equiv.) was added and the system was degassed again followed by heating at 100° C. for 16 h. The reaction mixture was cooled to ambient temperature and diluted by CH$_2$Cl$_2$. The solution was filtered through a pad of celite and the volatile components were removed on a rotary evaporator. The residue was purified by flash column chromatography. The title compound ZBA245 was isolated in 1.0 g. ESI-MS calculated for $C_{16}H_{22}BO_6$ [M+H]$^+$=321.15, Obtained: 321.44.

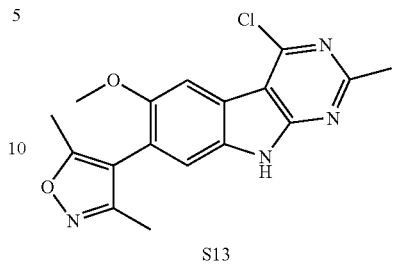

S13

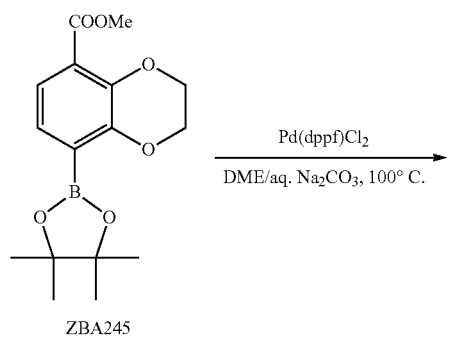

ZBA245

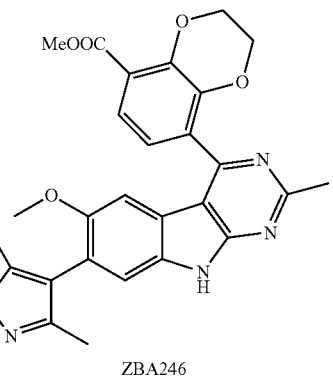

ZBA246

To a round-bottom flask, 4-(4-chloro-6-methoxy-2-methyl-9H-pyrimido[4,5-b]indol-7-yl)-3,5-dimethylisoxazole (S13, 5.4 g, 16 mmol, 1.0 equiv.) and ZBA245 (13.75 g, 37 mmol, 2.0 equiv.), 1,2-dimethoxyethane (150 mL), and Na$_2$CO$_3$ (2 M, 50 mL) were added. The system was degassed to remove oxygen and nitrogen was refilled. Pd(dppf)Cl$_2$—CH$_2$Cl$_2$ (1.3 g, 1.6 mmol, 0.1 equiv.) was added and the system was degassed and refilled with nitrogen. The reaction mixture was heated at reflux for 16 h. The reaction was quenched with water and the aqueous layer was extracted with ethyl acetate. The organic layers were combined and the volatile components were removed on a rotary evaporator. The residue was purified by flash column chromatography to yield the title compound ZBA246 in 2.1 g (26.5% yield over two steps). ESI-MS calculated for $C_{27}H_{25}N_4O_6$ [M+H]=501.17, Obtained: 501.35.

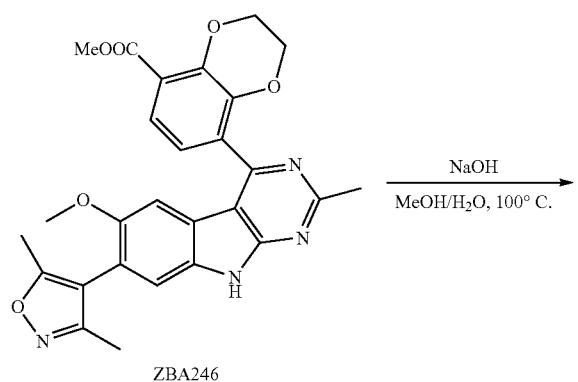

ZBA246

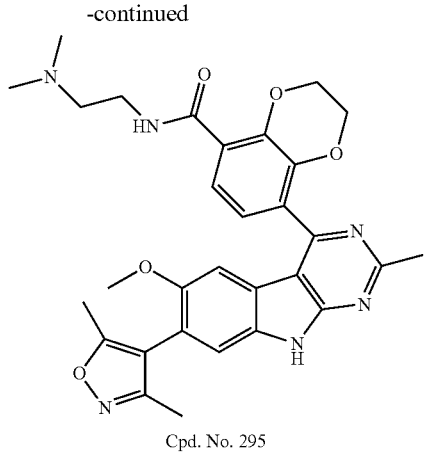

Cpd. No. 295

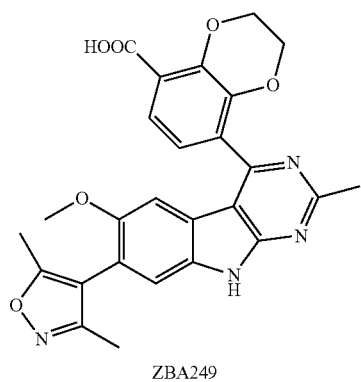

ZBA249

To a round-bottom flask, ZBA246 (110 mg, 0.22 mmol) was dissolved in MeOH (5 mL) and water (5 mL). NaOH (26 mg, 0.66 mmol, 3 equiv.) was added and solution was stirred for 3 h at 100° C. The reaction mixture was extracted with ethyl acetate. Subsequently, the aqueous layer was neutralized to pH=2 and was extracted with ethyl acetate. The organic extracts of acidic aqueous solution were combined and concentrated on a rotary evaporator. The remaining residue was freeze-dried to yield the title compound in 90 mg. ESI-MS calculated for $C_{26}H_{23}N_4O_6$ [M+H]$^+$= 487.16, Obtained: 487.35.

(amide condensation): ZBA249 (20 mg, 0.05 mmol), EDCI-HCl (100 mg, 0.5 mmol), and HOBt-H$_2$O (70 mg, 0.5 mmol) were added to a round-bottom flask. EtN(i-Pr)$_2$ (0.1 mL) was added followed by addition of DMF (2.5 mL). N,N-dimethylethylenediamine (40 mg) was added and the reaction mixture was stirred for 12 h. The reaction was quenched with NaHCO$_3$ saturated solution and the aqueous layer was extracted with ethyl acetate. The combined organic layers were concentrated on a rotary evaporator. The remaining residue was purified by reverse phase HPLC affording the title compound Cpd. No. 295 as a salt of CF$_3$CO$_2$H (69% yield). ESI-MS calculated for $C_{30}H_{33}N_6O_5$ [M+H]$^+$=557.25, Obtained: 557.44. $^1$H NMR (300 MHz, MeOD) δ 7.85 (d, J=8.2 Hz, 1H), 7.58 (s, 1H), 7.50 (d, J=8.2 Hz, 1H), 7.19 (s, 1H), 4.61-4.54 (m, 2H), 4.45-4.40 (m, 2H), 3.89 (t, J=5.9 Hz, 2H), 3.71 (s, 3H), 3.47 (t, J=5.9 Hz, 2H), 3.04 (s, 6H), 2.98 (s, 3H), 2.33 (s, 3H), 2.15 (s, 3H).

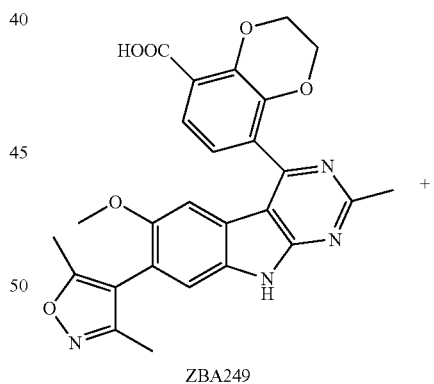

ZBA249

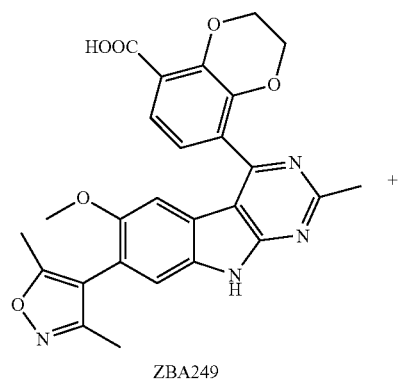

ZBA249

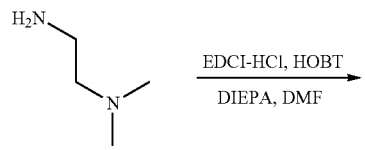

EDCI-HCl, HOBT
DIEPA, DMF

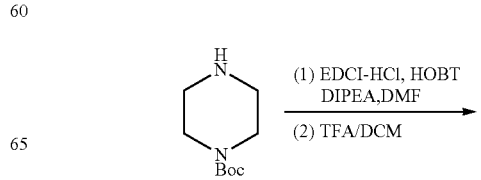

(1) EDCI-HCl, HOBT
DIPEA, DMF
(2) TFA/DCM

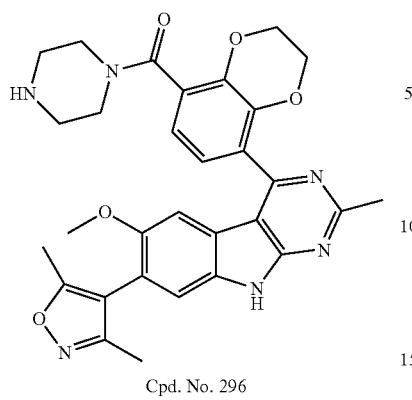

Cpd. No. 296

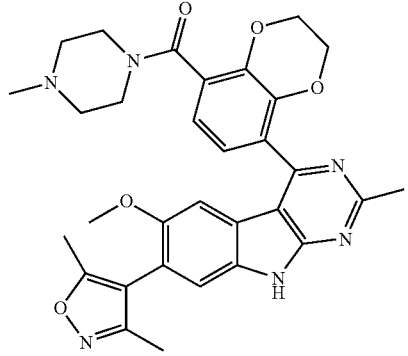

Cpd. No. 297

ZBA249 (20 mg, 0.05 mmol), EDCI-HCl (100 mg, 0.5 mmol), and HOBt-H$_2$O (70 mg, 0.5 mmol) were added to a round-bottom flask. EtN(i-Pr)$_2$ (0.1 mL) was added followed by addition of DMF (2.5 mL). 1-Boc-piperazine (40 mg) was added and the reaction mixture was stirred for 12 h. The reaction was quenched with NaHCO$_3$ saturated solution and the aqueous layer was extracted with ethyl acetate. The combined organic layers were concentrated on a rotary evaporator. The remaining residue was dissolved in TFA (2 mL) and DCM (2 mL). The mixture was stirred for 3 hours and was concentrated on a rotary evaporator. The remaining residue was purified by reverse phase HPLC affording the Cpd. No. 296 as a salt of CF$_3$CO$_2$H (15 mg). ESI-MS calculated for C$_{30}$H$_{31}$N$_6$O$_5$ [M+H]$^+$=555.23, Obtained: 555.44. $^1$H NMR (300 MHz, MeOD) δ 7.58 (s, 1H), 7.51 (d, J=7.9 Hz, 1H), 7.29 (d, J=7.9 Hz, 1H), 7.21 (s, 1H), 4.59-4.37 (m, 4H), 4.23-3.96 (m, 2H), 3.82-3.62 (m, 5H), 3.51-3.30 (m, 4H), 2.99 (s, 3H), 2.33 (s, 3H), 2.15 (s, 3H).

Cpd. No. 297-TFA salt was prepared from amide condensation of ZBA249 and 1-methylpiperazine using EDCI-HOBT condition. 75% yield. ESI-MS calculated for C$_{31}$H$_{33}$N$_6$O$_5$ [M+H]$^+$=569.25, Obtained: 569.64. $^1$H NMR (300 MHz, MeOD) δ 7.56 (s, 1H), 7.50 (d, J=7.9 Hz, 1H), 7.29 (d, J=7.9 Hz, 1H), 7.19 (s, 1H), 4.55-4.37 (m, 4H), 3.92-3.32 (m, 11H), 3.02 (s, 3H), 2.98 (s, 3H), 2.34 (s, 3H), 2.16 (s, 3H).

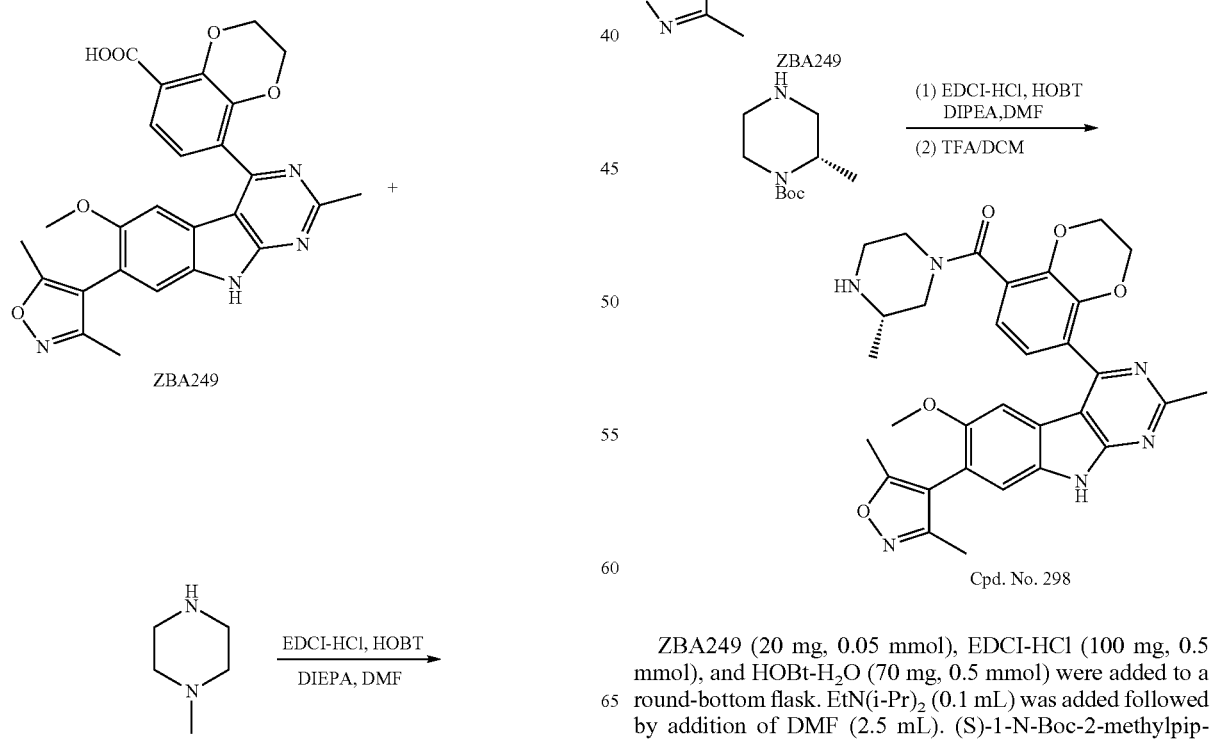

Cpd. No. 298

ZBA249 (20 mg, 0.05 mmol), EDCI-HCl (100 mg, 0.5 mmol), and HOBt-H$_2$O (70 mg, 0.5 mmol) were added to a round-bottom flask. EtN(i-Pr)$_2$ (0.1 mL) was added followed by addition of DMF (2.5 mL). (S)-1-N-Boc-2-methylpiperazine (40 mg) was added and the reaction mixture was stirred for 12 h. The reaction was quenched with NaHCO₃ saturated solution and the aqueous layer was extracted with ethyl acetate. The combined organic layers were concentrated on a rotary evaporator. The remaining residue was dissolved in TFA (2 mL) and DCM (2 mL). The mixture was stirred for 3 hours and was concentrated on a rotary evaporator. The remaining residue was purified by reverse phase HPLC affording the Cpd. No. 298 as a salt of CF₃CO₂H (17 mg). ESI-MS calculated for $C_{31}H_{33}N_6O_5$ [M+H]⁺=569.25, Obtained: 569.55.

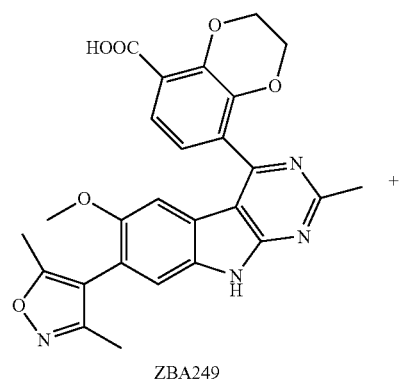

ZBA249

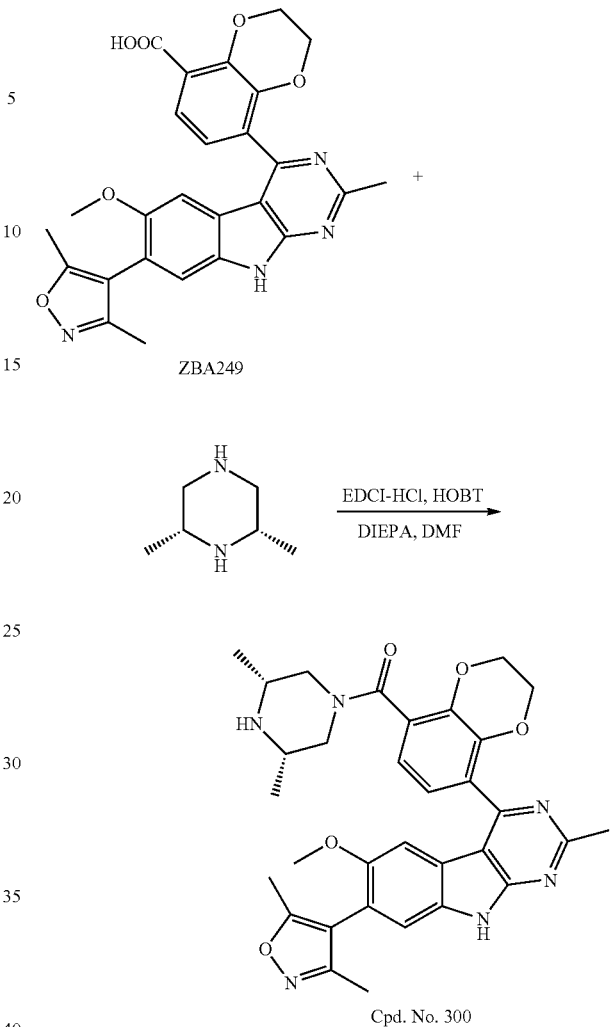

ZBA249

Cpd. No. 300

Cpd. No. 300-TFA salt was prepared from amide condensation of ZBA249 and cis-2,6-dimethylpiperazine dihydrochloride using EDCI-HOBT condition. 80% yield. ESI-MS calculated for $C_{32}H_{35}N_6O_5$ [M+H]⁺=583.26, Obtained: 583.47. ¹H NMR (300 MHz, MeOD) δ 7.58 (s, 1H), 7.51 (d, J=5.5 Hz, 1H), 7.36-7.18 (m, 2H), 4.91 (brs, 1H), 4.55-4.36 (m, 4H), 3.88-3.69 (m, 4H), 3.63-3.20 (m, 3H), 3.06-2.86 (m, 4H), 2.34 (s, 3H), 2.16 (s, 3H), 1.47 (d, J=6.5 Hz, 3H), 1.40-1.27 (m, 3H).

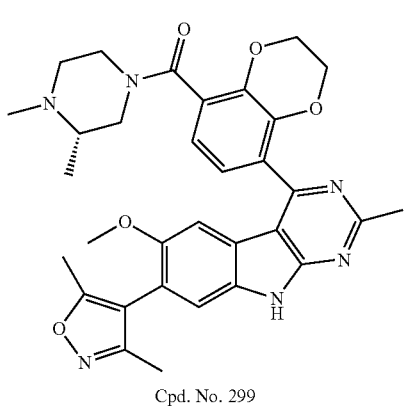

Cpd. No. 299

Cpd. No. 299-TFA salt was prepared from amide condensation of ZBA249 and (S)-1,2-dimethylpiperazine dihydrochloride using EDCI-HOBT condition. 75% yield. ESI-MS calculated for $C_{32}H_{35}N_6O_5$ [M+H]⁺=583.26, Obtained: 583.37. ¹H NMR (300 MHz, MeOD) δ 7.58 (s, 1H), 7.51 (d, J=7.9 Hz, 1H), 7.33-7.18 (m, 2H), 4.60-4.35 (m, 4H), 3.96-3.31 (m, 10H), 3.06-2.96 (m, 6H), 2.34 (s, 3H), 2.16 (s, 3H), 1.59-1.32 (m, 3H).

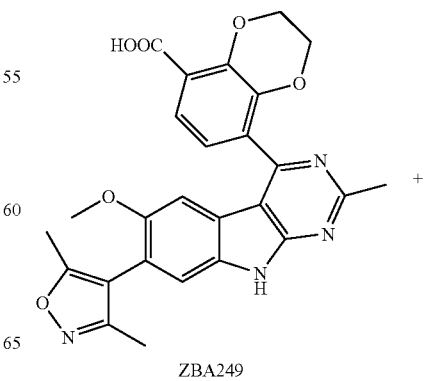

ZBA249

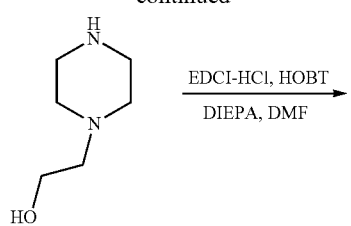

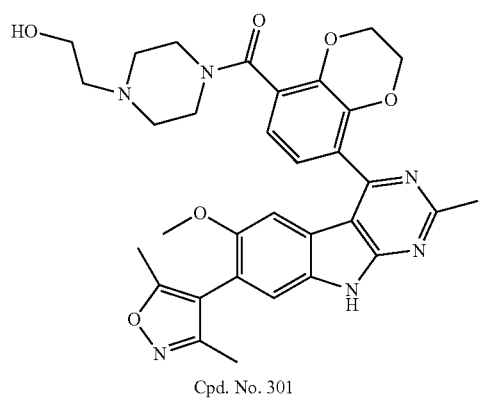

Cpd. No. 301

Cpd. No. 301-TFA salt was prepared from amide condensation of ZBA249 and 1-(2-hydroxyethyl)piperazine using EDCI-HOBT condition. 80% yield. ESI-MS calculated for $C_{32}H_{35}N_6O_6$ [M+H]$^+$=599.26, Obtained: 599.66. $^1$H NMR (300 MHz, MeOD) δ 7.57 (s, 1H), 7.51 (d, J=7.9 Hz, 1H), 7.29 (d, J=7.9 Hz, 1H), 7.21 (s, 1H), 4.59-4.37 (m, 4H), 4.01-3.92 (m, 2H), 3.89-3.35 (m, 13H), 2.99 (s, 3H), 2.34 (s, 3H), 2.16 (s, 3H).

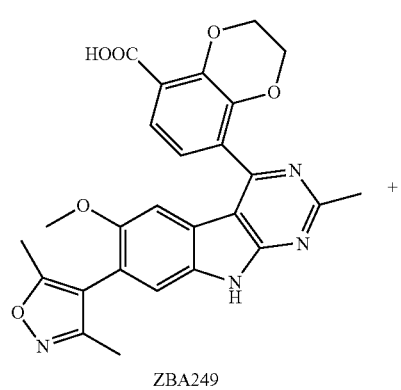

ZBA249

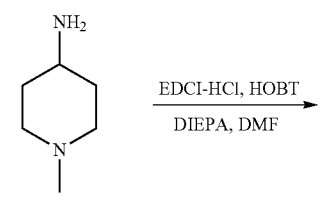

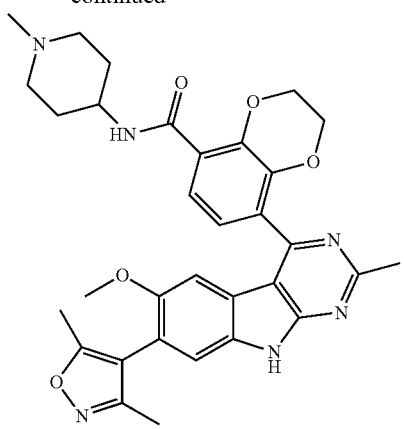

Cpd. No. 302

Cpd. No. 302-TFA salt was prepared from amide condensation of ZBA249 and 1-methyl-4-piperidinamine using EDCI-HOBT condition. 75% yield. ESI-MS calculated for $C_{32}H_{35}N_6O_5$ [M+H]=583.26, Obtained: 583.37. $^1$H NMR (300 MHz, MeOD) δ 7.64 (d, J=8.1 Hz, 1H), 7.58 (s, 1H), 7.48 (d, J=8.0 Hz, 1H), 7.19 (s, 1H), 4.63-4.33 (m, 4H), 4.37-4.14 (m, 1H), 3.72 (s, 3H), 3.70-3.50 (m, 2H), 3.22 (dd, J=13.2, 10.6 Hz, 2H), 2.98 (s, 3H), 2.93 (s, 3H), 2.38-2.24 (d, J=8.3 Hz, 5H), 2.16 (s, 3H), 2.08-1.90 (m, 2H).

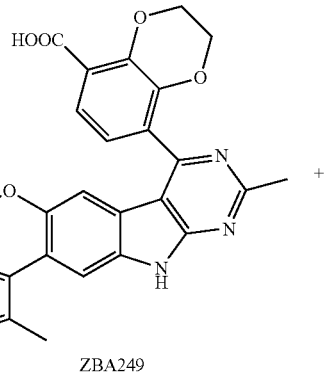

ZBA249

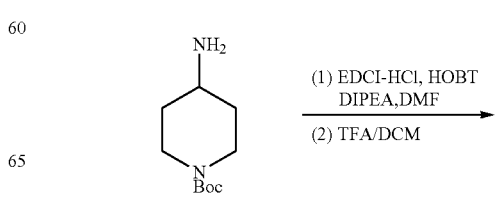

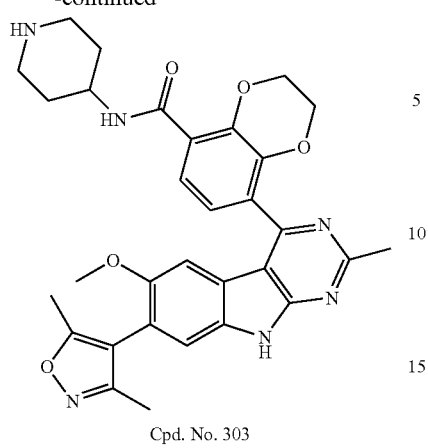

Cpd. No. 303

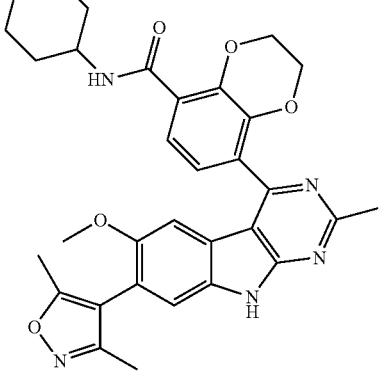

Cpd. No. 304

ZBA249 (20 mg, 0.05 mmol), EDCI-HCl (100 mg, 0.5 mmol), and HOBt-H$_2$O (70 mg, 0.5 mmol) were added to a round-bottom flask. EtN(i-Pr)$_2$ (0.1 mL) was added followed by addition of DMF (2.5 mL). 4-Amino-1-Boc-piperidine (40 mg) was added and the reaction mixture was stirred for 12 h. The reaction was quenched with NaHCO$_3$ saturated solution and the aqueous layer was extracted with ethyl acetate. The combined organic layers were concentrated on a rotary evaporator. The remaining residue was dissolved in TFA (2 mL) and DCM (2 mL). The mixture was stirred for 3 hours and was concentrated on a rotary evaporator. The remaining residue was purified by reverse phase HPLC affording the Cpd. No. 303 as a salt of CF$_3$CO$_2$H (20 mg). ESI-MS calculated for C$_{31}$H$_{33}$N$_6$O$_5$ [M+H]$^+$=569.25, Obtained: 569.45. $^1$H NMR (300 MHz, MeOD) δ 7.64 (d, J=8.1 Hz, 1H), 7.58 (s, 1H), 7.48 (d, J=8.1 Hz, 1H), 7.19 (s, 1H), 4.63-4.48 (m, 2H), 4.44-4.38 (m, 2H), 4.34-4.17 (m, 1H), 3.72 (s, 3H), 3.52 (dd, J=9.7, 3.6 Hz, 2H), 3.22 (td, J=12.7, 2.8 Hz, 2H), 2.98 (s, 3H), 2.37-2.23 (m, 5H), 2.16 (s, 3H), 2.02-1.85 (m, 2H).

Cpd. No. 304-TFA salt was prepared from amide condensation of ZBA249 and 2-(4-aminopiperidin-1-yl)ethanol using EDCI-HOBT condition. 75% yield. ESI-MS calculated for C$_{33}$H$_{37}$N$_6$O$_6$ [M+H]$^+$=613.27, Obtained: 613.57. $^1$H NMR (300 MHz, MeOD) δ 7.64 (d, J=8.1 Hz, 1H), 7.58 (s, 1H), 7.48 (d, J=8.1 Hz, 1H), 7.19 (s, 1H), 4.64-4.17 (m, 5H), 3.98-3.88 (m, 2H), 3.85-3.66 (m, 5H), 3.62-3.36 (m, 2H), 3.30-3.15 (m, 2H), 2.98 (s, 3H), 2.41-1.90 (m, 10H).

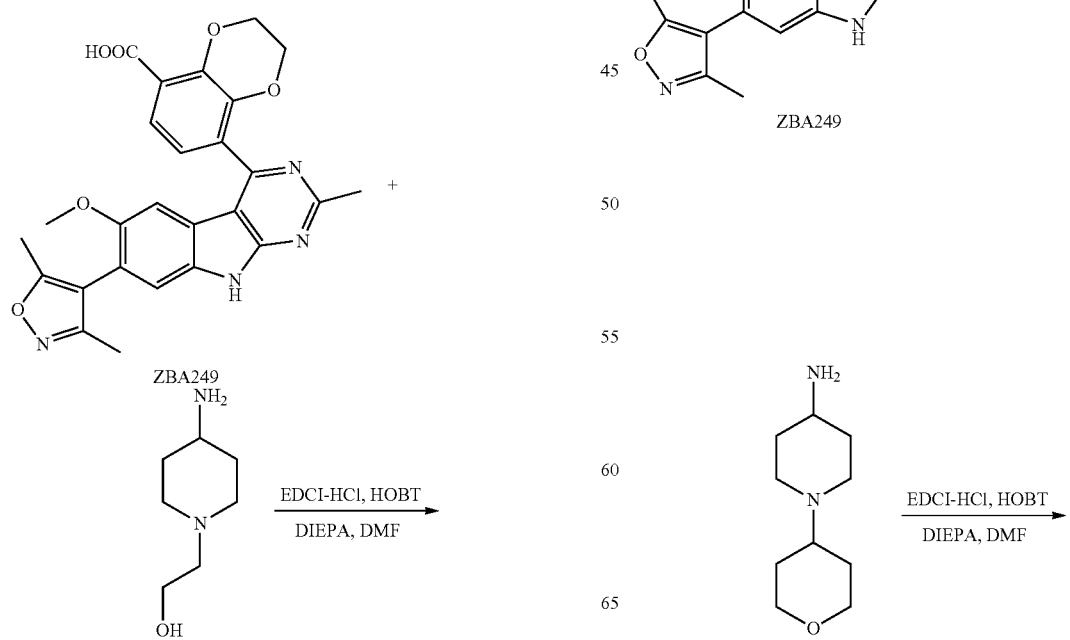

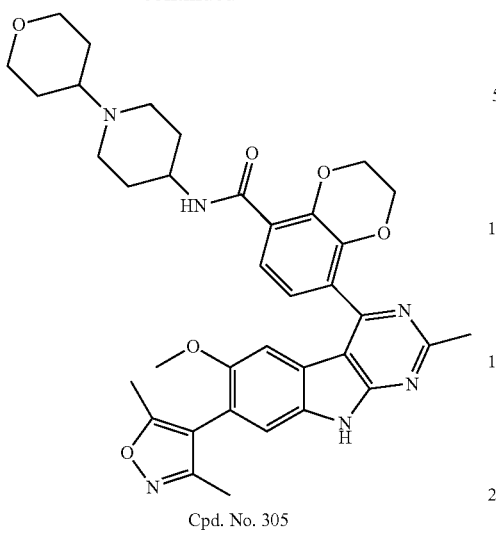

Cpd. No. 305

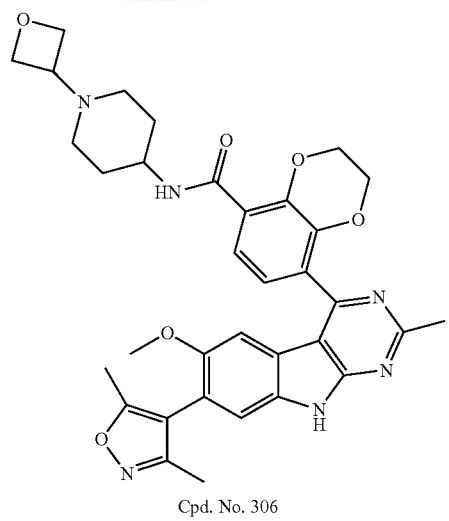

Cpd. No. 306

Cpd. No. 305-TFA salt was prepared form amide condensation of ZBA249 and 1-(tetrahydro-2H-pyran-4-yl)-4-piperidinamine using EDCI-HOBT condition. 80% yield. ESI-MS calculated for $C_{36}H_{41}N_6O_6$ [M+H]$^+$=653.30, Obtained: 653.55. $^1$H NMR (300 MHz, MeOD) δ 7.64 (d, J=8.1 Hz, 1H), 7.58 (s, 1H), 7.47 (d, J=8.1 Hz, 1H), 7.19 (s, 1H), 4.62-4.35 (m, 4H), 4.32-4.18 (m, 1H), 4.11 (dd, J=11.3, 4.1 Hz, 2H), 3.78-3.66 (m, 5H), 3.48 (t, J=11.3 Hz, 3H), 3.30-3.17 (m, 2H), 2.98 (s, 3H), 2.43-2.26 (m, 5H), 2.16 (s, 3H), 2.13-1.70 (m, 6H).

Cpd. No. 306-TFA salt was prepared from amide condensation of ZBA249 and 1-(oxetan-3-yl)piperidin-4-amine using EDCI-HOBT condition. 80% yield. ESI-MS calculated for $C_{34}H_{37}N_6O_6$ [M+H]$^+$=625.27, Obtained: 625.37. $^1$H NMR (300 MHz, MeOD) δ 7.63 (d, J=8.1 Hz, 1H), 7.58 (s, 1H), 7.47 (d, J=8.1 Hz, 1H), 7.19 (s, 1H), 4.89 (d, J=6.5 Hz, 4H), 4.63-4.18 (m, 6H), 3.72 (s, 3H), 3.65-3.45 (m, 2H), 3.22-3.02 (m, 2H), 2.98 (s, 3H), 2.45-1.91 (m, 10H).

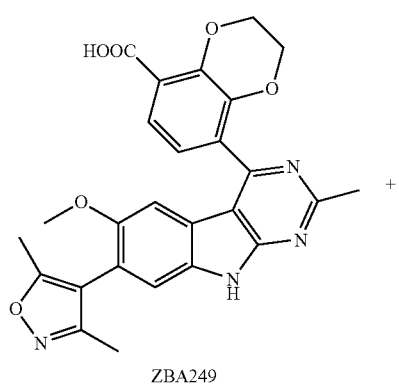

ZBA249

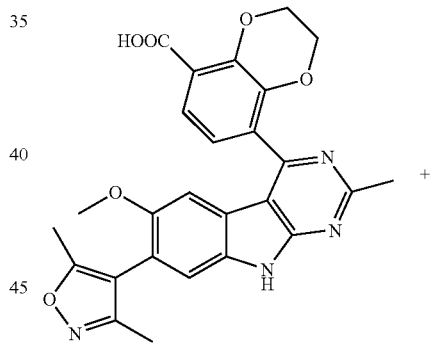

ZBA249

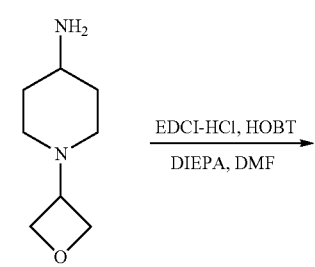

EDCI-HCl, HOBT
DIEPA, DMF
→

EDCI-HCl, HOBT
DIEPA, DMF
→

3.98-3.88 (m, 2H), 3.74 (s, 3H), 3.66-3.47 (m, 2H), 3.43-3.25 (m, 4H), 3.00 (s, 3H), 2.92 s, 3H), 2.33 (s, 3H), 2.15 (s, 3H).

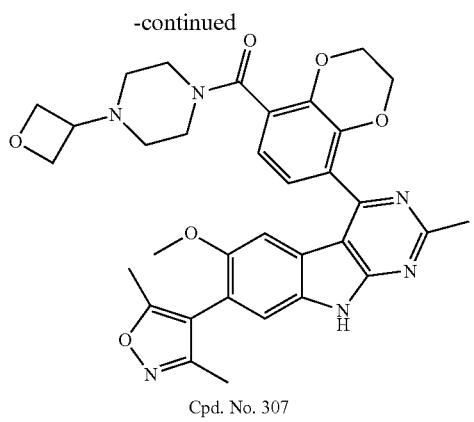

Cpd. No. 307

Cpd. No. 307-TFA salt was prepared from amide condensation of ZBA249 and 1-(oxetan-3-yl)piperazine using EDCI-HOBT condition. 70% yield. ESI-MS calculated for $C_{33}H_{35}N_6O_6$ [M+H]$^+$=611.26, Obtained: 611.37. $^1$H NMR (300 MHz, MeOD) δ 7.58 (s, 1H), 7.51 (d, J=7.9 Hz, 1H), 7.29 (d, J=7.9 Hz, 1H), 7.19 (d, J=10.4 Hz, 1H), 4.95-4.87 (m, 4H), 4.60-4.34 (m, 5H), 4.34-3.76 (m, 4H), 3.73 (s, 3H), 3.50-3.20 (m, 4H), 2.99 (s, 3H), 2.32 (s, 3H), 2.14 (s, 3H).

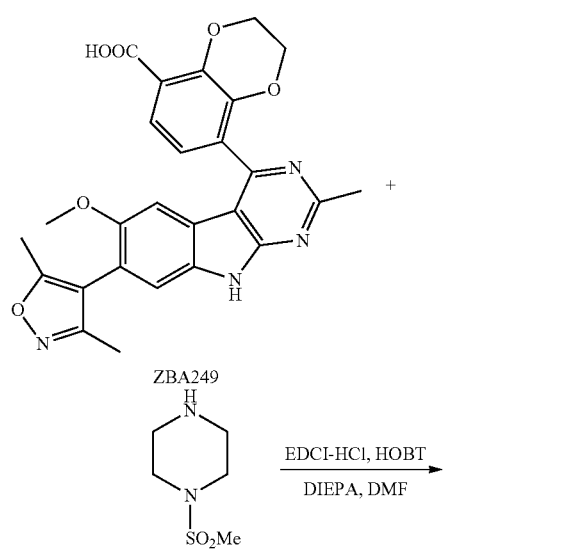

Cpd. No. 308

Cpd. No. 308-TFA salt was prepared from amide condensation of ZBA249 and 1-methylsulfonyl-piperazine using EDCI-HOBT condition. 80% yield. ESI-MS calculated for $C_{31}H_{33}N_6O_7S$[M+H]=633.21, Obtained: 633.44. $^1$H NMR (300 MHz, MeOD) δ 7.59 (s, 1H), 7.51 (d, J=7.9 Hz, 1H), 7.26 (d, J=7.9 Hz, 1H), 7.22 (s, 1H), 4.59-4.38 (m, 4H),

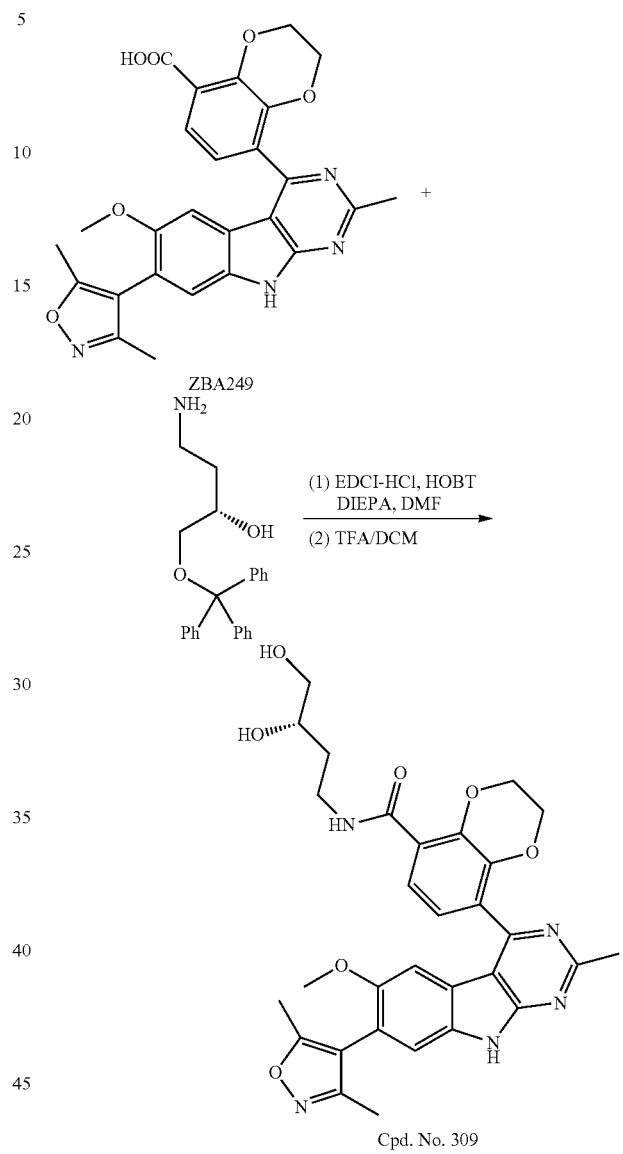

Cpd. No. 309

ZBA249 (20 mg, 0.05 mmol), EDCI-HCl (100 mg, 0.5 mmol), and HOBt-H$_2$O (70 mg, 0.5 mmol) were added to a round-bottom flask. EtN(i-Pr)$_2$ (0.1 mL) was added followed by addition of DMF (2.5 mL). (S)-4-Amino-1-(trityloxy)butan-2-ol (40 mg) was added and the reaction mixture was stirred for 12 h. The reaction was quenched with NaHCO$_3$ saturated solution and the aqueous layer was extracted with ethyl acetate. The combined organic layers were concentrated on a rotary evaporator. The remaining residue was dissolved in TFA (2 mL) and DCM (2 mL). The mixture was stirred for 3 hours and was concentrated on a rotary evaporator. The remaining residue was purified by reverse phase HPLC affording the Cpd. No. 309 as a salt of CF$_3$CO$_2$H (18 mg). ESI-MS calculated for $C_{30}H_{32}N_5O_7$ [M+H]$^+$=574.23, Obtained: 574.47. $^1$H NMR (300 MHz, MeOD) δ 7.77 (d, J=8.2 Hz, 1H), 7.57 (s, 1H), 7.47 (d, J=8.2 Hz, 1H), 7.18 (s, 1H), 4.61-4.51 (m, 2H), 4.45-4.37 (m, 2H), 3.85-3.52 (m, 8H), 2.98 (s, 3H), 2.34 (s, 3H), 2.16 (s, 3H), 2.00-1.61 (m, 2H).

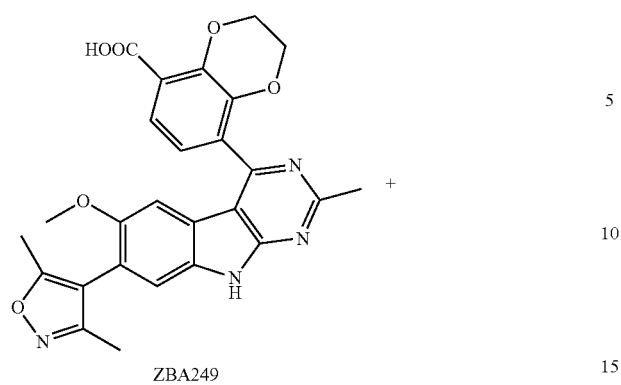

ZBA249

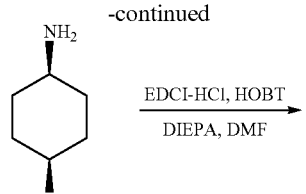

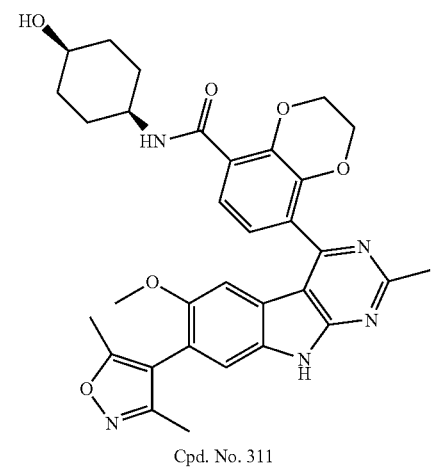

Cpd. No. 310

Cpd. No. 310-TFA salt was prepared from amide condensation of ZBA249 and 4-hydroxypiperidine using EDCI-HOBT condition. 80% yield. ESI-MS calculated for $C_{31}H_{32}N_5O_6$ [M+H]$^+$=570.23, Obtained: 570.4. $^1$H NMR (300 MHz, MeOD) δ 7.57 (s, 1H), 7.47 (dd, J=7.9, 3.6 Hz, 1H), 7.26-7.15 (m, 2H), 4.54-4.35 (m, 4H), 4.32-4.18 (m, 1H), 4.02-3.90 (m, 1H), 3.73 (s, 3H), 3.70-3.55 (m, 1H), 3.51-3.21 (m, 2H), 2.99 (s, 3H), 2.34 (s, 3H), 2.16 (s, 3H), 2.07-1.78 (m, 2H), 1.68-1.4256 (m, 2H).

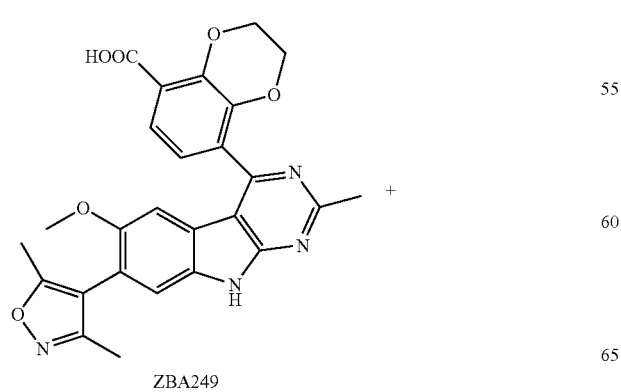

ZBA249

Cpd. No. 311

Cpd. No. 311-TFA salt was prepared from amide condensation of ZBA249 and cis-4-Amino-cyclohexanol using EDCI-HOBT condition. 80% yield. ESI-MS calculated for $C_{32}H_{34}N_5O_6$ [M+H]$^+$=584.25, Obtained: 584.5.

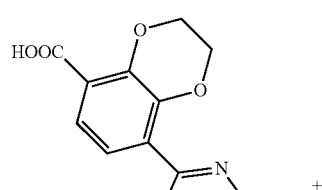

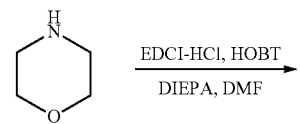

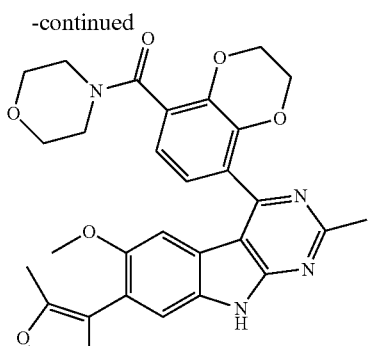

Cpd. No. 312

Cpd. No. 312-TFA salt was prepared from amide condensation of ZBA249 and morpholine using EDCI-HOBT condition. 80% yield. ESI-MS calculated for $C_{30}H_{30}N_5O_6$ [M+H]$^+$=556.21, Obtained: 556.4. $^1$H NMR (300 MHz, MeOD) δ 7.57 (s, 1H), 7.48 (d, J=7.9 Hz, 1H), 7.24 (d, J=7.9 Hz, 1H), 7.18 (s, 1H), 4.51-4.45 (m, 2H), 4.44-4.36 (m, 2H), 3.88-3.66 (m, 9H), 3.52-3.39 (m, 2H), 2.98 (s, 3H), 2.34 (s, 3H), 2.16 (s, 3H).

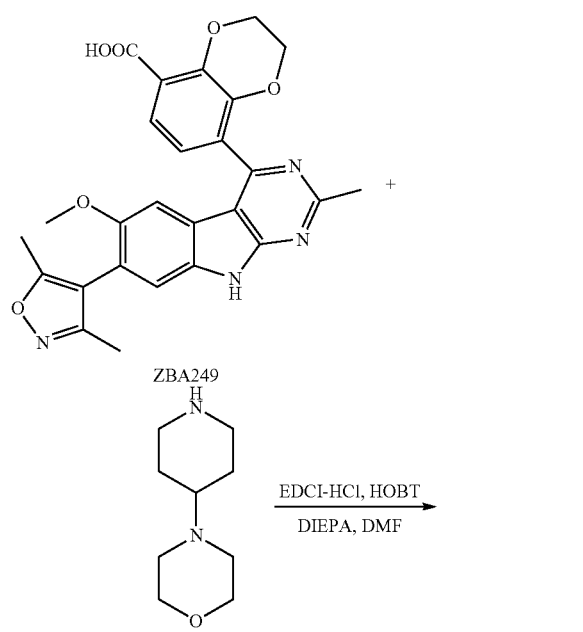

Cpd. No. 313

Cpd. No. 313-TFA salt was prepared from amide condensation of ZBA249 and 4-morpholinopiperidine using EDCI-HOBT condition. 80% yield. ESI-MS calculated for $C_{35}H_{39}N_6O_6$ [M+H]$^+$=639.29, Obtained: 639.5. $^1$H NMR (300 MHz, MeOD) δ 7.57 (s, 1H), 7.49 (d, J=7.9 Hz, 1H), 7.32-7.17 (m, 2H), 4.59-4.28 (m, 4H), 4.20-4.02 (m, 2H), 3.93-3.15 (m, 13H), 3.05-2.86 (m, 4H), 2.46-2.22 (m, 5H), 2.16 (s, 3H), 1.94-1.66 (m, 2H).

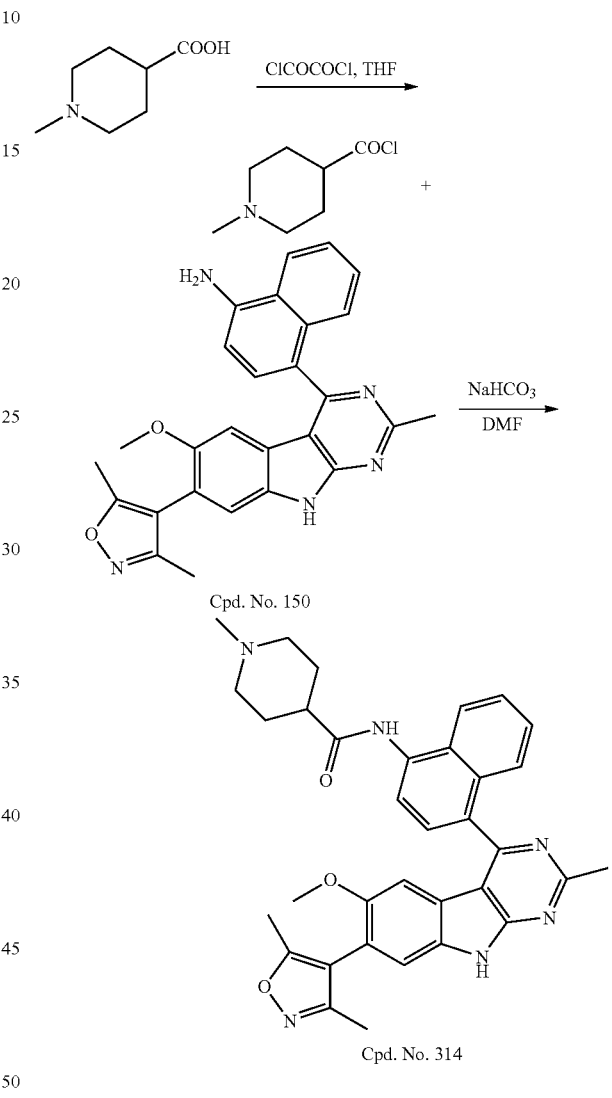

Cpd. No. 314

1-methyl-4-piperidinecarboxylic acid (57 mg, 0.4 mmol) and THF (10 mL) were added to a round-bottom flask. Oxalyl chloride (0.1 mL) was added followed by addition of DMF (1 drop). The reaction mixture was stirred for 3 h and then was concentrated on a rotary evaporator. The remaining residue was dissolved in DMF (1 mL). Then Cpd. No. 150 (20 mg) and NaHCO$_3$ (50 mg) was added. The mixture was stirred for 12 h at room temperature. The reaction was quenched with NaHCO$_3$ saturated solution and the aqueous layer was extracted with ethyl acetate. The combined organic layers were concentrated on a rotary evaporator. The remaining residue was purified by reverse phase HPLC affording the Cpd. No. 314 as a salt of CF$_3$CO$_2$H (13 mg). ESI-MS calculated for $C_{34}H_{35}N_6O_3$ [M+H]$^+$=575.27, Obtained: 575.47. $^1$H NMR (300 MHz, MeOD) δ 8.38 (d, J=8.4 Hz, 1H), 8.13 (d, J=7.8 Hz, 1H), 8.04 (d, J=7.8 Hz, 1H), 7.79 (t, J=8.7 Hz, 2H), 7.67-7.60 (m, 1H), 7.55 (s, 1H), 6.23 (s, 1H), 3.77-3.66 (m, 2H), 3.54 (d, J=7.3 Hz, 2H), 3.27-3.09 (m, 4H), 3.03 (s, 3H), 2.97 (s, 3H), 2.47-2.12 (m, 7H), 2.08 (s, 3H).

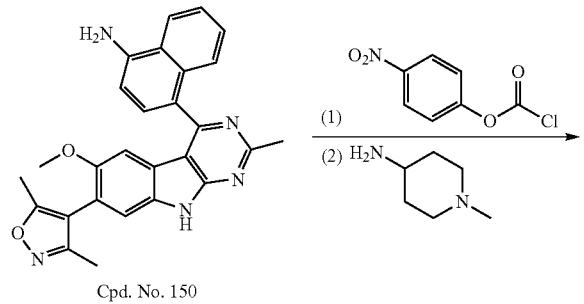

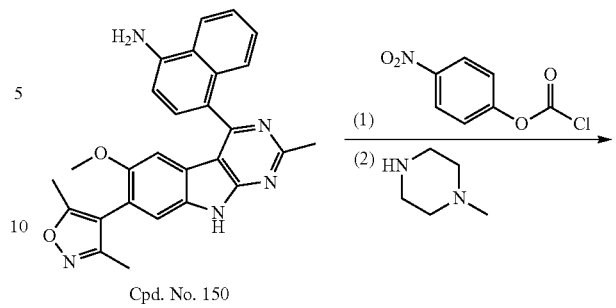

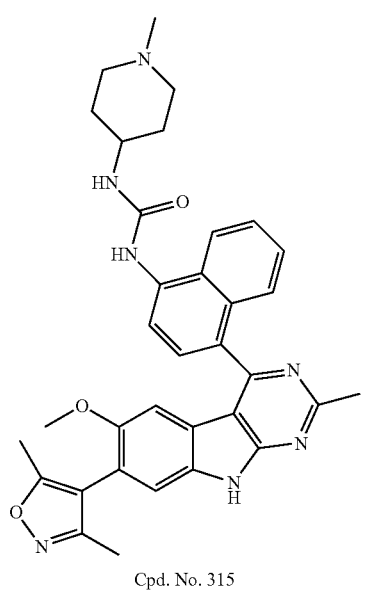

Cpd. No. 150 (50 mg) and pyridine (2 mL) were added to a round-bottom flask. 4-Nitrophenyl chloroformate (33 mg) was added. The reaction mixture was stirred for 5 h and then 1-methyl-4-piperidinamine (300 mg) and DBU (300 mg) was added. The mixture was stirred for 12 h at room temperature. The reaction was quenched with NaHCO₃ saturated solution and the aqueous layer was extracted with ethyl acetate. The combined organic layers were concentrated on a rotary evaporator. The remaining residue was purified by reverse phase HPLC affording the Cpd. No. 315 as a salt of CF₃CO₂H (30 mg). ESI-MS calculated for $C_{34}H_{36}N_7O_3$ [M+H]⁺=590.28 Obtained: 590.5. ¹H NMR (300 MHz, MeOD) δ 8.51-8.31 (m, 2H), 7.98 (d, J=8.1 Hz, 1H), 7.82-7.71 (m, 2H), 7.65-7.58 (m, 1H), 7.54 (s, 1H), 6.26 (s, 1H), 4.06-3.90 (m, 1H), 3.71-3.47 (m, 2H), 3.28-3.12 (m, 5H), 3.02 (s, 3H), 2.93 (s, 3H), 2.44-2.14 (m, 5H), 2.09 (s, 3H), 1.95-1.77 (m, 2H).

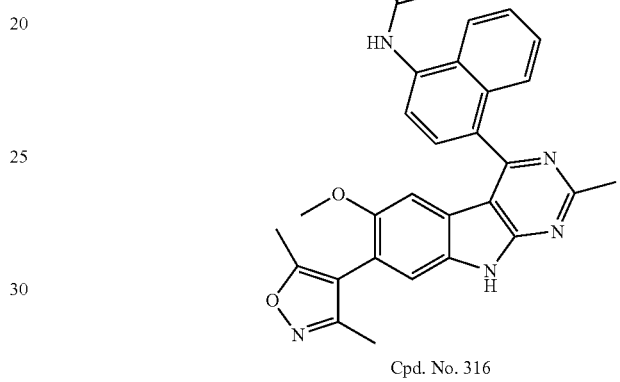

Cpd. No. 150 (50 mg) and pyridine (2 mL) were added to a round-bottom flask. 4-Nitrophenyl chloroformate (33 mg) was added. The reaction mixture was stirred for 5 h and then 1-methylpiperazine (300 mg) and DBU (300 mg) was added. The mixture was stirred for 12 h at room temperature. The reaction was quenched with NaHCO₃ saturated solution and the aqueous layer was extracted with ethyl acetate. The combined organic layers were concentrated on a rotary evaporator. The remaining residue was purified by reverse phase HPLC affording the Cpd. No. 316 as a salt of CF₃CO₂H (29 mg). ESI-MS calculated for $C_{33}H_{34}N_7O_3$ [M+H]⁺=576.27, Obtained: 576.5. ¹H NMR (300 MHz, MeOD) δ 8.34 (d, J=8.5 Hz, 1H), 8.02 (d, J=7.8 Hz, 1H), 7.87 (d, J=7.8 Hz, 1H), 7.81-7.69 (m, 2H), 7.65-7.56 (m, 1H), 7.55 (s, 1H), 6.26 (s, 1H), 4.70-4.34 (m, 2H), 3.81-3.24 (m, 6H), 3.20 (s, 3H), 3.04 (s, 3H), 3.03 (s, 3H), 2.28 (s, 3H), 2.09 (s, 3H).

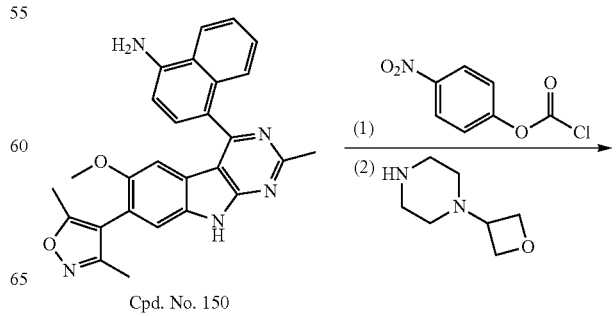

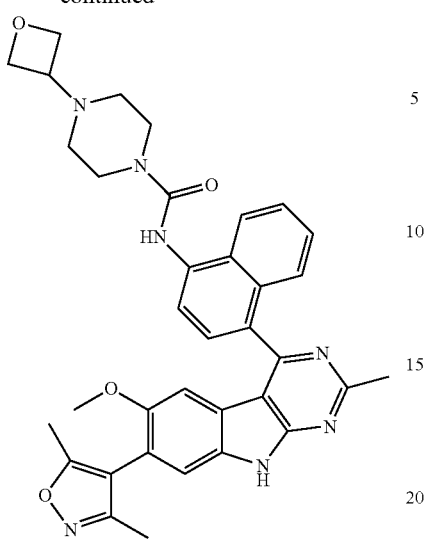

Cpd. No. 317

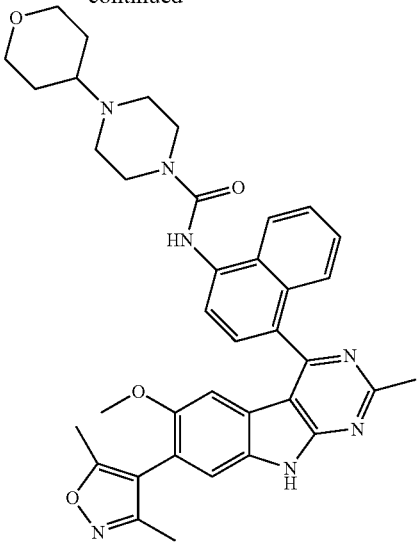

Cpd. No. 318

Cpd. No. 150 (50 mg) and pyridine (2 mL) were added to a round-bottom flask. 4-Nitrophenyl chloroformate (33 mg) was added. The reaction mixture was stirred for 5 h and then 1-(oxetan-3-yl)piperazine (300 mg) and DBU (300 mg) was added. The mixture was stirred for 12 h at room temperature. The reaction was quenched with NaHCO$_3$ saturated solution and the aqueous layer was extracted with ethyl acetate. The combined organic layers were concentrated on a rotary evaporator. The remaining residue was purified by reverse phase HPLC affording the Cpd. No. 317 as a salt of CF$_3$CO$_2$H (32 mg). ESI-MS calculated for C$_{35}$H$_{36}$N$_7$O$_4$ [M+H]$^+$=618.28, Obtained: 618.5. $^1$H NMR (300 MHz, MeOD) δ 8.33 (d, J=8.5 Hz, 1H), 8.01 (d, J=7.8 Hz, 1H), 7.87 (d, J=7.8 Hz, 1H), 7.82-7.69 (m, 2H), 7.66-7.57 (m, 1H), 7.55 (s, 1H), 6.26 (s, 1H), 5.01-4.84 (m, 4H), 4.57-4.46 (m, 1H), 4.13-3.97 (m, 4H), 3.44-3.36 (m, 4H), 3.19 (s, 3H), 3.03 (s, 3H), 2.28 (s, 3H), 2.08 (s, 3H).

Cpd. No. 150 (50 mg) and pyridine (2 mL) were added to a round-bottom flask. 4-Nitrophenyl chloroformate (33 mg) was added. The reaction mixture was stirred for 5 h and then 1-(tetrahydro-2H-pyran-4-yl)piperazine (300 mg) and DBU (300 mg) was added. The mixture was stirred for 12 h at room temperature. The reaction was quenched with NaHCO$_3$ saturated solution and the aqueous layer was extracted with ethyl acetate. The combined organic layers were concentrated on a rotary evaporator. The remaining residue was purified by reverse phase HPLC affording the Cpd. No. 318 as a salt of CF$_3$CO$_2$H (5 mg). ESI-MS calculated for C$_{37}$H$_{40}$N$_7$O$_4$ [M+H]$^+$=646.31, Obtained: 646.55.

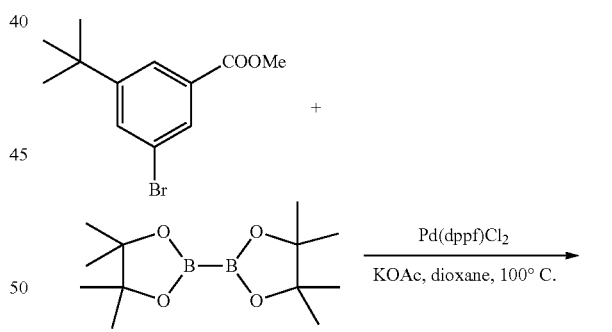

ZBA297

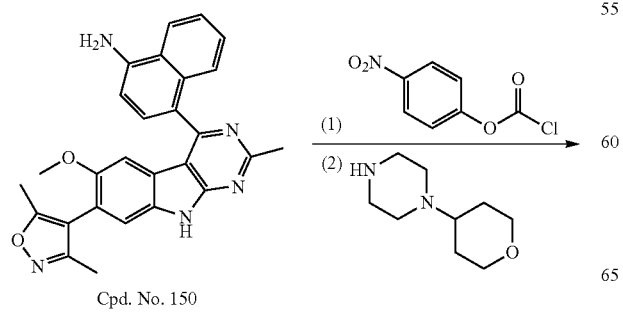

Cpd. No. 150

Methyl 3-bromo-5-(tert-butyl)benzoate (1.1 g, 4.16 mmol), bis(pinacolato)diboron (2.13 g, 8.4 mmol, 2.0 equiv.), and potassium acetate (1.6 g, 16 mmol, 4.0 equiv.) were added to a round-bottom flask. Anhydrous 1,4-dixoane (20 mL) was added via a syringe and the flask was degassed and refilled with nitrogen. Pd(dppf)Cl$_2$ (322 mg, 0.46 mmol, 0.1 equiv.) was added and the system was degassed again followed by heating at 100° C. for 16 h. The reaction mixture was cooled to ambient temperature and diluted by CH$_2$Cl$_2$. The solution was filtered through a pad of celite and the volatile components were removed on a rotary evaporator. The residue was purified by flash column chromatography. The title compound ZBA297 was isolated in 0.9 g. ESI-MS calculated for C$_{18}$H$_{28}$BO$_4$ [M+H]$^+$=319.20, Obtained: 319.4.

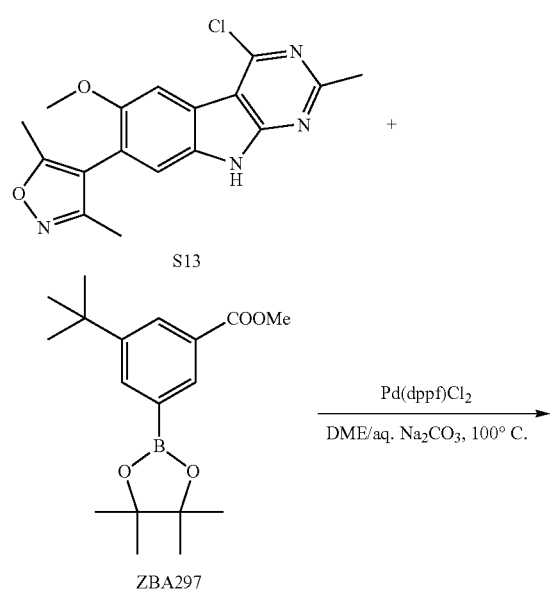

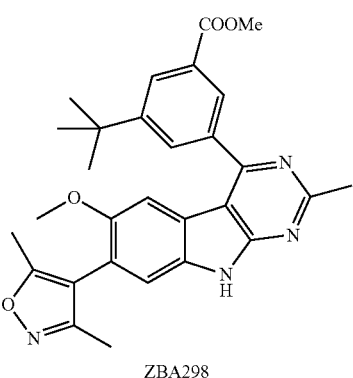

To a round-bottom flask, 4-(4-chloro-6-methoxy-2-methyl-9H-pyrimido[4,5-b]indol-7-yl)-3,5-dimethylisoxazole (S13, 5.4 g, 16 mmol, 1.0 equiv.) and ZBA297 (13.75 g, 37 mmol, 2.0 equiv.), 1,2-dimethoxyethane (150 mL), and Na$_2$CO$_3$ (2 M, 50 mL) were added. The system was degassed to remove oxygen and nitrogen was refilled. Pd(dppf)Cl$_2$—CH$_2$Cl$_2$ (1.3 g, 1.6 mmol, 0.1 equiv.) was added and the system was degassed and refilled with nitrogen. The reaction mixture was heated at reflux for 16 h. The reaction was quenched with water and the aqueous layer was extracted with ethyl acetate. The organic layers were combined and the volatile components were removed on a rotary evaporator. The residue was purified by flash column chromatography to yield the title compound ZBA298 in 2.2 g. ESI-MS calculated for C$_{29}$H$_{31}$N$_4$O$_4$ [M+H]$^+$=499.23, Obtained: 499.6. $^1$H NMR (300 MHz, DMSO) δ 12.28 (s, 1H), 8.37 (s, 1H), 8.22 (s, 2H), 7.40 (s, 1H), 7.31 (s, 1H), 3.91 (s, 3H), 3.62 (s, 3H), 2.76 (s, 3H), 2.30 (s, 3H), 2.09 (s, 3H), 1.42 (s, 9H).

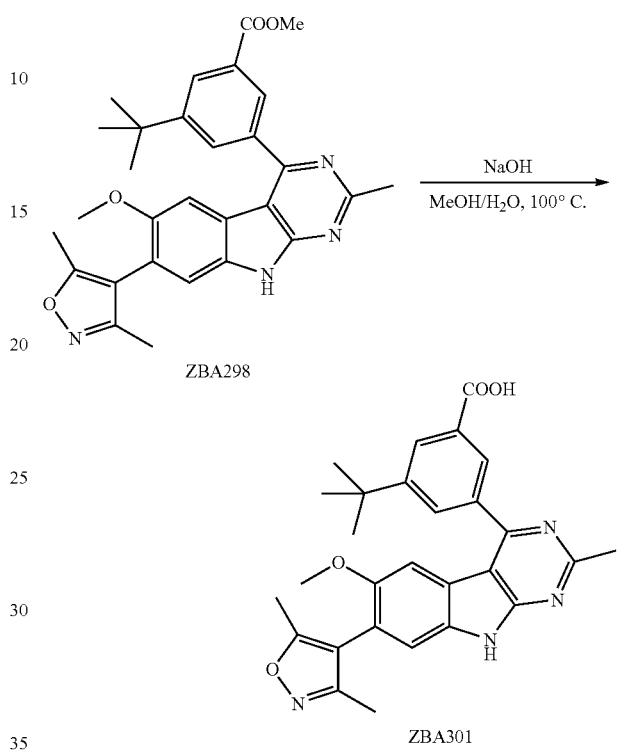

To a round-bottom flask, ZBA298 (110 mg, 0.22 mmol) was dissolved in MeOH (5 mL) and water (5 mL). NaOH (26 mg, 0.66 mmol, 3 equiv.) was added and solution was stirred for 3 h at 100° C. The reaction mixture was extracted with ethyl acetate. Subsequently, the aqueous layer was neutralized to pH=2 and was extracted with ethyl acetate. The organic extracts of acidic aqueous solution were combined and concentrated on a rotary evaporator. The remaining residue was freeze-dried to yield the title compound in 80 mg. ESI-MS calculated for C$_{28}$H$_{29}$N$_4$O$_4$ [M+H]$^+$= 485.21, Obtained: 485.5. $^1$H NMR (300 MHz, DMSO) δ 13.34 (brs, 1H), 12.56 (brs, 1H), 8.40 (t, J=1.4 Hz, 1H), 8.30-8.18 (m, 2H), 7.44 (s, 1H), 7.32 (s, 1H), 3.63 (s, 3H), 2.80 (s, 3H), 2.30 (s, 3H), 2.09 (s, 3H), 1.42 (s, 9H).

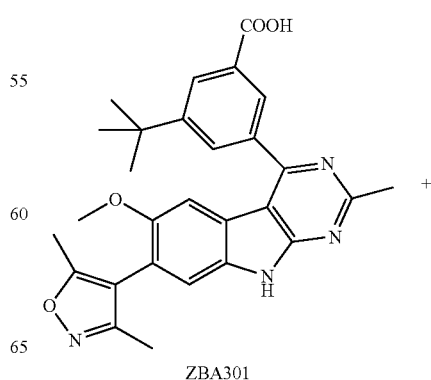

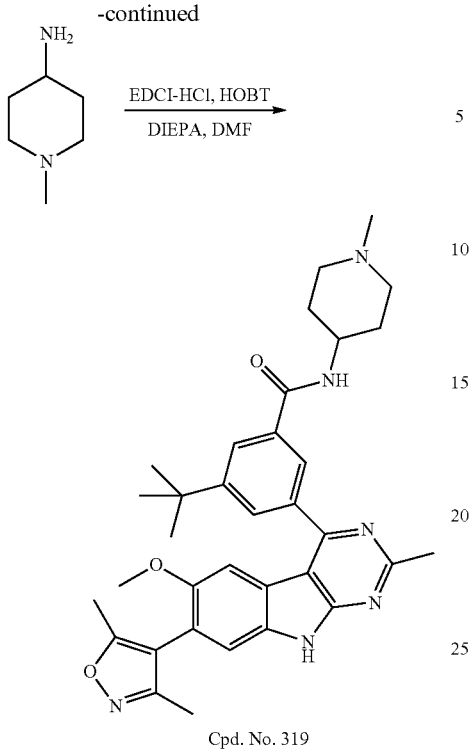

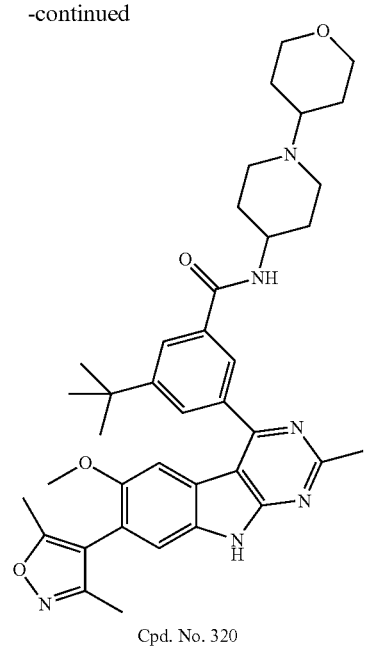

Cpd. No. 319

Cpd. No. 319-TFA salt was prepared from amide condensation of ZBA301 and 1-methyl-4-piperidinamine using EDCI-HOBT condition. 75% yield. ESI-MS calculated for $C_{34}H_{41}N_6O_3$ [M+H]$^+$=581.32, Obtained: 581.66. $^1$H NMR (300 MHz, MeOD) δ 8.42 (t, J=1.6 Hz, 1H), 8.38 (t, J=1.7 Hz, 1H), 8.23 (t, J=1.7 Hz, 1H), 7.59 (s, 1H), 7.29 (s, 1H), 4.38-4.17 (m, 1H), 3.74-3.57 (m, 5H), 3.21 (dd, J=13.2, 10.6 Hz, 2H), 3.00 (s, 3H), 2.92 (s, 3H), 2.35-2.22 (m, 5H), 2.15 (s, 3H), 2.10-1.88 (m, 2H), 1.52 (s, 9H).

Cpd. No. 320

Cpd. No. 320-TFA salt was prepared from amide condensation of ZBA301 and 1-(tetrahydro-2H-pyran-4-yl)-4-piperidinamine using EDCI-HOBT condition. 80% yield. ESI-MS calculated for $C_{38}H_{47}N_6O_4$ [M+H]$^+$=651.36, Obtained: 651.55. $^1$H NMR (300 MHz, MeOD) δ 8.42 (t, J=1.6 Hz, 1H), 8.39 (t, J=1.6 Hz, 1H), 8.23 (t, J=1.7 Hz, 1H), 7.59 (s, 1H), 7.30 (s, 1H), 4.35-4.20 (m, 1H), 4.15-4.05 (m, 2H), 3.80-3.65 (m, 5H), 3.55-3.40 (m, 3H), 3.22 (t, J=12.0 Hz, 2H), 3.00 (s, 3H), 2.40-2.20 (m, 5H), 2.15 (s, 3H), 2.12-1.69 (m, 6H), 1.52 (s, 9H).

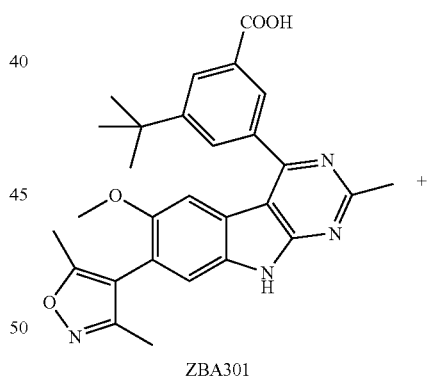

ZBA301

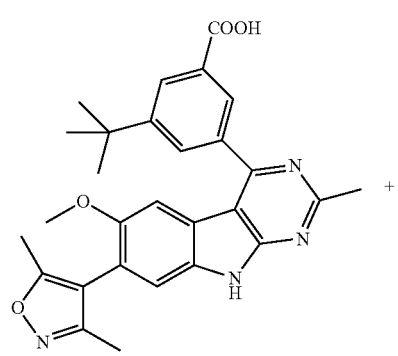

ZBA301

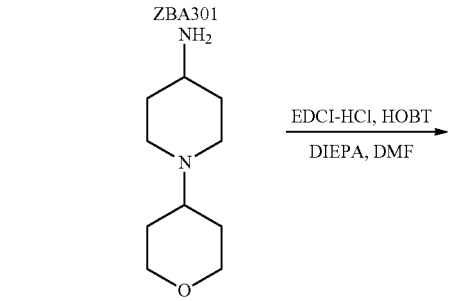

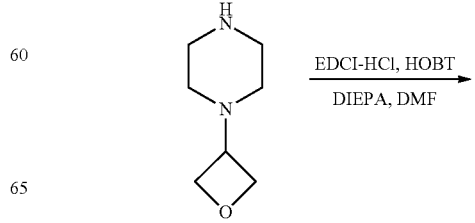

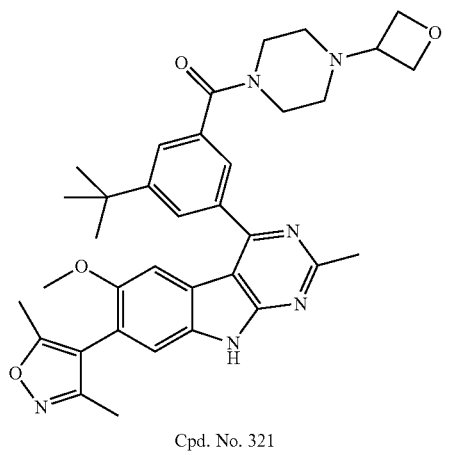

Cpd. No. 321

Cpd. No. 321-TFA salt was prepared from amide condensation of ZBA301 and 1-(oxetan-3-yl)piperazine using EDCI-HOBT condition. 80% yield. ESI-MS calculated for $C_{35}H_{41}N_6O_4$ [M+H]=609.31, Obtained: 609.46. $^1$H NMR (300 MHz, MeOD) δ 8.18 (t, J=1.7 Hz, 1H), 8.01 (s, 1H), 8.01 (s, 1H), 7.58 (s, 1H), 7.29 (s, 1H), 4.88 (d, J=6.4 Hz, 4H), 4.44 (p, J=6.3 Hz, 1H), 4.22-3.78 (m, 4H), 3.74 (s, 3H), 3.43-3.24 (m, 4H), 3.00 (s, 3H), 2.33 (s, 3H), 2.15 (s, 3H), 1.50 (s, 9H).

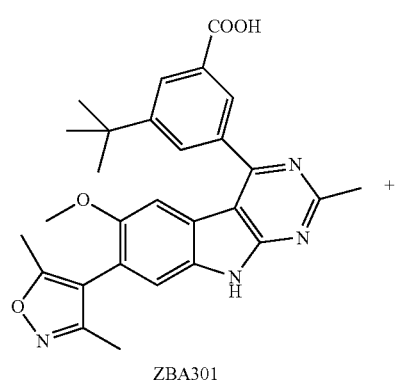

ZBA301

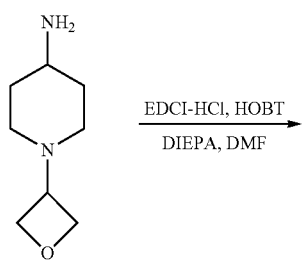

EDCI-HCl, HOBT
DIEPA, DMF →

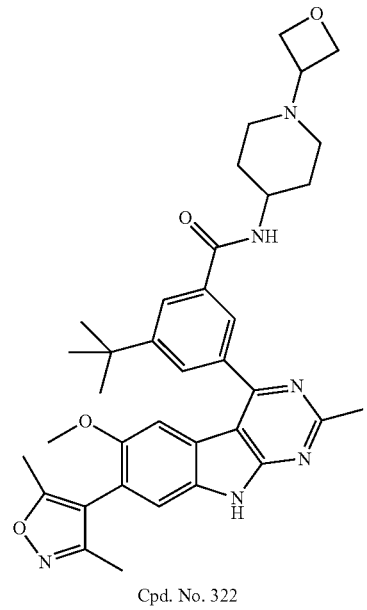

Cpd. No. 322

Cpd. No. 322-TFA salt was prepared from amide condensation of ZBA301 and 1-(oxetan-3-yl)piperidin-4-amine using EDCI-HOBT condition. 90% yield. ESI-MS calculated for $C_{36}H_{43}N_6O_4$ [M+H]$^+$=623.33, Obtained: 623.5. $^1$H NMR (300 MHz, MeOD) δ 8.42 (t, J=1.5 Hz, 1H), 8.39 (t, J=1.6 Hz, 1H), 8.22 (t, J=1.6 Hz, 1H), 7.59 (s, 1H), 7.28 (s, 1H), 4.88 (d, J=6.5 Hz, 4H), 4.53-4.40 (m, 1H), 4.35-4.20 (m, 1H), 3.68 (s, 3H), 3.65-3.50 (m, 2H), 3.25-3.02 (m, 2H), 3.00 (s, 3H), 2.35-2.25 (m, 5H), 2.20-2.00 (m, 5H), 1.51 (s, 9H).

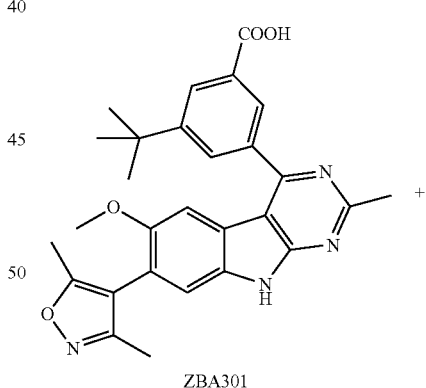

ZBA301

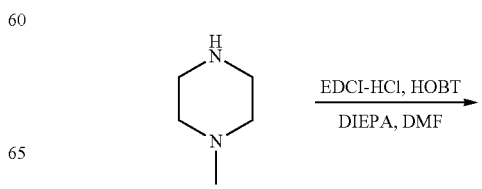

EDCI-HCl, HOBT
DIEPA, DMF →

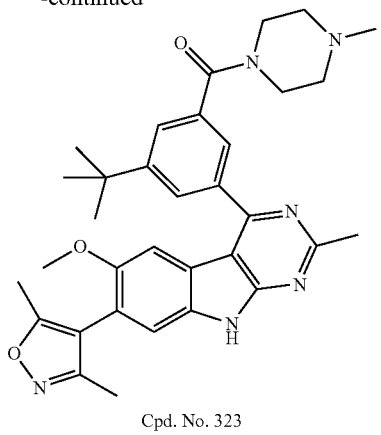

Cpd. No. 323

Cpd. No. 323-TFA salt was prepared from amide condensation of ZBA301 and 1-methylpiperazine using EDCI-HOBT condition. 70% yield. ESI-MS calculated for $C_{33}H_{39}N_6O_3$ [M+H]=567.30, Obtained: 567.5. $^1$H NMR (300 MHz, MeOD) δ 8.18 (t, J=1.7 Hz, 1H), 8.01 (s, 1H), 8.00 (s, 1H), 7.58 (s, 1H), 7.30 (s, 1H), 3.74 (s, 3H), 3.68-3.16 (m, 8H), 3.00 (s, 3H), 2.97 (s, 3H), 2.33 (s, 3H), 2.15 (s, 3H), 1.51 (s, 9H).

Cpd. No. 324-TFA salt was prepared from amide condensation of ZBA301 and 1-isopropylpiperazine using EDCI-HOBT condition. 80% yield. ESI-MS calculated for $C_{35}H_{43}N_6O_3$ [M+H]$^+$=595.33, Obtained: 595.55. $^1$H NMR (300 MHz, MeOD) δ 8.18 (t, J=1.7 Hz, 1H), 8.02 (s, 1H), 8.02 (s, 1H), 7.58 (s, 1H), 7.29 (s, 1H), 3.74 (s, 3H), 3.68-3.15 (m, 9H), 3.00 (s, 3H), 2.33 (s, 3H), 2.15 (s, 3H), 1.51 (s, 9H), 1.40 (d, J=6.6 Hz, 6H).

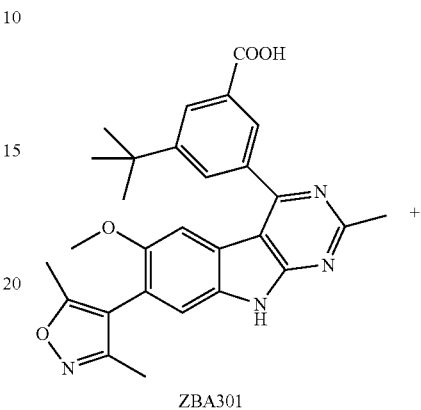

ZBA301

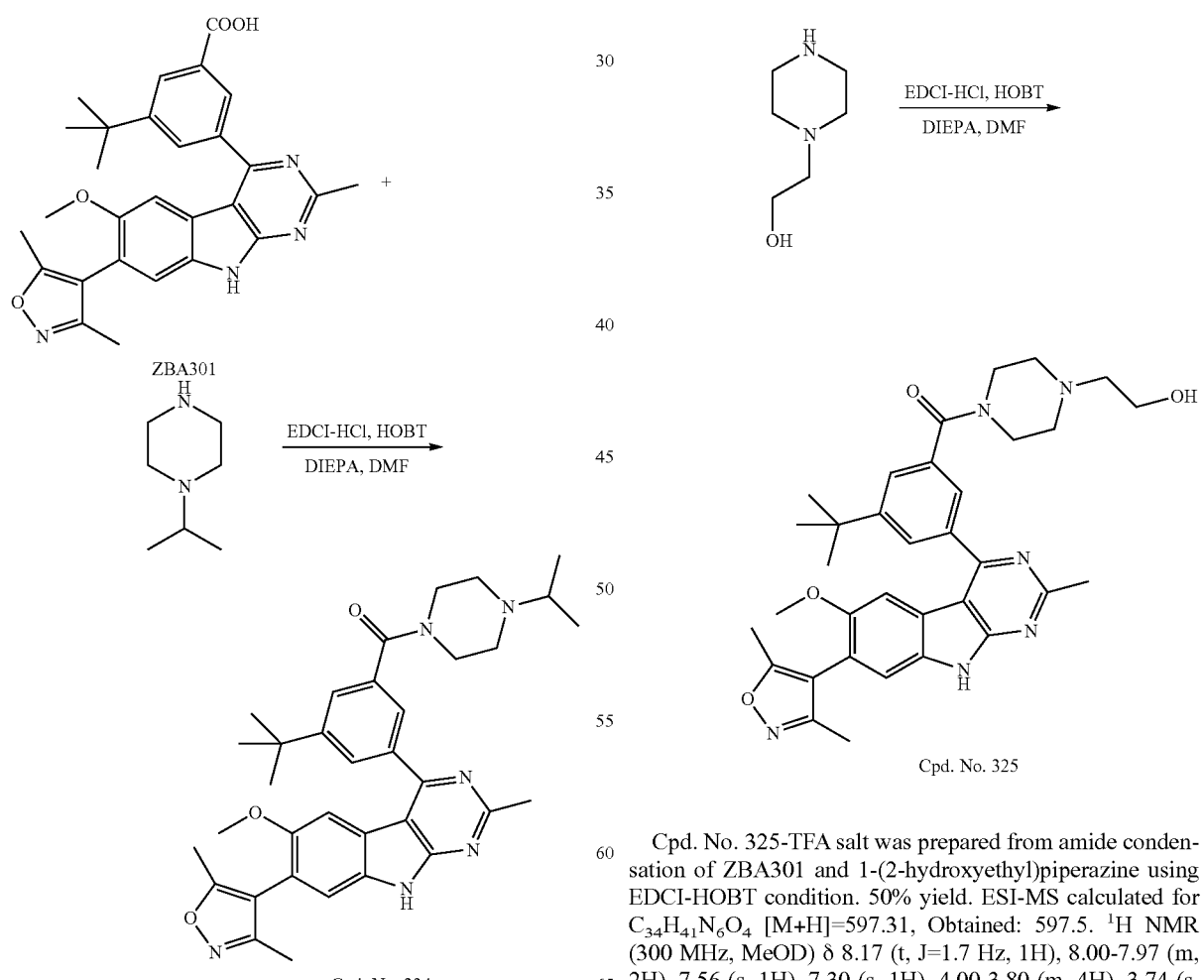

Cpd. No. 324

Cpd. No. 325

Cpd. No. 325-TFA salt was prepared from amide condensation of ZBA301 and 1-(2-hydroxyethyl)piperazine using EDCI-HOBT condition. 50% yield. ESI-MS calculated for $C_{34}H_{41}N_6O_4$ [M+H]=597.31, Obtained: 597.5. $^1$H NMR (300 MHz, MeOD) δ 8.17 (t, J=1.7 Hz, 1H), 8.00-7.97 (m, 2H), 7.56 (s, 1H), 7.30 (s, 1H), 4.00-3.80 (m, 4H), 3.74 (s, 3H), 3.68-3.18 (m, 8H), 2.98 (s, 3H), 2.33 (s, 3H), 2.15 (s, 3H), 1.51 (s, 9H).

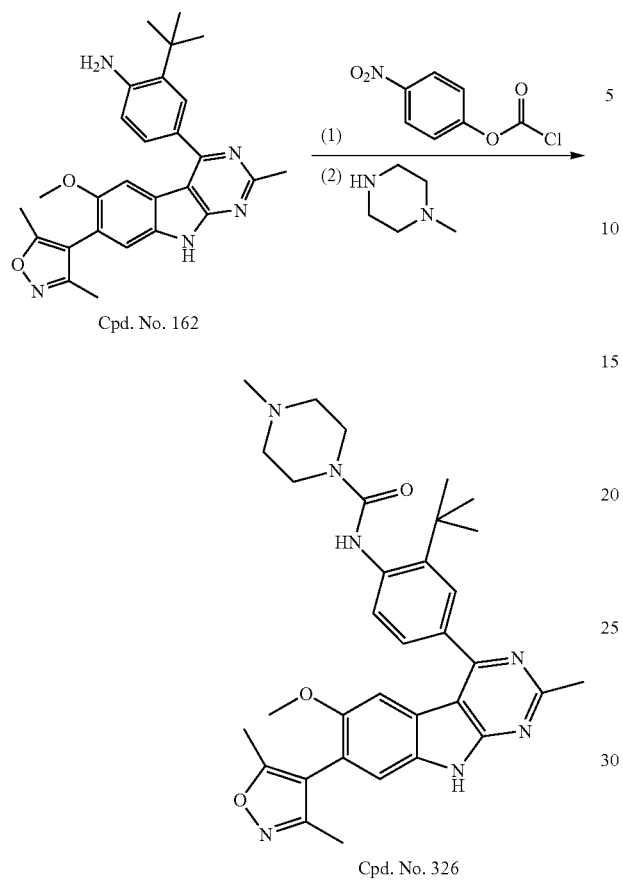

Cpd. No. 162

Cpd. No. 326

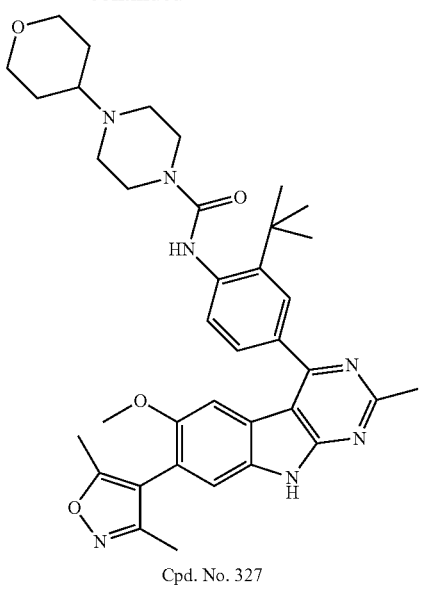

Cpd. No. 327

Cpd. No. 162 (50 mg) and pyridine (2 mL) were added to a round-bottom flask. 4-Nitrophenyl chloroformate (33 mg) was added. The reaction mixture was stirred for 5 h and then 1-methylpiperazine (300 mg) and DBU (300 mg) was added. The mixture was stirred for 12 h at room temperature. The reaction was quenched with NaHCO$_3$ saturated solution and the aqueous layer was extracted with ethyl acetate. The combined organic layers were concentrated on a rotary evaporator. The remaining residue was purified by reverse phase HPLC affording the Cpd. No. 326 as a salt of CF$_3$CO$_2$H (5 mg). ESI-MS calculated for C$_{33}$H$_{40}$N$_7$O$_3$ [M+H]$^+$=582.31, Obtained: 582.55. $^1$H NMR (300 MHz, MeOD) δ 7.85 (d, J=2.1 Hz, 1H), 7.76-7.69 (m, 2H), 7.61 (s, 1H), 7.05 (d, J=8.4 Hz, 1H), 4.27-3.25 (m, 11H), 3.05 (s, 3H), 2.98 (s, 3H), 2.35 (s, 3H), 2.17 (s, 3H), 1.52 (s, 9H).

Cpd. No. 162 (50 mg) and pyridine (2 mL) were added to a round-bottom flask. 4-Nitrophenyl chloroformate (33 mg) was added. The reaction mixture was stirred for 5 h and then 1-(tetrahydro-2H-pyran-4-yl)piperazine (300 mg) and DBU (300 mg) was added. The mixture was stirred for 12 h at room temperature. The reaction was quenched with NaHCO$_3$ saturated solution and the aqueous layer was extracted with ethyl acetate. The combined organic layers were concentrated on a rotary evaporator. The remaining residue was purified by reverse phase HPLC affording the Cpd. No. 327 as a salt of CF$_3$CO$_2$H (25 mg). ESI-MS calculated for C$_{37}$H$_{46}$N$_7$O$_4$ [M+H]$^+$=652.36, Obtained: 652.45. $^1$H NMR (300 MHz, MeOD) δ 7.86 (d, J=2.1 Hz, 1H), 7.76-7.71 (m, 2H), 7.61 (s, 1H), 7.07 (d, J=8.4 Hz, 1H), 4.39-3.39 (m, 16H), 2.99 (s, 3H), 2.35 (s, 3H), 2.20-2.08 (m, 5H), 1.99-1.69 (m, 2H), 1.52 (s, 9H).

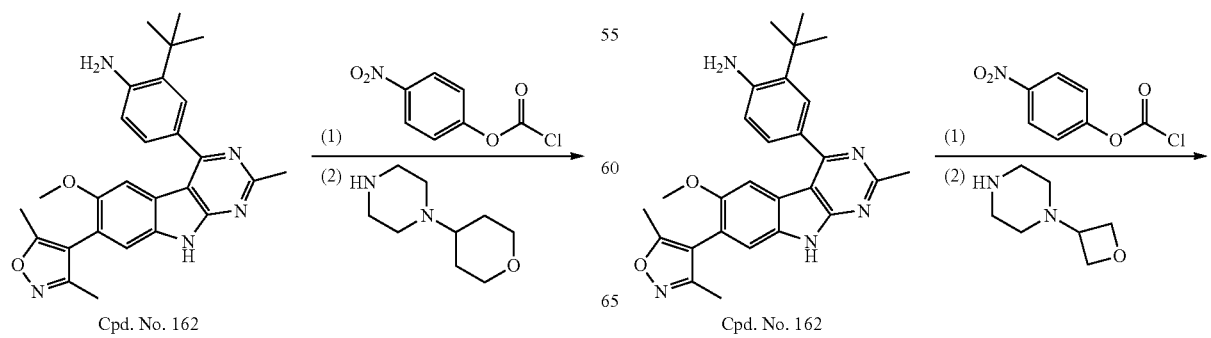

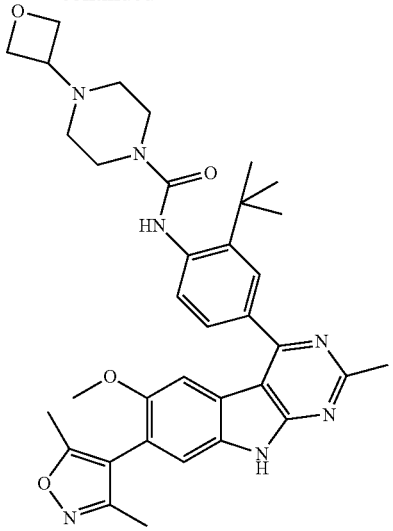

Cpd. No. 328

Cpd. No. 162 (50 mg) and pyridine (2 mL) were added to a round-bottom flask. 4-Nitrophenyl chloroformate (33 mg) was added. The reaction mixture was stirred for 5 h and then 1-(oxetan-3-yl)piperazine (300 mg) and DBU (300 mg) was added. The mixture was stirred for 12 h at room temperature. The reaction was quenched with NaHCO$_3$ saturated solution and the aqueous layer was extracted with ethyl acetate. The combined organic layers were concentrated on a rotary evaporator. The remaining residue was purified by reverse phase HPLC affording the Cpd. No. 328 as a salt of CF$_3$CO$_2$H (34 mg). ESI-MS calculated for C$_{35}$H$_{42}$N$_7$O$_4$ [M+H]$^+$=624.32, Obtained: 624.44. $^1$H NMR (300 MHz, MeOD) δ 7.86 (d, J=2.1 Hz, 1H), 7.76-7.71 (m, 2H), 7.61 (s, 1H), 7.06 (d, J=8.4 Hz, 1H), 4.91-4.81 (m, 4H), 4.47-4.33 (m, 1H), 4.30-3.10 (m, 11H), 2.99 (s, 3H), 2.35 (s, 3H), 2.16 (s, 3H), 1.52 (s, 9H).

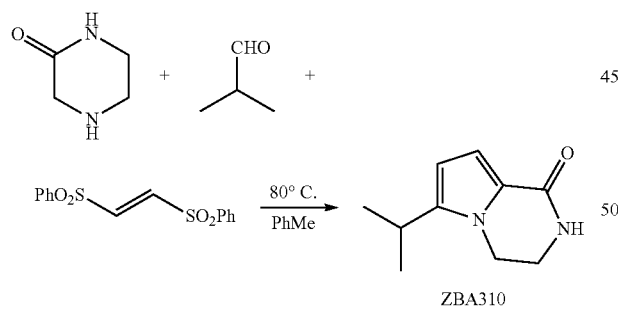

ZBA310

Isobutyl aldehyde (0.7 mL), 2-oxopiperazine (0.5 g) and trans-1,2-Bis(phenylsulfonyl)ethylene (1.7 g) were mixture in a round-bottom flask followed by addition of anhydrous PhMe (100 mL) and 4 A molecular sieve (1 g). The reaction mixture was stirred at 80° C. overnight. The solid was filter off and the solution was concentrated on a rotary evaporator. The remaining residue was dissolved in THF (20 mL) and DBU (1.5 mL) was added. The mixture was stirred at room temperature for 4 h. The mixture was diluted with ethyl acetate and wash with 1N HCl to remove DBU. The organic layer was dried, concentrated on a rotary evaporator. The remaining residue was purified by flash column chromatography to yield ZBA310 in 450 mg. ESI-MS calculated for C$_{10}$H$_{15}$N$_2$O [M+H]$^+$=179.11, Obtained: 179.33.

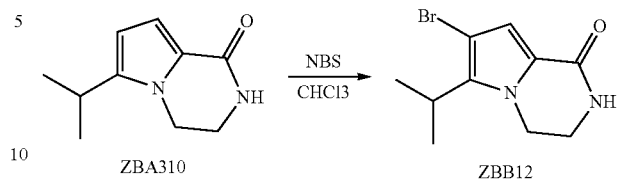

ZBA310 (350 mg) was dissolved in CHCl$_3$ (20 mL). NBS (350 mg) was added in small portions and the mixture was stirred at room temperature for 2 h. The volatile components were removed on a rotary evaporator. The remaining residue was purified by flash column chromatography to yield ZBB12 in 280 mg. ESI-MS calculated for C$_{10}$H$_{14}$BrN$_2$O [M+H]$^+$=257.02, Obtained: 257.15.

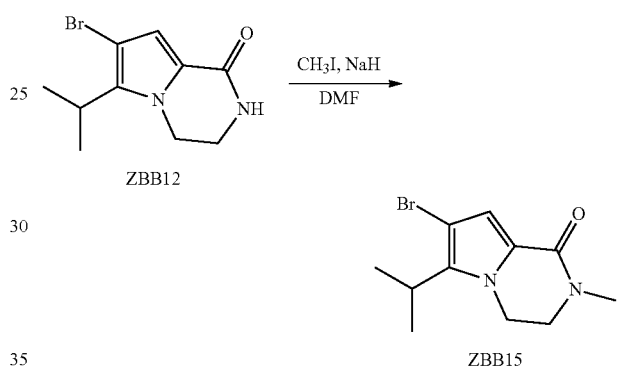

ZBB12 (250 mg) was dissolved in DMF (2 mL). NaH (40 mg) was added in small portions and then MeI (0.1 mL) was added. The mixture was stirred at room temperature for 2 h. The mixture was diluted with ethyl acetate and wash with aq. NaCl. The organic layer was dried, concentrated on a rotary evaporator. The remaining residue was purified by flash column chromatography to yield ZBB15 in 230 mg. ESI-MS calculated for C$_{11}$H$_{16}$N$_2$OBr [M+H]$^+$=271.04, Obtained: 271.32.

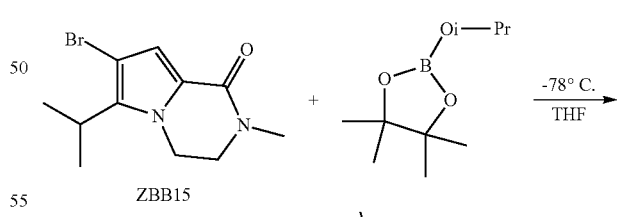

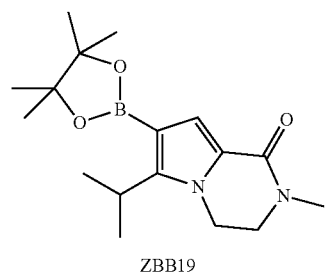

ZBB15 (250 mg) and 2-isopropoxy-4,4,5,5-tetramethyl-1,3,2-dioxaborolane (0.4 mL) were dissolved in anhydrous THF (20 mL). The solution was cooled to −78° C. for 15 min before BuLi (0.77 mL, 2.5 M in THF) was added via a syringe. The reaction was stirred at −78° C. for 6 h before quenching with saturated NH$_4$Cl aqueous solution. The aqueous layer was extracted with ethyl acetate and the combined organic layers were washed with brine, dried over anhydrous sodium sulfate, and concentrated on a rotary evaporator. The remaining residue was purified by flash column chromatography to yield the title compound ZBB19 in 180 mg. ESI-MS calculated for $C_{17}H_{28}N_2O_3B[M+H]^+$= 319.21, Obtained: 319.44.

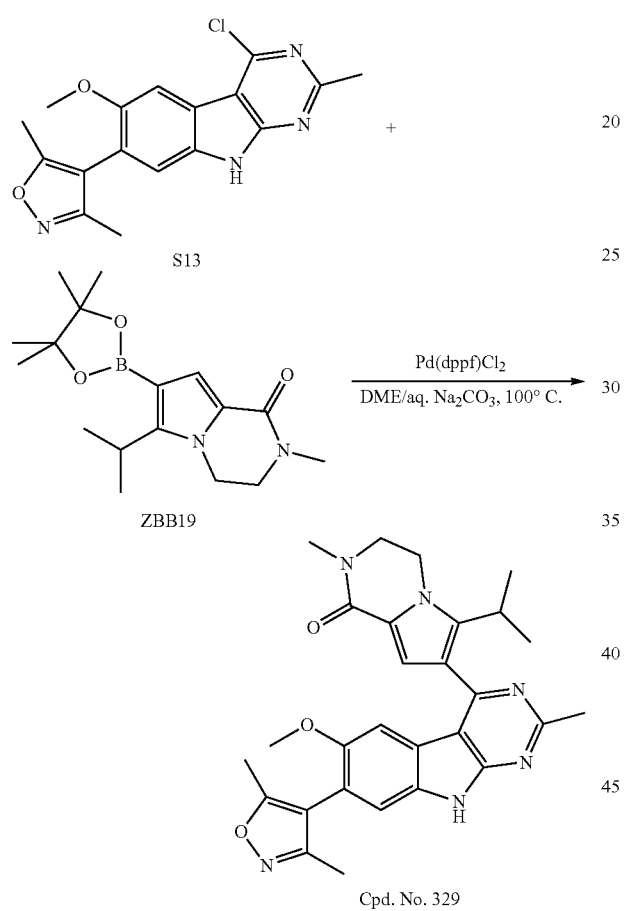

To a round-bottom flask, 4-(4-chloro-6-methoxy-2-methyl-9H-pyrimido[4,5-b]indol-7-yl)-3,5-dimethylisoxazole (S13, 70 mg) and ZBB19 (130 mg), 1,2-dimethoxyethane (150 mL), and Na$_2$CO$_3$ (2 M, 50 mL) were added. The system was degassed to remove oxygen and nitrogen was refilled. Pd(dppf)Cl$_2$—CH$_2$Cl$_2$ (25 mg) was added and the system was degassed and refilled with nitrogen. The reaction mixture was heated at reflux for 16 h. The reaction was quenched with water and the aqueous layer was extracted with ethyl acetate. The organic layers were combined and the volatile components were removed on a rotary evaporator. The residue was purified by flash column chromatography to yield the title compound Cpd. No. 329 in 15 mg. ESI-MS calculated for $C_{28}H_{31}N_6O_3$ [M+H]$^+$=499.24, Obtained: 499.55. $^1$H NMR (300 MHz, MeOD) δ 7.56 (s, 1H), 7.17 (s, 1H), 7.10 (s, 1H), 4.53-4.41 (m, 2H), 3.95-3.83 (m, 2H), 3.71 (s, 3H), 3.30-3.20 (m, 1H), 3.19 (s, 3H), 2.95 (s, 3H), 2.33 (s, 3H), 2.15 (s, 3H), 1.24 (d, J=7.2 Hz, 6H).

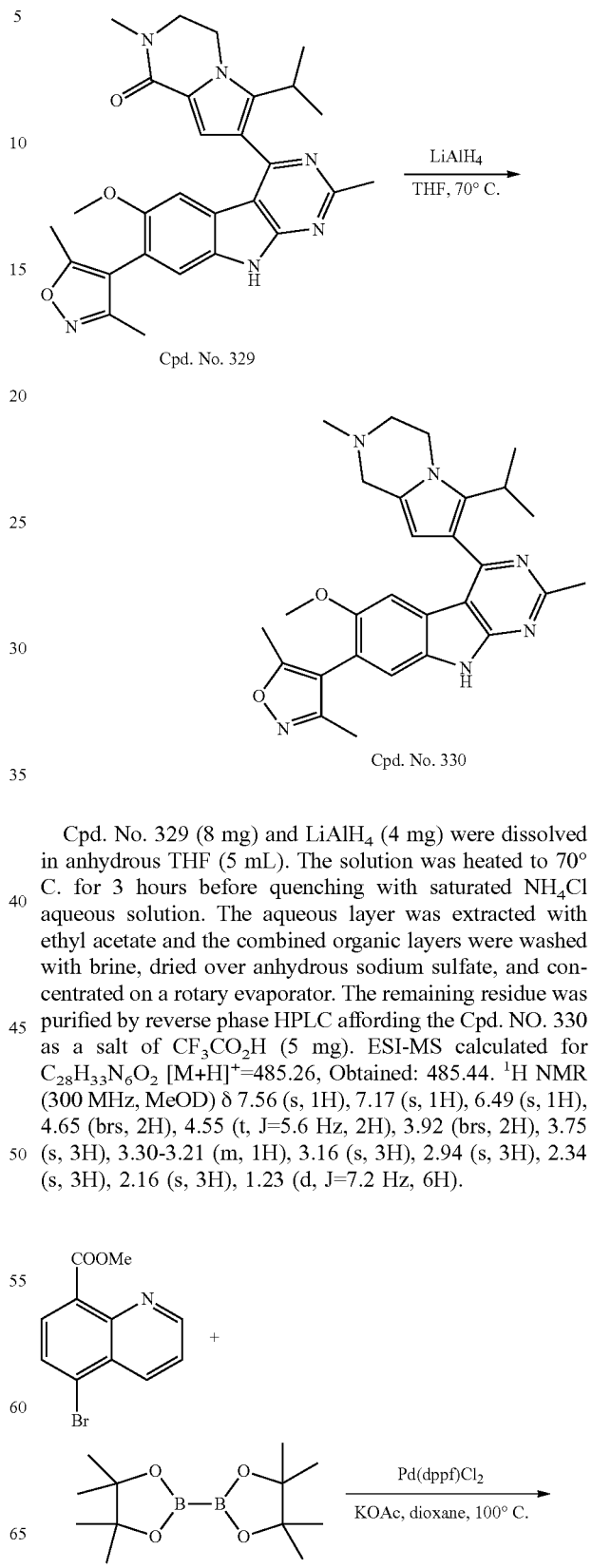

Cpd. No. 329 (8 mg) and LiAlH$_4$ (4 mg) were dissolved in anhydrous THF (5 mL). The solution was heated to 70° C. for 3 hours before quenching with saturated NH$_4$Cl aqueous solution. The aqueous layer was extracted with ethyl acetate and the combined organic layers were washed with brine, dried over anhydrous sodium sulfate, and concentrated on a rotary evaporator. The remaining residue was purified by reverse phase HPLC affording the Cpd. NO. 330 as a salt of CF$_3$CO$_2$H (5 mg). ESI-MS calculated for $C_{28}H_{33}N_6O_2$ [M+H]$^+$=485.26, Obtained: 485.44. $^1$H NMR (300 MHz, MeOD) δ 7.56 (s, 1H), 7.17 (s, 1H), 6.49 (s, 1H), 4.65 (brs, 2H), 4.55 (t, J=5.6 Hz, 2H), 3.92 (brs, 2H), 3.75 (s, 3H), 3.30-3.21 (m, 1H), 3.16 (s, 3H), 2.94 (s, 3H), 2.34 (s, 3H), 2.16 (s, 3H), 1.23 (d, J=7.2 Hz, 6H).

-continued

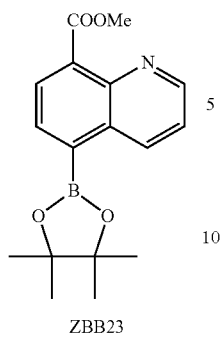

ZBB23

Methyl 5-bromoquinoline-8-carboxylate (1.1 g, 4.16 mmol), bis(pinacolato)diboron (2.13 g, 8.4 mmol, 2.0 equiv.), and potassium acetate (1.6 g, 16 mmol, 4.0 equiv.) were added to a round-bottom flask. Anhydrous 1,4-dixoane (20 mL) was added via a syringe and the flask was degassed and refilled with nitrogen. Pd(dppf)Cl$_2$ (322 mg, 0.46 mmol, 0.1 equiv.) was added and the system was degassed again followed by heating at 100° C. for 16 h. The reaction mixture was cooled to ambient temperature and diluted by CH$_2$Cl$_2$. The solution was filtered through a pad of celite and the volatile components were removed on a rotary evaporator. The residue was purified by flash column chromatography. The title compound ZBB23 was isolated in 0.7 g. ESI-MS calculated for C$_{17}$H$_{21}$BNO$_4$ [M+H]$^+$=314.15, Obtained: 314.33.

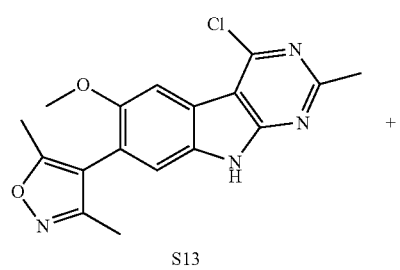

S13

+

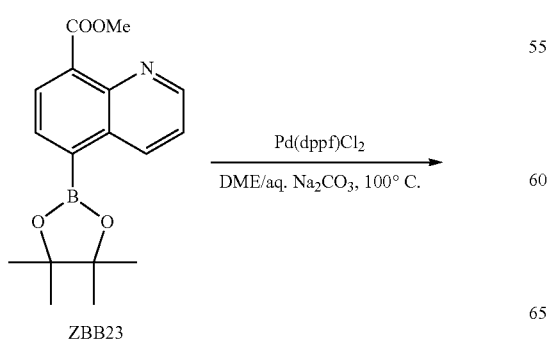

ZBB23

Pd(dppf)Cl$_2$
—————————→
DME/aq. Na$_2$CO$_3$, 100° C.

-continued

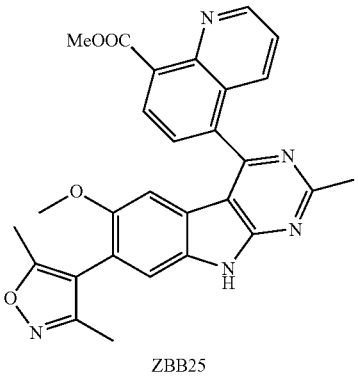

ZBB25

To a round-bottom flask, 4-(4-chloro-6-methoxy-2-methyl-9H-pyrimido[4,5-b]indol-7-yl)-3,5-dimethylisoxazole (S13, 5.4 g, 16 mmol, 1.0 equiv.) and ZBB23 (18.2 g, 37 mmol, 2.0 equiv.), 1,2-dimethoxyethane (150 mL), and Na$_2$CO$_3$ (2 M, 50 mL) were added. The system was degassed to remove oxygen and nitrogen was refilled. Pd(dppf)Cl$_2$—CH$_2$Cl$_2$ (1.3 g, 1.6 mmol, 0.1 equiv.) was added and the system was degassed and refilled with nitrogen. The reaction mixture was heated at reflux for 16 h. The reaction was quenched with water and the aqueous layer was extracted with ethyl acetate. The organic layers were combined and the volatile components were removed on a rotary evaporator. The residue was purified by flash column chromatography to yield the title compound ZBB25 in 3.7 g. ESI-MS calculated for C$_{28}$H$_{24}$N$_5$O$_4$ [M+H]$^+$=494.18, Obtained: 494.33.

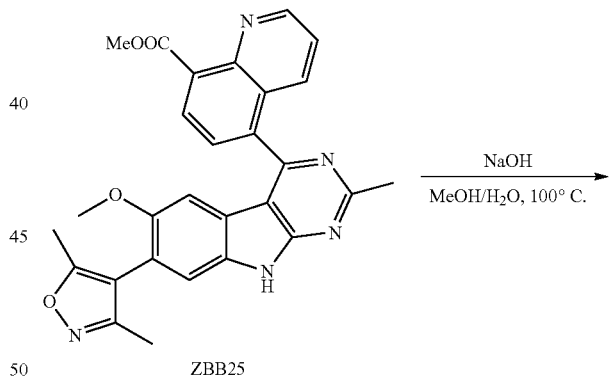

ZBB25

NaOH
—————————→
MeOH/H$_2$O, 100° C.

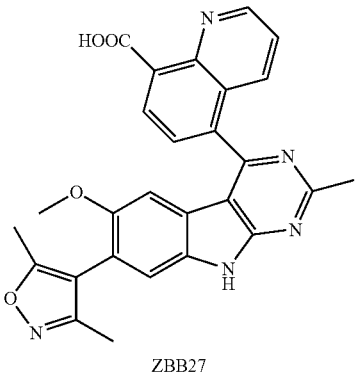

ZBB27

To a round-bottom flask, ZBB25 (110 mg, 0.22 mmol) was dissolved in MeOH (5 mL) and water (5 mL). NaOH (26 mg, 0.66 mmol, 3 equiv.) was added and solution was stirred for 3 h at 100° C. The reaction mixture was extracted with ethyl acetate. Subsequently, the aqueous layer was neutralized to pH=2 and was extracted with ethyl acetate. The organic extracts of acidic aqueous solution were combined and concentrated on a rotary evaporator. The remaining residue was freeze-dried to yield the title compound ZBB27 in 80 mg. ESI-MS calculated for $C_{27}H_{22}N_5O_4$ [M+H]$^+$=480.16, Obtained: 480.33. $^1$H NMR (300 MHz, MeOD) δ 9.26 (dd, J=4.5, 1.6 Hz, 1H), 9.05 (d, J=7.6 Hz, 1H), 8.59 (dd, J=8.7, 1.6 Hz, 1H), 8.38 (d, J=7.6 Hz, 1H), 7.86 (dd, J=8.7, 4.5 Hz, 1H), 7.56 (s, 1H), 6.39 (s, 1H), 3.33 (s, 3H), 3.02 (s, 3H), 2.29 (s, 3H), 2.10 (s, 3H).

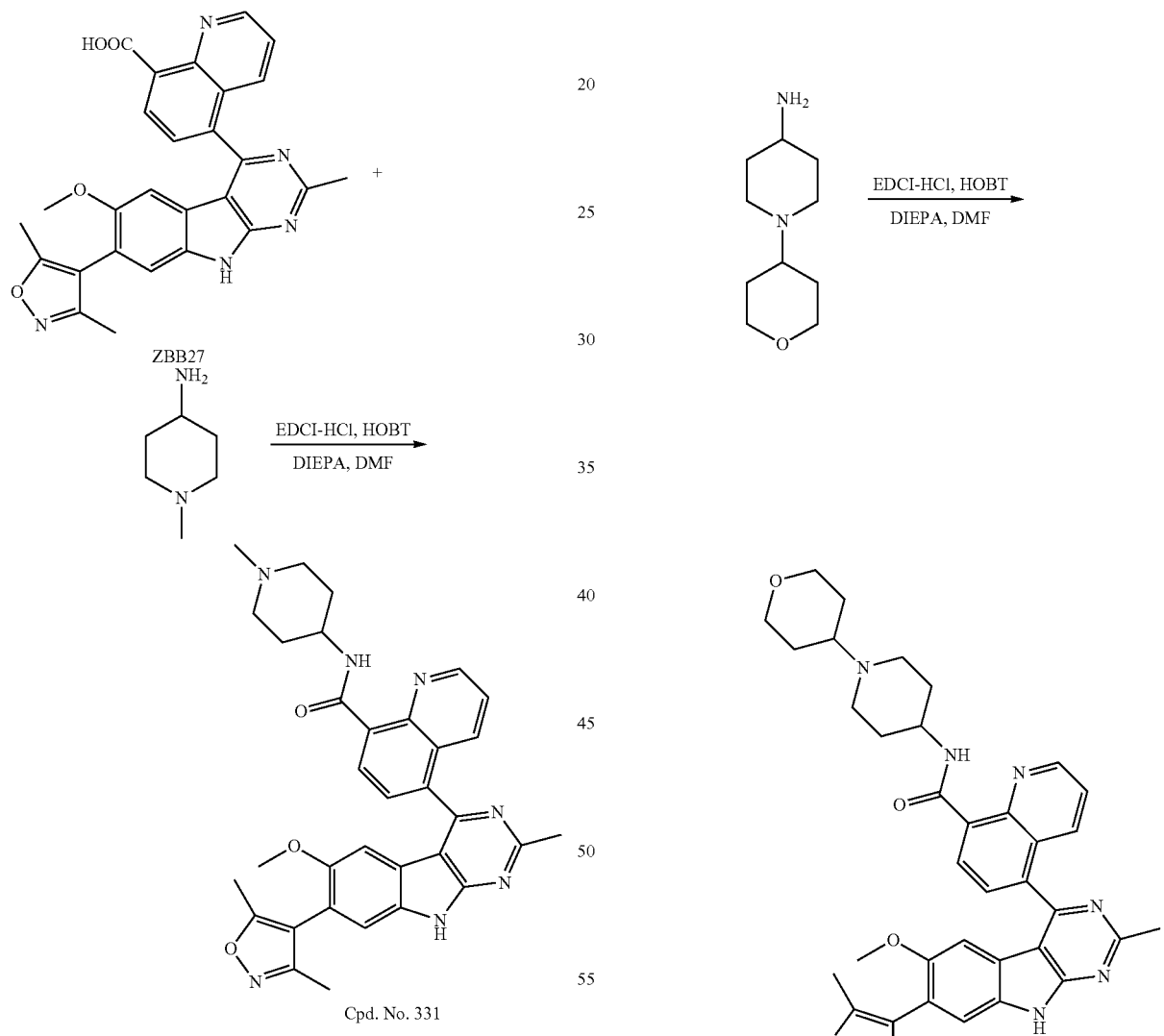

Cpd. No. 331 salt was prepared from amide condensation of ZBB27 and 1-methyl-4-piperidinamine using EDCI-HOBT condition. 75% yield. ESI-MS calculated for $C_{33}H_{34}N_7O_3$ [M+H]$^+$=576.27, Obtained: 576.44. $^1$H NMR (300 MHz, MeOD) δ 9.18 (d, J=2.8 Hz, 1H), 8.92 (d, J=7.6 Hz, 1H), 8.38 (dd, J=8.6, 1.5 Hz, 1H), 8.26 (d, J=7.6 Hz, 1H), 7.70 (dd, J=8.6, 4.3 Hz, 1H), 7.55 (s, 1H), 6.32 (s, 1H), 4.45-4.28 (m, 1H), 3.75-3.55 (m, 2H), 3.45-3.15 (m, 5H), 3.00 (s, 3H), 2.97 (s, 3H), 2.56-1.96 (m, 10H).

Cpd. No. 332 salt was prepared from amide condensation of ZBB27 and 1-(tetrahydro-2H-pyran-4-yl)-4-piperidinamine using EDCI-HOBT condition. 80% yield. ESI-MS calculated for $C_{37}H_{40}N_7O_4$ [M+H]$^+$=646.31, Obtained: 646.44.

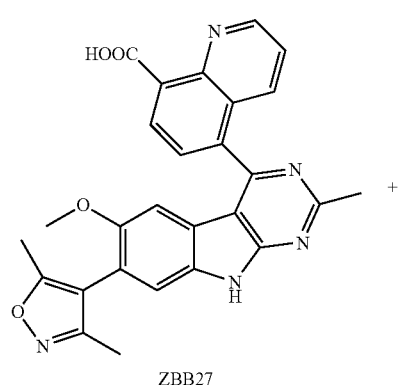

ZBB27

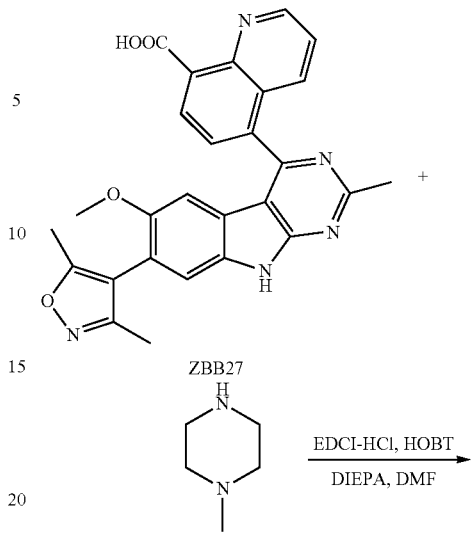

ZBB27

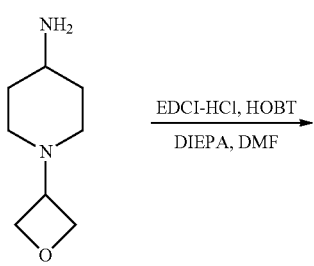

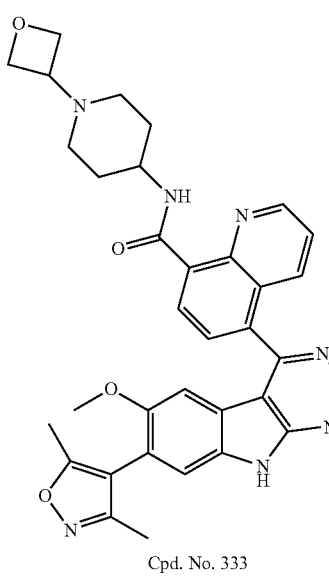

Cpd. No. 333

Cpd. No. 333 salt was prepared from amide condensation of ZBB27 and 1-(oxetan-3-yl)piperidin-4-amine using EDCI-HOBT condition. 80% yield. ESI-MS calculated for $C_{35}H_{36}N_7O_4$ [M+H]$^+$=618.28, Obtained: 618.33.

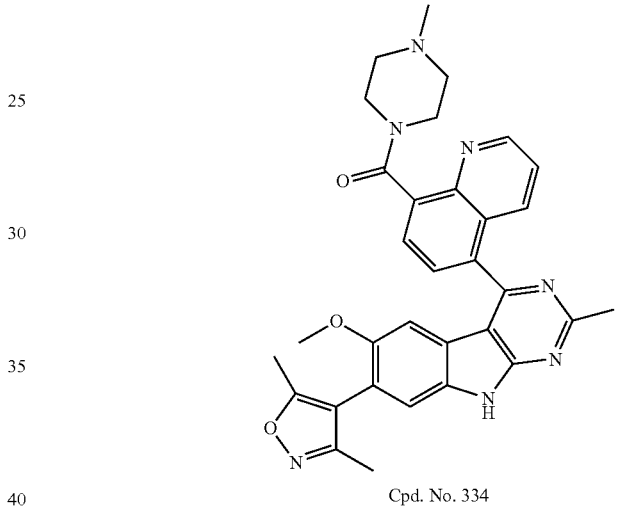

Cpd. No. 334

Cpd. No. 334 salt was prepared from amide condensation of ZBB27 and 1-methylpiperazine using EDCI-HOBT condition. 80% yield. ESI-MS calculated for $C_{32}H_{32}N_7O_4$3 [M+H]$^+$=562.25, Obtained: 562.33. $^1$H NMR (300 MHz, MeOD) δ 9.14 (d, J=3.1 Hz, 1H), 8.31 (d, J=8.3 Hz, 1H), 8.25-8.13 (m, 2H), 7.67 (dd, J=8.6, 4.2 Hz, 1H), 7.54 (s, 1H), 6.34 (s, 1H), 3.92-3.31 (m, 8H), 3.30 (s, 3H), 3.02 (s, 3H), 3.01 (s, 3H), 2.29 (s, 3H), 2.10 (s, 3H).

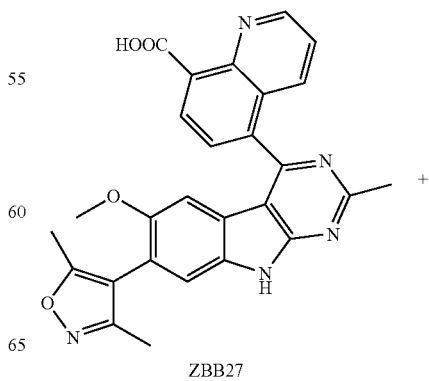

ZBB27

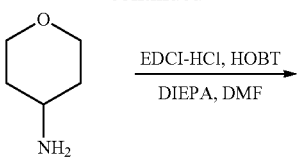

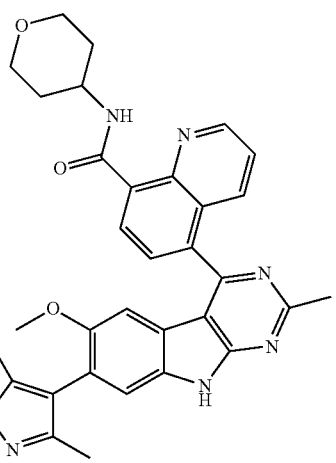

Cpd. No. 335

Cpd. No. 335 salt was prepared from amide condensation of ZBB27 and 4-aminotetrahydropyran using EDCI-HOBT condition. 70% yield. ESI-MS calculated for $C_{32}H_{31}N_6O_4$ [M+H]$^+$=563.24, Obtained: 563.33. $^1$H NMR (300 MHz, MeOD) δ 9.22 (dd, J=4.2, 1.7 Hz, 1H), 8.96 (d, J=7.6 Hz, 1H), 8.39 (dd, J=8.7, 1.7 Hz, 1H), 8.28 (d, J=7.6 Hz, 1H), 7.72 (dd, J=8.6, 4.3 Hz, 1H), 7.57 (s, 1H), 6.33 (s, 1H), 4.43-4.30 (m, 1H), 4.13-3.98 (m, 2H), 3.76-3.60 (m, 2H), 3.29 (s, 3H), 3.02 (s, 3H), 2.29 (s, 3H), 2.22-2.04 (m, 5H), 1.94-1.74 (m, 2H).

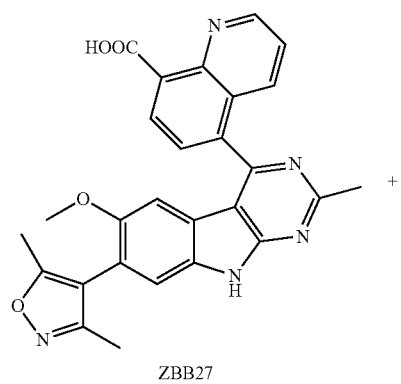

ZBB27

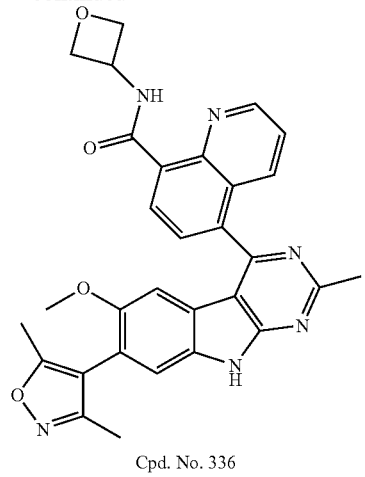

Cpd. No. 336

Cpd. No. 336 salt was prepared from amide condensation of ZBB27 and 3-oxetanamine using EDCI-HOBT condition. 80% yield. ESI-MS calculated for $C_{30}H_{27}N_6O_4$ [M+H]= 535.20, Obtained: 535.33.

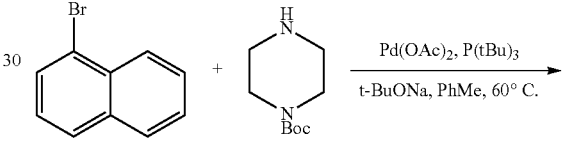

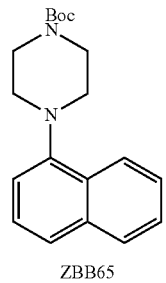

ZBB65

1-Bromonaphthalene (2.8 g), Pd(OAc)$_2$ (0.6 g), P(tBu)$_3$ (0.5 g) and tBuONa (2 g) were added to a round-bottom flask. Anhydrous PhMe (60 mL) was added via a syringe and the flask was degassed and refilled with nitrogen. 1-Boc-piperazine (4 g) was added and the system was degassed again followed by heating at 60° C. for 16 h. The reaction mixture was cooled to ambient temperature and diluted by CH$_2$Cl$_2$. The solution was filtered through a pad of celite and the volatile components were removed on a rotary evaporator. The residue was purified by flash column chromatography. The title compound ZBB65 was isolated in 3.5 g. ESI-MS calculated for $C_{19}H_{25}N_2O_2$ [M+H]$^+$=313.19, Obtained: 313.24.

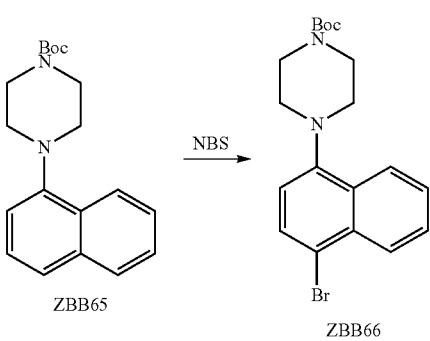 [SMILES: CC(C)(C)OC(=O)N1CCN(c2cccc3ccccc23)CC1 ; "NBS" ; CC(C)(C)OC(=O)N1CCN(c2ccc(Br)c3ccccc23)CC1]

ZBB65        ZBB66

ZBB65 (4.3 g) was dissolved in CH$_3$CN (80 mL). NBS (2.7 g) was added in small portions and the mixture was stirred at room temperature for 10 h. The volatile components were removed on a rotary evaporator. The remaining residue was purified by flash column chromatography to yield ZBB66 in 3.5 g. ESI-MS calculated for C$_{19}$H$_{24}$BrN$_2$O$_2$ [M+H]$^+$=391.10, Obtained: 391.22.

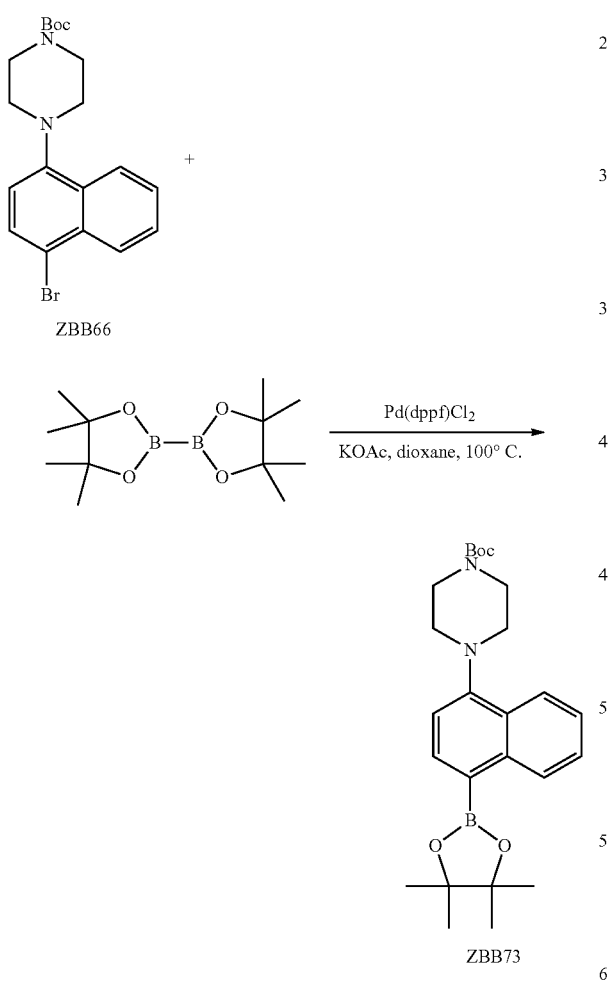

ZBB66 (1.6 g, 4.16 mmol), bis(pinacolato)diboron (2.13 g, 8.4 mmol, 2.0 equiv.), and potassium acetate (1.6 g, 16 mmol, 4.0 equiv.) were added to a round-bottom flask. Anhydrous 1,4-dioxane (20 mL) was added via a syringe and the flask was degassed and refilled with nitrogen. Pd(dppf)Cl$_2$ (322 mg, 0.46 mmol, 0.1 equiv.) was added and the system was degassed again followed by heating at 100° C. for 16 h. The reaction mixture was cooled to ambient temperature and diluted by CH$_2$Cl$_2$. The solution was filtered through a pad of celite and the volatile components were removed on a rotary evaporator. The residue was purified by flash column chromatography. The title compound ZBB73 was isolated in 1.3 g. ESI-MS calculated for C$_{25}$H$_{36}$BN$_2$O$_4$ [M+H]$^+$=439.27, Obtained: 439.33.

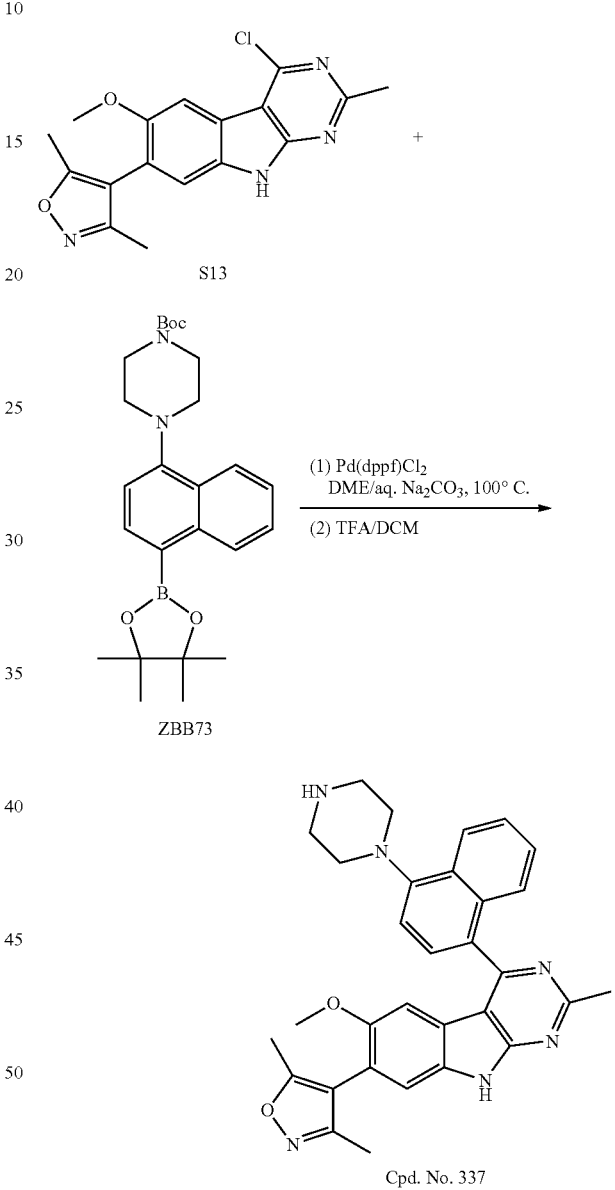

Cpd. No. 337

To a round-bottom flask, 4-(4-chloro-6-methoxy-2-methyl-9H-pyrimido[4,5-b]indol-7-yl)-3,5-dimethylisoxazole (S13, 5.4 g, 16 mmol, 1.0 equiv.) and ZBB73 (16.75 g, 37 mmol, 2.0 equiv.), 1,2-dimethoxyethane (150 mL), and Na$_2$CO$_3$ (2 M, 50 mL) were added. The system was degassed to remove oxygen and nitrogen was refilled. Pd(dppf)Cl$_2$—CH$_2$Cl$_2$ (1.3 g, 1.6 mmol, 0.1 equiv.) was added and the system was degassed and refilled with nitrogen. The reaction mixture was heated at reflux for 16 h. The reaction was quenched with water and the aqueous layer was extracted with ethyl acetate. The organic layers were combined and the volatile components were removed on a rotary evaporator. The residue was dissolved in $CH_2Cl_2$ (50 mL) and TFA (50 mL). The reaction mixture was stirred for 3 hours at room temperature. The volatile components were removed on a rotary evaporator and the residue was purified by flash column chromatography to yield the title compound Cpd. No. 337 in 2.0 g. ESI-MS calculated for $C_{31}H_{31}N_6O_2$ [M+H]=519.25, Obtained: 519.33. $^1$H NMR (300 MHz, MeOD) δ 8.52-8.47 (m, 1H), 8.01 (d, J=7.8 Hz, 1H), 7.81-7.72 (m, 2H), 7.64-7.52 (m, 3H), 6.20 (s, 1H), 3.68-3.50 (m, 8H), 3.17 (s, 3H), 3.02 (s, 3H), 2.26 (s, 3H), 2.07 (s, 3H).

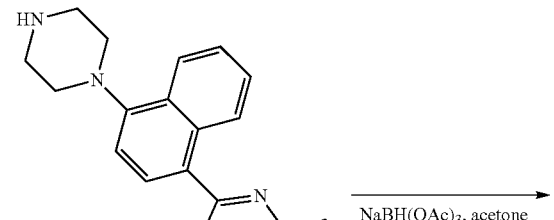

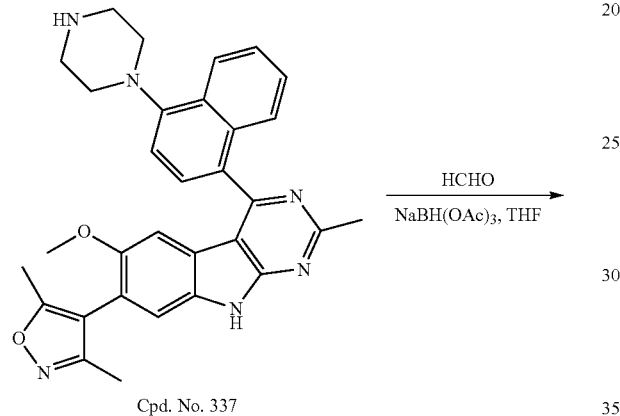

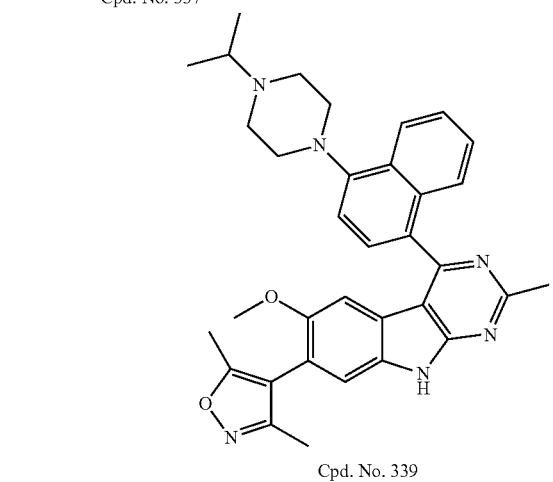

The Cpd. No. 337 (20 mg), formaldehyde (0.2 mL, 37% in $H_2O$) and $NaBH(OAc)_3$ (65 mg) was dissolved in $ClCH_2CH_2Cl$ (10 mL) and the mixture was stirred overnight. Then water and Ethyl acetate was slowly added. The aqueous layer was extracted with EtOAc. The combined EtOAc extracts were washed with $H_2O$, dried over $Na_2SO_4$, and concentrated under reduced pressure to afford Cpd. No. 338 (8 mg) after HPLC purification. ESI-MS calculated for $C_{32}H_{33}N_6O_2$ [M+H]$^+$=533.26, Obtained: 533.34.

The Cpd. No. 337 (20 mg), and $NaBH(OAc)_3$ (65 mg) was dissolved in acetone (1 mL) and the mixture was stirred overnight. Then water and Ethyl acetate was slowly added. The aqueous layer was extracted with EtOAc. The combined EtOAc extracts were washed with $H_2O$, dried over $Na_2SO_4$, and concentrated under reduced pressure to afford Cpd. No. 339 (12 mg) after HPLC purification. ESI-MS calculated for $C_{34}H_{37}N_6O_2$ [M+H]$^+$=561.29, Obtained: 561.33. $^1$H NMR (300 MHz, MeOD) δ 8.55-8.51 (m, 1H), 8.02 (d, J=7.8 Hz, 1H), 7.82-7.74 (m, 2H), 7.68-7.52 (m, 3H), 6.20 (s, 1H), 3.91-3.59 (m, 7H), 3.51-3.35 (m, 2H), 3.18 (s, 3H), 3.03 (s, 3H), 2.27 (s, 3H), 2.08 (s, 3H), 1.54 (d, J=6.7 Hz, 6H).

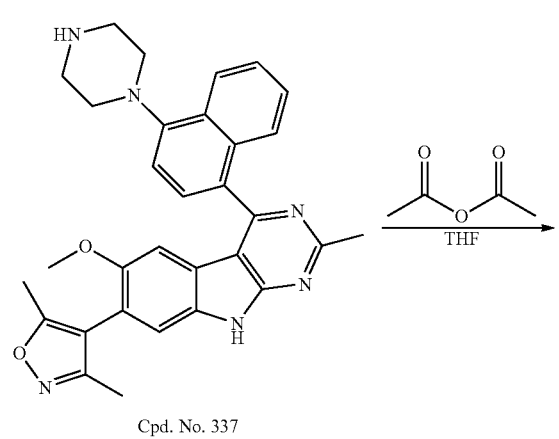

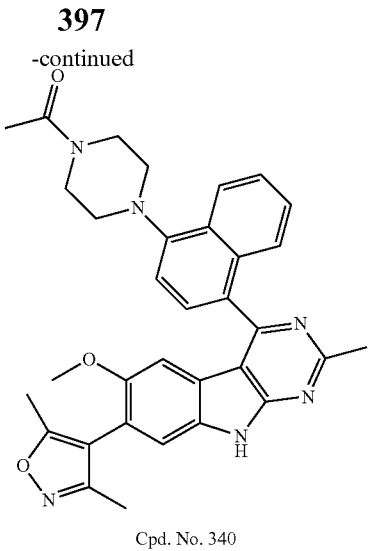

Cpd. No. 340

The Cpd. No. 337 (20 mg), and acetic anhydride (5 mg) was dissolved in THF (1 mL) and the mixture was stirred overnight. Then water and Ethyl acetate was slowly added. The aqueous layer was extracted with EtOAc. The combined EtOAc extracts were washed with H$_2$O, dried over Na$_2$SO$_4$, and concentrated under reduced pressure to afford Cpd. No. 340 (6 mg) after HPLC purification. ESI-MS calculated for C$_{33}$H$_{33}$N$_6$O$_3$ [M+H]$^+$=561.26, Obtained: 561.34. $^1$H NMR (300 MHz, MeOD) δ 8.58-8.50 (m, 1H), 7.97 (d, J=7.8 Hz, 1H), 7.79-7.72 (dd, J=11.1, 4.7 Hz, 2H), 7.65-7.56 (m, 1H), 7.54 (s, 1H), 7.51 (d, J=7.9 Hz, 1H), 6.23 (s, 1H), 4.12-3.86 (m, 4H), 3.36-3.22 (m, 4H), 3.20 (s, 3H), 3.02 (s, 3H), 2.28 (s, 3H), 2.23 (s, 3H), 2.09 (s, 3H).

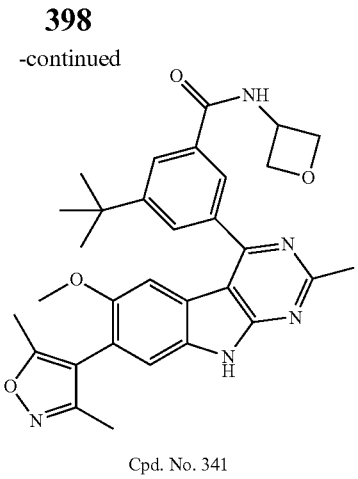

Cpd. No. 341

Cpd. No. 341-TFA salt was prepared from amide condensation of ZBA301 and 3-aminooxetane using EDCI-HOBT condition. 50% yield. ESI-MS calculated for C$_{31}$H$_{34}$N$_5$O$_4$ [M+H]$^+$=540.26, Obtained: 540.33. $^1$H NMR (300 MHz, MeOD) δ 8.65-8.49 (m, 2H), 8.34 (dt, J=6.4, 1.7 Hz, 1H), 7.59 (d, J=2.4 Hz, 1H), 7.24 (s, 1H), 4.93-4.57 (m, 3H), 3.95-3.70 (m, 2H), 3.67 (d, J=5.4 Hz, 3H), 3.00 (d, J=2.0 Hz, 3H), 2.33 (s, 3H), 2.15 (s, 3H), 1.52 (d, J=1.3 Hz, 9H).

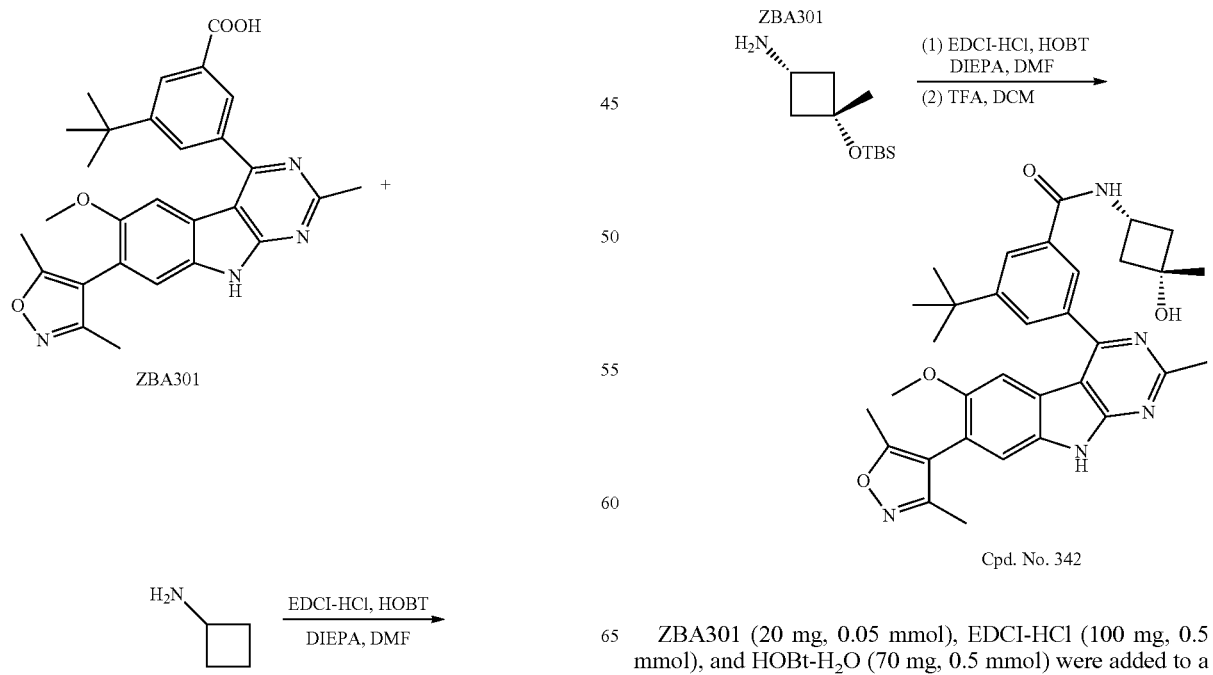

Cpd. No. 342

ZBA301 (20 mg, 0.05 mmol), EDCI-HCl (100 mg, 0.5 mmol), and HOBt-H$_2$O (70 mg, 0.5 mmol) were added to a round-bottom flask. EtN(i-Pr)$_2$ (0.1 mL) was added followed by addition of DMF (2.5 mL). 3-((tert-butyldimethylsilyl)oxy)-3-methylcyclobutan-1-amine (40 mg) was added and the reaction mixture was stirred for 12 h. The reaction was quenched with NaHCO₃ saturated solution and the aqueous layer was extracted with ethyl acetate. The combined organic layers were concentrated on a rotary evaporator. The remaining residue was dissolved in TFA (2 mL) and DCM (2 mL). The mixture was stirred for 3 hours and was concentrated on a rotary evaporator. The remaining residue was purified by reverse phase HPLC affording the Cpd. No. 342 as a salt of $CF_3CO_2H$ (9 mg). ESI-MS calculated for $C_{33}H_{35}N_5O_4$ $[M+H]^+$=568.29, Obtained: 568.44. ¹H NMR (300 MHz, MeOD) δ 8.40 (t, J=1.6 Hz, 1H), 8.37 (t, J=1.7 Hz, 1H), 8.22 (t, J=1.7 Hz, 1H), 7.58 (s, 1H), 7.31 (s, 1H), 4.23-4.08 (m, 1H), 3.69 (s, 3H), 3.00 (s, 3H), 2.60-2.45 (m, 2H), 2.33 (s, 3H), 2.23 (td, J=9.0, 2.2 Hz, 2H), 2.15 (s, 3H), 1.53 (s, 9H), 1.42 (s, 3H).

3.80-3.65 (m, 4H), 3.51-3.30 (m, 2H), 3.00 (s, 3H), 2.33 (s, 3H), 2.15 (s, 3H), 2.06-1.78 (m, 2H), 1.69-1.42 (m, 11H).

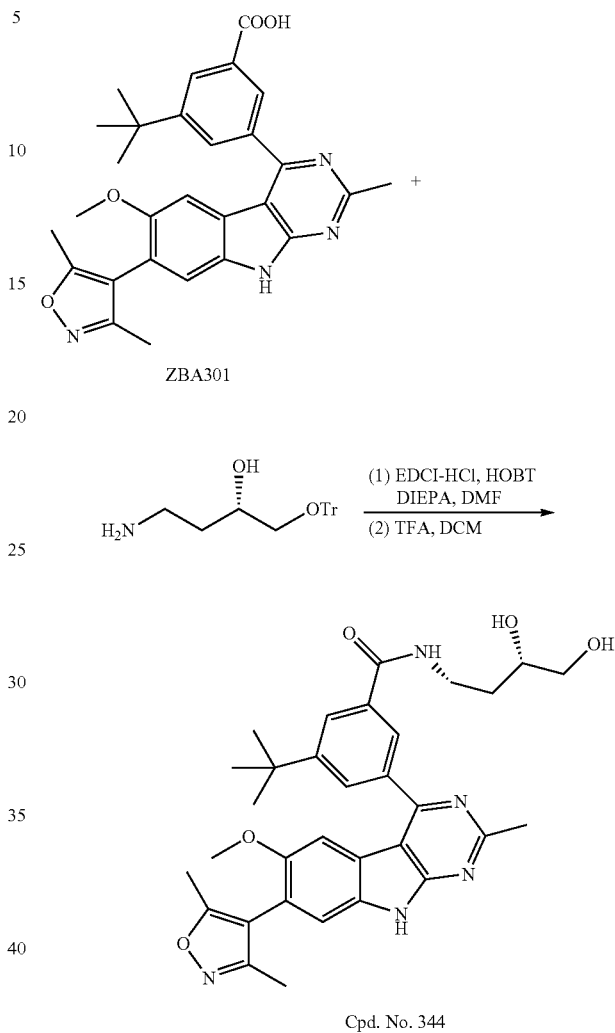

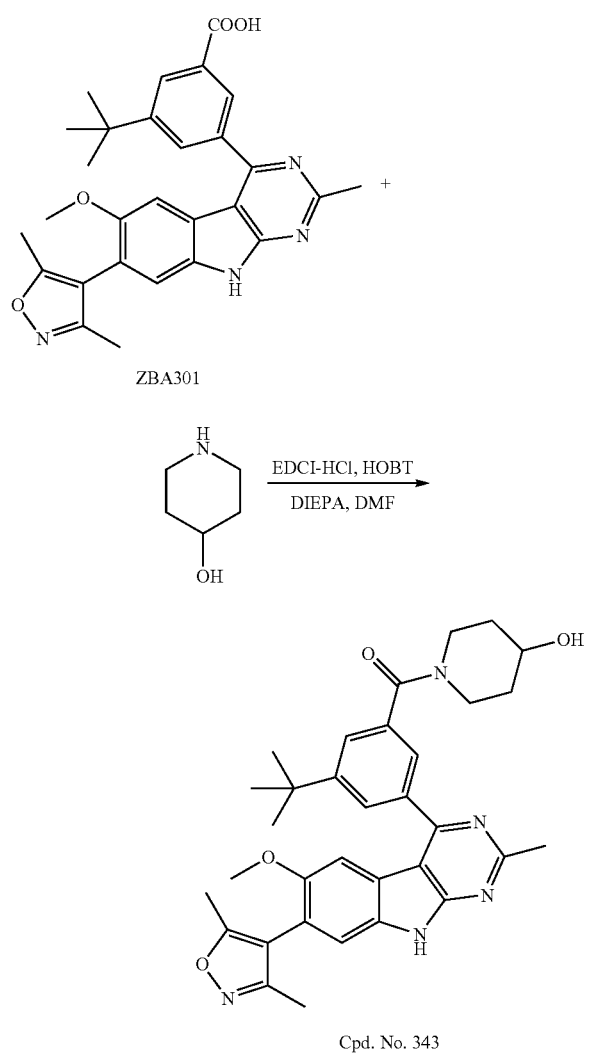

Cpd. No. 343-TFA salt was prepared from amide condensation of ZBA301 and piperidin-4-ol using EDCI-HOBT condition. 60% yield. ESI-MS calculated for $C_{33}H_{38}N_5O_4$ $[M+H]^+$=568.29, Obtained: 568.43. ¹H NMR (300 MHz, MeOD) δ 8.14 (t, J=1.7 Hz, 1H), 7.95-7.90 (m, 2H), 7.58 (s, 1H), 7.27 (s, 1H), 4.30-4.15 (m, 1H), 3.99-3.88 (m, 1H), ZBA301 (20 mg, 0.05 mmol), EDCI-HCl (100 mg, 0.5 mmol), and HOBt-H₂O (70 mg, 0.5 mmol) were added to a round-bottom flask. EtN(i-Pr)₂ (0.1 mL) was added followed by addition of DMF (2.5 mL). (S)-4-Amino-1-(trityloxy)butan-2-ol (40 mg) was added and the reaction mixture was stirred for 12 h. The reaction was quenched with NaHCO₃ saturated solution and the aqueous layer was extracted with ethyl acetate. The combined organic layers were concentrated on a rotary evaporator. The remaining residue was dissolved in TFA (2 mL) and DCM (2 mL). The mixture was stirred for 3 hours and was concentrated on a rotary evaporator. The remaining residue was purified by reverse phase HPLC affording the Cpd. No. 344 as a salt of $CF_3CO_2H$ (10 mg). ESI-MS calculated for $C_{32}H_{38}N_5O_5$ $[M+H]$=572.28, Obtained: 572.45. ¹H NMR (300 MHz, MeOD) δ 8.39 (t, J=1.6 Hz, 1H), 8.36 (t, J=1.7 Hz, 1H), 8.21 (t, J=1.7 Hz, 1H), 7.58 (s, 1H), 7.30 (s, 1H), 3.80-3.48 (m, 8H), 3.00 (s, 3H), 2.33 (s, 3H), 2.15 (s, 3H), 1.99-1.62 (m, 2H), 1.52 (s, 9H).

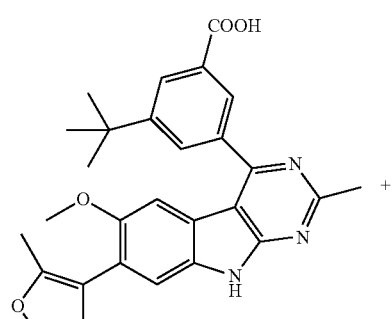

ZBA301

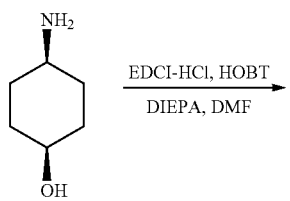

EDCI-HCl, HOBT
DIEPA, DMF

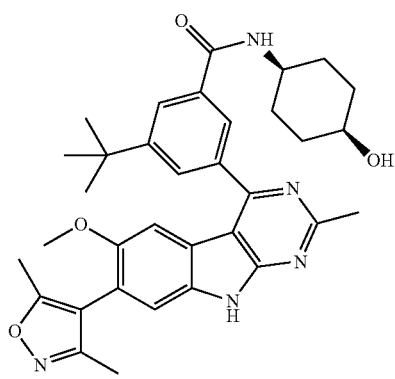

Cpd. No. 345

Cpd. No. 345-TFA salt was prepared from amide condensation of ZBA301 and cis-4-Amino-cyclohexanol using EDCI-HOBT condition. 60% yield. ESI-MS calculated for $C_{34}H_{40}N_5O_4$ [M+H]=582.30, Obtained: 582.55. $^1$H NMR (300 MHz, MeOD) δ 8.39 (t, J=1.6 Hz, 1H), 8.36 (t, J=1.7 Hz, 1H), 8.21 (t, J=1.7 Hz, 1H), 7.58 (s, 1H), 7.32 (s, 1H), 4.06-3.90 (m, 2H), 3.70 (s, 3H), 3.00 (s, 3H), 2.33 (s, 3H), 2.15 (s, 3H), 1.97-1.59 (m, 8H), 1.53 (s, 9H).

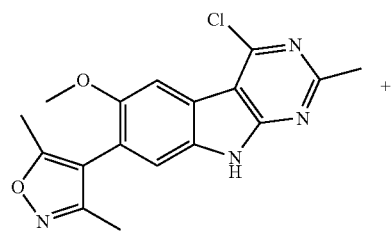

S13

-continued

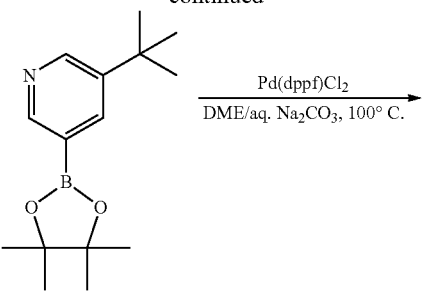

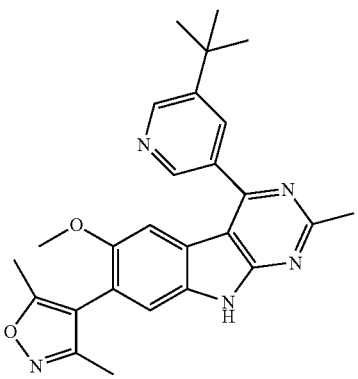

Cpd. No. 346

To a round-bottom flask, 4-(4-chloro-6-methoxy-2-methyl-9H-pyrimido[4,5-b]indol-7-yl)-3,5-dimethylisoxazole (S13, 54 mg, 1.0 equiv.) and 3-(tert-butyl)-5-(4,4,5,5-tetramethyl-1,3,2-dioxaborolan-2-yl)pyridine (137 mg, 2.0 equiv.), 1,2-dimethoxyethane (15 mL), and $Na_2CO_3$ (2 M, 5 mL) were added. The system was degassed to remove oxygen and nitrogen was refilled. Pd(dppf)Cl$_2$—CH$_2$Cl$_2$ (13 mg) was added and the system was degassed and refilled with nitrogen. The reaction mixture was heated at reflux for 16 h. The reaction was quenched with water and the aqueous layer was extracted with ethyl acetate. The organic layers were combined and the volatile components were removed on a rotary evaporator. The residue was purified by flash column chromatography to yield the title compound Cpd. No. 346 in 16 mg. ESI-MS calculated for $C_{26}H_{28}N_5O_2$ [M+H]=442.22, Obtained: 442.44. $^1$H NMR (300 MHz, MeOD) δ 9.13 (s, 2H), 8.69 (d, J=1.8 Hz, 1H), 7.58 (s, 1H), 7.21 (s, 1H), 3.72 (s, 3H), 2.98 (s, 3H), 2.33 (s, 3H), 2.15 (s, 3H), 1.55 (s, 9H).

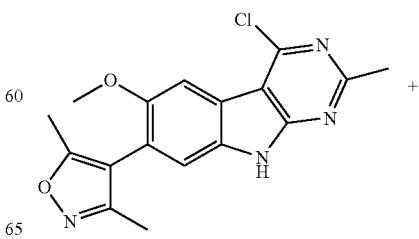

S13

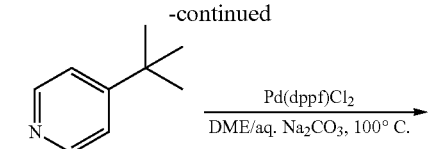

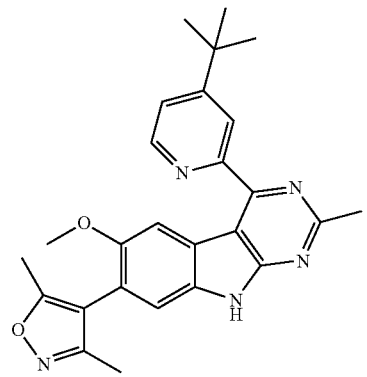

Cpd. No. 347

To a round-bottom flask, 4-(4-chloro-6-methoxy-2-methyl-9H-pyrimido[4,5-b]indol-7-yl)-3,5-dimethylisoxazole (S13, 54 mg, 1.0 equiv.) and 4-(tert-butyl)-2-(4,4,5,5-tetramethyl-1,3,2-dioxaborolan-2-yl)pyridine (137 mg, 2.0 equiv.), 1,2-dimethoxyethane (15 mL), and Na$_2$CO$_3$ (2 M, 5 mL) were added. The system was degassed to remove oxygen and nitrogen was refilled. Pd(dppf)Cl$_2$—CH$_2$Cl$_2$ (13 mg) was added and the system was degassed and refilled with nitrogen. The reaction mixture was heated at reflux for 16 h. The reaction was quenched with water and the aqueous layer was extracted with ethyl acetate. The organic layers were combined and the volatile components were removed on a rotary evaporator. The residue was purified by flash column chromatography to yield the title compound Cpd. No. 347 in 4 mg. ESI-MS calculated for C$_{26}$H$_{28}$N$_5$O$_2$ [M+H]=442.22, Obtained: 442.46. $^1$H NMR (300 MHz, MeOD) δ 8.98 (d, J=5.4 Hz, 1H), 8.35 (d, J=1.2 Hz, 1H), 7.91 (dd, J=5.3, 1.9 Hz, 1H), 7.82 (s, 1H), 7.55 (s, 1H), 3.81 (s, 3H), 3.00 (s, 3H), 2.35 (s, 3H), 2.17 (s, 3H), 1.51 (s, 9H).

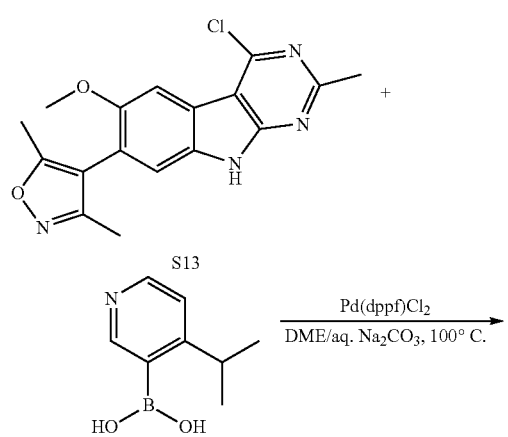

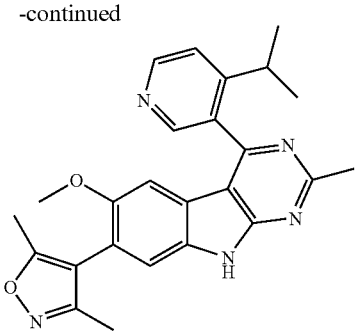

Cpd. No. 348

To a round-bottom flask, 4-(4-chloro-6-methoxy-2-methyl-9H-pyrimido[4,5-b]indol-7-yl)-3,5-dimethylisoxazole (S13, 54 mg, 1.0 equiv.) and (4-isopropylpyridin-3-yl)boronic acid (100 mg, 2.0 equiv.), 1,2-dimethoxyethane (15 mL), and Na$_2$CO$_3$ (2 M, 5 mL) were added. The system was degassed to remove oxygen and nitrogen was refilled. Pd(dppf)Cl$_2$—CH$_2$Cl$_2$ (13 mg) was added and the system was degassed and refilled with nitrogen. The reaction mixture was heated at reflux for 16 h. The reaction was quenched with water and the aqueous layer was extracted with ethyl acetate. The organic layers were combined and the volatile components were removed on a rotary evaporator. The residue was purified by flash column chromatography to yield the title compound Cpd. No. 348 in 10 mg. ESI-MS calculated for C$_{25}$H$_{26}$N$_5$O$_2$ [M+H]$^+$=428.20, Obtained: 428.45. $^1$H NMR (300 MHz, MeOD) δ 8.98 (d, J=5.5 Hz, 1H), 8.86 (s, 1H), 8.03 (d, J=5.6 Hz, 1H), 7.57 (s, 1H), 6.60 (s, 1H), 3.59 (s, 3H), 3.11-2.92 (m, 4H), 2.32 (s, 3H), 2.13 (s, 3H), 1.31 (d, J=6.7 Hz, 3H), 1.22 (d, J=6.6 Hz, 3H).

Synthesis of Cpd. No. 350 (TFA salt)

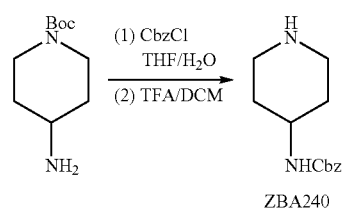

ZBA240

To a round-bottom flask, 4-Amino-1-Boc-piperidine (2 g) was dissolved in THF (30 mL) and water (30 mL). NaHCO$_3$ (8 g) and CbzCl (1.5 mL) was added and the solution was stirred for 10 h at rt. The reaction mixture was extracted with ethyl acetate. The organic extracts were combined and concentrated on a rotary evaporator. The remaining residue was dissolved in TFA (4 mL) and DCM (40 mL) and the solution was stirred for 4 h at rt. The solution was concentrated on a rotary evaporator. Then aq. NaHCO$_3$ (30 mL) and the reaction mixture was extracted with ethyl acetate. The organic extracts were combined and concentrated on a rotary evaporator to give ZBA240 (1.6 g) which was used directly in the next step.

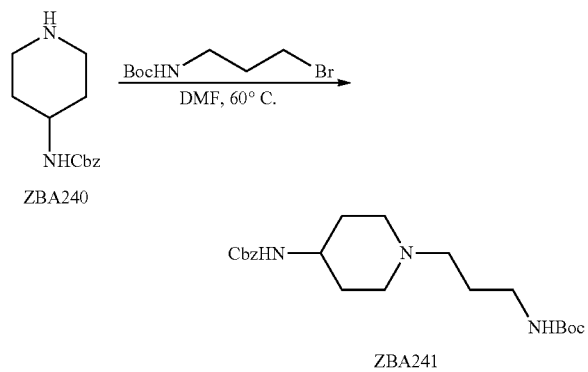

ZBA240

ZBA241

To a round-bottom flask, ZBA240 (2.3 g) was dissolved in DMF (30 mL). $K_2CO_3$ (2 g), tert-butyl (3-bromopropyl) carbamate (2.4 g) and NaI (750 mg) was added and the solution was stirred for 2 h at 60° C. The reaction mixture was extracted with ethyl acetate. The organic layers were combined and the volatile components were removed on a rotary evaporator. The residue was purified by flash column chromatography to yield the title compound ZBA241 in 1.8 g. ESI-MS calculated for $C_{21}H_{34}N_3O_4$ $[M+H]^+=392.25$, Obtained: 392.44.

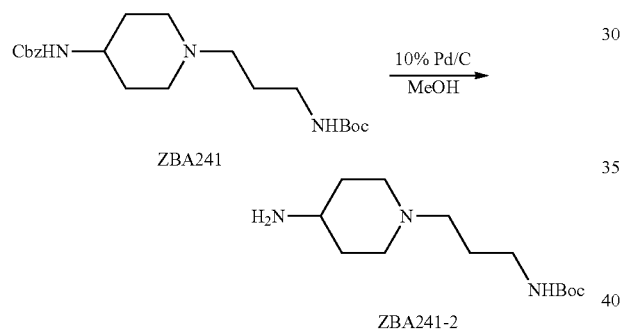

ZBA241

ZBA241-2

To a round-bottom flask, ZBA241 (300 mg), 10% Pd/C (100 mg), MeOH (20 mL) were added. The system was degassed to remove oxygen and hydrogen was refilled. the solution was stirred for 10 h at rt. The solution was filtered through a pad of celite and the volatile components were removed on a rotary evaporator. The residue ZBA241-2 was directly used next step without purification.

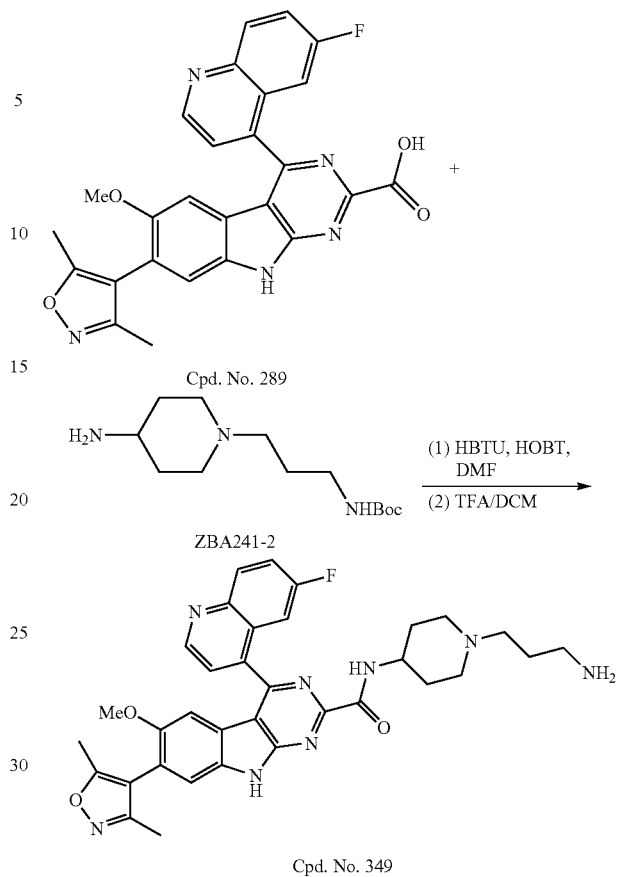

Cpd. No. 289

ZBA241-2

Cpd. No. 349

Cpd. No. 289 (20 mg), HBTU (24 mg), HOBt-$H_2O$ (6 mg) and DMF (1 mL) were added to a round-bottom flask. EtN(i-Pr)$_2$ (0.05 mL) was added followed by addition of ZBA241-2 (37 mg) was added and the reaction mixture was stirred for 12 h. The reaction was quenched with $NaHCO_3$ saturated solution and the aqueous layer was extracted with ethyl acetate. The combined organic layers were concentrated on a rotary evaporator. The remaining residue was dissolved in TFA (2 mL) and DCM (2 mL). The mixture was stirred for 3 hours and was concentrated on a rotary evaporator. The remaining residue was purified by reverse phase HPLC affording the Cpd. No. 349 as a salt of $CF_3CO_2H$ (10 mg). ESI-MS calculated for $C_{34}H_{36}FN_8O_3$ $[M+H]^+=623.28$, Obtained: 623.43.

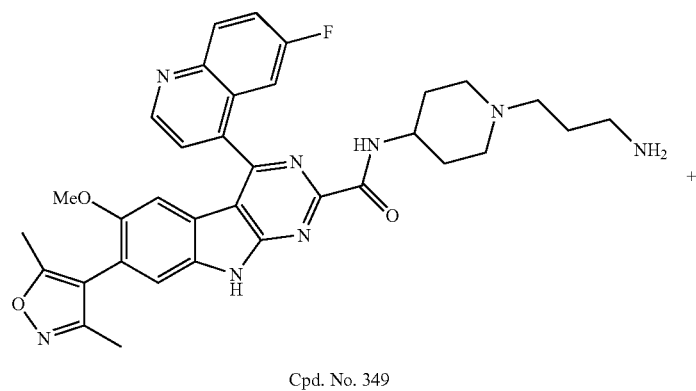

Cpd. No. 349

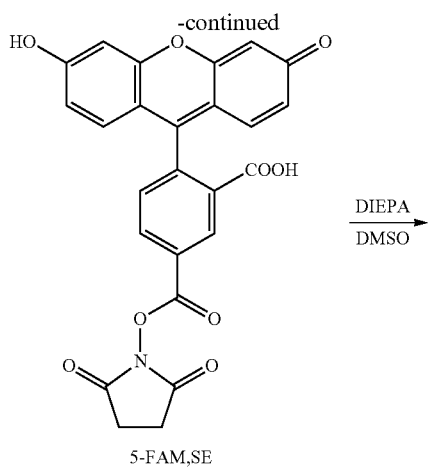

5-FAM,SE

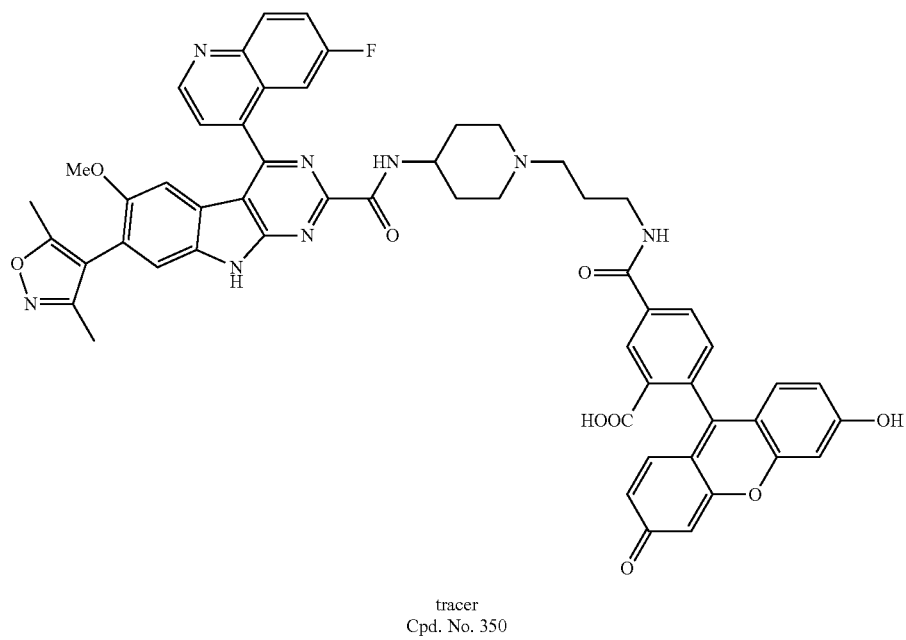

tracer
Cpd. No. 350

To a round-bottom flask, Cpd. No. 349 (19 mg) was dissolved in DMSO (1 mL). 5-FAM, SE (5-Carboxyfluorescein, Succinimidyl Ester) (43 mg), DIEPS (0.03 mL) was added and the solution was stirred for 2 h at rt. The mixture was purified by reverse phase HPLC affording the tracer Cpd. No. 350 as a salt of $CF_3CO_2H$ (6 mg). ESI-MS calculated for $C_{55}H_{46}FN_8O_9$ [M+H]$^+$=981.33, Obtained: 981.42. $^1$H NMR (300 MHz, MeOD) δ 9.20 (d, J=4.4 Hz, 1H), 8.51 (s, 1H), 8.36 (dd, J=9.3, 5.4 Hz, 1H), 8.26 (dd, J=8.1, 1.5 Hz, 1H), 7.99 (d, J=4.5 Hz, 1H), 7.82-7.72 (m, 1H), 7.54 (s, 1H), 7.44 (dd, J=9.7, 2.6 Hz, 1H), 7.36 (d, J=7.9 Hz, 1H), 6.75 (d, J=2.2 Hz, 2H), 6.66-6.56 (m, 4H), 6.40 (s, 1H), 4.45-4.25 (m, 1H), 3.80-3.70 (m, 2H), 3.64-3.54 (m, 2H), 3.32-3.16 (m, 4H), 2.45-2.24 (m, 5H), 2.23-1.99 (m, 7H).

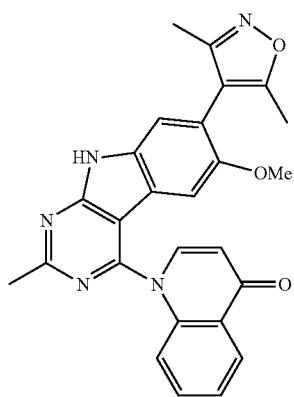

Cpd. No. 351

1-(7-(3,5-dimethylisoxazol-4-yl)-6-methoxy-2-methyl-9H-pyrimido[4,5-b]indol-4-yl)quinolin-4(1H)-one (Cpd. No. 351): $^1$H-NMR (300 MHz, CD$_3$OD) δ ppm 8.51 (dd, J=1.68, 7.77 Hz, 1H), 8.43 (d, J=7.78 Hz, 1H), 7.70-7.54 (m, 2H), 7.43 (s, 1H), 7.32 (dd, J=0.88, 8.13 Hz, 1H), 6.66 (d, J=7.76 Hz, 1H), 6.26 (s, 1H), 3.32 (s, 3H), 2.89 (s, 3H), 2.26 (s, 3H), 2.08 (s, 3H); ESI-MS m/z 452.50 (M+H)$^+$.

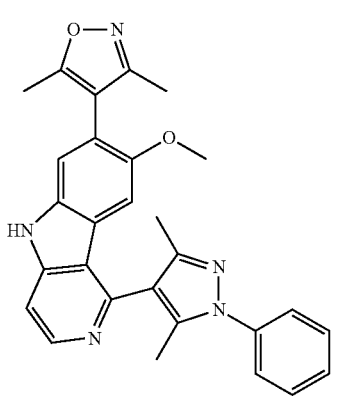

Cpd. No. 352

4-(1-(3,5-dimethyl-1-phenyl-1H-pyrazol-4-yl)-8-methoxy-5H-pyrido[4,3-b]indol-7-yl)-3,5-dimethylisoxazole was prepared as described in Section 3.2 above. $^1$HNMR (300 MHz, MeOD-d$_4$) δ 8.60 (d, 1H, J=6.6 Hz), 8.00 (d, 1H, J=6.9 Hz), 7.64-7.66 (m, 6H), 7.11 (s, 1H), 3.78 (s, 3H), 2.35 (s, 3H), 2.33 (s, 3H), 2.31 (s, 3H), 2.17 (s, 3H). $^{13}$CNMR (300 MHz, MeOD-d$_4$), δ 168.26, 161.16, 155.67, 149.62, 149.10, 142.49, 142.22, 140.20, 137.48, 136.42, 131.02, 130.49, 126.75, 123.83, 122.75, 121.30, 117.06, 114.60, 108.87, 103.95, 56.38, 12.56, 11.74, 11.69, 10.81. ESIMS m/z [M+H]$^+$ calcd.=464.54. found=464.42.

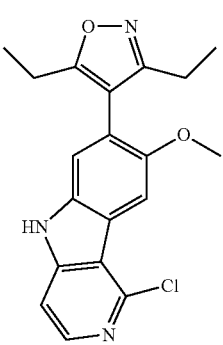

RX45

4-(1-chloro-8-methoxy-5H-pyrido[4,3-b]indol-7-yl)-3,5-diethylisoxazole was prepared as described in Section 4.3 above. $^1$HNMR (300 MHz, DMSO-d$_6$) δ 12.06 (s, 1H), 8.22 (d, 1H, J=5.7 Hz), 7.96 (s, 1H), 7.52 (d, 1H, J=5.7 Hz), 7.49 (s, 1H), 3.89 (s, 3H), 2.65 (q, 2H, J=7.5 Hz), 2.53 (q, 2H, J=7.5 Hz), 1.15 (t, 3H, J=7.5 Hz), 1.04 (t, 3H, J=7.5 Hz). $^{13}$CNMR (300 MHz, DMSO-d$_6$), δ 169.85, 163.67, 152.08, 145.84, 143.62, 143.55, 133.92, 119.93, 119.20, 116.06, 114.30, 111.86, 106.71, 103.19, 55.71, 18.94, 18.49, 11.81. ESIMS m/z [M+H]$^+$ calcd.=356.67. found=356.83.

To demonstrate the ability of the present BET bromodomain inhibitors to bind to BET bromodomain proteins, competitive FP binding assays were designed and performed for recombinant BRD2 BD2, BRD3 BD2, and BRD4 BD2 proteins.

The FAM labeled fluorescent probe (BRD-1F) was synthesized based on a known small-molecule BET bromodomain inhibitor. K$_d$ values of BRD-1F to these three proteins were determined by monitoring the total fluorescence polarization of mixtures composed with the fluorescent probe at a fixed concentration and proteins with increasing concentrations up to full saturation. Fluorescence polarization values were measured using the Infinite M-1000 plate reader (Tecan U.S., Research Triangle Park, N.C.) in Corning 384 well flat bottom black plates (Corning Life Science). Serial dilutions of testing protein were mixed with BRD-1F to a final volume of 80 μl in the assay buffer (100 mM potassium phosphate, pH 7.5, 100 μg/ml bovine γ-globulin, 0.02% sodium azide, Invitrogen, with 0.01% Triton X-100 and 2.5% Ethylene Glycol). Final BRD-1F concentration was 5 nM. Plates were incubated at room temperature for 1-2 hours with gentle shaking to assure equilibrium. The polarization values in millipolarization units (mP) were measured at an excitation wavelength of 485 nm and an emission wavelength of 530 nm. Equilibrium dissociation constants (K$_d$) were then calculated by fitting the sigmoidal dose-dependent FP increases as a function of protein concentrations using Graphpad Prism 5.0 software (Graphpad Software, San Diego, Calif.).

The IC50 and K$_i$ values of compounds were determined in a competitive binding experiment in which serial dilutions of compounds competed against fixed concentration of the fluorescent probe (BRD-1F) for binding to the protein with a fixed concentration (typically 2 to 3 times the K$_d$ values determined above) as well. Mixtures of 2 μl of the tested compounds in Ethylene Glycol and 78 μl of preincubated protein/probe complex solution in the assay buffer (100 mM potassium phosphate, pH 7.5, 100 μg/ml bovine γ-globulin, 0.02% sodium azide, Invitrogen with 0.01% Triton X-100) were added into assay plates and incubated at room temperature for 1 hour with gentle shaking. Final concentrations of proteins were 200 nM, 150 nM and 200 nM in assays for BRD2 BD2, BRD3 BD2, and BRD4 BD2, respectively. Final probe concentration is 5 nM in all assays. Negative controls containing protein/probe complex only (equivalent to 0% inhibition), and positive controls containing only free probes (equivalent to 100% inhibition), were included in each assay plate. FP values were measured as described above. IC$_{50}$ values were determined by nonlinear regression fitting of the competition curves. The K$_i$ values of competitive inhibitors were calculated using the derived equation described previously, based upon the measured IC$_{50}$ values, the K$_d$ values of the probe to different proteins, and the concentrations of the proteins and probes in the competitive assays.

Table 1 lists binding affinities of several representative compounds to BRD2 BD2 and BRD4 BD2 proteins.

TABLE 1
Binding affinities of representative compounds to BRD2 BD2 and BRD4 BD2 in FP competitive binding assays.
| Cpd. No. ID | Structure | Binding Affinities | | | |
| --- | --- | --- | --- | --- | --- |
| | | BRD2 BD2 | | BRD4 BD2 | |
| | | IC50 (nM) | Ki (nM) | IC50 (nM) | Ki (nM) |
| Cpd. No. 2 | 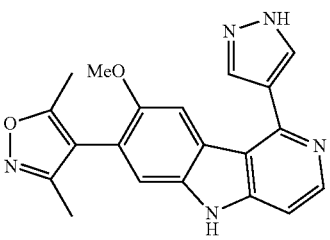 [SMILES: COc1cc2c(cc1-c1c(C)noc1C)[nH]c1ccnc(-c3cn[nH]c3)c12] | 286 ± 125 | 42.3 ± 32.0 | 608 ± 244 | 114 ± 87 |
| RX-7 | 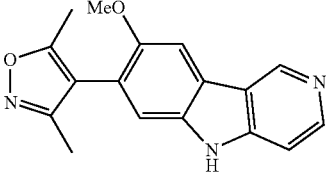 [SMILES: COc1cc2c(cc1-c1c(C)noc1C)[nH]c1ccncc12] | 1350 ± 212 | 366 ± 82 | 2902 | 850 |
| Cpd. No. 3 | 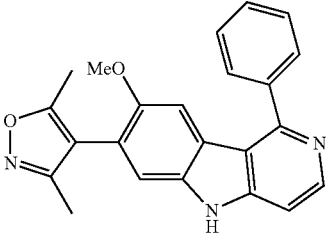 [SMILES: COc1cc2c(cc1-c1c(C)noc1C)[nH]c1ccnc(-c3ccccc3)c12] | 225 ± 114 | 34.9 ± 21.2 | 514 | 83.4 |
| Cpd. No. 4 | 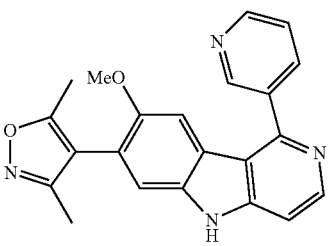 [SMILES: COc1cc2c(cc1-c1c(C)noc1C)[nH]c1ccnc(-c3cccnc3)c12] | 349 | 57.4 | 873 | 232 |
| Cpd. No. 17 | 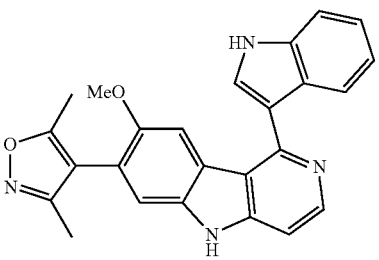 [SMILES: COc1cc2c(cc1-c1c(C)noc1C)[nH]c1ccnc(-c3c[nH]c4ccccc34)c12] | 142 ± 31 | <10 | 197 ± 99 | 16.4 |
| Cpd. No. 21 | 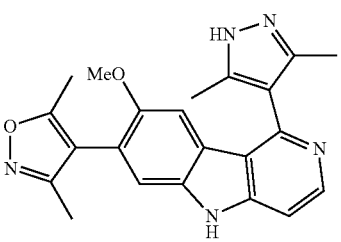 [SMILES: COc1cc2c(cc1-c1c(C)noc1C)[nH]c1ccnc(-c3c(C)n[nH]c3C)c12] | 92.8 ± 30.8 | <10 | 310 ± 71 | 37.9 ± 10.0 |

TABLE 1-continued

Binding affinities of representative compounds to BRD2 BD2 and BRD4 BD2 in FP competitive binding assays.

| Cpd. No. ID | Structure | BRD2 BD2 IC50 (nM) | BRD2 BD2 Ki (nM) | BRD4 BD2 IC50 (nM) | BRD4 BD2 Ki (nM) |
|---|---|---|---|---|---|
| Cpd. No. 34 | (structure) | 3197 | 1199 | 3666 | 775 |

Binding affinities of synthesized compounds to BRD2 BD1 and BD2, BRD3 BD1 and BD2, and BRD4 BD1 and BD2 were also determined by a label free binding assay using the OctetRED label free biolayer interferometry (BLI) binding assay.

BLI measures interference pattern changes of light reflected from an optical layer and a biolayer containing protein targets only or complexed with interacting partners. The assay principle is similar to the surface plasmon resonance (SPR) assay in which the target protein is immobilized on an optical surface and then exposed to potential binding partners in solution. The interaction between the binding partner and the immobilized protein changes the optical properties of the biosensors, resulting in the wavelength shift of reflecting light which will change the interference pattern. Association and dissociation rates can be obtained by fitting the real time wavelength shift of the based on a proper binding model, from which $K_D$ values can be obtained thereafter.

Biotin labeled BRD proteins (10 g/ml) in kinetic assay buffer (PBS, pH 7.4, 0.1% BSA and 0.01% Tween-20) were immobilized on Super Streptavidin (SSA) sensors for 15 minutes followed by washing in kinetic buffer for 10 minutes to eliminate any loose nonspecific immobilization. In the same 96-well plate serial dilutions of testing compounds with concentrations typically ranging from 0.1-10 times of expected $K_d$ values in the identical assay buffer were prepared. These protein coated sensors were then immersed into the testing compound solutions, starting from the one with the lowest concentration, where compound association occurs and then returned to the fresh buffer for the dissociation. The same operation was repeated for the next solution with higher concentration up to the one with the highest concentration. Identical procedure was performed again with control sensors that were immobilized with SAB4 inactive control protein prepared by following protocols from the manufacturer. Blank buffer controls were included in both BRD protein sensor and inactive protein sensor runs. For each kinetic cycle, kinetic curves for association and dissociation were obtained from raw sensorgrams by using the double reference subtraction protocol included in the analysis program (Data Analysis 7.0) provided by the manufacturer, in which nonspecific interaction and buffer drift were both corrected. The association and dissociation rate constants ($k_{on}$ and $k_{off}$) were determined using the global fitting protocol in the analysis program based on a reversible 1:1 binding model. The equilibrium association constant ($K_A$) was calculated thereafter. All binding data were collected at 30 degree. Assay plates were kept being shaken at 1000 RPM in the whole experiment time period to avoid mass transport effect.

Table 2 lists the binding affinities of several representative compounds to BRD2 BD1, BRD2 BD2, BRD3 BD1, BRD3 BD2, BRD4 BD1 and BRD4 BD2 proteins.

TABLE 2

Binding affinities of several representative BET bromodomain inhibitors to BRD2 BD1, BRD2 BD2, BRD3 BD1, BRD3 BD2, BRD4 BD1 and BRD4 BD2 proteins using the biolayer interferometry (BLI) binding assay.

| Kd (nM) | BRD2 | | BRD3 | | BRD4 | |
|---|---|---|---|---|---|---|
| | BD1 | BD2 | BD1 | BD2 | BD1 | BD2 |
| Cpd. No. 22 | 34.0 ± 2.1 | 24.4 ± 6.2 | 17.9 ± 8.8 | 18.7 ± 4.9 | 40.0 ± 6.4 | 27.9 ± 6.8 |
| Cpd. No. 23 | 25.6 ± 3.7 | 19.6 ± 4.1 | 17.6 ± 2.5 | 20.7 ± 3.6 | 29.0 ± 8.8 | 12.9 ± 2.1 |
| Cpd. No. 25 | 41.2 ± 2.2 | 35.9 ± 8.8 | 20.7 ± 7.8 | 42.4 ± 17.6 | 60.3 ± 17.6 | 36.3 ± 11.2 |
| Cpd. No. 44 | 33.8 ± 8.2 | 11.0 ± 4.7 | 17.0 ± 7.0 | 10.6 ± 1.1 | 27.0 ± 14.5 | 10.2 ± 4.5 |

Cell growth inhibitory activity of representative BET bromodomain inhibitors was determined using CellTiter-Glo® Luminescent Cell Viability Assay. For leukemia cell lines MV-4-11 (ATCC, Manassas, Va.) and MOLM-13 (DSMZ, Germany), cells were seeded in 96-well white opaque cell culture plates at a density of 10,000 cells/well with serially diluted compounds and incubated at 37° C. in an atmosphere of 95% air and 5% CO2 for 4 days. Cell viability was determined using the CellTiter-Glo® Luminescent Cell Viability Assay Kit (Promega, Madison, Wis.) according to the manufacture's instruction. Briefly, a volume of CellTiter-Glo® Reagent equal to the volume of cell culture medium was added to each well, and then the plates were incubated at room temperature for 10-20 minutes. The luminescent signal was measured using a Tecan Infinite M1000 multimode microplate reader (Tecan, Morrisville, N.C.). The half maximal inhibitory concentration (IC50) was calculated using the GraphPad Prism 5 software (GraphPad Software, La Jolla, Calif.).

For breast cancer cell lines, cells were seeded in 96-well cell culture plates at a density of 5,000-10,000 cells/well with serially diluted compounds and incubated at 37° C. in an atmosphere of 95% air and 5% CO2 for 4 days. All the breast cancer cell lines were obtained from the ATCC. Cell viability was determined using the WST-8 (2-(2-methoxy-4-nitrophenyl)-3-(4-nitrophenyl)-5-(2,4-disulfophenyl)-2H-tetrazolium, monosodium salt) based Cell Counting-8 Kit (Dojindo Molecular Technologies, Inc., Rockville, Md.) according to the manufacture's instruction. Briefly, WST-8 was added to each well at a final concentration of 10% (v/v), and then the plates were incubated at 37° C. for 1-2 hours for color development. The absorbance was measured at 450 nm using a SPECTRAmax PLUS plate reader (Molecular Devices, Sunnyvale, Calif.). The IC50 was calculated using the GraphPad Prism 5 software.

Table 3 lists the IC50 values for several representative BET bromodomain inhibitors in the present invention in inhibition of cell growth in leukemia cell lines. Table 4 lists cell growth inhibition of compound Cpd. No. 68 in breast cancer cell lines.

TABLE 3

Cell growth inhibition of several representative compounds in acute leukemia cell lines.

| Compounds | IC50 (nM) | |
|---|---|---|
| | MV-4-11 | Molm-13 |
| Cpd. No. 17 | <100 | <500 |
| Cpd. No. 21 | <100 | <500 |
| Cpd. No. 38 | <100 | <500 |
| Cpd. No. 44 | <100 | <100 |
| Cpd. No. 68 | <100 | <100 |

TABLE 4

Cell growth inhibition of compound Cpd. No. 68 in breast cancer cell lines.

| Cell Lines | IC50 (nM) |
|---|---|
| BT-474 | <300 |
| MDA-MB-157 | <300 |
| MDA-MB-231 | <300 |
| MDA-MB-436 | <300 |
| SK-BR-3 | <300 |

Fluorescence Polarization (FP) Competitive Binding Assays Using Cpd. No. 350

Fluorescence Polarization (FP) competitive binding studies (see above) were carried out using the FAM labeled fluorescent probe Cpd. No. 350 to determine binding affinities of representative compounds to both BD1 and BD2 of BRD2, BRD3, and BRD4 proteins. Equilibrium dissociation constants ($K_d$) values of Cpd. No. 350 to these six proteins were determined from protein saturation experiments by monitoring the total fluorescence polarization of mixtures composed with the fluorescent probe at a fixed concentration and proteins with increasing concentrations up to full saturation. Serial dilutions of testing protein were mixed with Cpd. No. 350 to a final volume of 200 µl in the assay buffer. In order to achieve large dynamic rages, particularly for BD1 bromodomains, 100 mM phosphate buffer (pH=6.5, 0.01% Triton X-100 (Sigma, 282103) being added right before assays) was used as the assay buffer. Final Cpd. No. 350 concentration was 1.5 nM for all proteins. Plates were incubated at room temperature for 30 minutes with gentle shaking to assure equilibrium. FP values in millipolarization units (mP) were measured using the Infinite M-1000 plate reader (Tecan U.S., Research Triangle Park, N.C.) in Microfluor 1 96-well, black, round-bottom plates (Thermo Scientific, Waltham, Mass.) at an excitation wavelength of 485 nm and an emission wavelength of 530 nm. $K_d$ values of Cpd. No. 350, which were calculated by fitting the sigmoidal dose-dependent FP increases as a function of protein concentrations using Graphpad Prism 6.0 software (Graphpad Software, San Diego, Calif.), are 2.0, 2.2, 6.5, 0.6, 5.5, and 3.0 nM to BRD2 BD1 and 2, BRD3 BD1 and 2, and BDR4 BD1 and 2, respectively.

The $IC_{50}$ and $K_i$ values of compounds were determined in a competitive binding experiment as described above. Mixtures of 10 µl of the tested compounds in assay buffer with 40% Ethylene Glycol and 190 µl of preincubated protein/probe complex solution in the assay buffer (100 mM potassium phosphate, pH 6.5, 0.01% Triton X-100) were added into assay plates which were incubated at room temperature for 30 minutes with gentle shaking. Final concentrations of proteins were 3, 6, 15, 2, 10, and 6 nM in assays for BD1 and BD2 of BRD2, BRD3, and BRD4 BD2, respectively. Final probe concentration is 1.5 nM in all assays. Negative controls containing protein/probe complex only (equivalent to 0% inhibition), and positive controls containing only free probes (equivalent to 100% inhibition), were included in each assay plate. FP values were measured as described above. $IC_{50}$ values were determined by nonlinear regression fitting of the competition curves. Instead of being calculated from $IC_{50}$ values as described before, $K_i$ values of competitive inhibitors were obtained directly by nonlinear regression fitting as well, based upon the $K_d$ values of the probe to different proteins, and concentrations of the proteins and probes in the competitive assays (Wang, FEBS Lett. 360; 111 (1995); Zhang et al., Analytical Biochemistry, 331; 138 (2004)).

TABLE 5

Binding affinities of representative compounds to recombinant BD1 and BD2 domain proteins of BDR2, BRD3 and BRD4 in fluorescence-polarization based assays using Cpd. No. 350 as the probe

| | BRD2 | | BRD3 | | BRD4 | |
|---|---|---|---|---|---|---|
| Compound ID | BD1 $K_i$ (nM) | BD2 $K_i$ (nM) | BD1 $K_i$ (nM) | BD2 $K_i$ (nM) | BD1 $K_i$ (nM) | BD2 $K_i$ (nM) |
| RX-3 | 215 ± 34 | 109 ± 10 | 144 ± 17 | 63.8 ± 6.0 | 305 ± 26 | 194 ± 24 |
| RX-7 | 650 ± 125 | 498 ± 11 | 730 ± 146 | 241 ± 6 | 1644 ± 71 | 824 ± 25 |
| Cpd. No. 1 | 31.6 ± 8.2 | 34.5 ± 2.1 | 14.7 ± 1.0 | 14.3 ± 0.5 | 47.8 ± 1.0 | 70.1 ± 2.0 |
| Cpd. No. 2 | 138 ± 8 | 89.7 ± 6.4 | 151 ± 20 | 48.7 ± 3.3 | 247 ± 29 | 201 ± 5 |
| Cpd. No. 21 | 48.3 ± 1.3 | 57.7 ± 8.1 | 31.9 ± 4.0 | 25.9 ± 1.8 | 98.8 ± 11.6 | 100 ± 16 |
| Cpd. No. 24 | 58.4 ± 1 | 92.1 ± 3.3 | 38.2 ± 1 | 50.9 ± 5.8 | 116 ± 5 | 134 ± 42 |
| Cpd. No. 352 | 62.6 ± 9.0 | 52.9 ± 2.7 | 31.8 ± 1.5 | 35.0 ± 2.0 | 103 ± 3 | 98.1 ± 6.1 |
| Cpd. No. 22 | 21.0 ± 3.3 | 15.4 ± 3.2 | 12.9 ± 2.9 | 4.2 ± 0.4 | 44.1 ± 6.4 | 16.1 ± 2.8 |
| Cpd. No. 23 | 11.1 ± 1.0 | 11.7 ± 3.0 | 7.3 ± 0.1 | 3.2 ± 0.5 | 24.7 ± 1.0 | 12.2 ± 1.6 |
| Cpd. No. 25 | 12.2 ± 1.7 | 22.2 ± 2.8 | 10.4 ± 1.0 | 9.4 ± 1.0 | 26.9 ± 1.0 | 38.0 ± 2.2 |
| RX-38 | 760 ± 240 | 1884 ± 432 | 703 ± 432 | 1279 ± 1069 | 2814 ± 782 | 2182 ± 132 |
| RX-39 | 1716 ± 892 | 638 ± 70 | 668 ± 82 | 406 ± 192 | 1243 ± 549 | 478 ± 69 |
| Cpd. No. 33 | 1668 ± 448 | 909 ± 272 | 1219 ± 100 | 348 ± 12 | 1726 ± 17 | 867 ± 107 |
| RX-27 | 5452 ± 1916 | 2837 ± 574 | 5029 ± 1014 | 2047 ± 142 | 4842 ± 29 | 1948 ± 175 |
| RX-45 | | | | 3438 ± 1985 | >10000 | 8322 ± 1272 |
| Cpd. No. 68 | 3.2 | 2.7 | 5.1 | 0.65 | 7.3 | 1.7 |
| Cpd. No. 73 | 15.5 | 8.7 | 10.2 | 2.6 | 35.3 | 7.8 |
| Cpd. No. 183 | 5.2 | 8.8 | 6.1 | 4.7 | 7.9 | 11.7 |
| Cpd. No. 196 | 4.3 | 3.5 | 9.7 | 1.4 | 12.3 | 7.0 |
| Cpd. No. 197 | 6.2 | 3.6 | 10.5 | 1.3 | 17.1 | 8.9 |
| Cpd. No. 207 | 5.3 | 5.1 | 10.0 | 1.3 | 14.7 | 4.1 |
| Cpd. No. 211 | 5.7 | 4.9 | 10.8 | 1.2 | 17.2 | 5.2 |
| Cpd. No. 212 | 5.7 | 4.6 | 10.2 | 1.0 | 17.0 | 4.5 |
| Cpd. No. 213 | 10.5 | 7.1 | 14.0 | 2.2 | 20.8 | 6.5 |
| Cpd. No. 319 | 2.2 | 5.2 | 6.3 | 1.1 | 9.0 | 5.3 |
| Cpd. No. 322 | 3.2 | 7.4 | 7.7 | 2.3 | 10.2 | 7.4 |
| Cpd. No. 316 | 4.6 | 2.6 | 7.5 | 0.82 | 11.3 | 2.9 |
| Cpd. No. 317 | 16.7 | 7.8 | 22.9 | 3.5 | 38.6 | 7.1 |

Cell Viability Assays

The effect of representative BET bromodomain inhibitors on cell viability was determined in a 4-day proliferation assay. Cells were maintained in the appropriate culture medium with 10% FBS at 37° C. and an atmosphere of 5% CO2. All the cell lines were used within three months of thawing fresh vials.

Cells were seeded in 96-well flat bottom (Corning COSTAR, Corning, N.Y., cat#3595) or white opaque cell culture plates (BD Falcon, cat#353296) at a density of 3,000-10,000 cells/well in 75 µl of culture medium. Compounds were serially diluted in the appropriate medium, and 75 µl of the diluted compounds were added to the appropriate wells of the cell plate. After the addition of compounds, the cells were incubated at 37° C. in an atmosphere of 5% CO2 for 4 days. Cell viability was determined using the CellTiter-Glo® Luminescent Cell Viability Assay Kit (Promega, Madison, Wis.) for MOLM-13 cells and WST (2-(2-methoxy-4-nitrophenyl)-3-(4-nitrophenyl)-5-(2,4-disulfophenyl)-2H-tetrazolium, monosodium salt) Cell Counting-8 Kit (Dojindo Molecular Technologies, Inc., Rockville, Md.) for MDA-MB-436 cells according to the manufacturers' instructions.

For the WST assay, WST-8 reagent was added to each well at a final concentration of 10% (v/v), and then the plates were incubated at 37° C. for 1-2 hours for color development. The absorbance was measured at 450 nm using a SPECTRAmax PLUS plate reader (Molecular Devices, Sunnyvale, Calif.). The readings were normalized to the DMSO-treated cells and the half maximal inhibitory concentration (IC50) was calculated by nonlinear regression (four parameters sigmoid fitted with variable slope, least squares fit, and no constraint) analysis using the GraphPad Prism 5 software (GraphPad Software, La Jolla, Calif.).

For the CellTiter-Glo assay, 100 µl of CellTiter-Glo® Reagent was added to each well, and then the plates were incubated at room temperature for 10-20 minutes. The luminescent signal was measured using a Tecan Infinite M1000 multimode microplate reader (Tecan, Morrisville, N.C.). The readings were normalized to the DMSO-treated cells and the IC50 was calculated by nonlinear regression (four parameters sigmoid fitted with variable slope, least squares fit, and no constraint) analysis using the GraphPad Prism 5 software.

TABLE 6

Inhibition of cell growth by representative compounds in leukemia MOLM-13 and breast cancer MDA-MB-436 cell lines.

| | Cell Growth Inhibition ($IC_{50}$ (nM)) | |
|---|---|---|
| Compound ID No. | MOLM-13 Cell Line (CellTiter-Glo assay) | MDA-436 Cell Line (WST assay) |
| Cpd. No. 1 | 550 ± 303 | |
| Cpd. No. 2 | 1042 ± 158 | |
| Cpd. No. 21 | 311 ± 12 | |
| Cpd. No. 24 | 280 ± 35 | |
| Cpd. No. 22 | 183 ± 38 | |
| Cpd. No. 23 | 104 ± 16 | |
| Cpd. No. 25 | 343 ± 5 | 119.0 |
| Cpd. No. 26 | 431.1 | 696.5 |
| Cpd. No. 352 | 751.3 | 723.9 |
| Cpd. No. 183 | 20 | 93 |
| Cpd. No. 196 | 6.8 | 53 |

TABLE 6-continued

Inhibition of cell growth by representative compounds in leukemia MOLM-13 and breast cancer MDA-MB-436 cell lines.

| Compound ID No. | Cell Growth Inhibition (IC$_{50}$ (nM)) | |
|---|---|---|
| | MOLM-13 Cell Line (CellTiter-Glo assay) | MDA-436 Cell Line (WST assay) |
| Cpd. No. 197 | 17.3 | 101 |
| Cpd. No. 207 | 5.3 | 58.1 |
| Cpd. No. 211 | 10.4 | 140 |
| Cpd. No. 212 | 22 | 100 |
| Cpd. No. 213 | 48 | 225 |
| Cpd. No. 319 | 10 | 67.4 |
| Cpd. No. 322 | 19.4 | 63.9 |
| Cpd. No. 316 | 7.4 | 45.2 |
| Cpd. No. 317 | 31.6 | 169.1 |

TABLE 7

Cell growth inhibition of representative compounds in the prostate VCaP cell line (cells were treated with drug for 4 days and cell viability was measured by Cell TiterGLO assay).

| Compound ID | VCaP cells (IC$_{50}$(nM)) |
|---|---|
| JQ1 | 48 |
| I-BET762 | 500 |
| I-BET151 | 862 |
| Cpd. No. 23 | 117 |
| Cpd. No. 68 | 148 |
| Cpd. No. 73 | 156 |
| Cpd. No. 90 | 20 |
| Cpd. No. 101 | 25 |

TABLE 8

Cell growth inhibition of representative compounds in the leukemia MV4; 11, AML-2 and K562 cell lines.

| Cpd. ID No. | MV4; 11 (IC$_{50}$(nM)) | AML-2 (IC$_{50}$(nM)) | K562 (IC$_{50}$(nM)) |
|---|---|---|---|
| Cpd. No. 1 | 178 ± 114 | 148 ± 64 | >2000 |
| Cpd. No. 2 | 1074 ± 195 | 217 ± 61 | >2000 |
| Cpd. No. 21 | 124 ± 39 | 216 ± 43 | >2000 |
| Cpd. No. 24 | 83 ± 41 | 173 ± 89 | >2000 |
| Cpd. No. 22 | 61 ± 28 | 101 ± 22 | >2000 |
| Cpd. No. 23 | 17 ± 3 | 104 ± 5 | >2000 |
| Cpd. No. 25 | 65 ± 24 | 163 ± 2 | >2000 |

What is claimed:

1. A method of reducing or ameliorating cancer, the method comprising administering a therapeutically effective amount of a compound having formula (I):

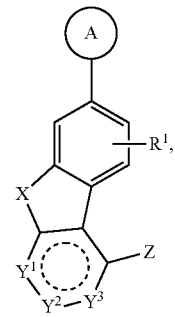

(I)

wherein:
X is N(R$^a$);
Y$^1$ and Y$^3$, independently, are CH or N;
Y$^2$ is CH, CR$^a$, or N;
Z is H,

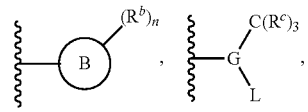

halo, or OH;
A is

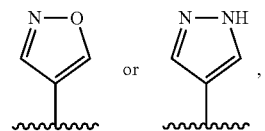

each unsubstituted or substituted;
B is aryl, CH(R$^a$)-aryl, C$_{3-10}$cycloalkyl, CH(R$^a$)—C$_{3-10}$cycloalkyl, heteroaryl, CH(R$^a$)-heteroaryl, C$_{3-10}$heterocycloalkyl, or CH(R$^a$)—C$_{3-10}$heterocycloalkyl, each unsubstituted or substituted;
G is N, O, or S;
L is null, H, or C(R$^d$)$_3$;
R$^1$ is H, halo, OH, OR$^e$, or N(R$^a$)$_2$;
R$^a$, independently, is H, C$_{1-3}$alkyl, or benzyl;
R$^b$, independently, is C$_{1-6}$alkyl, halo, aryl, unsubstituted or substituted CH$_2$-aryl, unsubstituted or substituted C$_{3-10}$cycloalkyl, unsubstituted or substituted CH$_2$—C$_{3-10}$cycloalkyl, heteroaryl, unsubstituted or substituted CH$_2$-heteroaryl, unsubstituted or substituted C$_{3-10}$heterocycloalkyl, or unsubstituted or substituted CH$_2$—C$_{3-10}$heterocycloalkyl, or CHO;
n is an integer 0, 1, 2, or 3; and
R$^c$ and R$^d$, each independently, are hydrogen, C$_{1-6}$alkyl, unsubstituted or substituted aryl, unsubstituted or substituted CH$_2$-aryl, unsubstituted or substituted C$_{3-10}$cycloalkyl, unsubstituted or substituted CH$_2$—C$_{3-10}$cycloalkyl, heteroaryl, unsubstituted or substituted CH$_2$-heteroaryl, unsubstituted or substituted C$_{3-10}$heterocycloalkyl, or unsubstituted or substituted CH$_2$—C$_{3-10}$heterocycloalkyl;
or a pharmaceutically acceptable salt, hydrate, or solvate thereof, to an individual in need thereof.

2. The method of claim 1 further comprising administering a therapeutically effective amount of a second therapeutic agent useful in the treatment of cancer.

3. The method of claim 2 wherein the compound having formula (I) and the second therapeutic agent are administered separately.

4. The method of claim 2 wherein the second therapeutic agent is one or more of surgery, a chemotherapeutic agent, and radiation.

5. The method of claim 1 wherein the cancer is breast cancer, leukemia, or prostate cancer.

6. The method of claim 2 wherein the compound having formula (I) and the second therapeutic agent are administered from separate compositions.

7. The method of claim 3 wherein the compound having formula (I) is administered prior to the second therapeutic agent.

8. The method of claim 3 wherein the compound having formula (I) is administered after the second therapeutic agent.

9. The method of claim 1, wherein ring A is:

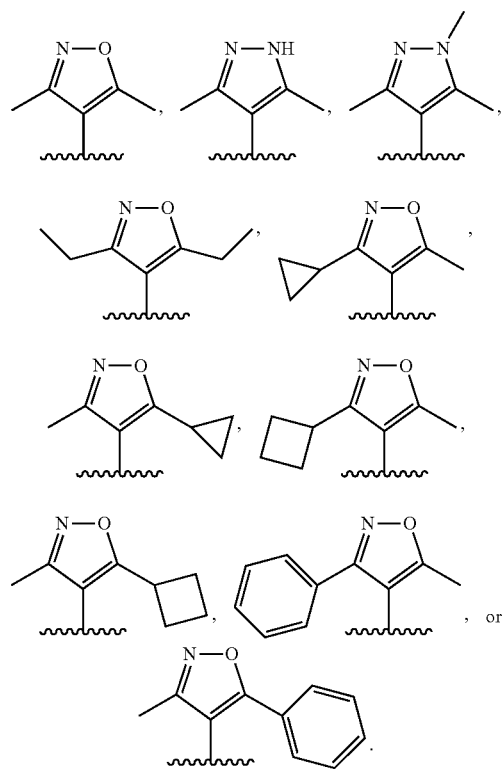

10. The method of claim 1, wherein $R^1$ is —OCH$_3$.

11. The method of claim 1, wherein the ring system

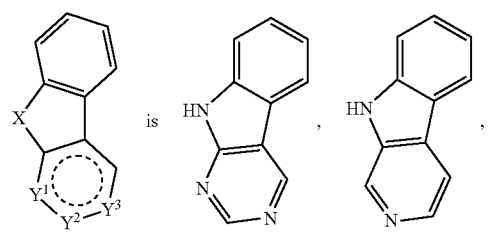

is

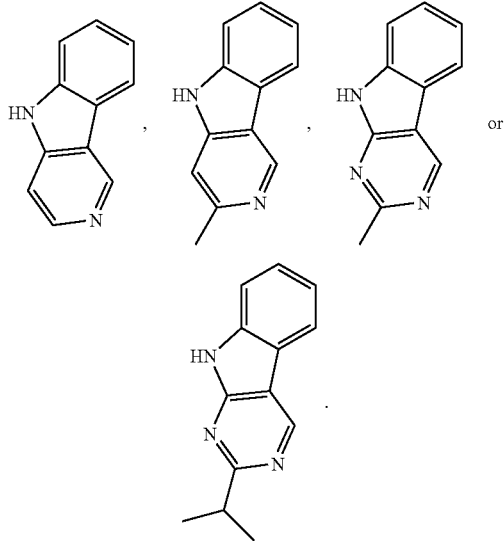

12. The method of claim 1, wherein Z is

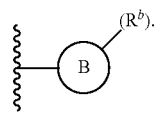

13. The method of claim 12, wherein the B ring, substituted or unsubstituted, is selected from the group consisting of:

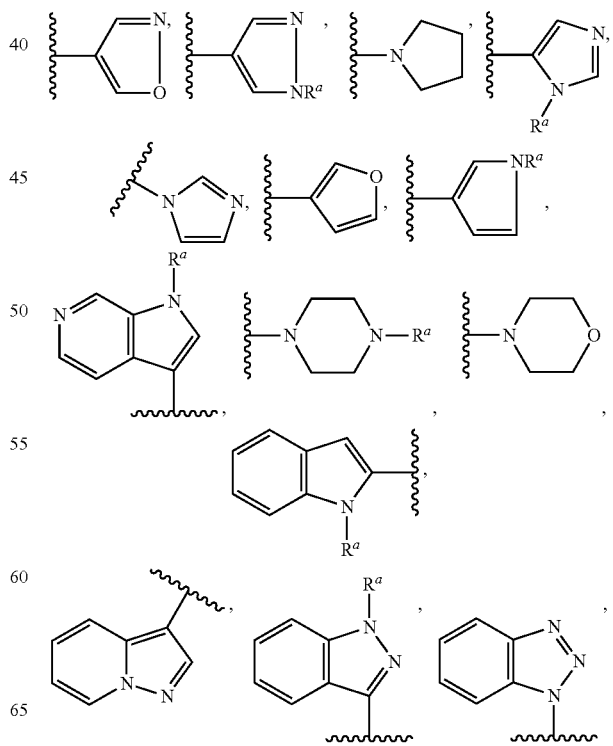

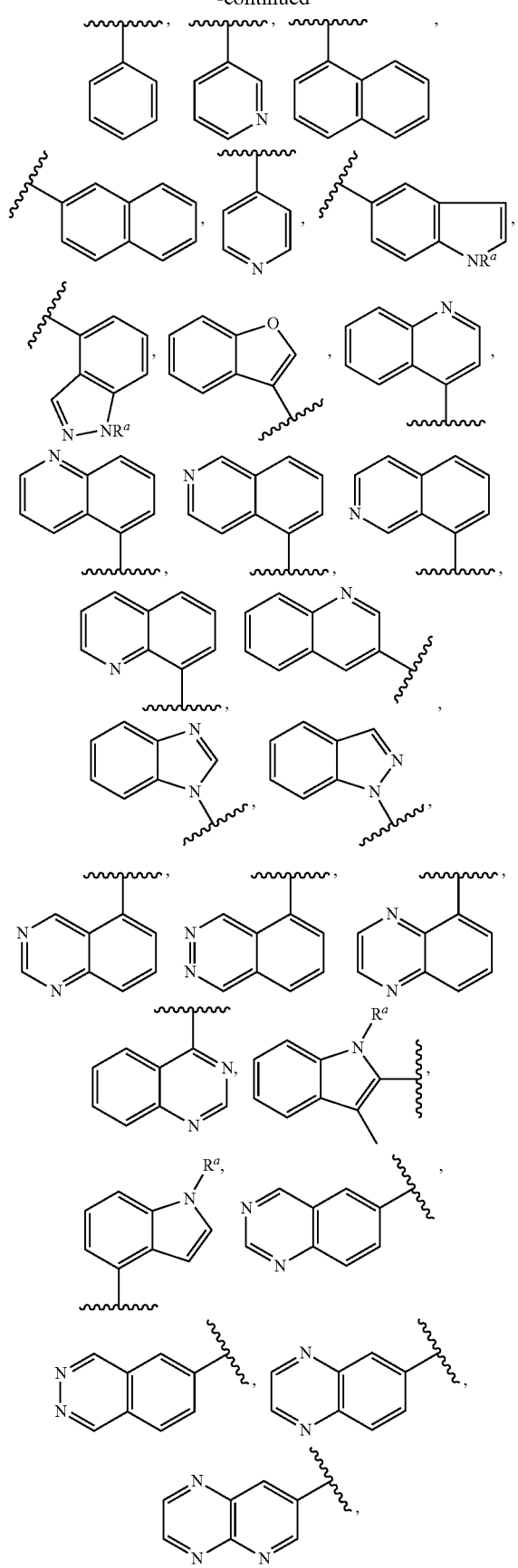
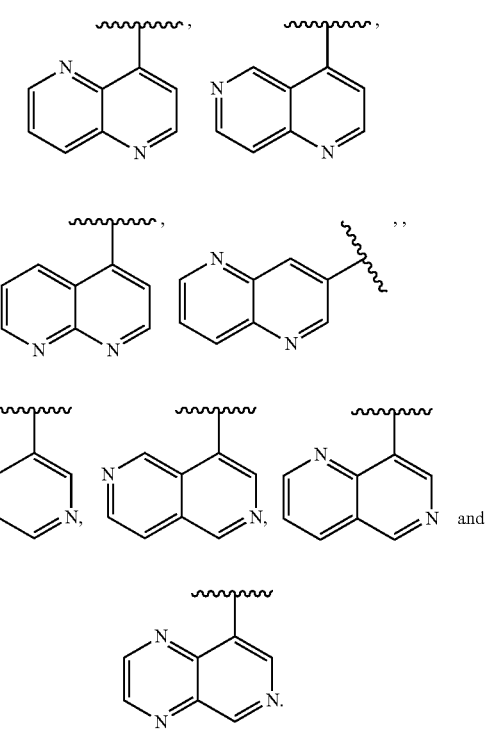
14. The method of claim 13, wherein the B ring is substituted with one to three of methyl, phenyl, fluoro, pyridinyl, chloro, isopropyl, cyclopropyl, or ethyl.
15. The method of claim 1 wherein the compound having formula (I) is selected from the group consisting of:
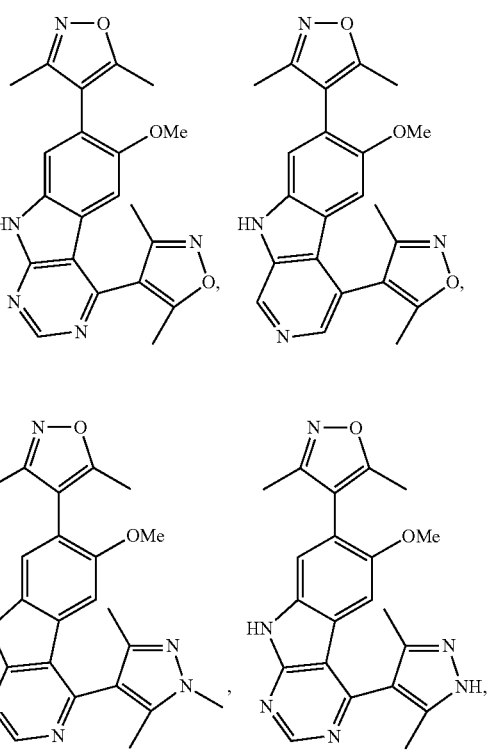

-continued
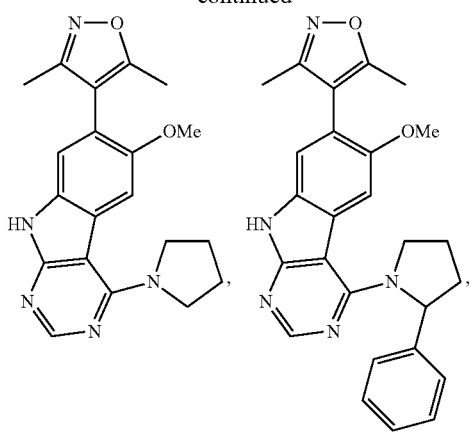
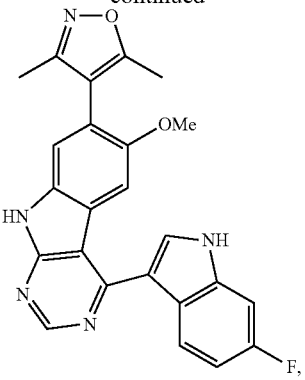
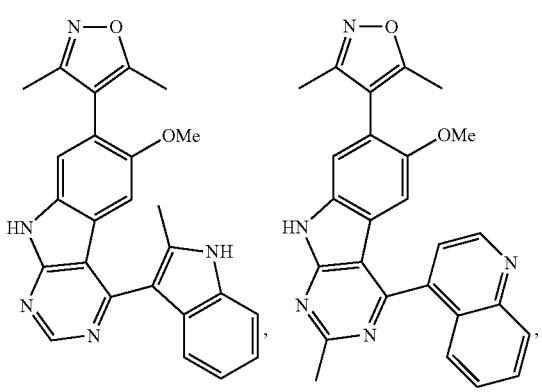
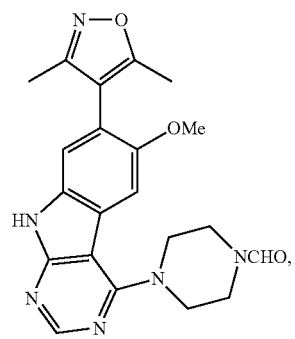
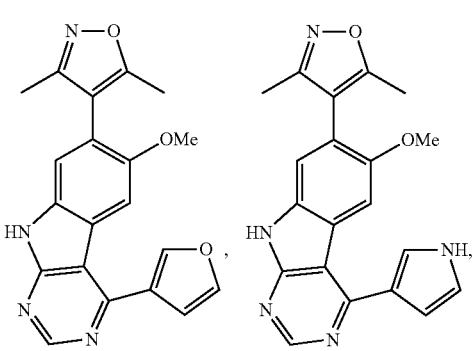
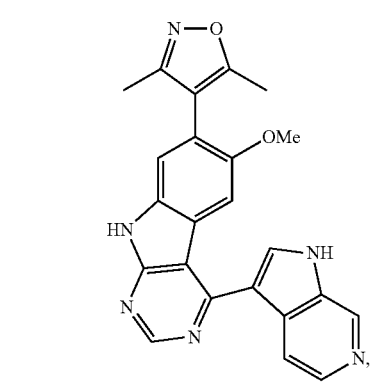
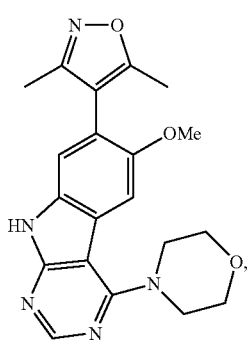

427
-continued
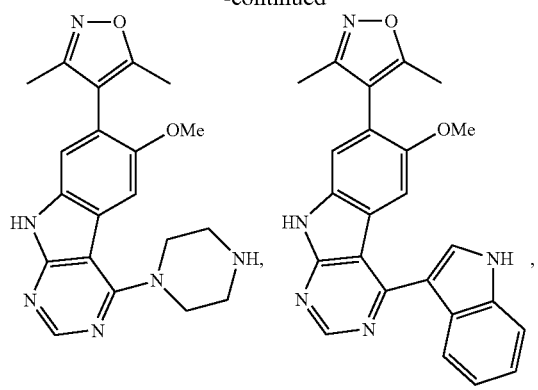
428
-continued
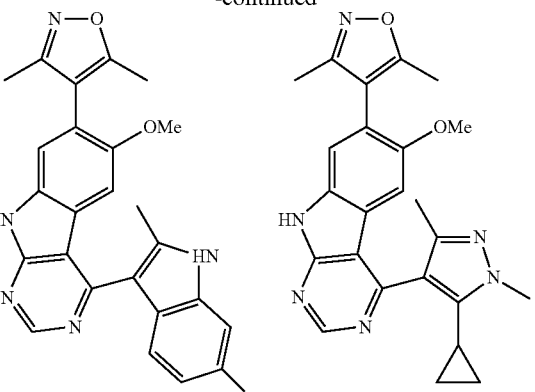
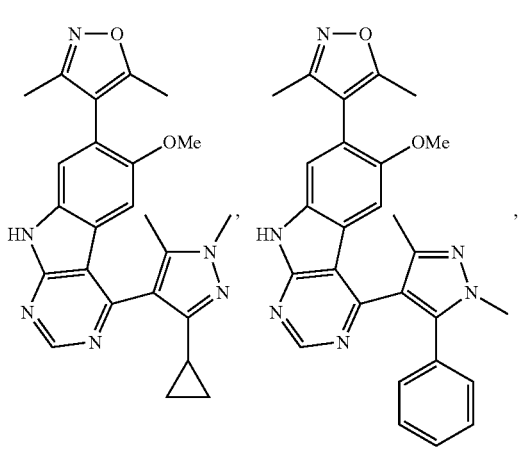
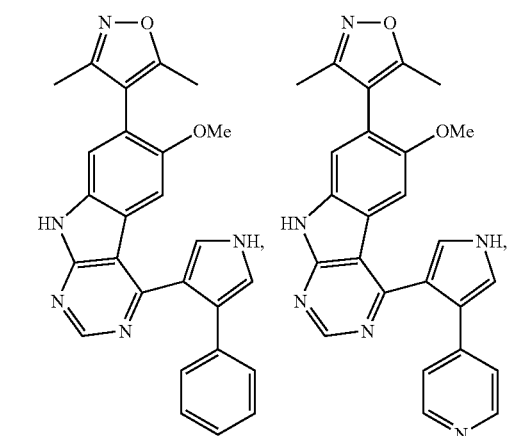
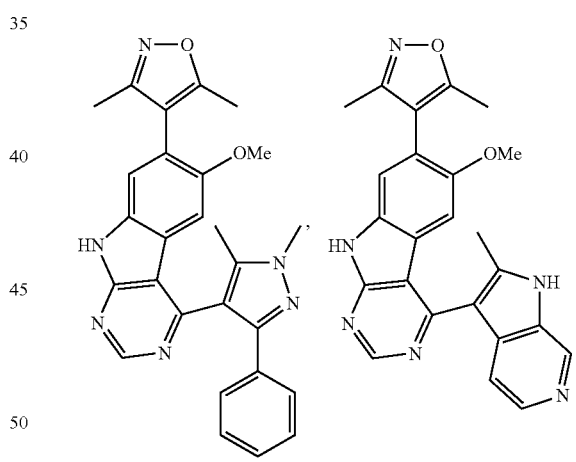
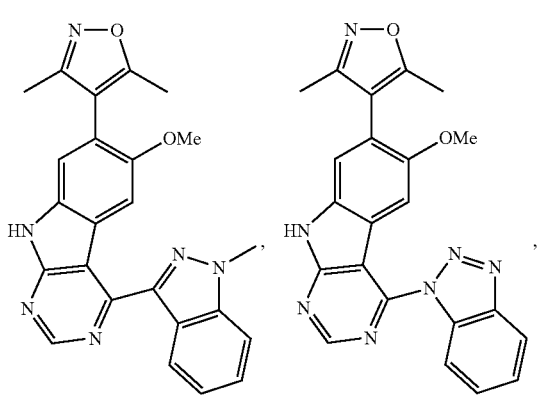
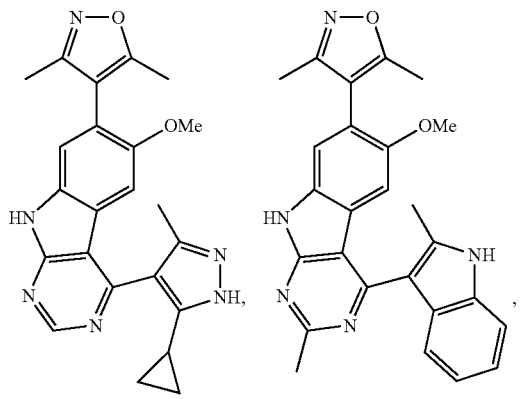

429
-continued
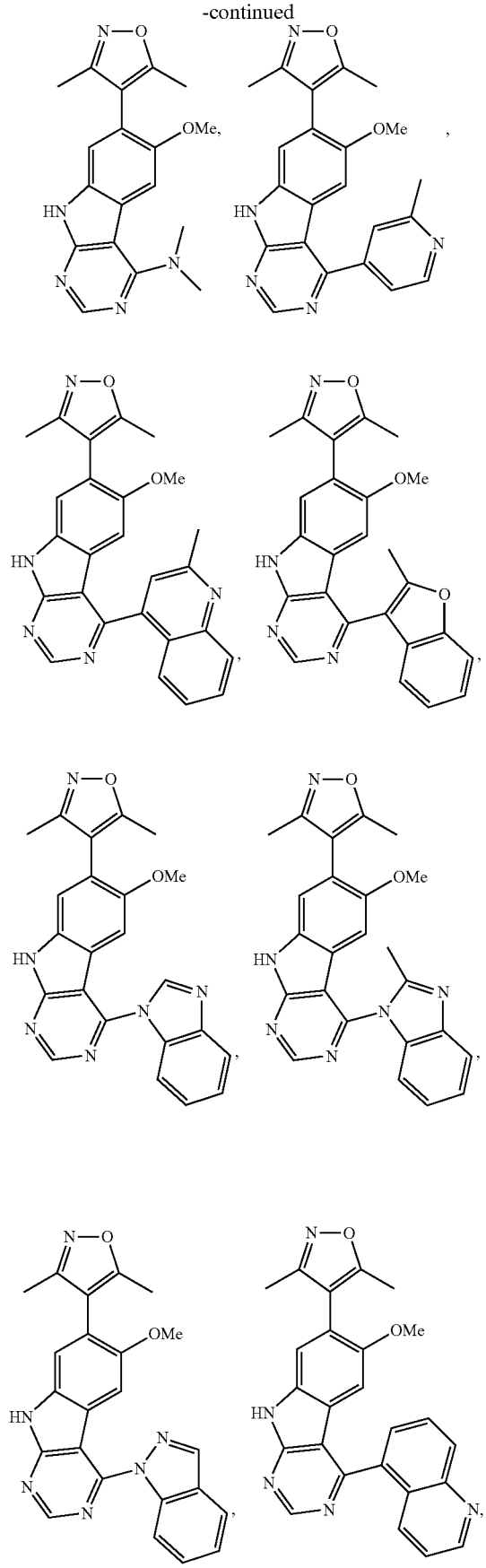
430
-continued
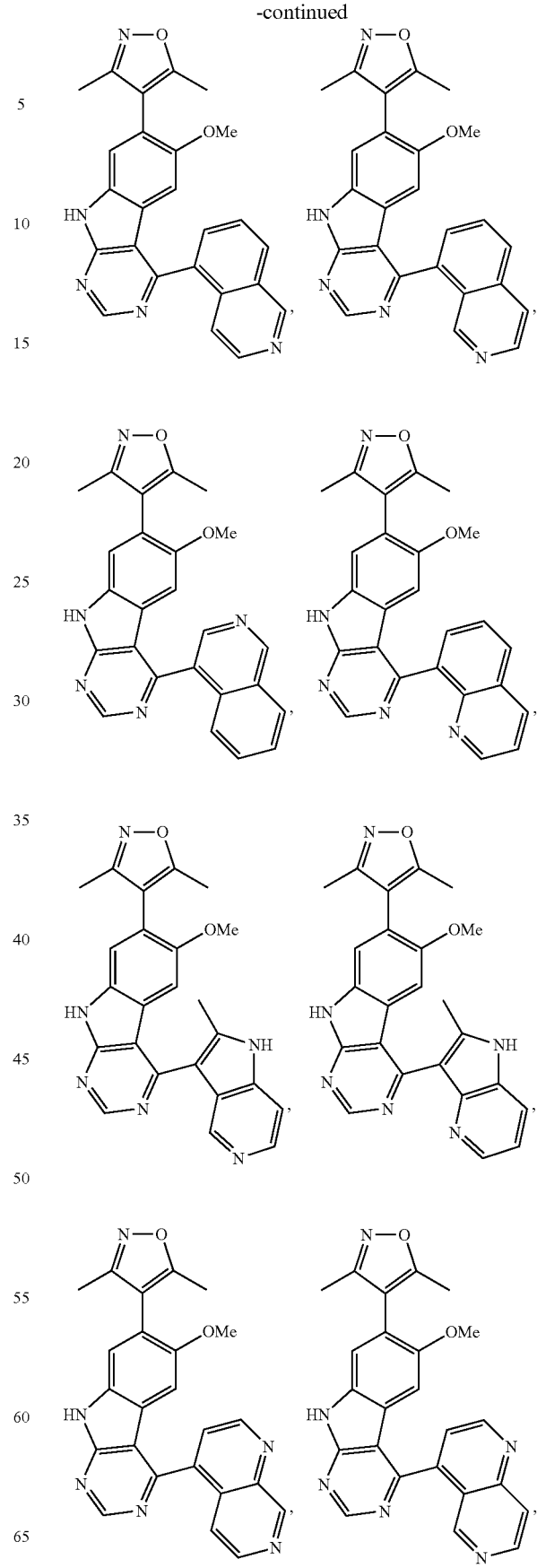

431
-continued
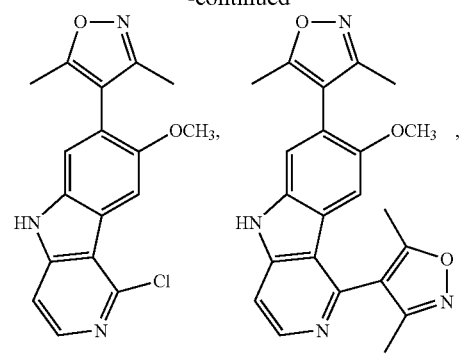
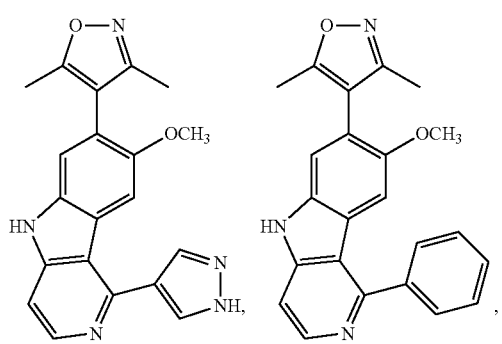
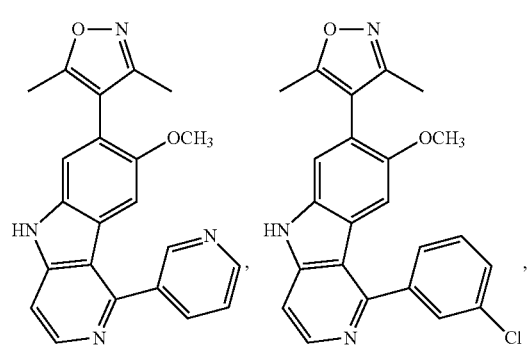
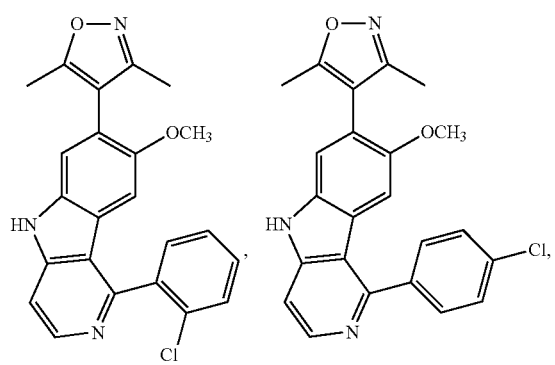
432
-continued
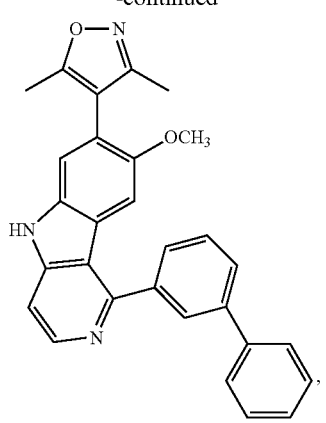
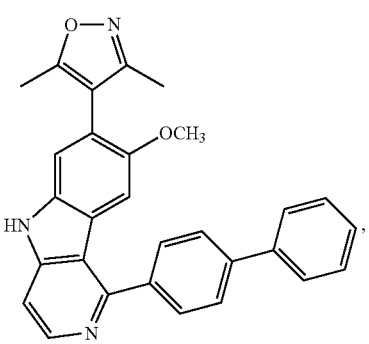
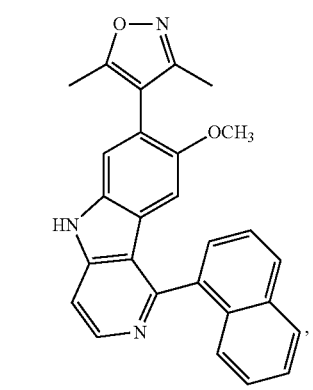
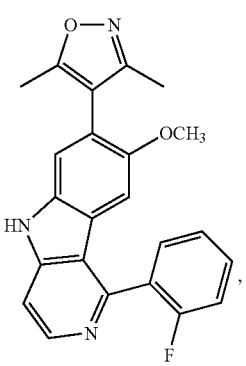

-continued
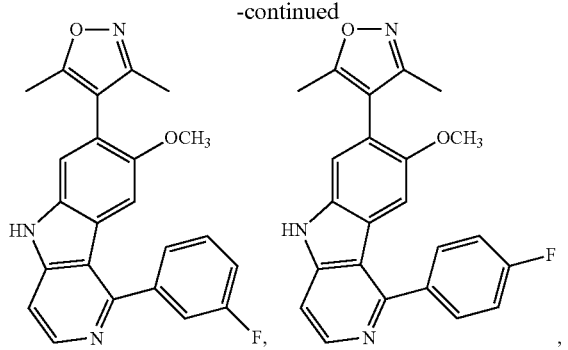
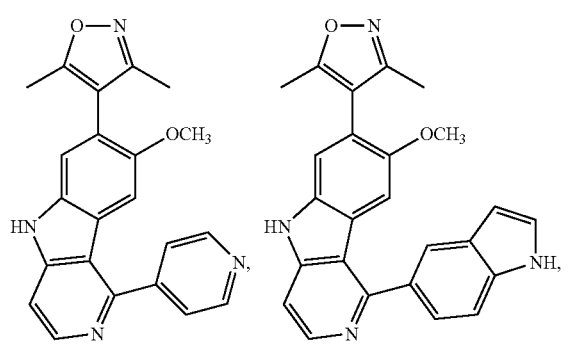
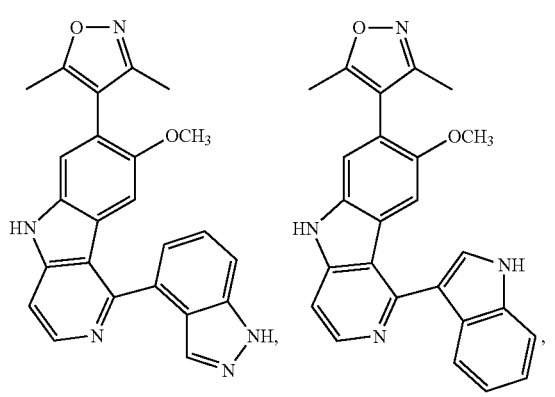
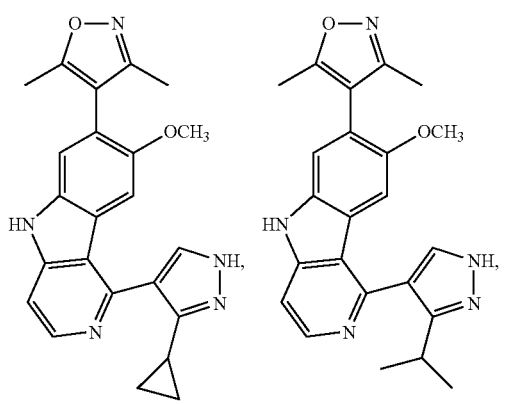
-continued
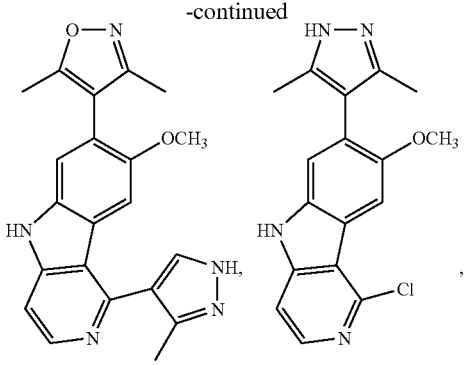
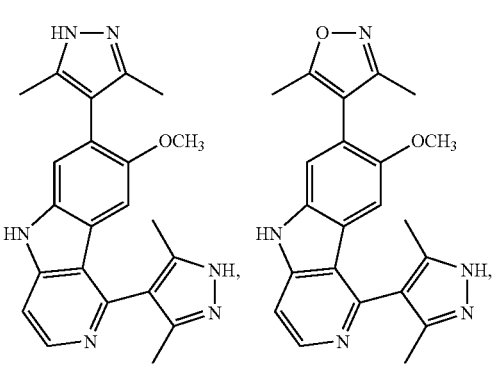
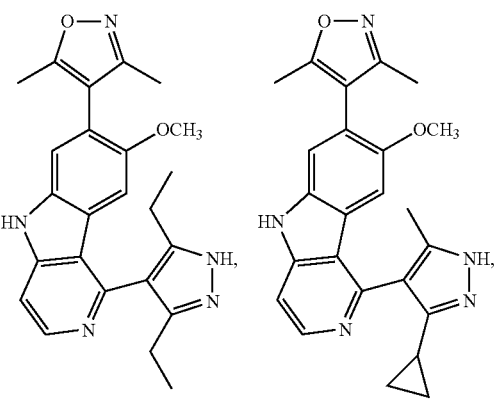
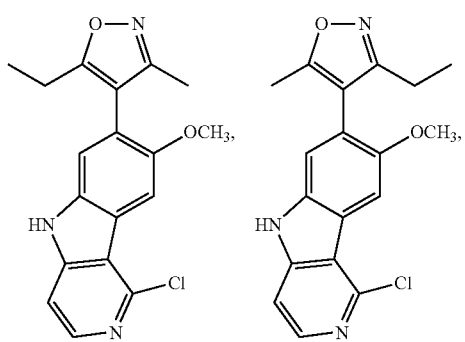

-continued

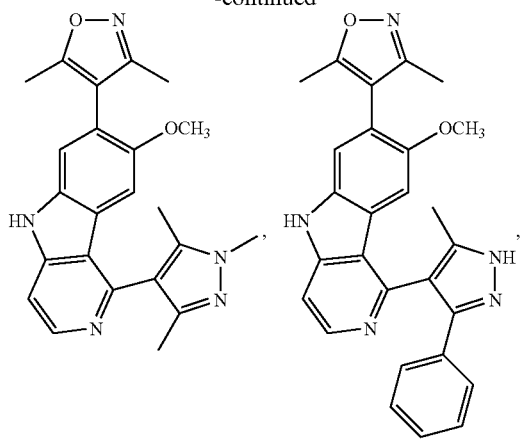

or a pharmaceutically acceptable salt, hydrate, or solvate thereof.

16. The method of claim 15 wherein the compound having formula (I) is:

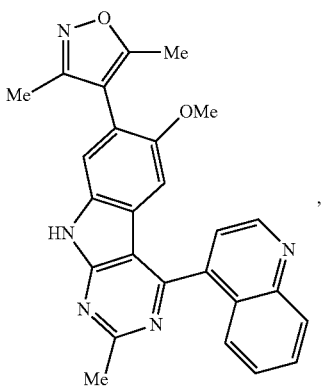

or a pharmaceutically acceptable salt, hydrate, or solvate thereof.

17. A method of reducing or ameliorating a proliferative disorder, the method comprising administering a therapeutically effective amount of a compound having formula (I):

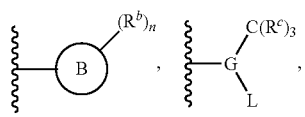

(I)

wherein:
X is N($R^a$);
$Y^1$ and $Y^3$, independently, are CH or N;
$Y^2$ is CH, $CR^a$, or N;
Z is H,

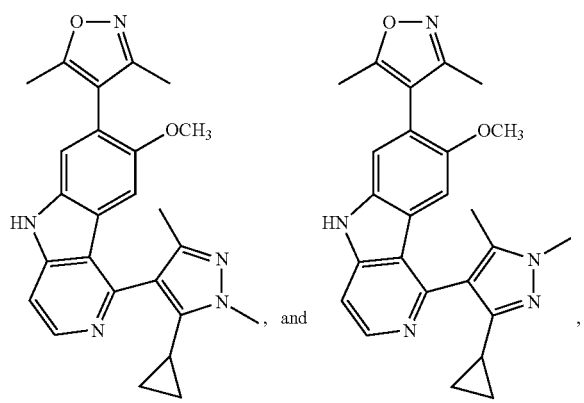

halo, or OH;
A is each unsubstituted or substituted;
B is aryl, CH($R^a$)-aryl, $C_{3-10}$cycloalkyl, CH($R^a$)—$C_{3-10}$cycloalkyl, heteroaryl, CH($R^a$)-heteroaryl, $C_{3-10}$heterocycloalkyl, or CH($R^a$)—$C_{3-10}$heterocycloalkyl, each unsubstituted or substituted;
G is N, O, or S;
L is null, H, or C($R^d$)$_3$;
$R^1$ is H, halo, OH, ORE, or N($R^a$)$_2$;
$R^a$, independently, is H, $C_{1-3}$alkyl, or benzyl;
$R^b$, independently, is $C_{1-6}$alkyl, halo, aryl, unsubstituted or substituted $CH_2$-aryl, unsubstituted or substituted $C_{3-10}$cycloalkyl, unsubstituted or substituted $CH_2$—$C_{3-10}$cycloalkyl, heteroaryl, unsubstituted or substituted $CH_2$-heteroaryl, unsubstituted or substituted $C_{3-10}$heterocycloalkyl, or unsubstituted or substituted $CH_2$—$C_{3-10}$heterocycloalkyl, or CHO;
n is an integer 0, 1, 2, or 3; and
$R^c$ and $R^d$, each independently, are hydrogen, $C_{1-6}$alkyl, unsubstituted or substituted aryl, unsubstituted or substituted $CH_2$-aryl, unsubstituted or substituted $C_{3-10}$cycloalkyl, unsubstituted or substituted $CH_2$—$C_{3-10}$cycloalkyl, heteroaryl, unsubstituted or substituted $CH_2$-heteroaryl, unsubstituted or substituted $C_{3-10}$heterocycloalkyl, or unsubstituted or substituted $CH_2$—$C_{3-10}$heterocycloalkyl;
or a pharmaceutically acceptable salt, hydrate, or solvate thereof,
to an individual in need thereof.

18. A method of reducing or ameliorating an autoimmune disorder, the method comprising administering a therapeutically effective amount of a compound having formula (I):

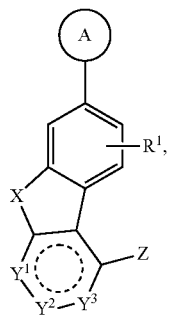

(I)

wherein:

X is N($R^a$);

$Y^1$ and $Y^3$, independently, are CH or N;

$Y^2$ is CH, ORE, or N;

Z is H,

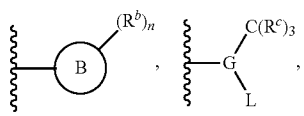

halo, or OH;

A is

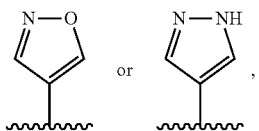 [SMILES: *c1cnoc1 ; *c1cn[nH]c1]

each unsubstituted or substituted;

B is aryl, CH($R^a$)-aryl, $C_{3-10}$cycloalkyl, CH($R^a$)—$C_{3-10}$cycloalkyl, heteroaryl, CH($R^a$)-heteroaryl, $C_{3-10}$heterocycloalkyl, or CH($R^a$)—$C_{3-10}$heterocycloalkyl, each unsubstituted or substituted;

G is N, O, or S;

L is null, H, or C($R^d$)$_3$;

$R^1$ is H, halo, OH, ORE, or N($R^a$)$_2$;

$R^a$, independently, is H, $C_{1-3}$alkyl, or benzyl;

$R^b$, independently, is $C_{1-6}$alkyl, halo, aryl, unsubstituted or substituted CH$_2$-aryl, unsubstituted or substituted $C_{3-10}$cycloalkyl, unsubstituted or substituted CH$_2$—$C_{3-10}$cycloalkyl, heteroaryl, unsubstituted or substituted CH$_2$-heteroaryl, unsubstituted or substituted $C_{3-10}$heterocycloalkyl, or unsubstituted or substituted CH$_2$—$C_{3-10}$heterocycloalkyl, or CHO;

n is an integer 0, 1, 2, or 3; and $R^c$ and $R^d$, each independently, are hydrogen, $C_{1-6}$alkyl, unsubstituted or substituted aryl, unsubstituted or substituted CH$_2$-aryl, unsubstituted or substituted $C_{3-10}$cycloalkyl, unsubstituted or substituted CH$_2$—$C_{3-10}$cycloalkyl, heteroaryl, unsubstituted or substituted CH$_2$-heteroaryl, unsubstituted or substituted $C_{3-10}$heterocycloalkyl, or unsubstituted or substituted CH$_2$—$C_{3-10}$heterocycloalkyl;

or a pharmaceutically acceptable salt, hydrate, or solvate thereof, to an individual in need thereof.

* * * * *

UNITED STATES PATENT AND TRADEMARK OFFICE
CERTIFICATE OF CORRECTION

PATENT NO. : 10,391,175 B2  
APPLICATION NO. : 15/619671  
DATED : August 27, 2019  
INVENTOR(S) : Shaomeng Wang et al.

Page 1 of 1

It is certified that error appears in the above-identified patent and that said Letters Patent is hereby corrected as shown below:

In the Claims

At Column 420, Line 45, "ORE," should be -- OR$^a$, --.

At Column 436, Line 47, "ORE," should be -- OR$^a$, --.

At Column 437, Line 26, "ORE," should be -- OR$^a$, --.

At Column 438, Line 17, "ORE," should be -- OR$^a$, --.

Signed and Sealed this  
Sixteenth Day of June, 2020

Andrei Iancu  
*Director of the United States Patent and Trademark Office*